(12) United States Patent
DeGoey et al.

(10) Patent No.: US 8,921,514 B2
(45) Date of Patent: Dec. 30, 2014

(54) ANTI-VIRAL COMPOUNDS

(75) Inventors: David A. DeGoey, Salem, WI (US);
Warren M. Kati, Gurnee, IL (US);
Charles W. Hutchins, Green Oaks, IL (US); Pamela L. Donner, Mundelein, IL (US); Allan C. Krueger, Gurnee, IL (US); John T. Randolph, Libertyville, IL (US); Christopher E. Motter, Oak Creek, WI (US); Lissa T. Nelson, Highland Park, IL (US); Sachin V. Patel, Round Lake, IL (US); Mark A. Matulenko, Libertyville, IL (US); Ryan G. Keddy, Beach Park, IL (US); Tammie K. Jinkerson, Pleasant Prairie, WI (US); Yi Gao, Vernon Hills, IL (US); Dachun Liu, Vernon Hills, IL (US); John K. Pratt, Kenosha, WI (US); Todd W. Rockway, Grayslake, IL (US); Clarence J. Maring, Palatine, IL (US); Douglas K. Hutchinson, Antioch, IL (US); Charles A. Flentge, Salem, WI (US); Rolf Wagner, Antioch, IL (US); Michael D. Tufano, Chicago, IL (US); David A. Betebenner, Grayslake, IL (US); Kathy Sarris, Mundelein, IL (US); Kevin R. Woller, Antioch, IL (US); Seble H. Wagaw, Evanston, IL (US); Jean C. Califano, Whitefish Bay, WI (US); Wenke Li, Gurnee, IL (US); Daniel D. Caspi, Evanston, IL (US); Mary E. Bellizzi, Lake Forest, IL (US); William A. Carroll, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 974 days.

(21) Appl. No.: 12/964,027

(22) Filed: Dec. 9, 2010

(65) Prior Publication Data
US 2011/0207699 A1 Aug. 25, 2011

Related U.S. Application Data

(63) Continuation-in-part of application No. 12/903,822, filed on Oct. 13, 2010, now abandoned, which is a continuation of application No. 12/813,301, filed on Jun. 10, 2010, now Pat. No. 8,691,938.

(60) Provisional application No. 61/186,291, filed on Jun. 11, 2009, provisional application No. 61/242,836, filed on Sep. 16, 2009, provisional application No. 61/243,596, filed on Sep. 18, 2009.

(51) Int. Cl.
*A61K 31/66* (2006.01)
*C07K 16/00* (2006.01)
*C07D 453/00* (2006.01)
*C07D 401/14* (2006.01)
*C07D 403/14* (2006.01)
*C07D 405/14* (2006.01)
*C07D 413/14* (2006.01)
*C07D 491/113* (2006.01)

(52) U.S. Cl.
CPC ............ *C07D 401/14* (2013.01); *C07D 403/14* (2013.01); *C07D 405/14* (2013.01); *C07D 453/00* (2013.01); *C07D 413/14* (2013.01); *C07D 491/113* (2013.01)
USPC .............. 530/206; 514/80; 514/107; 544/247

(58) Field of Classification Search
None
See application file for complete search history.

(56) References Cited

U.S. PATENT DOCUMENTS

| | | | |
|---|---|---|---|
| 5,683,999 | A | 11/1997 | Jadhav et al. |
| 5,830,867 | A | 11/1998 | Bhatnagar et al. |
| 5,935,982 | A | 8/1999 | Dykstra et al. |
| 6,042,847 | A | 3/2000 | Kerc et al. |
| 6,235,493 | B1 | 5/2001 | Bissell et al. |
| 6,369,091 | B1 | 4/2002 | Sircar et al. |
| 6,388,093 | B1 | 5/2002 | Chamberlain et al. |
| 6,599,528 | B1 | 7/2003 | Rosenberg et al. |
| 6,703,403 | B2 | 3/2004 | Norbeck et al. |
| 6,846,802 | B2 | 1/2005 | Chen et al. |
| 6,881,741 | B2 | 4/2005 | Chan Chun Kong et al. |
| 6,919,366 | B2 | 7/2005 | Sircar et al. |
| 6,923,988 | B2 | 8/2005 | Patel et al. |
| 7,065,453 | B1 | 6/2006 | Diller et al. |
| 7,141,574 | B2 | 11/2006 | Beaulieu et al. |
| 7,183,270 | B2 | 2/2007 | Cherney et al. |
| 7,488,832 | B2 | 2/2009 | Cole et al. |

(Continued)

FOREIGN PATENT DOCUMENTS

| | | |
|---|---|---|
| BR | PI0401908 A | 1/2006 |
| DE | 75755 C | 3/1893 |

(Continued)

OTHER PUBLICATIONS

Kelly et. al., Bisubstrate Reaction Templates. Examination of Consequences of Identical versus Different bonding Sites. J. Am. Chem. Soc. 1990, 112, 8024-8034).*
Abagyan R., et al., "ICM—A New Method for Protein Modeling and Design: Applications to Docking and Structure Prediction from the Distorted Native Conformation," Journal of Computational Chemistry, 1994, vol. 15 (5), pp. 488-506.
Altschuel S.F., et al., "Basic Local Alignment Search Tool," Journal of Molecular Biology, 1990, 215 (3), 403-410.
Altschul S.F., et al., "Gapped BLAST and PSI-BLAST: A New Generation of Protein Database Search Programs," Nucleic Acids Research, 1997, 25 (17), 3389-3402.

(Continued)

*Primary Examiner* — James H Alstrum Acevedo
*Assistant Examiner* — Jeanette Lieb
(74) *Attorney, Agent, or Firm* — Xu Zhang

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

7 Claims, No Drawings

(56) References Cited

U.S. PATENT DOCUMENTS

| | | |
|---|---|---|
| 7,659,270 B2 | 2/2010 | Bachand et al. |
| 7,704,992 B2 | 4/2010 | Bachand et al. |
| 7,728,027 B2 | 6/2010 | Pack et al. |
| 7,732,457 B2 | 6/2010 | Malamas et al. |
| 7,741,347 B2 | 6/2010 | Bachand et al. |
| 7,745,636 B2 | 6/2010 | Bachand et al. |
| 7,759,495 B2 | 7/2010 | Bachand et al. |
| 7,763,731 B2 | 7/2010 | Rockway et al. |
| 7,906,655 B2 | 3/2011 | Belema et al. |
| 8,101,643 B2 | 1/2012 | Qiu et al. |
| 8,691,938 B2 | 4/2014 | Degoey et al. |
| 2002/0183319 A1 | 12/2002 | Liang et al. |
| 2003/0004203 A1 | 1/2003 | Sircar et al. |
| 2003/0100582 A1 | 5/2003 | Sircar et al. |
| 2004/0013697 A1 | 1/2004 | Berndl et al. |
| 2004/0034189 A1* | 2/2004 | Cho et al. ............... 528/394 |
| 2005/0075343 A1 | 4/2005 | Sircar et al. |
| 2005/0084529 A1 | 4/2005 | Rosenberg et al. |
| 2005/0197375 A1 | 9/2005 | Sircar et al. |
| 2006/0003942 A1 | 1/2006 | Tung et al. |
| 2006/0052602 A1 | 3/2006 | Kim et al. |
| 2006/0058317 A1 | 3/2006 | Gravestock et al. |
| 2006/0105997 A1 | 5/2006 | Arrington et al. |
| 2007/0004741 A1 | 1/2007 | Apodaca et al. |
| 2007/0142434 A1 | 6/2007 | Sandanayaka et al. |
| 2007/0197558 A1 | 8/2007 | Betebenner et al. |
| 2007/0232627 A1 | 10/2007 | Betebenner et al. |
| 2007/0232645 A1 | 10/2007 | Rockway et al. |
| 2007/0299068 A1 | 12/2007 | Karp et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0075696 A1* | 3/2008 | Parsons et al. ............ 424/85.6 |
| 2008/0221107 A1 | 9/2008 | Giordanetto et al. |
| 2008/0299075 A1 | 12/2008 | Bachand et al. |
| 2008/0311075 A1 | 12/2008 | Bachand et al. |
| 2009/0004111 A1 | 1/2009 | Rice et al. |
| 2009/0041716 A1 | 2/2009 | Kim et al. |
| 2009/0043107 A1 | 2/2009 | Pack et al. |
| 2009/0068140 A1 | 3/2009 | Bachand et al. |
| 2009/0093456 A1 | 4/2009 | Arnold et al. |
| 2009/0104151 A1 | 4/2009 | Hanson et al. |
| 2009/0202478 A1 | 8/2009 | Bachand et al. |
| 2009/0202483 A1 | 8/2009 | Bachand et al. |
| 2010/0021540 A1 | 1/2010 | Gopinathan et al. |
| 2010/0029666 A1 | 2/2010 | Harper et al. |
| 2010/0055071 A1 | 3/2010 | Leivers et al. |
| 2010/0068176 A1 | 3/2010 | Belema et al. |
| 2010/0080772 A1 | 4/2010 | Belema et al. |
| 2010/0143499 A1 | 6/2010 | Condon |
| 2010/0158862 A1 | 6/2010 | Kim et al. |
| 2010/0160355 A1 | 6/2010 | DeGoey et al. |
| 2010/0168138 A1 | 7/2010 | DeGoey et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2010/0317568 A1 | 12/2010 | Degoey et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0189129 A1 | 8/2011 | Qiu et al. |
| 2011/0195044 A1 | 8/2011 | Romine |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2012/0004196 A1 | 1/2012 | Degoey et al. |
| 2012/0028978 A1 | 2/2012 | Zhong et al. |
| 2012/0040977 A1 | 2/2012 | Li et al. |
| 2012/0076756 A1 | 3/2012 | Qiu et al. |
| 2012/0114600 A1 | 5/2012 | Mckinnell et al. |
| 2012/0122864 A1 | 5/2012 | Zhong et al. |
| 2012/0172290 A1 | 7/2012 | Krueger et al. |

FOREIGN PATENT DOCUMENTS

| | | |
|---|---|---|
| EP | 2242751 A1 | 10/2010 |
| JP | 2003282270 A | 10/2003 |
| JP | 2003282270 A | 10/2003 |
| JP | 2007320925 A | 12/2007 |
| JP | 2010126571 A | 6/2010 |
| RU | 2286343 C2 | 10/2006 |
| WO | WO9427627 A1 | 12/1994 |
| WO | WO9961020 A1 | 12/1999 |
| WO | WO-0000179 A1 | 1/2000 |
| WO | WO0012521 A1 | 3/2000 |
| WO | WO-0214314 A2 | 2/2002 |
| WO | WO-03068738 | 8/2003 |
| WO | WO-03068738 A1 | 8/2003 |
| WO | WO03082186 A2 | 10/2003 |
| WO | WO2004005283 A1 | 1/2004 |
| WO | WO2004014313 A2 | 2/2004 |
| WO | WO2004014852 A2 | 2/2004 |
| WO | WO2004014852 A3 | 4/2004 |
| WO | WO2004014313 A3 | 12/2005 |
| WO | WO2006020951 A1 | 2/2006 |
| WO | WO2006033703 A1 | 3/2006 |
| WO | WO-2006093867 A1 | 9/2006 |
| WO | WO2006133326 A1 | 12/2006 |
| WO | WO2007070556 A2 | 6/2007 |
| WO | WO2007070600 A2 | 6/2007 |
| WO | WO2007076034 A2 | 7/2007 |
| WO | WO2007076035 A2 | 7/2007 |
| WO | WO-2007081517 A2 | 7/2007 |
| WO | WO2007082554 A1 | 7/2007 |
| WO | WO2007070556 A3 | 8/2007 |
| WO | WO2007081517 C1 | 9/2007 |
| WO | WO2007070600 A3 | 11/2007 |
| WO | WO2007131366 A1 | 11/2007 |
| WO | WO2007144174 A1 | 12/2007 |
| WO | WO2008014236 A1 | 1/2008 |
| WO | WO2008014238 A2 | 1/2008 |
| WO | WO2008021927 A2 | 2/2008 |
| WO | WO2008021928 A2 | 2/2008 |
| WO | WO2008021936 A2 | 2/2008 |
| WO | WO2008021928 A3 | 3/2008 |
| WO | WO2008021936 A3 | 4/2008 |
| WO | WO2008021927 A3 | 5/2008 |
| WO | WO2008064218 A2 | 5/2008 |
| WO | WO2008070447 A2 | 6/2008 |
| WO | WO2008074450 A2 | 6/2008 |
| WO | WO2008064218 A3 | 10/2008 |

(56) References Cited

FOREIGN PATENT DOCUMENTS

| | | |
|---|---|---|
| WO | WO2008128121 A1 | 10/2008 |
| WO | WO2008133753 A2 | 11/2008 |
| WO | WO2008144380 A1 | 11/2008 |
| WO | WO2009003009 A1 | 12/2008 |
| WO | WO2009020534 A2 | 2/2009 |
| WO | WO2009020825 A1 | 2/2009 |
| WO | WO2009020828 A1 | 2/2009 |
| WO | WO2008070447 A3 | 3/2009 |
| WO | WO2009093082 A1 | 7/2009 |
| WO | WO2009094224 A1 | 7/2009 |
| WO | WO2009102318 A1 | 8/2009 |
| WO | WO2009102325 A1 | 8/2009 |
| WO | WO2009102568 A1 | 8/2009 |
| WO | WO2009102633 A1 | 8/2009 |
| WO | WO2009102694 A1 | 8/2009 |
| WO | WO2009136290 A1 | 11/2009 |
| WO | WO2009143361 A1 | 11/2009 |
| WO | WO2009155709 A1 | 12/2009 |
| WO | WO2010015090 A1 | 2/2010 |
| WO | WO-2010017035 A2 | 2/2010 |
| WO | WO2010017401 A1 | 2/2010 |
| WO | WO2010039793 A1 | 4/2010 |
| WO | WO2010059858 A1 | 5/2010 |
| WO | WO2010062821 A1 | 6/2010 |
| WO | WO2010065668 A1 | 6/2010 |
| WO | WO2010065674 A1 | 6/2010 |
| WO | WO2010065681 A1 | 6/2010 |
| WO | WO2010075376 A2 | 7/2010 |
| WO | WO2010091413 A1 | 8/2010 |
| WO | WO2010096302 A1 | 8/2010 |
| WO | WO2010096462 A1 | 8/2010 |
| WO | WO2010096777 A1 | 8/2010 |
| WO | WO2010099527 A1 | 9/2010 |
| WO | WO2010111483 A1 | 9/2010 |
| WO | WO2010111534 A1 | 9/2010 |
| WO | WO2010111673 A1 | 9/2010 |
| WO | WO2010115767 A1 | 10/2010 |
| WO | WO2010117635 A1 | 10/2010 |
| WO | WO2010117704 A1 | 10/2010 |
| WO | WO2010117977 A1 | 10/2010 |
| WO | WO2010120621 A1 | 10/2010 |
| WO | WO2010120935 A1 | 10/2010 |
| WO | WO2010122162 A1 | 10/2010 |
| WO | WO2010132538 A1 | 11/2010 |
| WO | WO2010132601 A1 | 11/2010 |
| WO | WO2010138368 A1 | 12/2010 |
| WO | WO2010138488 A1 | 12/2010 |
| WO | WO2010138790 A1 | 12/2010 |
| WO | WO2010138791 A1 | 12/2010 |
| WO | WO2010144646 A2 | 12/2010 |
| WO | WO2010148006 A1 | 12/2010 |
| WO | WO2011004276 A1 | 1/2011 |
| WO | WO2011009084 A2 | 1/2011 |
| WO | WO2011015658 A1 | 2/2011 |
| WO | WO2011026920 A1 | 3/2011 |
| WO | WO2011028596 A1 | 3/2011 |
| WO | WO2011031904 A1 | 3/2011 |
| WO | WO2011031934 A1 | 3/2011 |
| WO | WO2011050146 A1 | 4/2011 |
| WO | WO2011054834 A1 | 5/2011 |
| WO | WO2011059850 A1 | 5/2011 |
| WO | WO2011059887 A1 | 5/2011 |
| WO | WO2011060000 A1 | 5/2011 |
| WO | WO2011066241 A1 | 6/2011 |
| WO | WO2011068941 A2 | 6/2011 |
| WO | WO2011075439 A1 | 6/2011 |
| WO | WO2011075607 A1 | 6/2011 |
| WO | WO2011075615 A1 | 6/2011 |
| WO | WO2011079327 A1 | 6/2011 |
| WO | WO2011081918 A1 | 7/2011 |
| WO | WO2011082077 A1 | 7/2011 |
| WO | WO2011087740 A1 | 7/2011 |
| WO | WO2011091417 A1 | 7/2011 |
| WO | WO2011091446 A1 | 7/2011 |
| WO | WO2011091532 A1 | 8/2011 |
| WO | WO2011112429 A1 | 9/2011 |
| WO | WO2011119853 A1 | 9/2011 |
| WO | WO2011119858 A1 | 9/2011 |
| WO | WO2011119860 A1 | 9/2011 |
| WO | WO2011119870 A1 | 9/2011 |
| WO | WO2011127350 A1 | 10/2011 |
| WO | WO 2011146401 A1 | 11/2011 |
| WO | WO 2011150243 A1 | 12/2011 |
| WO | WO 2011156543 A2 | 12/2011 |
| WO | WO-2011156578 A1 | 12/2011 |
| WO | WO-2012039717 A1 | 3/2012 |
| WO | WO-2012040389 A2 | 3/2012 |
| WO | WO-2012040923 A1 | 4/2012 |
| WO | WO-2012040924 A1 | 4/2012 |
| WO | WO-2012041014 A1 | 4/2012 |
| WO | WO-2012041227 A1 | 4/2012 |
| WO | WO-2012050848 A1 | 4/2012 |
| WO | WO-2012050850 A1 | 4/2012 |
| WO | WO-2012068234 A2 | 5/2012 |
| WO | WO-2012074437 A2 | 6/2012 |
| WO | WO-2012087976 A2 | 6/2012 |

OTHER PUBLICATIONS

Baker D., et al., "Protein Structure Prediction and Structural Genomics," Science, 2001, vol. 294 (5540), pp. 93-96.
Bartenschlager R., "Hepatitis C Virus Molecular Clones: From cDNA to Infectious Virus Particles in Cell Culture," Current Opinion in Microbiology, 2006, vol. 9 (4), pp. 416-422.
Bartenschlager R., "Hepatitis C Virus Replicons: Potential Role for Drug Development," Nature Reviews Drug Discovery, 2002, vol. 1 (11), pp. 911-916.
Bohm H.J., "The Computer Program LUDI: A New Method for the De Novo Design of Enzyme Inhibitors," Journal of Computer-Aided Molecular Design, vol. 6, pp. 61-78, 1992.
Breitenbach J., et al., "Confocal Raman-Spectroscopy: Analytical Approach to Solid Dispersions and Mapping of Drugs," 1999, vol. 16 (7), pp. 1109-1113.
Brunger A.T., et al., "Recent Developments for the Efficient Crystallographic Refinement of Macromolecular Structures," Current Opinion in Structural Biology, 1998, vol. 8, pp. 606-611.
Bundgaard H., "Design of Prodrugs", Elsevier Science Publishers, 1985, pp. 7-9 & 1-6 & 21-24.
Chiou W.L., et al., "Pharmaceutical Applications of Solid Dispersion Systems," Journal of Pharmaceutical Science, 1971, vol. 60 (9), pp. 1281-1302.
Co-pending U.S. Appl. No. 13/404,429, filed Feb. 24, 2012.
Cornell, W.D., et al., "A Second Generation Force Field for the Simulation of Proteins, Nucleic Acids, and Organic Molecules," Journal of the American Chemical Society, 1995, vol. 117, pp. 5179-5197.
De Francesco R., et al., "Challenges and Successes in Developing New Therapies for Hepatitis C," Nature, 2005, vol. 436 (7053), pp. 953-960.
Eldridge M.D., et al., "Empirical Scoring Functions: I. The Development of a Fast Empirical Scoring Function to Estimate the Binding Affinity of Ligands in Receptor Complexes," Journal of Computer Aided Molecular Design, 1997, vol. 11 (5), pp. 425-445.
Eswar N., et al., "Comparative Protein Structure Modeling Using Modeller," Current Protocols in Bioinformatics, 2006, Suppl. 15, 5.6.1-5.6.30.
European Search Report for Application No. EP12155991, mailed on Mar. 29, 2012, 2 pages.
Excipients & Activities for Pharma, ExAct, No. 20, May 2008.
Feig M., et al., "Performance Comparison of Generalized Born and Poisson Methods in the Calculation of Electrostatic Solvation Energies for Protein Structures," Journal of Computational Chemistry, 2004, vol. 25 (2), pp. 265-284.
Fiser A., et al., "Modeling of Loops in Protein Structures," Protein Science, 2000, vol. 9 (9), pp. 1753-1773.
Forster A., et al., "Selection of Excipients for Melt Extrusion with Two Poorly Water-Soluble Drugs by Solubility Parameter Calculation and Thermal Analysis," 2001, vol. 226, pp. 147-161.
Galun E., et al., "Hepatitis C Virus Viremia in SCID-BNX Mouse Chimera," Journal of Infectious Diseases, 1995, vol. 172 (1), pp. 25-30.

(56) References Cited

OTHER PUBLICATIONS

Gastreich M., et al., "Ultrafast De Novo Docking Combining Pharmacophores and Combinatorics," Journal of Computer-Aided Molecular Design, 2006, vol. 20 (12), pp. 717-734.
Gillet V., et al., "Sprout: A Program for Structure Generation," Journal of Computer-Aided Molecular Design, 1993, vol. 7 (2), pp. 127-153.
Gohlke H., et al., "Approaches to the Description and Prediction of the Binding Affinity of Small-Molecule Ligands to Macromolecular Receptors," Angewandte Chemie International Edition, 2002, vol. 41 (15), pp. 2644-2676.
Goodford P.J., "A Computational Procedure for Determining Energetically Favorable Binding Sites on Biologically Important Macromolecules," Journal of Medicinal Chemistry, 1985, vol. 28 (7), pp. 849-857.
Goodsell D.S., et al., "Automated Docking of Substrates to Proteins by Simulated Annealing," Proteins, 1990, vol. 8 (3), pp. 195-202.
Greene T.W., et al., in: Protective Groups in Organic Synthesis, 3rd Edition, John Wiley and Sons, Inc., 1999, Preface, Table of Contents, Abbreviations.
Halperin I., et al., "Principles of Docking: An Overview of Search Algorithms and a Guide to Scoring Functions," Proteins, 2002, vol. 47 (4), pp. 409-443.
Hubbard S.R., et al., "Src Autoinhibition: Let us Count the Ways," Nature Structural Biology, 1999, vol. 6 (8), pp. 711-714.
International Preliminary Report on Patentability and Written Opinion for Application No. PCT/US2009/069188, mailed on Jun. 29, 2011, 10 pages.
International Preliminary Report on Patentability for Application No. PCT/US2009/069177, mailed on Jun. 29, 2011, 1 page.
International Search Report for Application No. PCT/US2011/039769, mailed on Oct. 6, 2011, 4 pages.
International Search Report for Application No. PCT/US2011/056045, mailed on Apr. 2, 2012, 4 pages.
International Search Report for Application No. PCT/US2011/065206, mailed on May 22, 2012, 3 pages.
International Search Report for Application No. PCT/US2011/065215, mailed on Jun. 12, 2012, 3 pages.
International Search Report for Application No. PCT/US2011/065224, mailed on Jun. 12, 2012, 3 pages.
International Search Report for Application No. PCT/US2011/065239, mailed on Jul. 30, 2012, 3 pages.
International Search Report for Application No. PCT/US2011/065242, mailed on May 22, 2012, 3 pages.
International Search Report for Application No. PCT/US2011/065247, mailed on Jun. 12, 2012, 3 pages.
International Search Report for Application No. PCT/US2011/065468, mailed on Mar. 26, 2012, 3 pages.
Jones G., et al., "Development and Validation of a Genetic Algorithm for Flexible Docking," Journal of Molecular Biology, 1997, vol. 267 (3), pp. 727-748.
Jones G., et al., "Docking Small-Molecule Ligands into Active Sites," Current Opinion in Biotechnology, 1995, vol. 6 (6), pp. 652-656.
Jones G., et al., "Molecular Recognition of Receptor Sites using a Genetic Algorithm with a Description of Desolvation," Journal of Molecular Biology, 1995, vol. 245 (1), pp. 43-53.
Kolykhalov A.A., et al., "Transmission of Hepatitis C by Intrahepatic Inoculation with Transcribed RNA," Science, 1997, vol. 277 (5325), pp. 570-574.
Kuntz I.D., et al., "A Geometric Approach to Macromolecule-Ligand Interactions," Journal of Molecular Biology, 1982, vol. 161 (2), pp. 269-288.
Lattman, E., "Use of the Rotation and Translation Functions," Meth. in Enzymol., 1985, 115, 55-77.
Marti-Renom M.A., et al., "Comparative Protein Structure Modeling of Genes and Genomes," Annual Review of Biophysics and Biomolecular Structure, 2000, vol. 29, pp. 291-325.
Mercer D.F., et al., "Hepatitis C Virus Replication in Mice with Chimeric Human Livers," Nature Medicine, 2001, vol. 7 (8), pp. 927-933.
Miranker A., et al., "Functionality Maps of Binding Sites: A Multiple Copy Simultaneous Search Method," Proteins, 1991, vol. 11 (1), pp. 29-34.
Navaza J., "AMoRe: An Automated Package for Molecular Replacement," Acta Crystallographica, 1994, vol. A50 (2), pp. 157-163.
Nishibata Y., et al., "Confirmation of Usefulness of a Structure Construction Program Based on Three-Dimensional Receptor Structure for Rational Lead Generation," Journal of Medicinal Chemistry, 1993, vol. 36 (20), pp. 2921-2928.
Rao S.N., et al., "Validation Studies of the Site-Directed Docking Program LibDock," Journal of Chemical Information and Modeling, 2007, vol. 47 (6), pp. 2159-2171.
Rarey M., et al., "A Fast Flexible Docking Method using an Incremental Construction Algorithm," Journal of Molecular Biology, 1996, vol. 261 (3), pp. 470-489.
Rosenberg J., et al., "Novel Therapeutic Delivery System," Journal of Controlled Release, 2003, vol. 87, pp. 264-267.
Rossmann M.G., "The Molecular Replacement Method: A Collection of Papers on the Use of Non-Crystallographic Symmetry" Gordon and Breach Science Publishers, 1972, Table of Contents.
Sali A., et al., "Comparative Protein Modelling by Satisfaction of Spatial Restraints," Journal of Molecular Biology, 1993, vol. 234 (3), pp. 779-815.
Sato H., et al., "Prediction of Multiple Binding Modes of the CDK2 Inhibitors, Anilinopyrazoles, Using the Automated Docking Programs GOLD, FlexX, and LigandFit: An Evaluation of Performance," Journal of Chemical Information and Modeling, 2006, vol. 46 (6), pp. 2552-2562.
Serajuddin A.T., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.
Sousa S.F., et al., "Protein-Ligand Docking: Current Status and Future Challenges," Proteins, 2006, vol. 65 (1), pp. 15-26.
Thayer A. M., "Finding Solutions, Custom manufacturers take on drug solubility issues to help pharmaceutical firms move products through development," Chemical & Engineering News, 2010, vol. 88 (22), pp. 13-18.
Vagin A., et al., "MOLREP: An Automated Program for Molecular Replacement," Journal of Applied Crystallography, 1997, vol. 30, pp. 1022-1025.
Voigt R., "Pharmaceutical Technology" for Students and Professionals, 7th revised Edition, 2000, pp. 80-85.
Warren G.L., et al., "A Critical Assessment of Docking Programs and Scoring Functions," Journal of Medicinal Chemistry, 2006, vol. 49 (20), pp. 5912-5931.
Wu G.Y., et al., "A Novel Immunocompetent Rat Model of HCV Infection and Hepatitis," Gastroenterology, 2005, vol. 128 (5), pp. 1416-1423.
Xie Z.C., et al., "Transmission of Hepatitis C Virus Infection to Tree Shrews," Virology, 1998, vol. 244 (2), pp. 513-520.
Yanagi M., et al., "Transcripts from a Single Full-Length cDNA Clone of Hepatitis C Virus are Infectious when Directly Transfected into the Liver of a Chimpanzee," Proceedings of the National Academy of Sciences, 1997, vol. 94 (16), pp. 8738-8743.
Yu H., et al., "The Discovery of Novel Vascular Endothelial Growth Factor Receptor Tyrosine Kinases Inhibitors: Pharmacophore Modeling, Virtual Screening and Docking Studies," Chemical Biology and Drug Design, 2007, vol. 69 (3), pp. 204-211.
Zhu Q., et al., "Novel Robust Hepatitis C Virus Mouse Efficacy Model," Antimicrobial Agents and Chemotherapy, 2006, vol. 50 (10), pp. 3260-3268.
Zuckerman E., et al., "Management of Hepatitis C Virus-related Arthritis," BioDrugs, 2001, vol. 15 (9), pp. 573-584.
European Search Report for Application No. EP11160830, mailed on Aug. 12, 2011, 2 pages.
European Search Report for Application No. EP13191041, mailed on Dec. 9, 2013, 2 pages.
European Search Report for Application No. EP13191049, mailed on Dec. 13, 2013, 2 pages.
Extended European Search Report for Application No. EP13167828, mailed on Jun. 21, 2013, 6 pages.

(56) References Cited

OTHER PUBLICATIONS

International Search Report for Application No. PCT/US2012/026456, mailed on Jun. 22, 2012, 3 pages.
Aldous D.J., et al., "A Simple Enantioselective Preparation of (2S,5S)-2,5-diphenylpyrrolidine and Related Diaryl Amines," Tetrahedron Asymmetry, 2000, vol. 11, pp. 2455-2462.
Angiolini M., et al., "Synthesis of Azabicycloalkane Amino Acid Scaffolds as Reverse-Turn Inducer Dipeptide Mimics," European Journal Organization Chemistry, 2000, pp. 2571-2581.
Boehm T., et al., "Uber Die Bildung Von Gamma-Piperidonderivaten Aus Azetessigester, Aromatischen Aldehyden and Aminen, Eine Modifikation Der Hantzschschen Pyridinsynthese," Pharmaceutical,1943, vol. 281, pp. 62-77.
Bundgaard H., "Design of Pro Drugs," 1985, pp. 1-6.
Chong J.M., et al., "Asymmetric Synthesis of trans.2,5-Diphenylpyrrolidine: A C2-Symmetric Chirai Amine," Tetrahedron Asymmetry, 1995, vol. 6 (2), pp. 409-418.
Clarke P.A., et al., "Pot, Atom and Step Economic (Pase) Synthesis of Highly Functionalized Piperidines: A Five-Component Condensation," Tetrahedron Letters, 2007, vol. 48, pp. 5209-5212.
Clarke P.A., et al., "Pot, Atom and Step Economic (PASE) Synthesis of Highly Substituted Piperidines:A Five-Component Condensation," Synthesis, 2008, No. 28, pp. 3530-3532.
Collado I., et al, "Stereoselective Addition of Grignard-Derived Organocopper Reagents to N-Acyliminium Ions: Synthesis of Enantiopure 5- and 4,5-Substituted Prolinates," Journal of Organic Chemistry, 1995, vol. 60, pp. 5011-5015.
Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.
Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.
Gordon T.D., et al, "Synthetic Approaches to the Azole Peptide Mimetics," Tetrahedron Letters, 1993, vol. 34(12), pp. 1901-1904.
Greene T.W., et al., "Protection for the Amino group," Protective Groups in Organic Synthesis, 1999, Third Edition, pp. 494-653.
Hoover J.E, Remington's Pharmaceutical Sciences, Tbl of Cont, 1975.
International Search Report and Written Opinion for Application No. PCT/US2009/038077, mailed on Jan. 21, 2011, 16 pages.
International Search Report and Written Opinion for Application No. PCT/US2009/069177, mailed on Aug. 10, 2010, 17 pages.
International Search Report for Application No. PCT/US2009/069188, mailed on Jun. 8, 2010, 4 pages.
International Search Report for the Application No. PCT/US2010/031102, mailed on Sep. 1, 2010, 4 pages.
Jacques et al., "Enantiomers, Racemates, and Resolutions," J. Wiley & Sons, Chapter 3, pp. 197-213, 1981.
Jing Q., et al., "Bulky Achiral Triarylphosphines Mimic BINAP in Ru(II)—Catalyzed Asymmetric Hydrogenation of Ketones," Advanced Synthesis & Catalysis, 2005, vol. 347, pp. 1193-1197.
Khan A.T., et al., "Effects of Substituents in the ?-Position of 1,3-Dicarbonyl Compounds in Bromodimethylsulfonium Bromide-Catalyzed Multicomponent Reactions: A Facile Access to Functionalized Piperidines," Journal of organic chemistry, 2008, vol. 73, pp. 8398-8402.
Li Chuan-Ying., et al., "Olefination of Ketenes for the Enantioselective Synthesis of Allenes via an Ylide Route," Tetrahedron, 2007, vol. 63, pp. 8046-8053.
Lieberman L., et al., eds., Pharmaceutical Dosage Forms, vol. 1, Marcel Dekker, Inc., 1980, Table of Contents.
Masui M., et al., "A Practical Method for Asymmetric Borane Reduction of Prochiral Ketones Using Chiral Amino Alcohols and Trimethyl Borate," Synlett, 1997, pp. 273-274.
Misra M., et al., "Organocatalyzed Highly Atom Economic One Pot Synthesis of Tetrahydropyridines as Antimalarials," Bioorganic & Medicinal Chemistry, 2009, vol. 17, pp. 625-633.

Moinet C., et al., "Novel Non-Peptide Ligands for the Somatostatin sst3 Receptor," Bioorganic & Medicinal Chemistry Letters, 2001, vol. 11 (8), pp. 991-995.
Muri E.M.F., et al., "Pseudo-Peptides Derived From Isomannide as Potential Inhibitors of Serine Proteases," Amino Acids, 2005, vol. 28 (4), pp. 413-419.
Naylor E.M., et al., "3-Pyridylethanolamines: Potent and Selective Human 63 Adrenergic Receptor Agonists," Bioorganic & Medicinal Chemistry Letters, 1998, vol. 8 (21), pp. 3087-3092.
Nevar N.M., et al., "One Step Preparation of 1,4-Diketones from Methyl Ketones and a-Bromomethyl Ketones in the Presence of $ZnCl_2$•t-BuOH•$Et_2NR$ as a Condensation Agent," Synthesis, 2000, vol. 9, pp. 1259-1262.
Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.
Penning T.D., et al, "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer," Bioorganic & Medicinal Chemistry, 2008, vol. 16(14), pp. 6965-6975.
Sato M., et al., "Efficient Preparation of Optically Pure C2-Symmetrical Cyclic Amines for Chiral Auxiliary," Synthesis, 2004, vol. 9, pp. 1434-1438.
Sawyer J.S., et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.
Smith D.C., et al., "Reissert Compound Chemistry. XXVI. The Syntheses of Bis-Benzylisoquinolines," Journal of Heterocyclic Chemistry, 1976, vol. 13, pp. 573-576.
Takagi S., et al., "Antimicrobial Agents From *Bletilla striata*," Phyrochemisrry, 1983, vol. 22 (4), pp. 1011-1015.
Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.
Xiao D., et al., "A Practical Synthetic Pathway to Polysubstituted Tetrahydropyridines via Multicomponent Reactions Catalyzed by $BF_3$•OEt2," Synlett, 2005, vol. 10, pp. 1531-1534.
Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Journal of the American Chemical Society, 2002, vol. 4(23), pp. 4029-4032.
Adjabeng G., et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.
Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.
Alesso E.N., et al., "Synthesis of Diastereoisomeric 1,2,3-Triphenylindans," Australian Journal of Chemistry, 1997, vol. 50, pp. 149-152.
Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.
Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51 (17), pp. 5243-5263.
Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.

(56) References Cited

OTHER PUBLICATIONS

Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.

Effenberger F., et al., "Synthesis, Structure, and Spectral Behavior of Donor-Acceptor Substituted Biphenyls," The Journal of Organic Chemistry, 1983, vol. 48, pp. 4649-4658.

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.

Hartwig J.F., et al., "III.3.2 Palladium-Catalyzed Amination of Aryl Halides and Related Reactions," Handbook of Organopalladium Chemistry for Organic Synthesis, 2002, pp. 1051-1096.

International Preliminary Report on Patentability and Written Opinion for the Application No. PCT/US2010/031102, mailed on Oct. 18, 2011, 7 pages.

Jeffrey J.L., et al., "Concise Synthesis of Pauciflorol F Using a Larock Annulation," Organic Letters, 2009, vol. 11 (23), pp. 5450-5453.

Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67 (17), pp. 5993-6000.

Louie J., et al., "Palladium-Catalyzed Amination of Aryl Triflates and Importance of Triflate Addition Rate," Journal of Organic Chemistry, 1997, vol. 62 (5), pp. 1268-1273.

L-selectride, Retrieved from the Internet<URL: http://en.wikipedia.org/w/index.php?oldid=488453454>.

Lucas S., et al.,"In Vivo Active Aldosterone Synthase Inhibitors with Improved Aelectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.

Masters K., "Spray Drying Handbook" 4th Edition, John Wiley & Sons, 1985, Table of Contents.

Matzeit A., "Radical Tandem Cyclizations by Anodic Decarboxylation of Carboxylic Acids," Synthesis, 1995, pp. 1432-1444.

Muci A.R., et al., "Practical Palladium Catalysts for C—N and C—O Bond Formation," Topics in Current Chemistry, 2002, vol. 219, pp. 131-209.

Peng T., et al., "Construction of a Library of Rhodol Fluorophores for Developing New Fluorescent Probes," Organic Letters, 2010, vol. 12 (3), pp. 496-499.

Polymer Handbook, Brandrup J., et al., Eds., Interscience Publishers, 1975, Table of Contents.

Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.

Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.

Sperling L. H., "Introduction to Physical Polymer Science," 2nd Edition, John Wiley & Sons, Inc., 1992, Table of Contents.

Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.

Tellinghuisen T.L., et al., "Structure of the Zinc-Binding Domain of an Essential Component of the Hepatitis C Virus Replicase," Nature, 2005, vol. 435 (7040), pp. 374-379.

Vallee R.J., et al., "Photoannelation Reactions of 3-(Alk-1-ynyl)cyclohept-2-en-1-ones," Helvetica Chimica Acta, 2010, vol. 93 (1), pp. 17-24.

Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.

Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.

Wolfe J.P., et al., "Palladium-Catalyzed Amination of Aryl Triflates," Journal of Organic Chemistry, 1997, vol. 62 (5), pp. 1264-1267.

\* cited by examiner

ANTI-VIRAL COMPOUNDS

The present application is a continuation-in-part of U.S. patent application Ser. No. 12/903,822, filed Oct. 13, 2010 and now U.S. Patent Application Publication No. 2011/0092415, which is a continuation-in-part of U.S. patent application Ser. No. 12/813,301, filed Jun. 10, 2010 and now U.S. Pat. No. 8,691,938, which claims the benefit from U.S. Provisional Application Ser. No. 61/186,291, filed Jun. 11, 2009, U.S. Provisional Application Ser. No. 61/242,836, filed Sep. 16, 2009, and U.S. Provisional Application Ser. No. 61/243,596, filed Sep. 18, 2009. All of these applications and patents are incorporated herein by reference in their entireties.

FIELD

The present invention relates to compounds effective in inhibiting replication of Hepatitis C virus ("HCV"). The present invention also relates to compositions comprising these compounds and methods of using these compounds to treat HCV infection.

BACKGROUND

HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY

The present invention features compounds of Formulae I, $I_A$, $I_B$, $I_C$, $I_D$, $I_E$, $I_F$ and $I_G$ and pharmaceutically acceptable salts thereof. These compounds and salts can inhibit the replication of HCV and therefore are useful for treating HCV infection.

The present invention also features compositions comprising the compounds or salts of the present invention. The compositions can also include additional therapeutic agents, such as HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features compounds having Formula I, and pharmaceutically acceptable salts thereof,

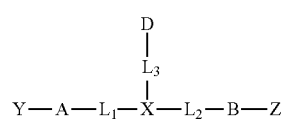

wherein:
  X is $C_3$-$C_{12}$carbocycle or 3- to 12-membered heterocycle, and is optionally substituted with one or more $R_A$ or $R_F$;
  $L_1$ and $L_2$ are each independently selected from bond; or $C_1$-$C_6$alkylene, $C_2$-$C_6$alkenylene or $C_2$-$C_6$alkynylene, each of which is independently optionally substituted at each occurrence with one or more $R_L$;
  $L_3$ is bond or -$L_S$-K-$L_S'$-, wherein K is selected from bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B'$)—, —N($R_B$)SO$_2$N($R_B'$)—, or —N($R_B$)S(O)N($R_B'$)—;
  A and B are each independently $C_3$-$C_{12}$carbocycle or 3- to 12-membered heterocycle, and are each independently optionally substituted with one or more $R_A$;
  D is $C_3$-$C_{12}$carbocycle or 3- to 12-membered heterocycle, and is optionally substituted with one or more $R_A$; or D is $C_3$-$C_{12}$carbocycle or 3- to 12-membered heterocycle which is substituted with J and optionally substituted with one or more $R_A$, where J is $C_3$-$C_{12}$carbocycle or 3- to 12-membered heterocycle and is optionally substituted with one or more $R_A$, or J is —SF$_5$; or D is hydrogen or $R_A$;
  Y is selected from -T'-C($R_1R_2$)N($R_5$)-T-$R_D$, -T'-C($R_3R_4$)C($R_6R_7$)-T-$R_D$, -$L_K$-T-$R_D$, or -$L_K$-E;
  $R_1$ and $R_2$ are each independently $R_C$, and $R_5$ is $R_B$; or $R_1$ is $R_C$, and $R_2$ and $R_5$, taken together with the atoms to which they are attached, form a 3- to 12-membered heterocycle which is optionally substituted with one or more $R_A$;
  $R_3$, $R_4$, $R_6$, and $R_7$ are each independently $R_C$; or $R_3$ and $R_6$ are each independently $R_C$, and $R_4$ and $R_7$, taken together with the atoms to which they are attached, form a 3- to 12-membered carbocycle or heterocycle which is optionally substituted with one or more $R_A$;

Z is selected from -T'-C($R_8R_9$)N($R_{12}$)-T-$R_D$, -T'-C($R_{10}R_{11}$)C($R_{13}R_{14}$)-T-$R_D$, -$L_K$-T-$R_D$, or -$L_K$-E;

$R_8$ and $R_9$ are each independently $R_C$, and $R_{12}$ is $R_B$; or $R_8$ is $R_C$, and $R_9$ and $R_{12}$, taken together with the atoms to which they are attached, form a 3- to 12-membered heterocycle which is optionally substituted with one or more $R_A$;

$R_{10}$, $R_{11}$, $R_{13}$, and $R_{14}$ are each independently $R_C$; or $R_{10}$ and $R_{13}$ are each independently $R_C$, and $R_{11}$ and $R_{14}$, taken together with the atoms to which they are attached, form a 3- to 12-membered carbocycle or heterocycle which is optionally substituted with one or more $R_A$;

T and T' are each independently selected at each occurrence from bond, -$L_S$-, -$L_S$-M-$L_S$'-, or -$L_S$-M-$L_S$'-M'-$L_S$''-, wherein M and M' are each independently selected at each occurrence from bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B$')—, —N($R_B$)SO$_2$N($R_B$')—, —N($R_B$)S(O)N($R_B$')—, $C_3$-$C_{12}$carbocycle or 3- to 12-membered heterocycle, and wherein said $C_3$-$C_{12}$carbocycle and 3- to 12-membered heterocycle are each independently optionally substituted at each occurrence with one or more $R_A$;

$L_K$ is independently selected at each occurrence from bond, -$L_S$-N($R_B$)C(O)-$L_S$'- or -$L_S$-C(O)N($R_B$)-$L_S$'-; or $C_1$-$C_6$alkylene, $C_2$-$C_6$alkenylene or $C_2$-$C_6$alkynylene, each of which is independently optionally substituted at each occurrence with one or more $R_L$; or $C_3$-$C_{12}$carbocycle or 3- to 12-membered heterocycle, each of which is independently optionally substituted at each occurrence with one or more $R_A$;

E is independently selected at each occurrence from $C_3$-$C_{12}$carbocycle or 3- to 12-membered heterocycle, and is independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or -$L_S$-$R_E$, wherein two adjacent $R_A$, taken together with the atoms to which they are attached and any atoms between the atoms to which they are attached, can optionally form carbocycle or heterocycle;

$R_B$ and $R_B$' are each independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_B$ or $R_B$' is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_C$ is independently selected at each occurrence from hydrogen, halogen, hydroxy, mercapto, amino, carboxy, nitro, oxo, phosphonoxy, phosphono, thioxo, formyl or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_C$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_E$ is independently selected at each occurrence from —O—$R_S$, —S—$R_S$, —C(O)$R_S$, —OC(O)$R_S$, C(O)OR$_S$, —N($R_SR_S$'), —S(O)$R_S$, —SO$_2R_S$, —C(O)N($R_SR_S$'), —N($R_S$)C(O)$R_S$', —N($R_S$)C(O)N($R_S$'$R_S$''), —N($R_S$)SO$_2R_S$', —SO$_2$N($R_SR_S$'), —N($R_S$)SO$_2$N($R_S$'$R_S$''), —N($R_S$)S(O)N($R_S$'$R_S$''), —OS(O)—$R_S$, —OS(O)$_2$—$R_S$, —S(O)$_2$OR$_S$, —S(O)OR$_S$, —OC(O)OR$_S$, —N($R_S$)C(O)OR$_S$', —OC(O)N($R_SR_S$'), —N($R_S$)S(O)—$R_S$', —S(O)N($R_SR_S$'), —P(O)(OR$_S$)$_2$, or —C(O)N($R_S$)C(O)—$R_S$'; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$, or —N($R_SR_S$');

$R_F$ is independently selected at each occurrence from $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is independently optionally substituted with one or more $R_L$; or —($R_X$-$R_Y$)$_Q$—($R_X$-$R_Y$'), wherein Q is 0, 1, 2, 3 or 4, and each $R_X$ is independently O, S or N($R_B$), wherein each $R_Y$ is independently $C_1$-$C_6$alkylene, $C_2$-$C_6$alkenylene or $C_2$-$C_6$alkynylene each of which is independently optionally substituted with one or more substituents selected from halogen, hydroxy, mercapto, amino, carboxy, nitro, oxo, phosphonoxy, phosphono, thioxo, formyl or cyano, and wherein each $R_Y$' is independently $C_1$-$C_6$alkyl, $C_2$-$C_6$alkenyl or $C_2$-$C_6$alkynyl each of which is independently optionally substituted with one or more substituents selected from halogen, hydroxy, mercapto, amino, carboxy, nitro, oxo, phosphonoxy, phosphono, thioxo, formyl or cyano;

$R_L$ is independently selected at each occurrence from halogen, nitro, oxo, phosphonoxy, phosphono, thioxo, cyano, —O—$R_S$, —S—$R_S$, —C(O)$R_S$, —OC(O)$R_S$, —C(O)OR$_S$, —N($R_SR_S$'), —S(O)$R_S$, —SO$_2R_S$, —C(O)N($R_SR_S$') or —N($R_S$)C(O)$R_S$'; or $C_3$-$C_6$carbocycle 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; wherein two adjacent $R_L$, taken together with the atoms to which they are attached and any atoms between the atoms to which they are attached, can optionally form carbocycle or heterocycle;

$L_S$, $L_S'$ and $L_S''$ are each independently selected at each occurrence from bond; or $C_1$-$C_6$alkylene, $C_2$-$C_6$alkenylene or $C_2$-$C_6$alkynylene, each of which is independently optionally substituted at each occurrence with one or more $R_L$; and $R_S$, $R_S'$ and $R_S''$ are each independently selected at each occurrence from hydrogen; $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —O—$C_1$-$C_6$alkyl, —O—$C_1$-$C_6$alkylene-O—$C_1$-$C_6$alkyl, or 3- to 6-membered carbocycle or heterocycle; or 3- to 6-membered carbocycle or heterocycle; wherein each 3- to 6-membered carbocycle or heterocycle in $R_S$, $R_S'$ or $R_S'$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

A and B preferably are independently selected from $C_5$-$C_6$carbocycle (e.g., phenyl), 5- to 6-membered heterocycle (e.g., pyridinyl or thiazolyl), or 8- to 12-membered bicycles such as

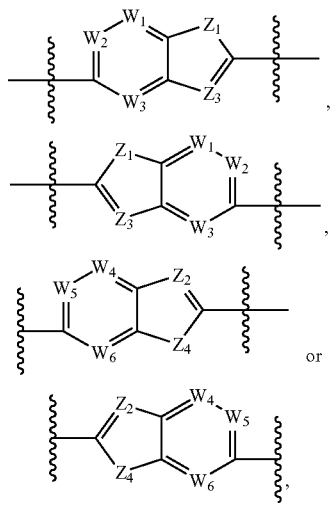

where $Z_1$ is independently selected at each occurrence from O, S, NH or $CH_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from $C_5$-$C_6$carbocycle, 5- to 6-membered heterocycle,

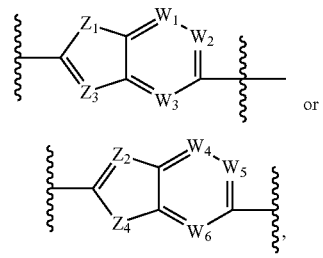

and is optionally substituted with one or more $R_A$; B is selected from $C_5$-$C_6$carbocycle, 5- to 6-membered heterocycle,

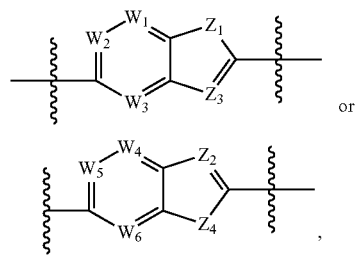

and is optionally substituted with one or more $R_A$; where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from

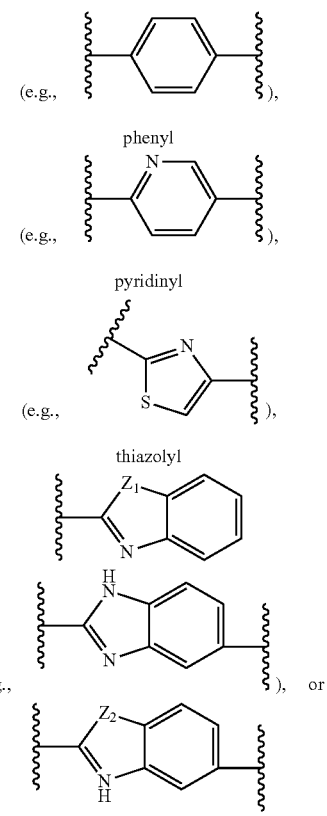

(e.g., 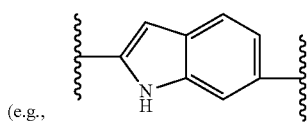 or 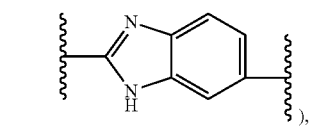),
and is optionally substituted with one or more $R_A$; and B can be selected from phenyl
phenyl (e.g., 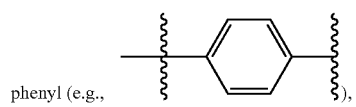),
pyridinyl (e.g., 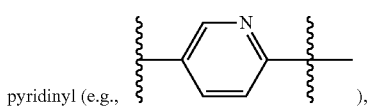),
thiazolyl (e.g., 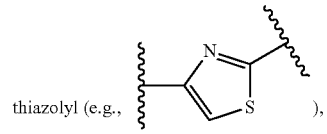),
(e.g., 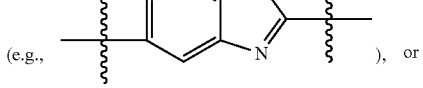),
(e.g.,  or
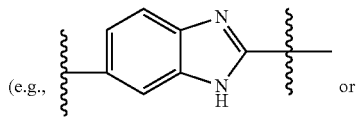),
and is optionally substituted with one or more $R_A$. Highly preferably, both A and B are phenyl (e.g., both A and B are
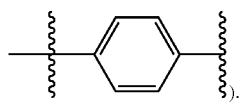).
Also highly preferably, A is
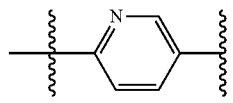
and B is
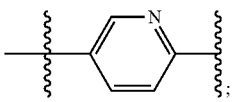;
or A is
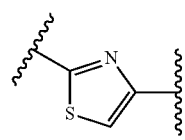 [SMILES: *c1csc(*)n1]
and B is
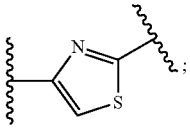 [SMILES: *c1csc(*)n1];
or A is
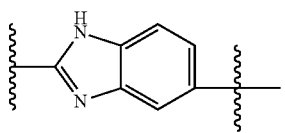 [SMILES: *c1ccc2[nH]c(*)nc2c1]
and B is
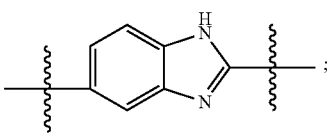;
or A is
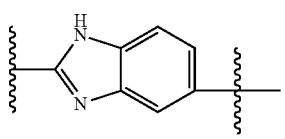 [SMILES: *c1ccc2[nH]c(*)nc2c1]

and B is

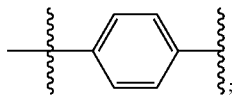

or A is

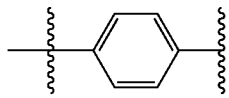

and B is

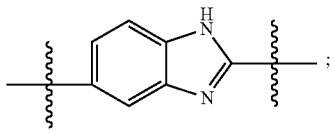

wherein each A and B is independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle (e.g., phenyl), 5- to 6-membered heterocycle (e.g., pyridinyl, pyrimidinyl, thiazolyl), or 6- to 12-membered bicycles (e.g., indanyl, 4,5,6,7-tetrahydrobenzo[d]thiazolyl, benzo[d]thiazolyl, indazolyl, benzo[d][1,3]dioxol-5-yl), and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

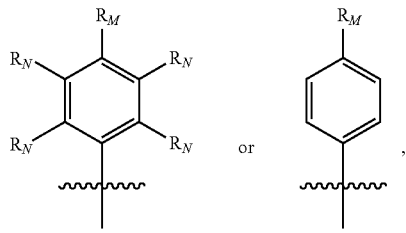

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably D is

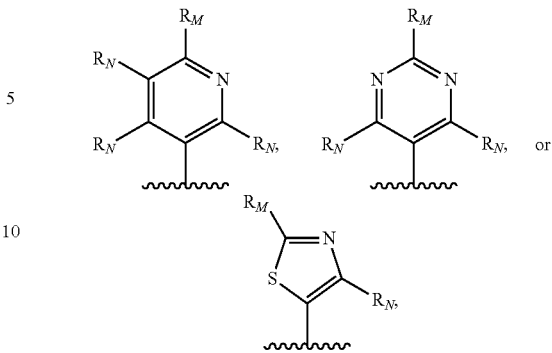

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

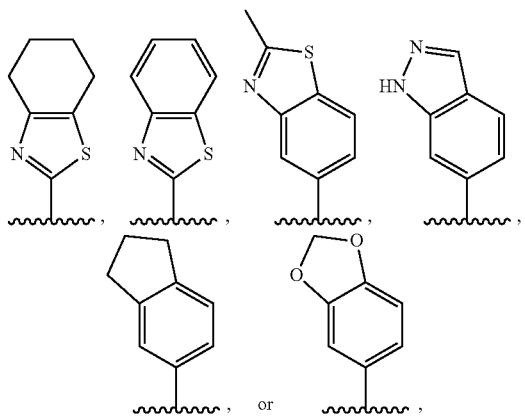

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is $-L_S-R_E$, wherein $L_S$ is a bond or $C_1$-$C_6$alkylene, and $R_E$ is $-N(R_S R_S')$, $-O-R_S$, $-C(O)R_S$, $-C(O)OR_S$, $-C(O)N(R_S R_S')$, $-N(R_S)C(O)R_S'$, $-N(R_S)C(O)OR_S'$, $-N(R_S)SO_2R_S'$, $-SO_2R_S$, $-SR_S$, or $-P(O)(OR_S)_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, $-O-C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $-C(O)OR_S$, or $-N(R_S R_S')$. More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, $-C(CF_3)_2-OH$, $-C(CH_3)_2-CN$, $-C(CH_3)_2-CH_2OH$, or $-C(CH_3)_2-CH_2NH_2$. Also preferably $R_M$ is $-L_S-R_E$ where $L_S$ is a bond and $R_E$ is $-N(R_S R_S)$, $-O-R_S$, $-N(R_S)C(O)OR_S'$, $-N(R_S)SO_2R_S'$, $-SO_2R_S$, or $-SR_S$. For example where $L_S$ is a bond, $R_E$ is $-N(C_1$-$C_6$alkyl$)_2$ (e.g., $-NMe_2$); $-N(C_1$-$C_6$alkylene-O-$C_1$-$C_6$alkyl$)_2$ (e.g. $-N(CH_2CH_2OMe)_2$); $-N(C_1$-$C_6$alkyl)($C_1$-$C_6$alkylene-O-$C_1$-$C_6$alkyl) (e.g. $-N(CH_3)(CH_2CH_2OMe)$); $-O-C_1$-$C_6$alkyl (e.g., $-O$-Me, $-O$-Et, $-O$-isopropyl, $-O$-tert-butyl, $-O$-n-hexyl); $-O-C_1$-$C_6$haloalkyl (e.g., $-OCF_3$, $-OCH_2CF_3$); $-O-C_1$-$C_6$alkylene-piperidine (e.g. $-O-CH_2CH_2$-1-piperidyl); $-N(C_1$-$C_6$alkyl)C(O)OC_1$-$C_6$alkyl (e.g., $-N(CH_3)C(O)O-CH_2CH(CH_3)_2$), $-N(C_1$-$C_6$alkyl)$SO_2C_1$-$C_6$alkyl (e.g., $-N(CH_3)SO_2CH_3$); $-SO_2C_1$-$C_6$alkyl (e.g., $-SO_2Me$); $-SO_2C_1$-$C_6$haloalkyl (e.g., $-SO_2CF_3$); or $-S-C_1$-$C_6$haloalkyl (e.g., $SCF_3$). Also preferably $R_M$ is $-L_S-R_E$ where $L_S$ is $C_1$-$C_6$alkylene (e.g., $-CH_2-$, $-C(CH_3)_2-$, $-C(CH_3)_2-CH_2-$) and $R_E$ is $-O-R_S$, $-C(O)OR_S$, $-N(R_S)C(O)OR_S'$, or $-P(O)(OR_S)_2$. For example $R_M$ is $-C_1$-$C_6$alkylene-O-$R_S$ (e.g., $-C(CH_3)_2-CH_2-OMe$); $-C_1$-$C_6$alkylene-C(O)OR$_S$ (e.g., $-C(CH_3)_2-C(O)OMe$); $-C_1$-$C_6$alkylene-N(R$_S$)C(O)OR$_S'$ (e.g., $-C(CH_3)_2-CH_2-NHC(O)OCH_3$); or $-C_1$-$C_6$alkylene-P(O)(OR$_S$)$_2$ (e.g., $-CH_2-P(O)(OEt)_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $-C(O)OR_S$, or $-N(R_S R_S')$. For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkenyl, $C(O)OR_S$ or $-N(R_S R_S')$, and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or $-N(R_S R_S')$. Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or $-N(R_S R_S')$. Highly preferably, D is

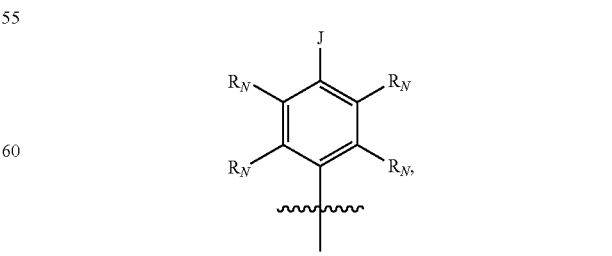

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$. Also preferably, D is

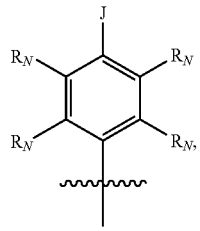

wherein each $R_N$ is independently selected from $R_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$, and J can also be optionally substituted with one or more $R_A$. Also preferably, D is

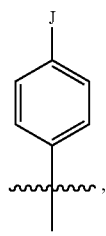

and J is $C_3$-$C_6$carbocycle or 3- to 6-membered heterocycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$.

X preferably is $C_5$-$C_6$carbocycle, 5- to 6-membered heterocycle, or 6- to 12-membered bicycles, and is optionally substituted with one or more $R_A$ or $R_F$. X can also be $C_5$-$C_6$carbocycle or 5- to 6-membered heterocycle which is optionally substituted with one or more $R_A$ or $R_F$, wherein two adjacent $R_A$ on X, taken together with the ring atoms to which they are attached, optionally form a 5- to 6-membered carbocycle or heterocycle. Also preferably, X is

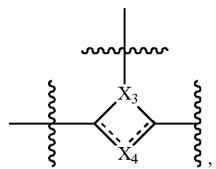

wherein $X_3$ is C(H) or preferably N and is directly appended to -$L_3$-D; $X_4$ is $C_2$-$C_4$alkylene, $C_2$-$C_4$alkenylene or $C_2$-$C_4$alkynylene, each of which optionally contains one or two heteroatoms selected from O, S or N; and X is optionally substituted with one or more $R_A$ or $R_F$, and two adjacent $R_A$ on X, taken together with the ring atoms to which they are attached, can optionally form a 5- to 6-membered carbocycle or heterocycle. In addition, X can be

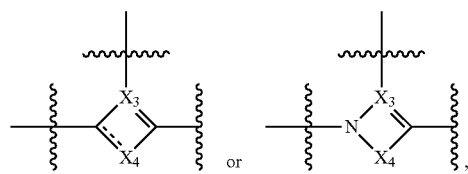

wherein $X_3$ is C and is directly linked to -$L_3$-D, $X_4$ is $C_2$-$C_4$alkylene, $C_2$-$C_4$alkenylene or $C_2$-$C_4$alkynylene each of which optionally contains one or two heteroatoms selected from O, S or N, and X is optionally substituted with one or more $R_A$ or $R_F$, and two adjacent $R_A$ on X, taken together with the ring atoms to which they are attached, optionally form a 5- to 6-membered carbocycle or heterocycle. Moreover, X can be

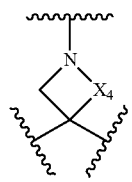

wherein N is directly linked to $L_3$-D, $X_4$ is $C_2$-$C_4$alkylene, $C_2$-$C_4$alkenylene or $C_2$-$C_4$alkynylene each of which optionally contains one or two heteroatoms selected from O, S or N, and X is optionally substituted with one or more $R_A$ or $R_F$, and two adjacent $R_A$ on X, taken together with the ring atoms to which they are attached, optionally form a 5- to 6-membered carbocycle or heterocycle.

For instance, X can be

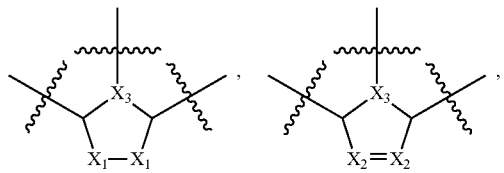

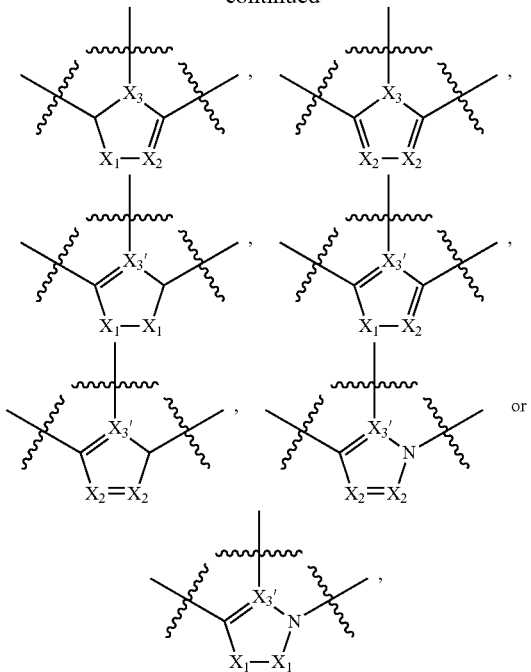

wherein $X_1$ is independently selected at each occurrence from $CH_2$, O, S or NH, $X_2$ is independently selected at each occurrence from CH or N, $X_3$ is N and is directly linked to -$L_3$-D, and $X_3'$ is C and is directly linked to -$L_3$-D; and X is optionally substituted with one or more $R_A$ or $R_F$, and two adjacent $R_A$ on X, taken together with the ring atoms to which they are attached, optionally form a 5- to 6-membered carbocycle or heterocycle. For another example, X is

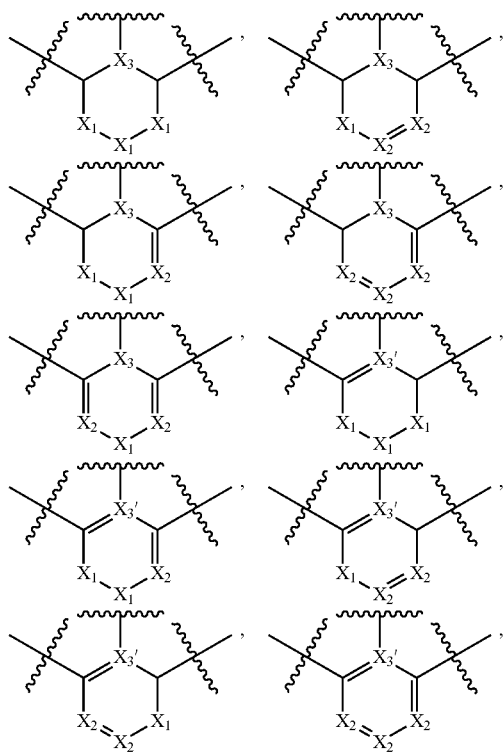

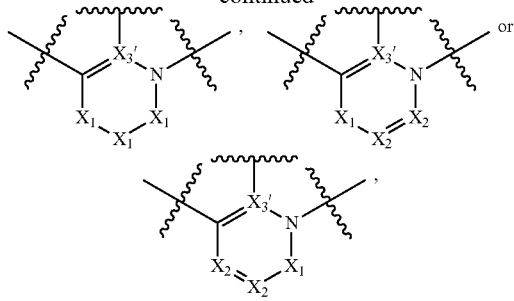

wherein $X_1$ is independently selected at each occurrence from $CH_2$, O, S or NH, $X_2$ is independently selected at each occurrence from CH or N, $X_3$ is N and is directly linked to -$L_3$-D, and $X_3'$ is C and is directly linked to -$L_3$-D; and wherein X is optionally substituted with one or more $R_A$ or $R_F$, and two adjacent $R_A$ on X, taken together with the ring atoms to which they are attached, optionally form a 5- to 6-membered carbocycle or heterocycle.

Highly preferably, X is

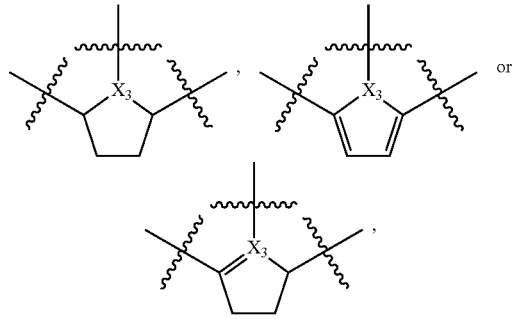

wherein $X_3$ is C(H) or N and is directly linked to -$L_3$-D, $X_3'$ is C and is directly linked to -$L_3$-D, and wherein X is optionally substituted with one or more $R_A$ or $R_F$, and two adjacent $R_A$ on X, taken together with the ring atoms to which they are attached, optionally form a 5- to 6-membered carbocycle or heterocycle. More preferably, $X_3$ is N.

Non-limiting examples of X include:

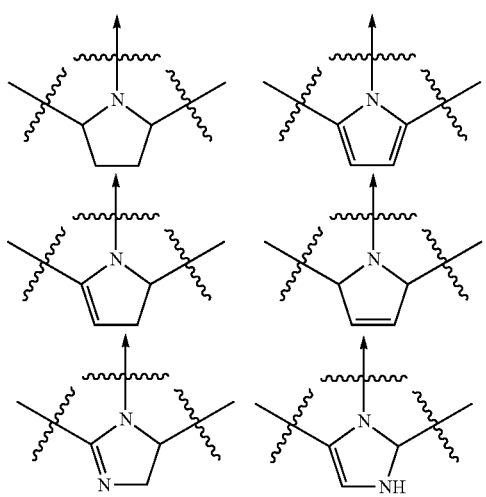

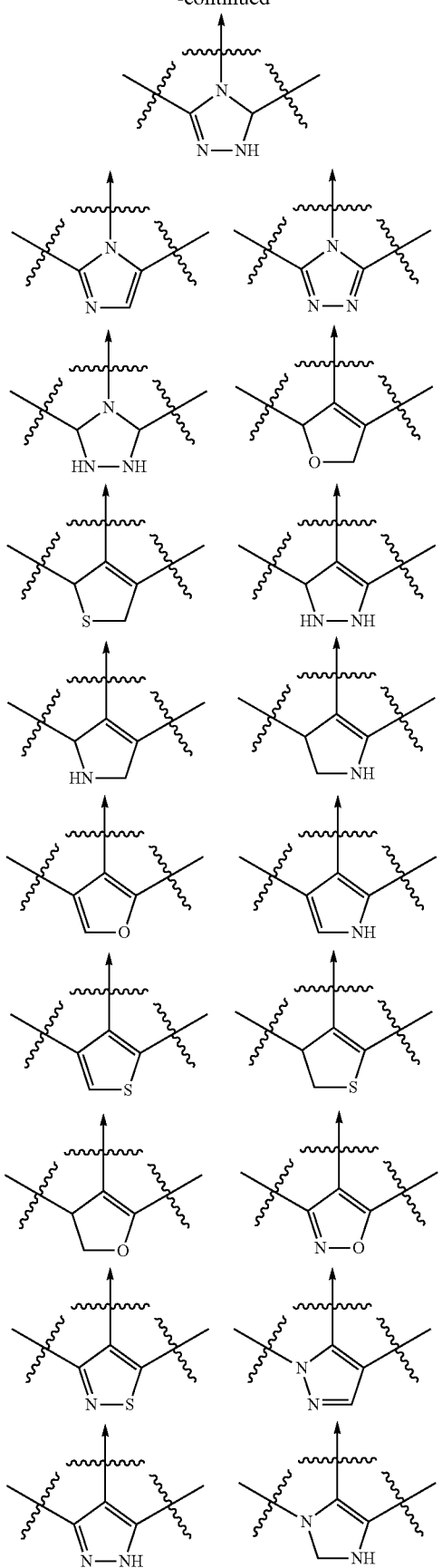
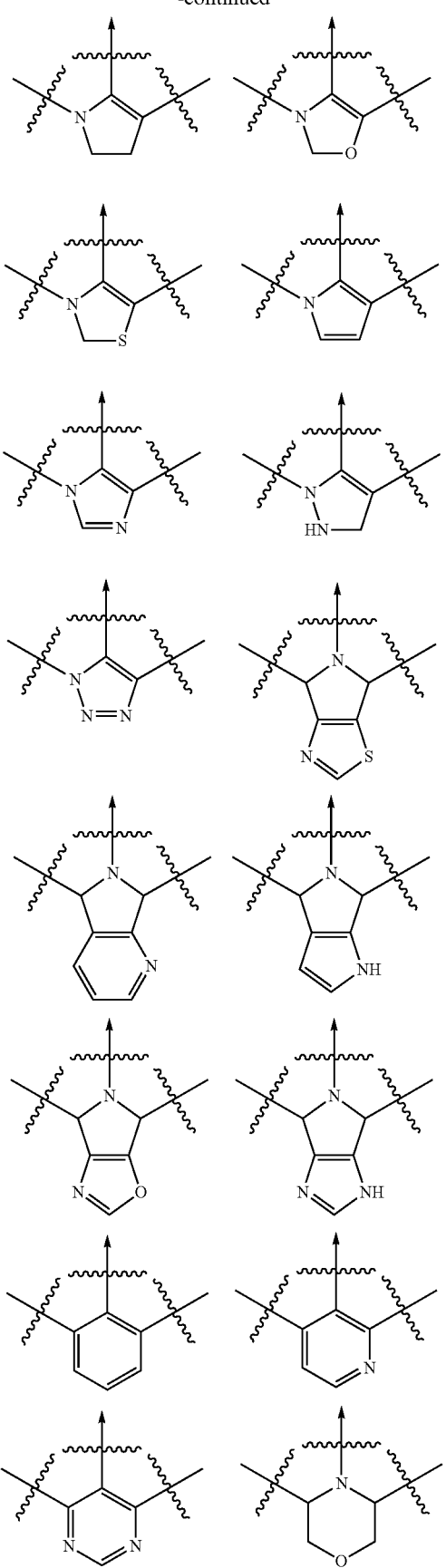

-continued

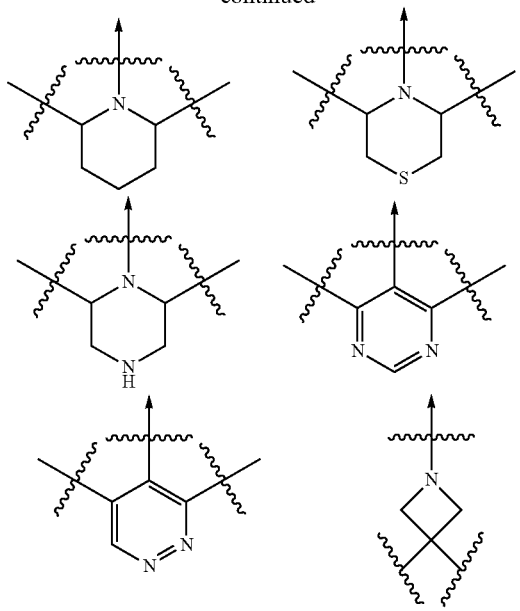

wherein "→" indicates the covalent attachment to -L₃-D. Each X can be optionally substituted with one or more $R_A$ or $R_F$, and two adjacent $R_A$ on X, taken together with the ring atoms to which they are attached, optionally form a 5- to 6-membered carbocycle or heterocycle.

Non-limiting examples of preferred X include the following pyrrolidine rings, each of which is optionally substituted with one or more $R_A$ or $R_F$:

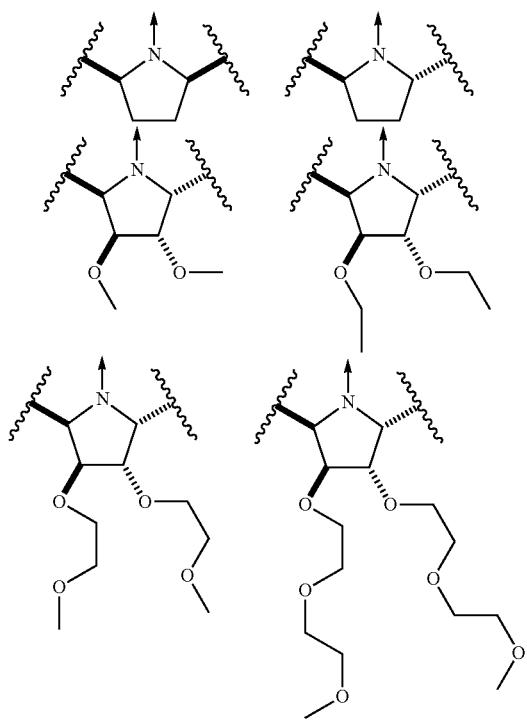

As shown, the relative stereochemistry at the 2- and 5-positions of the above pyrrolidine ring may be either cis or trans. The stereochemistries of optional substituents $R_A$ at the 3- or 4-positions of the pyrrolidine may vary relative to any substituent at any other position on the pyrrolidine ring. Depending on the particular substituents attached to the pyrrolidine, the stereochemistry at any carbon may be either (R) or (S).

Non-limiting examples of preferred X also include the following pyrrole, triazole or thiomorpholine rings, each of which is optionally substituted with one or more $R_A$ or $R_F$:

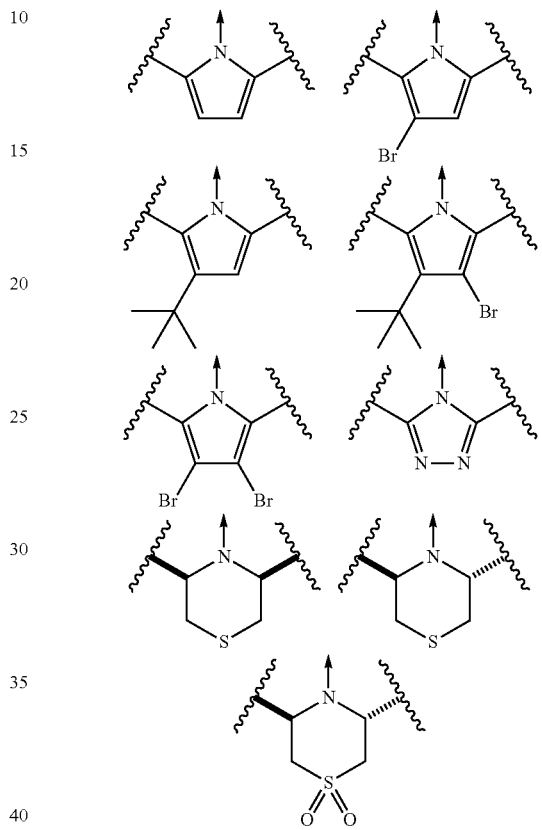

As shown, the relative stereochemistry at the 3- and 5-positions of the thiomorpholine ring may be either cis or trans. Depending on the particular substituents attached to the thiomorpholine, the stereochemistry at any carbon may be either (R) or (S).

Also preferably, X is

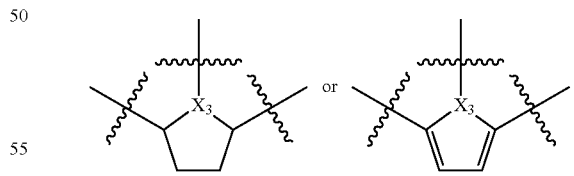

wherein $X_3$ is N and is directly linked to -L₃-D, and X is optionally substituted with one or more $R_A$ or $R_F$. Preferably, $R_F$ is $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is independently optionally substituted with one or more substituents selected from halogen, hydroxy, mercapto, amino, carboxy, nitro, oxo, phosphonoxy, phosphono, thioxo, formyl or cyano. Also preferably, $R_F$ is $C_1$-$C_{10}$alkyl, $C_2$-$C_{10}$alkenyl or $C_2$-$C_{10}$alkynyl, each of which contains 0, 1, 2, 3, 4 or 5 O and is independently optionally substituted with one or more $R_L$. Also preferably, $R_F$ is —$(R_X$-$R_Y)_Q$—$(R_X$-$R_Y')$, wherein Q is 0, 1, 2, 3 or 4; each $R_X$ is independently O, S or N($R_B$); each $R_Y$ is independently $C_1$-$C_6$alkylene, $C_2$-$C_6$alkenylene or $C_2$-$C_6$alkynylene each of which is independently optionally substituted with one or more substituents selected from halogen, hydroxy, mercapto, amino, carboxy, nitro, oxo, phosphonoxy, phosphono, thioxo, formyl or cyano; and each $R_Y'$ is independently $C_1$-$C_6$alkyl, $C_2$-$C_6$alkenyl or $C_2$-$C_6$alkynyl each of which is independently optionally substituted with one or more substituents selected from halogen, hydroxy, mercapto, amino, carboxy, nitro, oxo, phosphonoxy, phosphono, thioxo, formyl or cyano. Preferably, each $R_X$ is O. More preferably, X is optionally substituted with one or more $R_A$ or $R_F$, each $R_F$ is independently selected from $C_1$-$C_{10}$alkyl, $C_2$-$C_{10}$alkenyl or $C_2$-$C_{10}$alkynyl, each of which contains 0, 1, 2 or 3 O and is independently optionally substituted with one or more substituents selected from halogen, hydroxy, mercapto, amino, carboxy, nitro, oxo, phosphonoxy, phosphono, thioxo, formyl or cyano. Also preferably, X is optionally substituted with one or more $R_A$ or $R_F$, each $R_F$ is independently selected from —(O—$C_1$-$C_6$alkylene)$_Q$-(O—$C_1$-$C_6$alkyl), wherein Q preferably is 0, 1, 2 or 3.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —$CH_2$— or —$CH_2CH_2$—), and are each independently optionally substituted with one or more $R_L$. Highly preferably, $L_1$, $L_2$ and $L_3$ are bond.

Y is preferably selected from -$L_S$-C($R_1R_2$)N($R_5$)-T-$R_D$, -$L_S$-C($R_3R_4$)C($R_6R_7$)-T-$R_D$, -G-C($R_1R_2$)N($R_5$)-T-$R_D$, -G-C($R_3R_4$)C($R_6R_7$)-T-$R_D$, —N($R_B$)C(O)C($R_1R_2$)N($R_5$)-T-$R_D$, —N($R_B$)C(O)C($R_3R_4$)C($R_6R_7$)-T-$R_D$, —C(O)N($R_B$)C($R_1R_2$)N($R_5$)-T-$R_D$, —C(O)N($R_B$)C($R_3R_4$)C($R_6R_7$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

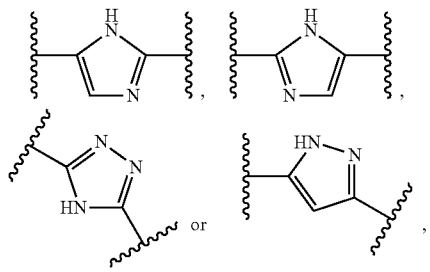

and is optionally substituted with one or more $R_A$ (e.g., one or more chloro or bromo). E preferably is a 7- to 12-membered bicycle (such as,

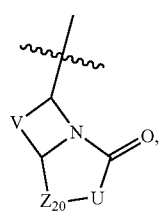

wherein U is independently selected at each occurrence from —($CH_2$)— or —(NH)—; V and $Z_{20}$ are each independently selected from $C_1$-$C_4$alkylene, $C_2$-$C_4$alkenylene or $C_2$-$C_4$alkynylene, in which at least one carbon atom can be independently optionally replaced with O, S or N), and is independently optionally substituted with one or more $R_A$. More preferably, $R_1$ is $R_C$, and $R_2$ and $R_5$, taken together with the atoms to which they are attached, form a 5- to 6-membered heterocycle or 6- to 12-membered bicycle

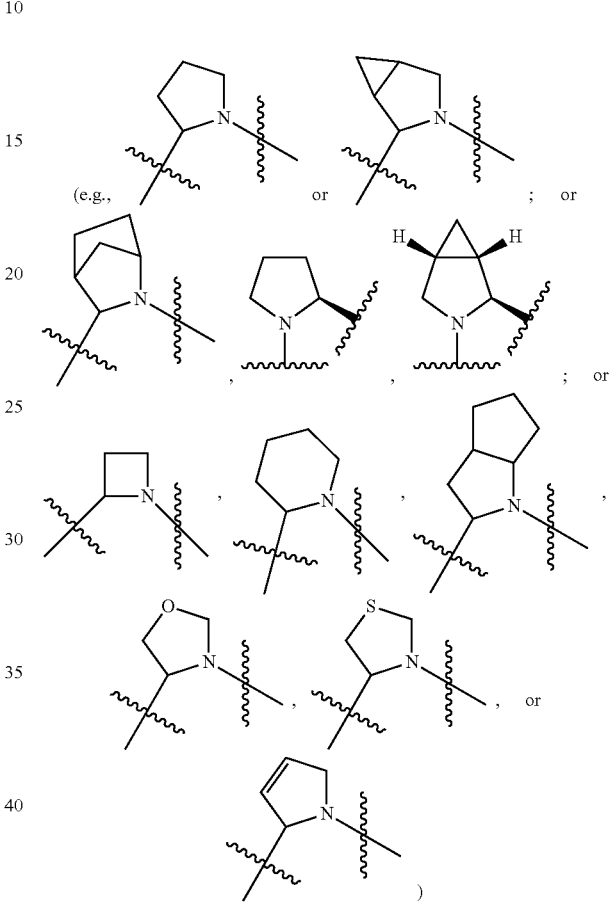

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_3$ and $R_6$ are each independently $R_C$, and $R_4$ and $R_7$, taken together with the atoms to which they are attached, form a 5- to 6-membered carbocycle/heterocycle or 6- to 12-membered bicycle

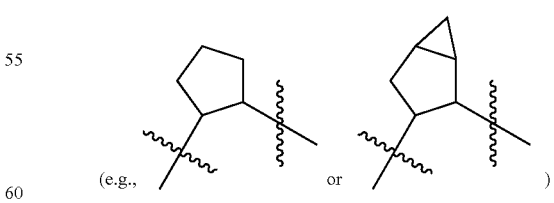

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Y can also be selected from -M-C($R_1R_2$)N($R_5$)—C(O)-$L_Y'$-M'-$R_D$, -M-C($R_1R_2$)N($R_5$)-$L_Y'$-M'-$R_D$, -$L_S$-C($R_1R_2$)N($R_5$)—C(O)-$L_Y'$-M'-$R_D$, -$L_S$-C($R_1R_2$)N($R_5$)-$L_Y'$-M'-$R_D$, -M-C(R$_3$R$_4$)C(R$_6$R$_7$)—C(O)-L$_Y$'-M'-R$_D$, -M-C(R$_3$R$_4$)C(R$_6$R$_7$)-L$_Y$'-M'-R$_D$, -L$_S$-C(R$_3$R$_4$)C(R$_6$R$_7$)—C(O)-L$_Y$'-M'-R$_D$, or -L$_S$-C(R$_3$R$_4$)C(R$_6$R$_7$)-L$_Y$'-M'-R$_D$, wherein M preferably is bond, —C(O)N(R$_B$)— or —N(R$_B$)C(O)—, M' preferably is bond, —C(O)N(R$_B$)—, —N(R$_B$)C(O)O—, —N(R$_B$)C(O)O—, N(R$_B$)C(O)N(R$_B$')—, —N(R$_B$)S(O)— or —N(R$_B$)S(O)$_2$—, and L$_Y$' preferably is C$_1$-C$_6$alkylene which is optionally substituted with one or more R$_L$. L$_Y$', for example, is a C$_1$-C$_6$alkylene such as, but not limited to,

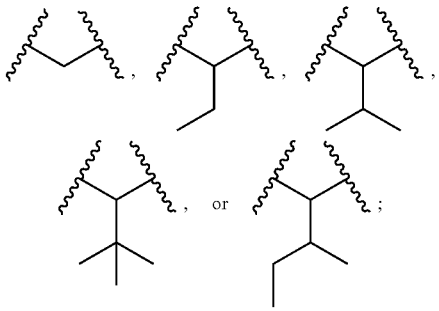

and the optional R$_L$ is a substituent such as, but not limited to phenyl, —SMe, or methoxy. Any stereochemistry at a carbon within the group L$_Y$' can be either (R) or (S). More preferably, R$_1$ is R$_C$, and R$_2$ and R$_5$, taken together with the atoms to which they are attached, form a 5- to 6-membered heterocycle or 6- to 12-membered bicycle

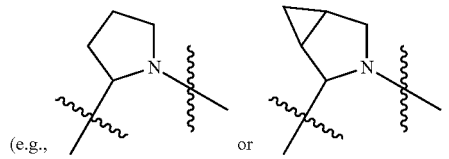

which is optionally substituted with one or more R$_A$ (e.g., one or more hydroxy); and R$_3$ and R$_6$ are each independently R$_C$, and R$_4$ and R$_7$, taken together with the atoms to which they are attached, form a 5- to 6-membered carbocycle/heterocycle or 6- to 12-membered bicycle

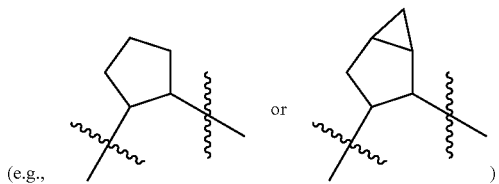 [SMILES: *C1CCCC1* ; *C1CC2CC2C1*]

which is optionally substituted with one or more R$_A$.

Also preferably, Y is selected from —N(R$_B$)CO—C(R$_1$R$_2$)N(R$_5$)—C(O)-L$_Y$'-N(R$_B$)C(O)O—R$_D$, —N(R$_B$)CO—C(R$_1$R$_2$)N(R$_5$)—C(O)-L$_Y$'-N(R$_B$)C(O)—R$_D$, —N(R$_B$)CO—C(R$_1$R$_2$)N(R$_5$)—C(O)-L$_Y$'-N(R$_B$)S(O)$_2$—R$_D$, —N(R$_B$)CO—C(R$_1$R$_2$)N(R$_5$)—C(O)-L$_Y$'-N(R$_B$R$_B$')—R$_D$, —N(R$_B$)CO—C(R$_1$R$_2$)N(R$_5$)—C(O)-L$_Y$'-O—R$_D$, —N(R$_B$)CO—C(R$_1$R$_2$)N(R$_5$)—C(O)-L$_Y$'-R$_D$, —N(R$_B$)CO—C(R$_1$R$_2$)N(R$_5$)—R$_D$, -L$_S$-C(R$_1$R$_2$)N(R$_5$)—C(O)-L$_Y$'—N(R$_B$)C(O)O—R$_D$, -L$_S$-C(R$_1$R$_2$)N(R$_5$)—C(O)-L$_Y$'-N(R$_B$)C(O)—R$_D$, -L$_S$-C(R$_1$R$_2$)N(R$_5$)—C(O)-L$_Y$'—N(R$_B$)S(O)$_2$—R$_D$, -L$_S$-C(R$_1$R$_2$)N(R$_5$)—C(O)-L$_Y$'-N(R$_B$R$_B$')—R$_D$, -L$_S$-C(R$_1$R$_2$)N(R$_5$)—C(O)-L$_Y$'-O—R$_D$, -L$_S$-C(R$_1$R$_2$)N(R$_5$)—C(O)-L$_Y$'-R$_D$, -L$_S$-C(R$_1$R$_2$)N(R$_5$)—R$_D$, —N(R$_B$)CO—C(R$_3$R$_4$)C(R$_6$R$_7$)—C(O)-L$_Y$'-N(R$_B$)C(O)O—R$_D$, —N(R$_B$)CO—C(R$_3$R$_4$)C(R$_6$R$_7$)—C(O)-L$_Y$'-N(R$_B$)C(O)—R$_D$, —N(R$_B$)CO—C(R$_3$R$_4$)C(R$_6$R$_7$)—C(O)-L$_Y$'-N(R$_B$)S(O)$_2$—R$_D$, —N(R$_B$)CO—C(R$_3$R$_4$)C(R$_6$R$_7$)—C(O)-L$_Y$'-N(R$_B$R$_B$')—R$_D$, —N(R$_B$)CO—C(R$_3$R$_4$)C(R$_6$R$_7$)—C(O)-L$_Y$'-O—R$_D$, —N(R$_B$)CO—C(R$_3$R$_4$)C(R$_6$R$_7$)—C(O)-L$_Y$'-R$_D$, —N(R$_B$)CO—C(R$_3$R$_4$)C(R$_6$R$_7$)—R$_D$, -L$_S$-C(R$_3$R$_4$)C(R$_6$R$_7$)—C(O)-L$_Y$'-N(R$_B$)C(O)O—R$_D$, -L$_S$-C(R$_3$R$_4$)C(R$_6$R$_7$)—C(O)-L$_Y$'-N(R$_B$)C(O)—R$_D$, -L$_S$-C(R$_3$R$_4$)C(R$_6$R$_7$)—C(O)-L$_Y$'-N(R$_B$)S(O)$_2$—R$_D$, -L$_S$-C(R$_3$R$_4$)C(R$_6$R$_7$)—C(O)-L$_Y$'-N(R$_B$R$_B$')—R$_D$, -L$_S$-C(R$_3$R$_4$)C(R$_6$R$_7$)—C(O)-L$_Y$'-O—R$_D$, -L$_S$-C(R$_3$R$_4$)C(R$_6$R$_7$)—C(O)-L$_Y$'-R$_D$, or -L$_S$-C(R$_3$R$_4$)C(R$_6$R$_7$)—R$_D$, wherein L$_Y$' preferably is C$_1$-C$_6$alkylene which is optionally substituted with one or more R$_L$. R$_1$ may be R$_C$, and R$_2$ and R$_5$, taken together with the atoms to which they are attached, may form a 5- to 6-membered heterocycle or 6- to 12-membered bicycle

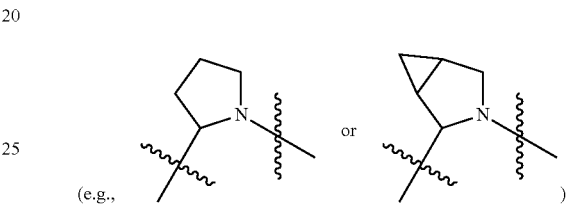

which is optionally substituted with one or more R$_A$; and R$_3$ and R$_6$ may be each independently R$_C$, and R$_4$ and R$_7$, taken together with the atoms to which they are attached, may form a 5- to 6-membered carbocycle/heterocycle or 6- to 12-membered bicycle

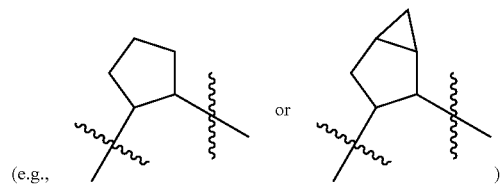 [SMILES: *C1CCCC1* ; *C1CC2CC2C1*]

which is optionally substituted with one or more R$_A$.

Highly preferably, Y is selected from —N(R$_B$")CO—C(R$_1$R$_2$)N(R$_5$)—C(O)-L$_Y$'-N(R$_B$")C(O)-L$_S$-R$_E$ or —C(R$_1$R$_2$)N(R$_5$)—C(O)-L$_Y$-N(R$_B$")C(O)-L$_S$-R$_E$, or Y is -G-C(R$_1$R$_2$)N(R$_5$)—C(O)-L$_Y$-N(R$_B$")C(O)-L$_S$-R$_E$, wherein L$_Y$ is C$_1$-C$_6$alkylene optionally substituted with one or more R$_L$, and R$_B$" is each independently R$_B$. R$_B$" and R$_1$ are each preferably hydrogen or C$_1$-C$_6$alkyl, and R$_2$ and R$_5$, taken together with the atoms to which they are attached, preferably form a 5- to 6-membered heterocycle or 6- to 12-membered bicycle

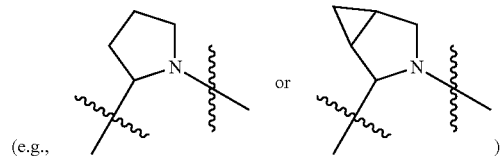 [SMILES: *C1CCCN1* ; *C1C2CC2CN1*]

which is optionally substituted with one or more R$_A$ (such as, but not limited to hydroxy, halo (e.g., fluoro), C$_1$-C$_6$alkyl (e.g., methyl), or C$_2$-C$_6$alkenyl (e.g., allyl)). Preferably, L$_Y$ is $C_1$-$C_6$alkylene substituted with one or more $R_L$ such as a $C_3$-$C_6$carbocycle 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Highly preferably, $L_Y$ is a $C_1$-$C_6$alkylene such as, but not limited to,

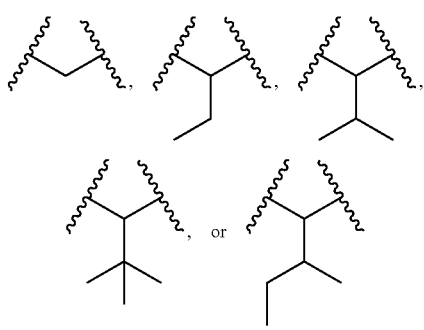

(stereochemistry at a carbon within the group $L_Y$ can be either (R) or (S)), $L_Y$ is independently optionally substituted with one or more $R_L$, (e.g., one or more phenyl or methoxy), G preferably is

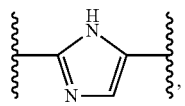 [SMILES: *c1cnc(*)[nH]1]

$R_B''$ is hydrogen; —C($R_1R_2$)N($R_5$)— is

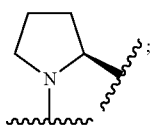 [SMILES: *[C@@H]1CCCN1*]

$L_S$ is a bond; and $R_E$ is methoxy.

Non-limiting examples of preferred Y include:

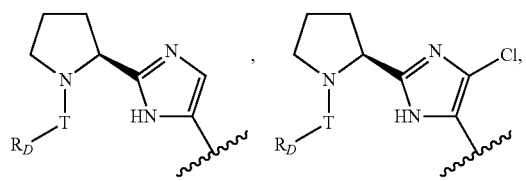

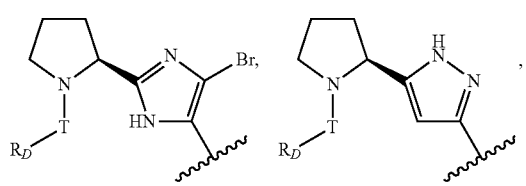

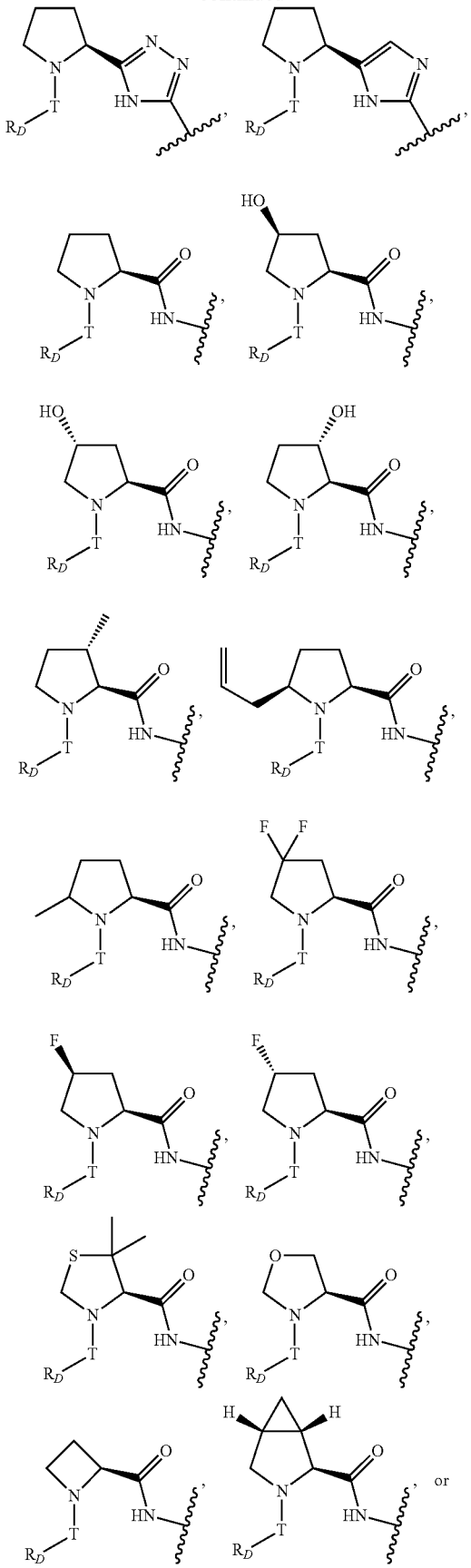

-continued

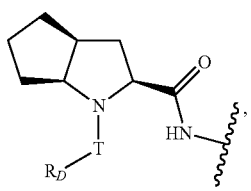

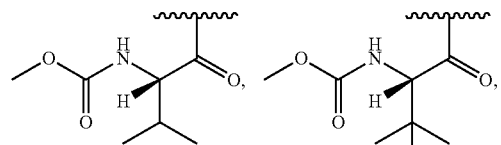

wherein T and $R_D$ are as defined herein. T, for example, can be $-L_S-M-L_S'-M'-L_S''-$ where $L_S$ is a bond; M is C(O); $L_S'$ is $C_1-C_6$alkylene such as, but not limited to,

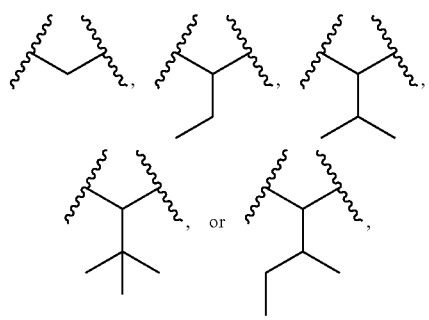

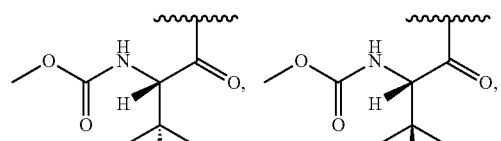

where $L_S'$ is independently optionally substituted with one or more $R_L$; $R_L$ is a substituent such as, but not limited to phenyl or methoxy; M' is —NHC(O)— or —NMeC(O)—; and $L_S''$ is a bond. Any stereochemistry at a carbon within the group $L_S'$ can be either (R) or (S). $R_D$, for example is methoxy. T-$R_D$ includes, but is not limited to:

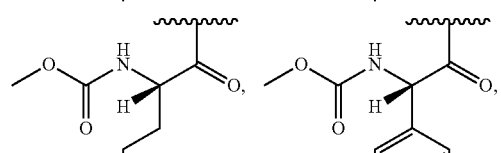

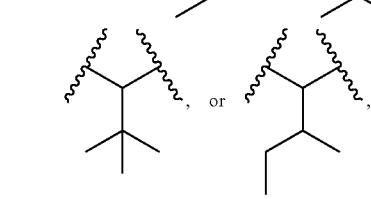

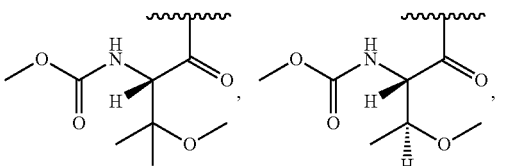

T-$R_D$ may also include certain stereochemical configurations; thus T-$R_D$ includes, but is not limited to:

Non-limiting examples of preferred Y also include:

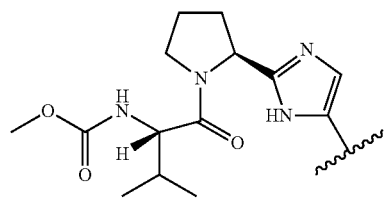

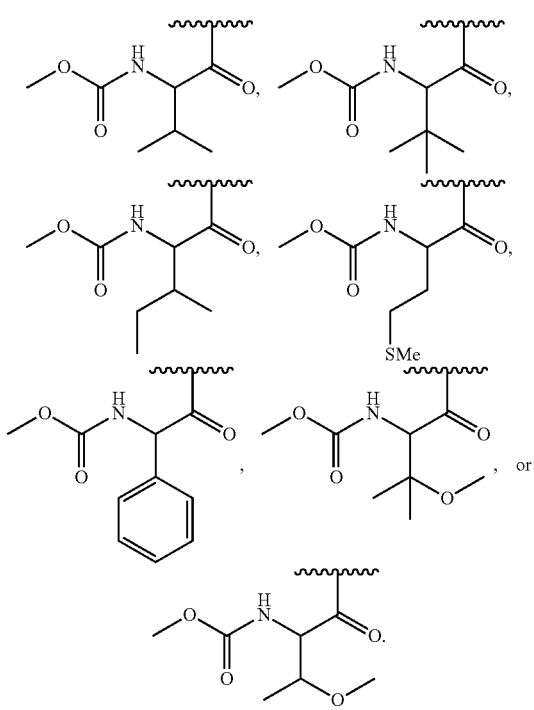

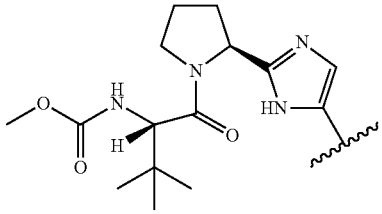

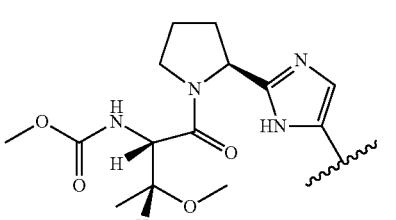

, or

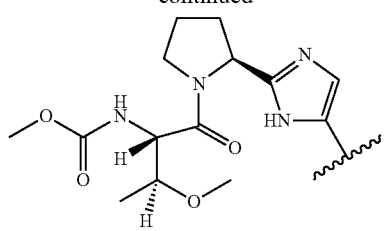
,
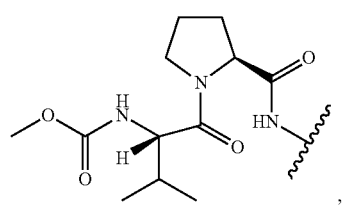
,
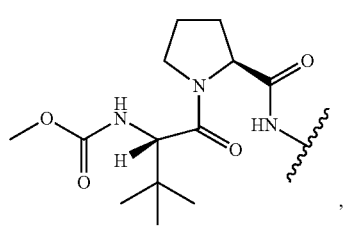
,
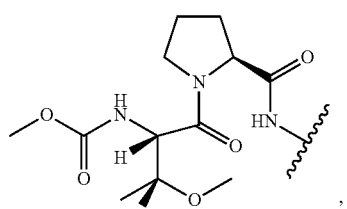
,
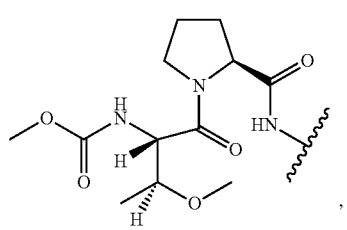
,
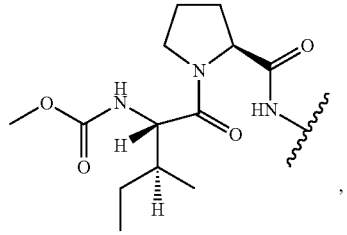
,
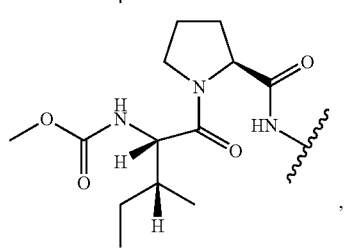
,

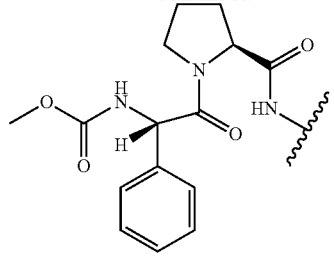
, or

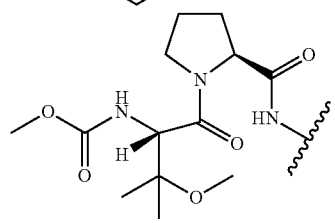
,

Z is preferably selected from $-L_S-C(R_8R_9)N(R_{12})-T-R_D$, $-L_S-C(R_{10}R_{11})C(R_{13}R_{14})-T-R_D$, $-G-C(R_8R_9)N(R_{12})-T-R_D$, $-G-C(R_{10}R_{11})C(R_{13}R_{14})-T-R_D$, $—N(R_B)C(O)C(R_8R_9)N(R_{12})-T-R_D$, $—N(R_B)C(O)C(R_{10}R_{11})C(R_{13}R_{14})-T-R_D$, $—C(O)N(R_B)C(R_8R_9)N(R_{12})-T-R_D$, $—C(O)N(R_B)C(R_{10}R_{11})C(R_{13}R_{14})-T-R_D$, $—N(R_B)C(O)-L_S-E$, or $—C(O)N(R_B)-L_S-E$. G is $C_5-C_6$ carbocycle or 5- to 6-membered heterocycle, such as

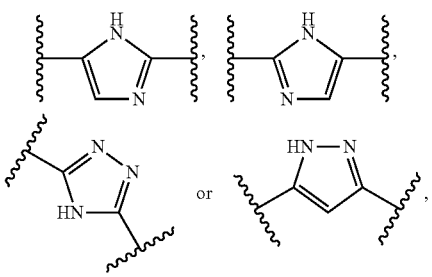

and is optionally substituted with one or more $R_A$ (e.g., one or more chloro or bromo). E preferably is a 8- to 12-membered bicycle (such as

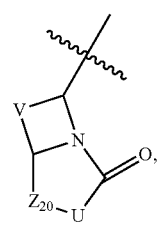

wherein U is independently selected at each occurrence from $—(CH_2)—$ or $—(NH)—$; and V and $Z_{20}$ are each independently selected from $C_1-C_4$ alkylene, $C_2-C_4$ alkenylene or $C_2-C_4$ alkynylene, in which at least one carbon atom is independently optionally replaced with O, S or N), and is independently optionally substituted with one or more $R_A$. More preferably, $R_8$ is $R_C$, and $R_9$ and $R_{12}$, taken together with the atoms to which they are attached, form a 5- to 6-membered heterocycle or 6- to 12-membered bicycle (e.g.,

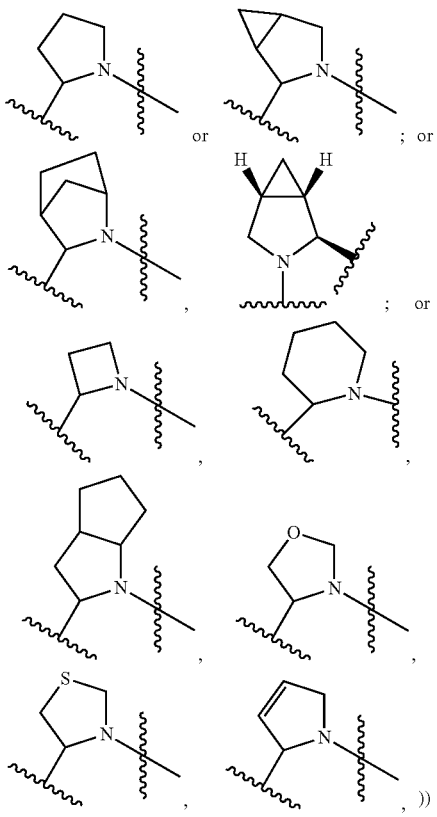

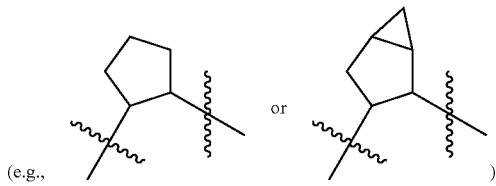 [SMILES: *C1CCCC1* ; *C1CC2CC2C1*]

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle

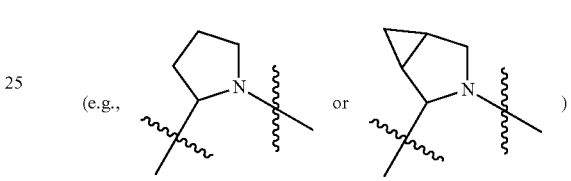

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Z can also be selected from -M-C($R_8R_9$)N($R_{12}$)—C(O)-$L_Y$'-M'-$R_D$, -M-C($R_8R_9$)N($R_{12}$)-$L_Y$'-M'-$R_D$, -$L_S$-C($R_8R_9$)N($R_{12}$)—C(O)-$L_Y$'-M'-$R_D$, -$L_S$-C($R_8R_9$)N($R_{12}$)-$L_Y$'-M'-$R_D$, -M-C($R_{10}R_{11}$)C($R_{13}R_{14}$)—C(O)-$L_Y$'-M'-$R_D$, -M-C($R_{10}R_{11}$)C($R_{13}R_{14}$)-$L_Y$', M'-$R_D$, -$L_S$-, C($R_{10}R_{11}$)C($R_{13}R_{14}$)—C(O)-$L_Y$'-M'-$R_D$, or -$L_S$-C($R_{10}R_{11}$)C($R_{13}R_{14}$)-$L_Y$'-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$')—, —N($R_B$)S(O)— or —N($R_B$)S(O)$_2$—, and $L_Y$' preferably is $C_1$-$C_6$alkylene which is independently optionally substituted with one or more $R_L$. $L_Y$', for example, is a $C_1$-$C_6$alkylene such as, but not limited to,

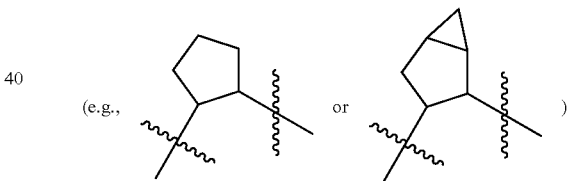

and the optional $R_L$ is a substituent such as, but not limited to phenyl, —SMe, or methoxy. Any stereochemistry at a carbon within the group $L_Y$' can be either (R) or (S). More preferably, $R_8$ is $R_C$, and $R_9$ and $R_{12}$, taken together with the atoms to which they are attached, form a 5- to 6-membered heterocycle or 6- to 12-membered bicycle which is optionally substituted with one or more $R_A$ (e.g., one or more hydroxy); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle which is optionally substituted with one or more $R_A$.

Also preferably, Z is selected from —N($R_B$)CO—C($R_8R_9$) N($R_{12}$)—C(O)-$L_Y$'-N($R_B$)C(O)O—$R_D$, —N($R_B$)CO—C ($R_8R_9$)N($R_{12}$)—C(O)-$L_Y$'-N($R_B$)C(O)—$R_D$, —N($R_B$)CO—C($R_8R_9$)N($R_{12}$)—C(O)-$L_Y$'-N($R_B$)S(O)$_2$—$R_D$, —N($R_B$) CO—C($R_8R_9$)N($R_{12}$)—C(O)-$L_Y$'-N($R_BR_B$')—$R_D$, —N($R_B$) CO—C($R_8R_9$)N($R_{12}$)—C(O)-$L_Y$'-O—$R_D$, —N($R_B$)CO—C ($R_8R_9$)N($R_{12}$)—C(O)-$L_Y$'-$R_D$, —N($R_B$)CO—C($R_8R_9$)N ($R_{12}$)—$R_D$, -$L_S$-C($R_8R_9$)N($R_{12}$)—C(O)-$L_Y$'—N($R_B$)C(O) O—$R_D$, -$L_S$-C($R_8R_9$)N($R_{12}$)—C(O)-$L_Y$'-N($R_B$)C(O)—$R_D$, -$L_S$-C($R_8R_9$)N($R_{12}$)—C(O)-$L_Y$'-N($R_B$)S(O)$_2$—$R_D$, -$L_S$-C ($R_8R_9$)N($R_{12}$)—C(O)-$L_Y$'-N($R_BR_B$')—$R_D$, -$L_S$-C($R_8R_9$)N ($R_{12}$)—C(O)-$L_Y$'-O—$R_D$, -$L_S$-C($R_8R_9$)N($R_{12}$)—C(O)-$L_Y$'-$R_D$, -$L_S$-C($R_8R_9$)N($R_{12}$)—$R_D$, —N($R_B$)CO—C($R_{10}R_{11}$)C ($R_{13}R_{14}$)—C(O)-$L_Y$'-N($R_B$)C(O)O—$R_D$, —N($R_B$)CO—C ($R_{10}R_{11}$)C($R_{13}R_{14}$)—C(O)-$L_Y$'-N($R_B$)C(O)—$R_D$, —N($R_B$) CO—C($R_{10}R_{11}$)C($R_{13}R_{14}$)—C(O)-$L_Y$-N($R_B$)S(O)$_2$—$R_D$, —N($R_B$)CO—C($R_{10}R_{11}$)C($R_{13}R_{14}$)—C(O)-$L_Y$'-N ($R_BR_B$')—$R_D$, —N($R_B$)CO—C($R_{10}R_{11}$)C($R_{13}R_{14}$)—C(O)-$L_Y$'-O—$R_D$, —N($R_B$)CO—C($R_{10}R_{11}$)C($R_{13}R_{14}$)—C(O)-$L_Y$'-$R_D$, —N($R_B$)CO—C($R_{10}R_{11}$)C($R_{13}R_{14}$)—$R_D$, -$L_S$-C ($R_{10}R_{11}$)C($R_{13}R_{14}$)—C(O)-$L_Y$'-N($R_B$)C(O)O—$R_D$, -$L_S$-C (R₁₀R₁₁)C(R₁₃R₁₄)—C(O)-L_Y'-N(R_B)C(O)—R_D,   -L_S-C
(R₁₀R₁₁)C(R₁₃R₁₄)—C(O)-L_Y'-N(R_B)S(O)₂—R_D,  -L_S-C
(R₁₀R₁₁)C(R₁₃R₁₄)—C(O)-L_Y'-N(R_BR_B')—R_D,   -L_S-C
(R₁₀R₁₁)C(R₁₃R₁₄)—C(O)-L_Y'-O—R_D,  -L_S-C(R₁₀R₁₁)C
(R₁₃R₁₄)—C(O)-L_Y'-R_D, or -L_S-C(R₁₀R₁₁)C(R₁₃R₁₄)—R_D,
wherein L_Y' preferably is C₁-C₆alkylene which is independently optionally substituted with one or more R_L. R₈ may be R_C, and R₉ and R₁₂, taken together with the atoms to which they are attached, may form a 5- to 6-membered heterocycle or 6- to 12-membered bicycle

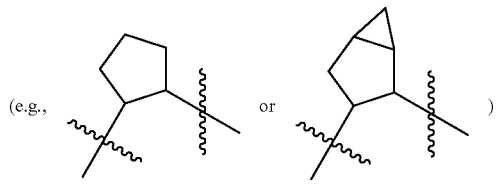 [SMILES: *C1CCCC1* ; *C1CC2CC2C1*]

(e.g., ... or ...)

which is optionally substituted with one or more R₄; and R₁₀ and R₁₃ may be each independently R_C, and R₁₁ and R₁₄, taken together with the atoms to which they are attached, may form a 5- to 6-membered carbocycle/heterocycle or 6- to 12-membered bicycle

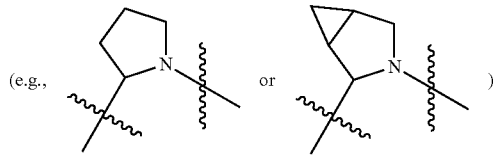 [SMILES: *C1CCCN1* ; *C1C2CC2CN1*]

(e.g., ... or ...)

which is optionally substituted with one or more R₄.

Highly preferably, Z is selected from —N(R_B")CO—C(R₈R₉)N(R₁₂)—C(O)-L_Y-N(R_B")C(O)-L_S-R_E or —C(R₈R₉)N(R₁₂)—C(O)-L_Y-N(R_B")C(O)-L_S-R_E, or Z is -G-C(R₈R₉)N(R₁₂)—C(O)-L_Y-N(R_B")C(O)-L_S-R_E,  wherein L_Y is C₁-C₆alkylene optionally substituted with one or more R_L, and R_B" is each independently R_B. R_B" and R₈ are each preferably hydrogen or C₁-C₆alkyl, R₉ and R₁₂, taken together with the atoms to which they are attached, preferably form a 5- to 6-membered heterocycle or 6- to 12-membered bicycle

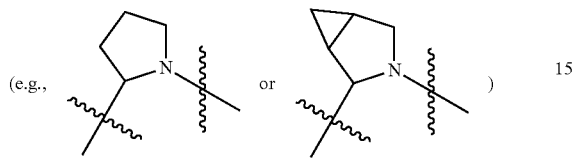

(e.g., ... or ...)

which is optionally substituted with one or more R₄ (such as, but not limited to hydroxy, halo (e.g., fluoro), C₁-C₆alkyl (e.g., methyl), or C₂-C₆alkenyl (e.g., allyl)). Preferably, L_Y is C₁-C₆alkylene substituted with one or more R_L such as a C₃-C₆carbocycle 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C₁-C₆alkyl, C₂-C₆alkenyl, C₂-C₆alkynyl, C₁-C₆haloalkyl, C₂-C₆haloalkenyl or C₂-C₆haloalkynyl. Highly preferably, L_Y is a C₁-C₆alkylene such as, but not limited to,

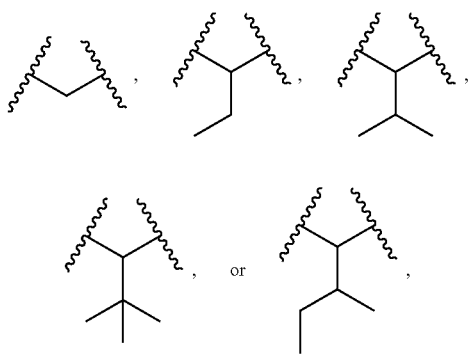

(stereochemistry at a carbon within the group L_Y can be either (R) or (S)); L_Y is independently optionally substituted with one or more R_L (e.g., one or more phenyl or methoxy); G preferably is

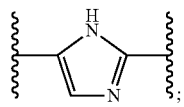

R_B" is hydrogen; —C(R₈R₉)N(R₁₂)— is

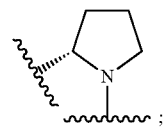 [SMILES: *[C@@H]1CCCN1*]

L_S is a bond; and R_E is methoxy. Non-limiting examples of preferred Z include:

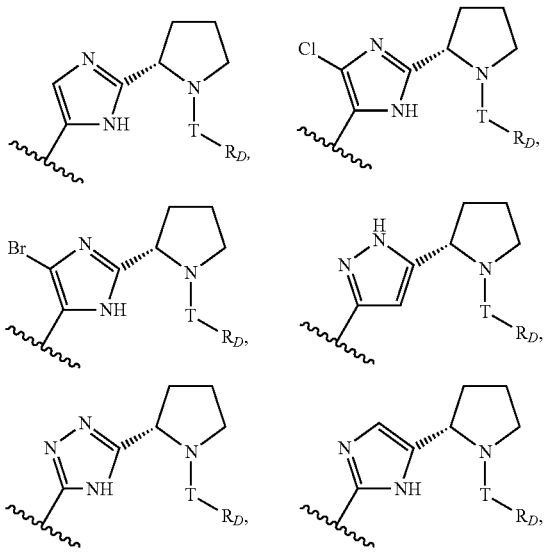

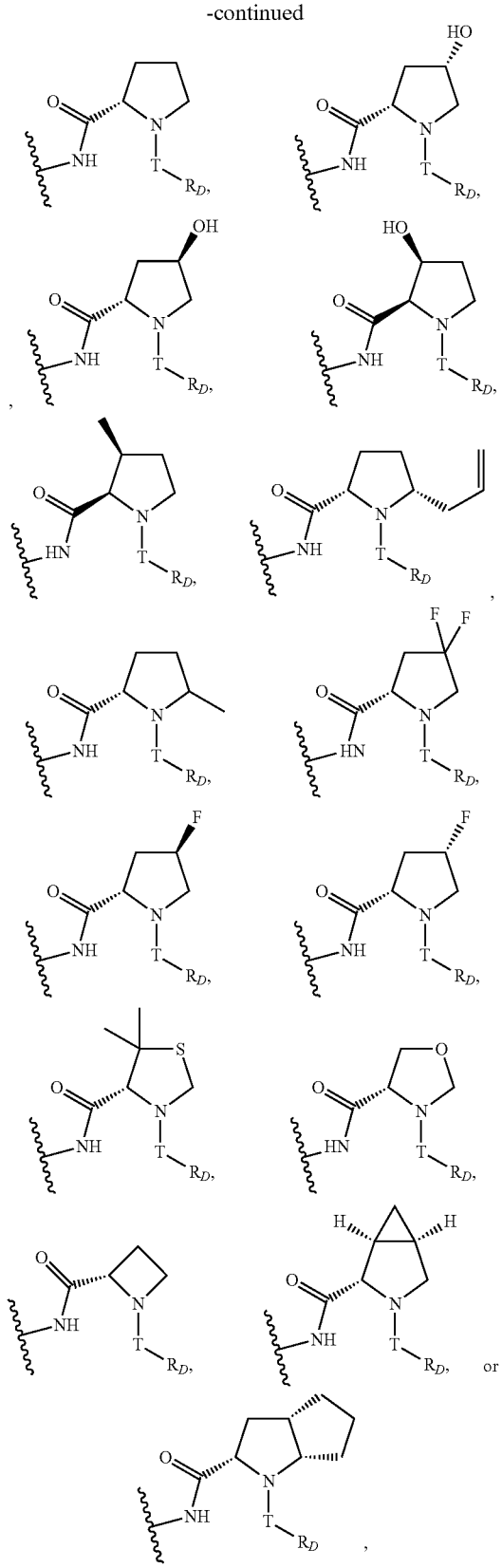

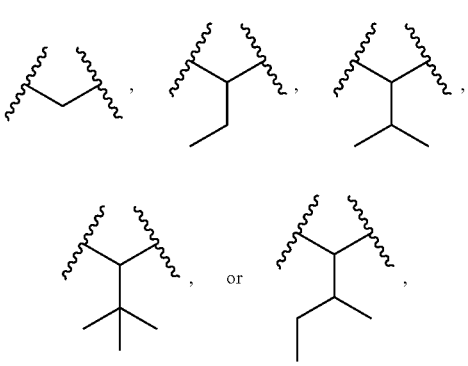

where $L_S'$ is independently optionally substituted with one or more $R_L$; the optional $R_L$ is a substituent such as, but not limited to phenyl or methoxy; M' is —NHC(O)— or —NMeC(O)—; and $L_S''$ is a bond. Any stereochemistry at a carbon within the group $L_S'$ can be either (R) or (S). $R_D$, for example is methoxy. T-$R_D$ includes, but is not limited to:

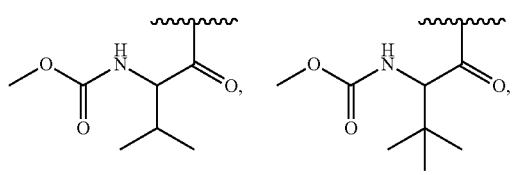

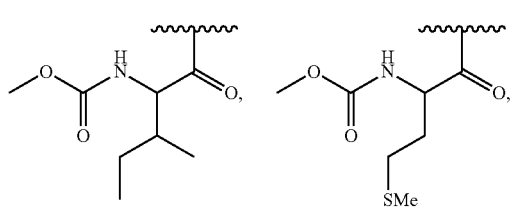

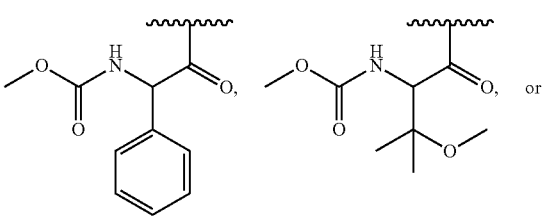

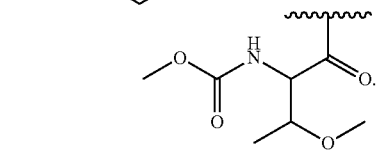

T-$R_D$ may also include certain stereochemical configurations; thus T-$R_D$ includes, but is not limited to:

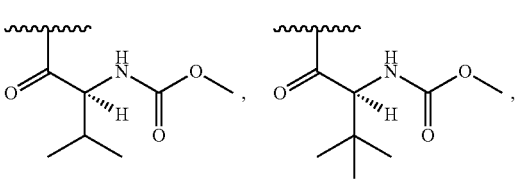

wherein T and $R_D$ are as defined herein. T, for example, can be -$L_S$-M-$L_S'$-M'-$L_S''$- where $L_S$ is a bond; M is C(O); $L_S'$ is $C_1$-$C_6$alkylene such as, but not limited to, -continued
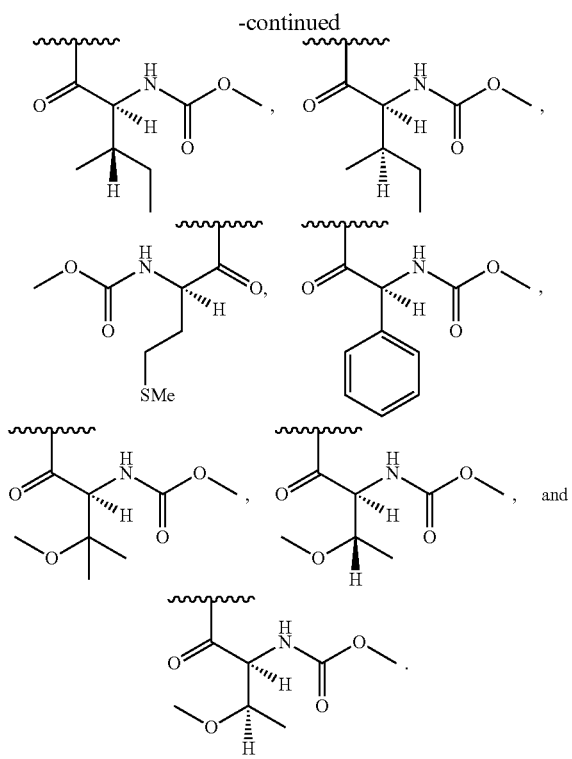
Non-limiting examples of preferred Z also include:
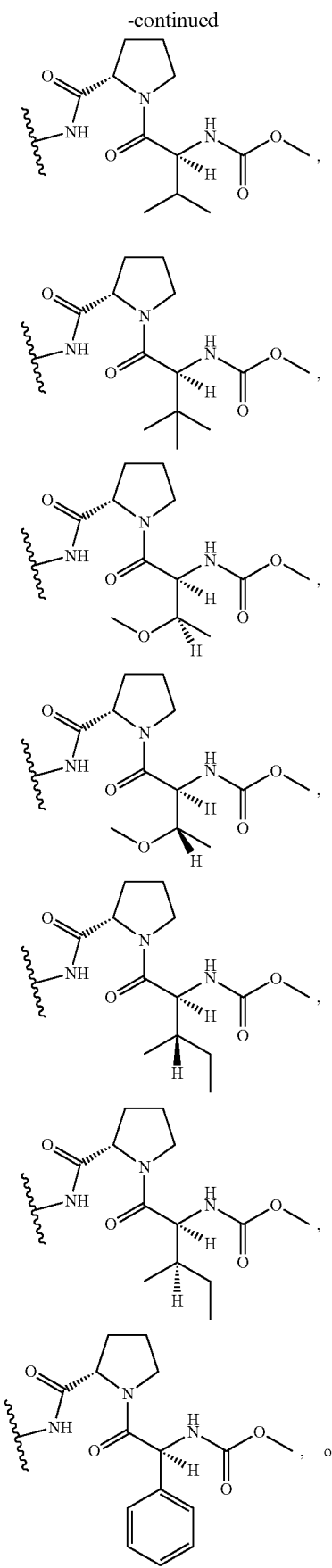

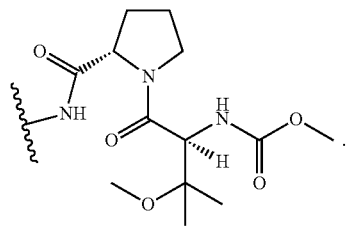

T can be, without limitation, independently selected at each occurrence from —C(O)-L$_S$'-, —C(O)O-L$_S$'-, —C(O)-L$_S$'-N(R$_B$)C(O)-L$_S$"-, —C(O)-L$_S$'-N(R$_B$)C(O)O-L$_S$"-, —N(R$_B$)C(O)-L$_S$'-N(R$_B$)C(O)-L$_S$"-, —N(R$_B$)C(O)-L$_S$'-N(R$_B$)C(O)O-L$_S$"-, or —N(R$_B$)C(O)-L$_S$'-N(R$_B$)-L$_S$"-. Preferably, T is independently selected at each occurrence from —C(O)-L$_S$'-M'-L$_S$"- or —N(R$_B$)C(O)-L$_S$'-M'-L$_S$'-. More preferably, T is independently selected at each occurrence from —C(O)-L$_S$'-N(R$_B$)C(O)-L$_S$- or —C(O)-L$_S$'-N(R$_B$)C(O)O-L$_S$"-.

T can also be, for example, -L$_S$-M-L$_S$'-M'-L$_S$"- where L$_S$ is a bond; M is C(O); L$_S$' is C$_1$-C$_6$alkylene (e.g., 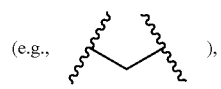 ), where L$_S$' is independently optionally substituted with R$_T$; the optional R$_T$ is a substituent selected from —C$_1$-C$_6$alkyl, —C$_2$-C$_6$alkenyl, —C$_1$-C$_6$alkyl-OH, —C$_1$-C$_6$alkyl-O—C$_1$-C$_6$alkyl, 3- to 6-membered heterocycle (e.g., tetrahydrofuranyl), or C$_3$-C$_6$carbocyclyl (e.g., phenyl, cyclohexyl); M' is —NHC(O)—, —N(Et)C(O)— or —N(Me)C(O)—; and L$_S$" is a bond. R$_D$ preferably is hydrogen, —C$_1$-C$_6$alkyl (e.g., methyl), —O—C$_1$-C$_6$alkyl (e.g., methoxy, tert-butoxy), methoxymethyl, or —N(C$_1$-C$_6$alkyl)$_2$ (e.g., —NMe$_2$).

T-R$_D$ can be, without limitation,

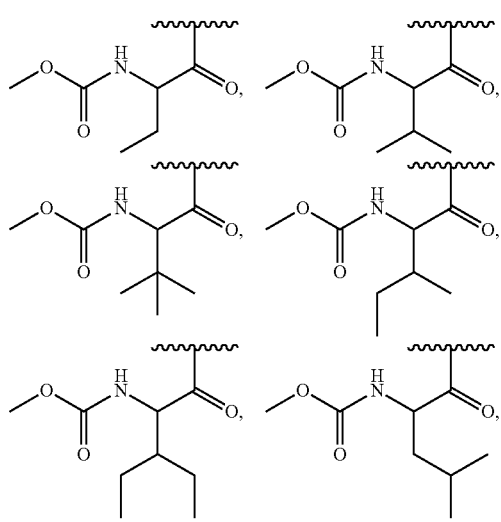

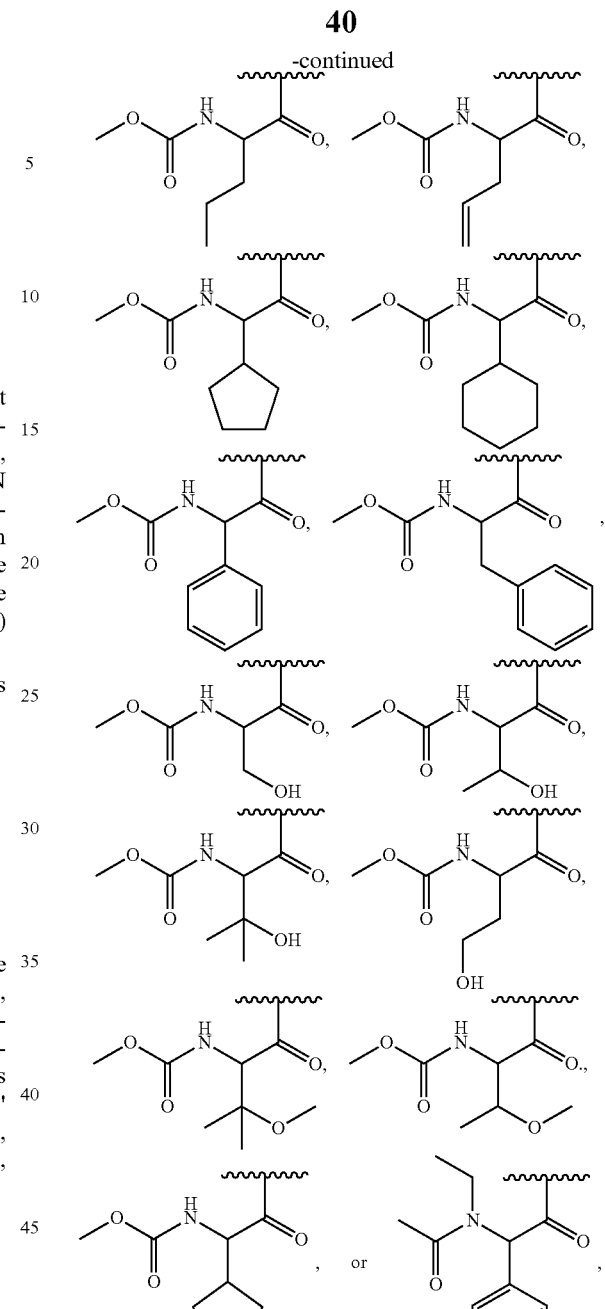

wherein the stereochemistry at a carbon within the group T-R$_D$ can be either (R) or (S).

T can also be, without limitation, -L$_S$-M-L$_S$'- where L$_S$ is a bond; M is C(O); L$_S$' is C$_1$-C$_6$alkylene (e.g., 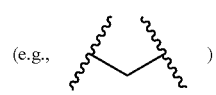 )

where L$_S$' is independently optionally substituted with R$_T$; the optional R$_T$ is a substituent selected from —C$_1$-C$_6$alkyl, —C$_1$-C$_6$alkyl-OH, —C$_1$-C$_6$alkyl-O—C$_1$-C$_6$alkyl, or a C$_3$-C$_6$carbocyclyl (e.g., phenyl, cyclohexyl). R$_D$, for example is —OH; —OC(O)Me; —NH(C$_1$-C$_6$alkyl) (e.g., —NHMe, —NHEt); —N($C_1$-$C_6$alkyl)$_2$ (e.g., —NMe$_2$, —NEt$_2$); a 3- to 10-membered heterocyclyl (e.g., pyrrolidinyl, imidazolidinyl, hexahydropyrimidinyl, morpholinyl, piperidinyl) optionally substituted with one or more halogen, oxo; $C_3$-$C_{10}$carbocycle (e.g., cyclopentyl) optionally substituted with —OH; —$C_1$-$C_6$alkyl (e.g., isopropyl, 3-pentyl) optionally substituted with —OH; or NHR$_T$ where R$_T$ is a 3- to 6-membered heterocyclyl (e.g., thiazolyl, pyrimidinyl). T-R$_D$ includes, but is not limited to:

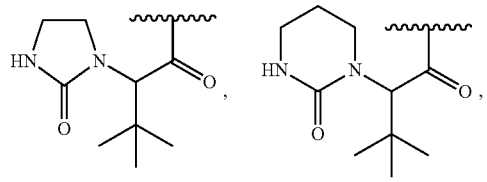

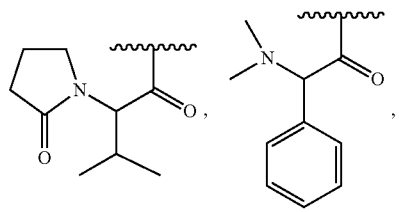

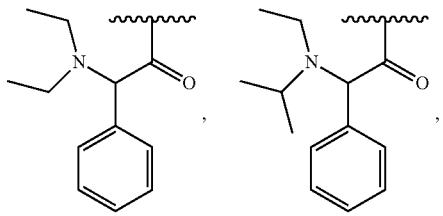

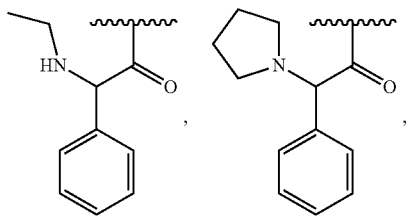

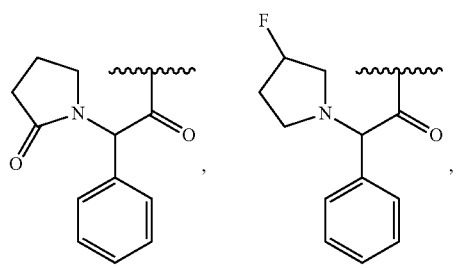

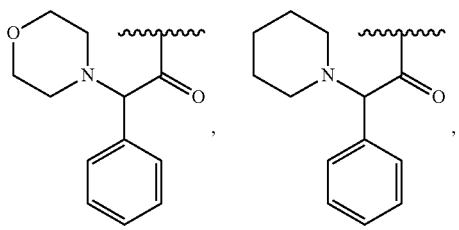

-continued

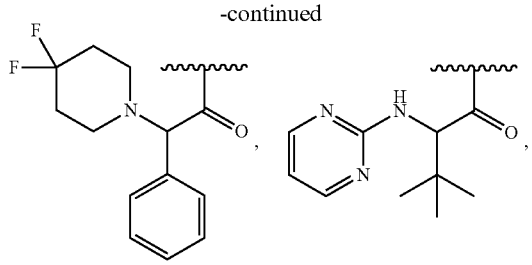

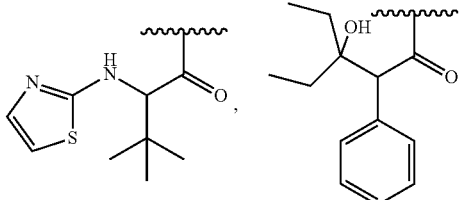

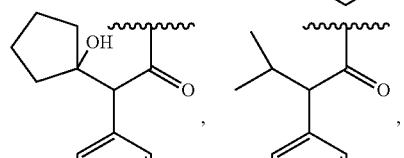

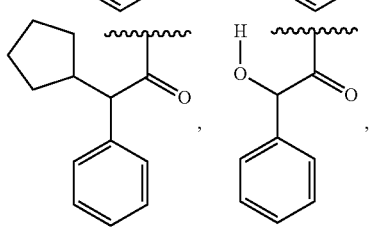

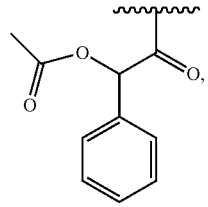, or wherein the stereochemistry at a carbon within the group T-R$_D$ can be either (R) or (S).

For each compound of Formula I, L$_K$ can also be independently selected at each occurrence from a bond; -L$_S$'-N(R$_B$)C(O)-L$_S$-; -L$_S$'-C(O)N(R$_B$)-L$_S$-; or $C_1$-$C_6$alkylene, $C_2$-$C_6$alkenylene, $C_2$-$C_6$alkynylene, $C_3$-$C_{10}$carbocycle or 3- to 10-membered heterocycle, each of which is independently optionally substituted at each occurrence with one or more substituents selected from halogen, R$_T$, —O—R$_S$, —S—R$_S$, N(R$_S$R$_S$'), —OC(O)R$_S$, —C(O)OR$_S$, nitro, oxo, phosphonoxy, phosphono, thioxo, formyl or cyano, wherein R$_T$, R$_B$, R$_S$, R$_S$', L$_S$ and L$_S$' are as defined above.

For Formula I as well as Formulae I$_A$, I$_B$, I$_C$, I$_D$, I$_E$, I$_F$ or I$_G$ described below, including each and every embodiment described thereunder, R$_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S'$), -$L_A$-S(O)$R_S$, -$L_A$-SO$_2 R_S$, -$L_A$-C(O)N($R_S R_S'$), -$L_A$-N($R_S$)C(O)$R_S'$, -$L_A$-N($R_S$)C(O)N($R_S' R_S''$), -$L_A$-N($R_S$)SO$_2 R_S'$, -$L_A$-SO$_2$N($R_S R_S'$), -$L_A$-N($R_S$)SO$_2$N($R_S' R_S''$), -$L_A$-N($R_S$)S(O)N($R_S' R_S''$), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-OC(O)O$R_S'$, -$L_A$-OC(O)N($R_S R_S'$), -$L_A$-N($R_S$)S(O)—$R_S'$, -$L_A$-S(O)N($R_S R_S'$) or -$L_A$-C(O)N($R_S$)C(O)—$R_S'$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$, or Y and Z, or Y-A- and Z—B—, or -A-$L_1$- and —B-$L_2$-, can be the same or different. In some instances, Y-A-$L_1$- is identical to Z—B-$L_2$-. In some other instances, Y-A-$L_1$- is different from Z—B-$L_2$-.

In one embodiment, A and B are each independently 5- or 6-membered carbocycle or heterocycle

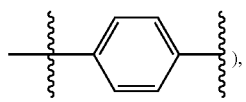, and are each independently optionally substituted with one or more $R_A$. X is 5- or 6-membered carbocycle or heterocycle or 6- to 12-membered bicycle

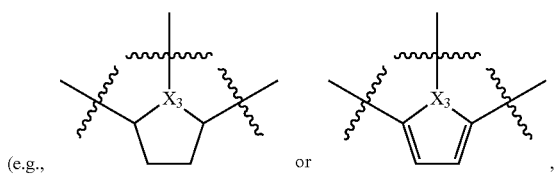

wherein $X_3$ is N and is directly linked to -$L_3$-D) and is optionally substituted with one or more $R_A$. Specific examples of X are described hereinabove. D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$), and J can also be optionally substituted with one or more $R_A$.

Preferably, D is

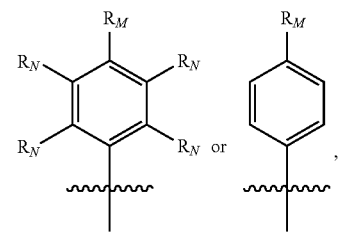

wherein $R_M$ and $R_N$ are as defined above. Also preferably, D is

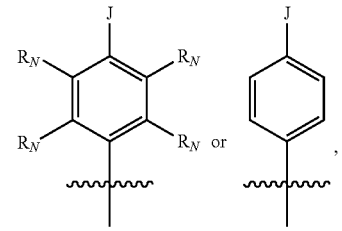

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1 R_2$)N($R_5$)-T-$R_D$, or —N($R_B$)C(O)C($R_3 R_4$)C($R_6 R_7$)-T-$R_D$, and Z is —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring (e.g., 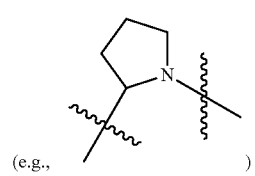 )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

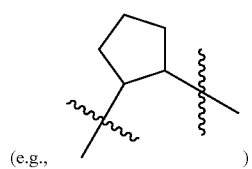

(e.g., )

which is optionally substituted with one or more $R_A$. $R_8$ is $R_C$, and $R_9$ and $R_{12}$, taken together with the atoms to which they are attached, form a 5- to 6-membered heterocyclic ring (e.g., )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., )

which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, at least one of Y and Z is, or both Y and Z are independently,

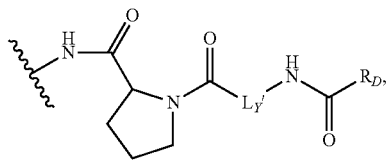

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another embodiment, A is

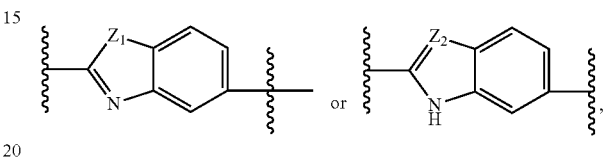

and is optionally substituted with one or more $R_A$; B is

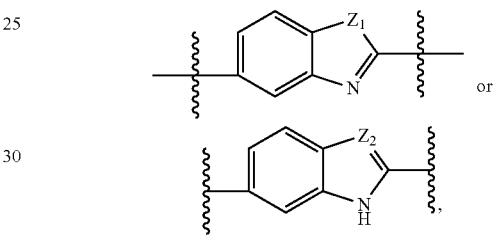

and is optionally substituted with one or more $R_A$. $Z_1$ is independently selected at each occurrence from O, S, NH or CH$_2$; and $Z_2$ is independently selected at each occurrence from N or CH. X is 5- or 6-membered carbocycle or heterocycle or 6- to 12-membered bicycle

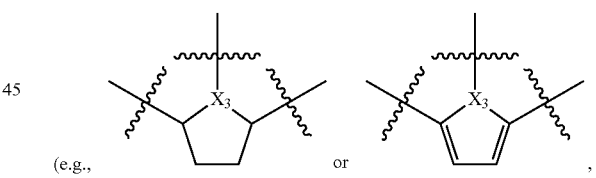

wherein $X_3$ is N and is directly linked to -$L_3$-D) and is optionally substituted with one or more $R_A$. Specific examples of X are described hereinabove. D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O) OR$_S$ or —N($R_S R_S$'), and J can also be optionally substituted with one or more $R_A$. Preferably, D is

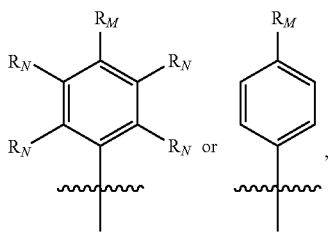

wherein $R_M$ and $R_N$ are as defined above. Also preferably, D is

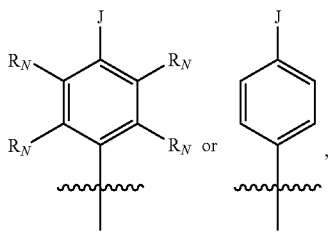

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -$L_S$-C($R_1R_2$)N($R_5$)-T-$R_D$ or -$L_S$-C($R_3R_4$)C($R_6R_7$)-T-$R_D$, and Z is -$L_S$-C($R_8R_9$)N($R_{12}$)-T-$R_D$ or -$L_S$-C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g.,  )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., 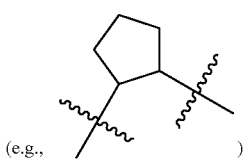 [SMILES: *C1CCCC1*] )

which is optionally substituted with one or more $R_A$. $R_8$ is $R_C$, and $R_9$ and $R_{12}$, taken together with the atoms to which they are attached, form a 5- to 6-membered heterocyclic ring (e.g., 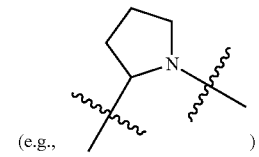 [SMILES: *C1CCCN1*] )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 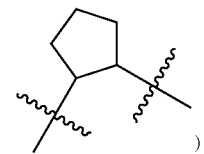 )

which is optionally substituted with one or more $R_A$. T is preferably independently selected at each occurrence from —C(O)-$L_{Y'}$-N($R_B$)C(O)-$L_S''$- or —C(O)-$L_{Y'}$—N($R_B$)C(O)O-$L_S''$-. $L_{Y'}$ is each independently $L_S'$ and, preferably, is independently $C_1$-$C_6$alkylene (e.g., —CH$_2$—) and optionally substituted with one or more substituents selected from $R_L$. T can also be, without limitation, selected from —C(O)-$L_{Y'}$-$L_S''$-, —C(O)-$L_{Y'}$-O-$L_S''$-, —C(O)-$L_{Y'}$-N($R_B$)-$L_S''$-, or —C(O)-$L_{Y'}$-N($R_B$)S(O)$_2$-$L_S''$-. In some cases, at least one of Y and Z is, or both Y and Z are independently,

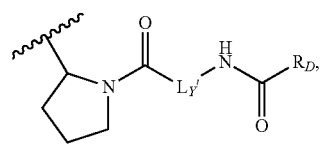

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_{Y'}$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In still yet another embodiment, A and B are each independently 5- or 6-membered carbocycle or heterocycle (e.g., A and B are each independently phenyl, such as

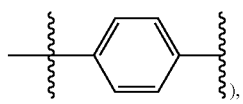

and are each independently optionally substituted with one or more $R_A$. X is 5- or 6-membered carbocycle or heterocycle or 6- to 12-membered bicycle

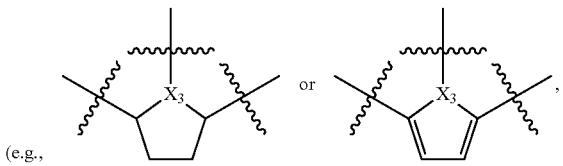

(e.g., wherein $X_3$ is N and is directly linked to -$L_3$-D) and is optionally substituted with one or more $R_A$. Specific examples of X are described hereinabove. D can be, for example, $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)$OR_S$ or —N($R_S R_S'$), and J can also be optionally substituted with one or more $R_A$. Preferably, D is

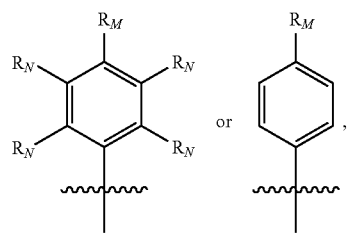

wherein $R_M$ and $R_N$ are as defined above. Also preferably, D is

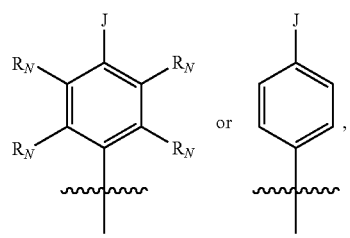

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -G-C($R_1 R_2$)N($R_5$)-T-$R_D$ or -G-C($R_3 R_4$)C($R_6 R_7$)-T-$R_D$, and Z is -G-C($R_8 R_9$)N($R_{12}$)-T-$R_D$ or -G-C($R_{10} R_{11}$)C($R_{13} R_{14}$)-T-$R_D$. G is independently $C_5$-$C_6$carbocycle or 5- to 6-membered heterocycle, such as

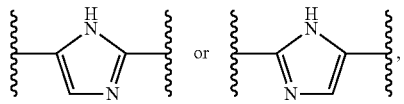 [SMILES: *c1cnc(*)[nH]1 ; *c1cnc(*)[nH]1]

and is independently optionally substituted with one or more $R_A$. $R_1$ is $R_C$, and $R_2$ and $R_5$, taken together with the atoms to which they are attached, form a 5- to 6-membered heterocyclic ring

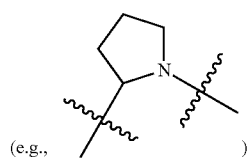 [SMILES: *C1CCCN1*]

(e.g., which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

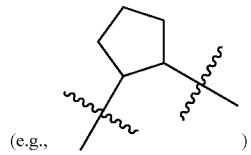 [SMILES: *C1CCCC1*]

(e.g., which is optionally substituted with one or more $R_A$. $R_8$ is $R_C$, and $R_9$ and $R_{12}$, taken together with the atoms to which they are attached, form a 5- to 6-membered heterocyclic ring

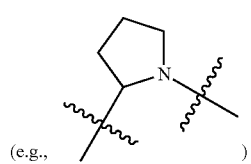 [SMILES: *C1CCCN1*]

(e.g., which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

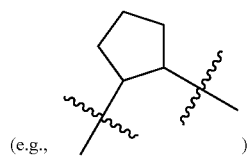 [SMILES: *C1CCCC1*]

(e.g., which is optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —$CH_2$—) and optionally substituted with one or more substituents selected from $R_L$. T can also be, without limitation, selected from —C(O)-$L_{Y'}$-$L_S''$-, —C(O)-$L_{Y'}$-O-$L_S''$-, —C(O)-$L_{Y'}$-N($R_B$)-$L_S''$-, or —C(O)-$L_{Y'}$-N($R_B$)S(O)$_2$-$L_S''$-. In some cases, at least one of Y and Z is and Z are independently,

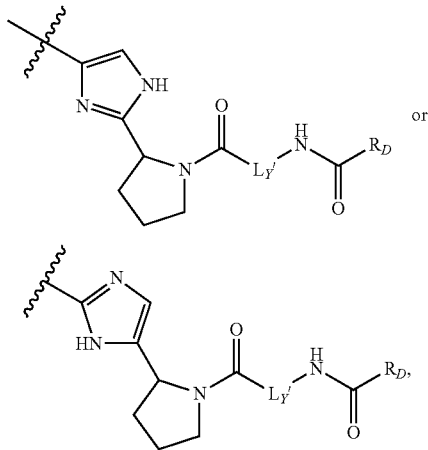

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_{Y'}$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In yet another embodiment, A and B are each independently 5- or 6-membered carbocycle or heterocycle (e.g., A and B are each independently phenyl, such as

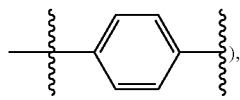

and are each independently optionally substituted with one or more $R_A$. X is 5- or 6-membered carbocycle or heterocycle or 6- to 12-membered bicycle

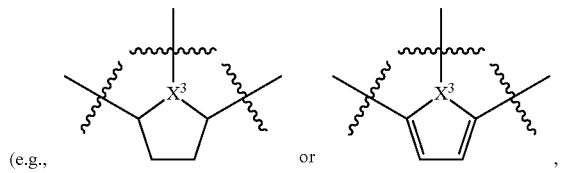

wherein $X_3$ is N and is directly linked to -$L_3$-D) and is optionally substituted with one or more $R_A$. Specific examples of X are described hereinabove. D can be, for example, $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O) OR$_S$ or —N($R_S R_S'$), and J can also be optionally substituted with one or more $R_A$. Preferably, D is

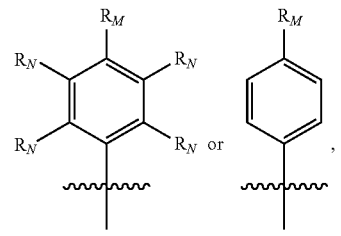

wherein $R_M$ and $R_N$ are as defined above. Also preferably, D is

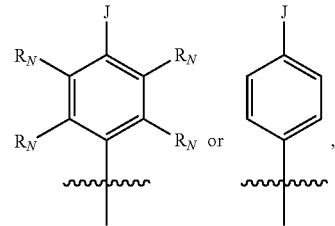

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1 R_2$)N($R_5$)-T-$R_D$ or —N($R_B$)C(O)C($R_3 R_4$)C($R_6 R_7$)-T-$R_D$, and Z is -G-C($R_8 R_9$)N($R_{12}$)-T-$R_D$ or -G-C($R_{10} R_{11}$)C($R_{13} R_{14}$)-T-$R_D$; or Y is -G-C($R_1 R_2$)N($R_5$)-T-$R_D$ or -G-C($R_3 R_4$)C($R_6 R_7$)-T-$R_D$, and Z is —N($R_B$)C(O)C($R_8 R_9$)N($R_{12}$)-T-$R_D$ or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring (e.g., 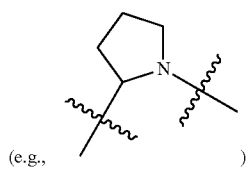)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., )

which is optionally substituted with one or more $R_A$. $R_8$ is $R_C$, and $R_9$ and $R_{12}$, taken together with the atoms to which they are attached, form a 5- to 6-membered heterocyclic ring (e.g., 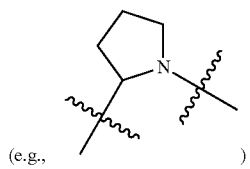)

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 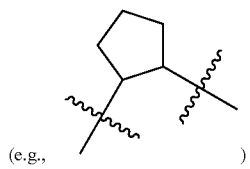)

which is optionally substituted with one or more $R_A$. G is independently $C_5$-$C_6$carbocycle or 5- to 6-membered heterocycle, such as

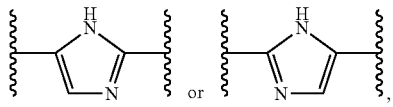

and is independently optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, Y is

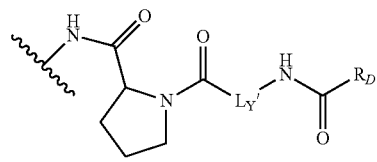

as described above, and Z is

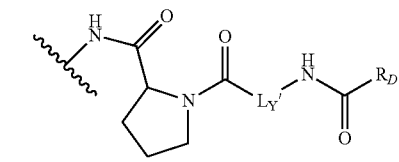

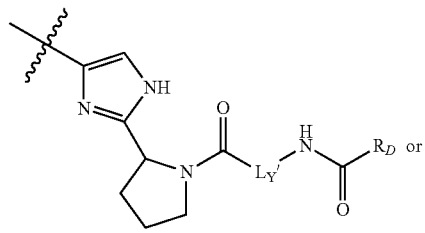

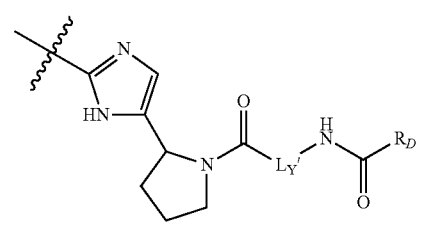

as described above. In some other cases, Y is

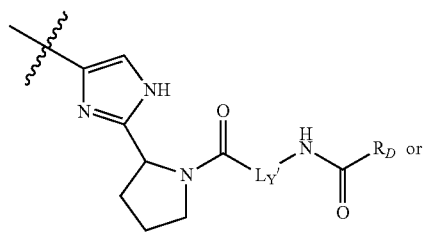

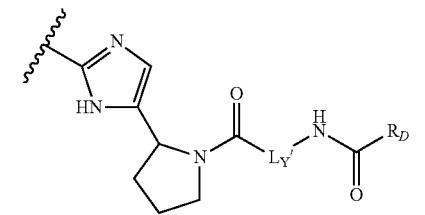

as described above, and Z is

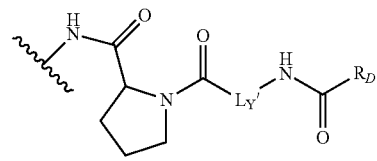

as described above.

In still another embodiment, A is 5- or 6-membered carbocycle or heterocycle (e.g., phenyl such as

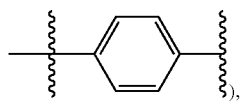

and B is

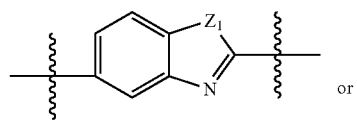

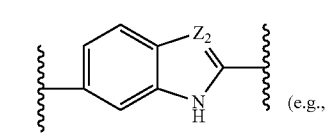 (e.g., and B is 5- or 6-membered carbocycle or heterocycle (e.g., phenyl such as

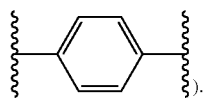 [SMILES: *c1ccc(*)cc1]

A and B are each independently optionally substituted with one or more $R_A$. $Z_1$ is independently selected at each occurrence from O, S, NH or $CH_2$; and $Z_2$ is independently selected at each occurrence from N or CH. X is 5- or 6-membered carbocycle or heterocycle or 6- to 12-membered bicycle

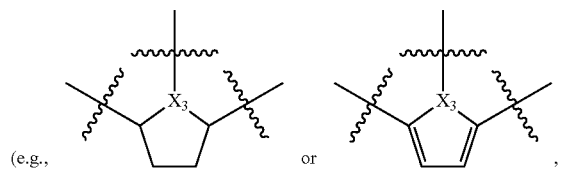

(e.g., or , wherein $X_3$ is N and is directly linked to -$L_3$-D) and is optionally substituted with one or more $R_A$. Specific examples of X are described hereinabove. D is $C_5$-$C_6$ carbocycle or 5- to 6-membered heterocycle (e.g., phenyl), and is optionally substituted with one or more $R_A$, or is substituted with J and optionally substituted with one or more $R_A$, wherein J is $C_3$-$C_6$ carbocycle, 3- to 6-membered heterocycle or 6- to 12-membered bicycle and is optionally substituted with one or more $R_A$. Preferably, J is substituted with a $C_3$-$C_6$ carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, C(O)$OR_S$ or —N($R_S R_S'$), and J can also be optionally substituted with one or more $R_A$. Preferably, D is

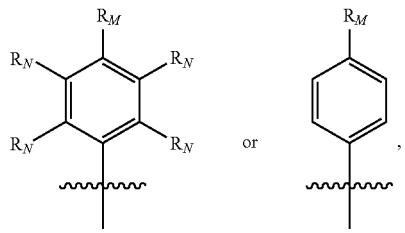 or 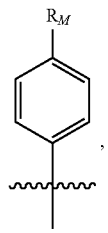 , wherein $R_M$ and $R_N$ are as defined above. Also preferably, D is

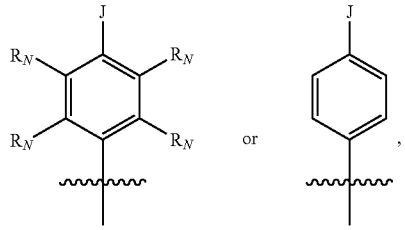 or 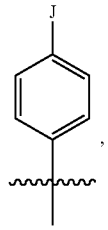 , wherein J and $R_N$ are as defined above. $L_1$ and $L_2$ are each independently bond or $C_1$-$C_6$ alkylene, and $L_3$ is bond, $C_1$-$C_6$ alkylene or —C(O)—, and $L_1$, $L_2$, and $L_3$ are each independently optionally substituted with one or more $R_L$. Preferably, $L_1$, $L_2$, and $L_3$ are bond. When A is 5- or 6-membered carbocycle or heterocycle (e.g., phenyl such as

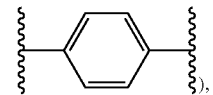),

Y is —N($R_B$)C(O)C($R_1R_2$)N($R_S$)-T-$R_D$, —N($R_B$)C(O)C($R_3R_4$)C($R_6R_7$)-T-$R_D$, -G-C($R_1R_2$)N($R_S$)-T-$R_D$ or -G-C($R_3R_4$)C($R_6R_7$)-T-$R_D$, and Z is -$L_S$-C($R_8R_9$)N($R_{12}$)-T-$R_D$ or -$L_S$-C($R_{10}R_{11}$)C($R_{13}R_{14}$)-T-$R_D$.

When B is 5- or 6-membered carbocycle or heterocycle (e.g., phenyl such as

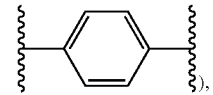),

Y is -$L_S$-C($R_1R_2$)N($R_S$)-T-$R_D$ or -$L_S$-C($R_3R_4$)C($R_6R_7$)-T-$R_D$, and Z is —N($R_B$)C(O)C($R_8R_9$)N($R_{12}$)-T-$R_D$, —N($R_B$)C(O)C($R_{10}R_{11}$)C($R_{13}R_{14}$)-T-$R_D$, -G-C($R_8R_9$)N($R_{12}$)-T-$R_D$ or -G-C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g., 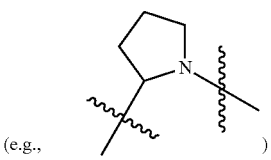 [SMILES: *C1CCCN1*] )

which is optionally substituted with one or more $R_4$; $R_3$ and $R_6$ are each independently $R_C$, and $R_4$ and $R_7$, taken together with the atoms to which they are attached, form a 5- to 6-membered carbocyclic or heterocyclic ring (e.g., 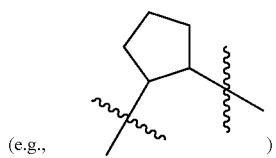 [SMILES: *C1CCCC1*] )

which is optionally substituted with one or more $R_4$. $R_8$ is $R_C$, and $R_9$ and $R_{12}$, taken together with the atoms to which they are attached, form a 5- to 6-membered heterocyclic ring (e.g., 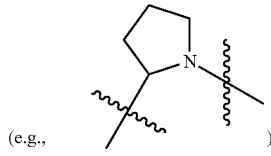 [SMILES: *C1CCCN1*] )

which is optionally substituted with one or more $R_4$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 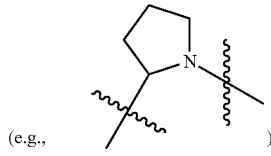 [SMILES: *C1CCCN1*] )

which is optionally substituted with one or more $R_4$. G is independently $C_5$-$C_6$carbocycle or 5- to 6-membered heterocycle, such as

and is independently optionally substituted with one or more $R_4$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases when A is 5- or 6-membered carbocycle or heterocycle (e.g., phenyl such as

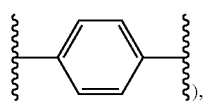),

Y is

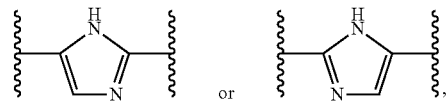

as described above, and Z is

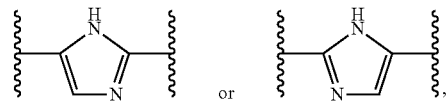

as described above. In some other cases when B is 5- or 6-membered carbocycle or heterocycle (e.g., phenyl such as

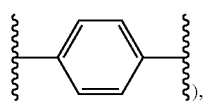),

Y is

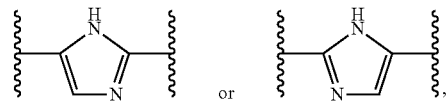

as described above, and Z is

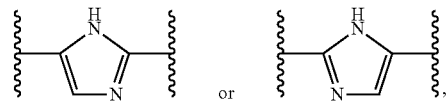

-continued

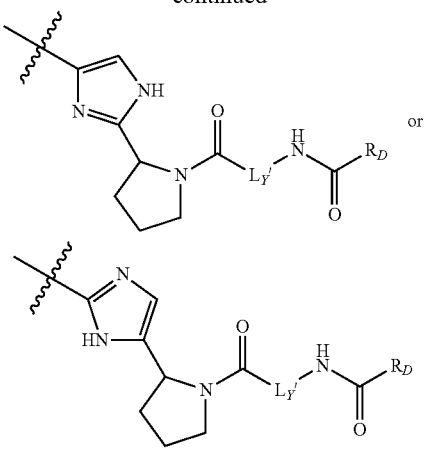

or as described above.

The present invention also features compounds of Formulae I, $I_A$, $I_B$, $I_C$ and $I_D$ as described herein (including each embodiment described hereunder) and pharmaceutically acceptable salts thereof, wherein:

D is $C_3$-$C_{12}$carbocycle or 3- to 12-membered heterocycle, and is optionally substituted with one or more $R_A$; or D is $C_3$-$C_{12}$carbocycle or 3- to 12-membered heterocycle which is substituted with J and optionally substituted with one or more $R_A$, where J is $C_3$-$C_{15}$carbocycle or 3- to 15-membered heterocycle (e.g., a 3- to 6-membered monocycle, a 6- to 12-membered fused, bridged or spiro bicycle, a 10- to 15-membered tricycle containing fused, bridged or spiro rings, or a 13- to 15-membered carbocycle or heterocycle) and is optionally substituted with one or more $R_A$, or J is —$SF_5$; or D is hydrogen or $R_A$;

$R_E$ is independently selected at each occurrence from —O—$R_S$, —S—$R_S$, —C(O)$R_S$, —OC(O)$R_S$, —C(O)O$R_S$, —N($R_SR_S'$), —S(O)$R_S$, —SO$_2R_S$, —C(O)N($R_SR_S'$), —N($R_S$)C(O)$R_S'$, —N($R_S$)C(O)N($R_S'R_S''$), —N($R_S$)SO$_2R_S'$, —SO$_2$N($R_SR_S'$), —N($R_S$)SO$_2$N($R_S'R_S''$), —N($R_S$)S(O)N($R_S'R_S''$), —OS(O)—$R_S$, —OS(O)$_2$—$R_S$, —S(O)$_2$O$R_S$, —S(O)O$R_S$, —OC(O)O$R_S$, —N($R_S$)C(O)O$R_S'$, —OC(O)N($R_SR_S'$), —N($R_S$)S(O)—$R_S'$, —S(O)N($R_SR_S'$), —P(O)(O$R_S$)$_2$, =C($R_SR_S'$), or —C(O)N($R_S$)C(O)—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle (e.g., 7- of 12-membered carbocycle or heterocycle), each of which is independently optionally substituted at each occurrence with one or more substituents selected from halogen, hydroxy, mercapto, amino, carboxy, nitro, oxo, phosphonoxy, phosphono, thioxo, formyl, cyano, trimethylsilyl, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —O—$R_S$, —S—$R_S$, —C(O)$R_S$, —C(O)O$R_S$, or —N($R_SR_S'$).

In one embodiment, A and B are each independently 5- or 6-membered carbocycle or heterocycle (preferably, A and B are each independently phenyl such as

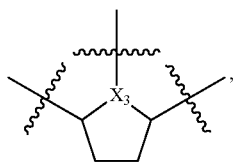

and are each independently optionally substituted with one or more $R_A$ (preferably, A and B are each independently substituted with at least one halo such as F). X is 5- or 6-membered carbocycle or heterocycle or 6- to 12-membered bicycle (preferably, X is

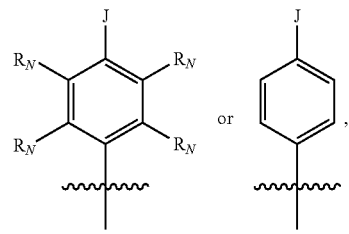

wherein $X_3$ is N and is directly linked to -$L_3$-D), and is optionally substituted with one or more $R_A$. D is a $C_5$-$C_6$carbocycle or 5- to 6-membered heterocycle (e.g., phenyl), and is substituted with J and optionally substituted with one or more $R_A$. J is $C_3$-$C_6$carbocycle, 3- to 6-membered heterocycle, 6- to 12-membered bicycle, 10- to 15-membered tricycle, or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$ or —N($R_SR_S'$), or (2) trimethylsilyl, —O—$R_S$, —S—$R_S$, —C(O)$R_S$; and J can also be optionally substituted with one or more $R_A$. Preferably, D is wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1R_2$)N($R_5$)-T-$R_D$, —N($R_B$)C(O)C($R_3R_4$)C($R_6R_7$)-T-$R_D$, -G-C($R_1R_2$)N($R_5$)-T-$R_D$ or -G-C($R_3R_4$)C($R_6R_7$)-T-$R_D$. Z is —N($R_B$)C(O)C($R_8R_9$)N($R_{12}$)-T-$R_D$, —N($R_B$)C(O)C($R_{10}R_{11}$)C($R_{13}R_{14}$)-T-$R_D$, -G-C($R_8R_9$)N($R_{12}$)-T-$R_D$ or -G-C($R_{10}R_{11}$)C($R_{13}R_{14}$)-T-$R_D$. $R_1$ is $R_C$; and $R_2$ and $R_5$, taken together with the atoms to which they are attached, form a 5- to 6-membered heterocyclic ring (e.g., 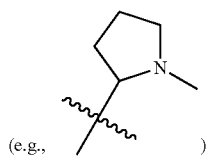 [SMILES: *C1CCCN1C] )

or 6- to 12-membered bicycle (e.g.,

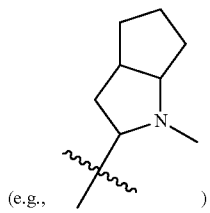 [SMILES: *C1CC2CCCC2N1C]

(e.g., )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

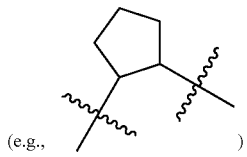 [SMILES: *C1CCCC1*]

(e.g., )

or 6- to 12-membered bicycle which is optionally substituted with one or more $R_A$. $R_8$ is $R_C$; and $R_9$ and $R_{12}$, taken together with the atoms to which they are attached, form a 5- to 6-membered heterocyclic ring

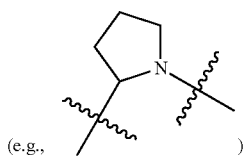 [SMILES: *C1CCCN1*]

(e.g., )

or 6- to 12-membered bicycle

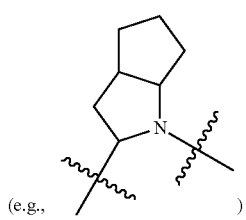 [SMILES: *C1CC2CCCC2N1*]

(e.g., )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 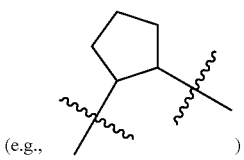 [SMILES: *C1CCCC1*] )

or 6- to 12-membered bicycle which is optionally substituted with one or more $R_A$. G is independently $C_5$-$C_6$carbocycle or 5- to 6-membered heterocycle, such as

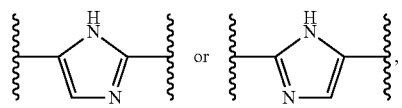 [SMILES: *c1cnc(*)[nH]1 ; *c1cnc(*)[nH]1]

and is independently optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, Y is

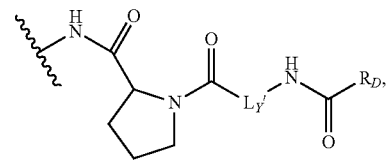

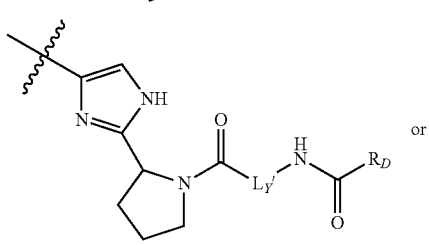

or

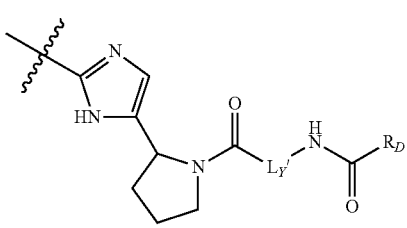

as described above, and Z is

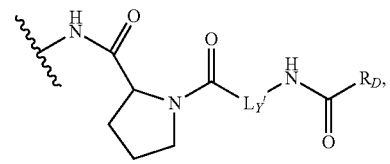

-continued

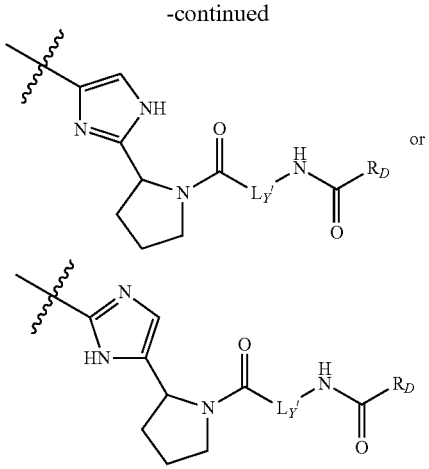

as described above.

In another embodiment, A is

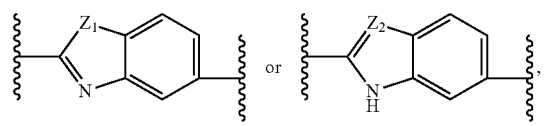

and is optionally substituted with one or more $R_A$; B is

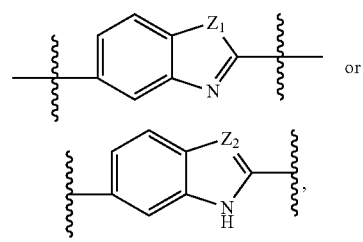

and is optionally substituted with one or more $R_A$. $Z_1$ is independently selected at each occurrence from O, S, NH or $CH_2$; and $Z_2$ is independently selected at each occurrence from N or CH. Preferably, A and B are each independently substituted with at least one halo such as F. X is 5- or 6-membered carbocycle or heterocycle or 6- to 12-membered bicycle (preferably, X is

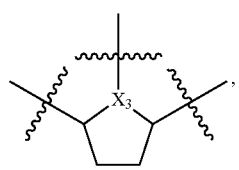

wherein $X_3$ is N and is directly linked to -$L_3$-D), and is optionally substituted with one or more $R_A$. D is a $C_5$-$C_6$carbocycle or 5- to 6-membered heterocycle (e.g., phenyl), and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$, or —C(O)R$_S$; and J can also be optionally substituted with one or more $R_A$. Preferably, D is

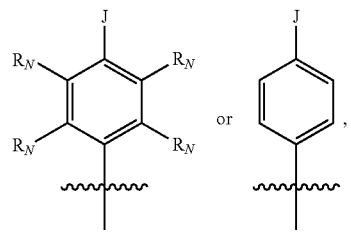

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -$L_S$-C($R_1R_2$)N($R_5$)-T-$R_D$ or -$L_S$-C($R_3R_4$)C($R_6R_7$)-T-$R_D$. Z is -$L_S$-C($R_8R_9$)N($R_{12}$)-T-$R_D$ or -$L_S$-C($R_{10}R_{11}$)C($R_{13}R_{14}$)-T-$R_D$. $R_1$ is $R_C$; and $R_2$ and $R_5$, taken together with the atoms to which they are attached, form a 5- to 6-membered heterocyclic ring

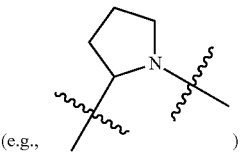 [SMILES: *C1CCCN1*]
(e.g., )

or 6- to 12-membered bicycle

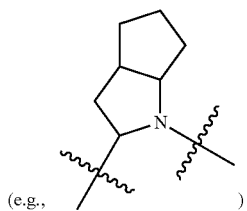 [SMILES: *C1CC2CCCC2N1*]
(e.g., )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

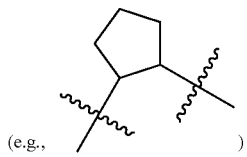 [SMILES: *C1CCCC1*]
(e.g., )

or 6- to 12-membered bicycle which is optionally substituted with one or more $R_A$. $R_8$ is $R_C$; and $R_9$ and $R_{12}$, taken together with the atoms to which they are attached, form a 5- to 6-membered heterocyclic ring

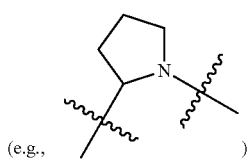 [SMILES: *C1CCCN1*]

(e.g., )

or 6- to 12-membered bicycle

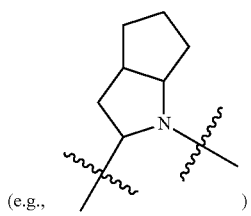 [SMILES: *C1CC2CCCC2N1*]

(e.g., )

which is optionally substituted with one or more $R_4$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

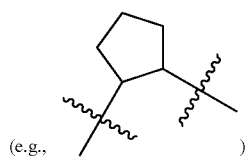 [SMILES: *C1CCCC1*]

(e.g., )

or 6- to 12-membered bicycle which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$", —C(O)-$L_Y$'-N($R_B$)-$L_S$"-, or —C(O)-$L_Y$'-N($R_B$)S(O)$_2$-$L_S$"-. In some cases, Y and Z are independently

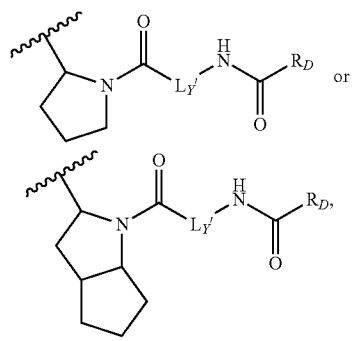

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another aspect, the present invention features compounds of Formula $I_A$ and pharmaceutically acceptable salts thereof.

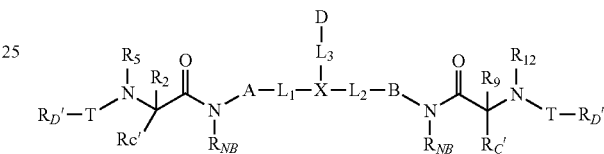

wherein:
$R_{NB}$ is each independently selected from $R_B$;
$R_C$' is each independently selected from $R_C$;
$R_D$' is each independently selected from $R_D$;
$R_2$ and $R_5$, taken together with the atoms to which they are attached, form a 3- to 12-membered heterocycle which is optionally substituted with one or more $R_4$;
$R_9$ and $R_{12}$, taken together with the atoms to which they are attached, form a 3- to 12-membered heterocycle which is optionally substituted with one or more $R_4$;
A, B, D, X, $L_1$, $L_2$, $L_3$, T, $R_4$, $R_B$, $R_C$, and $R_D$ are as described above in Formula I.

In this aspect, A and B preferably are independently selected from $C_5$-$C_6$carbocycle or 5- to 6-membered heterocycle, and are each independently optionally substituted with one or more $R_4$. More preferably, at least one of A and B is phenyl

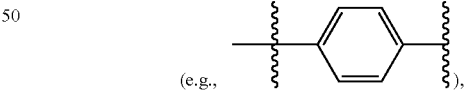

(e.g., ), and is optionally substituted with one or more $R_4$. Highly preferably, both A and B are each independently phenyl

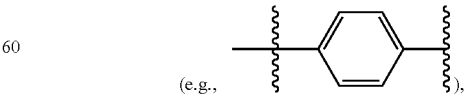

(e.g., ), and are each independently optionally substituted with one or more $R_4$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

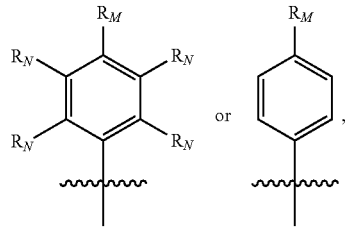

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

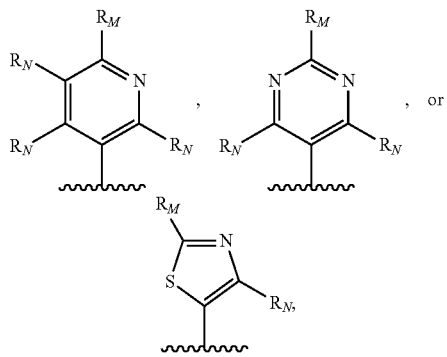

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

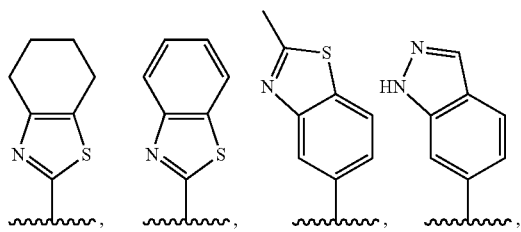

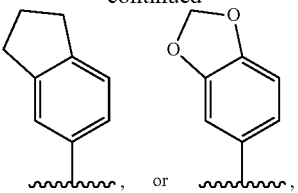

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is independently optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), N($R_S$)C(O)$R_S'$, N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$);

—N($C_1$-$C_6$alkyl)($C_1$-$C_6$alkylene-O—$C_1$-$C_6$alkyl) (e.g. —N($CH_3$)($CH_2CH_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —$OCF_3$, —$OCH_2CF_3$); —O—$C_1$-$C_6$alkylene-piperidine (e.g., —O—$CH_2CH_2$-1-piperidyl); —N($C_1$-$C_6$alkyl)C(O)O$C_1$-$C_6$alkyl (e.g., —N($CH_3$)C(O)O—$CH_2$CH($CH_3$)$_2$), —N($C_1$-$C_6$alkyl)$SO_2C_1$-$C_6$alkyl (e.g., —N($CH_3$)$SO_2CH_3$); —$SO_2C_1$-$CH_6$alkyl (e.g., —$SO_2$Me), —$SO_2C_1$-$C_6$haloalkyl (e.g., —$SO_2CF_3$); or —S—$C_1$-$C_6$haloalkyl (e.g., $SCF_3$). Also preferably $R_M$ is -$L_S$-$R_E$ where $L_S$ is $C_1$-$C_6$alkylene (e.g., —$CH_2$—, —C($CH_3$)$_2$—, —C($CH_3$)$_2$—$CH_2$—) and $R_E$ is —O—$R_S$, —C(O)O$R_S$, —N($R_S$)C(O)O$R_S$', or —P(O)(O$R_S$)$_2$. For example $R_M$ is —$C_1$-$C_6$alkylene-O—$R_S$ (e.g., —C($CH_3$)$_2$—$CH_2$—OMe); —$C_1$-$C_6$alkylene-C(O)O$R_S$ (e.g., —C($CH_3$)$_2$—C(O)OMe); —$C_1$-$C_6$alkylene-N($R_S$)C(O)O$R_S$' (e.g., —C($CH_3$)$_2$—$CH_2$—NHC(O)O$CH_3$); or —$C_1$-$C_6$alkylene-P(O)(O$R_S$)$_2$ (e.g., —$CH_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$ or —N($R_SR_S$'). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is independently optionally substituted with one or more substituents selected from halogen, hydroxy, mercapto, amino or carboxy (e.g., tert-butyl, $CF_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_SR_S$'), and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_SR_S$'). Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_SR_S$'). Highly preferably, D is

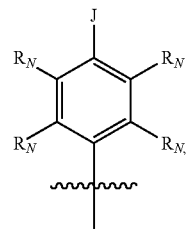

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_SR_S$'). Also preferably, D is

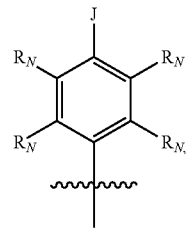

wherein each $R_N$ is independently selected from $R_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_SR_S$'), and J can also be optionally substituted with one or more $R_A$. Also preferably, D is

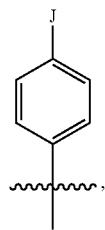

and J is $C_3$-$C_6$carbocycle or 3- to 6-membered heterocycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_S R_S')$.

X preferably is $C_5$-$C_6$carbocycle, 5- to 6-membered heterocycle, or 6- to 12-membered bicycles

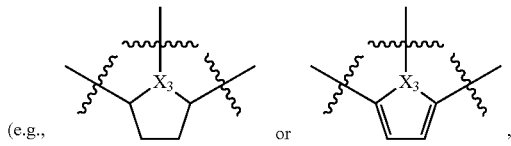

wherein $X_3$ is N and is directly linked to -$L_3$-D), and is optionally substituted with one or more $R_A$ or $R_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —$CH_2$— or —$CH_2CH_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

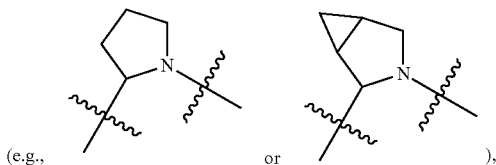 [SMILES: *C1CCCN1* ; *C1C2CC2CN1*]

which is optionally substituted with one or more $R_A$.

$R_9$ and $R_{12}$, taken together with the atoms to which they are attached, preferably form a 5- to 6-membered heterocycle or 6- to 12-membered bicycle

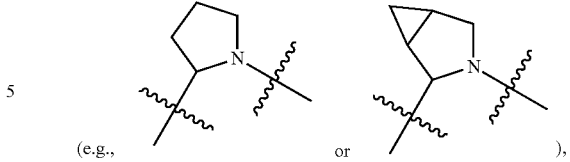

which is optionally substituted with one or more $R_A$.

-T-$R_D$' can be, without limitation, independently selected at each occurrence from —C(O)-$L_Y$'-, —C(O)O-$L_Y$'-$R_D$', —C(O)-$L_{Y'-N(RB)}$C(O)-$L_S$''-$R_D$', —C(O)-$L_Y$'-N($R_B$)C(O)O-$L_S$''-$R_D$'', —N($R_B$)C(O)-$L_Y$'-N($R_B$)C(O)-$L_S$''-$R_D$', —N($R_B$)C(O)-$L_Y$'-N($R_B$)C(O)O-$L_S$''-$R_D$', or —N($R_B$)C(O)-$L_Y$'-N($R_B$)-$L_S$''-$R_D$', wherein $L_Y$' is each independently $L_S$' and, preferably, is each independently $C_1$-$C_6$alkylene (e.g., —$CH_2$—) and optionally substituted with one or more substituents selected from $R_L$. Preferably, -T-$R_D$' is independently selected at each occurrence from —C(O)-$L_Y$'-M'-$L_S$''-$R_D$' or —N($R_B$)C(O)-$L_Y$'-M'-$L_S$''-$R_D$'. More preferably, -T-$R_D$' is independently selected at each occurrence from —C(O)-$L_Y$'-N($R_B$)C(O)-$L_S$''-$R_D$' or —C(O)-$L_Y$'-N($R_B$)C(O)O-$L_S$''-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —$CH_2$—) and optionally substituted with one or more substituents selected from $R_L$.

$R_{NB}$ and $R_C$' are preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S'$), -$L_A$-S(O)$R_S$, -$L_A$-SO$_2$$R_S$, -$L_A$-C(O)N($R_S R_S'$), -$L_A$-N($R_S$)C(O)$R_S'$, -$L_A$-N($R_S$)C(O)N($R_S'R_S''$), -$L_A$-N($R_S$)SO$_2$$R_S'$, -$L_A$-SO$_2$N($R_S R_S'$), -$L_A$-N($R_S$)SO$_2$N($R_S'R_S''$), -$L_A$-N($R_S$)S(O)N($R_S'R_S''$), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S'$, -$L_A$-OC(O)N($R_S R_S'$), -$L_A$-N($R_S$)S(O)—$R_S'$, -$L_A$-S(O)N($R_S R_S'$) or -$L_A$-C(O)N($R_S$)C(O)—$R_S'$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A and B are each independently phenyl, and are each independently optionally substituted with one or more $R_A$; D is phenyl, and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N($R_S R_S'$), and J can also be optionally substituted with one or more $R_A$.

Preferably, D is

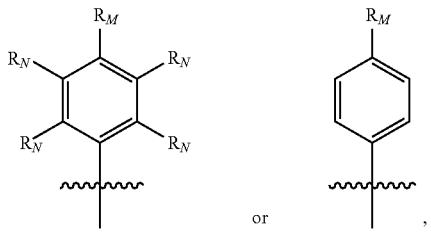

wherein $R_M$ and $R_N$ are as defined above. Also preferably, D is

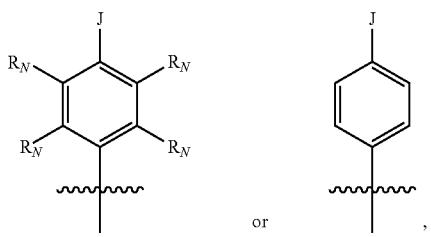

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D'$ is independently selected at each occurrence from —C(O)-$L_Y'$-N($R_B$)C(O)-$L_S''$-$R_D'$ or —C(O)-$L_Y'$-N($R_B$)C(O)O-$L_S''$-$R_D'$, wherein $L_Y'$ is $C_1$-$C_6$alkylene (e.g., —CH$_2$—) and optionally substituted with one or more substituents selected from $R_L$, and $L_S''$ preferably is bond. -T-$R_D'$ can also be, without limitation, selected from —C(O)-$L_Y'$-$L_S''$-$R_D'$, —C(O)-$L_Y'$-O-$L_S''$-$R_D'$, —C(O)-$L_Y'$-N($R_B$)-$L_S''$-$R_D'$, or —C(O)-$L_Y'$-N($R_B$)S(O)$_2$-$L_S''$-$R_D'$. Preferably, $R_2$ and $R_5$, taken together with the atoms to which they are attached, form

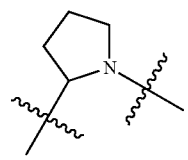 [SMILES: *C1CCCN1*]

which is optionally substituted with one or more $R_A$; $R_9$ and $R_{12}$, taken together with the atoms to which they are attached, form

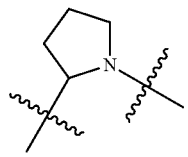 [SMILES: *C1CCCN1*]

which is optionally substituted with one or more $R_A$.

In another embodiment of this aspect, A and B are each independently phenyl

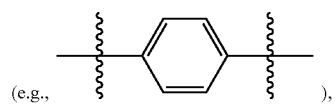 [SMILES: *c1ccc(*)cc1]

(e.g., ), and are each independently optionally substituted with one or more $R_A$ (preferably, A and B are each independently substituted with at least one halo such as F). X is

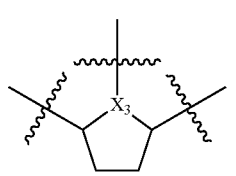

wherein $X_3$ is N and is directly linked to -$L_3$-D, and X is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$ or —C(O)R$_S$; and J can also be optionally substituted with one or more R$_4$. Preferably, D is

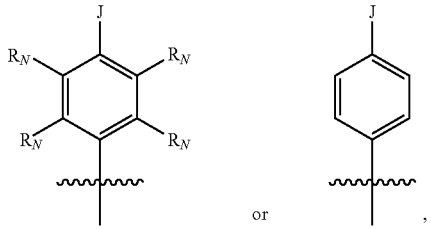

or wherein J is as defined above, and each R$_N$ is independently selected from R$_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more R$_L$. Preferably, $L_1$, $L_2$, and $L_3$ are bond. -T-R$_D$' is independently selected at each occurrence from —C(O)-L$_Y$'-N(R$_B$)C(O)-L$_S$''-R$_D$' or —C(O)-L$_Y$'-N(R$_D$)C(O)O-L$_S$''-R$_D$', wherein L$_Y$' is $C_1$-$C_6$alkylene (e.g., —CH$_2$—) and optionally substituted with one or more substituents selected from R$_L$, and L$_S$'' preferably is bond. -T-R$_D$' can also be, without limitation, selected from —C(O)-L$_Y$'-L$_S$''-R$_D$', —C(O)-L$_Y$'-O-L$_S$''-R$_D$', —C(O)-L$_Y$'-N(R$_B$)-L$_S$''-R$_D$', or —C(O)-L$_Y$'-N(R$_B$)S(O)$_2$-L$_S$''-R$_D$'. $R_2$ and $R_5$, taken together with the atoms to which they are attached, form a 5- to 6-membered heterocyclic ring

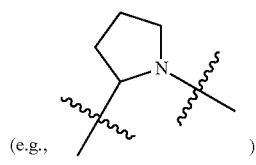 [SMILES: *C1CCCN1*]

or 6- to 12-membered bicycle which

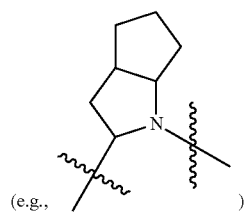 [SMILES: *C1CC2CCCC2N1*]

is optionally substituted with one or more R$_4$; and $R_9$ and $R_{12}$, taken together with the atoms to which they are attached, form a 5- to 6-membered heterocyclic ring

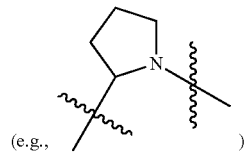 [SMILES: *C1CCCN1*]

or 6- to 12-membered bicycle

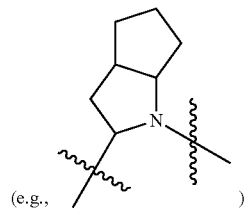

which is optionally substituted with one or more R$_4$.

In still another aspect, the present invention features compounds of Formula I$_B$ and pharmaceutically acceptable salts thereof:

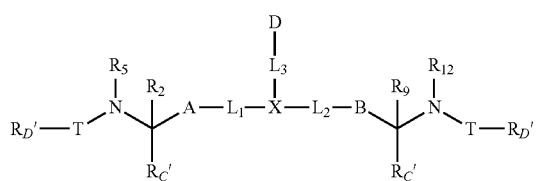

I$_B$ wherein:
R$_C$' is each independently selected from R$_C$;
R$_D$' is each independently selected from R$_D$;
$R_2$ and $R_5$, taken together with the atoms to which they are attached, form a 3- to 12-membered heterocycle which is optionally substituted with one or more R$_4$;
$R_9$ and $R_{12}$, taken together with the atoms to which they are attached, form a 3- to 12-membered heterocycle which is optionally substituted with one or more R$_4$;
A, B, D, X, $L_1$, $L_2$, $L_3$, T, R$_4$, R$_C$, and R$_D$ are as described above in Formula I.

In this aspect, A and B preferably are independently selected from 8- to 12-membered bicycles such as

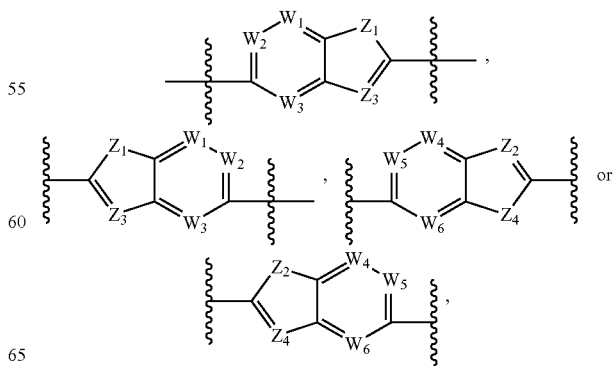

where $Z_1$ is independently selected at each occurrence from O, S, NH or $CH_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from

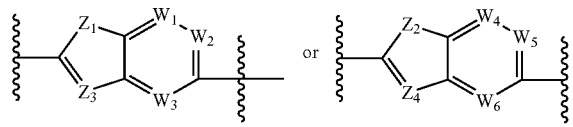

and is optionally substituted with one or more $R_A$; B is selected from

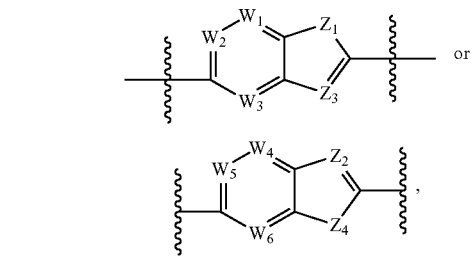

and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from

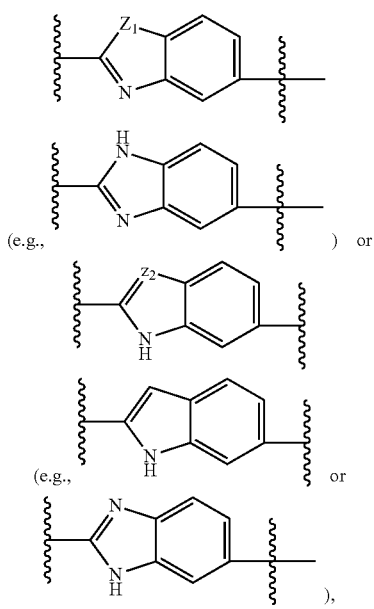

and is optionally substituted with one or more $R_A$; and B can be selected from

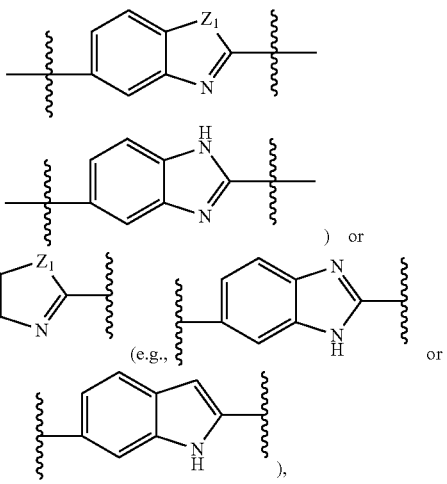

and is optionally substituted with one or more $R_A$.

Also preferably, A is

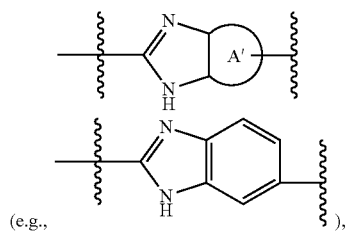

and B is

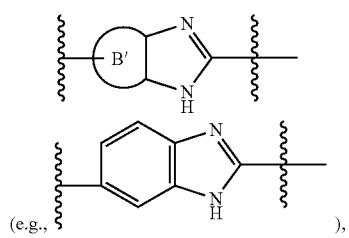

wherein A' and B' are independently selected from $C_5$-$C_6$carbocycle or 5- to 6-membered heterocycle, and A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

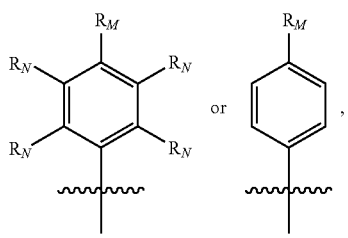

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

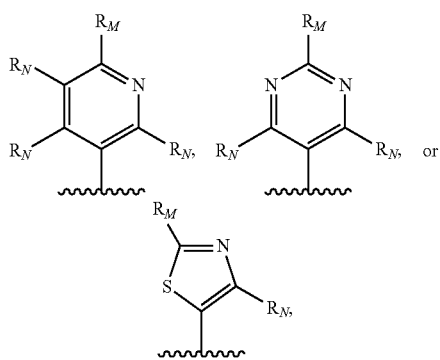

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

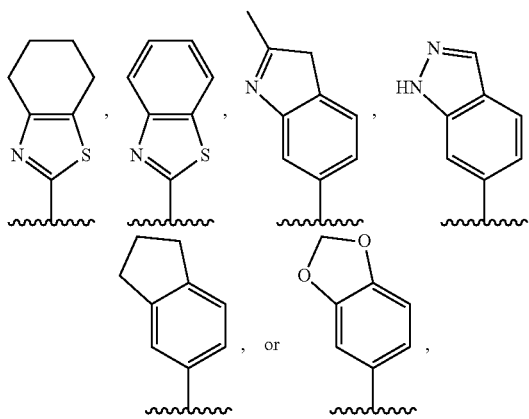

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)OC$_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—

CH$_2$—OMe); —C$_1$-C$_6$alkylene-C(O)OR$_S$ (e.g., —C(CH$_3$)$_2$—C(O)OMe); —C$_1$-C$_6$alkylene-N(R$_S$)C(O)OR$_S$' (e.g., —C(CH$_3$)$_2$—CH$_2$—NHC(O)OCH$_3$); or —C$_1$-C$_6$alkylene-P(O)(OR$_S$)$_2$ (e.g., —CH$_2$—P(O)(OEt)$_2$). Also more preferably R$_M$ is C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, —C(O)OR$_S$, or —N(R$_S$R$_S$'). For example R$_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, R$_M$ is C$_1$-C$_6$alkyl which is optionally substituted with one or more substituents selected from halogen, hydroxy, mercapto, amino or carboxy (e.g., tert-butyl, CF$_3$).

More preferably, D is C$_5$-C$_6$carbocycle, 5- to 6-membered heterocycle or 6- to 12-membered bicycle and is substituted with J and optionally substituted with one or more R$_4$, wherein J is C$_3$-C$_6$carbocycle, 3- to 6-membered heterocycle or 6- to 12-membered bicycle and is optionally substituted with one or more R$_4$. Preferably, J is substituted with a C$_3$-C$_6$carbocycle or 3- to 6-membered heterocycle, wherein said C$_3$-C$_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'), and J can also be optionally substituted with one or more R$_4$. Also preferably, D is C$_5$-C$_6$carbocycle or 5- to 6-membered heterocycle and is substituted with J and optionally substituted with one or more R$_4$, and J is C$_3$-C$_6$carbocycle or 3- to 6-membered heterocycle and is optionally substituted with one or more R$_4$, and preferably, J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Also preferably, D is C$_5$-C$_6$carbocycle or 5- to 6-membered heterocycle and is substituted with J and optionally substituted with one or more R$_4$, and J is 6- to 12-membered bicycle (e.g., a 7- to 12-membered fused, bridged or spiro bicycle comprising a nitrogen ring atom through which J is covalently attached to D) and is optionally substituted with one or more R$_4$. More preferably, D is phenyl and is substituted with J and optionally substituted with one or more R$_4$, and J is C$_3$-C$_6$carbocycle, 3- to 6-membered heterocycle or 6- to 12-membered bicycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Highly preferably, D is

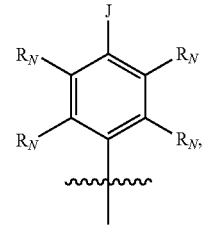

wherein each R$_N$ is independently selected from R$_D$ and preferably is hydrogen or halogen, and J is C$_3$-C$_6$carbocycle, 3- to 6-membered heterocycle or 6- to 12-membered bicycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Also preferably, D is

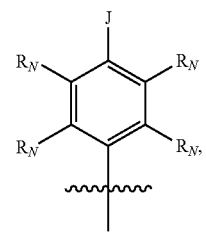

wherein each R$_N$ is independently selected from R$_D$ and preferably is hydrogen or halogen, and J is C$_3$-C$_6$carbocycle or 3- to 6-membered heterocycle and is substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'), and J can also be optionally substituted with one or more R$_4$. Also preferably, D is

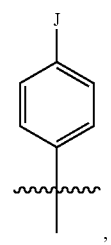

and J is C$_3$-C$_6$carbocycle or 3- to 6-membered heterocycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$').

X preferably is $C_5$-$C_6$carbocycle, 5- to 6-membered heterocycle, or 6- to 12-membered bicycles

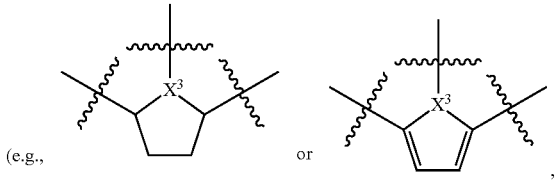

(e.g., or , wherein $X_3$ is N and is directly linked to -$L_3$-D), and is optionally substituted with one or more $R_A$ or $R_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

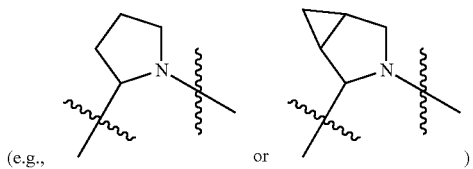

(e.g., or )

which is optionally substituted with one or more $R_A$. $R_9$ and $R_{12}$, taken together with the atoms to which they are attached, preferably form a 5- to 6-membered heterocycle or 6- to 12-membered bicycle

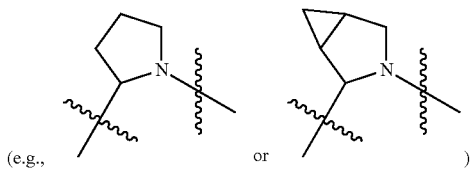

(e.g., or )

which is optionally substituted with one or more $R_A$.

-T-$R_D$' can be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$''-$R_D$', —C(O)-$L_Y$'-N($R_B$)C(O)O-$L_S$''-$R_D$', —N($R_B$)C(O)-$L_Y$'-N($R_B$)C(O)-$L_S$''-$R_D$', —N($R_B$)C(O)-$L_Y$'-N($R_B$)C(O)O-$L_S$''-$R_D$', or —N($R_B$)C(O)-$L_Y$'-N($R_B$)-$L_S$''-$R_D$', wherein $L_Y$' is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$''-$R_D$' or —N($R_B$)C(O)-$L_Y$'-M'-$L_S$''-$R_D$'. More preferably, -T-$R_D$' is independently selected at each occurrence from —C(O)-$L_Y$'-N($R_B$)C(O)-$L_S$''-$R_D$' or —C(O)-$L_Y$'-N($R_B$)C(O)O-$L_S$''-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_C$' is preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S$$R_S$'), -$L_A$-S(O)$R_S$, -$L_A$-SO$_2$$R_S$, -$L_A$-C(O)N($R_S$$R_S$'), -$L_A$-N($R_S$)C(O)$R_S$', -$L_A$-N($R_S$)C(O)N($R_S$'$R_S$''), -$L_A$-N($R_S$)SO$_2$$R_S$', -$L_A$-SO$_2$N($R_S$$R_S$'), -$L_A$-N($R_S$)SO$_2$N($R_S$'$R_S$''), -$L_A$-N($R_S$)S(O)N($R_S$'$R_S$''), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S$$R_S$'), -$L_A$-N($R_S$)S(O)—$R_S$', -$L_A$-S(O)N($R_S$$R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$'' preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A is

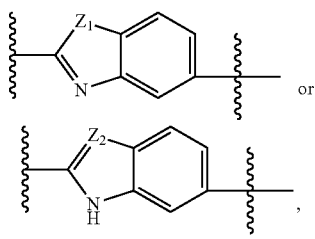

or

, and is optionally substituted with one or more $R_A$; B is

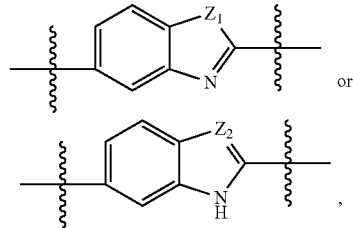

or

, and is optionally substituted with one or more $R_A$; and D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_S R_S')$, and J can also be optionally substituted with one or more $R_A$. Preferably, D is

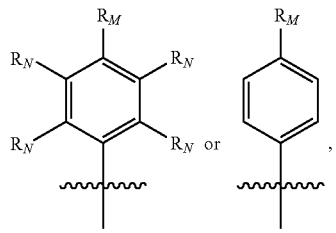

wherein $R_M$ and $R_N$ are as defined above. Also preferably, D is

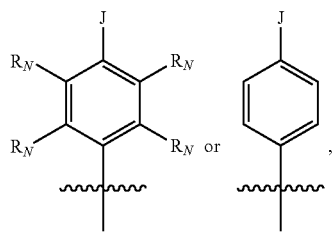

wherein J and $R_N$ are as defined above. $Z_1$ is independently selected at each occurrence from O, S, NH or $CH_2$; and $Z_2$ is independently selected at each occurrence from N or CH. $L_1$ and $L_2$ are each independently bond or $C_1$-$C_6$alkylene, and $L_3$ is bond, $C_1$-$C_6$alkylene or —C(O)—, and $L_1$, $L_2$, $L_3$ are each independently optionally substituted with one or more $R_L$. Preferably, $L_1$, $L_2$, and $L_3$ are bond. -T-$R_D'$ is independently selected at each occurrence from —C(O)-$L_Y'$-N($R_B$)C(O)-$L_S''$-$R_D'$ or —C(O)-$L_Y'$-N($R_B$)C(O)O-$L_S''$-$R_D'$, wherein $L_Y'$ is $C_1$-$C_6$alkylene (e.g., —$CH_2$—) and optionally substituted with one or more substituents selected from $R_L$, and $L_S''$ preferably is bond. -T-$R_D'$ can also be, without limitation, selected from —C(O)-$L_Y'$-$L_S''$-$R_D'$, —C(O)-$L_Y'$-O-$L_S''$-$R_D'$, —C(O)-$L_Y'$-N($R_B$)-$L_S''$-$R_D'$, or —C(O)-$L_Y'$-N($R_B$)S(O)$_2$-$L_S''$-$R_D'$.

In another embodiment of this aspect, A is

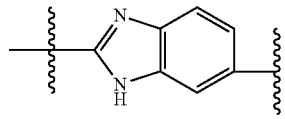

and optionally substituted with one or more $R_A$ (e.g., halogen); B is

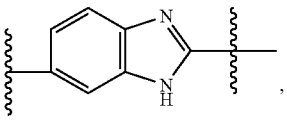

, and is optionally substituted with one or more $R_A$ (e.g., halogen); and D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_S R_S')$, and J can also be optionally substituted with one or more $R_A$. Preferably, D is

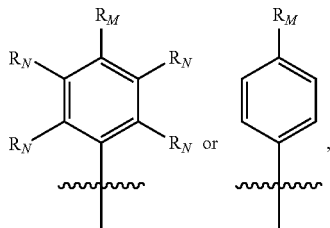

wherein $R_M$ and $R_N$ are as defined above. Also preferably, D is

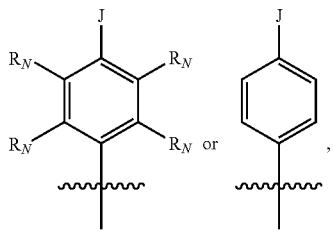

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —$CH_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'. $R_2$ and $R_5$, taken together with the atoms to which they are attached, preferably form a 5- to 6-membered heterocycle or 6- to 12-membered bicycle

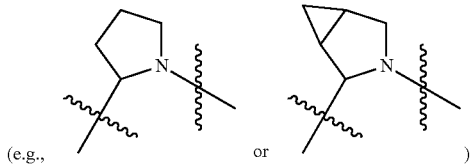

(e.g., or )

which is optionally substituted with one or more $R_A$. $R_9$ and $R_{12}$, taken together with the atoms to which they are attached, preferably form a 5- to 6-membered heterocycle or 6- to 12-membered bicycle

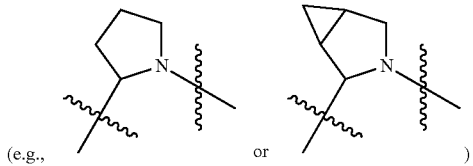

(e.g., or )

which is optionally substituted with one or more $R_A$. More preferably, $R_2$ and $R_5$, taken together with the atoms to which they are attached, form

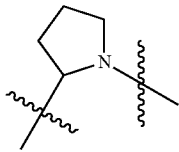 [SMILES: *C1CCCN1*]

which is optionally substituted with one or more $R_A$; $R_9$ and $R_{12}$, taken together with the atoms to which they are attached, form

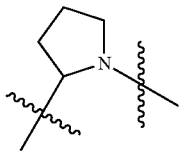 [SMILES: *C1CCCN1*]

which is optionally substituted with one or more $R_A$.

In still another embodiment of this aspect, A is

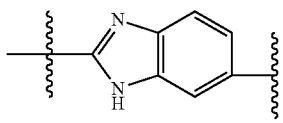

and optionally substituted with one or more $R_A$ (preferably, A is substituted with at least one halogen such as F); B is

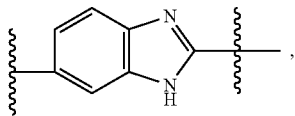

and is optionally substituted with one or more $R_A$ (preferably, B is substituted with at least one halogen such as F). X is

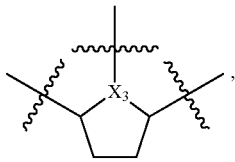

wherein $X_3$ is N and is directly linked to -$L_3$-D, and X is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$ or —N($R_S R_S$'), or (2) trimethylsilyl, —O—$R_S$, —S—$R_S$ or —C(O)$R_S$; and J can also be optionally substituted with one or more $R_A$. Preferably, D is

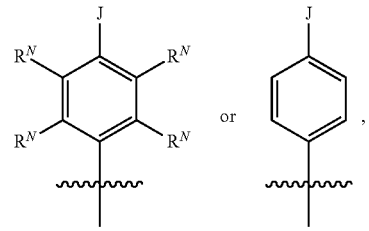

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —$CH_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'. $R_2$ and $R_5$, taken together with the atoms to which they are attached, preferably form a 5- to 6-membered heterocycle or 6- to 12-membered bicycle

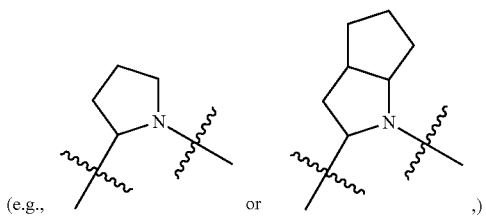 [SMILES: *C1CCCN1* ; *C1CC2CCCC2N1*]

(e.g., ... or ... ,)

which is optionally substituted with one or more $R_4$. $R_9$ and $R_{12}$, taken together with the atoms to which they are attached, preferably form a 5- to 6-membered heterocycle or 6- to 12-membered bicycle

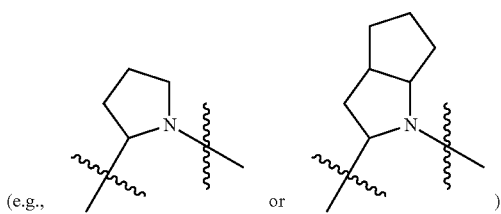 [SMILES: *C1CCCN1* ; *C1CC2CCCC2N1*]

(e.g., ... or ... )

which is optionally substituted with one or more $R_4$. More preferably, $R_2$ and $R_5$, taken together with the atoms to which they are attached, form

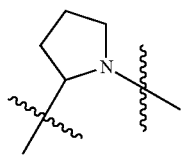 [SMILES: *C1CCCN1*]

which is optionally substituted with one or more $R_4$; $R_9$ and $R_{12}$, taken together with the atoms to which they are attached, form

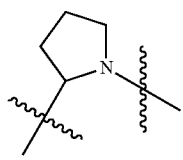 [SMILES: *C1CCCN1*]

which is optionally substituted with one or more $R_4$.

In yet another aspect, the present invention further features compounds of Formula $I_C$ and pharmaceutically acceptable salts thereof.

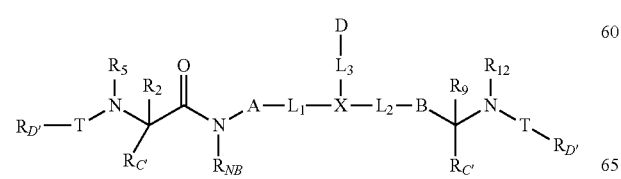

$I_C$ wherein:

$R_{NB}$ is $R_B$;

$R_C{}'$ is each independently selected from $R_C$;

$R_D{}'$ is each independently selected from $R_D$;

$R_2$ and $R_5$, taken together with the atoms to which they are attached, form a 3- to 12-membered heterocycle which is optionally substituted with one or more $R_4$;

$R_9$ and $R_{12}$, taken together with the atoms to which they are attached, form a 3- to 12-membered heterocycle which is optionally substituted with one or more $R_4$;

A, B, D, X, $L_1$, $L_2$, $L_3$, T, $R_4$, $R_B$, $R_C$, and $R_D$ are as described above in Formula I.

In this aspect, A preferably is $C_5$-$C_6$carbocycle or 5- to 6-membered heterocycle, and is optionally substituted with one or more $R_4$; and B preferably is 8- to 12-membered bicycle (such as

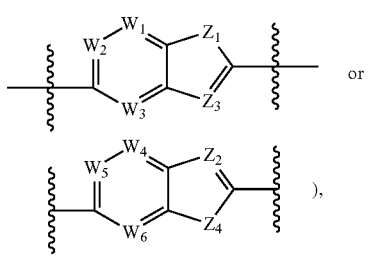

or

), and is optionally substituted with one or more $R_4$. $Z_1$ is O, S, NH or $CH_2$; $Z_2$ is N or CH; $Z_3$ is N or CH; $Z_4$ is O, S, NH or $CH_2$; and $W_1$, $W_2$, $W_3$, $W_4$, $W_5$ and $W_6$ are each independently selected from CH or N.

More preferably, A is phenyl

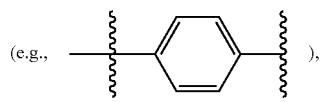

(e.g., ), and is optionally substituted with one or more $R_4$; and B is

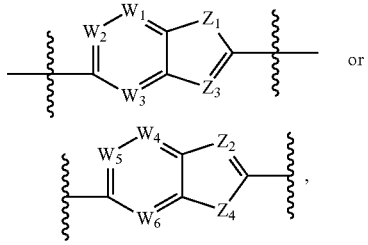

or

, and is optionally substituted with one or more $R_4$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, B can be

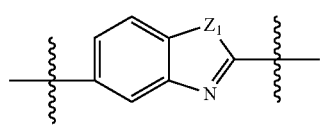

-continued

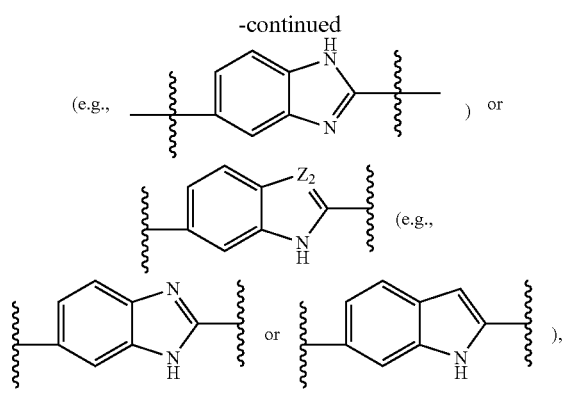

and is optionally substituted with one or more $R_A$.

Also preferably, A is $C_5$-$C_6$carbocycle (e.g., phenyl such as

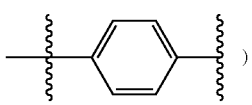)

or 5- to 6-membered heterocycle; and B is

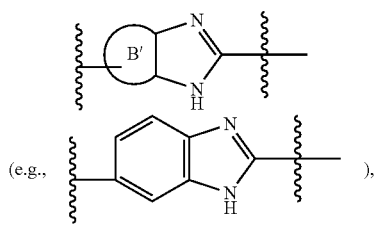

wherein B' is selected from $C_5$-$C_6$carbocycle or 5- to 6-membered heterocycle. A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

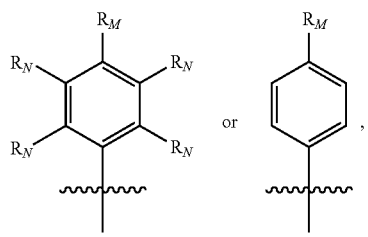

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

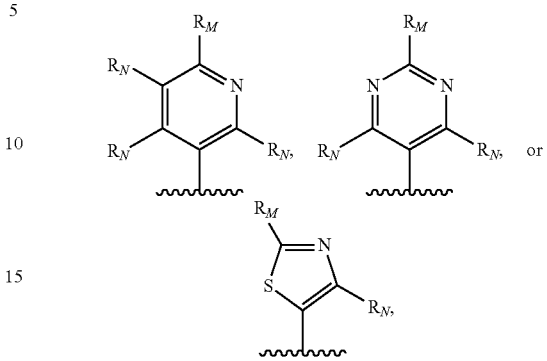

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

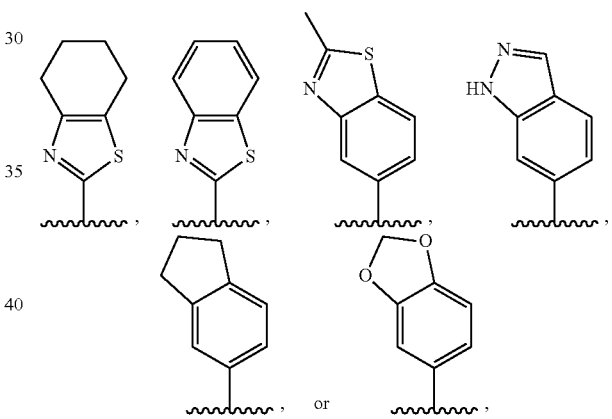

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is $-L_S-R_E$, wherein $L_S$ is a bond or $C_1$-$C_6$alkylene, and $R_E$ is $-N(R_SR_S')$, $-O-R_S$, $-C(O)R_S$, $-C(O)OR_S$, $-C(O)N(R_SR_S')$, $-N(R_S)C(O)R_S'$, $-N(R_S)C(O)OR_S'$, $-N(R_S)SO_2R_S'$, $-SO_2R_S$, $-SR_S$, or $-P(O)(OR_S)_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, $-O-C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $-C(O)OR_S$, or $-N(R_SR_S')$. More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, $-C(CF_3)_2-OH$, $-C(CH_3)_2-CN$, $-C(CH_3)_2-CH_2OH$, or $-C(CH_3)_2-CH_2NH_2$. Also preferably $R_M$ is $-L_S-R_E$ where $L_S$ is a bond and $R_E$ is $-N(R_SR_S')$, $-O-R_S$, $-N(R_S)C(O)OR_S'$, $-N(R_S)SO_2R_S'$, $-SO_2R_S$, or $-SR_S$. For example where $L_S$ is a bond, $R_E$ is $-N(C_1$-$C_6$alkyl$)_2$ (e.g., $-NMe_2$); $-N(C_1$-$C_6$alkylene-$O-C_1$-$C_6$alkyl$)_2$ (e.g. $-N(CH_2CH_2OMe)_2$); $-N(C_1$-$C_6$alkyl)($C_1$-$C_6$alkylene-$O-C_1$-$C_6$alkyl) (e.g. $-N(CH_3)(CH_2CH_2OMe)$); $-O-C_1$-$C_6$alkyl (e.g., $-O$-Me, $-O$-Et, $-O$-isopropyl, $-O$-tert-butyl, $-O$-n-hexyl); $-O-C_1$-$C_6$haloalkyl (e.g., $-OCF_3$, $-OCH_2CF_3$); $-O-C_1$-$C_6$alkylene-piperidine (e.g., $-O-CH_2CH_2$-1-piperidyl); $-N(C_1$-$C_6$alkyl)$C(O)OC_1$-$C_6$alkyl (e.g., $-N(CH_3)C(O)O-CH_2CH(CH_3)_2$), $-N(C_1$-$C_6$alkyl)$SO_2C_1$-$C_6$alkyl (e.g., $-N(CH_3)SO_2CH_3$); $-SO_2C_1$-$C_6$alkyl (e.g., $-SO_2Me$); $-SO_2C_1$-$C_6$haloalkyl (e.g., $-SO_2CF_3$); or $-S-C_1$-$C_6$haloalkyl (e.g., $SCF_3$). Also preferably $R_M$ is $-L_S-R_E$ where $L_S$ is $C_1$-$C_6$alkylene (e.g., $-CH_2-$, $-C(CH_3)_2-$, $-C(CH_3)_2-CH_2-$) and $R_E$ is $-O-R_S$, $-C(O)OR_S$, $-N(R_S)C(O)OR_S'$, or $-P(O)(OR_S)_2$. For example $R_M$ is $-C_1$-$C_6$alkylene-$O-R_S$ (e.g., $-C(CH_3)_2-CH_2-OMe$); $-C_1$-$C_6$alkylene-$C(O)OR_S$ (e.g., $-C(CH_3)_2-C(O)OMe$); $-C_1$-$C_6$alkylene-$N(R_S)C(O)OR_S'$ (e.g., $-C(CH_3)_2-CH_2-NHC(O)OCH_3$); or $-C_1$-$C_6$alkylene-$P(O)(OR_S)_2$ (e.g., $-CH_2-P(O)(OEt)_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $-C(O)OR_S$, or $-N(R_SR_S')$. For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or $-N(R_SR_S')$, and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or $-N(R_SR_S')$. Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or $-N(R_SR_S')$. Highly preferably, D is

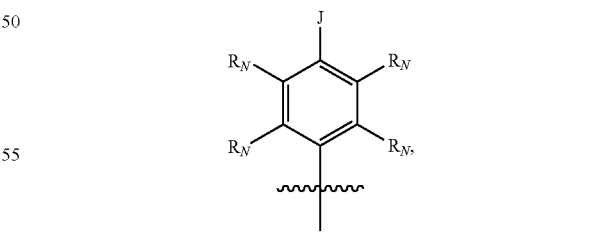

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Also preferably, D is

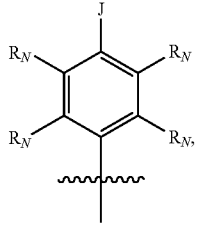

wherein each R$_N$ is independently selected from R$_D$ and preferably is hydrogen or halogen, and J is C$_3$-C$_6$carbocycle or 3- to 6-membered heterocycle and is substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'), and J can also be optionally substituted with one or more R$_A$. Also preferably, D is

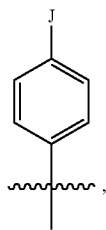

and J is C$_3$-C$_6$carbocycle or 3- to 6-membered heterocycle and is optionally substituted with one or more R$_A$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$').

X preferably is C$_5$-C$_6$carbocycle, 5- to 6-membered heterocycle, or 6- to 12-membered bicycles (e.g., 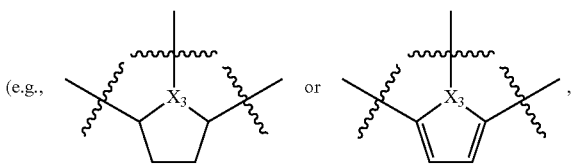

wherein X$_3$ is N and is directly linked to -L$_3$-D), and is optionally substituted with one or more R$_A$ or R$_F$. Non-limiting examples of X are described hereinabove.

L$_1$ and L$_2$ are preferably independently bond or C$_1$-C$_6$alkylene, L$_3$ is preferably selected from bond, C$_1$-C$_6$alkylene or —C(O)—, and L$_1$, L$_2$, and L$_3$ are each independently optionally substituted with one or more R$_L$. More preferably, L$_1$, L$_2$ and L$_3$ are each independently bond or C$_1$-C$_6$alkylene (e.g., —CH$_2$— or —CH$_2$CH$_2$—), and are each independently optionally substituted with one or more R$_L$. Highly preferably, L$_1$, L$_2$ and L$_3$ are bond. L$_1$ and L$_2$ can be the same or different.

R$_2$ and R$_5$, taken together with the atoms to which they are attached, preferably form a 5- to 6-membered heterocycle or 6- to 12-membered bicycle (e.g., 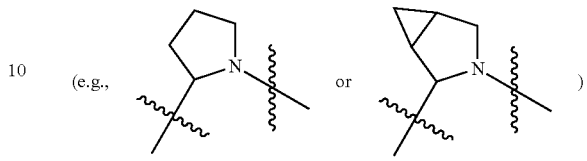 )

which is optionally substituted with one or more R$_A$. R$_9$ and R$_{12}$, taken together with the atoms to which they are attached, preferably form a 5- to 6-membered heterocycle or 6- to 12-membered bicycle (e.g., 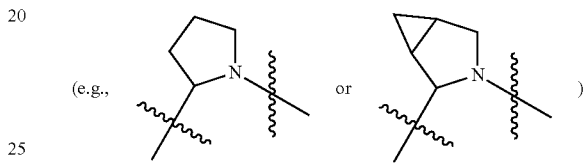 )

which is optionally substituted with one or more R$_A$.

-T-R$_D$' can be, without limitation, independently selected at each occurrence from —C(O)-L$_Y$'-R$_D$', —C(O)O-L$_Y$'-R$_D$', —C(O)-L$_Y$'-N(R$_B$)C(O)-L$_S$''-R$_D$', —C(O)-L$_Y$'-N(R$_B$)C(O)O-L$_S$''-R$_D$', —N(R$_B$)C(O)-L$_Y$'-N(R$_B$)C(O)-L$_S$''-R$_D$', —N(R$_B$)C(O)-L$_Y$'-N(R$_B$)C(O)O-L$_S$''-R$_D$', or —N(R$_B$)C(O)-L$_Y$'-N(R$_B$)-L$_S$''-R$_D$', wherein L$_Y$' is each independently L$_S$' and, preferably, is each independently C$_1$-C$_6$alkylene (e.g., —CH$_2$—) and optionally substituted with one or more substituents selected from R$_L$. Preferably, -T-R$_D$' is independently selected at each occurrence from —C(O)-L$_Y$'-M'-L$_S$''-R$_D$' or —N(R$_B$)C(O)-L$_Y$'-M'-L$_S$''-R$_D$'. More preferably, -T-R$_D$' is independently selected at each occurrence from —C(O)-L$_Y$'-N(R$_B$)C(O)-L$_S$''-R$_D$' or —C(O)-L$_Y$'-N(R$_B$)C(O)O-L$_S$''-R$_D$'. Highly preferably, -T-R$_D$' is independently selected at each occurrence from —C(O)-L$_Y$'-N(R$_B$)C(O)—R$_D$' or —C(O)-L$_Y$'-N(R$_B$)C(O)O—R$_D$', wherein L$_Y$' preferably is each independently C$_1$-C$_6$alkylene (e.g., —CH$_2$—) and optionally substituted with one or more substituents selected from R$_L$.

R$_{NB}$ and R$_C$' are preferably hydrogen, and R$_D$' preferably is independently selected at each occurrence from R$_E$. More preferably, R$_D$' is independently selected at each occurrence from C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, C$_3$-C$_6$carbocycle or 3- to 6-membered heterocycle; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

R$_A$ preferably is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S'$), -$L_A$-S(O)$R_S$, -$L_A$-SO$_2 R_S$, -$L_A$-C(O)N($R_S R_S'$), -$L_A$-N($R_S$)C(O)$R_S'$, -$L_A$-N($R_S$)C(O)N($R_S' R_S''$), -$L_A$-N($R_S$)SO$_2 R_S'$, -$L_A$-SO$_2$N($R_S R_S'$), -$L_A$-N($R_S$)SO$_2$N($R_S' R_S''$), -$L_A$-N($R_S$)S(O)N($R_S' R_S''$), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S'$, -$L_A$-OC(O)N($R_S R_S'$), -$L_A$-N($R_S$)S(O)—$R_S'$, -$L_A$-S(O)N($R_S R_S'$) or -$L_A$-C(O)N($R_S$)C(O)—$R_S'$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

In one embodiment of this aspect, A is phenyl, and is optionally substituted with one or more $R_A$; and B is

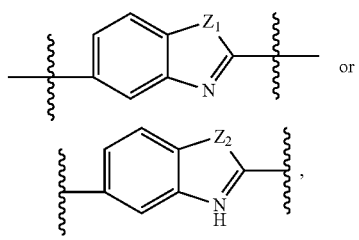

and is optionally substituted with one or more $R_A$, wherein $Z_1$ is O, S, NH or CH$_2$; and $Z_2$ is N or CH. D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$), and J can also be optionally substituted with one or more $R_A$. Preferably, D is

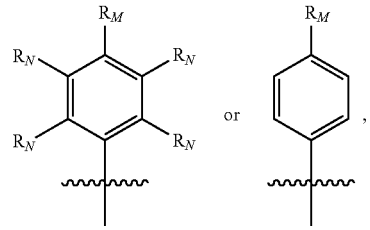

wherein $R_M$ and $R_N$ are as defined above. Also preferably, D is

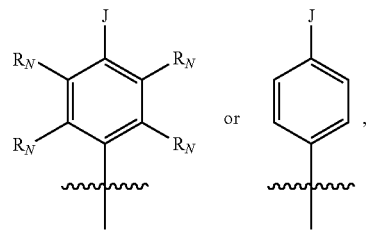

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D'$ is independently selected at each occurrence from —C(O)-$L_Y'$-N($R_B$)C(O)-$L_S''$-$R_D'$ or —C(O)-$L_Y'$-N($R_B$)C(O)O-$L_S''$-$R_D'$, wherein $L_Y'$ is $C_1$-$C_6$alkylene (e.g., —CH$_2$—) and optionally substituted with one or more substituents selected from $R_L$, and $L_S''$ preferably is bond. -T-$R_D'$ can also be, without limitation, selected from —C(O)-$L_Y'$-$L_S''$-$R_D'$, —C(O)-$L_Y'$-O-$L_S''$-$R_D'$, —C(O)-$L_Y'$-N($R_B$)-$L_S''$-$R_D'$, or —C(O)-$L_Y'$-N($R_B$)S(O)$_2$-$L_S''$-$R_D'$. Preferably, $R_2$ and $R_5$, taken together with the atoms to which they are attached, form

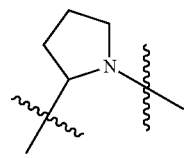 [SMILES: *C1CCCN1*]

which is optionally substituted with one or more $R_A$; $R_9$ and $R_{12}$, taken together with the atoms to which they are attached, form

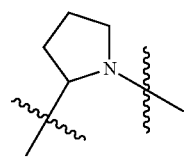 [SMILES: *C1CCCN1*]

which is optionally substituted with one or more $R_A$.

In another embodiment of this aspect, A is phenyl

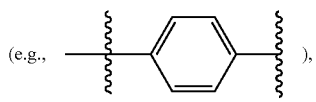

(e.g.,             ), and is optionally substituted with one or more $R_A$ (preferably, A is substituted with at least one halogen such as F); and B is

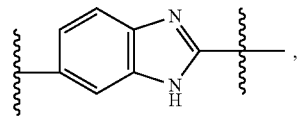

and is optionally substituted with one or more $R_A$ (preferably, B is substituted with at least one halogen such as F). X is

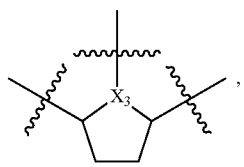

wherein $X_3$ is N and is directly linked to $-L_3-D$, and X is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR_S or —N(R_SR_S'), or (2) trimethylsilyl, —O—R_S, —S—R_S or —C(O)R_S; and J can also be optionally substituted with one or more $R_A$. Preferably, D is

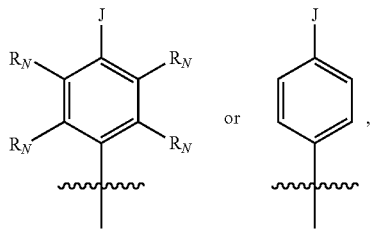

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-L_Y'-N(R_B)C(O)-L_S''-R_D' or —C(O)-L_Y'-N(R_B)C(O)O-L_S''-R_D', wherein $L_Y'$ is $C_1$-$C_6$alkylene (e.g., —CH$_2$—) and optionally substituted with one or more substituents selected from $R_L$, and $L_S''$ preferably is bond. -T-$R_D$' can also be, without limitation, selected from —C(O)-L_Y'-L_S''-R_D', —C(O)-L_Y'-O-L_S''-R_D', —C(O)-L_Y'-N(R_B)-L_S''-R_D', or —C(O)-L_Y'-N(R_B)S(O)$_2$-L_S''-R_D'. Preferably, $R_2$ and $R_5$, taken together with the atoms to which they are attached, form a 5- to 6-membered heterocyclic ring

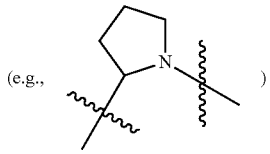 [SMILES: *C1CCCN1*]

(e.g.,             )

or 6- to 12-membered bicycle

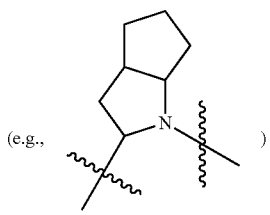 [SMILES: *C1CC2CCCC2N1*]

(e.g.,             )

which is optionally substituted with one or more $R_A$; $R_9$ and $R_{12}$, taken together with the atoms to which they are attached, form a 5- to 6-membered heterocyclic ring

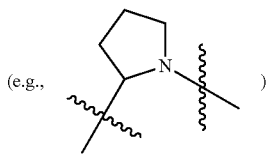 [SMILES: *C1CCCN1*]

(e.g.,             )

or 6- to 12-membered bicycle

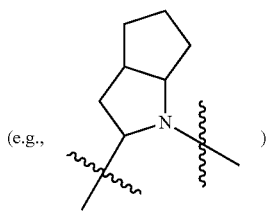 [SMILES: *C1CC2CCCC2N1*]

(e.g.,             )

which is optionally substituted with one or more $R_A$.

In yet another aspect, the present invention features compounds of Formula $I_D$ and pharmaceutically acceptable salts thereof.

$I_D$

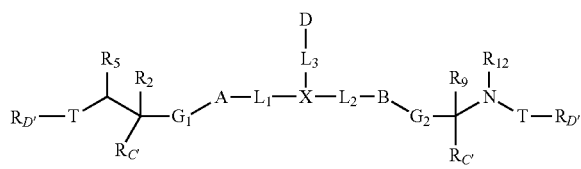

wherein:
$G_1$ and $G_2$ are each independently selected from $C_5$-$C_6$carbocycle or 5- to 6-membered heterocycle, and are each independently optionally substituted with one or more $R_A$;
$R_C$' is each independently selected from $R_C$;
$R_D$' is each independently selected from $R_D$;

$R_2$ and $R_5$, taken together with the atoms to which they are attached, form a 3- to 12-membered heterocycle which is optionally substituted with one or more $R_A$;

$R_9$ and $R_{12}$, taken together with the atoms to which they are attached, form a 3- to 12-membered heterocycle which is optionally substituted with one or more $R_A$;

A, B, D, X, $L_1$, $L_2$, $L_3$, T, $R_A$, $R_C$, and $R_D$ are as described above in Formula I.

In this aspect, A and B preferably are independently selected from $C_5$-$C_6$carbocycle or 5- to 6-membered heterocycle, and are each independently optionally substituted with one or more $R_A$. More preferably, at least one of A and B is phenyl

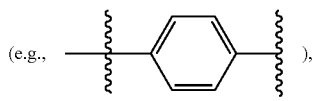
(e.g., ), and is optionally substituted with one or more $R_A$. Highly preferably, both A and B are each independently phenyl

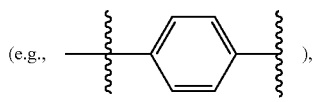
(e.g., ), and are each independently optionally substituted with one or more $R_A$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or $-L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

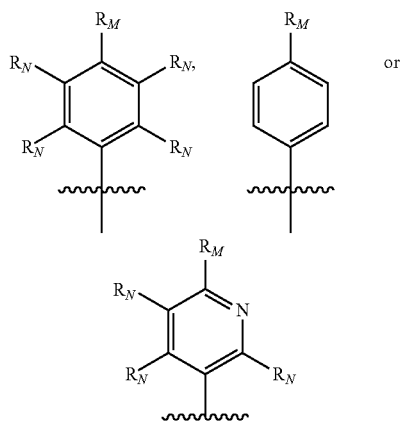

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

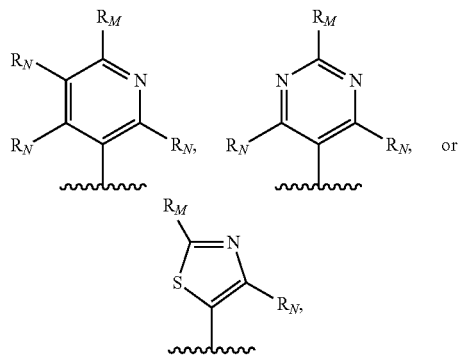

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

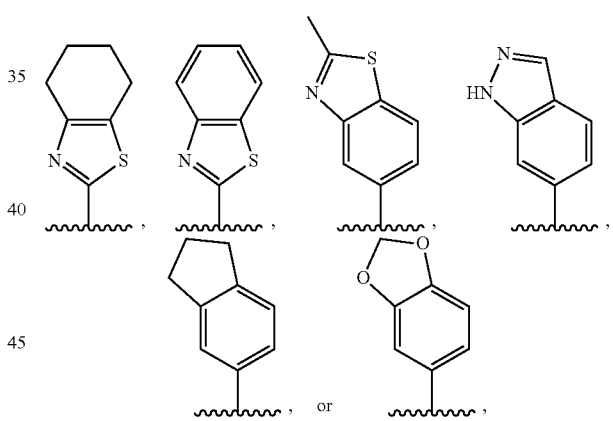

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)OC$_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$ (e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, CF$_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$), and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$). Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$). Highly preferably, D is

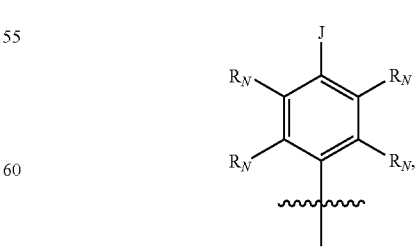

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$. Also preferably, D is

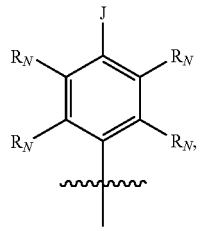

wherein each $R_N$ is independently selected from $R_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$, and J can also be optionally substituted with one or more $R_A$. Also preferably, D is

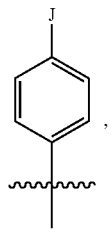

and J is $C_3$-$C_6$carbocycle or 3- to 6-membered heterocycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$.

X preferably is $C_5$-$C_6$carbocycle, 5- to 6-membered heterocycle, or 6- to 12-membered bicycles

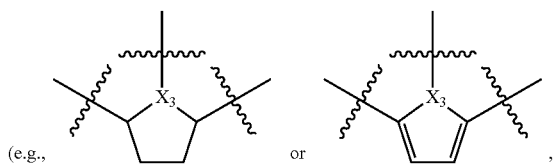

wherein $X_3$ is N and is directly linked to -$L_3$-D), and is optionally substituted with one or more $R_A$ or $R_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —$CH_2$— or —$CH_2CH_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

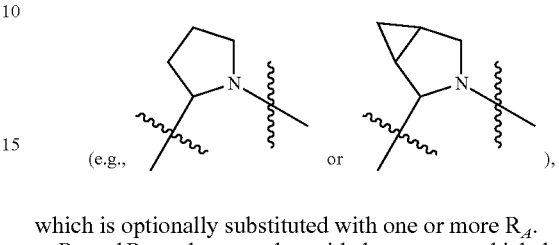

which is optionally substituted with one or more $R_A$.

$R_9$ and $R_{12}$, taken together with the atoms to which they are attached, preferably form a 5- to 6-membered heterocycle or 6- to 12-membered bicycle

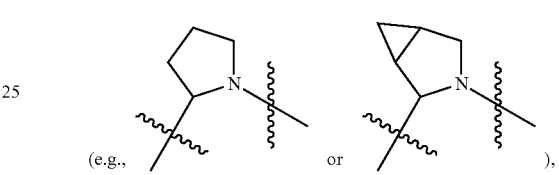

which is optionally substituted with one or more $R_A$.

$G_1$ and $G_2$ preferably are each independently selected from

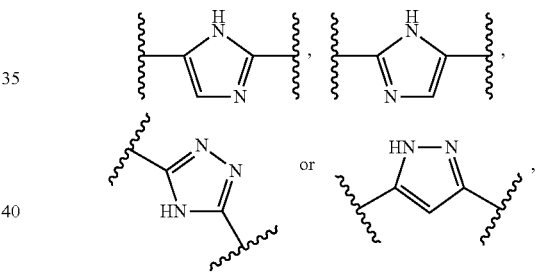

and are each independently optionally substituted with one or more $R_A$ (e.g., one or more chloro or bromo). More preferably, $G_1$ is

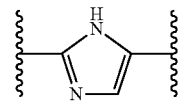

(including any tautomer thereof), and $G_2$ is

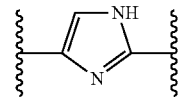

(including any tautomer thereof), and each $G_1$ and $G_2$ is independently optionally substituted with one or more $R_A$ (e.g., one or more chloro or bromo).

-T-$R_D$' can be, without limitation, independently selected at each occurrence from —C(O)-$L_Y$'-, —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or N($R_B$)C(O)-$L_Y$'—N($R_B$)-$L_S$"-$R_D$', wherein $L_Y$' is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_C$' is preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_4$-O—$R_S$, -$L_4$-S—$R_S$, -$L_4$-C(O)$R_S$, -$L_4$-OC(O)$R_S$, -$L_4$-C(O)O$R_S$, -$L_4$-N($R_S$$R_S$'), -$L_4$-S(O)$R_S$, -$L_4$-SO$_2$$R_S$, -$L_4$-C(O)N($R_S$$R_S$'), -$L_4$-N($R_S$)C(O)$R_S$', -$L_4$-N($R_S$)C(O)N($R_S$'$R_S$"), -$L_4$-N($R_S$)SO$_2$$R_S$', -$L_4$-SO$_2$N($R_S$$R_S$'), -$L_4$-N($R_S$)SO$_2$N($R_S$'$R_S$"), -$L_4$-N($R_S$)S(O)N($R_S$'$R_S$"), -$L_4$-OS(O)—$R_S$, -$L_4$-OS(O)$_2$—$R_S$, -$L_4$-S(O)$_2$O$R_S$, -$L_4$-S(O)O$R_S$, -$L_4$-OC(O)O$R_S$, -$L_4$-N($R_S$)C(O)O$R_S$', -$L_4$-OC(O)N($R_S$$R_S$'), -$L_4$-N($R_S$)S(O)—$R_S$', -$L_4$-S(O)N($R_S$$R_S$') or -$L_4$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A and B are each independently phenyl, and are each independently optionally substituted with one or more $R_A$; D is phenyl, and is independently optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S$$R_S$'), and J can also be optionally substituted with one or more $R_A$; and $G_1$ is

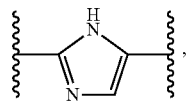

$G_2$ is

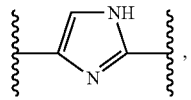 [SMILES: *c1c[nH]c(*)n1]

and each $G_1$ and $G_2$ is independently optionally substituted with one or more $R_A$ (e.g., one or more chloro or bromo). Preferably, D is

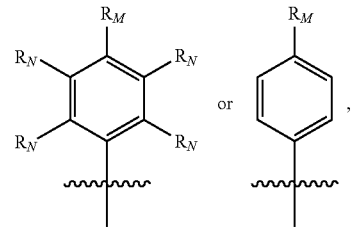

wherein $R_M$ and $R_N$ are as defined above. Also preferably, D is

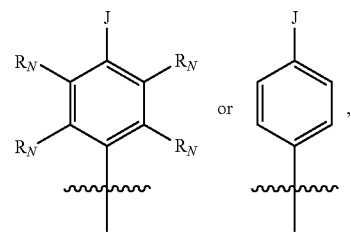

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'. Preferably, $R_2$ and $R_5$, taken together with the atoms to which they are attached, form

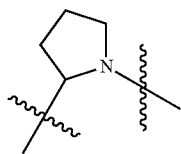 [SMILES: *C1CCCN1*]

which is optionally substituted with one or more $R_A$; $R_9$ and $R_{12}$, taken together with the atoms to which they are attached, form

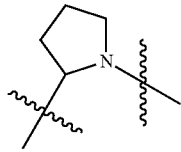 [SMILES: *C1CCCN1*]

which is optionally substituted with one or more $R_A$.

In another embodiment of this aspect, A and B are each independently phenyl (e.g., 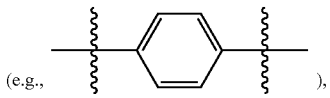 ), and are each independently optionally substituted with one or more $R_A$ (preferably, A and B are each independently substituted with at least one halogen such as F). X is

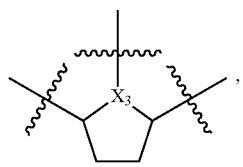

wherein $X_3$ is N and is directly linked to -$L_3$-D, and X is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$ or —N($R_S R_S$'), or (2) trimethylsilyl, —O—$R_S$, —S—$R_S$ or —C(O)$R_S$; and J can also be optionally substituted with one or more $R_A$. Preferably, D is

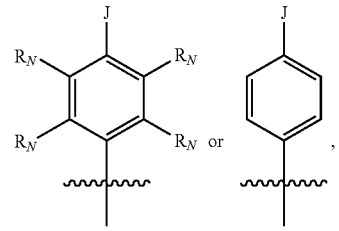

wherein J is as defined above, and each $R_N$ is independently selected from $R_D$ and preferably is hydrogen or halo such as F. $G_1$ is

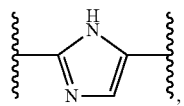 [SMILES: *c1cnc(*)[nH]1 ; ","]

$G_2$ is

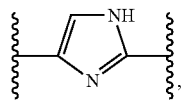

and each $G_1$ and $G_2$ is independently optionally substituted with one or more $R_A$ (e.g., one or more chloro or bromo). $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'. Preferably, $R_2$ and $R_5$, taken together with the atoms to which they are attached, form a 5- to 6-membered heterocyclic ring (e.g., 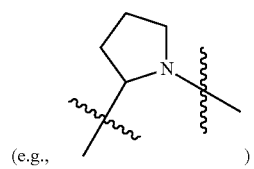 )

or 6- to 12-membered bicycle

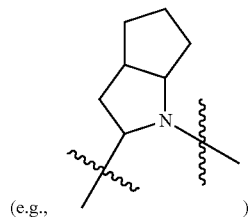

(e.g., )

which is optionally substituted with one or more $R_A$; $R_9$ and $R_{12}$, taken together with the atoms to which they are attached, form a 5- to 6-membered heterocyclic ring

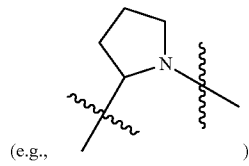

(e.g., )

or 6- to 12-membered bicycle

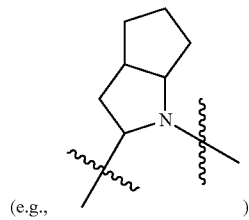

(e.g., )

which is optionally substituted with one or more $R_A$.

In another aspect, the present invention features compounds having Formula $I_E$ and pharmaceutically acceptable salts thereof,

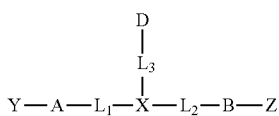

$I_E$ wherein:
X is 4- to 8-membered heterocycle, and is optionally substituted with one or more $R_A$;
$L_1$ and $L_2$ are each independently selected from bond or $C_1$-$C_6$alkylene which is independently optionally substituted at each occurrence with one or more halo, hydroxy, —O—$C_1$-$C_6$alkyl, or —O—$C_1$-$C_6$haloalkyl;
$L_3$ is bond or $C_1$-$C_6$alkylene;
A and B are each independently phenyl, pyridinyl, thiazolyl, or

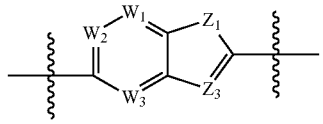

where $Z_1$ is independently selected at each occurrence from O, S, NH or $CH_2$, $Z_3$ is independently selected at each occurrence from N or CH, and $W_1$, $W_2$, and $W_3$ are each independently selected at each occurrence from CH or N; A and B are each independently optionally substituted with one or more $R_A$.

D is $C_6$-$C_{10}$carbocycle or 5- to 12-membered heterocycle, each of which is optionally substituted with one or more $R_M$;

Y is -T'-C($R_1R_2$)N($R_5$)-T-$R_D$;

Z is -T'-C($R_8R_9$)N($R_{12}$)-T-$R_D$;

$R_1$ is hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl;

$R_2$ and $R_5$ are each independently hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl; or $R_2$ and $R_5$, taken together with the atoms to which they are attached, form a 3- to 12-membered heterocycle which is optionally substituted with one or more $R_A$ (e.g., 1, 2, 3, or 4 $R_A$);

$R_8$ is hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl;

$R_9$ and $R_{12}$ are each independently hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl; or $R_9$ and $R_{12}$, taken together with the atoms to which they are attached, form a 3- to 12-membered heterocycle which is optionally substituted with one or more $R_A$ (e.g., 1, 2, 3, or 4 $R_A$);

T is independently selected at each occurrence from bond or —C(O)-$L_S$'-;

T' is independently selected at each occurrence from bond, —C(O)N($R_B$)—, —N($R_B$)C(O)—, or 3- to 12-membered heterocycle, wherein said 3- to 12-membered heterocycle is independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or -$L_S$-$R_E$;

$R_B$ and $R_B$' are each independently selected at each occurrence from hydrogen; or $C_1$-$C_6$alkyl which is independently optionally substituted at each occurrence with one or more substituents selected from halogen or 3- to 6-membered carbocycle or heterocycle; or 3- to 6-membered carbocycle or heterocycle; wherein each 3- to 6-membered carbocycle or heterocycle in $R_B$ or $R_B$' is independently optionally substituted at each occurrence with one or more substituents selected from halogen, hydroxy, $C_1$-$C_6$alkyl, $C_1$-$C_6$haloalkyl, —O—$C_1$-$C_6$alkyl, or —O—$C_1$-$C_6$haloalkyl;

$R_E$ is independently selected at each occurrence from —O—$R_S$, —S—$R_S$, —C(O)$R_S$, —OC(O)$R_S$, —C(O)OR$_S$, —N($R_S R_S'$), —S(O)$R_S$, —SO$_2 R_S$, —C(O)N($R_S R_S'$), —N($R_S$)C(O)$R_S'$, —N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$OR$_S$, —S(O)OR$_S$, —OC(O)OR$_S$, —N($R_S$)C(O)OR$_S'$, —OC(O)N($R_S R_S'$), —N($R_S$)S(O)—$R_S'$, —S(O)N($R_S R_S'$), —C(O)N($R_S$)C(O)—$R_S'$, or =C($R_S R_S'$); or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_L$ is independently selected at each occurrence from halogen, nitro, oxo, phosphonoxy, phosphono, thioxo, cyano, —O—$R_S$, —S—$R_S$, —C(O)$R_S$, —OC(O)$R_S$, —C(O)OR$_S$, —N($R_S R_S'$), —S(O)$R_S$, —SO$_2 R_S$, —C(O)N($R_S R_S'$), or —N($R_S$)C(O)$R_S'$; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$L_S$ is independently selected at each occurrence from bond; or $C_1$-$C_6$alkylene, $C_2$-$C_6$alkenylene or $C_2$-$C_6$alkynylene, each independently optionally substituted with halogen;

$L_S'$ is independently selected at each occurrence from bond; or $C_1$-$C_6$alkylene, $C_2$-$C_6$alkenylene or $C_2$-$C_6$alkynylene, each of which is independently optionally substituted at each occurrence with one or more $R_L$;

$R_S$, $R_S'$ and $R_S''$ are each independently selected at each occurrence from hydrogen; $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —O—$C_1$-$C_6$alkyl, —O—$C_1$-$C_6$haloalkyl, or 3- to 12-membered carbocycle or heterocycle; or 3- to 12-membered carbocycle or heterocycle; wherein each 3- to 12-membered carbocycle or heterocycle in $R_S$, $R_S'$ or $R_S''$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_M$ is independently selected at each occurrence from: halogen, hydroxy, mercapto, amino, carboxy, nitro, oxo, phosphonoxy, phosphono, thioxo, cyano, $SF_5$, —N($R_S R_S'$), —O—$R_S$, —OC(O)$R_S$, —OC(O)OR$_S$, —OC(O)N($R_S R_S'$), —C(O)$R_S$, —C(O)OR$_S$, —C(O)N($R_S R_S'$), —N($R_S$)C(O)$R_S'$, —N($R_S$)C(O)OR$_S'$, —N($R_S$)SO$_2 R_S'$, —S(O)$R_S$, —SO$_2 R_S$, —S(O)N($R_S R_S'$), —SR$_S$, —Si($R_S$)$_3$, or —P(O)(OR$_S$)$_2$;

$C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —N($R_S R_S'$), —O—$R_S$, —OC(O)$R_S$, —OC(O)OR$_S$, —OC(O)N($R_S R_S'$), —C(O)$R_S$, —C(O)OR$_S$, —C(O)N($R_S R_S'$), —N($R_S$)C(O)$R_S'$, —N($R_S$)C(O)OR$_S'$, —N($R_S$)SO$_2 R_S'$, —S(O)$R_S$, —SO$_2 R_S$, —S(O)N($R_S R_S'$), —SR$_S$, or —P(O)(OR$_S$)$_2$; or $G_2$, wherein $G_2$ is a $C_3$-$C_{12}$carbocycle or 3- to 12-membered heterocycle, each of which is independently optionally substituted at each occurrence with one or more $R_{G2}$, and each $R_{G2}$ is independently selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —O—$R_S$, —C(O)OR$_S$, —C(O)$R_S$, —N($R_S R_S'$), or -$L_4$-$G_3$;

$L_4$ is a bond, $C_1$-$C_6$alkylene, $C_2$-$C_6$alkenylene, $C_2$-$C_6$alkynylene, —O—, —S—, —N($R_B$)—, —C(O)—, —S(O)$_2$—, —S(O)—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —N($R_B$)C(O)N($R_B'$)—, —N($R_B$)SO$_2$N($R_B'$)—, or —N($R_B$)S(O)N($R_B'$)—;

$G_3$ is a $C_3$-$C_{12}$carbocycle or 3- to 12-membered heterocycle, and is optionally substituted with one or more $R_{G3}$; and $R_{G3}$ is each independently, at each occurrence, halogen, —$C_1$-$C_6$alkyl, —C(O)$C_1$-$C_6$alkyl, -$C_1$-$C_6$haloalkyl, —O—$C_1$-$C_6$alkyl, —O—$C_1$-$C_6$haloalkyl, $C_3$-$C_6$carbocycle, or 3- to 6-membered heterocycle.

As described hereinabove for compounds of Formula $I_E$ A and B are each phenyl, pyridinyl, thiazolyl, or

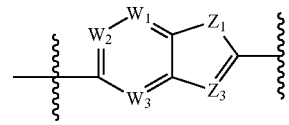

where $Z_1$ is independently selected at each occurrence from O, S, NH or $CH_2$, $Z_3$ is independently selected at each occurrence from N or CH, and $W_1$, $W_2$, and $W_3$ are each independently selected at each occurrence from CH or N; A and B are each independently optionally substituted with one or more $R_A$.

Preferably, A is selected from

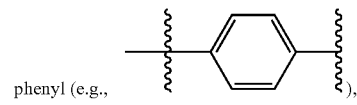

phenyl (e.g.,

-continued
pyridinyl (e.g., 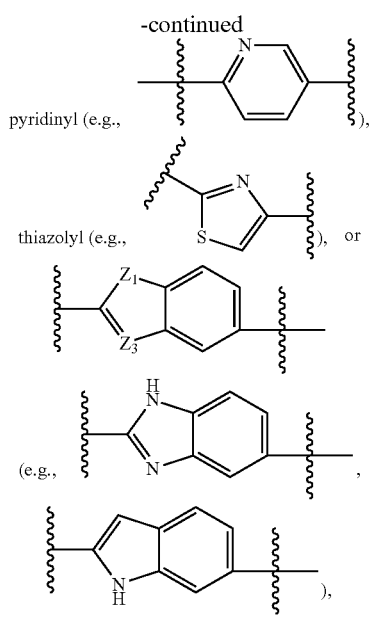), thiazolyl (e.g., ), or
(e.g., , ),
and is optionally substituted with one or more $R_A$.
Preferably, B is selected from
phenyl (e.g., ),
pyridinyl (e.g., ),
thiazolyl (e.g., ), or
(e.g., , ),
and is optionally substituted with one or more $R_A$.
Highly preferably, both A and B are phenyl (e.g., both A and B are
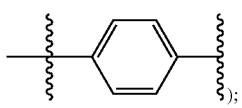);
or A is
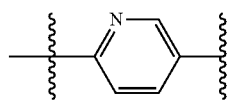
and B is
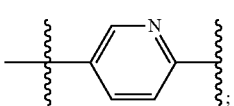;
or A is
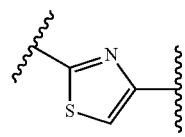 [SMILES: *c1csc(*)n1]
and B is
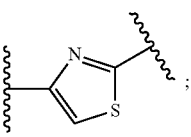 [SMILES: *c1csc(*)n1];
or A is
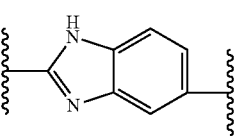 [SMILES: *c1ccc2[nH]c(*)nc2c1]
and B is
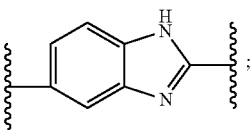 [SMILES: *c1ccc2[nH]c(*)nc2c1];
or A is
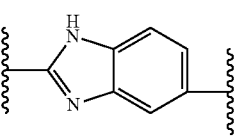 [SMILES: *c1ccc2[nH]c(*)nc2c1]

and B is

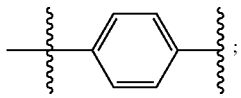

or A is

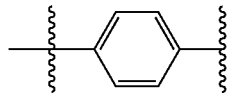

and B is


wherein each A and B is independently optionally substituted with one or more $R_A$.

In certain embodiments of this aspect of the invention, A and B are substituted by one or more $R_A$, wherein each $R_A$ is independently selected from halogen (e.g., fluoro, chloro), $L_S$-$R_E$ (where $L_S$ is bond and $R_E$ is —$C_1$-$C_6$alkyl (e.g., methyl), —O—$R_S$ (e.g., —O—$C_1$-$C_6$alkyl, —OCH$_3$), or —$C_1$-$C_6$alkyl optionally substituted with one or more halogen (e.g., —CF$_3$), or $L_S$-$R_E$ (where $L_S$ is $C_1$-$C_6$alkylene and $R_E$ is —O—$R_S$ (e.g., —$C_1$-$C_6$alkyl-O—$C_1$-$C_6$alkyl, —CH$_2$OCH$_3$)). For example, in certain embodiments A is

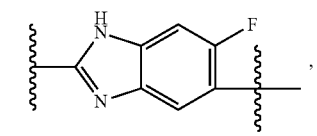,

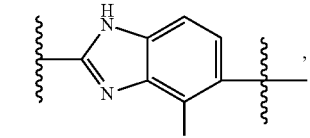,

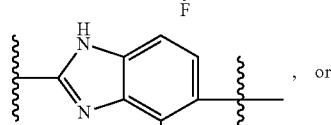, or

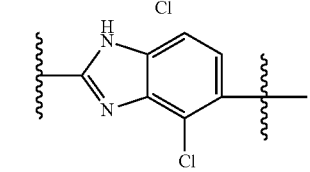

and B is as defined hereinabove. In certain other embodiments B is

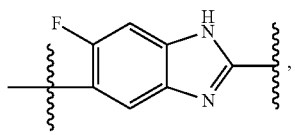,

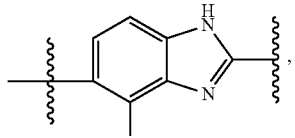,

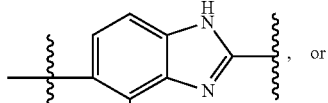, or

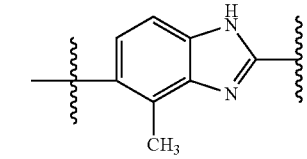

and A is as defined hereinabove. In still other embodiments A is

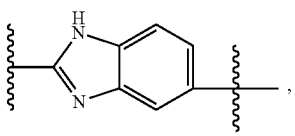,

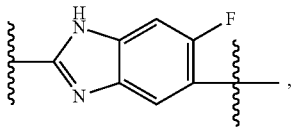,

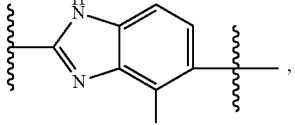,

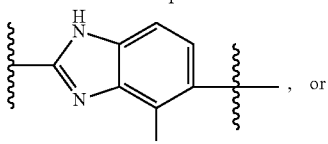, or

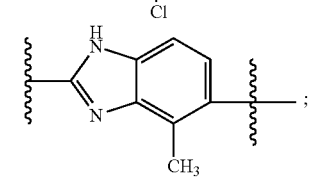;

and B is

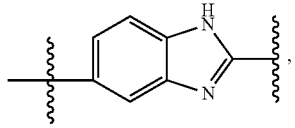 [SMILES: *c1ccc2[nH]c(*)nc2c1],

-continued

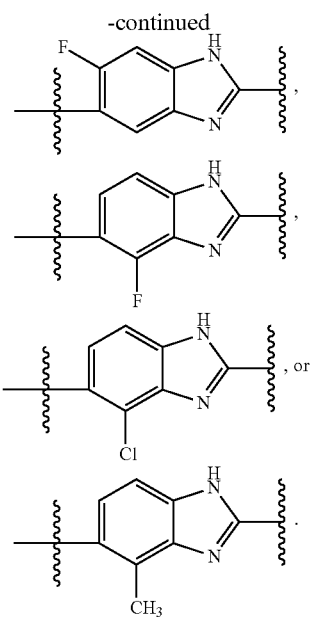

As described hereinabove for compounds of Formula $I_E$ D is $C_6$-$C_{10}$carbocycle or 3- to 12-membered heterocycle optionally substituted by one or more $R_M$. Preferably, D is $C_6$-$C_{10}$aryl (e.g., phenyl, naphthyl, indanyl), or 5- to 10-membered heteroaryl (pyridinyl, thiazolyl, 4,5,6,7-tetrahydrobenzo[d]thiazolyl, benzo[d]thiazolyl, indazolyl, benzo[d][1,3]dioxol-5-yl), and D is substituted with one or more $R_M$. For example, in certain embodiments D is preferably phenyl substituted by one or more $R_M$, wherein each $R_M$ is independently halogen (e.g., fluoro, chloro, bromo); $C_1$-$C_6$alkyl (e.g., tert-butyl); $C_1$-$C_6$alkyl substituted with one or more halogen (e.g., $CF_3$); —O—$R_S$ such as —O—$C_1$-$C_6$alkyl (e.g., —O—$CH_2CH_3$); or —O—$C_1$-$C_6$alkyl substituted at each occurrence with one or more halogen (e.g., —O—$CF_3$, —O—$CH_2CHF_2$) or —O—$C_1$-$C_6$alkyl (e.g., —O—$CH_2CH_2OCH_3$); —O—$R_S$ (e.g., —O—$C_1$-$C_6$alkyl, such as —O—$CH_2$) substituted with 3- to 12-membered heterocycle (e.g., 3-ethyloxetan-3-yl, 1,3-dioxolan-4-yl); —O—$R_S$ where $R_S$ is an optionally substituted 3- to 12-membered carbocycle or heterocycle (e.g., cyclopentyl, cyclohexyl, phenyl, 1,3-dioxan-5-yl); —N($R_S$)C(O)$R_S$' wherein $R_S$ and $R_S$' are each independently $C_1$-$C_6$alkyl (e.g., —N(t-Bu)C(O)Me); $SF_5$; —$SO_2R_S$ wherein $R_S$ is $C_1$-$C_6$alkyl (e.g., —$SO_2$Me); or $C_3$-$C_{12}$carbocycle (e.g., cyclopropyl, cyclohexyl, phenyl).

In certain embodiments of this aspect of the invention, D is preferably phenyl or pyridyl and is substituted by one or more $R_M$ where one $R_M$ is $G_2$. In certain embodiments where D is phenyl or pyridyl, D is substituted by $G_2$, $G_2$ is 3- to 12-membered heterocycle (e.g., pyridinyl, piperidinyl, pyrrolidinyl, azetidinyl, oxazolyl) and is optionally substituted with one or more halogen (e.g., fluoro, chloro), hydroxy, oxo, cyano, $C_1$-$C_6$alkyl (e.g., methyl), $C_2$-$C_6$alkenyl, $C_2$-$C_6$alkynyl, $C_1$-$C_6$haloalkyl (e.g., $CF_3$), $C_2$-$C_6$haloalkenyl, $C_2$-$C_6$haloalkynyl, —O—$C_1$-$C_6$alkyl (e.g., —O—$CH_3$), —C(O)$OR_S$ (e.g., —C(O)$OCH_3$), —C(O)$R_S$ (e.g., —C(O)$CH_3$), or —N($R_SR_S$'); and D is further optionally substituted by one or more $R_M$ where $R_M$ is halogen (e.g., fluoro, chloro), $C_1$-$C_6$alkyl (e.g., methyl), $C_1$-$C_6$haloalkyl (e.g., $CF_3$), or —O—$C_1$-$C_6$alkyl (e.g., —O—$CH_3$). In certain other embodiments D is phenyl or pyridyl and $G_2$ is, for example, a monocyclic 3-8 membered carbocycle or monocyclic 4-8 membered heterocycle substituted with $L_4$-$G_3$ and optionally substituted with one or more $R_{G2}$ wherein $L_4$, $G_3$ and $R_{G2}$ are as defined herein. $L_4$, for example is a bond, a $C_1$-$C_6$ alkylene (e.g., —$CH_2$—, —$CH_2CH_2$—, —$CH_2CH_2CH_2$—, etc.), —O—, or —S(O)$_2$—. $G_3$ is for example a $C_3$-$C_{12}$carbocycle optionally substituted with one or more $R_{G3}$. $R_{G2}$ and $R_{G3}$ are each independently at each occurrence halogen, —C(O)$C_1$-$C_6$alkyl, —$C_1$-$C_6$alkyl, —$C_1$-$C_6$haloalkyl, —O—$C_1$-$C_6$alkyl, or —O—$C_1$-$C_6$haloalkyl. In certain embodiments $G_2$ is

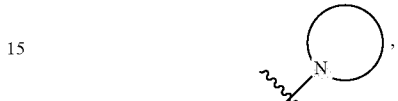

wherein

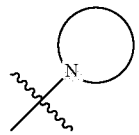

is a monocyclic 4-8 membered nitrogen-containing heterocycle (e.g., azetidinyl, pyrrolidinyl, piperidinyl, piperazinyl) attached to the parent molecular moiety through a nitrogen atom and substituted with one or two $L_4$-$G_3$ and optionally substituted with one or more $R_{G2}$. Thus, in certain embodiments where $L_4$ is a bond $G_2$ is

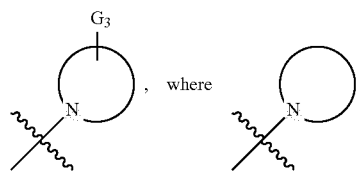, where is optionally substituted with $R_{G2}$ and $G_3$ is optionally substituted with $R_{G3}$. Thus

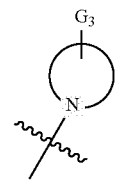

can be, for example, 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl, and wherein D can be further optionally substituted with one or more $R_M$ (e.g., fluoro, chloro, methyl, methoxy).

In certain other embodiments of this aspect of the invention, $L_4$ is a $C_1$-$C_6$ alkylene, —O—, or —S(O)$_2$—, and $G_2$ is

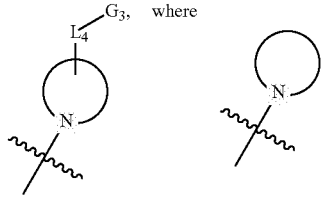

is as defined above and is optionally substituted with $R_{G2}$ and $G_3$ is as defined above and is optionally substituted with $R_{G3}$. Thus,

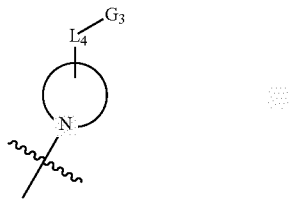

can be, for example, 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl.

In certain other embodiments of this aspect of the invention, D is phenyl or pyridyl, D is substituted by $G_2$ and $G_2$ is a spiro, bridged, or fused bicyclic carbocycle or heterocycle optionally substituted with $L_4$-$G_3$ and one or more $R_{G2}$, wherein D is optionally substituted with one or more $R_M$ and $R_M$, $L_4$, $G_3$, and $R_{G2}$ are as defined herein. In certain embodiments $G_2$ is

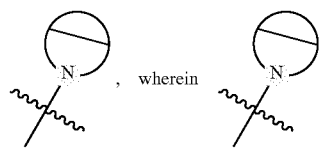

is a spiro, bridged, or fused bicyclic nitrogen-containing heterocycle (e.g., 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, 1,4-dioxa-8-azaspiro[4.5]dec-8-yl) attached to the parent molecular moiety through a nitrogen atom and optionally substituted with $G_3$ and one or more $R_{G2}$. Thus, $G_2$ is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl; $L_4$ is a bond and D is optionally substitute with one or more $R_M$ (e.g., fluoro, chloro, methyl, methoxy).

In certain embodiments of this aspect of the invention, D is

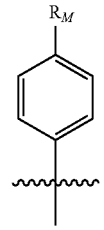

wherein $R_M$ is as defined above in connection with Formula $I_E$, and D is optionally substituted by one or more additional $R_M$. For instance, where D is

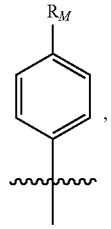

$R_M$ can be fluoro, chloro, tert-butyl, —O—CH$_2$CH$_3$, —O—CF$_3$, —O—CH$_2$CHF$_2$, —O—CH$_2$CH$_2$OCH$_3$, —O—CH$_2$-(3-ethyloxetan-3-yl), —O—CH$_2$-(1,3-dioxolan-4-yl), —O— cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D can be optionally substituted by one or more additional $R_M$ selected from the group consisting of halogen (e.g., fluoro, chloro) and $C_1$-$C_6$alkyl (e.g., methyl).

In certain embodiments, D is

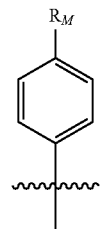

wherein $R_M$ is fluoro, chloro, tert-butyl, —O—CH$_2$CH$_3$, —O—CF$_3$, —O—CH$_2$CHF$_2$, —O—CH$_2$CH$_2$OCH$_3$, SF$_5$, —SO$_2$Me, or —N(t-Bu)C(O)Me and D is optionally substituted by one or more additional $R_M$ selected from the group consisting of halogen (e.g., fluoro, chloro) and $C_1$-$C_6$alkyl (e.g., methyl).

In certain embodiments, D is

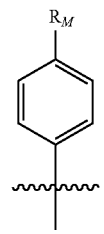

wherein $R_M$ is cyclopropyl, cyclohexyl, or phenyl and D is optionally substituted by one or more additional $R_M$ selected from the group consisting of halogen (e.g., fluoro, chloro) and $C_1$-$C_6$alkyl (e.g., methyl).

In certain embodiments, D is

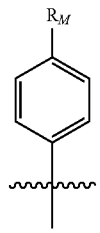

wherein $R_M$ is —O—CH$_2$-(3-ethyloxetan-3-yl), —O—CH$_2$-(1,3-dioxolan-4-yl), —O-cyclopentyl, —O-cyclohexyl, —O-phenyl, or —O-(1,3-dioxan-5-yl) and D is optionally substituted by one or more additional $R_M$ selected from the group consisting of halogen (e.g., fluoro, chloro) and $C_1$-$C_6$alkyl (e.g., methyl).

In certain embodiments, D is

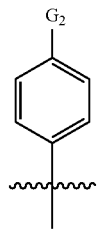

wherein $G_2$ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional $R_M$ selected from the group consisting of halogen (e.g., fluoro, chloro) and $C_1$-$C_6$alkyl (e.g., methyl).

In another embodiment of this aspect of the invention, D is

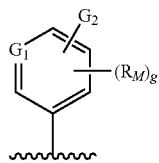

wherein $G_1$ is N, C—H, or C—$R_M$; $G_2$ is

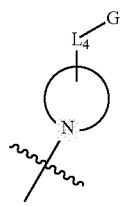 wherein 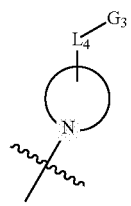

is a monocyclic 4-8 membered nitrogen-containing heterocycle (e.g., azetidinyl, pyrrolidinyl, piperidinyl) attached to the parent molecular moiety through a nitrogen atom and substituted by $L_4$-$G_3$ and optionally substituted with one or more $R_{G2}$; $L_4$ is a bond, $C_1$-$C_6$ alkylene, —O—, or —S(O)$_2$—; $G_3$ is aryl (e.g., phenyl), cycloalkyl (e.g., cyclohexyl), or heterocycle (e.g., thienyl) wherein each $G_3$ is optionally substituted with one or more $R_{G3}$; $R_{G2}$ and $R_{G3}$ at each occurrence are each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; g is 0, 1, 2, or 3; and $R_M$ is as defined above in connection with Formula I$_E$. In one group of compounds according to this embodiment, D is

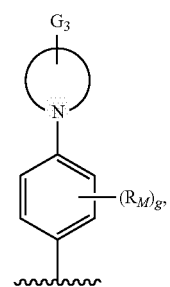

wherein $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

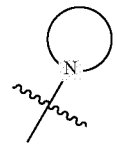

and $R_{G3}$ are as defined above. In a further subgroup of compounds of this embodiment, D is

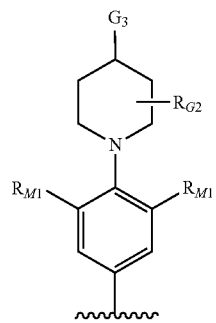

wherein $G_3$ is phenyl optionally substituted with one or two $R_{G3}$; $R_{M1}$ is each independently hydrogen, fluoro, chloro, or methyl; and $R_{G2}$ is an optional substituent as described herein. In another group of compounds according to this embodiment, D is

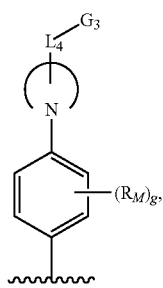

wherein L₄ is $C_1$-$C_6$ alkylene, —O—, or —S(O)₂—; G₃ is phenyl optionally substituted with one or two $R_{G3}$; g is 0, 1, or 2; $R_M$ is each independently fluoro, chloro, methyl, methoxy, trifluoromethyl, or trifluoromethoxy; and

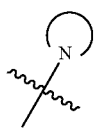

and $R_{G3}$ are as defined above.

In yet another embodiment of this aspect of the invention, D is

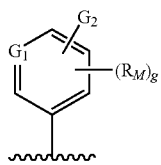

wherein G₁ is N, C—H, or C—$R_M$; G₂ is

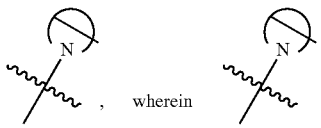

is a spiro, bridged, or fused bicyclic nitrogen-containing heterocycle (e.g., 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, 1,4-dioxa-8-azaspiro[4.5]dec-8-yl) attached to the parent molecular moiety through a nitrogen atom and optionally substituted with L₄-G₃ and one or more $R_{G2}$; L₄ is a bond, $C_1$-$C_6$ alkylene, —O—, or —S(O)₂—; G₃ is aryl (e.g., phenyl), cycloalkyl (e.g., cyclohexyl), or heterocycle (e.g., thienyl) wherein each G₃ is optionally substituted with one or more $R_{G3}$; $R_{G2}$ and $R_{G3}$ at each occurrence are each independently halogen, —C(O)$C_1$-$C_6$alkyl, —$C_1$-$C_6$alkyl, —$C_1$-$C_6$haloalkyl, —O—$C_1$-$C_6$alkyl, or —O—$C_1$-$C_6$haloalkyl; g is 0, 1, 2, or 3; and $R_M$ is as defined above in connection with Formula $I_E$. In one group of compounds according to this embodiment, D is

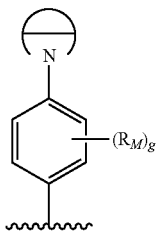

wherein g is 0, 1, or 2; $R_M$ is each independently fluoro, chloro, methyl, methoxy, trifluoromethyl, or trifluoromethoxy; and

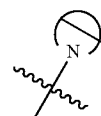

is as defined above. In a further subgroup of compounds D is

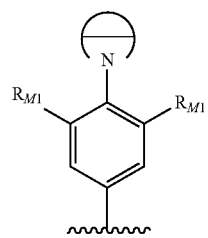

wherein $R_{M1}$ is each independently hydrogen, fluoro, chloro, or methyl, and

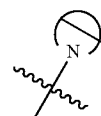

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In still another embodiment of this aspect of the invention, D is

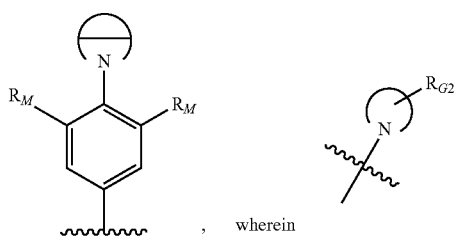

is a monocyclic 4-8 membered nitrogen-containing heterocycle (e.g., azetidinyl, pyrrolidinyl, piperidinyl) substituted with one or more $R_{G2}$, wherein $R_{G2}$ at each occurrence is each independently halogen, —C(O)$C_1$-$C_6$alkyl, —$C_1$-$C_6$alkyl, —$C_1$-$C_6$haloalkyl, —O—$C_1$-$C_6$alkyl, or —O—$C_1$-$C_6$haloalkyl; and $R_M$ is each independently halogen, -$C_1$-$C_6$alkyl, -$C_1$-$C_6$haloalkyl, —O—$C_1$-$C_6$alkyl, or —O—$C_1$-$C_6$haloalkyl. In one group of compounds according to this embodiment,

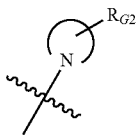

is azetidinyl, pyrrolidinyl, or piperidinyl substituted with one or two $R_{G2}$, wherein $R_{G2}$ at each occurrence is each independently methyl, ethyl, isopropyl, tert-butyl, fluoro, chloro, or trifluoromethyl; and $R_M$ is each independently fluoro, chloro, or methyl. For example

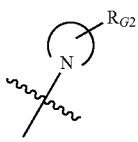

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

For compounds of Formula $I_E$

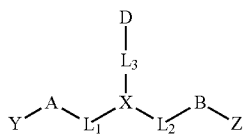

$I_E$ attachment of X to the remainder of the molecule can be conveniently depicted by the abbreviated structural Formula X', wherein the groups attached to X maintain the same relative spatial orientation as drawn in Formula $I_E$. It is understood that in subsequent depictions of the variable group X, the substituents of X will retain the same relative positions and orientation as in Formula $I_E$ and Formula X'.

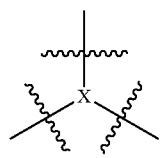

X'

Compounds of Formula $I_E$ include those where the variable X is selected from the group consisting of X-1, X-2, X-3, and X-4 wherein X-1, X-2, X-3, and X-4 retain the same orientation as structure X' relative to the remainder of the molecule; wherein the presence of ═══ in X-1, X-2, and X-3 represents single or double bonds, $X_1$ is $C_1$-$C_2$alkylene or $C_2$alkenylene, $X_2$ and $X_3$ are each $C_1$-$C_2$alkylene or $C_2$alkenylene, and $X_4$ is $C_1$-$C_2$ alkylene.

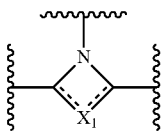

X-1

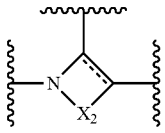

X-2

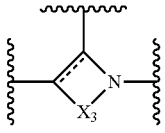

X-3

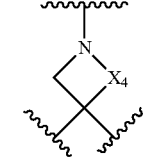

X-4

In accordance with the foregoing description, in certain embodiments of this aspect of the invention, X is pyrrolyl and is attached to the remainder of the molecule as shown in Formula $X_A$:

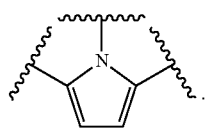

$X_A$

In certain embodiments, X is pyrrolidinyl and is attached to the remainder of the molecule as shown in Formula $X_B$:

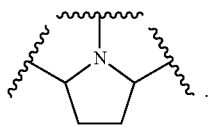

$X_B$

Embodiments according to Formula $X_B$ may exist in cis ($X_{B1}$) or trans ($X_{B2}$) forms:

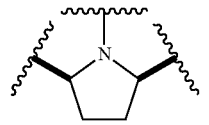

$X_{B1}$

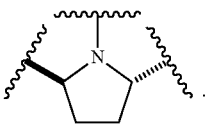

$X_{B2}$

Chiral carbon atoms in $X_B$, $X_{B1}$, and $X_{B2}$ may have either the (R) or (S) absolute stereochemistry.

In yet another embodiment of this aspect of the invention, X is pyrrolyl and is attached to the remainder of the molecule as shown in Formulae $X_{C1}$ or $X_{C2}$:

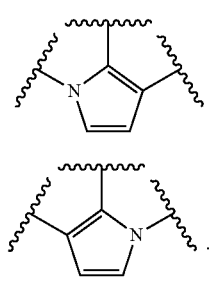

$X_{C1}$ $X_{C2}$

In certain embodiments, X is pyrrolidinyl and is attached to the remainder of the molecule as shown in Formulae $X_{D1}$ or $X_{D2}$:

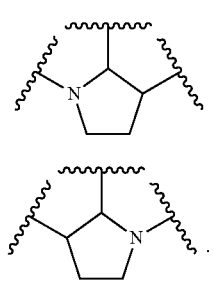

$X_{D1}$ $X_{D2}$

Embodiments according to Formulae $X_{D1}$ or $X_{D2}$ may exist in cis or trans forms and chiral carbon atoms in $X_{D1}$ and $X_{D2}$ may have either the (R) or (S) absolute stereochemistry. In certain embodiments, X is azetidinyl and is attached to the remainder of the molecule as shown in Formulae $X_{E1}$ or $X_{E2}$:

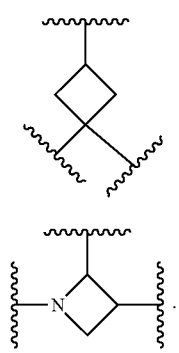

$X_{E1}$ $X_{E2}$

Chiral carbon atoms in $X_{E1}$ and $X_{E2}$ may independently have either the (R) or (S) absolute stereochemistry. In certain preferred embodiments of this aspect of the invention, X is $X_A$, $X_B$, $X_{B1}$, $X_{B2}$, $X_{C1}$, or $X_{C2}$ and $L_1$, $L_2$, and $L_3$ are each a bond. In certain other embodiments, X is $X_{D1}$, $X_{D2}$, $X_{E1}$, or $X_{E2}$ and $L_1$, $L_2$, and $L_3$ are each a bond. In another embodiment, X is $X_{E1}$ and $L_1$ and $L_2$ are each methylene (i.e. —CH$_2$—), and $L_3$ is a bond.

In compounds of Formula $I_E$, Y is -T'-C(R$_1$R$_2$)N(R$_S$)-T-R$_D$ and Z is -T'-C(R$_8$R$_9$)N(R$_{12}$)-T-R$_D$; wherein T', R$_1$, R$_2$, R$_5$, R$_8$, R$_9$, R$_{12}$, T, and R$_D$ are as defined herein.

Preferably R$_1$, R$_2$, R$_5$, R$_8$, R$_9$, and R$_{12}$ are each independently hydrogen; C$_1$-C$_6$alkyl; or 3- to 6-membered carbocycle or heterocycle, wherein each 3- to 6-membered carbocycle or heterocycle is independently optionally substituted at each occurrence with one or more substituents selected from halogen or C$_1$-C$_6$alkyl; wherein R$_2$ and R$_5$, taken together with the atoms to which they are attached, optionally form a 3- to 12-membered heterocycle which is substituted with 0, 1, 2, 3, or 4 R$_A$, and R$_9$ and R$_{12}$ taken together with the atoms to which they are attached, optionally form a 3- to 12-membered heterocycle which is substituted with 0, 1, 2, 3, or 4 R$_A$ wherein R$_A$ is as defined herein.

In certain embodiments of this aspect of the invention, R$_1$ is hydrogen and R$_2$ and R$_5$, taken together with the atoms to which they are attached form a 3- to 12-membered heterocycle

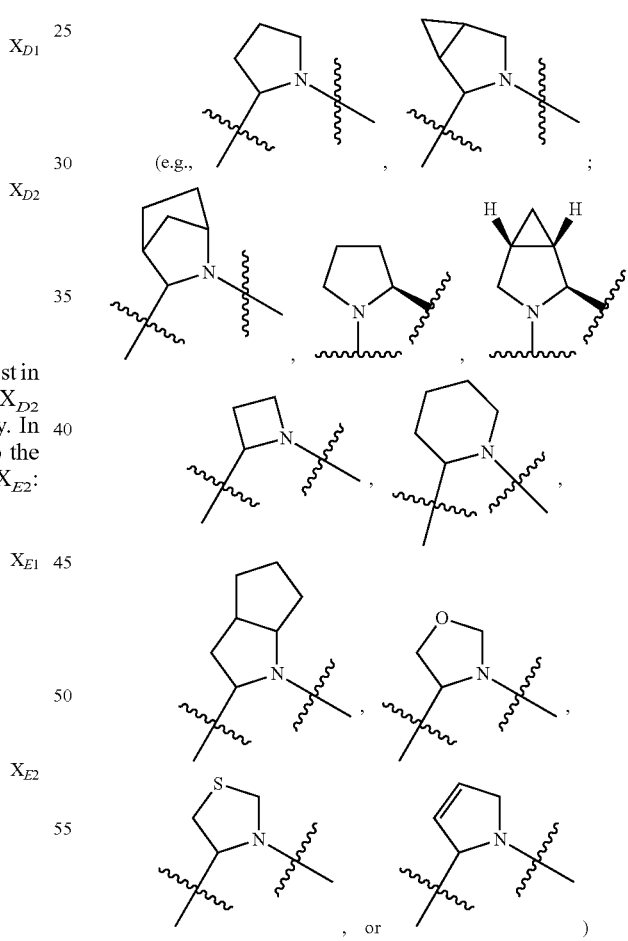

(e.g., , ;

, , ,

, ,

, or )

substituted with 0, 1, 2, 3, or 4 R$_A$ wherein R$_A$ is halogen (e.g., fluoro, chloro); cyano; L$_S$-R$_E$ where L$_S$ is a single bond and R$_E$ is C$_1$-C$_6$alkyl (e.g., methyl, ethyl), —O—C$_1$-C$_6$alkyl (e.g., methoxy), or —O—C$_1$-C$_6$haloalkyl (e.g., trifluoromethoxy); or L$_S$-R$_E$ where L$_S$ is a double bond and R$_E$ is =C(R$_S$R$_S$')

(e.g., 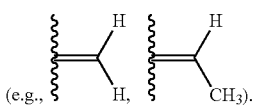).

In a preferred embodiment $R_2$ and $R_5$, taken together with the atoms to which they are attached form a pyrrolidine ring (i.e., )

substituted with 0 or 1 $R_A$ wherein $R_A$ is fluoro, methoxy, methyl, ethyl, or cyano. In another preferred embodiment $R_2$ and $R_5$, taken together with the atoms to which they are attached form a pyrrolidine ring (i.e., 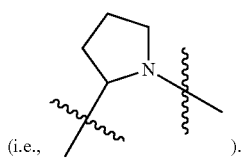).

In certain other embodiments of this aspect of the invention, $R_8$ is hydrogen and $R_9$ and $R_{12}$, taken together with the atoms to which they are attached form a 3- to 12-membered heterocycle (e.g.,

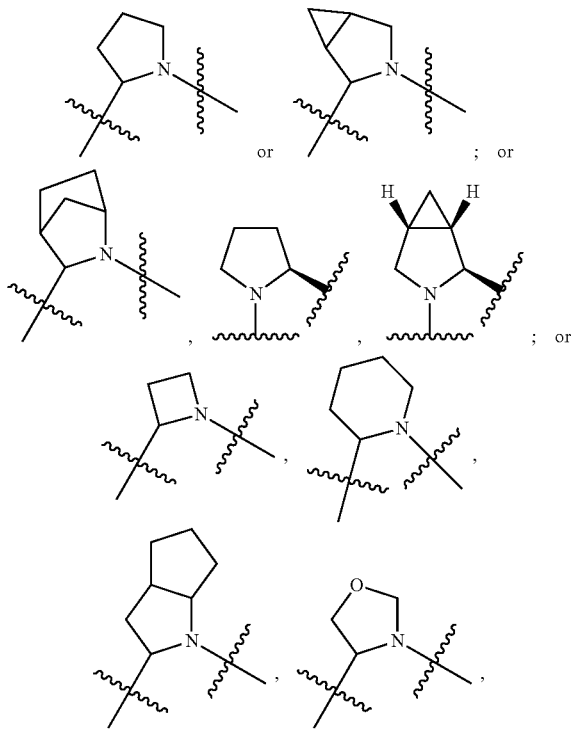

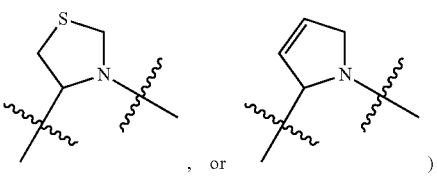

, or )

substituted with 0, 1, 2, 3, or 4 $R_A$ wherein $R_A$ is halogen (e.g., fluoro, chloro); cyano; $L_S$-$R_E$ where $L_S$ is a single bond and $R_E$ is $C_1$-$C_6$alkyl (e.g., methyl, ethyl), —O—$C_1$-$C_6$alkyl (e.g., methoxy), or —O—$C_1$-$C_6$haloalkyl (e.g., trifluoromethoxy); or $L_S$-$R_E$ where $L_S$ is a double bond and $R_E$ is =C($R_S R_S'$)

(e.g., 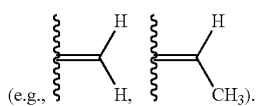).

In a preferred embodiment, $R_9$ and $R_{12}$, taken together with the atoms to which they are attached form a pyrrolidine ring (i.e., 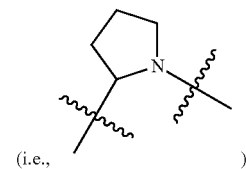 [SMILES: *C1CCCN1*])

substituted with 0 or 1 $R_A$ wherein $R_A$ is fluoro, methoxy, methyl, ethyl, or cyano. In another preferred embodiment $R_9$ and $R_{12}$, taken together with the atoms to which they are attached form a pyrrolidine ring (i.e., 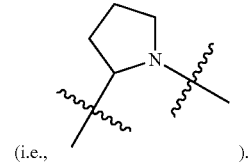 [SMILES: *C1CCCN1*]).

As used herein, a chiral carbon in any rings formed by joining $R_2$ and $R_5$ or $R_9$ and $R_{12}$ may possess either (R) or (S) stereochemistry. A pyrrolidine ring (i.e., 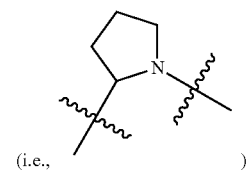 [SMILES: *C1CCCN1*])

formed from either $R_2$ and $R_5$ or $R_9$ and $R_{12}$ preferably possesses the (S) stereochemistry (i.e., 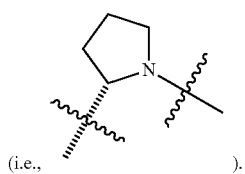 [SMILES: *[C@@H]1CCCN1*] ).

In this aspect of the invention, T' is independently selected at each occurrence from a bond, —C(O)N(R$_B$)—, —N(R$_B$)C(O)—, or 3- to 12-membered heterocycle, and wherein said 3- to 12-membered heterocycle is each independently optionally substituted at each occurrence with one or more R$_A$, and R$_A$ and R$_B$ are as described herein. In particular, where T' is —C(O)N(R$_B$)—, R$_B$ can be hydrogen (i.e., T' is —C(O)N(H)—). In certain embodiments, T' is imidazolyl (i.e., 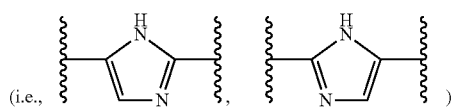 )

optionally substituted at each occurrence with one or more R$_A$ wherein R$_A$ is halogen (e.g., fluoro, chloro), C$_1$-C$_6$alkyl (e.g., methyl, ethyl), or C$_1$-C$_6$haloalkyl (e.g., trifluoromethyl). In certain embodiments, T' is imidazolyl (i.e.,  ).

This aspect of the invention contemplates particular combinations of A with Y and B with Z. Non-limiting examples of preferred Y when A is C$_5$-C$_6$carbocycle (e.g., phenyl) or 5- to 6-membered heterocycle (e.g., pyridinyl or thiazolyl) and preferred Z when B is C$_5$-C$_6$carbocycle (e.g., phenyl) or 5- to 6-membered heterocycle (e.g., pyridinyl or thiazolyl) include:

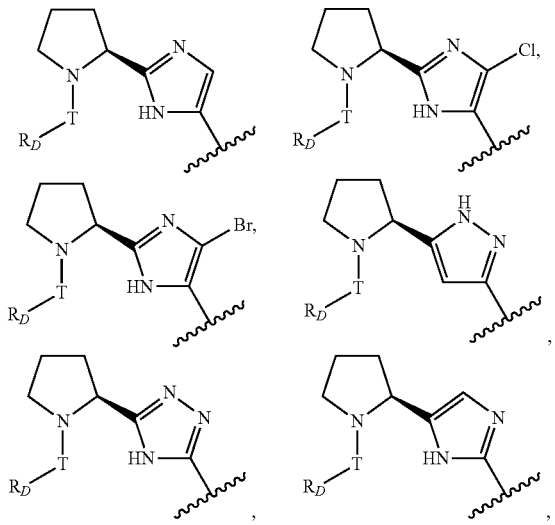

-continued

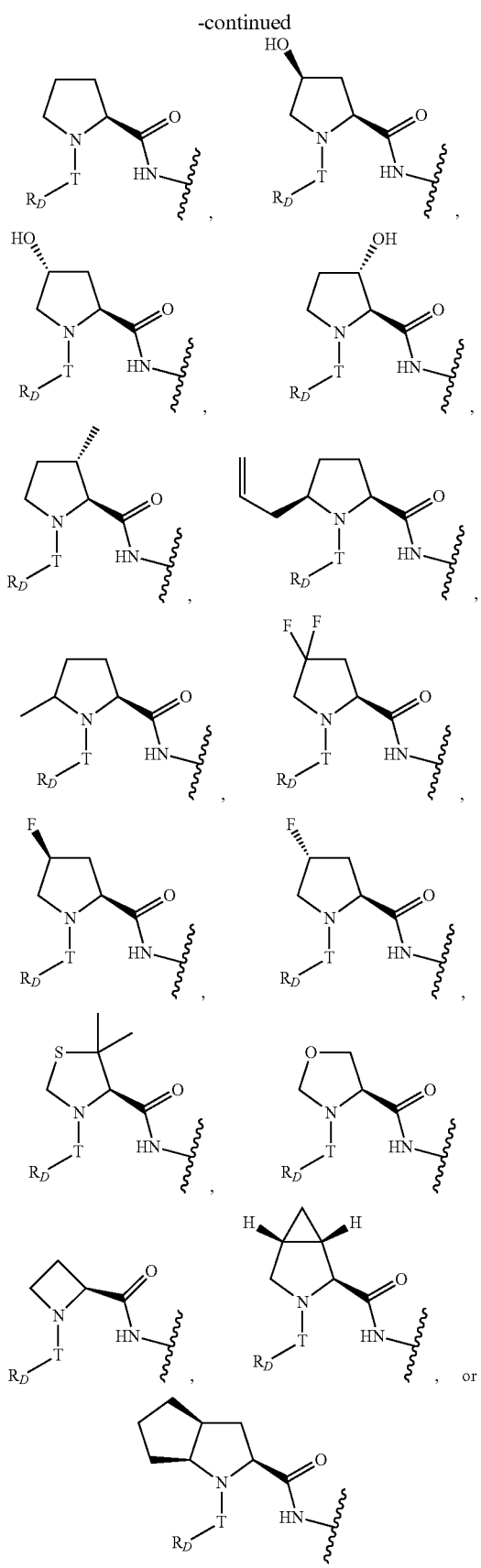

wherein T and R$_D$ are as defined herein.

In certain embodiments of this aspect of the invention, A is

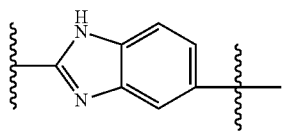 [SMILES: *c1ccc2[nH]c(*)nc2c1]

optionally substituted with one or more $R_A$ as described herein, or Y-A is

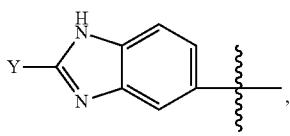

and non-limiting examples of preferred Y, where T' is a bond, include:

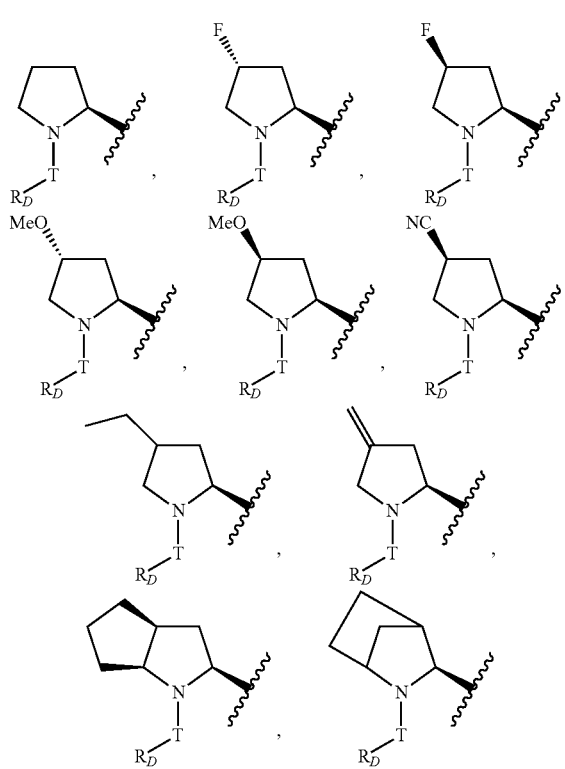

wherein T and $R_D$ are as defined herein.

In certain embodiments of this aspect of the invention, B is

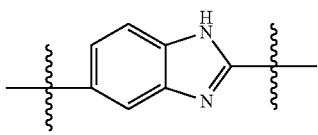 [SMILES: *c1ccc2[nH]c(*)nc2c1]

optionally substituted with one or more $R_A$ as described herein, or B—Z is

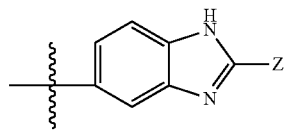

and non-limiting examples of preferred Z, where T' is a bond, include:

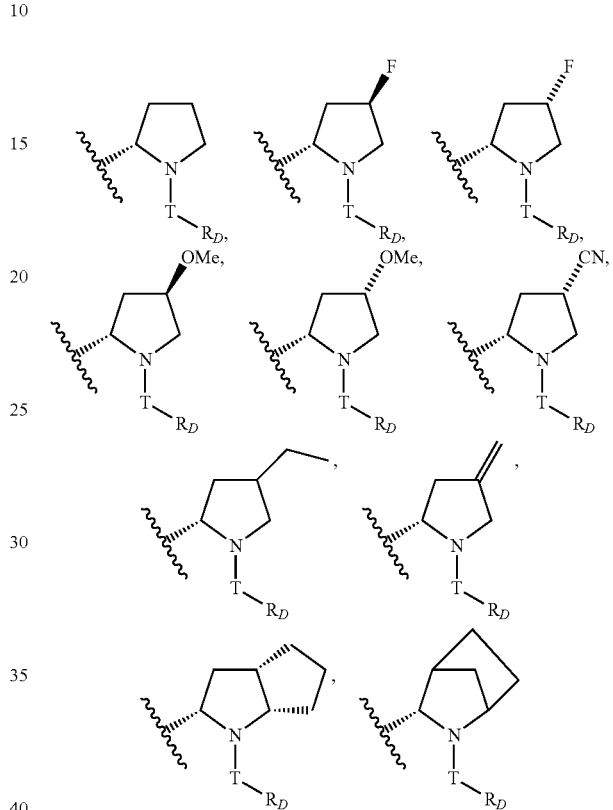

wherein T and $R_D$ are as defined herein.

T at each occurrence is independently a bond or —C(O)-$L_S'$-, wherein $L_S'$ is as defined herein. $L_S'$ includes, but is not limited to,

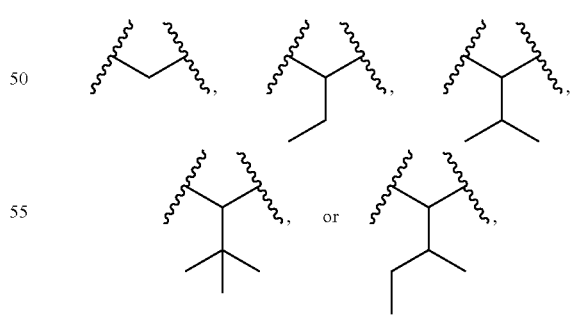

where $L_S'$ is optionally substituted with one or more $R_L$; and $R_L$ is a substituent such as, but not limited to carbocycle (e.g., cyclohexyl, cyclopentyl, cyclobutyl, cyclopropyl, phenyl), methoxy, or heterocycle (e.g., tetrahydropyranyl, tetrahydropyranyl).

$R_D$ is hydrogen or $R_A$ wherein $R_A$ is as defined herein. Thus $R_D$ includes, but is not limited to, $R_A$ wherein $R_A$ is $L_S$-$R_E$, and $L_S$ and $R_E$ are as defined herein. Thus $R_D$ includes, but is not limited to, $L_S$-$R_E$ wherein $L_S$ is a bond and $R_E$ is —N($R_S$$R_S$'), —N($R_S$)C(O)$R_S$', —N($R_S$)C(O)N($R_S$'$R_S$"), —N($R_S$)SO$_2$$R_S$', —N($R_S$)SO$_2$N($R_S$'$R_S$"), —N($R_S$)S(O)N($R_S$'$R_S$"), —N($R_S$)C(O)OR$_S$', or —N($R_S$)S(O)—$R_S$'; or $C_3$-$C_{12}$carbocycle or 3- to 12-membered heterocycle, each of which is independently optionally substituted at each occurrence with one or more substituents selected from halogen, hydroxy, cyano, $C_1$-$C_6$alkyl, $C_2$-$C_6$alkenyl, $C_2$-$C_6$alkynyl, or $C_1$-$C_6$haloalkyl.

In one embodiment of this aspect of the invention, $R_D$ is $L_S$-$R_E$ wherein $L_S$ is a bond and $R_E$ is —N($R_S$)C(O)OR$_S$' or 3- to 12-membered heterocycle (e.g., pyrrolidine, piperidine, azepanyl) wherein $R_S$ and $R_S$' are as defined herein. For example $R_D$ is preferably $L_S$-$R_E$ wherein $L_S$ is a bond and $R_E$ is —N(H)C(O)OMe.

Thus according to the foregoing description T-$R_D$ includes, but is not limited to:

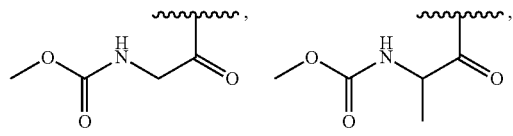

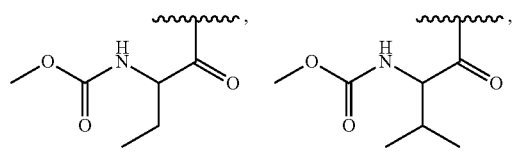

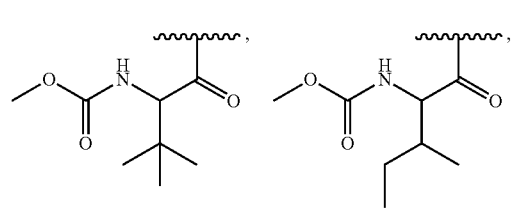

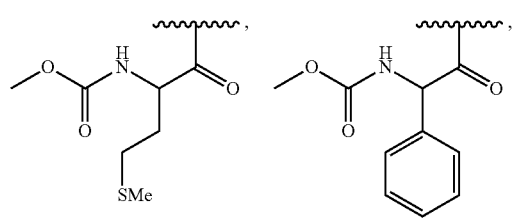

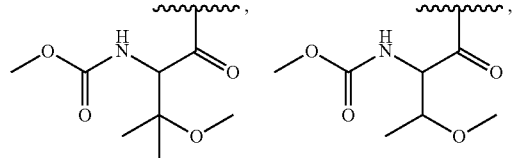

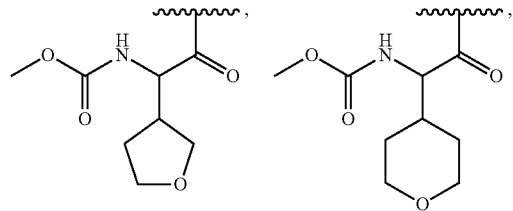

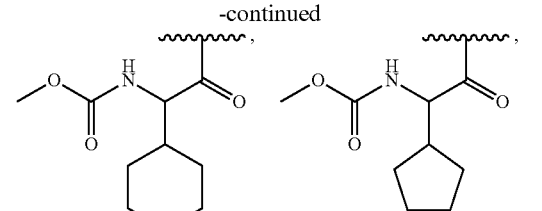

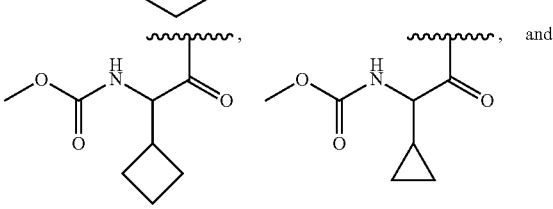

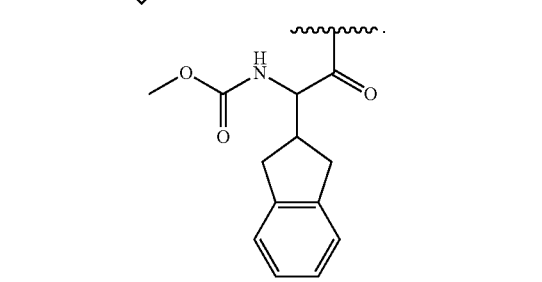

T-$R_D$ may also include particular stereochemical configurations; thus T-$R_D$ includes, but is not limited to:

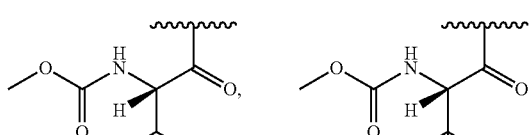

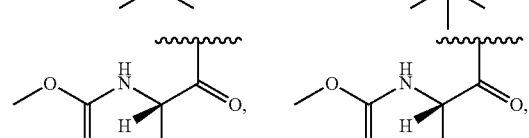

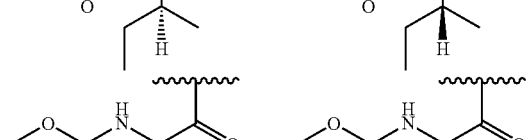

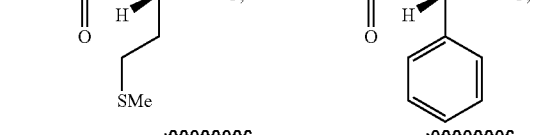

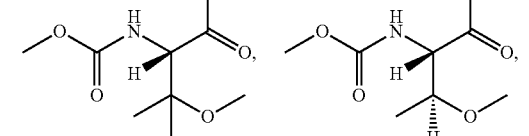

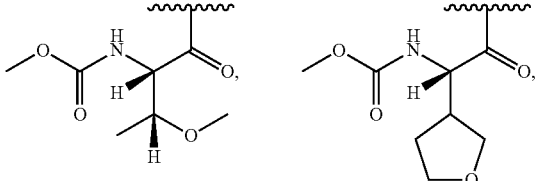

-continued
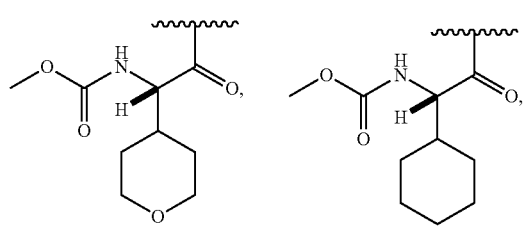
etc.
According to this aspect of the invention, non-limiting examples of preferred Y when A is $C_5$-$C_6$carbocycle (e.g., phenyl) or 5- to 6-membered heterocycle (e.g., pyridinyl or thiazolyl) and preferred Z when B is $C_5$-$C_6$carbocycle (e.g., phenyl) or 5- to 6-membered heterocycle (e.g., pyridinyl or thiazolyl) include:
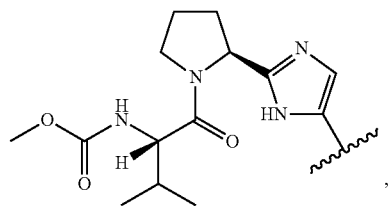
,
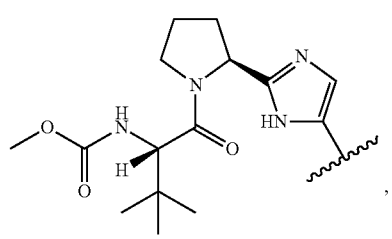
,
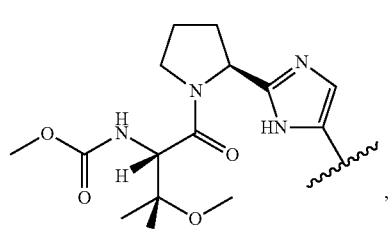
,
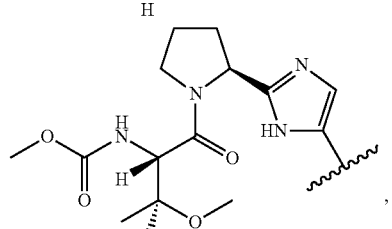
,
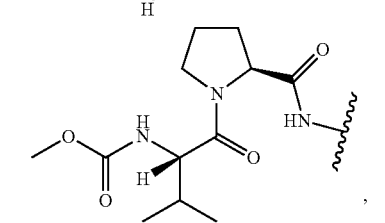
,
-continued
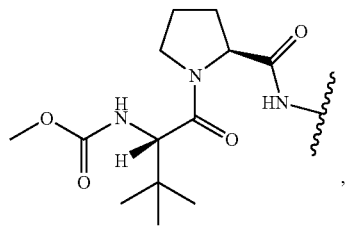
,
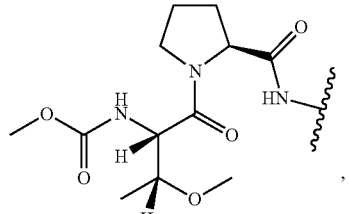
,
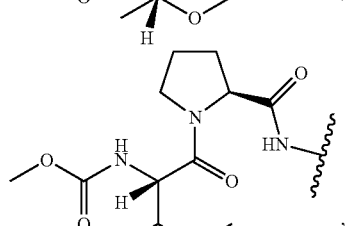
,
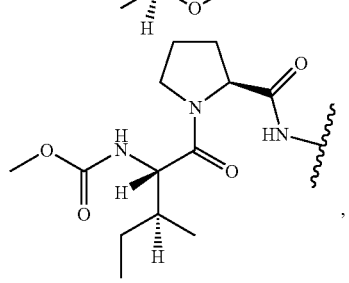
,
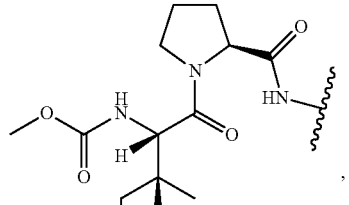
,
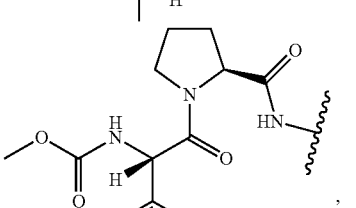
, and
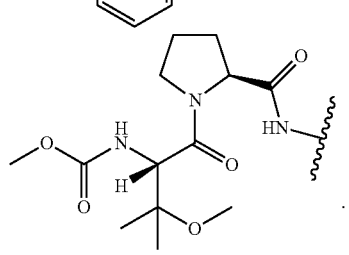
.

Non-limiting examples of preferred Y when A is
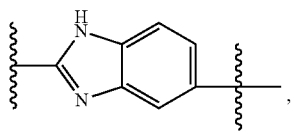 [SMILES: *c1ccc2[nH]c(*)nc2c1 ; ","]
optionally substituted with one or more $R_A$ as described herein, and Y-A is
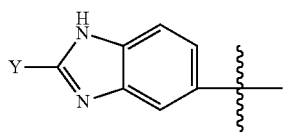
include:
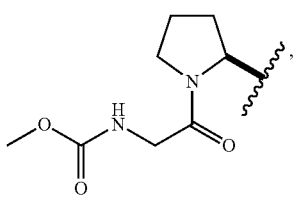
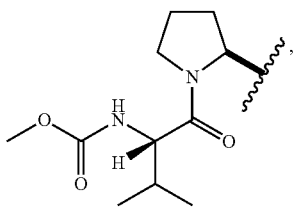
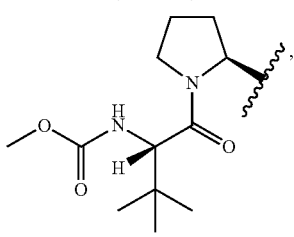
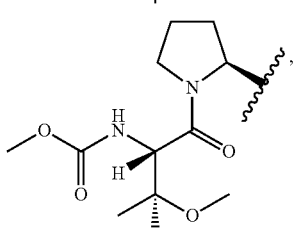
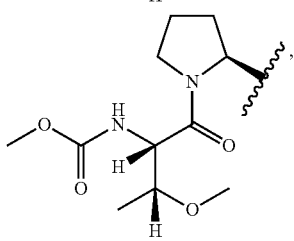
-continued
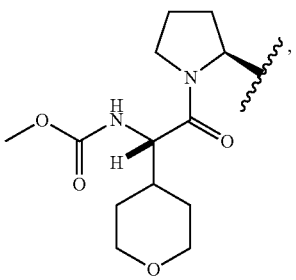
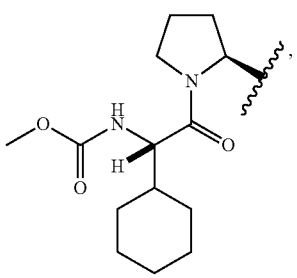
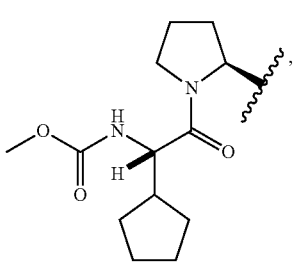
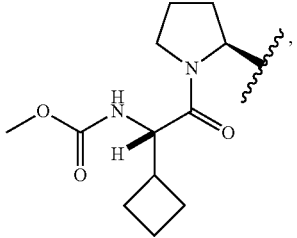
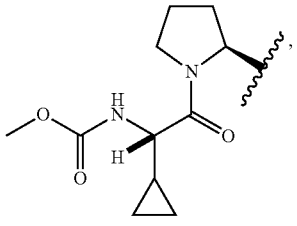
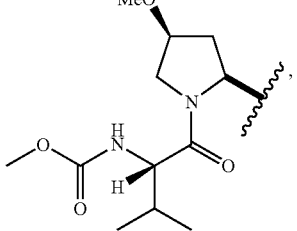

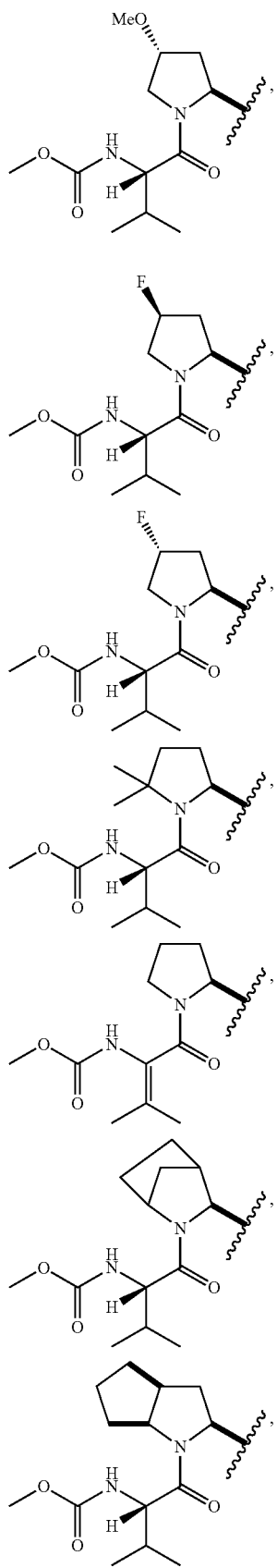
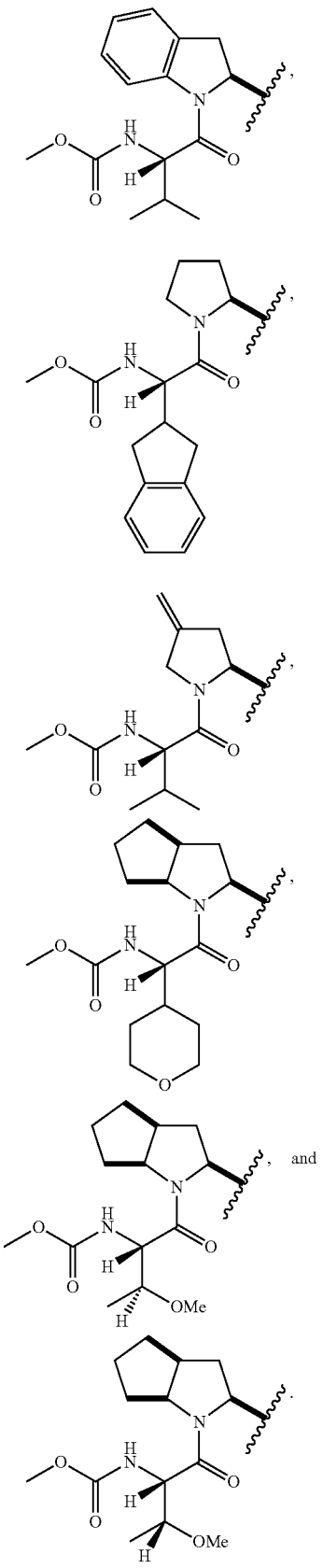

Non-limiting examples of preferred Z where B is
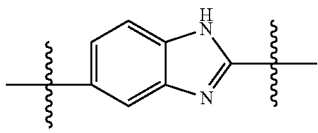
optionally substituted with one or more R$_A$ as described herein, and B—Z is
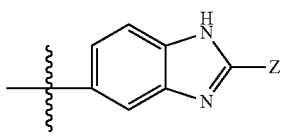
include:
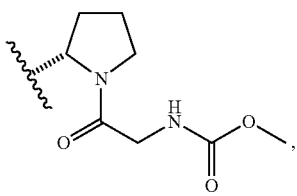
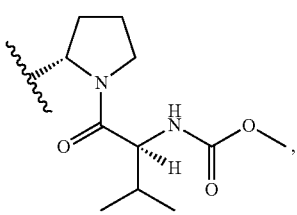
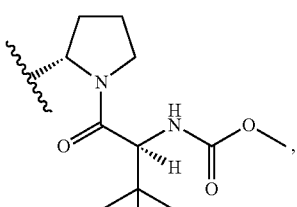
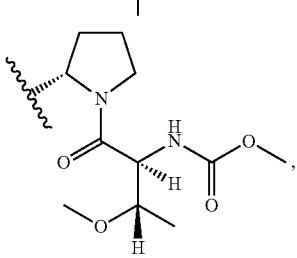
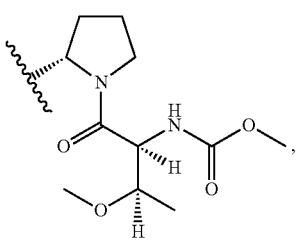
-continued
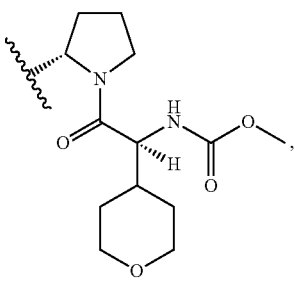
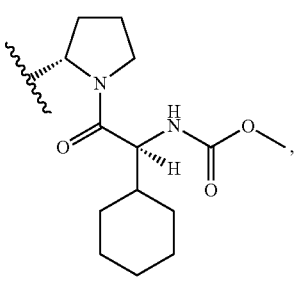
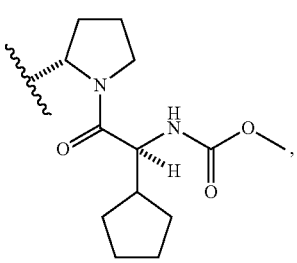
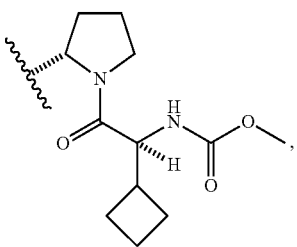
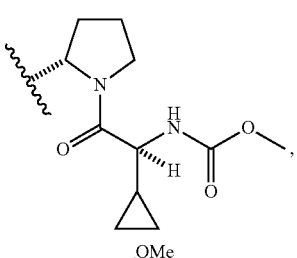
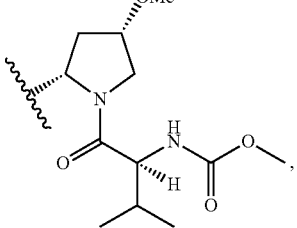

147
-continued
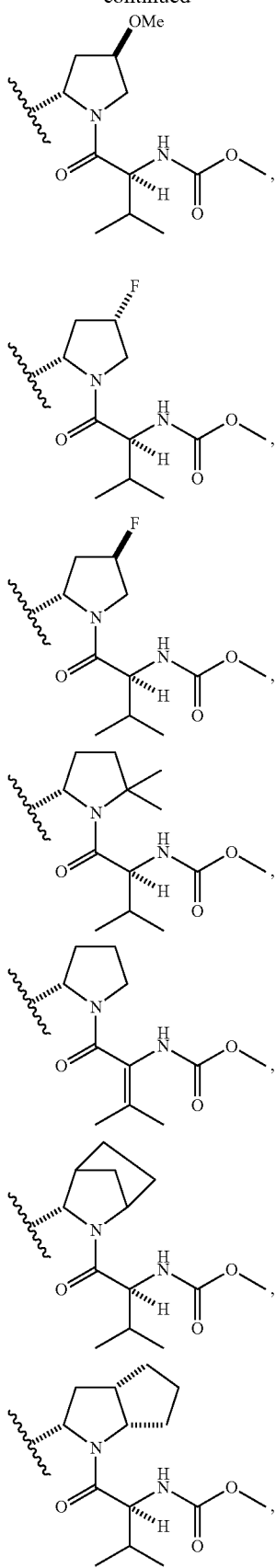
148
-continued
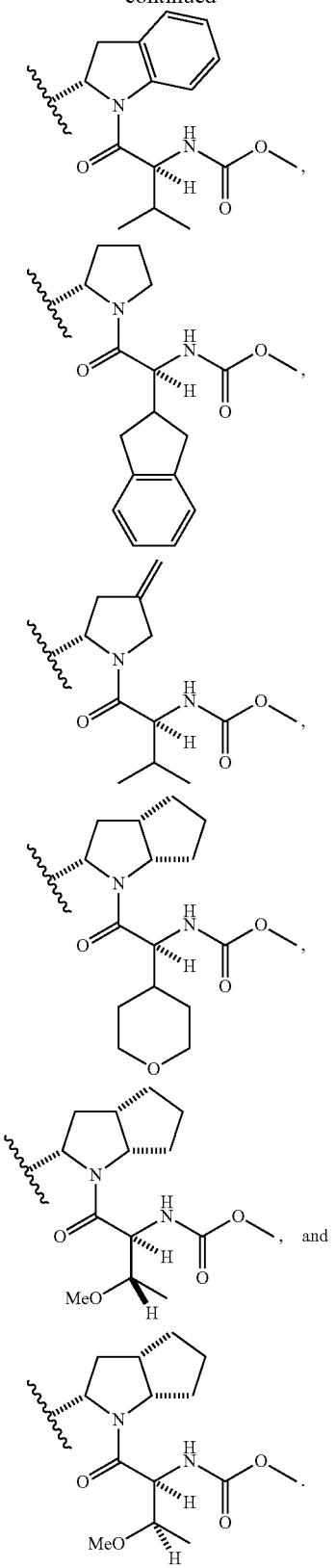
In still another aspect, the present invention features compounds of Formula $I_F$ and pharmaceutically acceptable salts thereof:

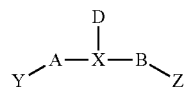

wherein:
X is

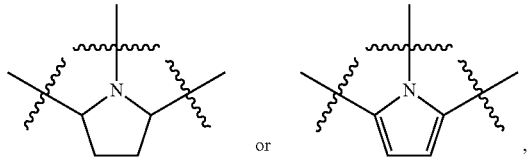

wherein X is optionally substituted with one or more $R_A$

A is

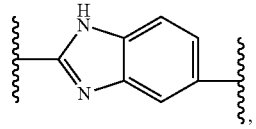

wherein A is optionally substituted with one or more $R_A$;
B is

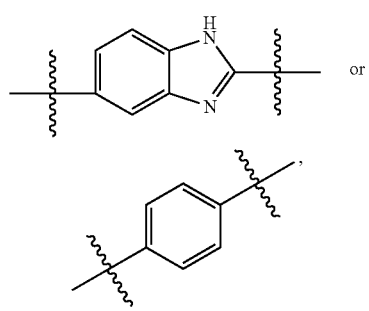

wherein B is optionally substituted with one or more $R_A$; and
Y, Z, $R_A$, and D are as described hereinabove (e.g., Y, Z, $R_A$, and D as described for Formula I, $I_A$, $I_B$, $I_C$, $I_D$, or $I_E$, preferably as described for Formula $I_E$).

In one embodiment of this aspect of the invention, X is

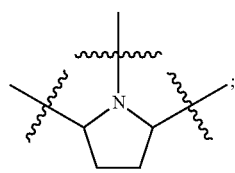 [SMILES: *C1CCC(*)N1*]

$I_F$

A is

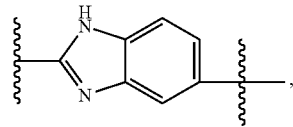

wherein A is optionally substituted with one or more $R_A$; B is

wherein B is optionally substituted with one or more $R_A$; Y is

Z is

-continued

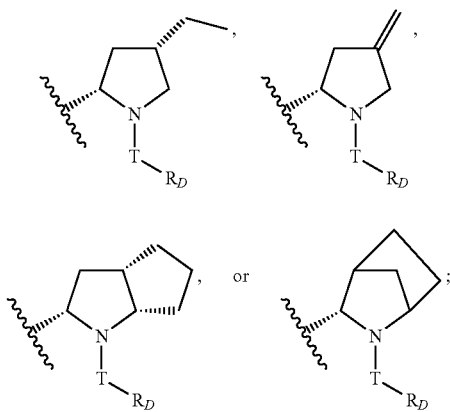

and D, $R_A$, T and $R_D$ are as defined hereinabove (e.g., as described for Formula I, $I_A$, $I_B$, $I_C$, $I_D$ or $I_E$, preferably as described for Formula $I_E$).

In another embodiment according to this aspect of the invention, A or B are optionally substituted with one or more substituents selected from: $R_A$ wherein $R_A$ is each independently halogen (e.g., fluoro, chloro); $L_S$-$R_E$ where $L_S$ is a single bond, and $R_E$ is —$C_1$-$C_6$alkyl (e.g., methyl), —O—$R_S$ (e.g., —O—$C_1$-$C_6$alkyl, —OCH$_3$), or —$C_1$-$C_6$alkyl optionally substituted with one or more halogen (e.g., —CF$_3$); or $L_S$-$R_E$ where $L_S$ is a $C_1$-$C_6$alkylene and $R_E$ is —O—$R_S$ (e.g., —$C_1$-$C_6$alkyl-O—$C_1$-$C_6$alkyl, —CH$_2$OCH$_3$). This embodiment includes compounds where A and B are both substituted by one $R_A$; compounds where A and B are both substituted by zero $R_A$; compounds where A is substituted by one $R_A$ and B is substituted by zero $R_A$; and compounds where A is substituted by zero $R_A$ and B is substituted by one $R_A$. Preferably, A is

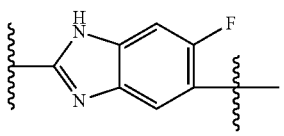 [SMILES: *c1nc2cc(*)c(F)cc2[nH]1]

and B is

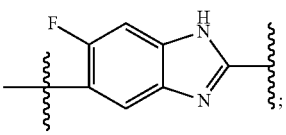 [SMILES: *c1nc2cc(*)c(F)cc2[nH]1]

or A is

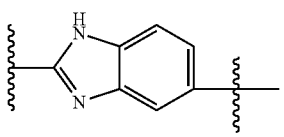 [SMILES: *c1ccc2[nH]c(*)nc2c1]

and B is

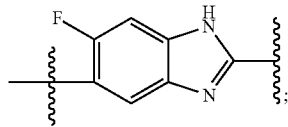 [SMILES: *c1nc2cc(*)c(F)cc2[nH]1]

or A is

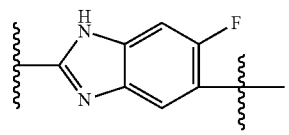 [SMILES: *c1nc2cc(*)c(F)cc2[nH]1]

and B is

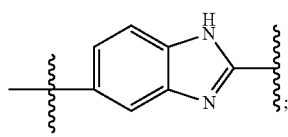 [SMILES: *c1ccc2[nH]c(*)nc2c1]

or A is

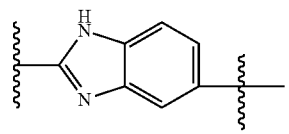 [SMILES: *c1ccc2[nH]c(*)nc2c1]

and B is

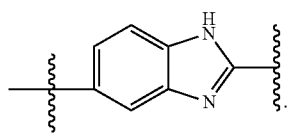 [SMILES: *c1ccc2[nH]c(*)nc2c1]

In a further embodiment of this aspect of the invention, T-$R_D$ is independently selected at each occurrence from the group consisting of

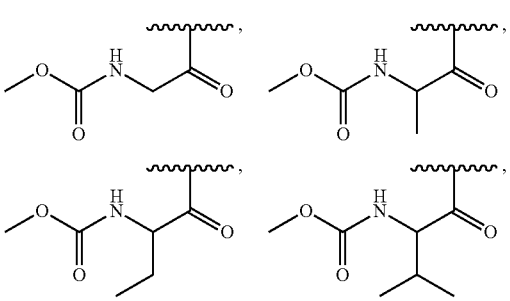

-continued

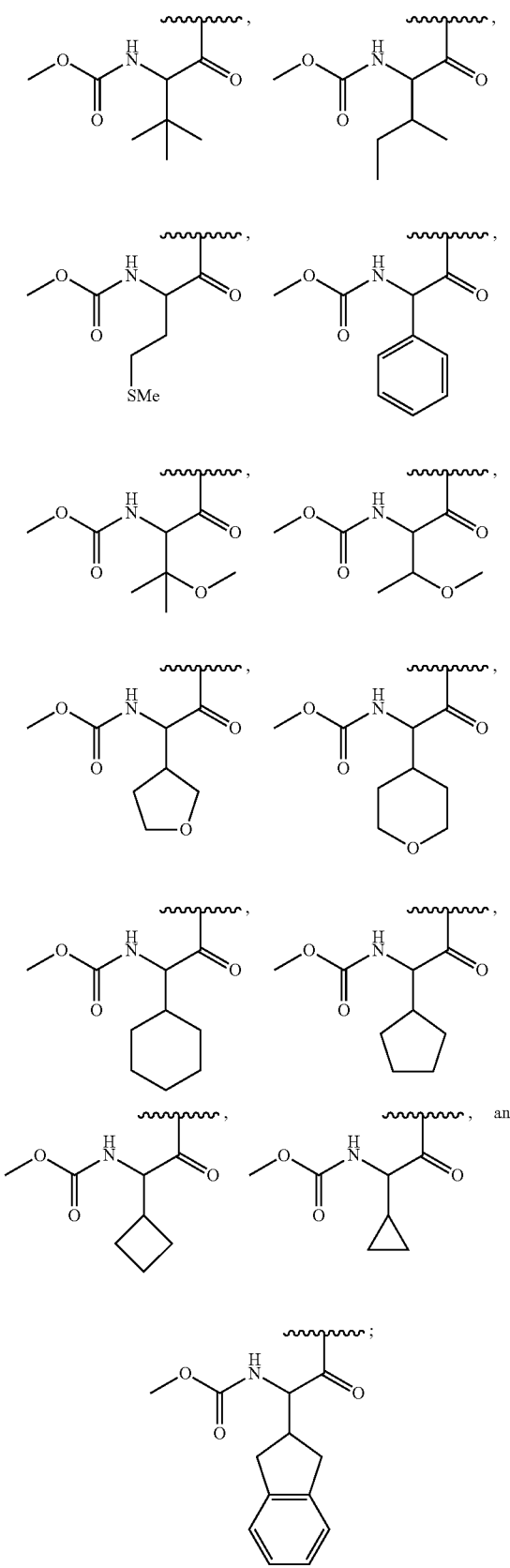

wherein compounds having (S) stereochemistry

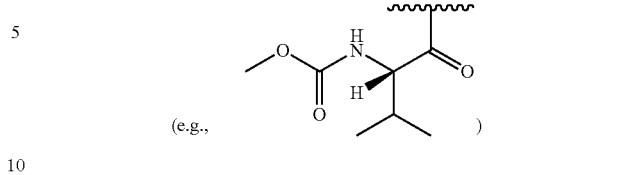

are preferred and wherein D is as defined hereinabove.

In another embodiment, this aspect of the invention features compound of Formula $I_F$ and pharmaceutically acceptable salts thereof, wherein:

X is

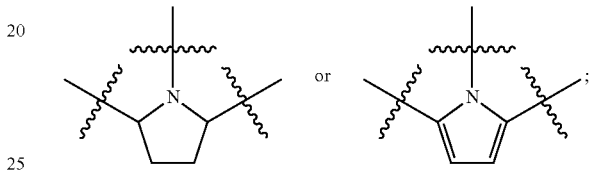

A is

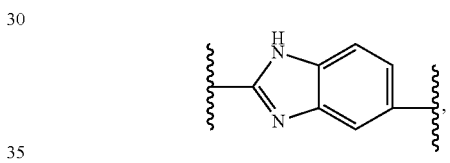

wherein A is optionally substituted with one or more $R_A$; B is

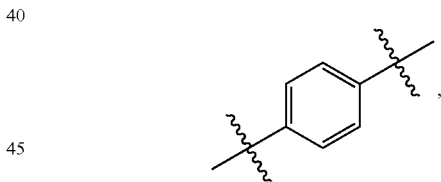

wherein B is optionally substituted with one or more $R_A$; Y is

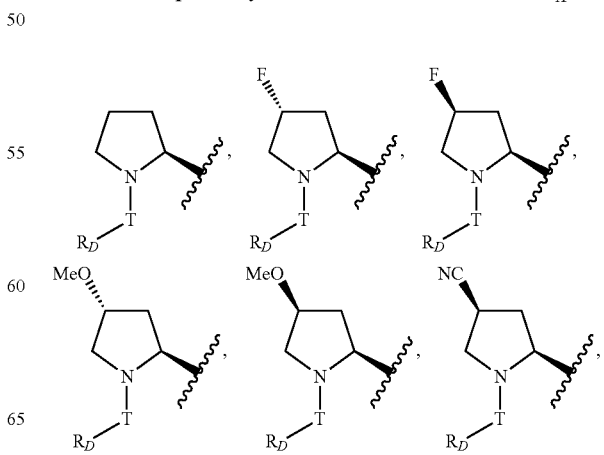

-continued

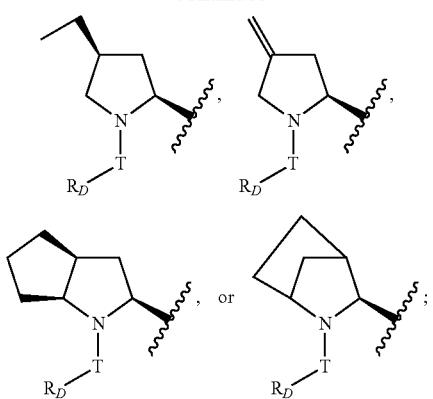

Z is

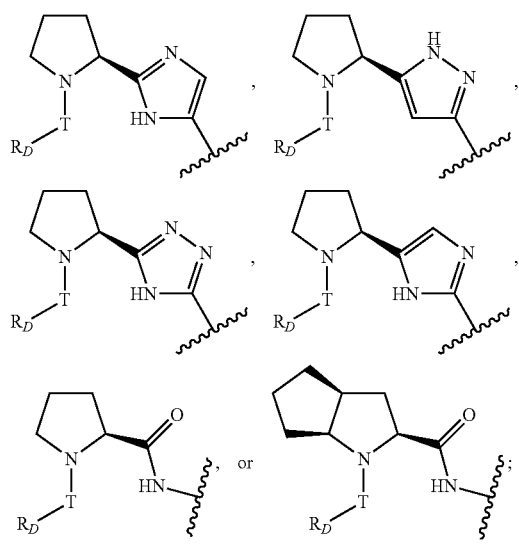

and D, $R_A$, T and $R_D$ are as defined hereinabove. A particular subgroup according to this embodiment includes compounds where A is

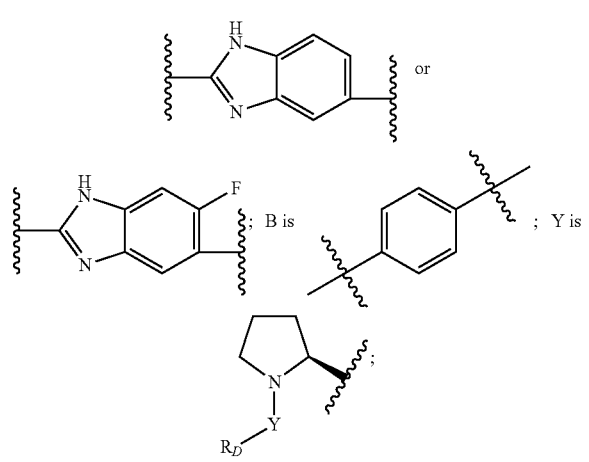

Z is

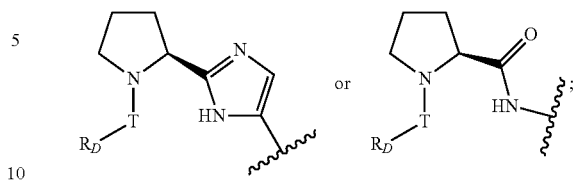

T-$R_D$ is each independently

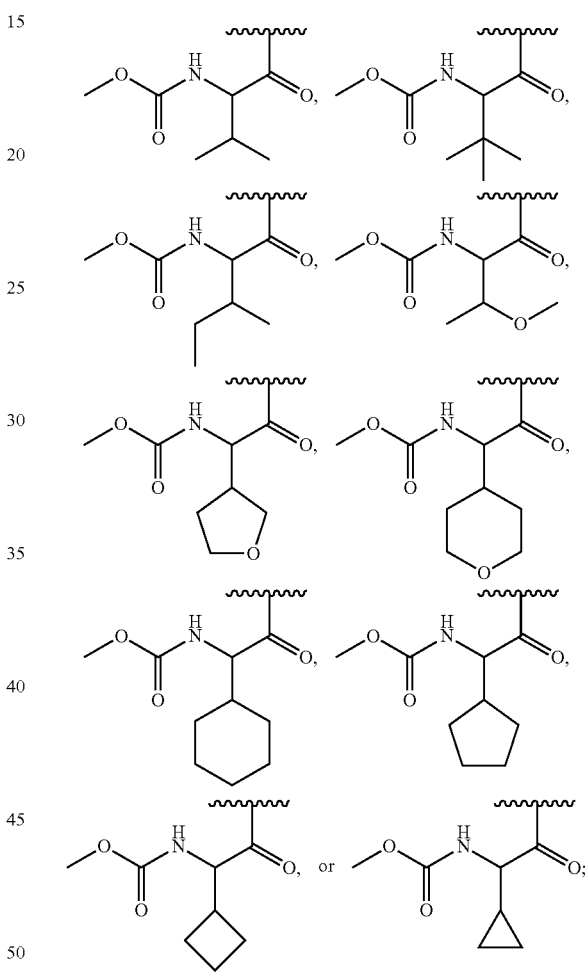

and D is as defined hereinabove.

In yet another embodiment, this aspect of the invention features compounds of Formula $I_F$ and pharmaceutically acceptable salts thereof, wherein: X is

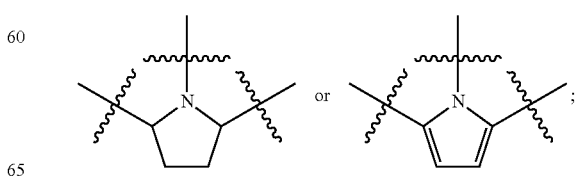

A and B are each

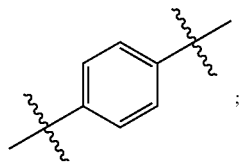 [SMILES: *c1ccc(*)cc1]

Y and Z are each independently

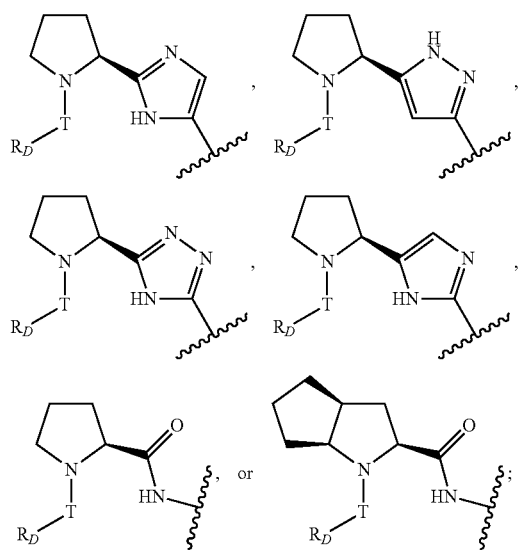

and D, T and $R_D$ are as defined hereinabove. A particular subgroup according to this embodiment includes compounds where T-$R_D$ is each independently selected from

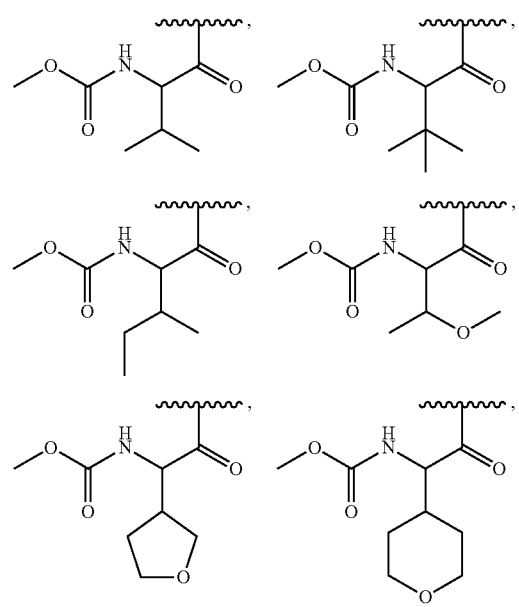

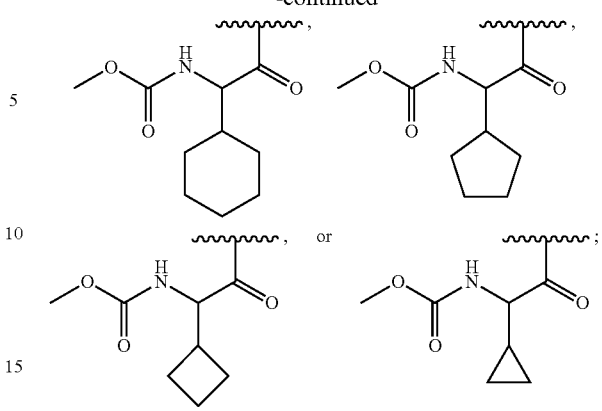

and D is as defined hereinabove.

According to each of the foregoing embodiments and description of this aspect of the invention of Formula $I_F$ are groups and subgroups of compounds having particular values for D. Included in each of the foregoing embodiments are groups and subgroups of compounds with the following particular values for D:

In certain groups of compounds according to Formula $I_F$ and the foregoing embodiments and description of this aspect of the invention, D is

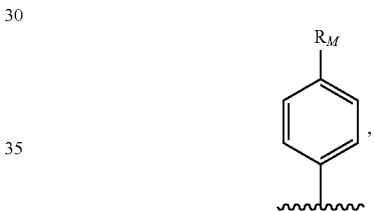

where $R_M$ is fluoro, chloro, tert-butyl, —O—CH$_2$CH$_3$, —O—CF$_3$, —O—CH$_2$CHF$_2$, —O—CH$_2$CH$_2$OCH$_3$, —O—CH$_2$-(3-ethyloxetan-3-yl), —O—CH$_2$-(1,3-dioxolan-4-yl), —O-cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D is optionally substituted by one or more additional $R_M$, selected from the group consisting of halogen (e.g., fluoro, chloro) or $C_1$-$C_6$alkyl (e.g., methyl).

In other groups of compounds according Formula $I_F$ and the foregoing embodiments and description of this aspect of the invention, D is

wherein $G_2$ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional $R_M$ selected from the group consisting of halogen (e.g., fluoro, chloro), or $C_1$-$C_6$alkyl (e.g., methyl). In particular according to these groups are compounds where D is

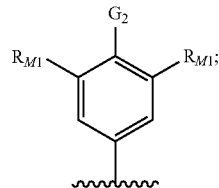

$G_2$ is piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl; and $R_{M1}$ is each independently hydrogen, fluoro, chloro, or methyl.

In other groups of compounds according Formula $I_F$ and the foregoing embodiments and description of this aspect of the invention, D is

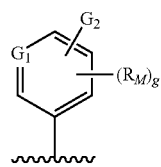

wherein $G_1$ is N, C—H, or C—$R_M$; $G_2$ is

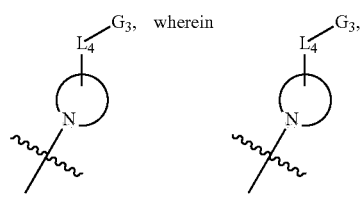

$R_M$, and g are as defined hereinabove. In particular according to these groups, $R_M$ is each independently fluoro, chloro, methyl, methoxy, trifluoromethyl, or trifluoromethoxy; g is 0, 1, or 2; and

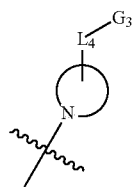

is as defined hereinabove. In further subgroups $L_4$ is a bond; $G_2$ is

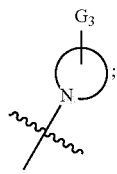

$R_M$ is each independently fluoro, chloro, methyl, methoxy, trifluoromethyl, or trifluoromethoxy; and g is 0, 1, or 2. In particular subgroups,

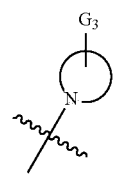

is 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl; $R_M$ is each independently fluoro, chloro, methyl, methoxy, trifluoromethyl, or trifluoromethoxy; and g is 0, 1, or 2. In other subgroups $L_4$ is $C_1$-$C_6$ alkylene, —O—, or —S(O)$_2$—; $G_2$ is

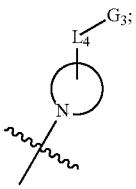

$R_M$ is each independently fluoro, chloro, methyl, methoxy, trifluoromethyl, or trifluoromethoxy; and g is 0, 1, or 2. In particular subgroups,

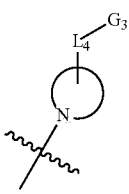

is 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl; $R_M$ is each independently fluoro, chloro, methyl, methoxy, trifluoromethyl, or trifluoromethoxy; and g is 0, 1, or 2. In further subgroups of compounds D is

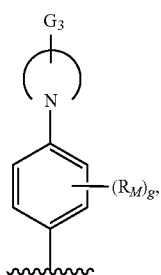

wherein G₃ is phenyl optionally substituted with one or two R_{G3}; g is 0, 1, or 2; R_M is each independently fluoro, chloro, methyl, methoxy, trifluoromethyl, or trifluoromethoxy; and

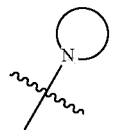

and R_{G3} are as defined above. In other groups of compounds D is

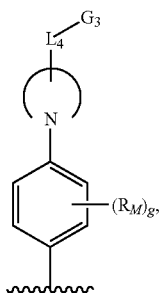

wherein L₄ is $C_1$-$C_6$ alkylene, —O—, or —S(O)₂—; G₃ is phenyl optionally substituted with one or two R_{G3}; g is 0, 1, or 2; R_M is each independently fluoro, chloro, methyl, methoxy, trifluoromethyl, or trifluoromethoxy; and

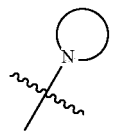

and R_{G3} are as defined above. In further subgroups of compounds D is

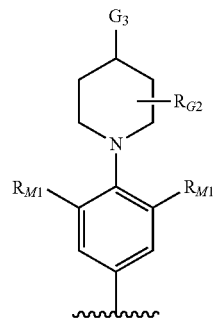

wherein G₃ is phenyl optionally substituted with one or two R_{G3} as defined hereinabove; R_{M1} is each independently hydrogen, fluoro, chloro, or methyl; and R_{G2} is an optional substituent, as described above, selected from the group consisting of —C(O)$C_1$-$C_6$alkyl, —$C_1$-$C_6$alkyl, —$C_1$-$C_6$haloalkyl, —O—$C_1$-$C_6$alkyl, and —O—$C_1$-$C_6$haloalkyl.

In other groups of compounds according Formula $I_F$ and the foregoing embodiments and description of this aspect of the invention, D is

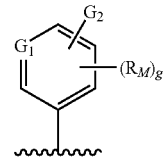

wherein G₁ is N, C—H, or C—R_M; G₂ is

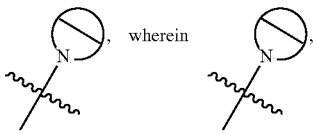, wherein

R_M, and g are as defined hereinabove. In particular according to these subgroups, R_M is each independently fluoro, chloro, methyl, methoxy, trifluoromethyl, or trifluoromethoxy; g is 0, 1, or 2; and

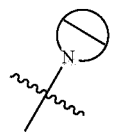

is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl. In further subgroups of compounds D is

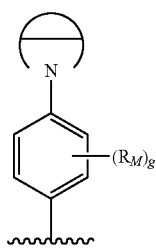

wherein g is 0, 1, or 2; R_M is each independently fluoro, chloro, methyl, methoxy, trifluoromethyl, or trifluoromethoxy; and

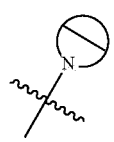

is as defined above. In further subgroups of compounds D is

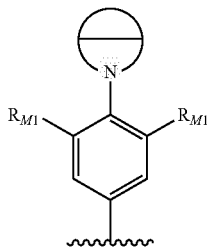

wherein $R_{M1}$ is each independently hydrogen, fluoro, chloro, or methyl and

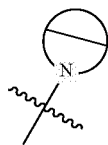

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In other groups of compounds according Formula $I_F$ and the foregoing embodiments and description of this aspect of the invention, D is

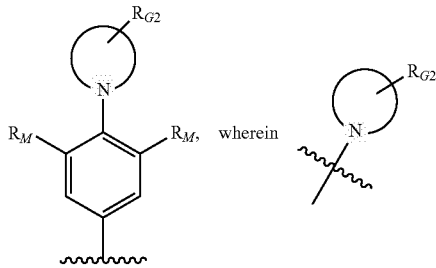

is a monocyclic 4-8 membered nitrogen-containing heterocycle (e.g., azetidinyl, pyrrolidinyl, piperidinyl) substituted with one or more $R_{G2}$, wherein $R_{G2}$ at each occurrence is each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; and $R_M$ is each independently halogen, —C$_1$-C$_6$alkyl, —C$_1$-C$_6$haloalkyl, —O—C$_1$-C$_6$alkyl, or —O—C$_1$-C$_6$haloalkyl. In each group of compounds according to the foregoing embodiments

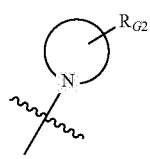

is azetidinyl, pyrrolidinyl, or piperidinyl substituted with one or two $R_{G2}$, wherein $R_{G2}$ at each occurrence is each methyl, ethyl, isopropyl, tert-butyl, fluoro, chloro, or trifluoromethyl; and $R_M$ is each independently fluoro, chloro, or methyl. For example

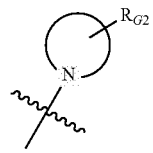

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

In still another aspect, the present invention features compounds of Formula $I_G$ and pharmaceutically acceptable salts thereof,
wherein:

$$I_G$$

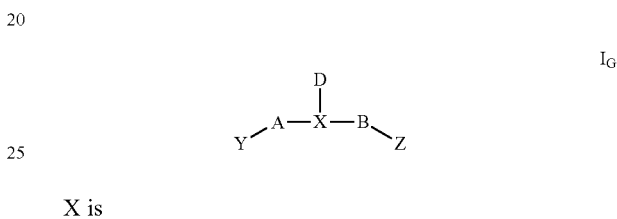

X is

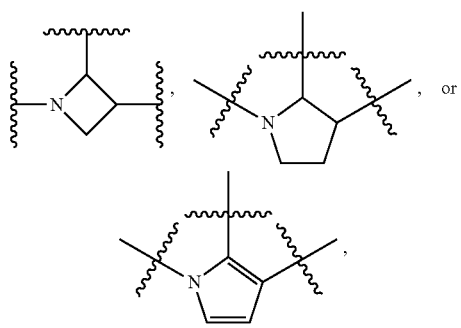

wherein X is optionally substituted with one or more $R_A$
A is

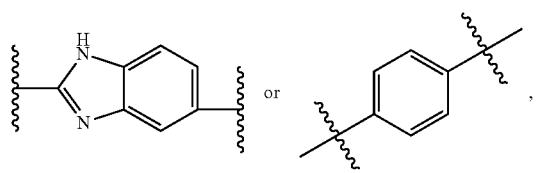

wherein A is optionally substituted with one or more $R_A$;
B is

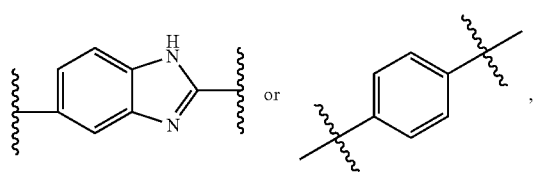

wherein B is optionally substituted with one or more $R_A$; and

Y, Z, $R_A$, and D are as described hereinabove (e.g., as described for Formula I, $I_A$, $I_B$, $I_C$, $I_D$, $I_E$ or $I_F$, preferably as described for Formula $I_E$).

In one embodiment, this aspect of the invention features compounds of Formula $I_G$ and pharmaceutically acceptable salts thereof, wherein: X is

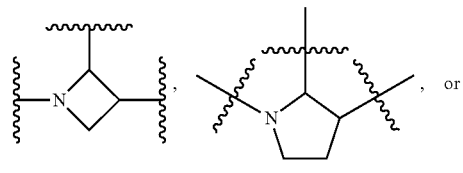, or

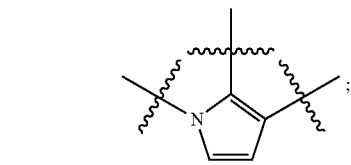;

A is

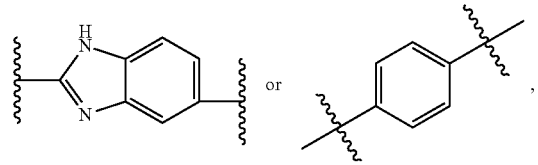

wherein A is optionally substituted with one $R_A$; B is

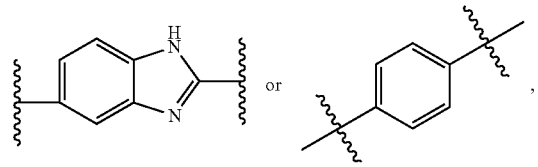

wherein B is optionally substituted with one $R_A$; $R_A$ is halogen (e.g., fluoro, chloro); $L_S$-$R_E$ where $L_S$ is a single bond and $R_E$ is —$C_1$-$C_6$alkyl (e.g., methyl), —O—$R_S$ (e.g., —O—$C_1$-$C_6$alkyl, —$OCH_3$), or —$C_1$-$C_6$alkyl optionally substituted with one or more halogen (e.g., —$CF_3$); or $L_S$-$R_E$ where $L_S$ is a $C_1$-$C_6$alkylene and $R_E$ is —O—$R_S$ (e.g., —$C_1$-$C_6$alkyl-O—$C_1$-$C_6$alkyl, —$CH_2OCH_3$); Y and Z are each independently

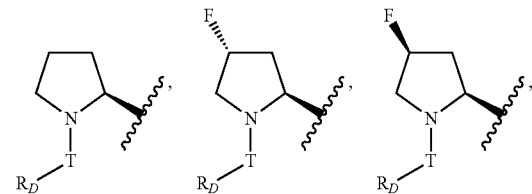

-continued

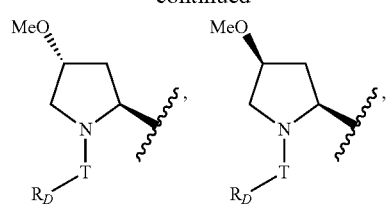

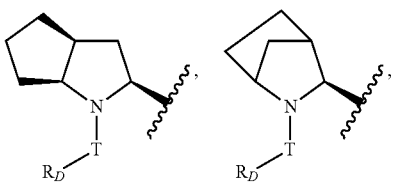

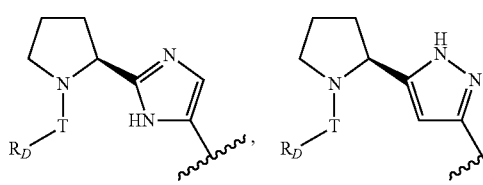

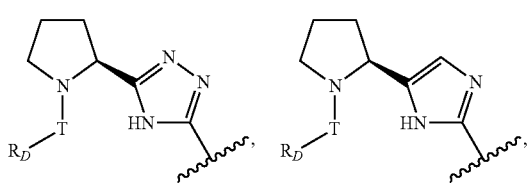

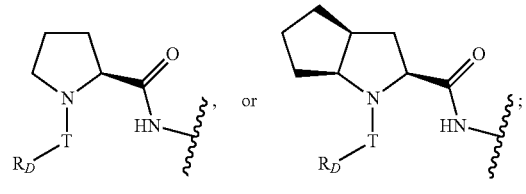

T-$R_D$ is each independently

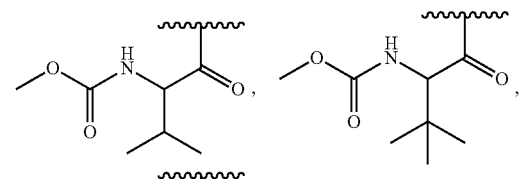

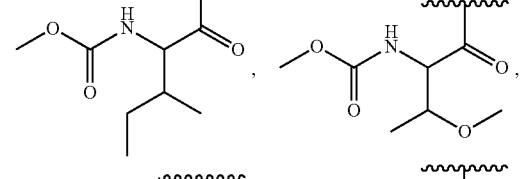

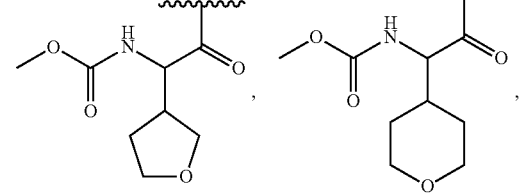

-continued

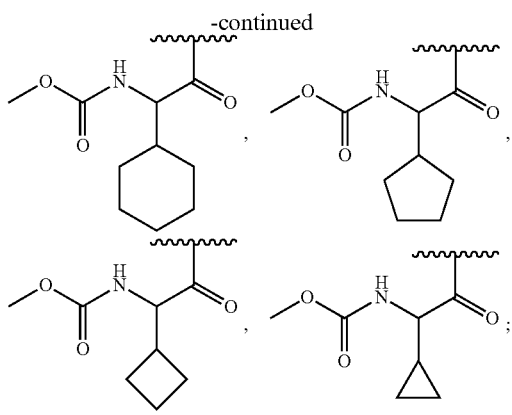

and D is as defined hereinabove.

In another embodiment, this aspect of the invention features compounds of Formula $I_G$ and pharmaceutically acceptable salts thereof, wherein X is

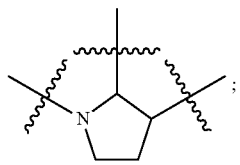 [SMILES: *C1CCN(*)C1*]

A is

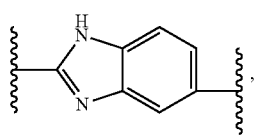

wherein A is optionally substituted with one $R_A$; B is

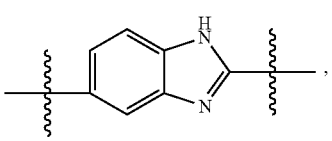

wherein B is optionally substituted with one $R_A$; $R_A$ is halogen (e.g., fluoro, chloro); $L_S$-$R_E$ where $L_S$ is a single bond and $R_E$ is —$C_1$-$C_6$alkyl (e.g., methyl), —O—$R_S$ (e.g., —O—$C_1$-$C_6$alkyl, —OCH$_3$), or —$C_1$-$C_6$alkyl optionally substituted with one or more halogen (e.g., —CF$_3$); or $L_S$-$R_E$ where $L_S$ is a $C_1$-$C_6$alkylene and $R_E$ is —O—$R_S$ (e.g., —$C_1$-$C_6$alkyl-O—$C_1$-$C_6$alkyl, —CH$_2$OCH$_3$); Y and Z are each independently

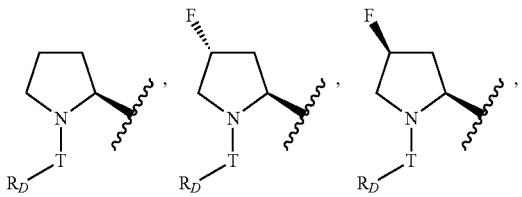

-continued

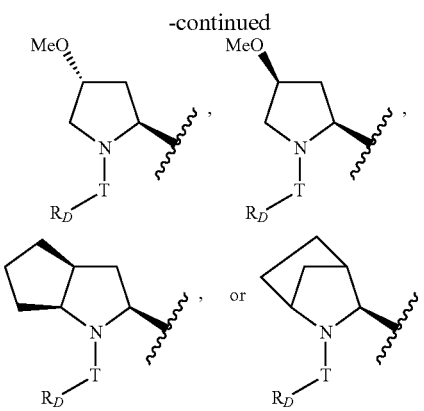

T-$R_D$ is each independently

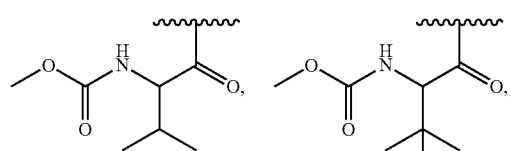

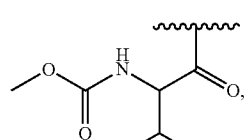 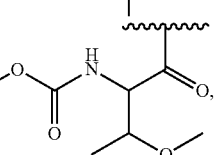

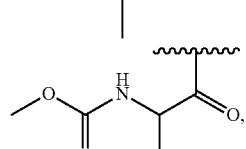 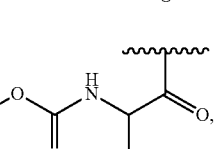

 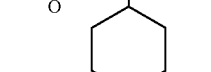

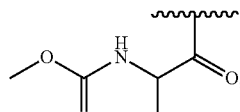 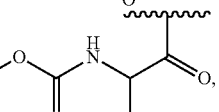

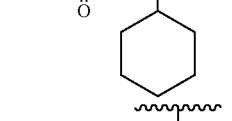 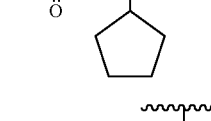

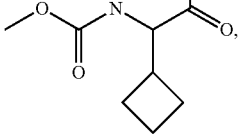, or 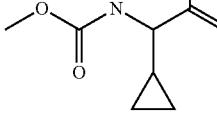.

wherein compounds having (S) stereochemistry (e.g., 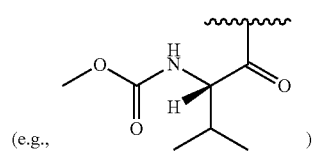 [SMILES: *C(=O)[C@@H](NC(=O)OC)C(C)C] )

are particularly contemplated; and D is as defined hereinabove. This subgroup includes compounds where A and B are both substituted by one $R_A$; compounds where A and B are both substituted by zero $R_A$; compounds where A is substituted by one $R_A$ and B is substituted by zero $R_A$; and compounds where A is substituted by zero $R_A$ and B is substituted by one $R_A$. In particular, according to this subgroup are included compounds where A is

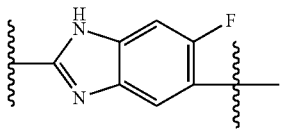

and B is

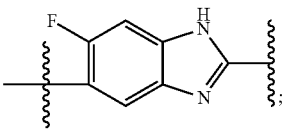 [SMILES: *c1nc2cc(*)c(F)cc2[nH]1]

or A is

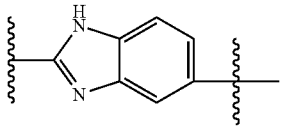

and B is

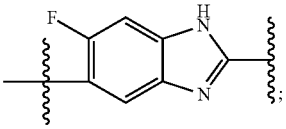 [SMILES: *c1nc2cc(*)c(F)cc2[nH]1]

or A is

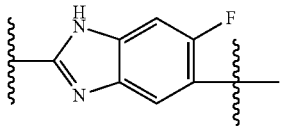

and B is

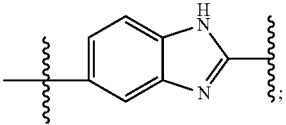

or A is

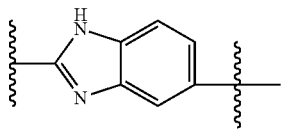

and B is

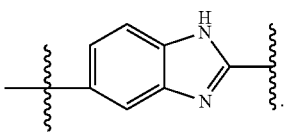 [SMILES: *c1ccc2[nH]c(*)nc2c1]

According to each of the foregoing embodiments and description of this aspect of the invention of Formula $I_G$ are groups and subgroups of compounds having particular values for D. Included in each of the foregoing embodiments are groups and subgroups of compounds with the following particular values for D:

Groups of compounds according to this aspect of the invention include compounds where D is $C_6$-$C_{10}$aryl (e.g., phenyl, naphthyl, indanyl), or 5- to 10-membered heteroaryl (pyridinyl, thiazolyl, 4,5,6,7-tetrahydrobenzo[d]thiazolyl, benzo[d]thiazolyl, indazolyl, benzo[d][1,3]dioxol-5-yl), and D is substituted with one or more $R_M$. Particular subgroups according to this aspect and these embodiments include compounds wherein $R_M$ is halogen (e.g., fluoro, chloro, bromo); $C_1$-$C_6$alkyl (e.g., tert-butyl); $C_1$-$C_6$alkyl substituted with one or more halogen (e.g., $CF_3$); —O—$C_1$-$C_6$alkyl (e.g., —O—$CH_2CH_3$); —O—$C_1$-$C_6$alkyl substituted at each occurrence with one or more halogen (e.g., —O—$CF_3$, —O—$CH_2CHF_2$) or —O—$C_1$-$C_6$alkyl (—O—$CH_2CH_2OCH_3$); —O—$C_1$-$C_6$alkyl (e.g., —O—$CH_2$) substituted with an optionally substituted 3- to 12-membered heterocycle (e.g., 3-ethyloxetan-3-yl, 1,3-dioxolan-4-yl); —O—$R_S$ where $R_S$ is an optionally substituted 3- to 12-membered carbocycle or heterocycle (e.g., cyclopentyl, cyclohexyl, phenyl, 1,3-dioxan-5-yl); —N($R_S$)C(O)$R_S'$ wherein $R_S$ and $R_S'$ are each independently $C_1$-$C_6$alkyl (e.g., —N(t-Bu)C(O)Me); $SF_5$; —$SO_2R_S$ wherein $R_S$ is $C_1$-$C_6$alkyl (e.g., —$SO_2Me$); or $C_3$-$C_{12}$carbocycle (e.g., cyclopropyl, cyclohexyl, phenyl). Other subgroups according to this embodiment include compounds wherein D is phenyl substituted by $G_2$ and optionally substituted by one or more $R_M$, wherein $G_2$ is a 3- to 12-membered heterocycle (e.g., pyridinyl, piperidinyl, pyrrolidinyl, azetidinyl, oxazolyl) wherein the heterocycle is optionally substituted with one or more substituents selected from halogen, hydroxy, oxo, cyano, $C_1$-$C_6$alkyl (e.g., methyl), $C_2$-$C_6$alkenyl, $C_2$-$C_6$alkynyl, $C_1$-$C_6$haloalkyl (e.g., $CF_3$), $C_2$-$C_6$haloalkenyl, $C_2$-$C_6$haloalkynyl, —O—$C_1$-$C_6$alkyl (e.g. —O—$CH_3$), —C(O)O$R_S$ (e.g., —C(O)O$CH_3$), —C(O)$R_S$ (e.g., —C(O)$CH_3$), —N($R_S R_S'$), or $L_4$-$G_3$; $R_M$ is halogen (e.g., fluoro, chloro), alkyl (e.g., methyl), haloalkyl (e.g., $CF_3$), or —O—$C_1$-$C_6$alkyl (e.g., —O—$CH_3$); and $L_4$, $G_3$, $R_S$, and $R_S'$ are as defined hereinabove.

In certain groups of compounds according to Formula $I_G$ and the foregoing embodiments and description of this aspect of the invention, D is

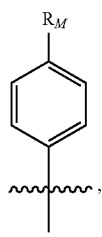

where $R_M$ is fluoro, chloro, tert-butyl, —O—CH$_2$CH$_3$, —O—CF$_3$, —O—CH$_2$CHF$_2$, —O—CH$_2$CH$_2$OCH$_3$, —O—CH$_2$-(3-ethyloxetan-3-yl), —O—CH$_2$-(1,3-dioxolan-4-yl), —O-cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D is optionally substituted by one or more additional $R_M$, selected from the group consisting of halogen (e.g., fluoro, chloro) or C$_1$-C$_6$alkyl (e.g., methyl).

In other groups of compounds according Formula I$_G$ and the foregoing embodiments and description of this aspect of the invention, D is

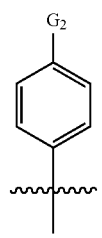

wherein G$_2$ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional $R_M$ selected from the group consisting of halogen (e.g., fluoro, chloro), or C$_1$-C$_6$alkyl (e.g., methyl). In particular according to these groups are compounds where D is

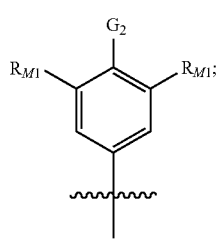

G$_2$ is piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl; and $R_{M1}$ is each independently hydrogen, fluoro, chloro, or methyl.

In other groups of compounds according Formula I$_G$ and the foregoing embodiments and description of this aspect of the invention, D is

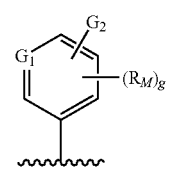

wherein G$_1$ is N, C—H, or C—R$_M$; G$_2$ is

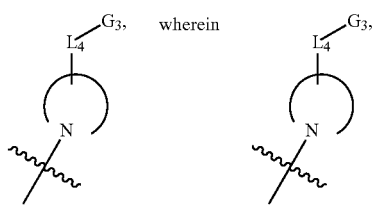

$R_M$, and g are as defined hereinabove. In particular according to these groups, $R_M$ is each independently fluoro, chloro, methyl, methoxy, trifluoromethyl, or trifluoromethoxy; g is 0, 1, or 2; and

is as defined hereinabove. In further subgroups L$_4$ is a bond; G$_2$ is

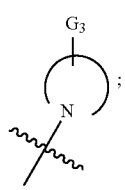

$R_M$ is each independently fluoro, chloro, methyl, methoxy, trifluoromethyl, or trifluoromethoxy; and g is 0, 1, or 2. In particular subgroups,

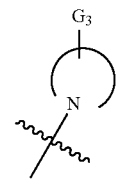

is 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl; $R_M$ is each independently fluoro, chloro, methyl, methoxy, trifluoromethyl, or trifluoromethoxy; and g is 0, 1, or 2. In other subgroups $L_4$ is $C_1$-$C_6$ alkylene, —O—, or —S(O)$_2$—; $G_2$ is

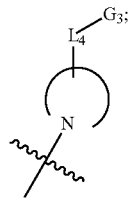

$R_M$ is each independently fluoro, chloro, methyl, methoxy, trifluoromethyl, or trifluoromethoxy; and g is 0, 1, or 2. In particular subgroups,

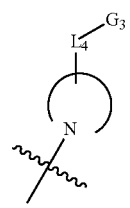

is 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl; $R_M$ is each independently fluoro, chloro, methyl, methoxy, trifluoromethyl, or trifluoromethoxy; and g is 0, 1, or 2. In further subgroups of compounds D is

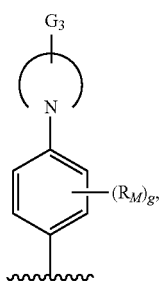

wherein $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

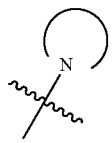 [SMILES: *N]

and $R_{G3}$ are as defined above. In other groups of compounds D is

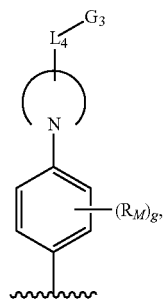

wherein $L_4$ is $C_1$-$C_6$ alkylene, —O—, or —S(O)$_2$—; $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

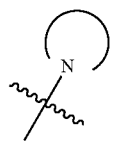

and $R_{G3}$ are as defined above. In further subgroups of compounds D is

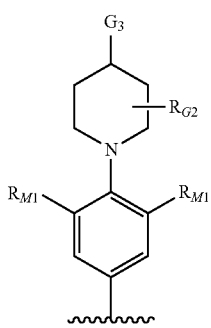

wherein $G_3$ is phenyl optionally substituted with one or two $R_{G3}$ as defined hereinabove; $R_{M1}$ is each independently hydrogen, fluoro, chloro, or methyl; and $R_{G2}$ is an optional substituent, as described above, selected from the group consisting of —C(O)C$_1$-C$_6$alkyl, —C$_1$-C$_6$alkyl, —C$_1$-C$_6$haloalkyl, —O—C$_1$-C$_6$alkyl, and —O—C$_1$-C$_6$haloalkyl.

In other groups of compounds according Formula $I_G$ and the foregoing embodiments and description of this aspect of the invention, D is

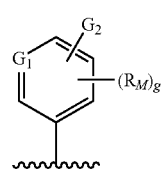

wherein G₁ is N, C—H, or C—R$_M$; G₂ is

 , wherein  ,

R$_M$, and g are as defined hereinabove. In particular according to these subgroups, R$_M$ is each independently fluoro, chloro, methyl, methoxy, trifluoromethyl, or trifluoromethoxy; g is 0, 1, or 2; and

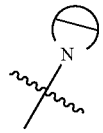 [SMILES: *N]

is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl. In further subgroups of compounds D is

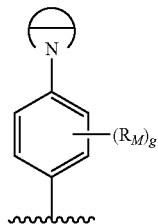

wherein g is 0, 1, or 2; R$_M$ is each independently fluoro, chloro, methyl, methoxy, trifluoromethyl, or trifluoromethoxy; and

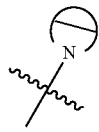

is as defined above. In further subgroups of compounds D is

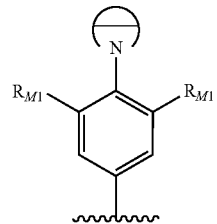

wherein R$_{M1}$ is each independently hydrogen, fluoro, chloro, or methyl and

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In other groups of compounds according Formula I$_G$ and the foregoing embodiments and description of this aspect of the invention, D is

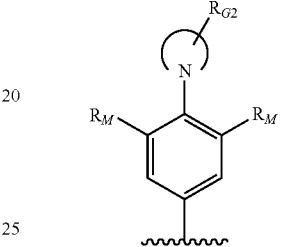 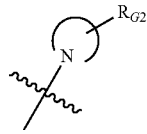 wherein is a monocyclic 4-8 membered nitrogen-containing heterocycle (e.g., azetidinyl, pyrrolidinyl, piperidinyl) substituted with one or more R$_{G2}$, wherein R$_{G2}$ at each occurrence is each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; and R$_M$ is each independently halogen, —C$_1$-C$_6$alkyl, —C$_1$-C$_6$haloalkyl, —O—C$_1$-C$_6$alkyl, or —O—C$_1$-C$_6$haloalkyl. In each group of compounds according to the foregoing embodiments

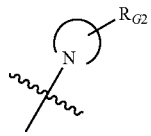

is azetidinyl, pyrrolidinyl, or piperidinyl substituted with one or two R$_{G2}$, wherein R$_{G2}$ at each occurrence is each methyl, ethyl, isopropyl, tert-butyl, fluoro, chloro, or trifluoromethyl; and R$_M$ is each independently fluoro, chloro, or methyl. For example

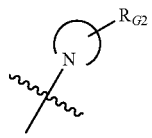

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

The present invention also features compounds of Formulae I$_E$, I$_F$ and I$_G$ as described herein (including each embodiment described hereunder) and pharmaceutically acceptable salts thereof, wherein:

$R_E$ is independently selected at each occurrence from —O—$R_S$, —S—$R_S$, —C(O)$R_S$, —C(O)$R_S$, —C(O)O$R_S$, —N($R_SR_S'$), —S(O)$R_S$, —SO$_2R_S$, —C(O)N($R_SR_S'$), —N($R_S$)C(O)$R_S'$, —N($R_S$)C(O)N($R_S'R_S''$), —N($R_S$)SO$_2R_S'$, —SO$_2$N($R_SR_S'$), —N($R_S$)SO$_2$N($R_S'R_S''$), —N($R_S$)S(O)N($R_S'R_S''$), —OS(O)—$R_S$, —OS(O)$_2$—$R_S$, —S(O)$_2$O$R_S$, —OC(O)O$R_S$, —N($R_S$)C(O)O$R_S'$, —OC(O)N($R_SR_S'$), —N($R_S$)S(O)—$R_S'$, —S(O)N($R_SR_S'$), —P(O)(O$R_S$)$_2$, =C($R_SR_S'$), or —C(O)N($R_S$)C(O)—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, trimethylsilyl, $C_1$-$C_6$alkyl, $C_2$-$C_6$alkenyl, $C_2$-$C_6$alkynyl, $C_1$-$C_6$haloalkyl, $C_2$-$C_6$-haloalkenyl, $C_2$-$C_6$haloalkynyl, —O—$R_S$, —S—$R_S$, —C(O)$R_S$, —C(O)O$R_S$, or —N($R_SR_S'$).

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibuytl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The invention encompasses each conformational isomer of these compounds and mixtures thereof.

Certain compounds of the invention may also exist in zwitterionic form and the invention encompasses each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., A, B, D, X, $L_1$, $L_2$, $L_3$, Y, Z, T, $R_A$ or $R_B$,). Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$carbocyclyl$C_1$-$C_6$alkyl refers to a $C_3$-$C_6$carbocyclyl appended to the parent molecular moiety through a $C_1$-$C_6$alkyl group.

Unless otherwise specified, when a linking element links two other elements in a depicted chemical structure, the leftmost-described component of the linking element is bound to the left element in the depicted structure, and the rightmost-described component of the linking element is bound to the right element in the depicted structure. To illustrate, if the chemical structure is -$L_S$-M-$L_S$'- and M is —N($R_B$)S(O)—, then the chemical structure is -$L_S$-N($R_B$)S(O)-$L_S$'-.

If a linking element in a depicted structure is a bond, then the element left to the linking element is joined directly to the element right to the linking element via a covalent bond. For example, if a chemical structure is depicted as -$L_S$-M-$L_S$'- and M is selected as bond, then the chemical structure will be -$L_S$-$L_S$'-. If two or more adjacent linking elements in a depicted structure are bonds, then the element left to these linking elements is joined directly to the element right to these linking elements via a covalent bond. For instance, if a chemical structure is depicted as -$L_S$-M-$L_S$'-M'-$L_S$"-, and M and $L_S$' are selected as bonds, then the chemical structure will be -$L_S$-M'-$L_S$"-. Likewise, if a chemical structure is depicted as -$L_S$-M-$L_S$'-M'-$L_S$"-, and M, $L_S$' and M' are bonds, then the chemical structure will be -$L_S$-$L_S$"-.

When a chemical formula is used to describe a moiety, the dash(s) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

Where a moiety is substituted with oxo or thioxo, it means that the moiety contains a carbon atom covalently bonded to at least two hydrogens (e.g., $CH_2$), and the two hydrogen radicals are substituted with oxo or thioxo to form C=O or C=S, respectively.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)═C(H)—, —C(H)═C(H)—CH$_2$—, —C(H)═C(H)—CH$_2$—CH$_2$—, —CH$_2$—C(H)═C(H)—CH$_2$—, —C(H)═C(H)—CH(CH$_3$)—, and —CH$_2$—C(H)═C(H)—CH(CH$_2$CH$_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple bonds. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—CH(CH$_2$CH$_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom. Where a carbocycle group is a divalent moiety linking two other elements in a depicted chemical structure (such as A in Formula I), the carbocycle group can be attached to the two other elements through any two substitutable ring atoms. Likewise, where a carbocycle group is a trivalent moiety linking three other elements in a depicted chemical structure (such as X in Formula I), the carbocycle group can be attached to the three other elements through any three substitutable ring atoms, respectively.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group. Where a heterocycle group is a divalent moiety that links two other elements in a depicted chemical structure (such as A in Formula I), the heterocycle group can be attached to the two other elements through any two substitutable ring atoms. Likewise, where a heterocycle group is a trivalent moiety that links three other elements in a depicted chemical structure (such as X in Formula I), the heterocycle group can be attached to the three other elements through any three substitutable ring atoms, respectively.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl"), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, thiomorpholinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl" or indazolyl), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, 4,5,6,7-tetrahydrobenzo[d]thiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may also be, without limitation, a spiro ring system, such as, for example, 1,4-dioxa-8-azaspiro[4.5]decanyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

═══ in a chemical formula refers to a single or double bond.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy, carboxy or phosphate group). Prodrugs often offer advantages of solubility, tissue compatibility, or delayed release in mammals (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention, or phosphate esters of the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS ($3^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

Abbreviations which have been used in the descriptions of the Schemes, Intermediates and Examples that follow are: Ac for acetyl; APCI for atmospheric pressure chemical ionization; aq or aq. for aqueous; atm for atmosphere; Boc for t-butoxycarbonyl; Bu for butyl; t-Bu or tert-butyl for tertiary-butyl; Cbz for benzyloxycarbonyl; dba for dibenzylidineacetone; DCI for desorption chemical ionization; DDQ for 2,3-dichloro-5,6-dicyano-p-benzoquinone; DEPBT for 3-(dietboxyphosphoryloxy)-1,2,3-berizotriazin-4(3H)-one; DIBAL for dfisobutylaiuminum hydride: DMA for N,N-dimethylacetamide; DME for 1,2-dimethoxyethane; DMF for N,N-dimethylformamide; DMSO for dimethyl sulfoxide; DMPU for 1,3-dimethyl-3,4,5,6-tetrahydro-2(1H)-pyrimidinone; dppf for 1,1'-bis(diphenylphosphino)ferrocene; EDC, EDAC or EDCI for N-(3-dimethylaminopropyl)-N'-ethylcarbodiimide hydrochloride; e.e. for enantiomeric excess; ELSD for evaporative light scattering detector; ESI for electrospray ionization; Et for ethyl; $Et_3N$ for triethylamine; EtOAc for ethyl acetate; EtOH for ethanol; $Et_2O$ for diethyl ether; eq or equiv for equivalents; Fmoc for 9-fluorenylmethoxycarbonyl; HATU for O-(7-azabenzotriazol-1-yl)-N,N,N',N'-tetramethyluronium hexafluorophosphate; HOBt for 1-hydroxybenzotriazole; HPLC for high performance liquid chromatography; HOBt for 1-hydroxybenzotriazole; LCMS for liquid chromatography/mass spectrometry; mCPBA for m-chloroperoxybenzoic acid; Me for methyl; MeOH for methanol; OAc for acetate; Ms for methanesulfonyl; OTF for triflate or trifluoromethanesulfonate; PDC for pyridinium dichromate; i-Pr for isopropyl; Ph for phenyl; PPh$_3$ for triphenylphosphine; psi or psig for pounds per square inch (gas); PTFE for polytetrafluoroethylene; PXPd for [(t-Bu)$_2$PCl]$_2$ PdCl$_2$, PyBOP for (benzotriazol-1-yloxy)tripyrrolidinophosphonium hexafluorophosphate; SEM for 2-(trimethylsilyl) ethoxymethyl; T3P for propane phosphonic acid anhydride; Tf for trifluorosulfonyl; TFA for trifluoroacetic acid; THF for tetrahydrofuran; TLC for thin layer chromatography; Troc for 2,2,2-trichloroethoxycarbonyl; v/v for volume/volume; wt % for weight percent; w/v for weight/volume; w/w for weight/weight; XantPhos for 4,5-bis(diphenylphosphino)-9,9-dimethylxanthene;

The compounds of the present invention can be prepared using a variety of methods. As a non-limiting example, the compounds of the present invention can be prepared according to Scheme I starting from compounds of Formula II (e.g., n=0 to 8), Formula V (X$_4$ can be, for example, O or NR$_A$, where R$_A$ is as described hereinabove and is preferably H or R$_E$ as defined above such as C1-C6alkyl, 3- to 12-membered carbocycle or heterocycle, —C(O)R$_S$, —C(O)OR$_S$, —C(O)N(R$_S$R$_S'$), —SO$_2$N(R$_S$R$_S'$), —S(O)$_2$OR$_S$, —S(O)OR$_S$, —S(O)N(R$_S$R$_S'$), or a suitable protecting group such as Boc or Fmoc), or Formula VIII (E can be, for example, 3- to 7-membered carbocycle or heterocycle and is optionally substituted with one or more R$_A$), wherein A, B, D, Y, Z and R$_A$ are as described above. The 1,4-diketones II, V, and VIII can be reduced to the 1,4-diols using the methods described below, and the resultant racemic, enantiomerically enriched, or meso 1,4-diols may be converted to the dimesylates III, VI, or IX, or alternatively to ditriflates, ditosylates, or dihalides by the methods described below. The dimesylates III, VI, and IX, ditriflates, ditosylates, or dihalides may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under the conditions described below to give the compounds of the invention. L$_1$ and L$_2$ can be readily introduced to Formulae II, V and VIII, as appreciated by those skilled in the art in light of the present invention. Likewise, D-L$_3$-NH$_2$ can be used instead of D-NH$_2$, as appreciated by those skilled in the art.

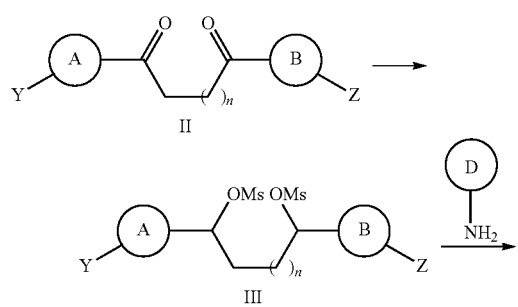

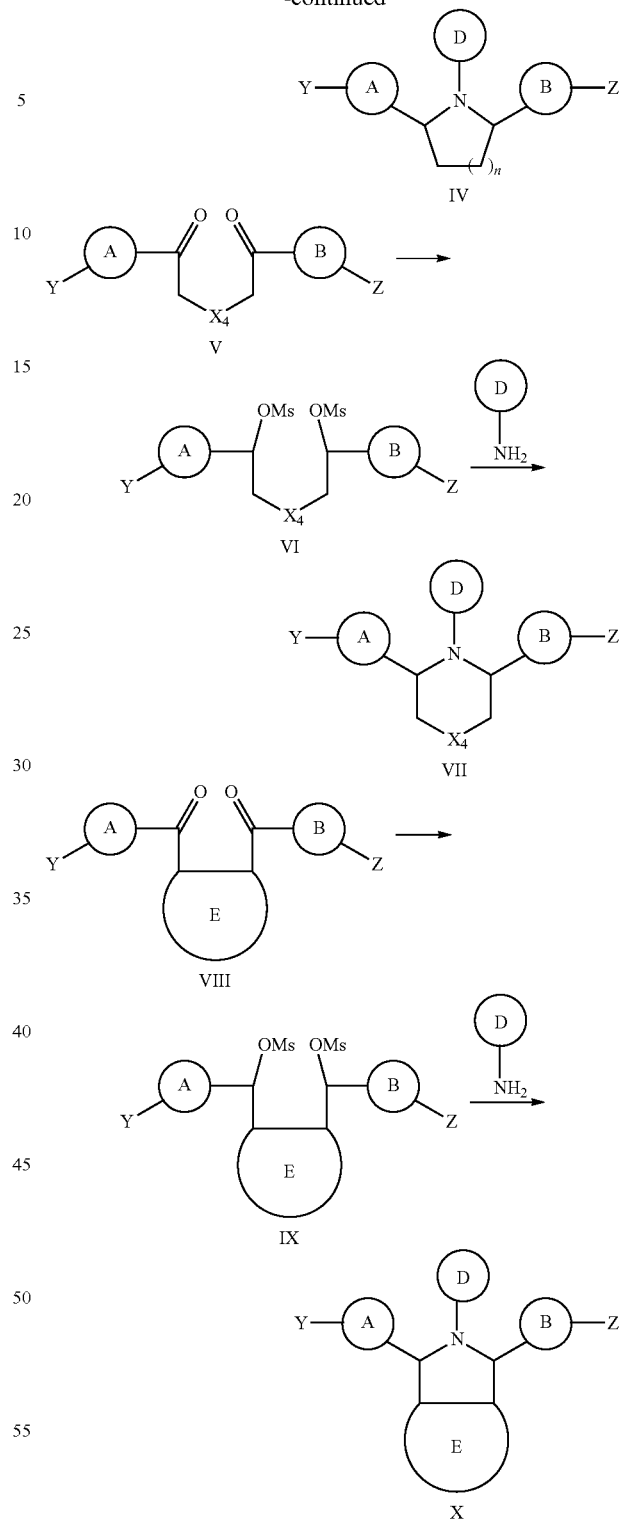

As another non-limiting example, the compounds of the present invention can be prepared starting from compounds of Formula II and Formula III as shown in Scheme II. The 1,4-diketones such as Formula IV may be prepared using known methods (see Nevar, et al., Synthesis: 1259-1262 (2000), such as the reaction of α-bromoketones such as Formula II with methyl ketones such as Formula III in the presence of a suitable Lewis acid such as ZnCl$_2$ or Ti(OiPr)$_4$. For example reaction of II (1 equivalent) with III (1.5 equivalents) in the presence of ZnCl$_2$ (2 equivalents), diethylamine (1.5 equivalents) and tert-butanol (1.5 equivalents) in a solvent such as benzene at around room temperature can provide the diketones IV. The 1,4-diketones IV may be reduced to the 1,4-diols such as V by the action of NaBH$_4$, LiAlH$_4$, or DIBAL. Alternatively, enantioselective reduction of 1,4-diketones such as Formula IV can be accomplished by analogy with reported methods (see Chong, et al., Tetrahedron: Asymmetry 6:409-418 (1995), Li, et al., Tetrahedron 63:8046-8053 (2007), Aldous, et al., Tetrahedron: Asymmetry 11:2455-2462 (2000), Masui, et al., Synlett: 273-274 (1997), Jing, et al., Adv. Synth. Catal. 347:1193-1197 (2005), Sato, et al., Synthesis: 1434-1438 (2004)), such as reduction with (−) or (+)-diisopinocamheylchloroborane (DIP-chloride), with borane and an oxazaborolidine catalyst, or with asymmetric hydrogenation in the presence of a suitable Ruthenium (II) catalyst, such as [RuCl2{(R)-BINAP} {(R, R)-DPEN}] (BINAP=2,2'-bis(diarylphosphino)-1,1'-binaphthyl; DPEN=1,2-diphenylethylenediamine). The diketones IV (1 equivalent) can be reduced by NaBH4 (3 equivalents) in solvents such as tetrahydrofuran with heating to about 50° C. The diketones IV (1 equivalent) can be enantioselectively reduced upon addition to a mixture made from N,N-diethylaniline borane (about 2 equivalents), trimethylborate (about 0.2 equivalents) and either (S) or (R) α,α-diphenyl-2-pyrrolidinemethanol (about 0.17 equivalents) in a solvent such as THF at temperatures ranging from about 10° C. to about 30° C. (Synthesis 2507-2510 (2003)). The resultant racemic, enantiomerically enriched, or meso 1,4-diols V may be reacted with methanesulfonyl chloride or methanesulfonic anhydride to provide the dimesylate Formula VI. For example, diols V (1 equivalent) can be reacted with methanesulfonic anhydride (about 2.5 equivalents) in the presence of a base such as diisopropylethylamine (about 4 equivalents) in a solvent such as tetrahydrofuran or 2-methyltetrahydrofuran at temperatures starting from about −15° C. to −25° C. and increasing to about room temperature. Alternatively Formula V may be converted to a ditriflate or ditosylate by the action of p-toluenesulfonyl chloride or triflic anhydride, or to a dihalide such as a dibromide or dichloride by the action of PPh$_3$ in the presence of CCl$_4$ or CBr$_4$, or by the action of SOCl$_2$, POCl$_3$, or PBr$_3$. The dimesylate, ditriflate, ditosylate, or dihalide may be reacted with an amine, such as 4-fluoroaniline (as shown for illustration in Scheme II), with or without a co-solvent such as DMF at room temperature to 100° C., to give the pyrrolidines such as Formula VII. The dimesylate VI (1 equivalent) (or in the alternative the ditriflate, ditosylate, or dihalide) may be reacted with between 1 to 20 equiv of an amine D-NH$_2$, such as, for example, a substituted aniline in solvents such as tetrahydrofuran or 2-methyltetrahydrofuran with or without a co-solvent such as DMF, at about room temperature to about 100° C., to give the pyrrolidines such as Formula VII. Where fewer equivalents of amine D-NH$_2$ are employed (i.e., 1-2 equivalents), a base such as diisopropylethylamine can be added to promote the reaction. In certain cases, the amine can be used in a large excess (i.e., as reaction solvent). For example, the reaction of a dimesylate (1 equivalent) with excess aniline (about 6.5 equivalents) can be conducted by heating to 65° C. in 2-methyltetrahydrofuran until completion of the reaction. Numerous substituted anilines can be reacted with the dimesylate Formula VI, including, but not limited to, 3-fluoro-4-(piperidin-1-yl)aniline, 3,5-difluoro-4-(piperidin-1-yl)aniline, 3,5-difluoro-4-(4-phenylpiperidin-1-yl)aniline, 3-difluoro-4-(4-phenylpiperidin-1-yl)aniline, 4-(4-phenylpiperidin-1-yl)aniline, 4-cyclopropylaniline, 4-cyclopropyl-2-fluoroaniline, 4-cyclopropyl-3,5-difluoroaniline, 4-cyclohexyl-3-fluoroaniline, biphenyl-4-amine, 4-(pyridin-2-yl)aniline, 3,5-dichloro-4-(piperidin-1-yl)aniline, 4-(4,4-dimethylpiperidin-1-yl)-3,5-difluoroaniline, 4-(4,4-fluoropiperidin-1-yl)-3,5-difluoroaniline, 3-methyl-4-(piperidin-1-yl)aniline, 2,5-difluoro-4-(piperidin-1-yl)aniline, 4-(3,5-dimethylpiperidin-1-yl)-3,5-difluoroaniline, 4-(2,6-dimethylpiperidin-1-yl)-3,5-difluoroaniline, 2,3,5-trifluoro-4-(piperidin-1-yl)aniline, 3,5-difluoro-4-(4-isopropylpiperidin-1-yl)aniline, 3,5-difluoro-4-(4-methylpiperidin-1-yl)aniline, 3,5-difluoro-4-(4-(trifluoromethyl)piperidin-1-yl)aniline, 4-(4-tert-butylpiperidin-1-yl)-3,5-difluoroaniline, 3,5-difluoro-4-(6-azaspiro[2.5]octan-6-yl)aniline, 4-(2-azabicyclo[2.2.2]octan-2-yl)-3,5-difluoroaniline, 4-(3,3-dimethylazetidin-1-yl)-3,5-difluoroaniline, 4-tert-butylaniline, 4-ethoxyaniline, 4-phenoxyaniline, 1-(4-aminophenyl)piperidin-2-one, 4-(cyclopentyloxy)-3-fluoroaniline, 3-chloro-4-(trifluoromethoxy)aniline, 2,5-difluoro-4-(trifluoromethyl)aniline, 4-(2,2-difluoroethoxy)aniline, 4-chloroaniline, 4-(2-methoxyethoxy)aniline, 4-(oxazol-2-yl)aniline, 4-(2-fluoropyridin-4-yl)aniline, 3,4-difluoroaniline, 4-chloro-3-fluoroaniline, 3-fluoro-4-(methylsulfonyl)aniline, 4-(3-azabicyclo[3.2.0]heptan-3-yl)-3,5-difluoroaniline, 4-((3-ethyloxetan-3-yl)methoxy)aniline, 4-cyclopropyl-3,5-difluoroaniline, 4-(1,3-dioxan-5-yloxy)aniline, 3,5-difluoro-4-(octahydroisoindol-2-yl)aniline, 4-((1,3-dioxolan-4-yl)methoxy)aniline, 4-((3-ethyloxetan-3-yl)methoxy)-3,5-difluoroaniline, 4-(pentafluorosulfanyl)aniline, N1-tert-butyl-2-fluorobenzene-1,4-diamine, heteroaryl amines, alkyl amines, cycloalkyl amines, substituted benzylamines, allylamine, or anilines that are listed in or can be made using General Procedures 1, 1.1, or 1.2. The dinitro Formula VII may be reduced to the diamino Formula VIII using Fe in the presence of NH$_4$Cl, HCl, or acetic acid, or by treatment with a hydride reducing agent, such as sodium borohydride (with or without the addition of a transition metal salt, such as BiCl$_3$, SbCl$_3$, NiCl$_2$, Cu$_2$Cl$_2$, or CoCl$_2$) in a solvent such as ethanol or THF. For example compounds VII (1 equivalent) can be reduced to VIII by reaction with iron powder (about 6 equivalents) and ammonium chloride in a 1:1 mix of THF and ethanol with heating to about 60-80° C. Alternatively, Formula VII can be reduced to the product Formula VIII by hydrogenation in the presence of a suitable catalyst, such as a palladium or platinum catalyst or Raney-nickel. For example reduction of VII to VIII can be effected by exposure to 30 psig hydrogen gas in the presence of Raney-nickel Grace 2800 in a solvent such as tetrahydrofuran with shaking. The diamine Formula VIII may be reacted with a suitably protected proline acid (Boc is shown, although Cbz, Troc, or Fmoc may be substituted) in the presence of a peptide coupling reagent, such as EDAC/HOBT, PyBOP, HATU, T3P or DEPBT, in a solvent such as THF, DMF, dichloromethane, ethyl acetate, or DMSO, with or without the addition of an amine base such as N-methylmorpholine, Hunig's base, pyridine, 2,6-lutidine, or triethylamine, to give Formula IX. For example, reaction of VIII (1 equivalent) with 1-(tert-butoxycarbonyl)pyrrolidine-2-carboxylic acid (2.5 equivalents) and HATU (2.5 equivalents) in the presence of diisopropylethylamine (3 equivalents) in DMSO at about room temperature can provide the product IX. Removal of the Boc protecting groups to give X may be accomplished by treatment with an acid, such as TFA, HCl, or formic acid. For example, reaction of IX (1 equivalent) with TFA:CH$_2$Cl$_2$ (1:1) at room temperature can provide compounds X. Compounds XI may be prepared by coupling of Formula X with an acid of choice using the standard peptide coupling reagents and conditions described above.

For example, X(1 equivalent) can be reacted with acids (2 equivalents) such as, but not limited to, 2-(methoxycarbonylamino)-3-methylbutanoic acid, 2-(methoxycarbonylamino)-3,3-dimethylbutanoic acid, 2-cyclohexyl-2-(methoxycarbonylamino)acetic acid, 2-(methoxycarbonylamino)-2-(tetrahydro-2H-pyran-4-yl)acetic acid, or acids listed under General Procedure 19. Alternately, diamine VIII may be reacted directly with an appropriately N-substituted proline in the presence of a peptide coupling reagent such as EDAC/HOBT, PyBOP, HATU, T3P, or DEPBT, in a solvent such as THF, DMF, dichloromethane, or DMSO, with or without the addition of an amine base such as N-methylmorpholine, Hunig's base, pyridine, 2,6-lutidine, or triethylamine, to directly give compounds XI. For example, VIII (1 equivalent) can be reacted directly with 1-(2-(methoxycarbonylamino)-3-methylbutanoyl)pyrrolidine-2-carboxylic acid (about 2 equivalents) and T3P (about 2.8 equivalents) in the presence of diisopropylethylamine (about 5.5 equivalents) in a solvent such as ethyl acetate at temperatures from about 0° C. to about room temperature to provide XI. The foregoing sequence illustrates the synthesis of particular compounds of the invention XI having a substituted proline group at Y and Z (i.e., $R_2$ and $R_5$ taken together with the atoms to which they are attached, and $R_9$ and $R_{12}$ taken together with the atoms to which they are attached, each form a 5-membered heterocycle). It is understood that analogous synthetic procedures can be used to make compounds of the invention where Y, Z, $R_2$, $R_5$, $R_9$, and $R_{12}$ are other than that shown and described in Scheme II.

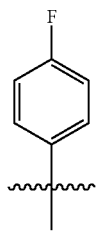

in each Formula within Scheme II can be replaced with

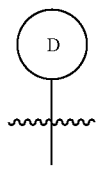

where D is defined above, and such compounds can be readily prepared according to the process described in Scheme II (including making compound XI directly from compound VIII). Likewise, compounds of Formula XII can be prepared from compounds of Formula X or directly from compounds of Formula VIII.

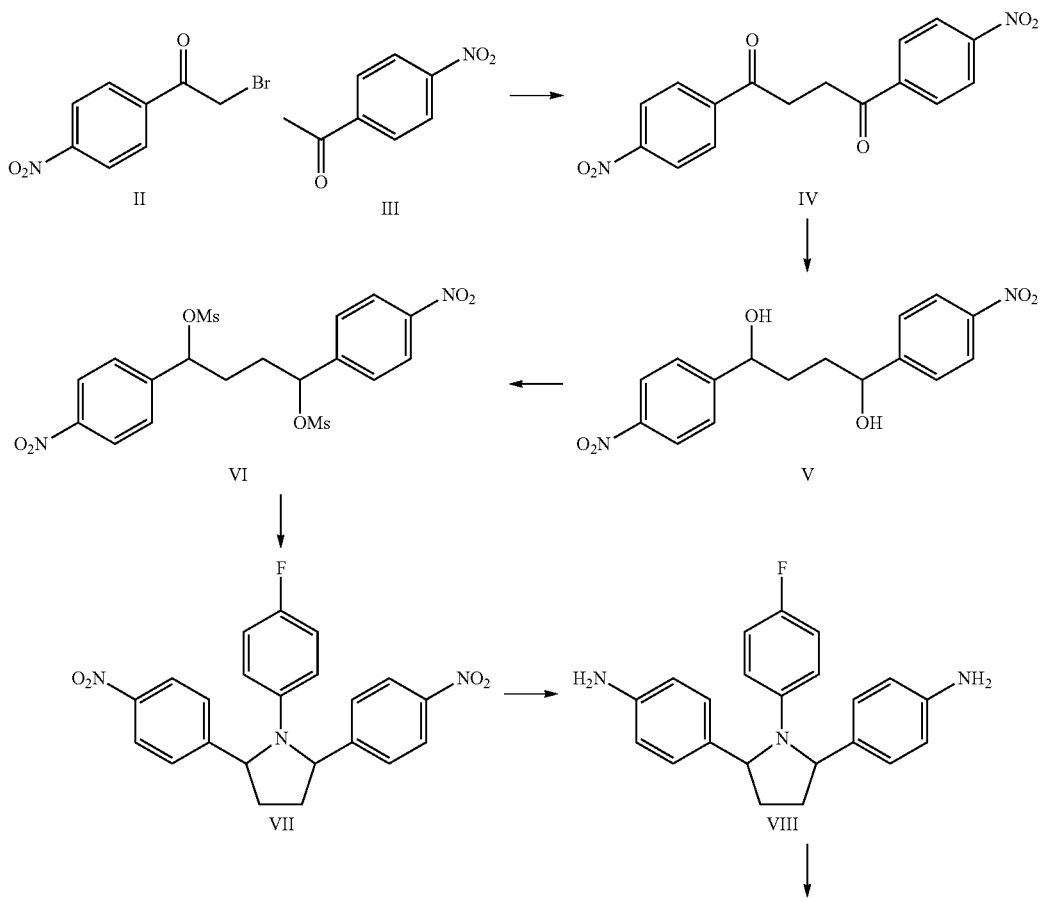

Scheme II

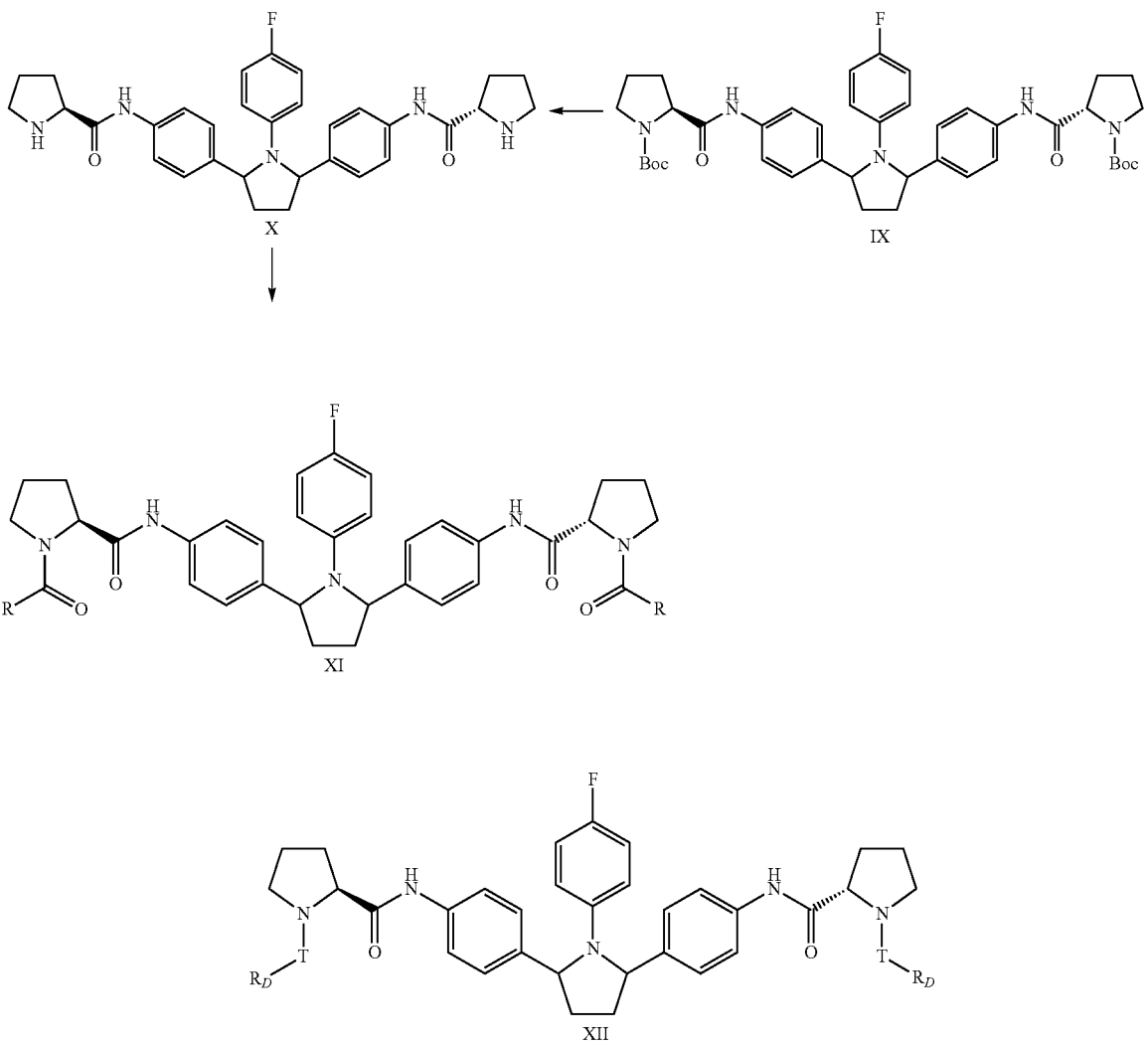

As yet another non-limiting example, the compounds of the present invention can be prepared starting from compounds of Formula II and Formula III as shown in Scheme III, where A, B, D, Y, and Z are as described above, using conditions similar to those described above for the preparation of IV in Scheme II. Similarly, the resulting 1,4-diketone IV may be reduced to the 1,4-diols V using the methods described above for Scheme II. The resultant racemic, enantiomerically enriched, or meso 1,4-diols V may be converted to the dimesylate VI or alternatively to a ditriflate, ditosylate, or dihalide by the methods described above. The dimesylate VI, ditriflate, ditosylate, or dihalide may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under the conditions described above the give the compounds of the invention. Alternatively, compounds such as VIII, where R is a group such as allyl, 4-methoxybenzyl, or 2,4-dimethoxybenzyl, may be treated with reagents useful for the removal of the R group (rhodium catalyst such as $Rh(Ph_3P)_3Cl$ for R=allyl, treatment with an acid such as TFA or HCl for R=4-methoxybenzyl or 2,4-dimethoxybenzyl, hydrogenolysis with a Pd catalyst for R=substituted benzyl) to generate compounds such as IX. Amine IX may be reacted with an aryl halide or triflate such as X (iodide shown for illustration) employing the Buchwald-Hartwig reaction in the presence of a palladium catalyst (such as $Pd(OAc)_2$ or $Pd_2(dba)_3$) and a phosphine ligand (such as triphenylphosphine or XantPhos) and a base (such as sodium bis(trimethylsilyl)amide, potassium tert-butoxide, or $K_3PO_4$) to give the compounds of the present invention. Alternatively, the compounds of the present invention may be obtained by reaction of IX with an aldehyde or ketone through reductive amination in the presence of a hydride reducing agent, such as sodium borohydride or sodium cyanoborohydride (with or without the addition of an acid, such as acetic acid) in a solvent such as ethanol, toluene, THF, or dichloromethane. Alternatively the reductive amination may be conducted through the use of hydrogenation in the presence of a suitable catalyst, such as a palladium or platinum catalyst or Raney nickel. Alternatively, amine IX may react with electrophilic reagents, such as alkyl halides, or with aryl electrophiles (suitably electron deficient aryl and heteroaryl halides and triflates) through nucleophilic aromatic substitution reactions to give the compounds of the present invention.

Scheme III

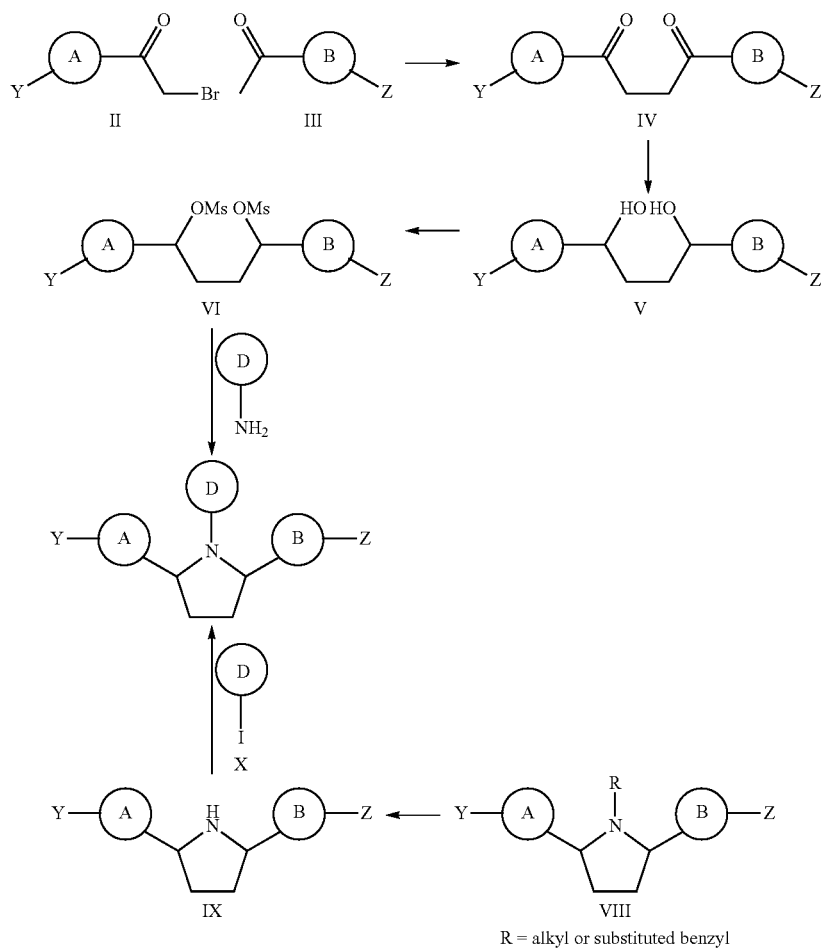

R = alkyl or substituted benzyl

As a further non-limiting example, the compounds of XIII can be prepared starting from compounds of Formula II and Formula III as shown in Scheme IV, where $X_5$ in Formula II and Formula III represents a halogen (e.g., Cl, Br, or F) or a nitro group. Additionally, each phenyl ring can be substituted with $X_{13}$, wherein $X_{13}$ is $X_5$, H, alkyl, haloalkyl, alkoxy, or haloalkoxy. The 1,4-diketones such as IV may be prepared using known methods described above for the preparation of IV for Scheme II. The 1,4-diketones IV may be reduced to the 1,4-diols such as V by the action of $NaBH_4$, $LiAlH_4$, or DIBAL. Alternatively, enantioselective reduction of 1,4-diketone such as IV can be accomplished by the methods described above for the preparation of V in Scheme II. The resultant racemic, enantiomerically enriched, or meso 1,4-diols V may be reacted with methansulfonyl chloride or methanesulfonic anhydride to provide the dimesylate VI. Alternatively V may be converted to a ditriflate or ditosylate by the methods described above for Scheme II. The dimesylate, ditriflate, ditosylate, or dihalide may be reacted, analogously to Scheme II, with an amine $D-NH_2$ including but not limited to those amines described or referred to in Scheme II to give VII. When $X_5$ in Formula VII is nitro, the nitro groups may be reduced to the tetraamino product IX using Fe in the presence of $NH_4Cl$, HCl, or acetic acid, or with a hydride reducing agent, such as sodium borohydride (with or without the addition of a transition metal salt, such as $BiCl_3$, $SbCl_3$, $NiCl_2$, $Cu_2Cl_2$, or $CoCl_2$) in a solvent such as ethanol or THF. Alternatively, VII ($X_5$=nitro) can be reduced to the product IX by hydrogenation in the presence of a suitable catalyst, such as a palladium or platinum catalyst or Raney nickel. Alternatively, compounds VII where $X_5$=halogen may be reacted with ammonia (R=H) or an amine bearing a suitable protecting group (R=substituted benzyl such as 4-methoxybenzyl or 2,4 dimethoxybenzyl or R=allyl). The resulting products VIII may be treated with a reagent useful for the removal of the R protecting group (rhodium catalyst such as $Rh(Ph_3P)_3Cl$ for R=allyl, treatment with an acid such as TFA or HCl for R=4-methoxybenzyl or 2,4-dimethoxybenzyl, hydrogenolysis with a Pd catalyst for R=substituted benzyl) to give the product IX. Formula IX may be reacted with a suitably protected proline acid (Boc is shown, although Cbz, Troc, or Fmoc may be substituted) in the presence of a peptide coupling reagent, such as EDAC/HOBT, PyBOP, HATU, T3P, or DEPBT, in a solvent such as THF, DMF, dichloromethane, or DMSO, with or without the addition of an amine base, such as N-methylmorpholine, Hunig's base, pyridine, 2,6-lutidine, or triethylamine, to give X as a mixture of the amide products. Although formula X depicts reaction taking place on a specific $NH_2$ group, the reaction may take place at either $NH_2$. Conversion to the benzimidazole compound XI may be accomplished by heating X in acetic acid (50-100° C.). Alternatively, XI may be prepared by reaction of IX with an aldehyde, followed by treatment with an oxidant, such as $Cu(OAc)_2$ or $MnO_2$ (see Penning, et al., Bioorg. Med. Chem.

2008, 16, 6965-6975. After removal of the Boc protecting groups from XI (accomplished by treatment with an acid, such as TFA, HCl, or formic acid), the compounds of the present invention may be prepared by coupling of the resulting diamine XII with an acid of choice using the standard peptide coupling reagents and conditions described above for Scheme II to give XIII.

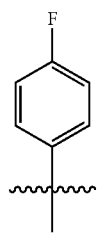

in each Formula within Scheme IV can be replaced with

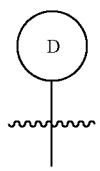

where D is defined above, and such compounds can be readily prepared according to the process described in Scheme IV. Compounds of Formula XIV can be similarly prepared from compounds of Formula XII.

Scheme IV

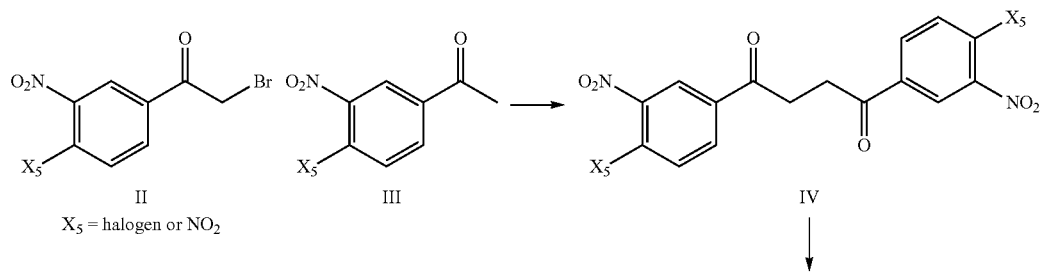

$X_5$ = halogen or $NO_2$

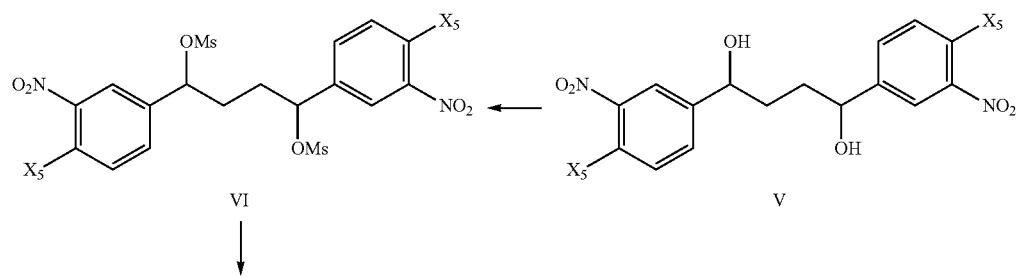

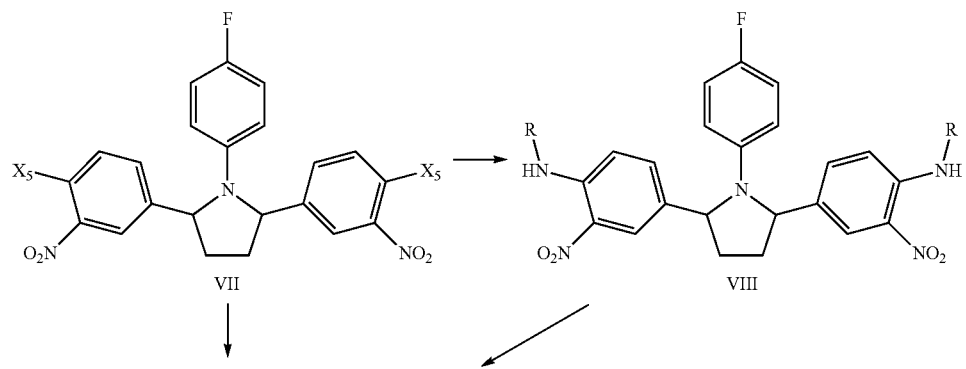

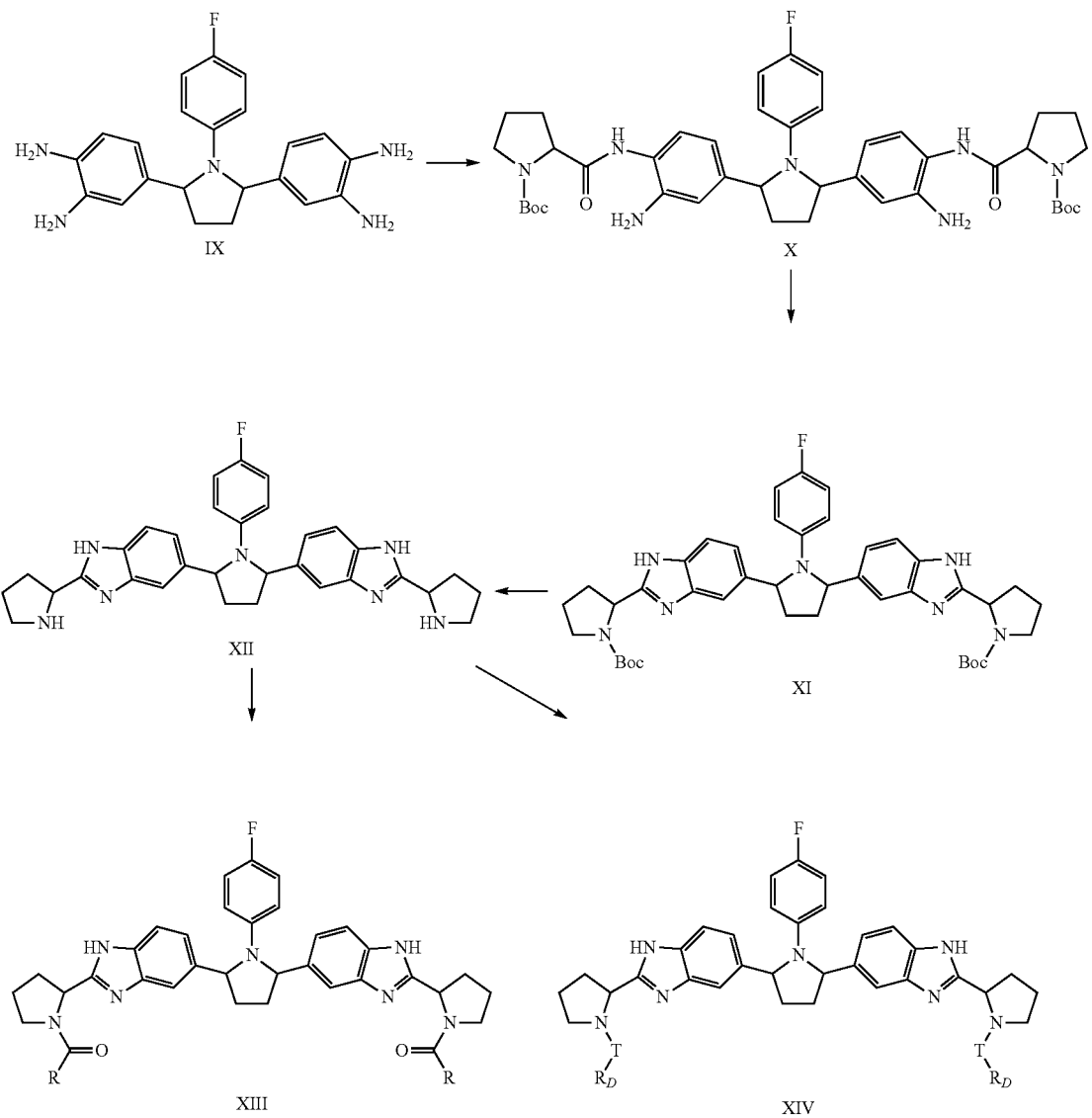

Alternatively IX in Scheme IV may be prepared from a compound of Formula II as shown in Scheme V. Compound VIII from Scheme II may be treated with an acylating agent such as acetyl chloride or acetic anhydride to give compound II (Scheme V). Nitration of compound II to provide III may be accomplished using known methods, such as treatment with nitric acid or potassium nitrate in the presence of an acid such as sulfuric acid or treatment with $NO_2BF_4$. Removal of the acetamide protecting group may be accomplished by treatment with Boc anhydride in the presence of DMAP to give IV, followed by sequential treatment of IV with hydroxide (such as NaOH, KOH, or LiOH) to remove the acetyl group and a strong acid such as TFA or HCl to remove the Boc protecting group to provide V. The nitro groups in V may be reduced to amino groups using the methods described above for Scheme IV to provide IX.

in each Formula within Scheme V can be replaced with

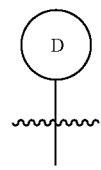

where D is defined above, and such compounds can be readily prepared according to the process described in Scheme V.

Scheme V

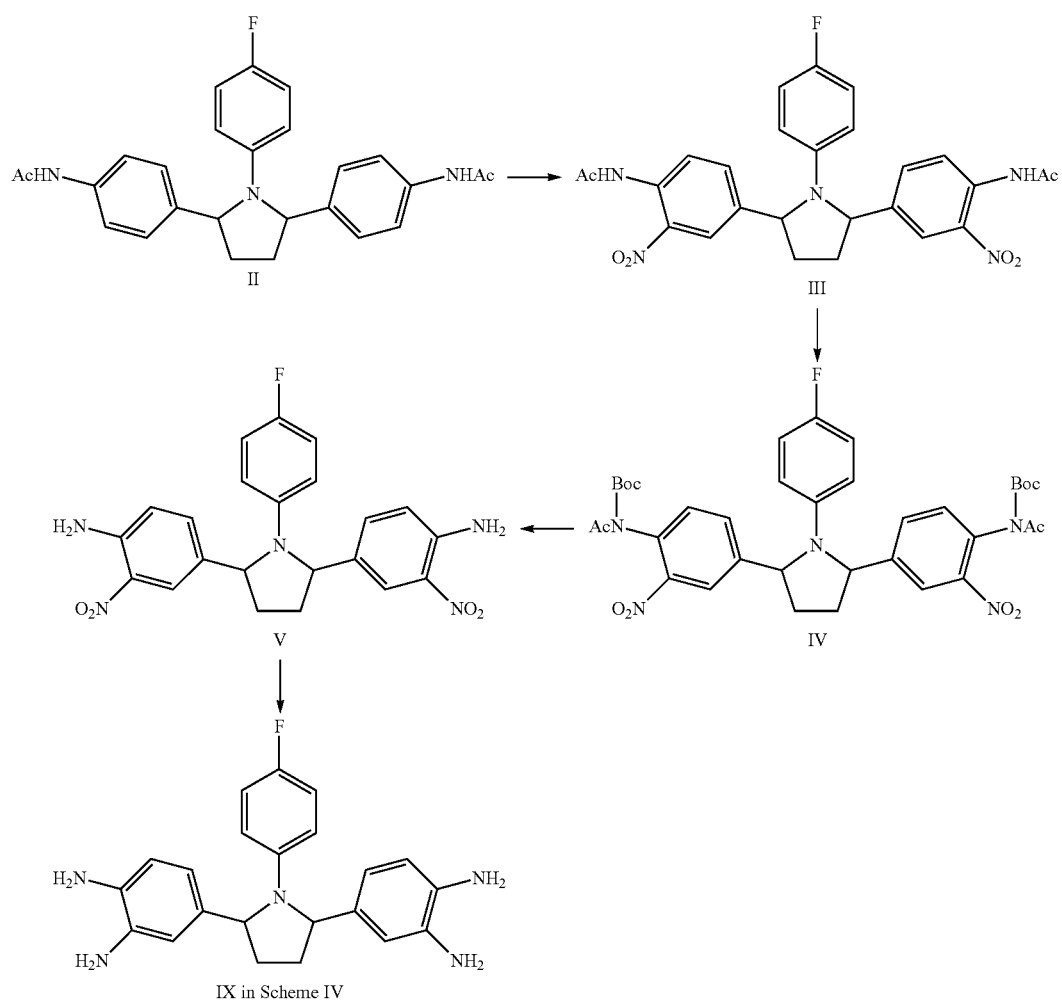

As still another non-limiting example, the compounds of the present invention can be prepared starting from compounds of Formula II as shown in Scheme VI, where A, B, D, Y, and Z are as described above. A 1,4-diketone compound of Formula II (prepared as described in Scheme III) may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under acid catalyzed conditions, such as acetic acid, TFA, formic acid or HCl, to give the compounds of the invention.

Scheme VI

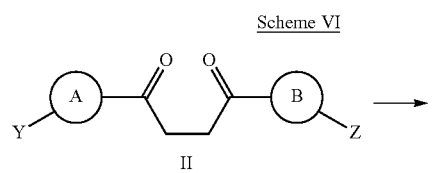

-continued

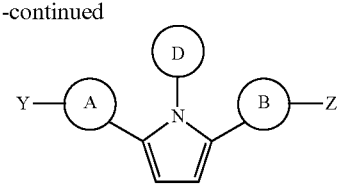

As a further non-limiting example, the compounds of the present invention can be prepared from a compound of Formula II as shown in Scheme VII. A compound of Formula II, where $R_X$ is a halogen, such as bromo, chloro, or iodo, or a triflate or a nonaflate may be converted to a boronic acid or ester such as Formula III, using the chemistry analogous to that of Scheme II to prepare VII (in Scheme II); for example, by starting with 1-(4-bromophenyl)ethanone and 2-bromo-1-(4-bromophenyl)ethanone. A compound of Formula II, where $R_X$ is a halogen, such as bromo, chloro, or iodo, or a triflate or a nonaflate may be converted to a boronic acid or ester such as Formula III, (e.g., a cyclic pinacolate ester) where R is hydrogen, methyl, ethyl, or a cyclic pinacolate ester. For example a compound of Formula II can be transformed to a compound of III by treatment with pinacolborane in the presence of a catalyst such as, for example, tris(dibenzylidineacetone)palladium (0), and a ligand such as, for example, tri-t-butylphosphine, in solvents such as, for example, tetrahydrofuran, dioxane, or toluene at temperatures ranging from ambient to about 130° C. Alternatively, compound II can be reacted with bis(pinacolato)diboron in the presence of a catalyst such as, for example, Combiphos-Pd6 (CombiPhos Catalysts, Inc. (NJ, USA), dichloro[1,1'-bis(diphenylphosphino)ferrocene]palladium (II) dichloromethane adduct, or palladium acetate in the presence of a ligand such as, for example, 2-dicyclohexylphosphino-2',4',6'-triisopropylbiphenyl (XPhos), and a base such as, for example, potassium acetate in solvents such as, for example, toluene, dioxane, tetrahydrofuran, dimethylformamide or dimethyl sulfoxide at temperatures from about 60 to about 130° C. to give compound III. Alternatively, a compound of Formula II may be reacted with an organolithium reagent, such as n-BuLi, sec-BuLi, or t-BuLi, followed by reaction with trimethyl borate or triethyl borate, to give a compound of Formula III.

A compound of Formula III in Scheme VII can be coupled with a compound of Formula IV, where $R_Y$ is a halogen, such as bromo, chloro or iodo, under Suzuki reaction conditions to provide a compound of Formula V. Such conditions include, for example, use of a palladium catalyst such as, for example, tris(dibenzylidineacetone)palladium (0), palladium acetate, bis(triphenylphosphine)palladium (II) chloride, tetrakis(triphenylphosphine)palladium, or dichloro[1,1'-bis(diphenylphosphino)ferrocene]palladium (II) dichloromethane adduct; base such as, for example, potassium carbonate, potassium phosphate, potassium t-butoxide, sodium carbonate, cesium carbonate, or cesium fluoride; and solvent such as, for example, toluene, ethanol, water, or tetrahydrofuran, or mixtures thereof heated in the temperature range from about 40 to about 130° C.

Removal of the Boc protecting groups from V may be accomplished by treatment with an acid, such as TFA, HCl, or formic acid. Certain compounds of the present invention such as VI may be prepared by coupling the resulting amino compounds with an acid of choice using the standard peptide coupling reagents, such as EDAC/HOBT, PyBOP, HATU, or DEPBT, in a solvent such as THF, DMF, dichloromethane, or DMSO, with or without the addition of an amine base such as N-methymorpholine, Hunig's base, pyridine, 2,6-lutidine, or triethylamine. Each $R_Z$ is independently $-L_Y'-M'-R_D$ (e.g., $-L_Y-N(R_B'')C(O)-L_S-R_E$), and D, $L_3$, $R_1$, $R_2$, $R_5$, $L_Y$, $R_B''$, $L_S$, $R_E$, $L_Y'$, M' and $R_D$ are as defined above. Alternatively, the functionality of $T-R_D$ can similarly be introduced following removal of the Boc protecting groups in V give compounds of Formula VII.

Scheme VII

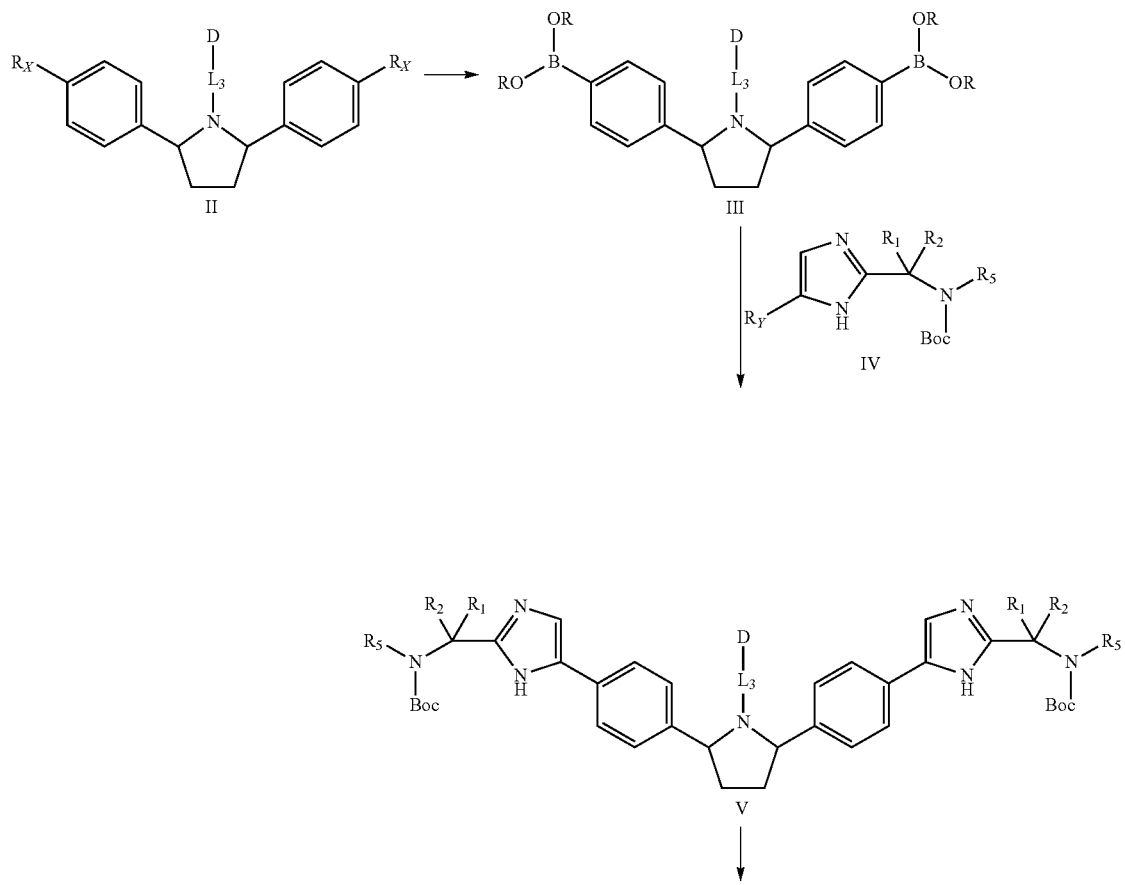

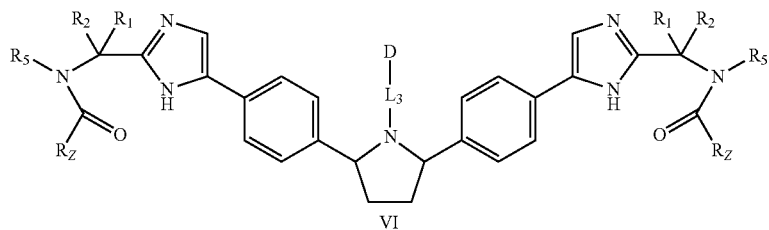

VI

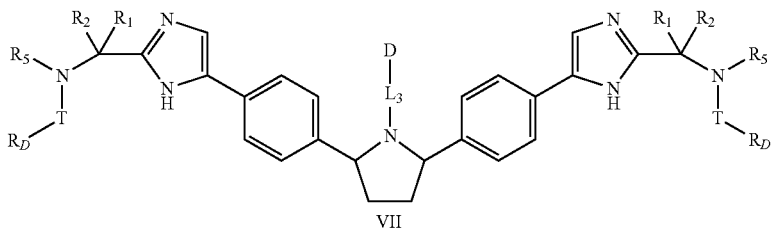

VII

As another non-limiting example, the compounds of the present invention can be prepared according to Scheme VIII starting from the compound of Formula II, initially cleaving the diol in oxidative fashion followed by subsequent acid hydrolysis of the acetonide. This dialdehyde intermediate is then treated with an aryl boronate or aryl boronic acid (compound IV where A and Y are as described previously, or compound VII) and aniline III (where W is $R_M$ or J, and $R_M$ and J are as defined above) resulting in the formation of Formula V or Formula VIII respectively. Formula V can be derivatized by deprotonating the hydroxyl groups with a strong base such as sodium hydride, butyl lithium, or potassium hydride, followed by alkylation with $R_S$-halogen. Alternatively Formula VIII can be deprotonated with a strong base (e.g., sodium hydride) and alkylated with $R_S$-halogen as well, followed by acid hydrolysis of the phenol protecting groups. The sulfonylation of the phenols with nonafluorobutylsulfonyl fluoride in the presence of a neutralizing agent such as potassium carbonate in a polar aprotic solvent such as DMF, followed by heating provides a compound of Formula IX. Boronate of Formula X is produced by heating Formula IX with bis(pinacolato)diboron in the presence of X-phos and a palladium catalyst, such as Pd2(dba)3 and a base such as potassium acetate in an organic solvent such as dioxane. Formula X is further derivatized to final product by heating a suitably substituted heteroarylhalide in the presence of a palladium catalyst such as PdCl2(dppf) in the presence of a base such as sodium carbonate in a mixture of toluene and ethanol. $R_S$ is as defined above.

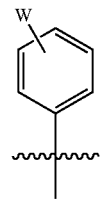

in each Formula within Scheme VIII can be replaced with

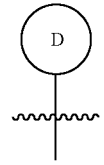

where D is defined above, and such compounds can be readily prepared according to the process described in Scheme VIII.

Scheme VIII

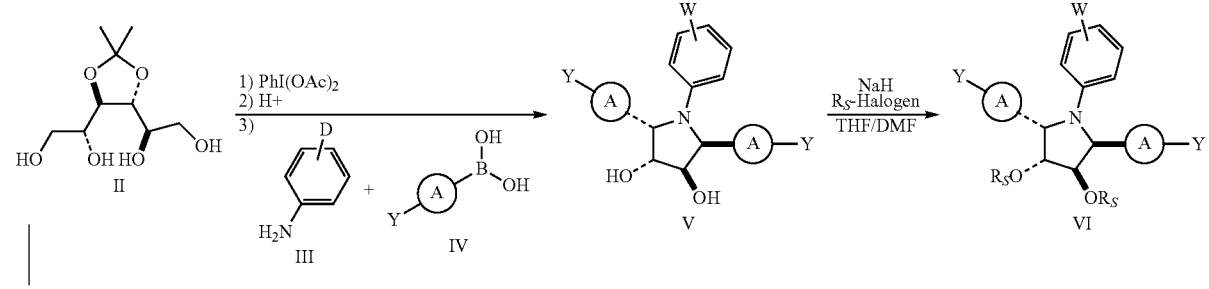

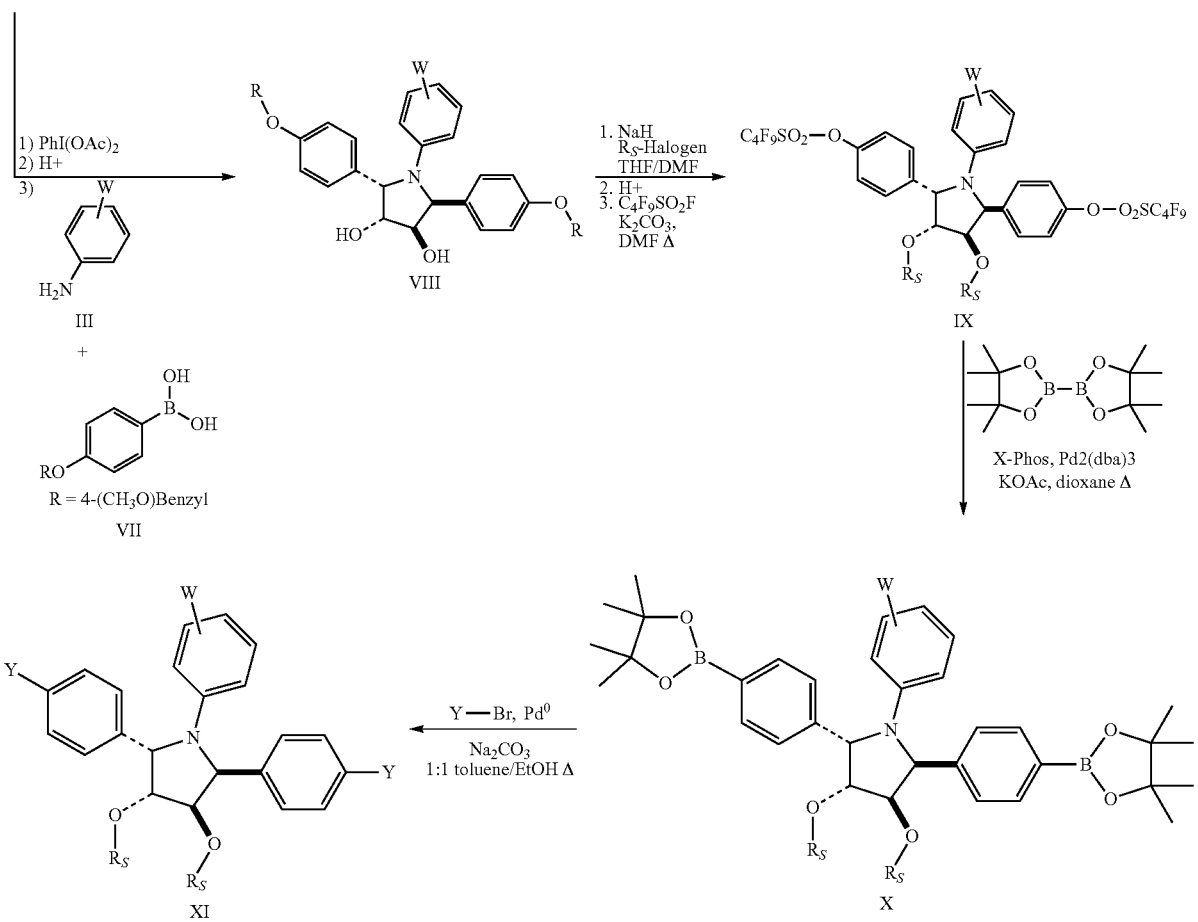

As yet another non-limiting example, the compounds of the present invention can be prepared according to Scheme IX starting from the compounds of Formula II and Formula III. Formula III carboxylic acid is activated towards coupling using reagents such as isobutylchloroformate, DCC, EDAC, or HATU in the presence of an organic base, such as diisopropylethylamine. Upon activation, dianiline of Formula II is added to the reaction, with the isolation of an intermediate amide, which is heated in acetic acid, preferably at 60° C., to yield the compound of Formula IV. The benzimidazole of Formula IV is treated with SEM-Cl in the presence of a base in an aprotic solvent such as THF, yielding two protected benzimidazole regioisomers V. The boronate esters VI are produced by heating Formula V with bis(pinacolato)diboron in the presence of a palladium catalyst, such as PdCl2(dppf), X-Phos, and a base such as potassium acetate in an organic solvent such as dioxane. Heating yields both benzimidazole regioisomers VI. Diol VII is cleaved in oxidative fashion followed by subsequent acid hydrolysis of the acetonide. This dialdehyde intermediate is then treated with an aryl boronate VI and aniline VIII (where W is $R_M$ or J, and $R_M$ and J are as defined above) resulting in the formation of the 3 benzimidazole regioisomers of Formula IX. Formula X is produced by deprotonating the hydroxyl groups with a strong base such as sodium hydride, butyl lithium, or potassium hydride, followed by alkylation with $R_S$-halogen, followed by acid hydrolysis of the pyrrolidine and benzimidazole protecting groups, preferably by treatment with mineral acid, such as hydrochloric acid in an alcoholic solvent such as methanol. The carboxylic acid $R_Z$—COOH is activated towards coupling using reagents such as isobutylchloroformate, DCC, EDAC, or HATU in the presence of an organic base, such as diisopropylethylamine. Upon activation, Formula X is added to the reaction, with the isolation of Formula XI.

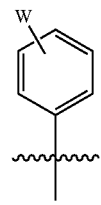

in each Formula within Scheme IX can be replaced with

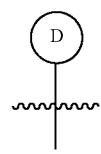

where D is defined above, and such compounds can be readily prepared according to the process described in Scheme IX.

Scheme IX

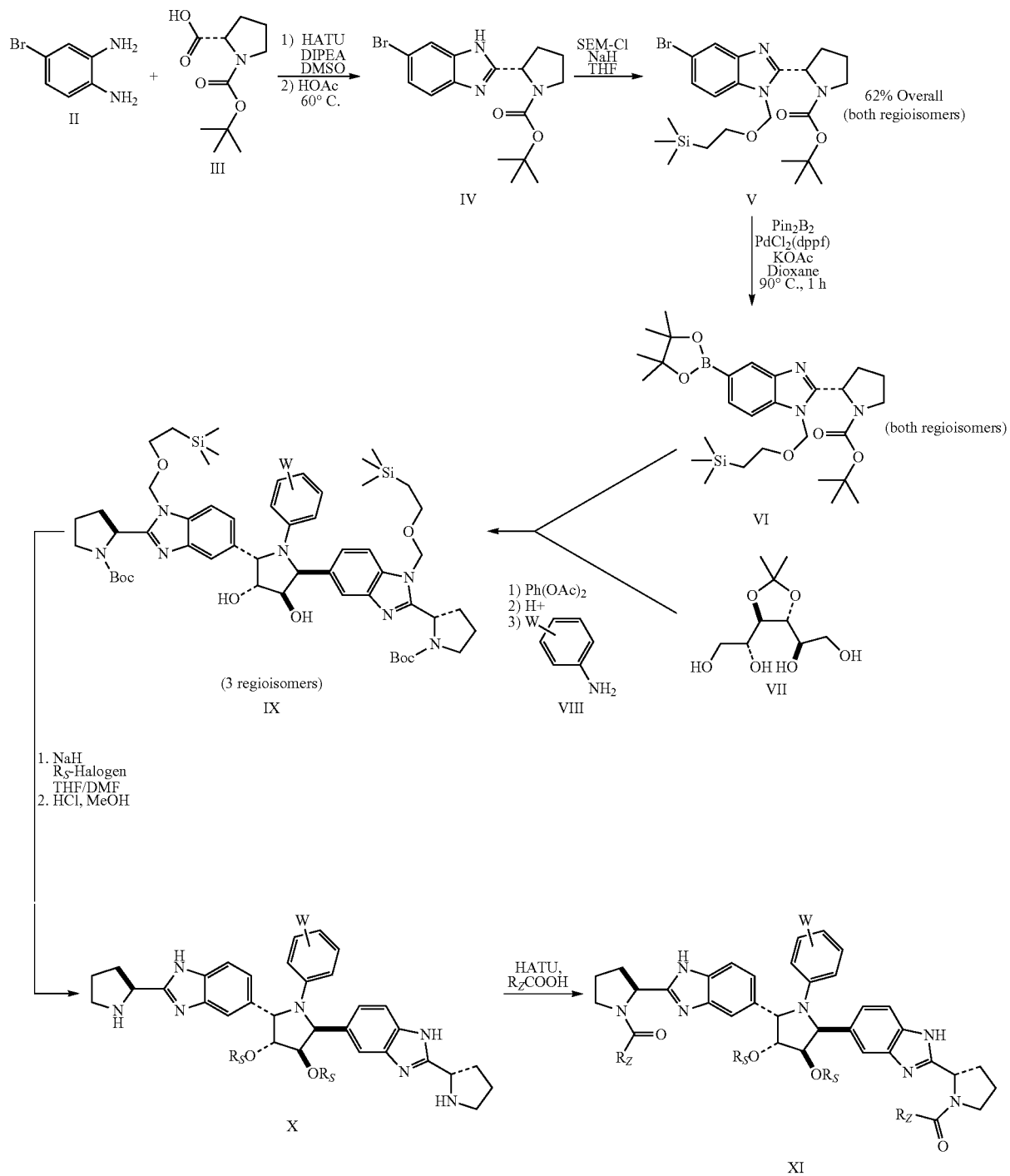

Certain compounds of the invention of general formula (8), where $R_{20}$ is -$L_S$'-M'-$L_S$"-$R_D$ and D is as described above, can be prepared according to the methods of Scheme X. The bromoalkylketone (1) can be reacted with an arylalkylketone (2) using the Lewis acid mediated conditions, described above in Scheme II, to give the diaryldiketone (3). The diketone (3) can be converted to the bisboronate (4) by reaction with bis(pinacolato)diborane in the presence of a base such as potassium acetate, a catalyst such as $PdCl_2$(dppf)-$CH_2Cl_2$, in a solvent such as DMSO, dimethoxyethane or dioxane with heating to between 60-100° C. Bisboronate (4) can be converted to the intermediate (5) by Suzuki reaction using, in analogous fashion, the Suzuki conditions described in Scheme VII. The intermediate (5) can be converted to (6) by reaction with an amine D-$NH_2$ under the analogous conditions described in Scheme VI. For example, reaction of (5) with D-$NH_2$ in the presence of an acid such as, but not limited to, TFA, in a solvent such as, but not limited to, toluene and with heating up to 110° C. can provide intermediates of general structure (6). Compounds (6) can be converted to compounds of general formulas (7) and then (8) using, in analogous fashion, the methods described in Scheme VII. Alternatively, the functionality of T-R$_D$ can be similarly introduced to compounds of Formula (7) to give compounds of Formula (X-1).

Scheme X

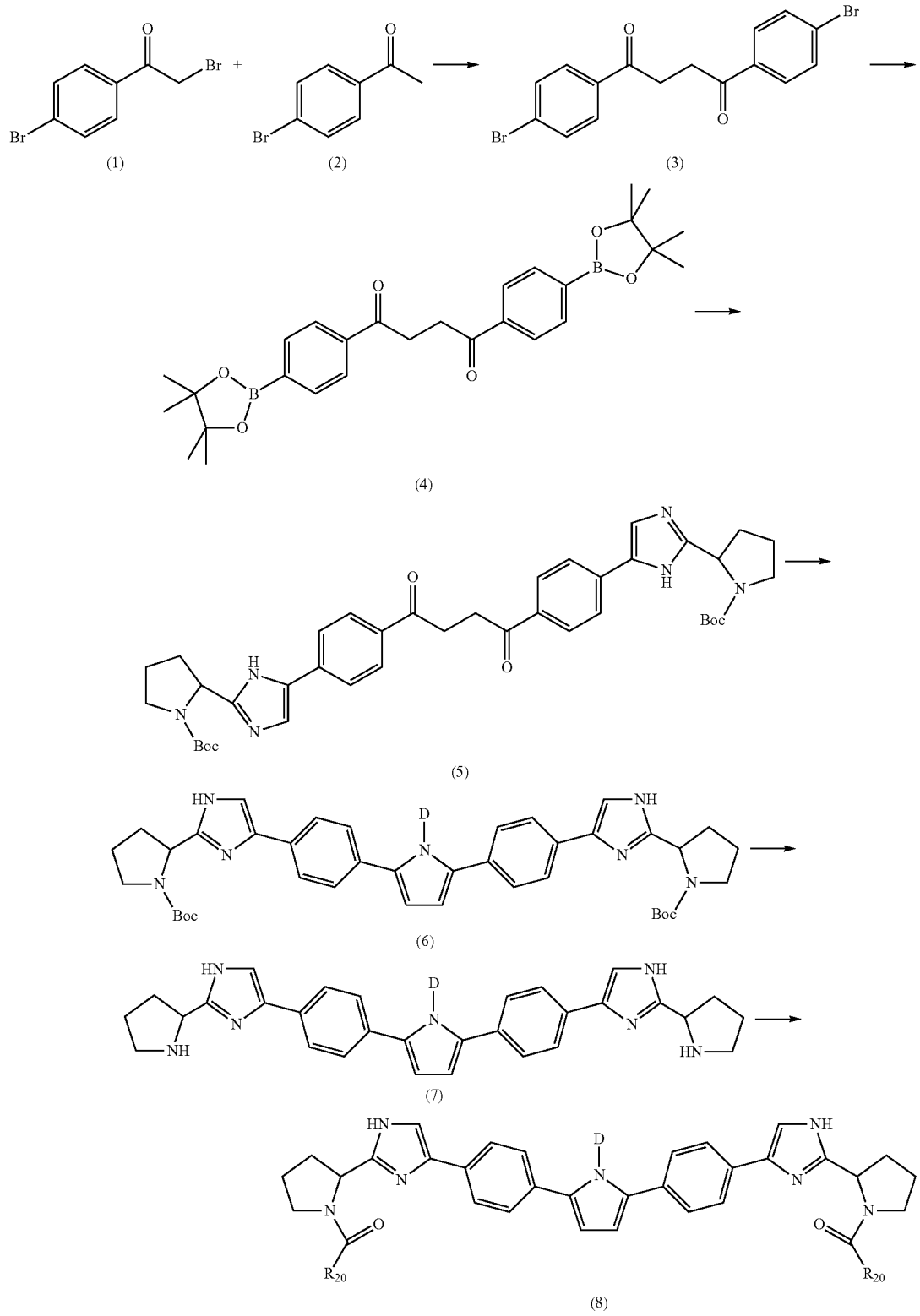

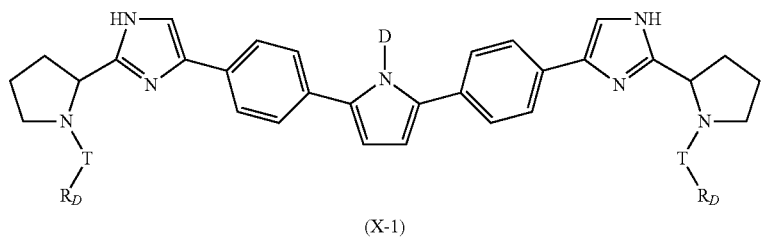

(X-1)

The intermediates (6) can also be prepared using the route depicted in Scheme XI. The intermediate (3) can be reacted with an amine D-NH$_2$ using, in analogous fashion, the conditions described in Schemes VI and X to provide intermediates (9), which can be converted to (10) using, analogously, conditions as described above in Scheme X; and (10), in turn, can be converted to compounds (6) using the Suzuki reaction conditions described in Scheme VII.

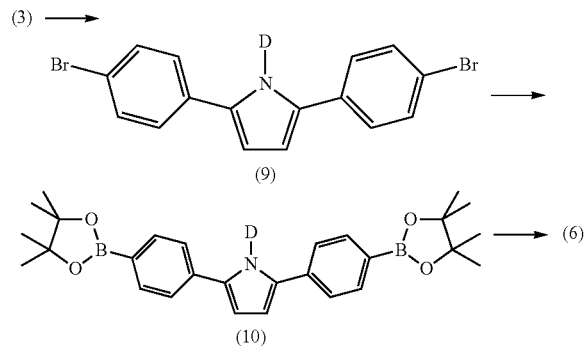

As still another non-limiting example, the compounds of the invention of general formula (15), where R$_{20}$ is -L$_S$'-M'-L$_S$''-R$_D$ and D is as described above, can be prepared as shown in Scheme XII. A 1,4-diketone compound (3) may be reacted with an amine D-NH$_2$, under acid catalyzed conditions, such as acetic acid, TFA, formic acid or HCl, to give the compounds (11). For example, a diketone (3) (1 equivalent) can be reacted with an aniline (1.2 equivalents) and TFA (2 equivalents) in a solvent such as toluene with heating to between around 80 and 120° C. to provide the compounds (11). Alternatively, a diketone (3) can be reacted with an aniline (about 10 equivalents) with heating in acetic acid to around about 70° C. to provide the compounds (11) Amines that can be reacted according to the foregoing description include but are not limited to, those amines described or referred to in Scheme II as suitable for reacting with intermediate (5). Compounds of formula (11) can be converted to compounds of formula (12) by reduction with iron in the presence of ammonium chloride. For example, reaction of compounds (11) (1 equivalent) with iron powder (about 6 equivalents) in the presence of ammonium chloride (about 3 equivalents) in a mixed solvent of ethanol:THF:water (1:1:0.25) at reflux can provide compounds (12). The conversion of (11) to (12) may also be effected by other methods described above in Scheme II to convert VII to VIII, for example by catalytic hydrogenation. Compounds (12) (1 equivalent) can be converted to compounds (13) using the peptide coupling condition described for the conversion of VIII to IX in Scheme II, for example using EDAC/HOBt (2 equivalents) and an appropriate acid in solvents such as DMF at around room temperature. Compounds (13) can be converted to compounds (14) using TFA/CH$_2$Cl$_2$ as described above for converting IX to X in Scheme II. Compounds (14) can be converted to compounds (15) using procedures analogous to those in Scheme II to convert X to XI, such as the coupling procedure to convert (12) to (13). Alternatively, the functionality of T-R$_D$ can be similarly introduced to compounds of Formula (14) to give compounds of Formula (XII-1).

Scheme XII

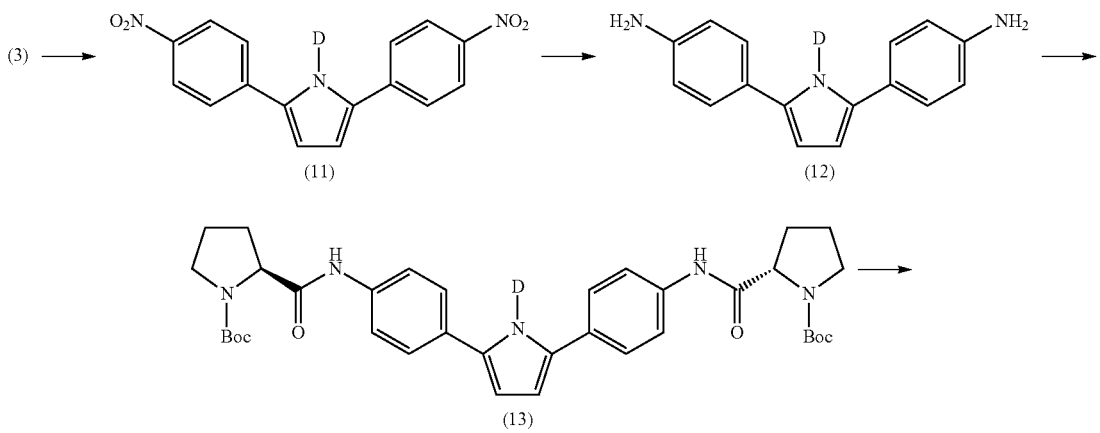

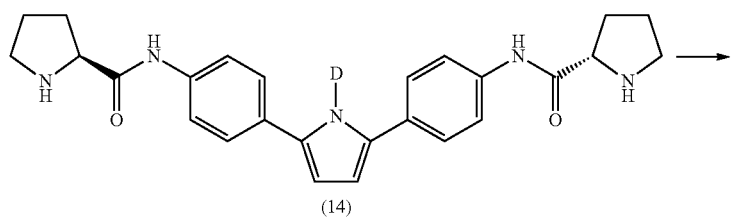

(14)

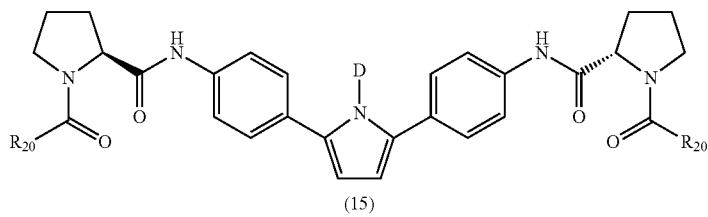

(15)

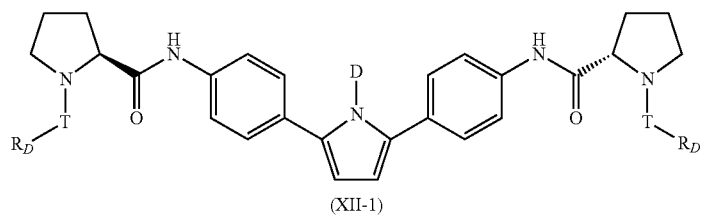

(XII-1)

Compounds of general formula (19), where D is as described above, can be prepared according to the methods of Scheme XIII. Compounds of general formula (16) can be converted to compounds of general formula (17) using a Buchwald reaction with tert-butyl-2-carbamoylpyrrolidine-1-carboxylate. This Buchwald reaction can be conducted in the presence of a base (e.g., cesium carbonate), a palladium catalyst (e.g., tris(dibenzylideneacetone)dipalladium(0)), a phosphine ligand (e.g., 4,5-bis(diphenylphosphino)-9,9-dimethylxanthene) in solvent such as dioxane with heating to about 80-120° C. The intermediate (17) can be reduced to (18) and cyclized to (19) using, in analogous fashion, the conditions described generally in Scheme IV. Compounds (19) can be further reacted as illustrated in Scheme IV to provide compounds of the invention. Each phenyl ring in the above structures can be substituted with $X_{13}$, wherein H, alkyl, haloalkyl, alkoxy, or haloalkoxy.

Scheme XIII

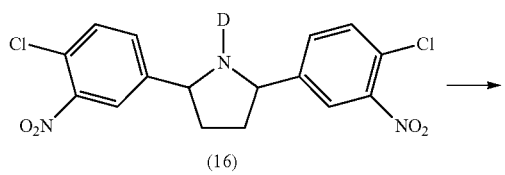

(16)

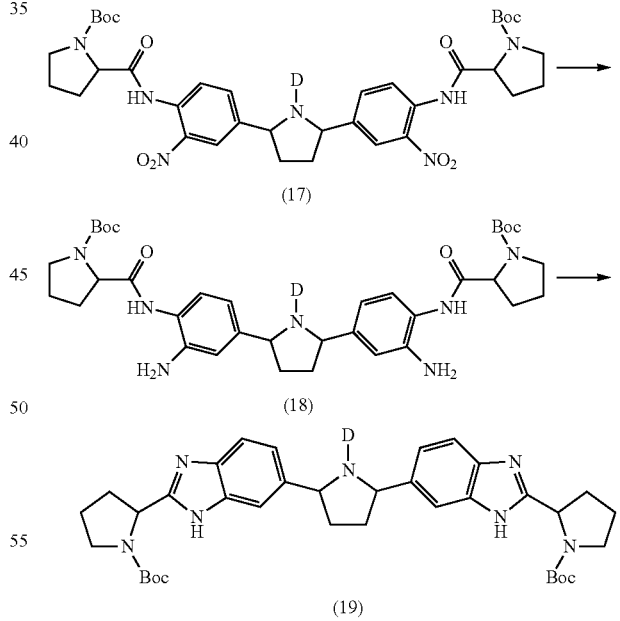

Certain compounds of the invention of general formula (23), where D is as described above, can be prepared according to the methods of Scheme XIV. Compounds (16) can be reacted with compound (20) using a Buchwald reaction as described generally in Scheme XIII to provide compounds (21). Compounds (21) can be reduced to compounds (22) and cyclized to (23) using, in analogous fashion, the conditions described generally in the foregoing Schemes.

Scheme XIV

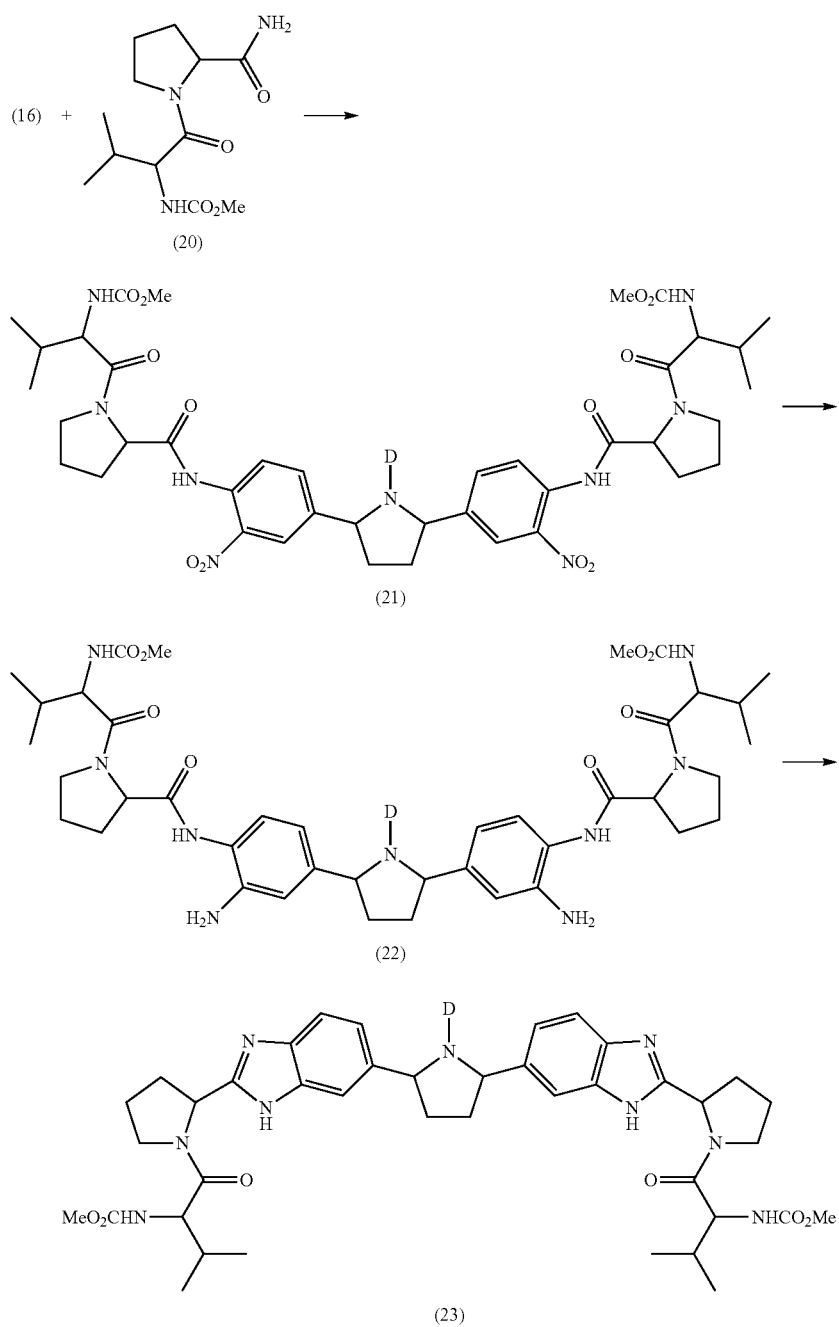

Certain compounds of the invention of general formula (29), where $R_{20}$ is $-L_S'-M'-L_S''-R_D$ and D is as described above, can be prepared according to the methods of Scheme XV. Compounds of formula (24) can be converted to compounds of formula (25) (Sonogashira reaction) by reaction with trimethylsilylacetylene, a palladium catalyst (e.g., bis(triphenylphosphine)palladium(II)chloride), a copper catalyst (e.g., copper(I)iodide), and a base (e.g., triethylamine) wherein an amine base can also be used as solvent. The compounds (25) can be desilylated to compounds (26) by reaction with a fluoride source (e.g., tetrabutylammonium fluoride) in a solvent such as THF. Compounds (26) can be converted to compounds (27) by formation of the dianion of (26) with n-butyllithium and subsequent reaction with a Weinreb amide (e.g., N-(tert-butoxycarbonyl)-L-proline-N'-methoxy-N'methylamide). This reaction can be conducted in an appropriate solvent such as THF or dimethoxyethane. Compounds (27) can be converted to compounds (28) by reaction with hydrazine in a solvent such as ethanol. The compounds (28) can be converted to compounds (29) using the methods described generally in the foregoing Schemes. Alternatively, the functionality of T-$R_D$ can be similarly introduced to compounds of Formula (28) to give compounds of Formula (XV-1).

Scheme XV

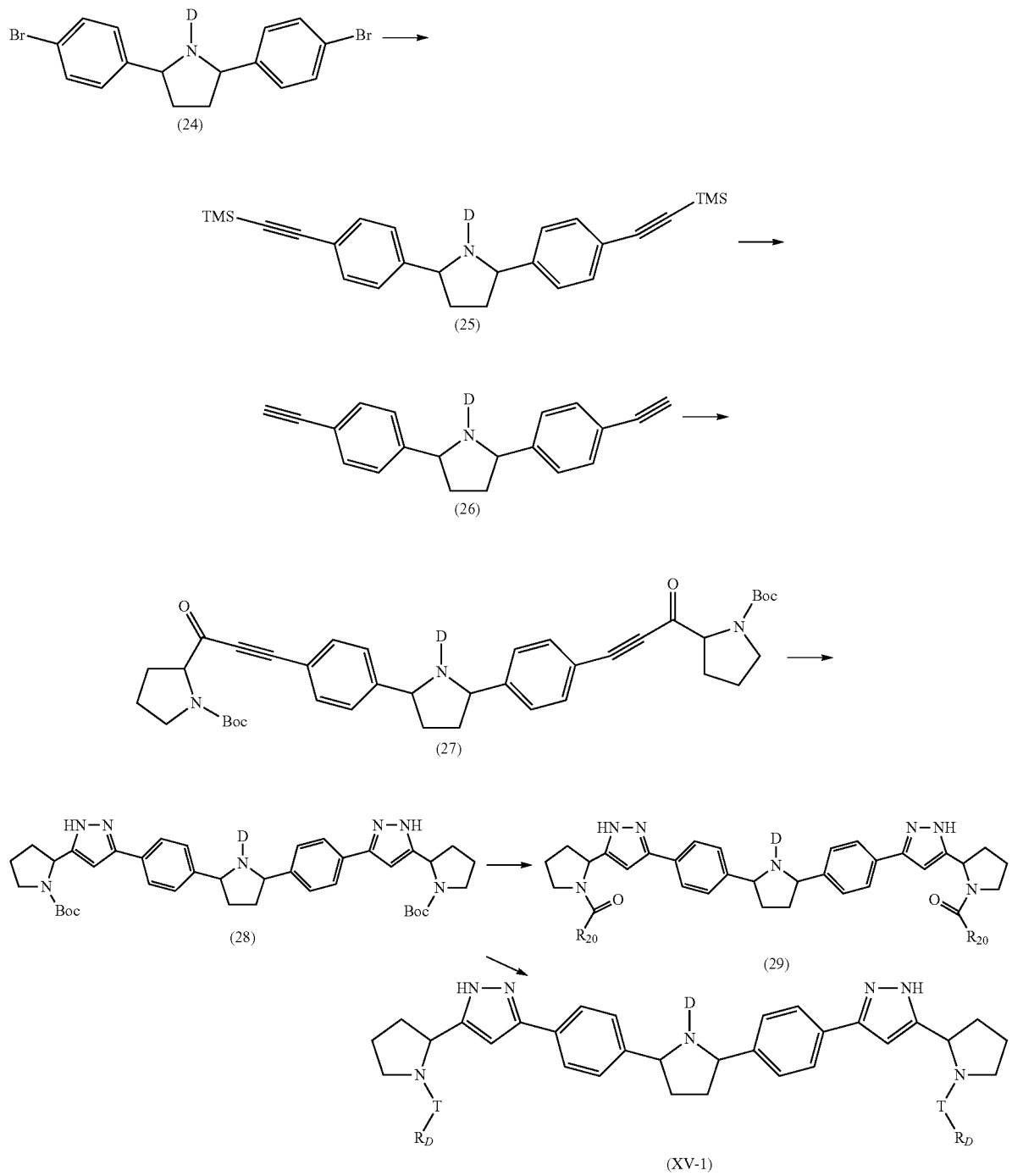

Certain compounds of the invention of general formula (34), where $R_{20}$ is -$L_S$'-M'-$L_S$"-$R_D$ and D is as described above, can be prepared according to the methods of Scheme XVI. Compounds (24) can be converted to compounds (30) by reaction of (24) with CO(g) under pressure (ca. 60 psi) in the presence of a palladium catalyst (e.g., $PdCl_2$(dppf)) in methanol as solvent and with heating to around 100° C. Compounds (30) can be converted to compounds (31) by reaction with hydrazine in a solvent such as methanol with heating to about 60-80° C. Compounds (31) can be converted to compounds (32) by reaction with N-Boc-2-cyano-pyrrolidine in the presence of a base (e.g., potassium carbonate) in a solvent such as butanol and with heating to around 150° C. with irradiation in a microwave reactor. Compounds (32) can be deprotected to compounds (33) and acylated to (34) using, in analogous fashion, the conditions described generally in the foregoing Schemes. Alternatively, the functionality of T-$R_D$ can be similarly introduced to compounds of Formula (33) to give compounds of Formula (XVI-1).

Scheme XVI

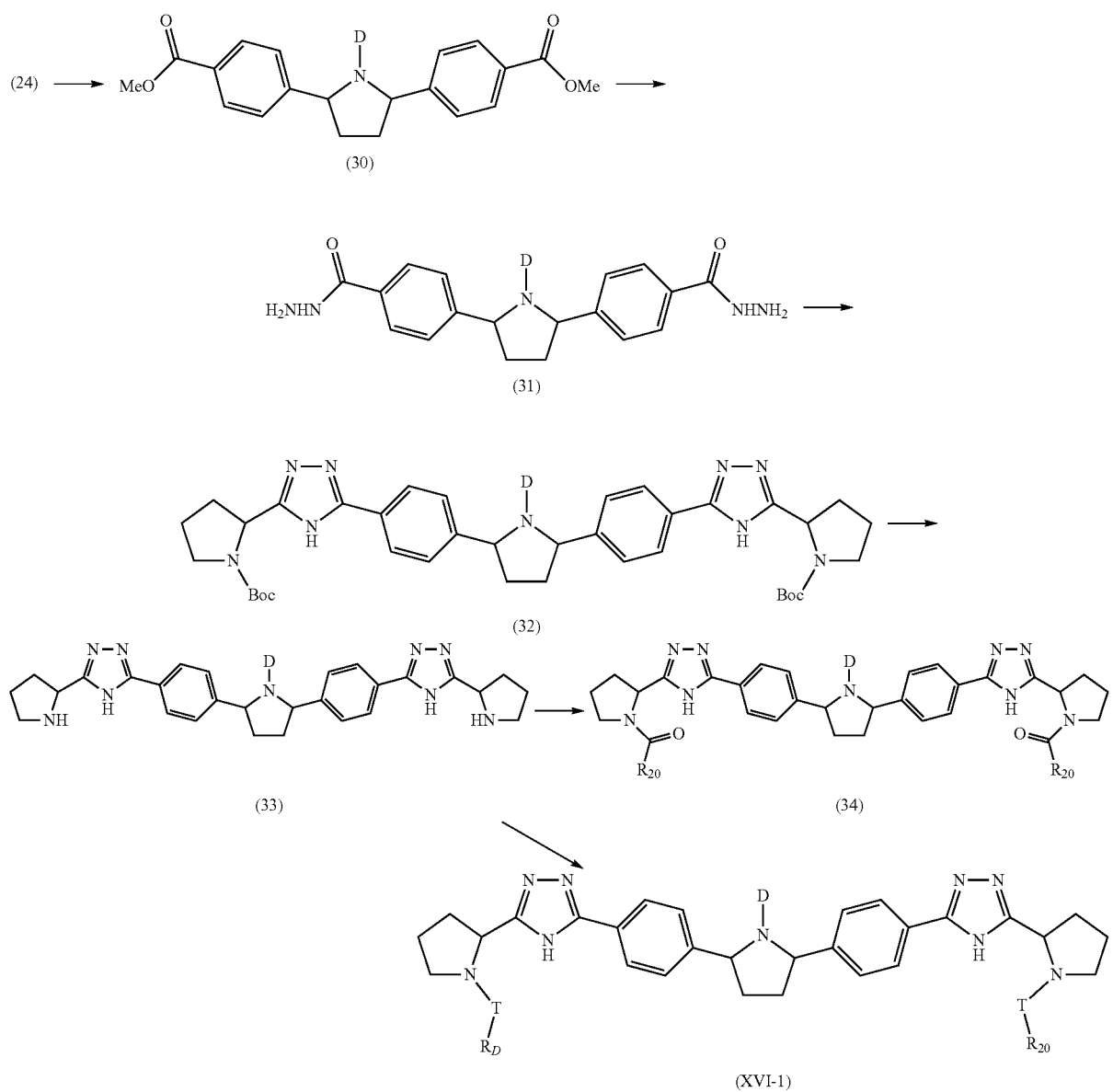

Certain compounds of the invention of general formula (38), where $R_{20}$ is $-L_S'-M'-L_S''-R_D$ and D is as described above, can be prepared according to the methods of Scheme XVII. Compounds of formula (24) can be converted to compounds (35) by reaction with CuCN in a solvent such as DMF and with heating to about 160° C. with microwave irradiation. Compounds (35) can be converted to compounds (36) by reaction with HCl(g) in anhydrous methanol at 0° C. with warming to room temperature. Compounds (36) can be converted to compounds (37) by reaction with $NH_3$(g) in anhydrous methanol at 0° C. with warming to room temperature. Compounds (37) can be converted to compounds (38) by reaction with (41) in THF in the presence of a base (e.g., potassium carbonate). Alternatively, the functionality of $T-R_D$ can be similarly introduced to compounds of Formula (33) to give compounds of Formula (XVII-1).

Scheme XVII

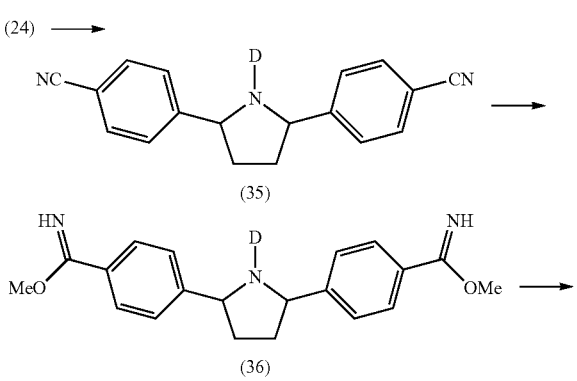

-continued

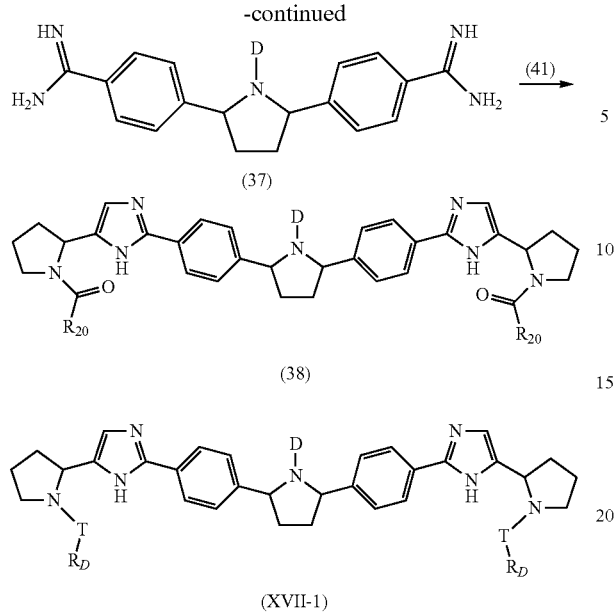

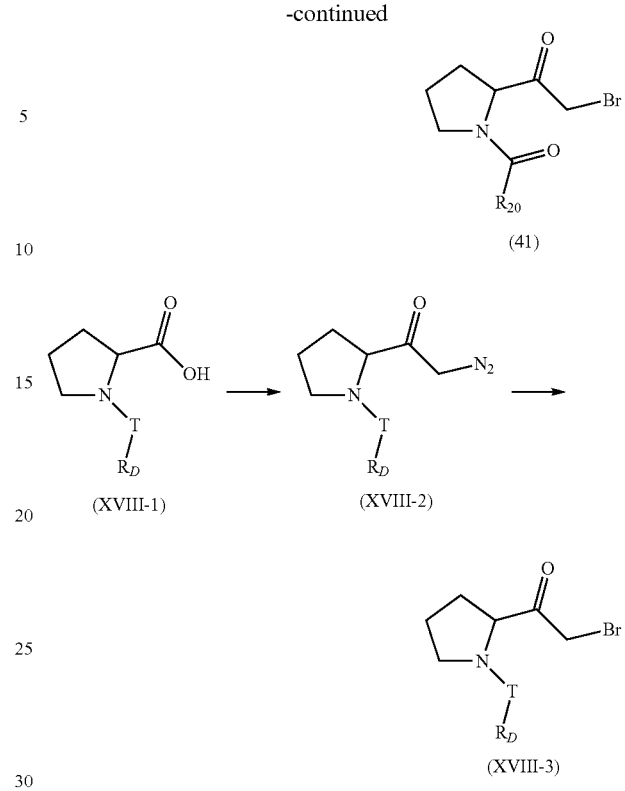

Compounds of formula (41), where $R_{20}$ is $-L_S'-M'-L_S''R_D$, can be prepared using the methods of Scheme XVIII. Compounds (39) can be converted to compounds (40) by sequential reaction of (39) with isobutylchloroformate in THF at 0° C. followed by diazomethane. Compounds (40) can be converted to compounds (41) by reaction with HBr in acetic acid. Similarly, compounds of formula (XVIII-1) can be converted to compounds of formula (XVIII-2) and then (XVIII-3), wherein T-$R_D$ are as defined above.

Scheme XVIII

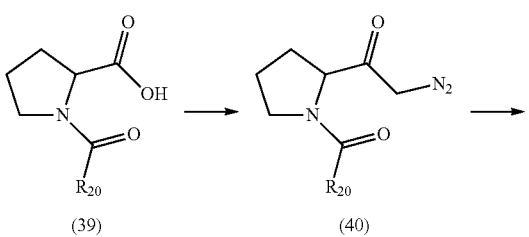

Certain compounds of the invention of general formula (48), where $R_{20}$ is $-L_S'-M'-L_S''-R_D$ and D is as described above, can be prepared according to the methods of Scheme XIX. Compound (42) can be reacted with compound (43) using, in analogous fashion, the Lewis acid mediated conditions described above in Scheme II to provide compound (44). Compound (44) can be converted sequentially to the diol (45), the mesylate (46) and the cyclic intermediate (47) using, in analogous fashion, the conditions of Scheme II. Compounds (47) can be converted to compounds (48) by reaction with (20) under Buchwald conditions such as those referred to Scheme XIV and described in Scheme XIII. Alternatively, the functionality of T-$R_D$, wherein T and $R_D$ are as defined above, can be similarly introduced to compounds of Formula (47) to give compounds of Formula (XIX-1).

Scheme XIX

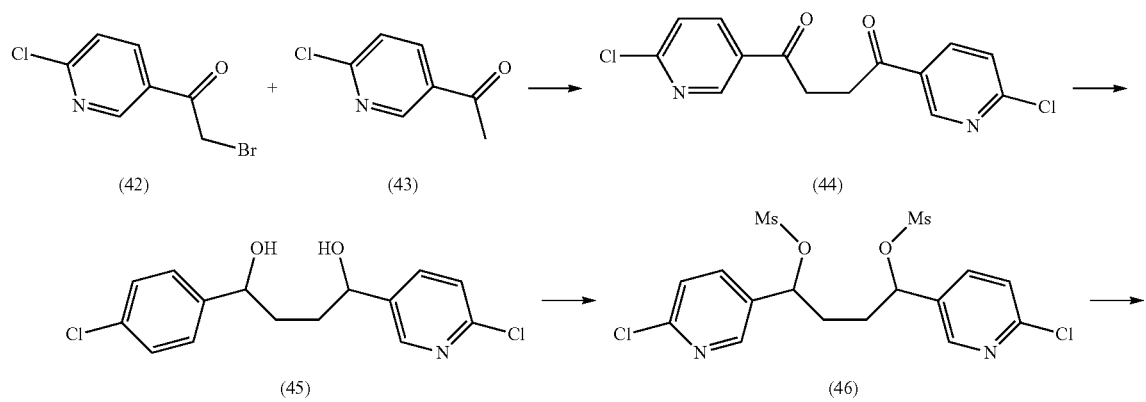

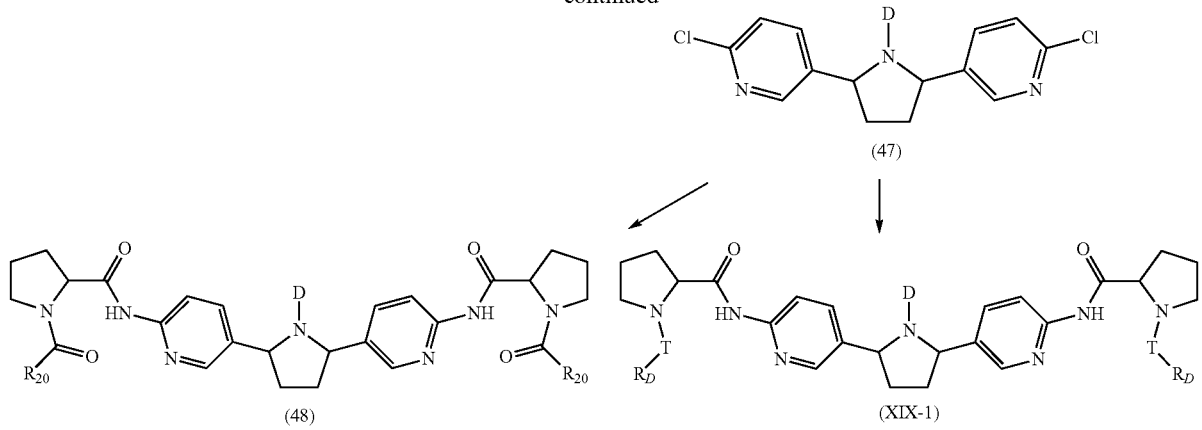

Certain compounds of the invention of general formula (55), where $R_{20}$ is $-L_S'-M'-L_S''-R_D$ and D is as described above, can be prepared according to the methods of Scheme XX. Diethyl meso-2,5-dibromoadipate (49) can be reacted with an amine $D-NH_2$ in a solvent such as THF, dioxane, or dimethoxyethane with heating from 50-100° C. to give compounds (50). Compounds (50) can be converted to (51) by alkaline hydrolysis with a base (e.g., NaOH, KOH) in an alcohol (e.g., methanol, ethanol) and water mixture for solvent. Compounds (51) can be converted to (52) by reaction first with oxalylchloride, and treatment of the intermediate acid chloride with diazomethane at 0° C. Compounds (52) can be converted to (53) by reaction with aqueous HBr. Compounds (53) can be converted to compounds (54) by reaction with thiourea in ethanol or like solvent. Compounds (54) can be converted to compounds (55) using, in analogous fashion, the conditions described above in Scheme II. Similarly, the functionality of $T-R_D$, wherein T and $R_D$ are as defined above, can be introduced to compounds of Formula (54) to give compounds of Formula (XX-1).

Scheme XX

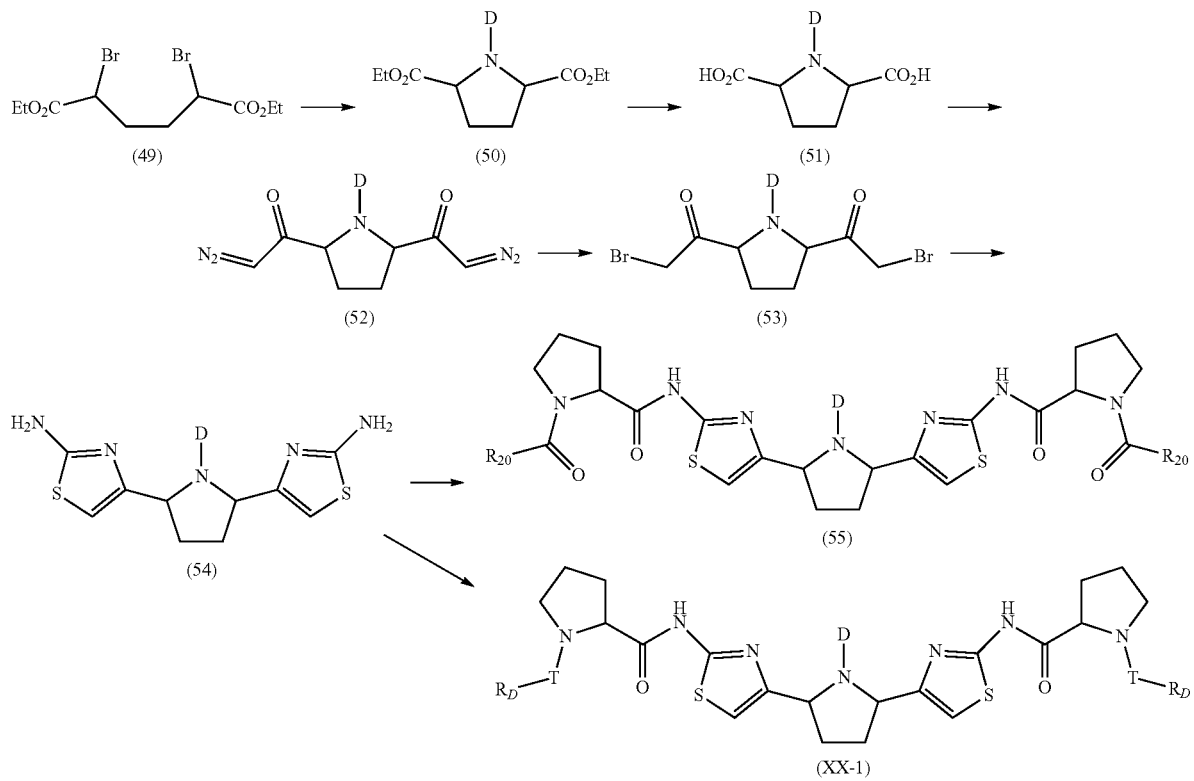

Certain compounds of the invention of general formula (60), where $R_{20}$ is $-L_S'-M'-L_S''-R_D$ and D is as described above, can be prepared according to the methods of Scheme XXI. Compound (56) can be reacted with compound (57) in pyridine with heating to about 135° C. to form compound (58). Compound (58) can be converted to compounds (59) by reaction of an amine D-NH$_2$ with POCl$_3$ followed by addition of (58) and heating at about 200° C. in 1,2-dichlorobenzene. Compounds (59) can be converted to compounds (60) using, in analogous fashion, the conditions described above in Scheme VII. Similarly, the functionality of T-R$_D$, wherein T and R$_D$ are as defined above, can be introduced to compounds of Formula (59) to give compounds of Formula (XXI-1).

-continued

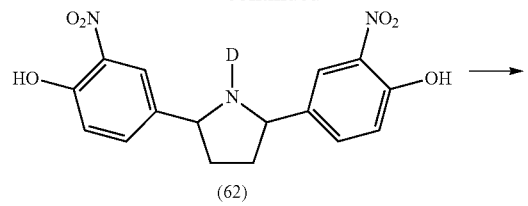

(62)

Scheme XXI

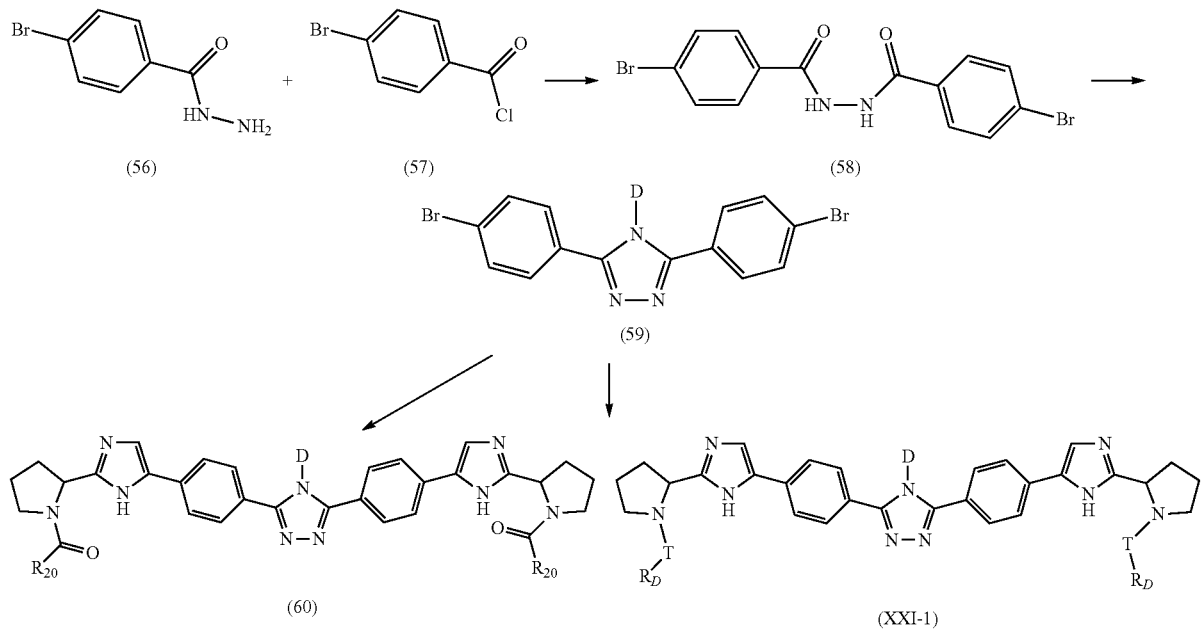

Certain compounds of the invention of general formula (66), where R$_{20}$ is -L$_S$'-M'-L$_S$"-R$_D$ and D are as described above, can be prepared according to the methods of Scheme XXII. Compounds of general formula (61) can be reacted with borontribromide in dichloromethane at 0° C. to give compounds (62), which can be subjected to hydrogenation conditions using platinum(II) oxide to give compounds (63). Coupling between compounds (63) and proline derivatives (64) can be carried out using standard coupling conditions described above to give compounds (65), which can be converted to (66) by the action of diethylazodicarboxylate and triphenylphosphine in THF.

-continued

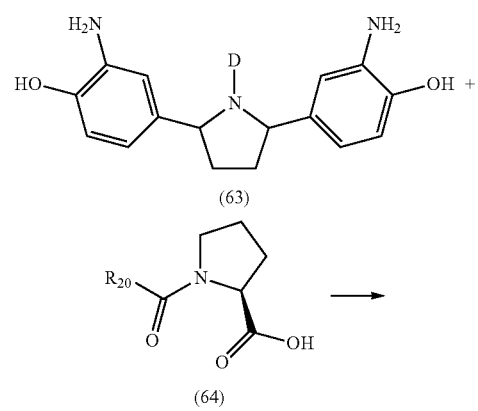

Scheme XXII

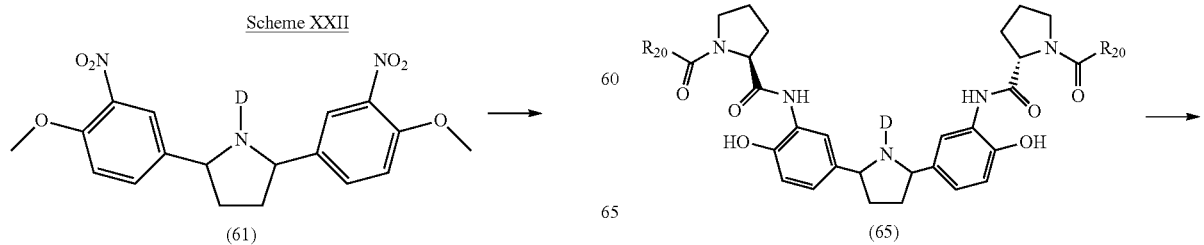

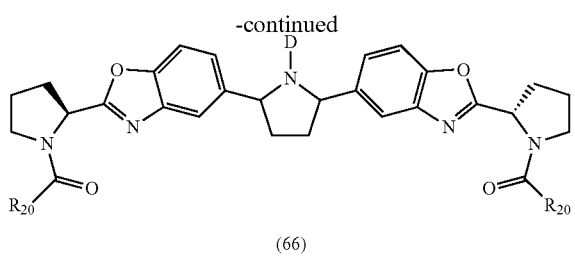

(66)

Certain compounds of the invention of general formula (74), where $R_{20}$ is $-L_S'-M'-L_S''-R_D$ and D is as described above, can be prepared according to the methods of Scheme XXIII. Compound (67) can be converted to (68) by reduction of the nitro group using tin(II) chloride in ethanol. Compound (69) can be made from (68) by peptide coupling with Boc-proline, followed by heating of the resulting amide in acetic acid at 80° C. Compound (69) can be reacted with SEM-Cl and diisopropylethylamine in dichloromethane to give (70), which can be coupled with (71) using a palladium catalyst such as PXPd using a base such as cesium fluoride in a solvent such as N,N-dimethylformamide at 100° C. to give (72). Compound (72) can be converted to (73) by reaction with Selectfluor in a mixture of THF and water, followed by hydrogenation using 3% Pt on carbon in ethylacetate and then reduction using sodium borohydride in methanol. Compound (73) can be reacted with methanesulfonyl chloride and triethylamine in dichloromethane at −10° C., followed by addition of an amine ($H_2N$-D) to give an intermediate that can be converted to (74) by deprotection using 4 N HCl in 1,4-dioxane and then coupling with $R_{20}CO_2H$ using peptide coupling procedures described above. Similarly, the functionality of T-$R_D$, wherein T and $R_D$ are as defined above, can be introduced to compounds of Formula (73) to give compounds of Formula (XXIII-1).

Scheme XXIII

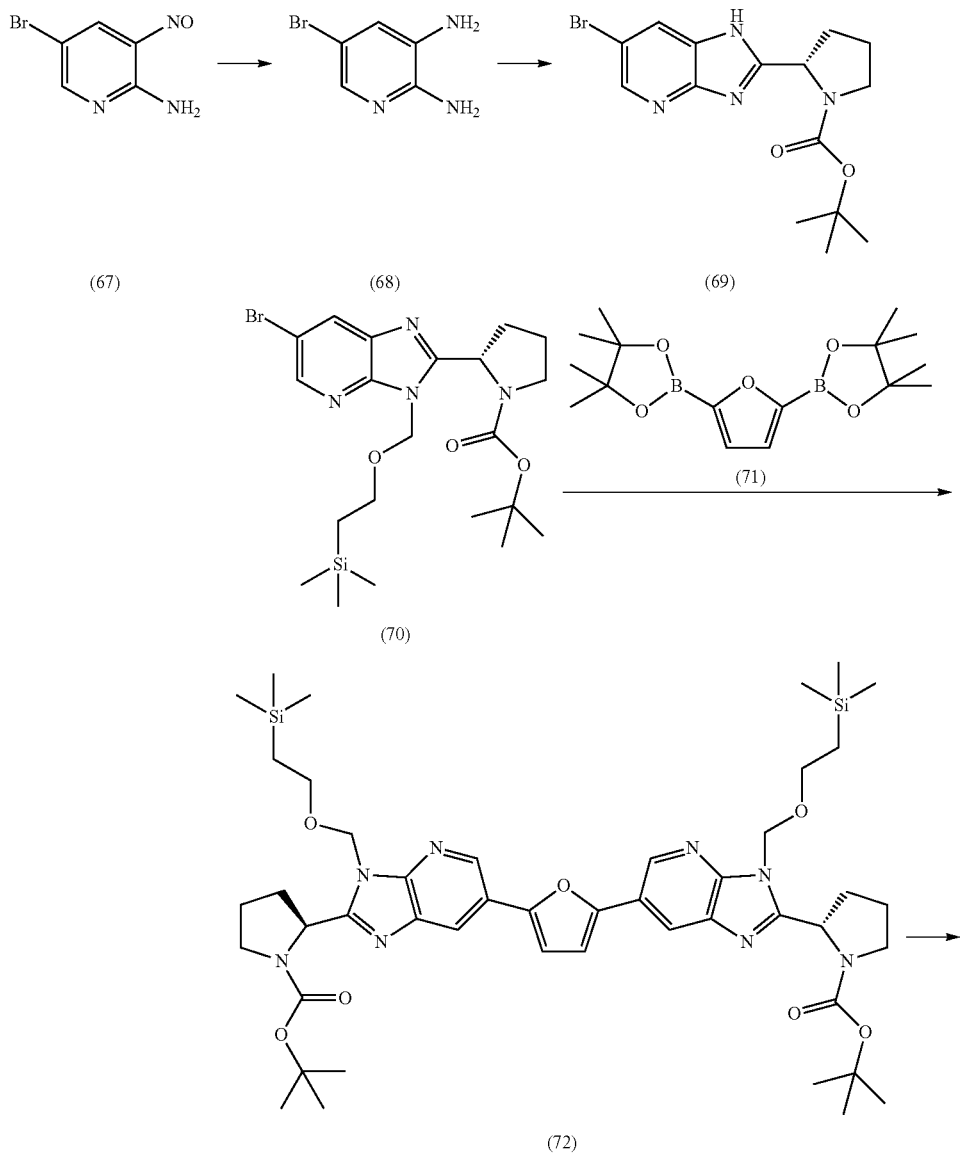

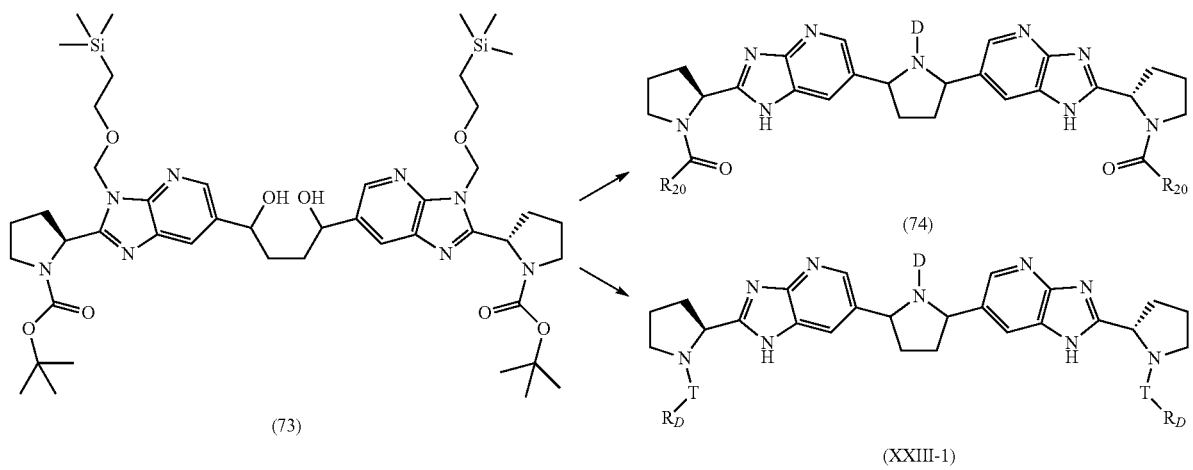

(73)

(74)

(XXIII-1)

Certain compounds of the invention of general formula (81), where $R_{20}$ is -$L_S$'-M'-$L_S$"-$R_D$ and D is as described above, can be prepared according to the methods of Scheme XXIV. Compound (75) can be converted to (76) using $SnCl_2$ in ethanol. Additionally, the phenyl ring of compound (75) can be substituted with $X_{13}$ at any position substituted with hydrogen or fluorine, wherein $X_{13}$ is H, alkyl, haloalkyl, alkoxy, or haloalkoxy, and those compounds carried through the subsequent sequence. Coupling of (76) with (64) using peptide coupling procedures described above to give an amide that can be heated in acetic acid at 100° C. to give (77). Compound (77) can be reacted with SEM-Cl and diisopropylethylamine in dichloromethane to give (78). For convenient illustration, the SEM protecting groups on the benzimidazoles are shown attached to particular nitrogens of the benzimidazole. The actual substitution positions of the SEM groups may be at either nitrogen (i.e., (78) may be a mixture of regioisomers). In subsequent compounds (79) through (80), the positional isomerism of the SEM group results in mixtures of SEM regioisomers that may or may not be separable. In practice the SEM regioisomers can be carried through as mixtures. Compound (78) can be reacted with (71) as described above to give (79). Compound (79) can be converted to (80) using Selectfluor in a mixture of THF and water, followed by hydrogenation with Pt on carbon in ethylacetate and reduction with sodium borohydride in methanol or chiral reduction conditions with (S) or (R) α,α-diphenyl-2-pyrrolidinemethanol, diethylaniline borane and trimethylborane. Compound (80) can be converted to compounds (81) by mesylation with methanesulfonyl chloride and triethylamine at temperatures less than 0° C., followed by reaction with primary amine $H_2N$-D and deprotection using 4 N HCl in 1,4-dioxane. Similarly, the functionality of T-$R_D$, wherein T and $R_D$ are as defined above, can be introduced to compounds of Formula (77) to give compounds of Formula (XXIV-1) at the end of the synthetic sequence.

Scheme XXIV

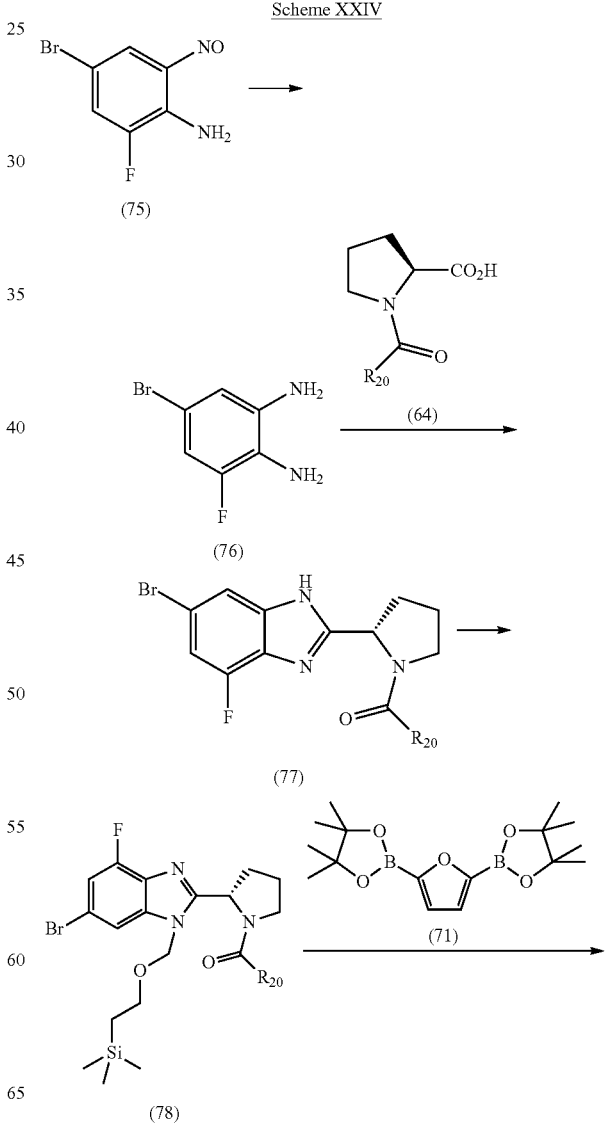

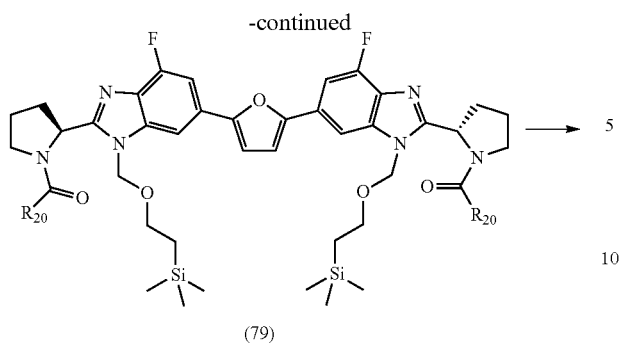

(79)

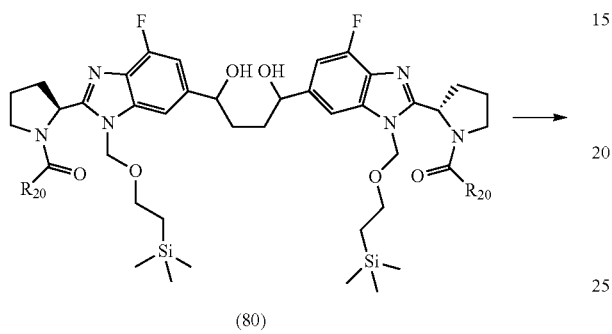

(80)

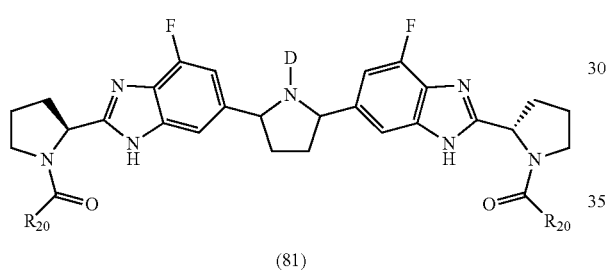

(81)

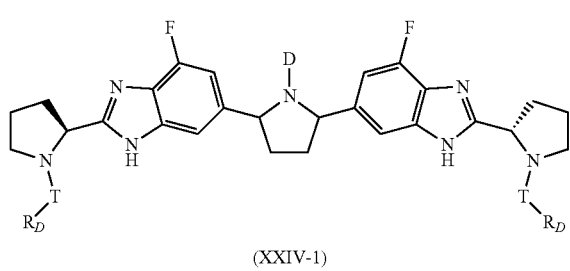

(XXIV-1)

Certain amines, D-NH$_2$, in the foregoing Schemes are represented by formula (84), and may be prepared according to the general method shown in Scheme XXV, wherein R$_N$ is as defined above (e.g., halogen, alkyl, haloalkyl) and R$_M$ is —N(R$_S$R$_S$') (e.g., —NEt$_2$), heterocyclyl (e.g., pyrrolidin-1-yl, piperidin-1-yl,

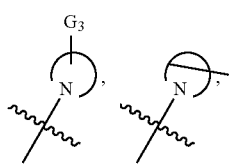

etc., wherein G$_3$ is defined above,

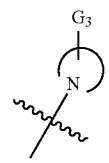

is a nitrogen containing heterocycle substituted with G$_3$, and

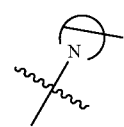

is a nitrogen containing bridged, bicyclic heterocycle), or —OR$_S$ (e.g., —O-t-butyl, —O-isopropyl, etc.). Fluoronitrobenzenes (82) can be reacted with an appropriate amine in the presence of dibasic potassium phosphate in a solvent such as DMSO optionally with heating to give intermediates (83), wherein R$_M$ is —N(R$_S$R$_S$') (e.g., —NEt$_2$) or heterocyclyl (e.g., pyrrolidin-1-yl, piperidin-1-yl,

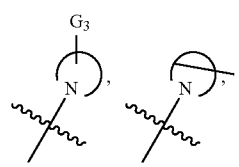

etc.). Fluoronitrobenzenes (82) can also be reacted with alkali metal alkoxides (e.g., potassium tert-butoxide) to give intermediates (83), wherein R$_M$ is —OR$_S$ (e.g., —O-t-butyl, —O-isopropyl, etc.). Intermediates (83) may be converted to (84) using well-known nitro reduction conditions. For example, (83) can be converted to (84) by catalytic hydrogenation using palladium on carbon. Alternatively, (83) can be converted to (84) by reaction with iron/ammonium chloride in THF/methanol/water as solvent. Other conditions for effecting nitro reduction include those described in the foregoing schemes and those generally known to one skilled in the art.

Scheme XXV

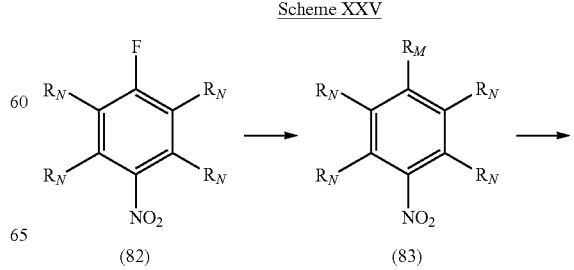

(82)    (83)

-continued

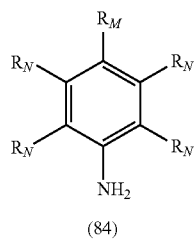

(84)

Certain compounds of the present invention (XXVI-10) can be prepared as shown generally in Scheme XXVI, where D, T, and $R_D$ are as described above. Reaction of compounds (1) with compounds (III), using the conditions described generally in Scheme II for the preparation of compounds (IV), can provide diketone compounds (XXVI-1). Compounds (XXVI-1) can be converted to compounds (XXVI-2) using the general conditions of Scheme II for the conversion of (IV) to (V). Compounds (XXVI-2) can be converted to compounds (XXVI-3) using the general conditions of Scheme II for the conversion of (V) to (VI). Compounds (XXVI-3) can be converted to compounds (XXVI-4) using the general conditions of Scheme II for the conversion of (VI) to (VII). Compounds of formula (XXVI-4) can be converted to compounds (XXVI-5) using the general conditions of Scheme VII for the conversion of (II) to (III). Compounds (XXVI-5) can be converted to compounds (XXVI-6) using the general conditions of Scheme VII for the conversion of (III) to (IV). Compounds (XXVI-6) can be converted to compounds (XXVI-7) using the general conditions of Scheme II for the conversion of (VII) to (VIII). For example, compounds (XXVI-6) (1 equivalent) can be reduced with hydrogen gas (1 atm) in the presence of $PtO_2$ (about 0.2 equivalents) in a solvent such as ethanol:THF (1:1). Compounds (XXVI-7) can be converted to compounds (XXVI-8) using the methods described generally in Scheme II for conversion of (VIII) to (IX). For example, reaction of (XXVI-7) (1 equivalent) with 1-(tert-butoxycarbonyl)pyrrolidine-2-carboxylic acid (1.5 to 3 equivalents) and HATU (about 1.6 equivalents) in the presence of diisopropylethylamine (3 equivalents) in DMSO at about room temperature can provide the compounds (XXVI-8). Compounds (XXVI-8) can be converted to compounds (XXVI-9) using the methods described generally in Scheme II for conversion of (IX) to (X). For example, reaction of (XXVI-8) (1 equivalent) with HCl in dioxane at about room temperature can provide the compounds (XXVI-9). Compounds (XXVI-9) can be converted to compounds (XXVI-10) by reaction with an appropriate acid using the methods described generally in Scheme II for the conversion of (X) to (XI). For example, reaction of (XXVI-9) (1 equivalent) with 2-(methoxycarbonylamino)-3-methylbutanoic acid (about 2 to 3 equivalents), HATU (about 2.5 to 3.5 equivalents), and diisopropylethylamine (about 10 equivalents) in a solvent such as DMSO can provide the products (XXVI-10).

Scheme XXVI

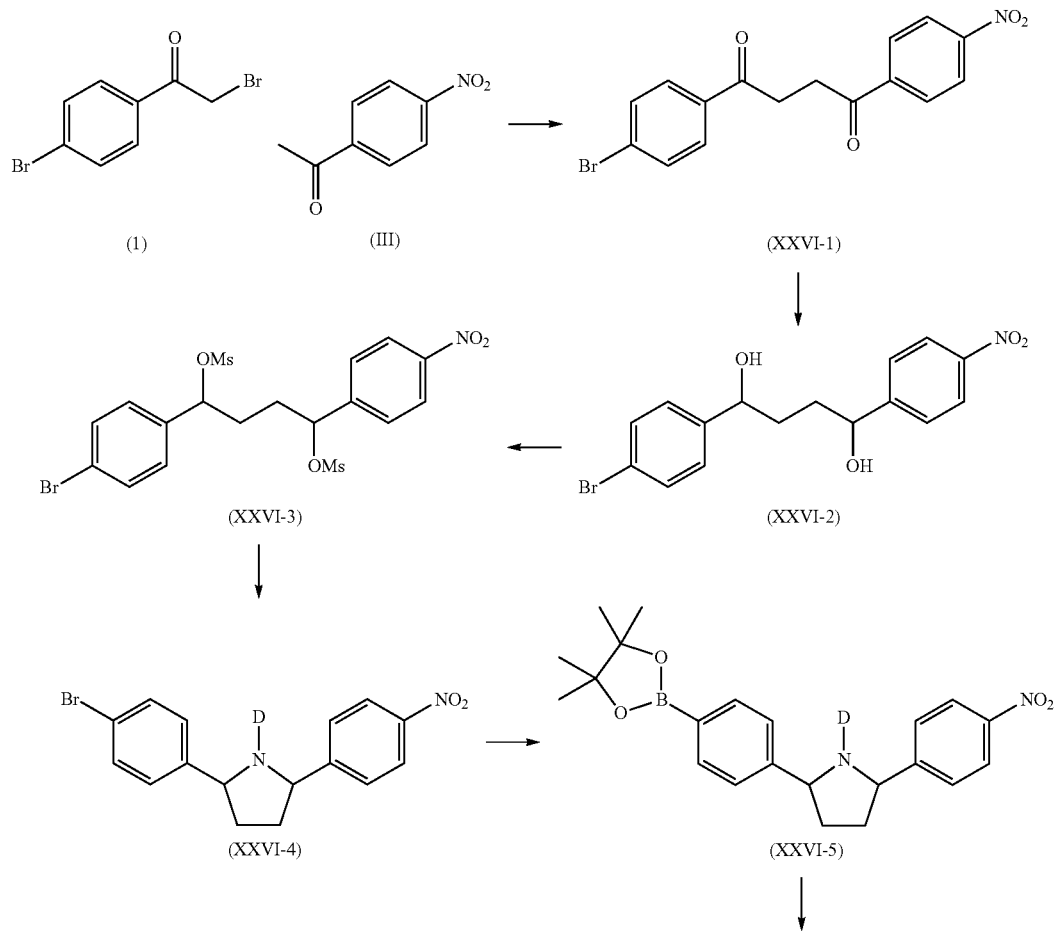

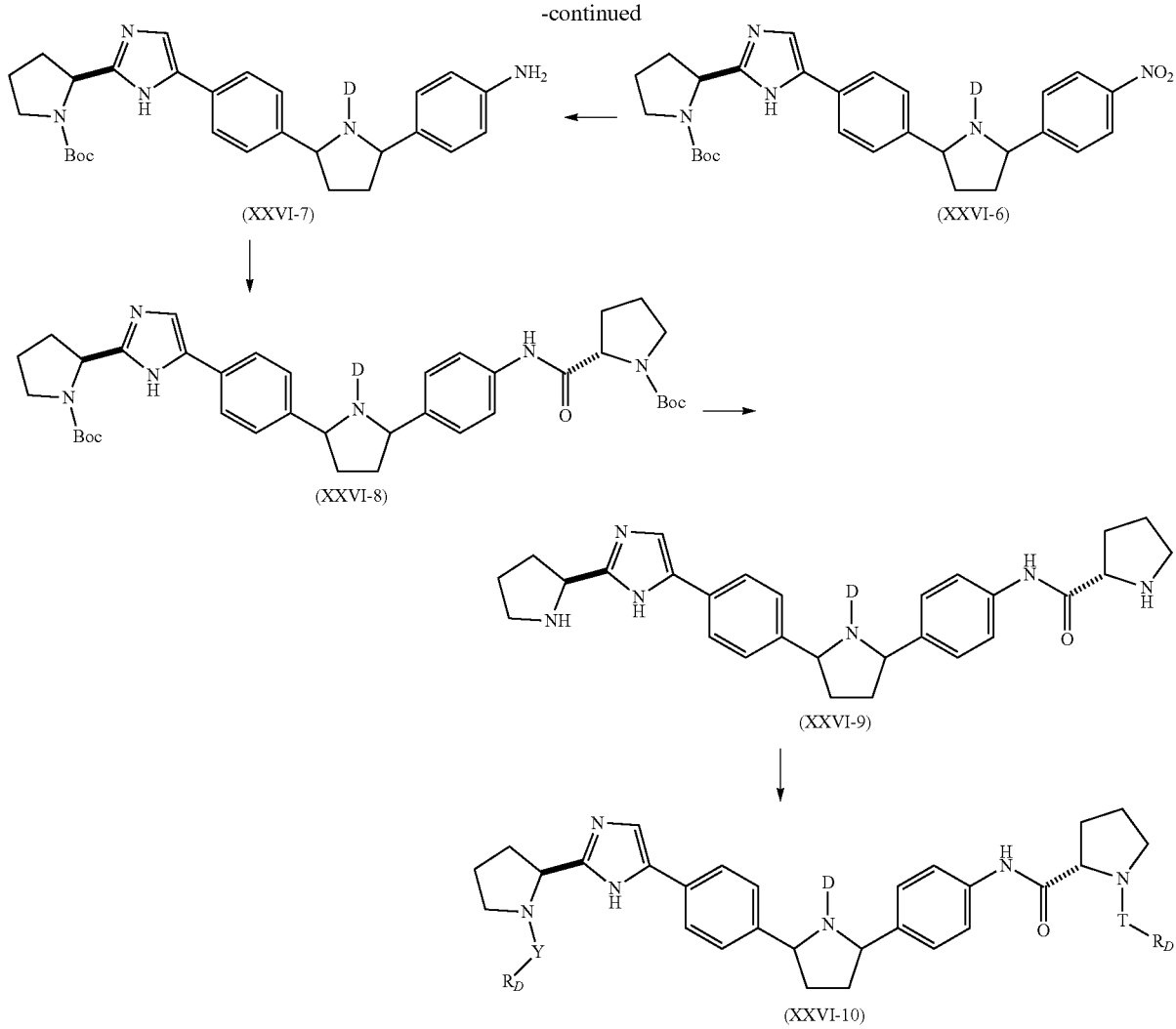

Certain compounds of the present invention (XXVII-7) can be prepared as shown generally in Scheme XXVII, where D, T, and $R_D$ are as described above. Compounds (XXVI-1) can be converted to compounds (XXVII-1) using the general conditions of Scheme XII for the conversion of (3) to (11). Compounds (XXVII-1) can be converted to compounds (XXVII-2) by reduction using conditions described generally above in Scheme II. For example (XXVII-1) (1 equivalent) can be reduced with iron powder (about 6 equivalents) and ammonium chloride (about 3 equivalents) in ethanol:THF:water (1:1:0.25) with heating up to the reflux temperature to provide (XXVII-2). Compounds (XXVII-2) can be converted to compounds (XXVII-3) using the conditions described above for conversion of VIII to IX in Scheme II, (12) to (13) in Scheme XII, or (XXVI-7) to (XXVI-8) in Scheme XXVI. Compounds (XXVII-3) can be converted sequentially to compounds (XXVII-4) and (XXVII-5) using the methods and conditions described generally in Scheme VII for the conversion of (II) to (III) to (V). Compounds (XXVII-5) can be converted sequentially to compounds (XXVII-6) and (XXVII-7) using the methods and conditions described generally above, for example using the methods to convert (IX) to (X) to (XI) in Scheme II.

Scheme XXVII

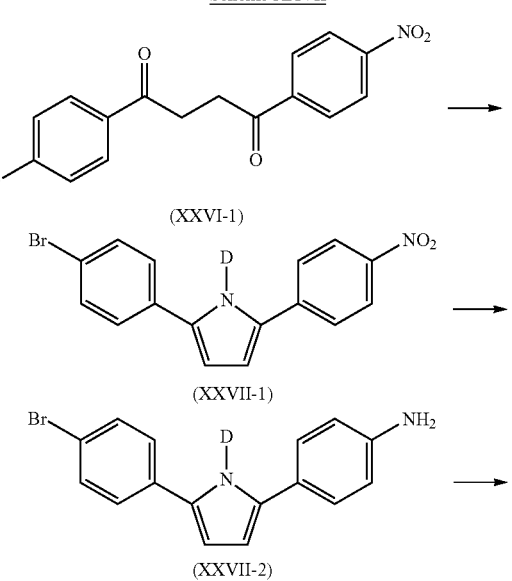

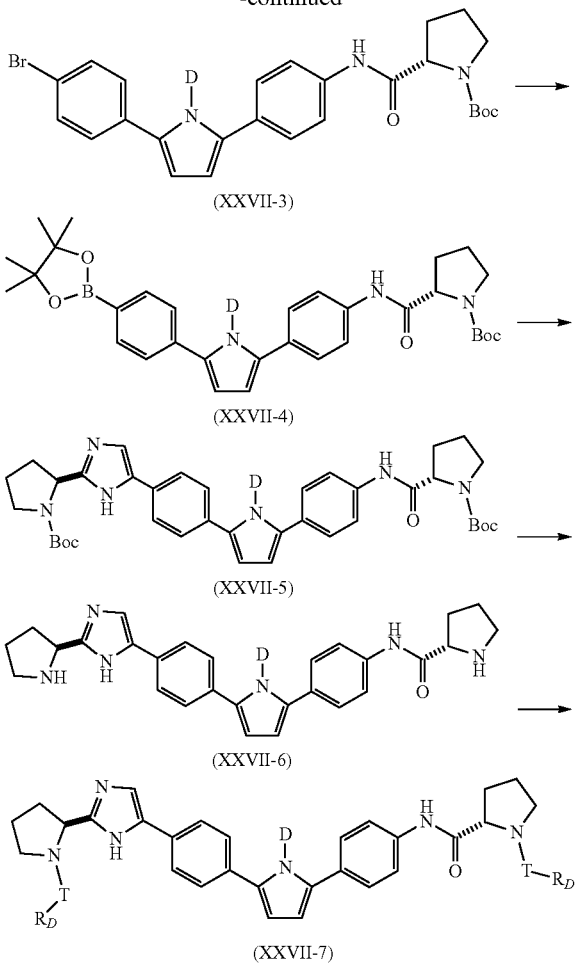

Certain compounds of the invention of general formula (XXVIII-7), where D, T, and $R_D$ are as described above, can be prepared according to the sequence of Scheme XXVIII. Compounds (XXVIII-1) can be prepared from 2-bromo-1-(4-nitrophenyl)ethanone, 1-(4-chloro-3-nitrophenyl)ethanone, and an amine D-NH$_2$ according to the methods described above to prepare compounds (VII) in Scheme II, (XXVI-4) in Scheme XXVI- and (VII) in Scheme IV. Compounds (XXVIII-1) (1 equivalent) can be converted to compounds (XXVIII-2) by reaction with neat 4-methoxybenzylamine (about 4-6 equivalents) with heating to around 140-150° C. Compounds (XXVIII-2) can be converted to compounds (XXVIII-3) by reduction according to the conditions described generally in Scheme II to prepare compounds (VIII). For example, reaction of (XXVIII-2) (1 equivalent) with PtO$_2$ (about 0.4-0.5 equivalents) in a solvent such as ethanol:THF (1:1) under a hydrogen atmosphere (1-4 atm) can provide compounds (XXVIII-3). Compounds (XXVIII-3) can be converted to compounds (XXVIII-4) according to the conditions described generally in Scheme II to prepare compounds (IX). For example, reaction of (XXVIII-3) (1 equivalent) with 1-(tert-butoxycarbonyl)pyrrolidine-2-carboxylic acid (about 2-3 equivalents), HATU (about 2-3 equivalents), and diisopropylethylamine (about 3 equivalents) in a solvent such as DMSO at room temperature can provide compounds (XXVIII-4). Compounds (XXVIII-4) (1 equivalent) can be converted to compounds (XXVIII-5) by reaction with DDQ (about 1.2 equivalents) in a solvent mixture of CH$_2$Cl$_2$:water (20:1) at room temperature. Compounds (XXVIII-5) can be converted to compounds (XXVIII-6) according to the general methods described in Scheme IV to prepare compounds (XI) (e.g., heating in acetic acid to around 60-70° C.). Compounds (XXVIII-6) can further be converted to compounds (XXVIII-7) by using the standard deprotection and coupling methods referred to in Scheme IV to prepare compounds (XIII) or (XIV).

Scheme XXVIII

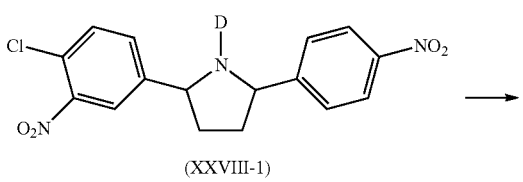

(XXVIII-1)

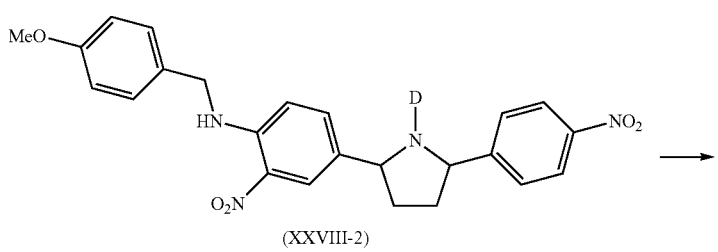

(XXVIII-2)

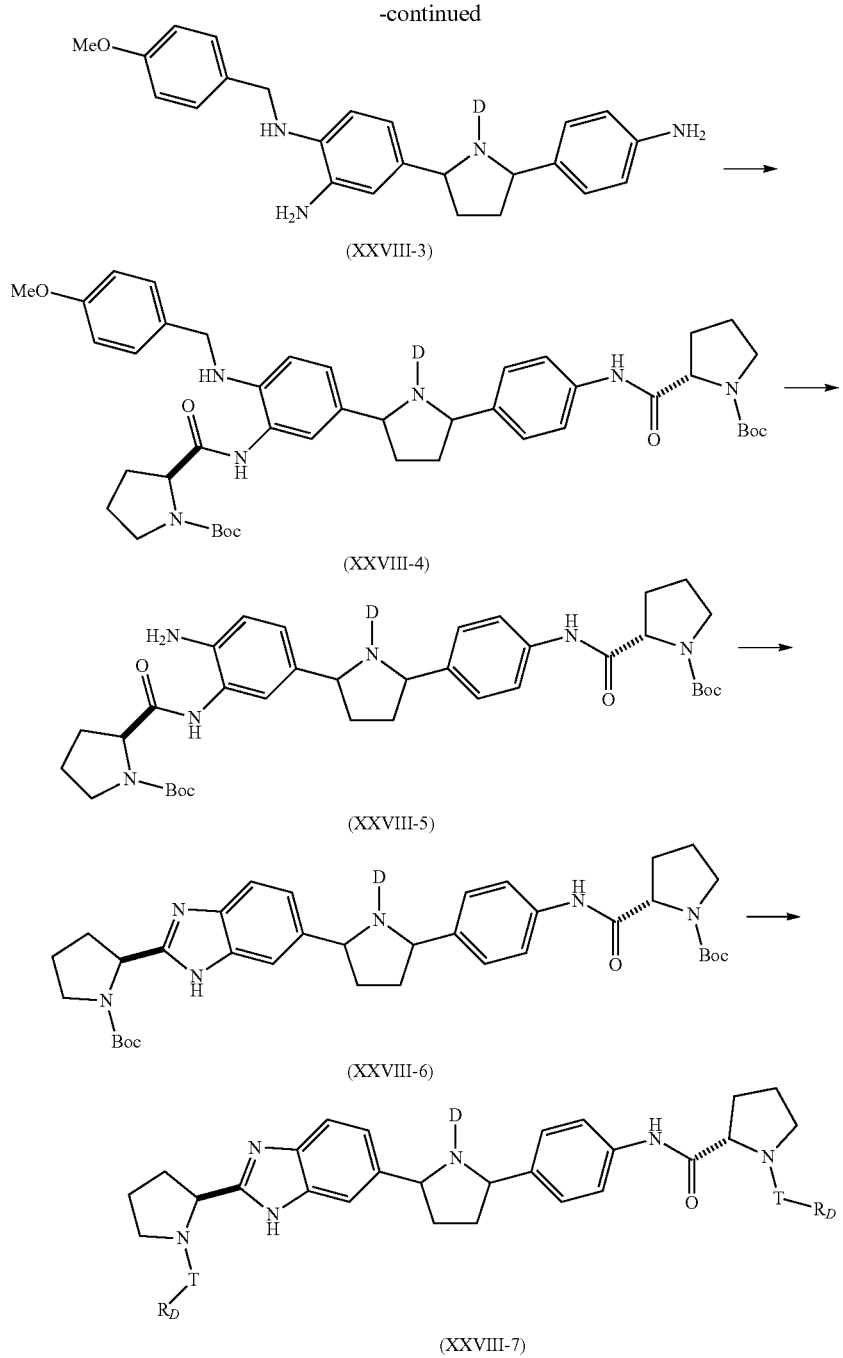

Certain compounds of the invention (XXIX-9) where D, T, and $R_D$ are as described above, can be prepared according to the sequence of Scheme XXIX. Compounds (XXIX-1) can be prepared from 2-bromo-1-(4-bromophenyl)ethanone, 1-(4-chloro-3-nitrophenyl)ethanone, and an amine D-NH₂ according to the methods described above to prepare compounds (VII) in Scheme II, (XXVI-4) in Scheme XXVI, and (VII) in Scheme IV. Compounds (XXIX-1) (1 equivalent) can be converted to compounds (XXIX-2) by reaction with neat 3,4-dimethoxybenzylamine (about 10 equivalents) with heating up to around 140-150° C. Compounds (XXIX-2) can be converted to compounds (XXIX-3) by reduction according to the conditions described generally in Scheme II to prepare compounds (VIII). For example, reaction of (XXIX-2) (1 equivalent) with $PtO_2$ (about 0.1 equivalent) in a solvent such as ethanol:THF:EtOAc (1:1) under a hydrogen atmosphere (e.g., 1 atm) can provide compounds (XXIX-3). Compounds (XXIX-3) can be converted to compounds (XXIX-4) according to the conditions described generally in Scheme II to prepare compounds (IX). For example, reaction of (XXIX-3) (1 equivalent) with a substituted proline like (S)-1-((S)-2-(methoxycarbonylamino)-3-methylbutanoyl)pyrrolidine-2-carboxylic acid (about 1.2-1.5 equivalents), HOBt (about 1.2-1.5 equivalents), EDAC (about 1.2-1.5 equivalents), and N-methylmorpholine (about 5-6 equivalents) in a solvent such as DMF at room temperature can provide compounds (XXIX-4). Compounds (XXIX-4) can be deprotected to compounds (XXIX-5) by reaction with excess TFA in solvents such as methylene chloride at about room temperature. Compounds (XXIX-5) can be converted to compounds (XXIX-6) according to the general methods described in Scheme IV to prepare compounds (XI) (e.g., heating in acetic acid to around 60-80° C.). Compounds (XXIX-6) can be converted to compounds (XXIX-7) according to the general conditions of Scheme VII to prepare compounds (III). For example, reaction of (XXIX-6) (1 equivalent) with PdCl$_2$(dppf) (about 0.1 equivalent), potassium acetate (about 3-5 equivalents), and bis(pinacolato)diboron (about 3 equivalents) in a solvent such as toluene with heating to 80-100° C. can provide compounds (XXIX-7). Compounds (XXIX-7) can be converted to compounds (XXIX-8) according to the general conditions of Scheme VII to prepare compounds (V). For example, reaction of compounds (XXIX-7) (1 equivalent) with Intermediate 1D (about 2 equivalents), 1M sodium carbonate (about 3 equivalents), and PdCl$_2$(dppf) (about 0.1 equivalent) in a solvent such as toluene at around 80-100° C. can provide compounds (XXIX-8). Compounds (XXIX-8) can further be converted to compounds (XXIX-9) by using the standard deprotection (e.g., HCl/dioxane) and coupling methods (e.g., carboxylic acid, HOBt, EDAC, and N-methylmorpholine) referred to in Scheme IV to prepare compounds (XIV).

Scheme XXIX

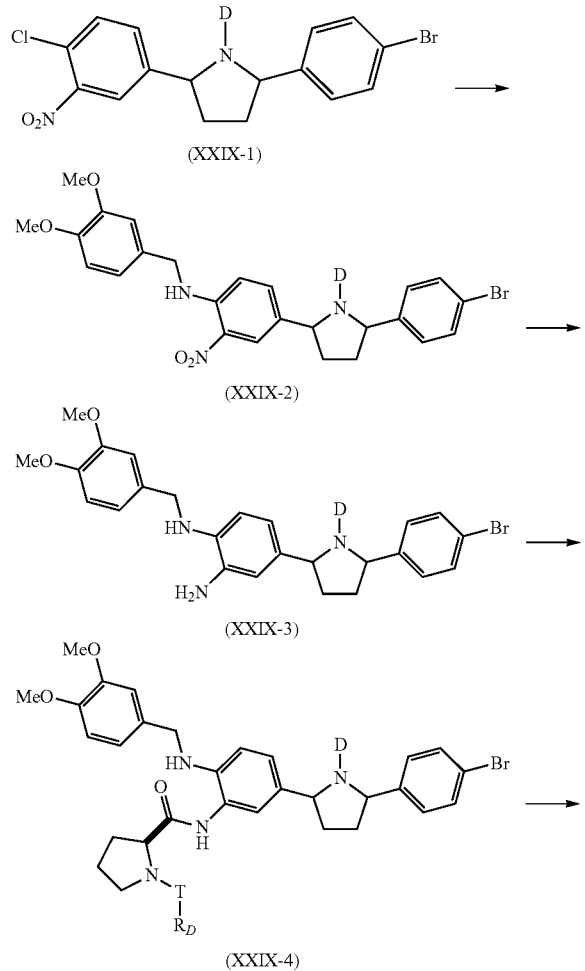

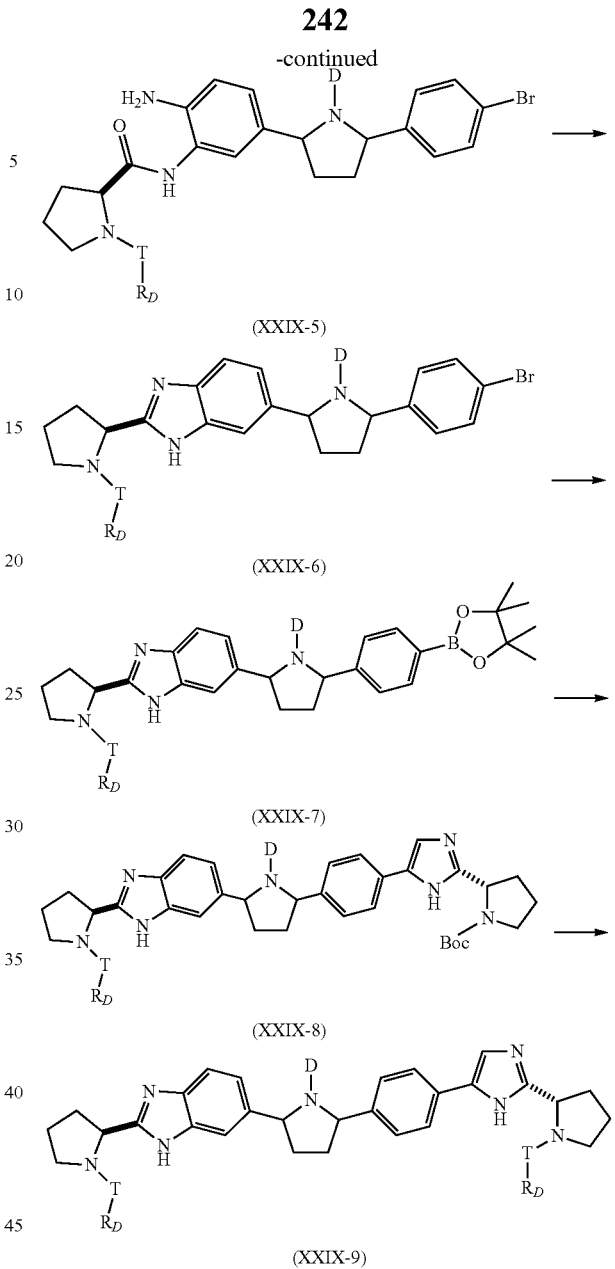

Certain compounds of the present invention (XXX-8) can be prepared as shown in Scheme XXX. An ester (XXX-1) can be reacted with a suitable reducing agent such as DIBAL-H, in a solvent such as THF, dichloromethane, or diethyl ether, to the corresponding alcohol then oxidized to the aldehyde (XXX-2) by employing a suitable oxidizing agent such as PDC in a solvent such as dichloromethane, THF or diethyl ether. A pyrrole of formula (XXX-4) can be prepared by reacting (XXX-3) (available from an aniline, an aldehyde and KCN using the Strecker reaction) together with aldehyde (XXX-2) with a base such as potassium hydroxide in a solvent such as ethanol (*Synlett,* 2003, pp 1427-1430). The bromine atoms in the pyrrole compounds (XXX-4) can be converted to a bis-borane compound (XXX-5) by utilization of palladium catalysis as described above in Scheme VII. The pyrrole compounds (XXX-5) can be reacted with bromoimidazoles like Intermediate 1D using Suzuki reaction conditions to give the phenylimidazole (XXX-6). A variety of reaction conditions are well known to those of skill in the art to be effective in mediating the Suzuki reaction. In particular, the reaction to produce (XXX-6) can be performed with Pd(dppf)Cl$_2$ catalyst and potassium carbonate in a mixture of toluene and water and with heating to about 100° C. Removal of the Boc protecting groups to give (XXX-7) can be accomplished by treatment with an acid, such as TFA, HCl, or formic acid. Certain compounds of the present invention (XXX-8), wherein T, R$_D$, and D are as described above, may be prepared by coupling of (XXX-7) with an acid of choice using the standard peptide coupling reagents and conditions described above.

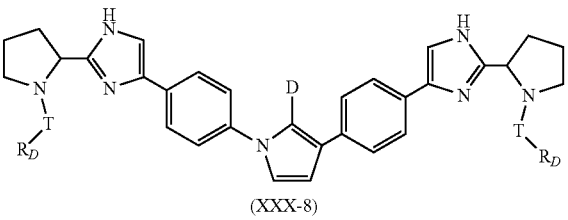

(XXX-8)

The present invention also contemplate Schemes XXXI-XXXIII to make a compound of the invention. For instance, compounds of the invention (XXXI-5) may be prepared using the sequence of steps outlined generally in Scheme XXXI. This sequence parallels that of Scheme XXX. A compound (XXXI-1) may be converted to a compound (XXXI-2) by sequential Heck reaction with ethylacrylate followed by reduction to an aldehyde (XXXI-2). An aldehyde like (XXXI-2) may be reacted with a compound (XXX-3) analogously to the conditions of Scheme XXX to provide compounds (XXXI-3). Compounds (XXXI-3) in turn may be converted to boronate compounds (XXXI-4) using the condition described above generally in Scheme VII. Compounds (XXXI-4) may be converted to compounds (XXXI-5) over several steps including Suzuki reaction, deprotection and coupling as described generally in the foregoing Schemes.

Scheme XXX

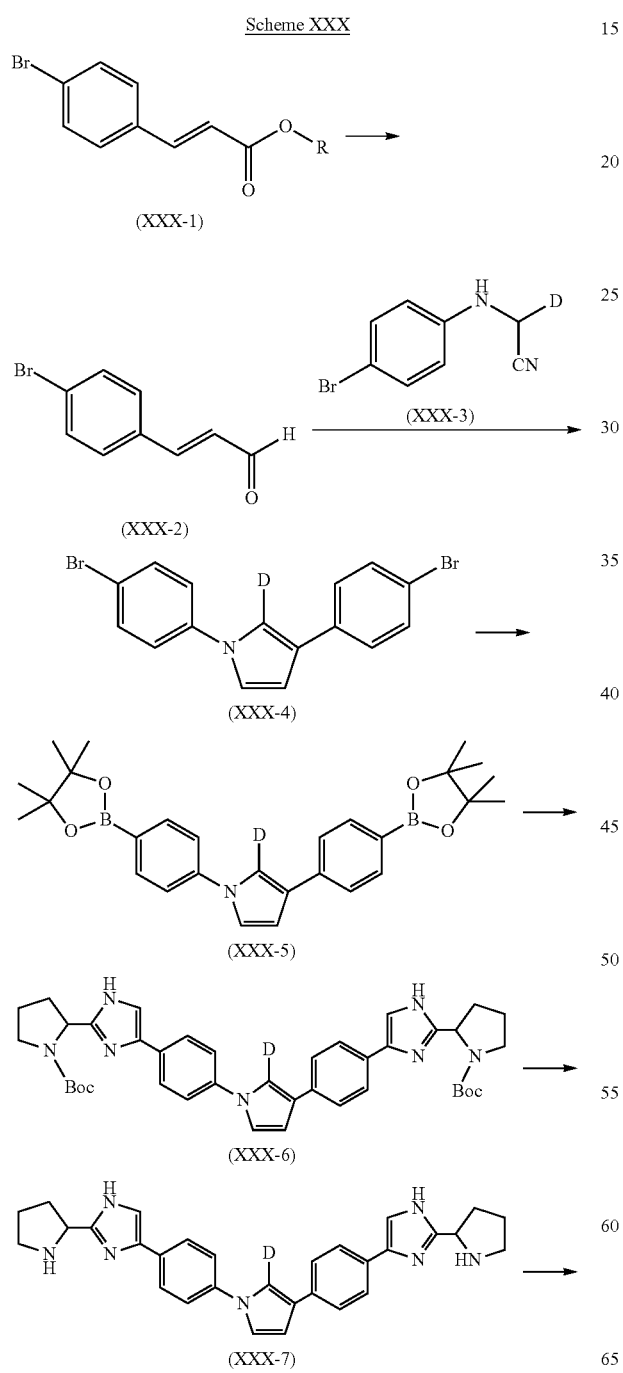

Scheme XXXI

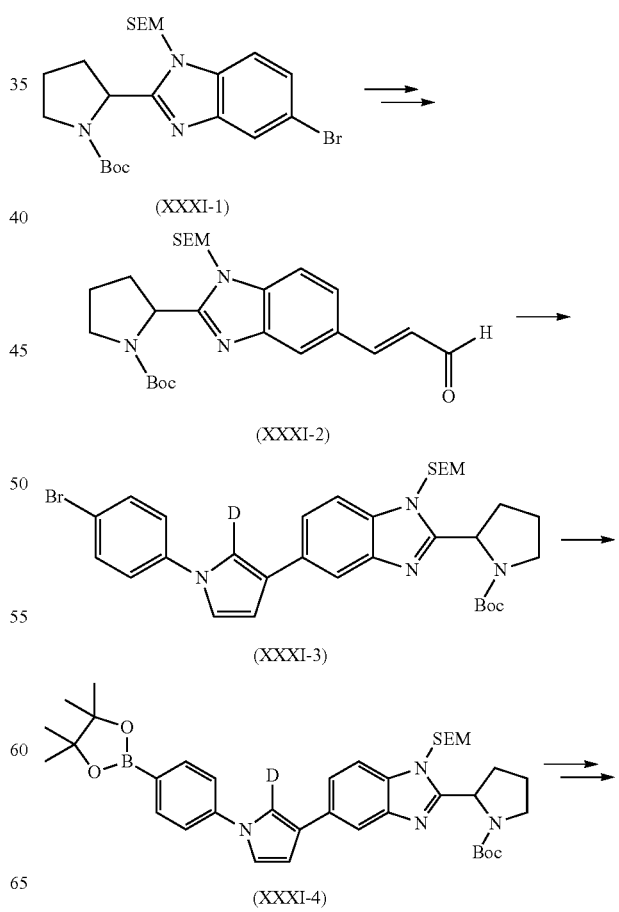

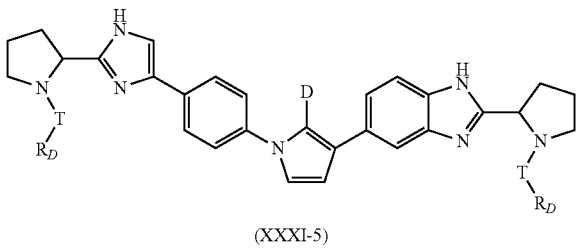

(XXXI-5)

As described in Meyer et al. *Synthesis,* 2005, pp. 945-956 and Meyer et al *Synlett,* 2003, pp 1427-1430, substituted α-aminonitriles can be reacted with α,β-unsaturated carbonyl compounds to provide substituted hydroxy-cyano pyrrolidines. In analogous fashion, a compound (XXXII-1) may be reacted with an α,β-unsaturated aldehyde (XXXII-2) to give a pyrrolidine (XXXII-3). The hydroxy and cyano groups of compounds such as (XXXII-3) may be reduced off using reagents such as NaBH$_3$CN or NaBH$_3$CN with FeSO$_4$ as described in *Synthesis,* 2005, pp. 945-956. The nitro group of compounds such as (XXXII-3) may be reduced using standard conditions such as catalytic hydrogenation or reduction with iron powder and ammonium chloride. Typical nitro reduction conditions are described elsewhere herein. The Boc group of compounds such as (XXXII-3) may be removed using standard conditions such as with TFA/CH$_2$Cl$_2$ or HCl in dioxane. Compounds such as (XXXII-4) may be reacted with an appropriate N-protected proline acid under standard conditions as described elsewhere herein to give compounds (XXXII-5). Compounds such as (XXXII-5) may be deprotected and coupled with an acid of choice as described herein to give compounds (XXXII-6) wherein T, R$_D$, and D are as described herein.

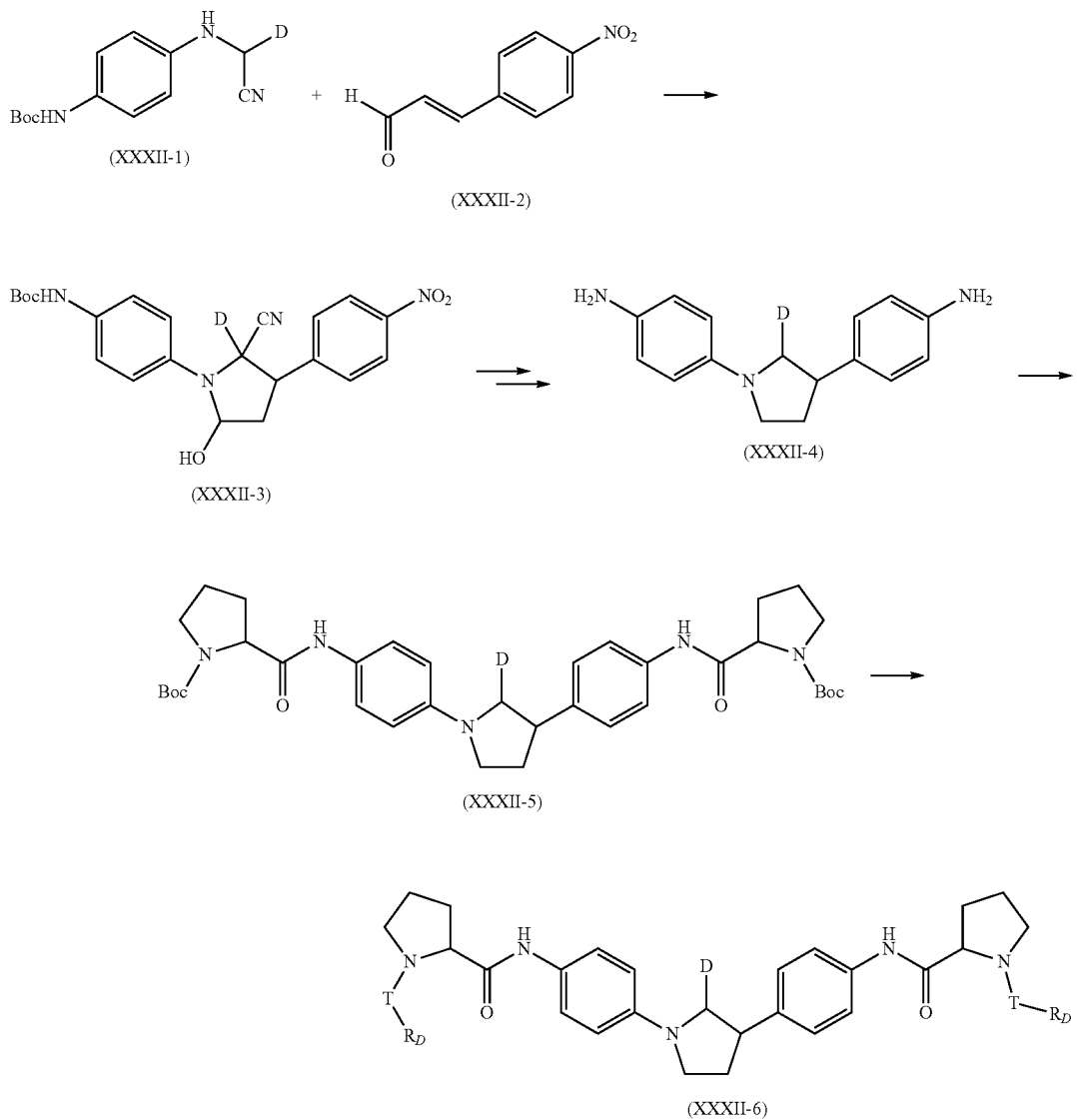

Scheme XXXII

Further compounds of the invention may be prepared as generally outlined in Scheme XXXIII. Compounds such as (XXXIII-1) may be prepared from 4-nitro-o-phenylenediamine by acylation with a protected proline acid (see *Tetrahedron* 2003, pp 2701-2712), cyclization (see *Tet. Lett.* 2003, 5807-5810), SEM protection, and nitro reduction. Compounds such as (XXXIII-1) may be converted to the Strecker product (XXXIII-2) by reaction with an aldehyde D-CHO and KCN in analogy with the process referred to in Scheme XXX. Compounds such as (XXXIII-2) may be condensed with compounds such as (XXXI-2) followed by reduction to give compounds such as (XXXIII-3) (see for example Meyer et al. *Synthesis*, 2005, pp. 945-956 and Meyer et al *Synlett*, 2003, pp 1427-1430). Compounds such as (XXXIII-3) may be deprotected using standard conditions for removal of Boc and SEM groups (see General Procedure 23) and the resultant amino compound reacted with an appropriate acid under conventional amide bond forming conditions to give compounds (XXXIII-4) wherein T, $R_D$, and D are as described herein.

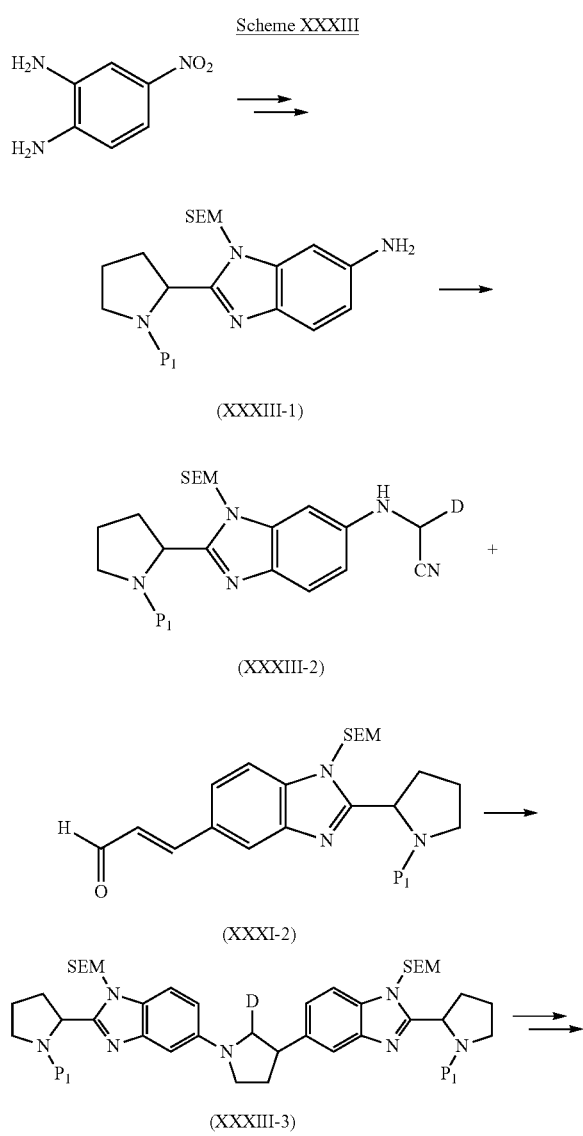

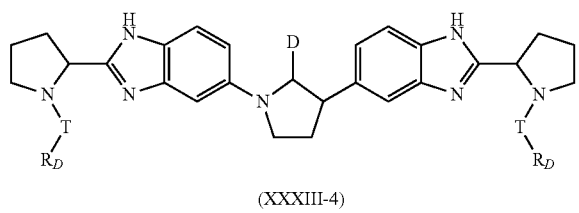

(XXXIII-4)

Certains compounds of the invention may also be prepared using the methods shown generally in Scheme XXXIV. The ketone XXXIV-1 (Reference: US20090076076; p 19, [0146]) can be homologated in two steps to the aldehyde XXXIV-3. In the first step, the ketone can be reacted with dimethylsulfonium methylide in dimethylsulfoxide to produce the epoxide XXXIV-2. The epoxide can be rearranged to the aldehyde by treatment with an acid such p-toluenesulfonic acid with heating in toluene at temperatures between around 80-110° C. (References: J. Am. Chem. Soc. (1965) 1353, 1358; J. Org. Chem. (1972) 4075, 4076, 4077; Bioorg. Med. Chem. Lett. (2009) 5684, 5686). The aldehyde XXXIV-3 can be converted to the diol XXXIV-4 with potassium carbonate and formaldehyde in ethanol as described generally in J. Am. Chem. Soc, 1951, 73, p 5171 and U.S. Pat. No. 5,095,153, Example 3a. The diol can be converted to the bismesylate XXXIV-5 by reaction with excess methanesulfonyl chloride and triethylamine in dichloromethane at 0° C. to room temperature. The bismesylate can be converted to the azide XXXIV-6 by reaction with sodium azide (about 1 equivalent) in DMPU and heating up to around 110° C. The azide can be converted to the phosphorimidate XXXIV-7 by reaction with freshly distilled triethylphosphite (about 1 equivalent) in anhydrous toluene/tetrahydrofuran at room temperature. The phosphorimidate can be converted to the azetidine-phosphonate XXXIV-8 by heating in o-xylene up to around 150° C. The azetidine-phosphonate can be converted to the azetidine XXXIV-9 by reaction with trifluoroacetic acid in dichloromethane at room temperature. The azetidine can be reacted with an appropriate aryl halide (e.g., iodide) using the Buchwald reaction to generate an N-arylazetidine XXXIV-10. Appropriate conditions include reaction with an aryliodide (about 2 equivalent), $Pd_2(dba)_3$ (about 0.025 equivalent), 4,5-bis(diphenylphosphino)-9,9-dimethylxanthene (Xantphos; about 0.1 equivalents) and sodium tert-butoxide (about 1.2 equivalent) with heating in a solvent such as dioxane to 80-100° C., optionally with microwave irradiation. The bisbromide may be converted to the bisboronate XXXIV-11 by reaction with bis(pinacolato)diborane, potassium acetate, and $PdCl_2(dppf)$ in a solvent such as DME, dioxane, or DMSO with heating up to around 85° C. The bisboronate can be converted to compounds of the invention XXXIV-12 by reaction with an appropriate halide (i.e. Suzuki reaction) such as methyl (S)-1-((S)-2-(5-bromo-1H -imidazol-2-yl)pyrrolidin-1-yl)-3-methyl-1-oxobutan-2ylcarbamate.

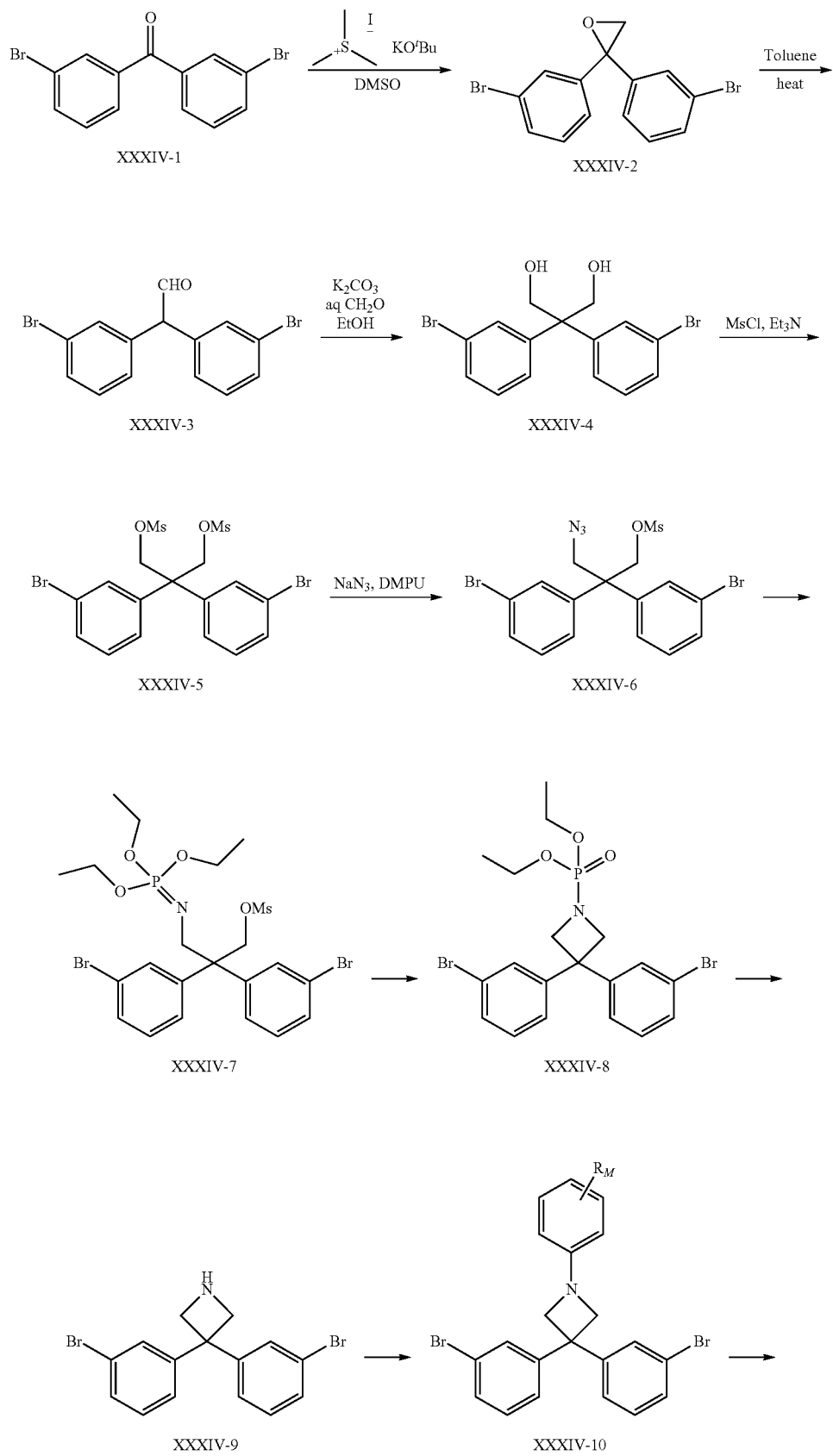
Scheme XXXIV

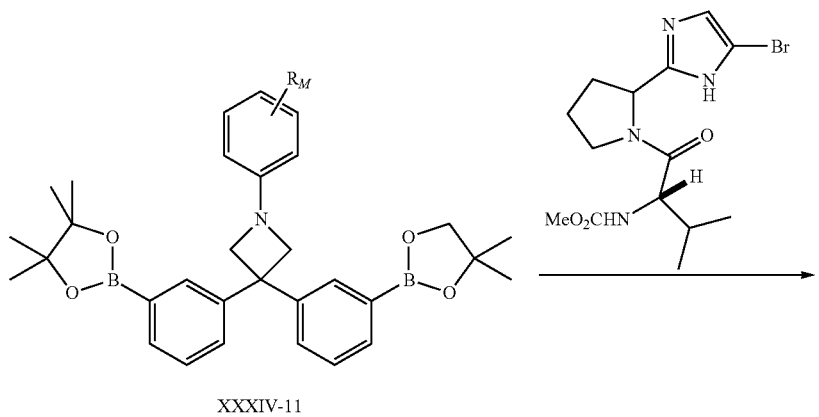

XXXIV-11

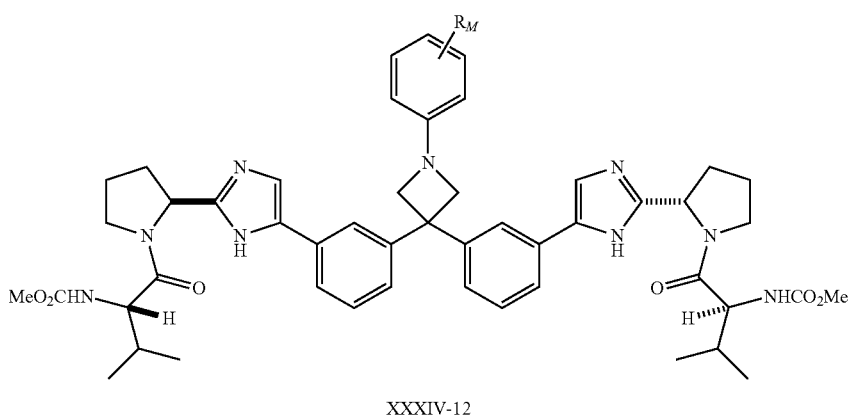

XXXIV-12

Certain compounds of the invention may also be prepared using the methods shown generally in Scheme XXXV. Compounds such as XXXV-1 can be prepared using known methods by alkylation of a malonate ester with a benzyl halide. Compound XXXV-1 can be converted to compound XXXV-2 by reduction with lithium aluminum hydride. Compound XXXV-2 can be converted to compound XXXV-3 by reaction with Ms$_2$O and a base such as diisopropylethylamine. Compound XXXV-3 may be converted to compound XXXV-4 using methods analogs to those to convert XXXIV-5 to XXXIV-9 (see Scheme XXXIV). Similarly compound XXXV-4 may be converted to compound XXXV-5 using a Buchwald reaction analogous to that of Scheme XXXIV. Compounds XXXV-5, in turn, may be converted to XXXV-6 by demethylation (e.g. with BBr$_3$) and triflate formation with Tf$_2$O. Compounds XXXV-6 may be converted to compounds XXXV-7 by analogy with the conversion of XXXIV-10 to XXXIV-11. Finally, compounds XXXV-7 may be converted to compounds XXXV-8 using the Suzuki coupling of Scheme XXXIV.

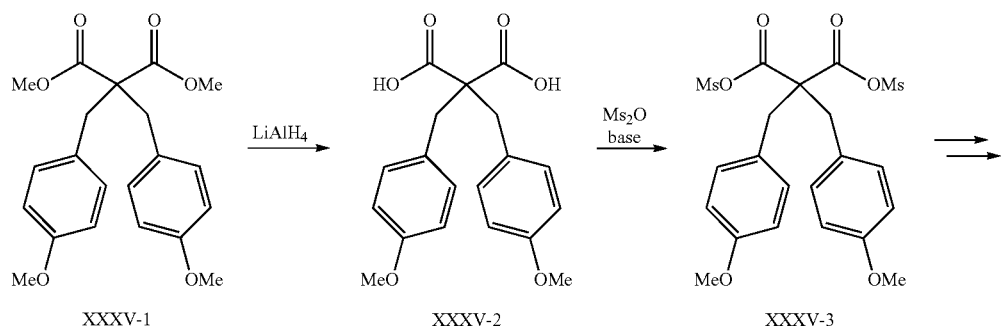

-continued

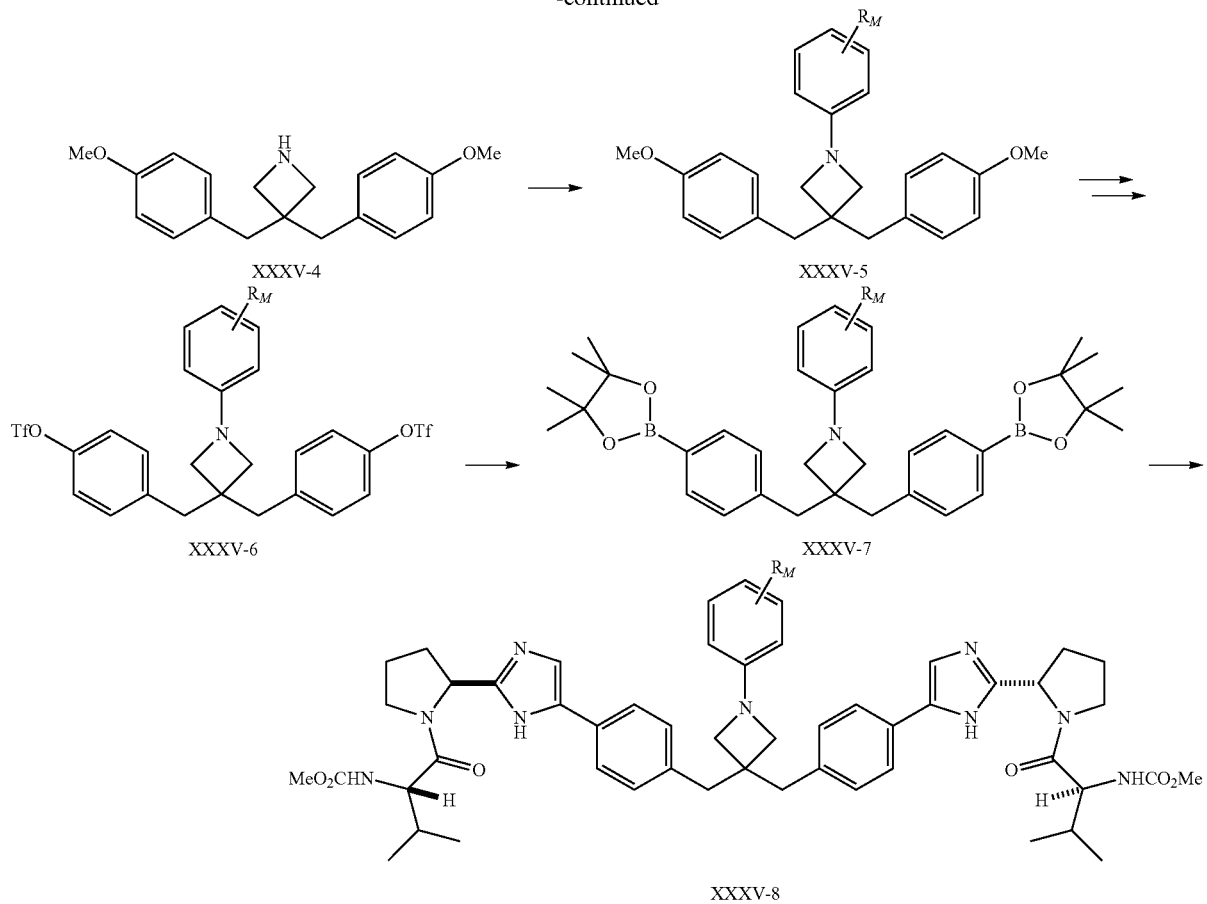

In the foregoing Schemes (Schemes I-XXXV), compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemsitry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —NH$_2$ or —OH) is not compatible with the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

Other compounds of the invention can be similarly prepared according to the above-described schemes as well as the procedures described in following Intermediates, General Procedures, and Examples, as appreciated by those skilled in the art. It should be understood that the above-described embodiments and schemes and the following Intermediates, General Procedures, and Examples are given by way of illustration, not limitation. Various changes and modifications within the scope of the present invention will become apparent to those skilled in the art from the present description.

Example compounds below were named using ACD Name version 12 (ACD Name v12). Other compounds were named using ChemDraw version 9.0 (v9), unless otherwise indicated as being named using ACD Name v12. Both naming programs may provide a chemical name that depends on the tautomeric structure chosen for naming. Structures may be shown or named as any chemically distinct tautomer.

For example, the tautomeric structure:

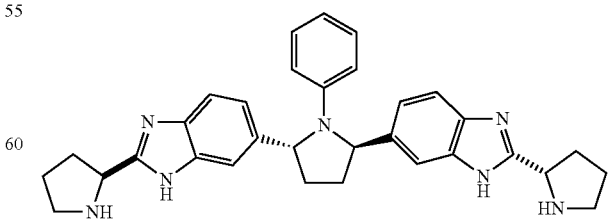

is given the following names:
(S)-6,6'-((2R,5R)-1-phenylpyrrolidine-2,5-diyl)bis(2-((S)-pyrrolidin-2-yl)-1H-benzo[d]imidazole) (Chemdraw v9);

6,6'-[(2R,5R)-1-phenylpyrrolidine-2,5-diyl]bis{2-[(2S)-pyrrolidin-2-yl]-1H-benzoimidazole} (ACD Name v12).

The tautomeric structure:

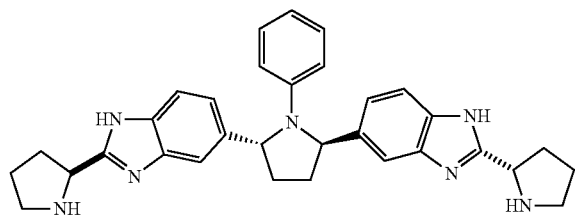

is given the following names:
(S)-5,5'-(2R,5R)-1-phenylpyrrolidine-2,5-diyl)bis(2-((S)-pyrrolidin-2-yl)-1H-benzo[d]imidazole) (Chemdraw v9);
5,5'-[(2R,5R)-1-phenylpyrrolidine-2,5-diyl]bis{2-[(2S)-pyrrolidin-2-yl]-1H-benzoimidazole} (ACD Name v12).

The tautomeric structure:

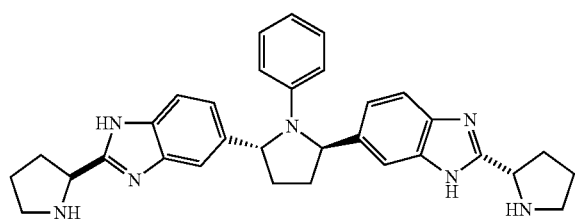

is given the following names:
(S)-5,5'-((2R,5R)-1-phenylpyrrolidine-2,5-diyl)bis(2-((S)-pyrrolidin-2-yl)-1H-benzo[d]imidazole) (Chemdraw v9);
5-[(2R,5R)-1-phenyl-5-{2-[(2S)-pyrrolidin-2-yl]-1H-benzimidazol-6-yl}pyrrolidin-2-yl]-2-[(2S)-pyrrolidin-2-yl]-1H-benzimidazole (ACD Name v12).

Certain compounds in the Examples below can be purified using reverse-phase HPLC. Purification can be conducted using either a C18 or C8 reverse-phase column. Compounds can be eluted using a gradient of about 10-100% acetonitrile in 0.1% aqueous TFA; about 60-100% methanol in 10 mM aqueous ammonium acetate; or about 10-95% methanol in 10 mM aqueous ammonium acetate. For purifications conducted with TFA, the product thus obtained may be in the form of a TFA salt. Compounds may be characterized as the TFA salt or as the free base following neutralization, extraction and isolation.

Certain compounds in the Examples below can be purified using normal phase silica gel chromatography including traditional flash chromatography or an automated purification system (e.g., Isco Combi-Flash, Analogix Intelliflash) using pre-packed silica gel columns (55 or 35 μm silica gel, Isco gold columns). Compounds can also be purified by prep-TLC.

Typical solvents for silica gel chromatography include: Ethyl acetate in hexanes, Diethyl ether in hexanes, THF in hexanes, Ethyl acetate in methylene chloride, Methanol in methylene chloride, Methanol in methylene chloride with NH₄OH, Acetone in hexanes, and Methylene chloride in hexanes.

Synthesis of Intermediates

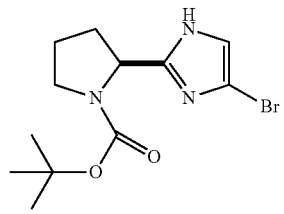 [SMILES: CC(C)(C)OC(=O)N1CCC[C@H]1c1nc(Br)c[nH]1]

Intermediate 1

(S)-tert-butyl 2-(4-bromo-1H-imidazol-2-yl)pyrrolidine-1-carboxylate

Intermediate 1A (S)-tert-butyl 2-formylpyrrolidine-1-carboxylate

To an oven-dried 500-mL 3-neck flask purged with nitrogen was added oxalyl chloride (5.32 mL, 60.8 mmol) and anhydrous dichloromethane (125 mL), and the solution was cooled to −78° C. A solution of anhydrous DMSO (7.30 mL, 103 mmol) in anhydrous dichloromethane (25 mL) was added dropwise from a constant-pressure addition funnel over a 20-minute period. A solution of (S)-tert-butyl 2-(hydroxymethyl)pyrrolidine-1-carboxylate (9.41 g, 46.8 mmol) in anhydrous dichloromethane (50 mL) was added dropwise from a constant-pressure addition funnel over a 20-minute period, and then the reaction mixture was stirred at −78° C. for 30 minutes. Triethylamine (32.6 mL, 234 mmol) was added dropwise via syringe over a 5-minute period and the thick white mixture was stirred in an ice-water bath for 30 minutes. The reaction was quenched with 10% (w/v) aq. citric acid (30 mL). The mixture was partitioned in a separatory funnel between Et₂O (550 mL) and 10% (w/v) aq citric acid. The layers were separated, and the organic phase was washed with water and brine. The organic phase was dried over anhydrous Na₂SO₄, filtered, and concentrated to afford a yellow oil (9.4 g), which was used directly in the next reaction.

Intermediate 1B (S)-tert-butyl 2-(1H-imidazol-2-yl)pyrrolidine-1-carboxylate

The product from Intermediate 1A (20 g, 100 mmol) was dissolved in methanol (50.2 mL) and ammonium hydroxide (50.2 mL) was added. To this solution glyoxal (40% in water; 24.08 mL, 211 mmol) was added, dropwise, over 10 minutes. The reaction was stirred at room temperature overnight. The reaction was concentrated under reduced pressure, diluted with 50 mL of water, and then extracted with ethyl acetate. The organic layer was washed with brine, dried (Na₂SO₄) and concentrated to a tan solid. The solid was treated with ether and concentrated. The solid was then triturated with 2:1 diethyl ether:hexanes (150 mL) to afford 17 g of solid, which was used directly in the next reaction. $^1$HNMR (400 MHz, DMSO-d₆) δ ppm 1.14/1.40 (s, 9H), 1.81-2.12 (m, 4H), 3.32-3.33 (m, 1H), 3.35-3.50 (m, 1H), 4.72-4.81 (m, 1H), 6.84 (s, 1H), 11.68 (s, 1H).

Intermediate 1C (S)-tert-butyl 2-(4,5-dibromo-1H-imidazol-2-yl)pyrrolidine-1-carboxylate N-Bromosuccinimide (108 mmol) was added to a cold (0° C.) solution of the product from Intermediate 1B (12.05 g, 50.8 mmol) in dichloromethane (200 mL). The mixture was stirred in ice bath for 2 hours and then concentrated, dissolved in ethyl acetate (250 mL), washed with water (3×150 mL) and brine (1×100 mL), dried (MgSO$_4$), and concentrated to very dark residue. The residue was mixed with and concentrated from dichloromethane/hexanes (1:1) to get brown solid (~19 g). The solid was triturated with ether (~100 mL) and filtered to isolate a tan solid (13.23 g, 65% yield). $^1$H NMR (400 MHz, CDCl$_3$) δ ppm 1.49 (s, 9H), 1.86-2.17 (m, 3H), 2.80-2.95 (m, 1H), 3.30-3.44 (m, 2H), 4.85 (dd, J=7.54, 2.55 Hz, 1H), 10.82 (s, 1H); MS (DCI+) m/z 394/396/398 (M+H)$^+$.

Intermediate 1D (S)-tert-butyl 2-(4-bromo-1H-imidazol-2-yl)pyrrolidine-1-carboxylate The product from Intermediate 1C (6.25 g, 15.82 mmol) was dissolved in dioxane (200 mL) and water (200 mL) in a 1 L round bottom flask equipped with a condenser and glass stopper. A solution of sodium sulfite (22.38 g, 174 mmol) in water (200 mL) was added, and the mixture was heated at reflux for 16 hours. The reaction mixture was cooled to room temperature, and dioxane and some water were removed by rotary evaporation. The residue was extracted with dichloromethane. The combined organic phases were washed with brine (50 mL), dried over anhydrous Na$_2$SO$_4$, filtered, and concentrated by rotary evaporation, co-evaporating with 2:1 hexanes/dichloromethane (100 mL) to give a beige foam (4.38 g). The foam was dissolved in dichloromethane (2 mL), hexanes (2 mL) were added, and the resultant solution was applied to a column, and purified by silica gel flash chromatography eluting with 30% to 80% ethyl acetate/hexanes to afford the title compound as a white solid (3.48 g). $^1$H NMR (400 MHz, CDCl$_3$) δ ppm 1.48 (s, 9H), 1.83-2.33 (m, 3H), 2.79-3.02 (m, 1H), 3.37 (dd, J=7.10, 5.37 Hz, 2H), 4.88 (dd, J=7.59, 2.49 Hz, 1H), 6.92 (s, 1H), 10.70 (br s, 1H); MS (ESI+) m/z 316/318 (M+H)$^+$.

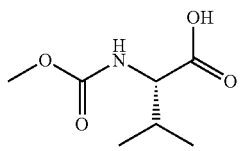

Intermediate 2

(S)-2-(methoxycarbonylamino)-3-methylbutanoic acid

To (S)-2-amino-3-methylbutanoic acid (57 g, 487 mmol) dissolved in dioxane (277 mL) was added a 2 N aqueous sodium hydroxide solution (803 mL, 1606 mmol) followed by the dropwise addition of methyl chloroformate (75 mL, 973 mmol) over 1 hour which caused warming of the solution to occur. After the addition, the mixture was heated at 60° C. for 22 hours, then cooled and extracted with dichloromethane (400 mL). The resultant aqueous layer was cooled in an ice bath, and then 12 N hydrochloric acid was added dropwise until the pH was 2. The resultant mixture was stirred at 0° C. for 2 hours, and then the resultant solid was collected by vacuum filtration, and dried in a vacuum oven to provide 80 g (94%) of the title compound as a colorless solid. $^1$H NMR (400 MHz, DMSO-d$_6$) δ ppm 12.50 (bs, 1H), 7.34 (d, J=8.6 Hz, 1H), 3.84 (dd, J=8.6, 6.0 Hz, 1H), 3.54 (s, 3H), 2.03 (m, 1H), 0.86 (t, J=7.0 Hz, 6H).

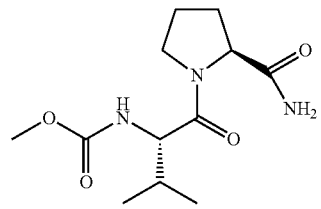 [SMILES: COC(=O)N[C@H](C(=O)N1CCC[C@H]1C(N)=O)C(C)C]

Intermediate 3 methyl (S)-1-((S)-2-carbamoylpyrrolidin-1-yl)-3-methyl-1-oxobutan-2-ylcarbamate

Intermediate 3A (S)-pyrrolidine-2-carboxamide hydrochloride salt

To (S)-tert-butyl 2-carbamoylpyrrolidine-1-carboxylate (29.8 g, 139 mmol) was added a solution of 4 N HCl in dioxane (209 mL, 836 mmol), and the resultant mixture was stirred at room temperature for 18 hours. The mixture was then concentrated and triturated with diethyl ether then vacuum filtered and dried under vacuum to provide 21.6 g (104%) of the title product as a colorless solid.

Intermediate 3B methyl (S)-1-((S)-2-carbamoylpyrrolidin-1-yl)-3-methyl-1-oxobutan-2-ylcarbamate Intermediate 3A (21.6 g, 144 mmol), Intermediate 2 (29.1 g, 166 mmol), 1H-benzo[d][1,2,3]triazol-1-ol hydrate (27.6 g, 180 mmol), N$^1$-((ethylimino)methylene)-N$^3$,N$^3$-dimethylpropane-1,3-diamine hydrochloride (34.6 g, 180 mmol) and 4-methylmorpholine (63.5 mL, 578 mmol) were dissolved in dichloromethane (960 mL) and stirred at room temperature for 18 hours. The resultant solution was then concentrated to a residue, water was then added and the solution extracted with a 25% isopropanol in chloroform solution (2×2000 mL). The organic layer was washed with brine, and then the organic extract was dried over MgSO$_4$, then concentrated to a yellow oil which was purified by column chromatography eluting with a gradient of 0-10% methanol in dichloromethane to provide 25 g (64%) of the title compound as a colorless solid. $^1$H NMR (400 MHz, DMSO-d$_6$) δ ppm 7.28 (m, 2H), 6.81 (s, 1H), 4.24 (dd, J=8.1, 4.4 Hz, 1H), 4.00 (t, J=8.4 Hz, 1H), 3.75 (m, 1H), 3.55 (m, 1H), 3.50 (s, 3H), 2.02 (m, 1H), 1.97 (m, 2H), 1.80 (m, 2H), 0.92 (d, J=6.7 Hz, 3H), 0.86 (d, J=8.6 Hz, 3H).

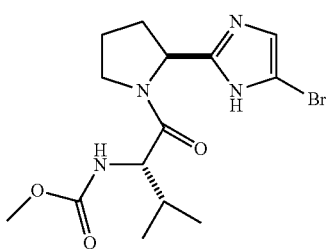 [SMILES: COC(=O)N[C@H](C(=O)N1CCC[C@H]1c1ncc(Br)[nH]1)C(C)C]

Intermediate 4 methyl (S)-1-((S)-2-(5-bromo-1H-imidazol-2-yl)pyrrolidin-1-yl)-3-methyl-1-oxobutan-2-ylcarbamate Intermediate 4A (S)-5-bromo-2-(pyrrolidin-2-yl)-1H-imidazole hydrochloride A mixture of Intermediate 1D (5.0 g, 15.8 mmol) in 4 M HCl/Dioxane (40 mL) was allowed to stir for one hour. The mixture was concentrated to afford 3.99 g (100%) of the title compound. MS (ESI) m/z 217 (M+H)$^+$.

Intermediate 4B methyl (S)-1-((S)-2-(5-bromo-1H-imidazol-2-yl)pyrrolidin-1-yl)-3-methyl-1-oxobutan-2-ylcarbamate A mixture of Intermediate 4A (3.99 g, 15.8 mmol), Intermediate 2 (2.77 g, 15.8 mmol), N-(3-dimethylaminopropyl)-N'-ethylcarbodiimide hydrochloride (3.63 g, 19.0 mmol), 1-hydroxybenzotriazole hydrate (2.90 g, 19.0 mmol) and N-methylmorpholine (12.2 mL, 111.0 mmol) in DMF (150 mL) were allowed to stir overnight. The mixture was diluted with H$_2$O and extracted with EtOAc (3×300 mL). The organic was washed with H$_2$O and brine. The organic phase was then dried (MgSO$_4$), filtered and concentrated. Purification by chromatography (silica gel, 75% EtOAc in hexanes) afforded 5.2 g (88%) of the title compound. $^1$H NMR (400 MHz, DMSO-d$_6$) δ ppm 0.79 (dd, J=6.67, 3.63 Hz, 6H), 1.84-1.96 (m, 3H), 2.02-2.14 (m, 2H), 3.51 (s, 3H), 3.66-3.80 (m, 2H), 3.96-4.03 (m, 1H), 4.91-4.99 (m, 1H), 7.06 (d, J=1.52 Hz, 1H), 7.26 (d, J=8.46 Hz, 1H), 12.01 (s, 1H); MS (ESI) m/z 373 (M+H)$^+$.

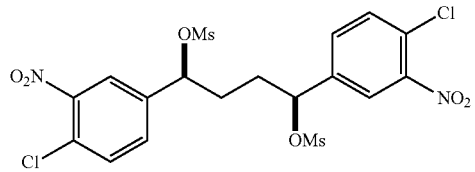 [SMILES: CS(=O)(=O)O[C@@H](CC[C@H](OS(C)(=O)=O)c1ccc(Cl)c([N+](=O)[O-])c1)c1ccc(Cl)c([N+](=O)[O-])c1]

Intermediate 5

(1S,4S)-1,4-bis(4-chloro-3-nitrophenyl)butane-1,4-diyl dimethanesulfonate

Intermediate 5A 2-bromo-1-(4-chloro-3-nitrophenyl)ethanone

Method A:
To a flask equipped with a magnetic stir bar and under an atmosphere of N$_2$ was added 4'-chloro-3'-nitroacetophenone (10.0 g, 50.1 mmol) and THF (100 mL). To this stirring mixture was added portion-wise phenyltrimethylammonium tribromide (19.78 g, 52.6 mmol) over a 15 minutes time period. The resultant mixture was then stirred with monitoring every hour via LCMS. After 3 hours, the mixture was then filtered and resulting solids washed with EtOAc. The organic solution was then concentrated, H$_2$O and 10% aq. NaHCO$_3$ were added, and the mixture was washed with EtOAc (2×300 mL). The combined organic layers were then washed with brine, dried (MgSO$_4$), filtered and concentrated. The residue material was then subjected to purification via crystallization. The residue was dissolved in EtOAc (100 mL) and hexanes were slowly added until the mixture was cloudy. After standing for a few hours, 2-bromo-1-(4-chloro-3-nitrophenyl)ethanone (9.81 g, 70%) was collected as an off white colored solid product. $^1$H NMR (500 MHz, DMSO-d$_6$) δ ppm 5.00 (s, 2H) 7.98 (d, J=8.54 Hz, 1H) 8.24 (dd, J=8.54, 2.14 Hz, 1H) 8.61 (d, J=1.98 Hz, 1H).

Method B:
In a 500 mL round-bottomed flask was added 1-(4-chloro-3-nitrophenyl)ethanone (11.98 g, 60 mmol) in benzene (75 mL) to give a white suspension. Bromine (9.59 g, 60.0 mmol) was added dropwise over 5 minutes to give a deep red solution. The mixture was stirred for 1 hour to give a yellow solution that was concentrated in vacuo to a yellow solid. Recrystallized from 9:1 hexane/ethyl acetate gave 2-bromo-1-(4-chloro-3-nitrophenyl)ethanone as yellow needles.

Intermediate 5B 1,4-bis(4-chloro-3-nitrophenyl)butane-1,4-dione

Zinc (II) chloride (14.68 g, 108 mmol) was added to toluene (81 mL) followed by diethylamine (8.35 mL, 81 mmol) and tert-butanol (7.73 mL, 81 mmol). The resultant heterogeneous solution was stirred at room temperature for approximately 2 hours. Afterwards Intermediate 5A (15.0 g, 53.9 mmol) and 4'-chloro-3'-nitroacetophenone (16.13 g, 81 mmol) were added to the solution in one portion, and the resultant mixture was stirred at room temperature for 42 hours. The reaction was then quenched with 5% aqueous sulfuric acid (500 mL) and stirred vigorously to induce solid formation. The resultant solid was collected by vacuum filtration, then washed with toluene, water, and methanol successively. Then the solid was added to a solution of hot ethyl acetate and resulting heterogeneous solution was stirred for 30 minutes. The solid was then collected and dried overnight in a vacuum oven to provide 16.6 g (78%) of the title compound. $^1$H NMR (400 MHz, DMSO-d$_6$) δ 8.61 (d, J=1.9 Hz, 2H), 8.27 (dd, J=8.4, 1.9 Hz, 2H), 7.96 (d, J=8.3 Hz, 2H), 3.48 (s, 4H).

Intermediate 5C (1S,4S)-1,4-bis(4-chloro-3-nitrophenyl)butane-1,4-diol (R)-(+)-α,α-Diphenyl-2-pyrrolidinemethanol (1.08 g, 4.28 mmol) was dissolved in 70 mL of THF at ambient temperature in a dry flask under nitrogen and trimethyl borate (650 uL, 5.54 mmol) was added dropwise. The resulting solution was stirred for 1 hour. The solution was cooled in a cold bath to ~10° C. and the N,N-diethylaniline borane (9.18 mL, 51.6 mmol) was added dropwise with some bubbling. After 15 minutes, this solution was transferred to an addition funnel and added dropwise to 1,4-bis(4-chloro-3-nitrophenyl)butane-1,4-dione (Intermediate 5B) (10.0 g, 25.2 mmol)

suspended in 200 mL of THF and cooled to ~10° C. Bubbling was observed. After the addition, the mixture was stirred at ambient temperature for 4 hours. The mixture was cooled in an ice bath and 30 mL or methanol was added dropwise until bubbling stopped, then the mixture was allowed to stir at ambient temperature for 30 minutes. The mixture was filtered to get rid of a trace of insoluble unreacted starting material. The filtrate was concentrated, poured into 1 N HCl and extracted into ethyl acetate, dried over sodium sulfate, and concentrated to give the title compound (9.9 g, 99%) as a yellow waxy solid. Chiral HPLC e.e. >99.9% (RR diol was undetectable). $^1$H NMR (400 MHz, DMSO-$d_6$) δ ppm 7.94 (d, J=1.9 Hz, 2H), 7.69 (d, J=8.4 Hz, 2H), 7.60 (dd, J=8.4, 1.9 Hz, 2H), 4.65 (m, 2H), 1.62 (m, 4H).

Intermediate 5D (1S,4S)-1,4-bis(4-chloro-3-nitrophenyl)butane-1,4-diyl dimethanesulfonate In a 1 L round-bottomed flask containing Intermediate SC (20.0 g, 49.9 mmol) was added 310 mL of dichloromethane with stirring and cooling in an ice bath. To the slurry was added triethylamine (20.84 mL, 150 mmol) and after 10 minutes stirring in the ice bath, a solution of methanesulfonyl chloride (8.5 mL, 110 mmol) in dichloromethane (10 mL) was added dropwise to the reaction. After complete addition, the flask was removed from the ice bath and stirred at room temperature for 3 hours. To the reaction was added water (400 mL) with vigorous stirring for 20 minutes. The solid was collected by filtration and washed thoroughly with water dichloromethane and diethyl ether. The solid was dried overnight in a vacuum drying oven at 60° C. to provide a white solid (20.49 g, 73.7% yield). $^1$H NMR (400 MHz, DMSO-$d_6$) δ ppm 1.81-1.91 (m, 2H) 2.06 (m, 2H) 3.18 (s, 6H) 5.73-5.84 (m, 2H) 7.71-7.77 (m, 2H) 7.80-7.85 (m, 2H) 8.13 (d, J=1.74 Hz, 2H).

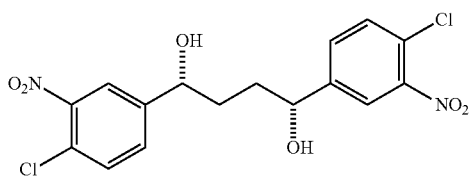 [SMILES: O=[N+]([O-])c1cc([C@H](O)CC[C@@H](O)c2ccc(Cl)c([N+](=O)[O-])c2)ccc1Cl]

Intermediate 5.1

(1R,4R)-1,4-bis(4-chloro-3-nitrophenyl)butane-1,4-diol (1R,4R)-1,4-bis(4-chloro-3-nitrophenyl)butane-1,4-diol can be prepared using (S)-(−)-α,α-diphenyl-2-pyrrolidinemethanol and the method of Intermediate 5C.

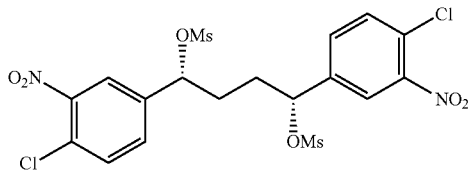 [SMILES: CS(=O)(=O)O[C@H](CC[C@@H](OS(C)(=O)=O)c1ccc(Cl)c([N+](=O)[O-])c1)c1ccc(Cl)c([N+](=O)[O-])c1]

Intermediate 5.2

(1R,4R)-1,4-bis(4-chloro-3-nitrophenyl)butane-1,4-diyl dimethanesulfonate (1R,4R)-1,4-bis(4-chloro-3-nitrophenyl)butane-1,4-diol can be transformed to (1R,4R)-1,4-bis(4-chloro-3-nitrophenyl)butane-1,4-diyl dimethanesulfonate as described under Intermediate 5D.

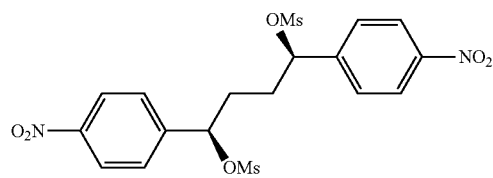 [SMILES: CS(=O)(=O)O[C@H](CC[C@@H](OS(C)(=O)=O)c1ccc([N+](=O)[O-])cc1)c1ccc([N+](=O)[O-])cc1]

Intermediate 6

(1R,4R)-1,4-bis(4-nitrophenyl)butane-1,4-diyl dimethanesulfonate

Intermediate 6A 1,4-Bis(4-nitrophenyl)butane-1,4-dione

Anhydrous zinc(II)chloride (2.73 g, 20.00 mmol) was stirred in dry benzene (15 mL) while diethylamine (1.558 mL, 15.00 mmol) and t-butanol (1.435 mL, 15.00 mmol) were added, and the resulting mixture was stirred at room temperature for 90 minutes to give a cloudy solution. To this mixture was added 2-bromo-1-(4-nitrophenyl)ethanone (2.44 g, 10.00 mmol) and 1-(4-nitrophenyl)ethanone (2.477 g, 15.00 mmol), and the resulting mixture was stirred at room temperature overnight. The mixture was poured into water (50 mL) and extracted with ethyl acetate (3×50 mL). The combined organic layers were dried over $Na_2SO_4$, filtered and concentrated. The resulting residue was triturated with dichloromethane to give an orange solid that was collected by filtration and dried to give the title compound (2.0 g, 61% yield).

Intermediate 6B (1R,4R)-1,4-bis(4-nitrophenyl)butane-1,4-diol

To (S)-(−)-α,α-diphenyl-2-pyrrolidinemethanol (2.71 g, 10.70 mmol) was added THF (80 mL) at 23° C. The very thin suspension was treated with trimethyl borate (1.44 g, 13.86 mmol) over 30 seconds, and the resulting solution was mixed at 23° C. for 1 hour. The solution was cooled to 16-19° C., and N,N-diethylaniline borane (21.45 g, 132 mmol) was added dropwise via syringe over 3-5 minutes (caution: vigorous $H_2$ evolution), while the internal temperature was maintained at 16-19° C. After 15 minutes, the $H_2$ evolution had ceased. To a separate vessel was added the product from Example 6A (22.04 g, 95 wt %, 63.8 mmol), followed by THF (80 mL), to form an orange slurry. After cooling the slurry to 11° C., the borane solution was transferred via cannula into the dione slurry over 3-5 minutes. During this period, the internal temperature of the slurry rose to 16° C. After the addition was complete, the reaction was maintained at 20-27° C. for an additional 2.5 hours. After reaction completion, the mixture was cooled to 5° C. and methanol (16.7 g, 521 mmol) was added dropwise over 5-10 minutes, maintaining an internal temperature <20° C. (note: vigorous H₂ evolution). After the exotherm had ceased (ca. 10 minutes), the temperature was adjusted to 23° C., and the reaction was mixed until complete dissolution of the solids had occurred. Ethyl acetate (300 mL) and 1 M HCl (120 mL) were added, and the phases were separated. The organic phase was then washed successively with 1 M HCl (2×120 mL), H₂O (65 mL), and 10% aq. NaCl (65 mL). The organics were dried over MgSO₄, filtered, and concentrated in vacuo. Crystallization of the product occurred during the concentration. The slurry was warmed to 50° C., and heptane (250 mL) was added over 15 minutes. The slurry was then allowed to mix at 23° C. for 30 minutes and filtered. The wet cake was washed with 3:1 heptane:ethyl acetate (75 mL), and the orange, crystalline solids were dried at 45° C. for 24 hours to provide the title compound (15.35 g, 99.3% ee, 61% yield), which was contaminated with 11% of the meso isomer (vs. dl isomer).

Intermediate 6C (1R,4R)-1,4-bis(4-nitrophenyl)butane-1,4-diyl dimethanesulfonate The product from Intermediate 6B (5.01 g, 13.39 mmol) was combined with 2-methyltetrahydrofuran (70 mL) and cooled to −5° C., and N,N-diisopropylethylamine (6.81 g, 52.7 mmol) was added over 30 seconds. Separately, a solution of methanesulfonic anhydride (6.01 g, 34.5 mmol) in 2-methyltetrahydrofuran (30 mL) was prepared and added to the diol slurry over 3 minutes, maintaining the internal temperature between −15° C. and −25° C. After mixing for 5 minutes at −15° C., the cooling bath was removed and the reaction was allowed to warm slowly to 23° C. and mixed for 30 minutes. After reaction completion, the crude slurry is used directly without purification or isolation.

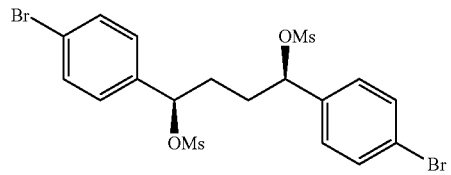 [SMILES: CS(=O)(=O)O[C@H](CC[C@@H](OS(C)(=O)=O)c1ccc(Br)cc1)c1ccc(Br)cc1]

Intermediate 7

((1R,4R)-1,4-bis(4-bromophenyl)butane-1,4-diyl dimethanesulfonate

Intermediate 7A 1,4-bis(4-bromophenyl)butane-1,4-dione

To a solution of zinc(II) chloride (19.62 g, 144 mmol) in benzene (108 mL) were added diethylamine (11.16 mL, 108 mmol) and 2-methylpropan-2-ol (10.32 mL, 108 mmol) and the mixture was stirred at room temperature for 2 hours. 2-Bromo-1-(4-bromophenyl)ethanone (20.0 g, (72 mmol) and 1-(4-bromophenyl)ethanone (21.48 g, 108 mmol) were added in one portion, and the mixture was stirred overnight (18 hours). The reaction mixture was quenched with 5% H₂SO₄ (500 mL) and stirred vigorously to induce precipitation of the product, which was collected by vacuum filtration and washed with benzene, water, methanol, and then dichloromethane, successively. The product was dried under vacuum to give the title compound as a white solid (11.15 g, 39.1% yield).

Intermediate 7B (1R,4R)-1,4-bis(4-bromophenyl)butane-1,4-diol

To (S)-(−)-α,α-diphenyl-2-pyrrolidinemethanol (3.81 g, 15.04 mmol) was added THF (140 mL) at 23° C. The thin slurry was treated with trimethyl borate (2.189 mL, 19.63 mmol) to form a clear solution. After stirring for 1.5 hours, the solution was cooled to 10-15° C., and N,N-diethylaniline borane (33.1 mL, 186 mmol) was added over 5-10 minutes via a syringe. A slight exotherm and H₂ evolution were observed. To a separate vessel was charged Intermediate 7A (35.045 g, 88 mmol), followed by THF (140 mL), to form a slurry. The slurry was cooled to 10° C. The cooled borane solution was transferred via cannula into the dione slurry over approximately 5 minutes, maintaining the internal temperature <25° C. After the transfer was complete, the slurry was held at 15° C. for 5 minutes and then the temperature was maintained at 23° C. for 3 hours. After reaction completion, the solution was cooled to 5° C., and methanol (31.6 mL, 780 mmol) was added slowly to maintain a temperature <20° C. (note: vigorous evolution of hydrogen). The hazy solution was mixed for an additional 1 hour in order to ensure complete quenching. The hazy solution was diluted with EtOAc (500 mL) and 1 M HCl (220 mL). The phases were separated, and the organic phase was washed successively with 1 M HCl (2×220 mL), H₂O (110 mL), and 25% aq. NaCl (110 mL). The organic layer was concentrated in vacuo; then the residue was dissolved in EtOAc, filtered, concentrated and crystallized from EtOAc/hexane to provide the title compound (16.92 g; 100% ee; 47% isolated yield).

Intermediate 7C (1R,4R)-1,4-bis(4-bromophenyl)butane-1,4-diyl dimethanesulfonate To Intermediate 7B (0.60 g, 1.500 mmol) in anhydrous CH₂Cl₂ (15 mL) at 0° C. was added Et₃N (0.627 mL, 4.50 mmol), and the resulting mixture was stirred at 0° C. for 10 minutes until a homogenous solution was obtained. To the cooled solution was added methanesulfonyl chloride (0.292 mL, 3.75 mmol) dropwise, and the resulting mixture was stirred at 0° C. for 1.5 hours until the reaction was complete as determined by TLC (1:1 EtOAc:hexanes). Solvent was removed in vacuo to give a solid, which was dried in vacuo.

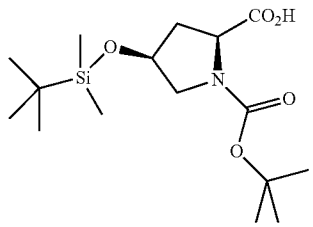 [SMILES: CC(C)(C)OC(=O)N1C[C@@H](O[Si](C)(C)C(C)(C)C)C[C@H]1C(=O)O]

Intermediate 8

(2S,4S)-1-(tert-butoxycarbonyl)-4-(tert-butyldimethylsilyloxy)pyrrolidine-2-carboxylic acid (2S,4S)-1-(tert-Butoxycarbonyl)-4-hydroxypyrrolidine-2-carboxylic acid (5.31 g, 22.96 mmol) and imidazole (7.82 g, 115 mmol) were combined in dichloromethane (106 mL) and dimethylformamide (22 mL) at ambient temperature and treated with portionwise addition of tert-butylchlorodimethylsilane (7.61 g, 50.5 mmol). The mixture was stirred for 18 hours then diluted with water and extracted into ethyl acetate and concentrated to provide the title compound.

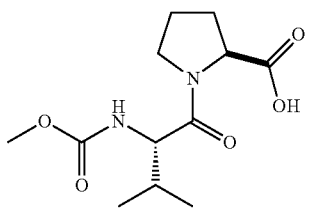 [SMILES: COC(=O)N[C@H](C(=O)N1CCC[C@H]1C(=O)O)C(C)C]

Intermediate 9

(S)-1-((S)-2-(methoxycarbonylamino)-3-methylbutanoyl)pyrrolidine-2-carboxylic acid Intermediate 2 (150 g, 856 mmol), HOBt hydrate (138 g, 899 mmol) and DMF (1500 mL) were charged to a flask. The mixture was stirred for 15 minutes to give a clear solution. EDC hydrochloride (172 g, 899 mmol) was charged and mixed for 20 minutes. The mixture was cooled to 13° C. and (L)-proline benzyl ester hydrochloride (207 g, 856 mmol) charged. Triethylamine (109 g, 1079 mmol) was then charged in 30 minutes. The resulting suspension was mixed at room temperature for 1.5 hours. The reaction mixture was cooled to 15° C. and 1500 mL of 6.7% NaHCO$_3$ charged in 1.5 hours, followed by the addition of 1200 mL of water over 60 minutes. The mixture was stirred at room temperature for 30 minutes, an then it was filtered and washed with water/DMF mixture (1:2, 250 mL) and then with water (1500 mL). The wet cake was dried at 55° C. for 24 hours to give 282 g of product (S)-benzyl 1-((S)-2-(methoxycarbonylamino)-3-methylbutanoyl)pyrrolidine-2-carboxylate as a white solid (90%).

(S)-Benzyl 1-((S)-2-(methoxycarbonylamino)-3-methylbutanoyl)pyrrolidine-2-carboxylate (40 g) and 5% Pd/Alumina were charged to a Parr reactor followed by THF (160 mL). The reactor was sealed and purged with nitrogen (6×20 psig) followed by a hydrogen purge (6×30 psig). The reactor was pressurized to 30 psig with hydrogen and agitated at room temperature for approximately 15 hours. The resulting slurry was filtered through a GF/F filter and concentrated to approximately 135 g solution. Heptane (120 mL) was added, and the solution was stirred until solids formed. After an addition 2-3 hours, additional heptane (240 mL) was added drop-wise, the slurry was stirred for approximately 1 hour, then filtered. The solids were dried to afford the title compound (S)-1-((S)-2-(methoxycarbonylamino)-3-methylbutanoyl)pyrrolidine-2-carboxylic acid.

Intermediate 10

4-Cyclohexyl-3-fluoroaniline hydrochloride

Intermediate 10A

3-Fluoro-4-iodoaniline

To a suspension of 3-fluoroaniline (1.0 mL, 1.16 g, 10.39 mmol) and solid sodium bicarbonate (1.75 g, 20.79 mmol) in 1:1 methanol-dichloromethane (20 mL) at 0° C. was added a solution of benzyl trimethylammonium dichloroiodate (3.62 g, 10.39 mmol) in dichloromethane (15 mL) over 30 minutes. The mixture was then allowed to warm to room temperature for 1 hour. The mixture was quenched by addition of water and the organic layer was extracted with water (2×). Drying (Na$_2$SO$_4$) and concentration in vacuo afforded an oil, which was chromatographed over a 100 g silica gel cartridge, eluting with 10-100% ethyl acetate in hexanes. These procedures afforded the title compound (2.20 g, 89%) as a pink solid. $^1$H NMR (400 MHz, CDCl$_3$) δ ppm 7.41 (dd, J=8.3, 7.3 Hz, 1H), 6.42 (dd, J=9.9, 2.5 Hz, 1H), 6.27 (dd, J=8.5, 2.5 Hz, 1H), 3.81 (s, 2H); MS+ESI m/z (rel abundance) 238 (100, M+H).

Intermediate 10B 4-(Cyclohexen-1-yl)-3-fluoroaniline

The procedure to prepare the title compound is described in General Procedure 1.2A.

Intermediate 10C

4-Cyclohexyl-3-fluoroaniline hydrochloride

A solution of 4-(cyclohexen-1-yl)-3-fluoroaniline (General Procedure 1.2A) (1.16 g, 6.07 mmol) in ethanol (30 mL) was treated with 10% palladium on carbon (300 mg) followed by hydrogenation at one atmosphere for 18 hours. The mixture was filtered through diatomaceous earth and concentrated to about one quarter volume and treated with a solution of hydrogen chloride in dioxane (4 N, 10 mL). The mixture was then partially concentrated in vacuo to about one quarter volume and diluted with ether (ca. 100 mL) and the solids were collected by filtration. After drying in a vacuum oven at 50° C. for 3 hours, these procedures afforded the title compound (1.13 g, 81%) as a light grey solid. $^1$H NMR (400 MHz, DMSO-d$_6$) δ ppm 7.35 (t, J=8.1 Hz, 1H), 7.03 (d, J=9.4 Hz, 2H), 2.76 (dd, J=15.6, 6.9 Hz, 1H), 1.74 (m, 5H), 1.40 (m, 4H), 1.21 (m, 1H). MS (DCI+) m/z (rel abundance) 194 (100, M+H), 211 (67, M+NH$_4$).

Intermediate 11A

N-(4-bromo-5-fluoro-2-nitrophenyl)-2,2,2-trifluoroacetamide

To a flask containing trifluoroacetic anhydride (10.0 mL, 70.5 mmol) at 0° C. was added 4-bromo-3-fluoroaniline (2.0, g, 10.5 mmol) and stirring was continued for 30 minutes (Charifson, P. S.; et al. J. Med. Chem. 2008, 51, 5243-5263). Potassium nitrate (1.3 g, 12.6 mmol) was added and the solution was allowed to warm to 25° C. The solution was concentrated, the residue dissolved in EtOAc and washed with 10% NaHCO$_3$, brine, dried (Na$_2$SO$_4$), and filtered. The filtrate was concentrated to give the title compound (3.5 g, 10.5 mmol, 100%).

Intermediate 11B 4-bromo-5-fluoro-2-nitroaniline

To N-(4-bromo-5-fluoro-2-nitrophenyl)-2,2,2-trifluoroacetamide (3.5 g, 10.5 mmol) was added CH$_3$OH (30 mL) followed by 1.0 M K$_2$CO$_3$ (10.5 mL, 10.5 mmol), and the solution was stirred for 30 minutes (Charifson, P. S.; et al. J. Med. Chem. 2008, 51, 5243-5263). The solution was diluted with H$_2$O and stirred for 1 hour. The resulting orange solid was collected by filtration and dried in a vacuum oven to give the title compound (2.1, g, 8.8 mmol, 84%).

Intermediate 11C 4-bromo-5-fluorobenzene-1,2-diamine

To a solution of 4-bromo-5-fluoro-2-nitroaniline (1.0 g, 4.3 mmol) in THF (9.0 mL), EtOH (9.0 mL) and H$_2$O (3 mL) was added iron powder (1.2 g, 21.3 mmol) and ammonium chloride (0.34 g, 6.4 mmol), and the mixture was heated at 95° C. for 4 hours. The cooled mixture was diluted with EtOH, filtered through diatomaceous earth until no further color came through the filter, and concentrated. The residue was dissolved in EtOAc, washed with H$_2$O, brine, dried (Na$_2$SO$_4$), filtered and concentrated. Hexane was added and the resulting solid collected by filtration to give the title compound (710 mg, 3.5 mmol, 81%).

Intermediate 12

4-bromo-3-chlorobenzene-1,2-diamine

Intermediate 12A 4-bromo-3-chloro-2-nitroaniline

3-Chloro-2-nitroaniline (5.00 g, 29.0 mmol) was dissolved in glacial acetic Acid (258 mL). N-Bromosuccinimide (5.06 g, 28.4 mmol) was added and the resulting mixture was refluxed for 1 hour. The reaction was cooled to room temperature and poured into water to give a precipitate that was filtered, rinsed with water and dried to constant weight to give the title compound (4.78 g, 67%). $^1$H NMR (400 MHz, CDCL$_3$) δ ppm 7.46 (d, J=9.0, 1H), 6.64 (d, J=9.0, 1H), 4.74 (s, 2H).

Intermediate 12B 4-bromo-3-chlorobenzene-1,2-diamine

4-Bromo-3-chloro-2-nitroaniline (4.78 g, 19.01 mmol) was dissolved in ethanol (112 mL). Tin (II) chloride (14.42 g, 76 mmol) was added, and the resulting mixture was stirred at reflux for 12 hours. The mixture was cooled to room temperature, poured into water, and adjusted to pH 5 with saturated sodium bicarbonate solution. The resulting solid was filtered and rinsed well with ethyl acetate. The filtrate was washed with water and brine, dried over Na$_2$SO$_4$, filtered and concentrated in vacuo. The crude product was purified by column chromatography on silica gel using a solvent gradient of 0-50% EtOAc in hexane to give the title compound (3.32 g, 79%). $^1$H NMR (400 MHz, CDCl$_3$) δ ppm 6.94 (d, 1H), 6.51 (d, J=7.0, 1H), 3.87 (br s, 2H), 3.46 (br s, 2H).

Intermediate 13

4-bromo-3-methylbenzene-1,2-diamine

Intermediate 13A

N-(3-bromo-2-methyl-6-nitrophenyl)-2,2,2-trifluoroacetamide

To a solution of 3-bromo-2-methylaniline (1.0 g, 5.37 mmol) in CH$_2$Cl$_2$ (4.0 mL) at 0° C. was added trifluoroacetic anhydride (2.0 mL, 14.2 mmol). The mixture was stirred at 0° C. for 30 minutes, and solid potassium nitrate (0.679 g, 6.72 mmol) was added. The cooling bath was removed, and the mixture was stirred at room temperature overnight. LCMS showed a single product formed. The mixture was concentrated in vacuo, and the residue was partitioned between water and CH$_2$Cl$_2$ (2×). The organic layers were combined and dried over Na$_2$SO$_4$. The drying agent was filtered off and the crude product was purified by crystallization from aq EtOH to give the title compound (1.3 g, 74%).

Intermediate 13B 3-bromo-2-methyl-6-nitroaniline

A solution of N-(3-bromo-2-methyl-6-nitrophenyl)-2,2,2-trifluoroacetamide (1.3 g, 3.97 mmol) in CH$_3$OH (30 mL) was treated with potassium carbonate (1.099 g, 7.95 mmol), and the mixture was stirred at 50° C. overnight. The mixture was cooled to room temperature and poured into water, 1N aq HCl was added to adjust to pH 6, and the mixture was extracted with CH$_2$Cl$_2$ (3×). The combined extracts were dried over Na$_2$SO$_4$, and the drying agent was filtered off and solvent was removed in vacuo to give the title compound as a yellow solid (0.57 g, 62%).

Intermediate 13C 4-bromo-3-methylbenzene-1,2-diamine

To a solution of 3-bromo-2-methyl-6-nitroaniline (0.45 g, 1.95 mmol) in EtOH (6 mL) was added tin(II) chloride (1.48 g, 7.8 mmol), and the resulting solution was stirred at 70° C. for 4 hours. The mixture was cooled to room temperature and poured into water, and 1 N aq. NaOH was added to adjust to pH>7. The resulting mixture was extracted with CH$_2$Cl$_2$ (2×), and the combined extracts were dried over Na$_2$SO$_4$. The drying agent was filtered off and solvent was removed in vacuo to give the title compound as an oil (0.34 g, 88%).

Intermediate 14

5-bromo-3-fluorobenzene-1,2-diamine

To a solution of 4-bromo-2-fluoro-6-nitroaniline (0.5 g, 2.1 mmol) in THF (4.6 mL), EtOH (4.6 mL) and H$_2$O (1.5 mL) was added iron powder (0.6 g, 10.6 mmol) and ammonium chloride (0.17 g, 3.2 mmol). The resulting mixture was stirred at 95° C. for 22 hours. The mixture was cooled to room temperature and filtered through diatomaceous earth. The solid was washed with EtOH until no further color came through the filter. The filtrate was concentrated and the residue was dissolved in EtOAc, washed with H$_2$O and brine, dried over Na$_2$SO$_4$, filtered and concentrated to give the title compound (0.43 g, 99%) as a brown, waxy solid.

Intermediate 15

4-bromo-3-fluorobenzene-1,2-diamine

Intermediate 15A 3-fluoro-2-nitroaniline

To a pressure tube was added 1,3-difluoro-2-nitrobenzene (2.8 mL, 26.4 mmol) and 7 N NH$_3$ in CH$_3$OH (10 mL, 70 mmol). The tube was sealed and the mixture was stirred at room temperature for 5 days. The solution was diluted with H$_2$O, extracted with CH$_2$Cl$_2$, and the combined extracts were washed with brine, dried over Na$_2$SO$_4$, filtered and concentrated to give an oil. The oil was triturated with hexane and the resulting orange solid was collected by filtration to give the title compound (2.1 g, 51%).

Intermediate 15B 4-bromo-3-fluoro-2-nitroaniline

To a solution of 3-fluoro-2-nitroaniline (2.1 g, 13.4 mmol) in DMF (30 mL) at 0° C. was added a solution of N-bromosuccinimide (2.4 g, 13.4 mmol) in DMF (20 mL). The resulting solution was stirred at 0° C. for 30 minutes and then warmed to room temperature over 1 hour. The solution was diluted with EtOAc, washed with H$_2$O and brine, dried over MgSO$_4$, filtered and concentrated to give the title compound (3.1 g, 97%).

Intermediate 15C 4-bromo-3-fluorobenzene-1,2-diamine

To a solution of 4-bromo-3-fluoro-2-nitroaniline (3.0 g, 12.8 mmol) in THF (30 mL) was added EtOH (30 mL) and H$_2$O (10 mL) followed by iron powder (3.6 g, 63.8 mmol) and ammonium chloride (1.0 g, 19.2 mmol). The resulting mixture was stirred at 80° C. for 16 hours. The mixture was cooled to room temperature and filtered through diatomaceous earth. The solid was washed with EtOH until no further color came through the filter. The filtrate was concentrated in vacuo and the crude product was purified by column chromatography on silica gel using a solvent gradient of 0-40% EtOAc in hexane to give the title compound (2.2 g, 84%).

Intermediate 16

4-cyclopropyl-2-fluoroaniline

4-Cyclopropyl-2-fluoro-1-nitrobenzene (prepared as described in General Procedure 1.2C) (2.2 g, 12.14 mmol) was dissolved in 7 mL of an ethanol:THF:water 3:3:1 (v/v) mixture. To this was added ammonium chloride (1.02 g, 19.07 mmol) followed by iron powder (3.50 g, 62.7 mmol). The resulting mixture was heated in a 90° C. oil bath under a nitrogen atmosphere with rapid stirring for one hour. The reaction mixture was vacuum filtered through a sand and diatomaceous earth plug. The filtrate was concentrated in vacuo and the residue partitioned between dichloromethane and water. The organic phase was washed with brine, dried (MgSO$_4$) and concentrated in vacuo to provide an orange oil (1.90 g).

Intermediate 17

2-(methoxycarbonylamino)-3-methylbut-2-enoic acid

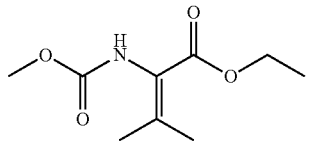

Intermediate 17A ethyl 2-(methoxycarbonylamino)-3-methylbut-2-enoate

A benzene solution (90 mL) of ethyl-3-methyl-2-oxobutanoate (4.03 g, 28.0 mmol), methyl carbamate (2.098 g, 28.0 mmol) and pyridine 4-methylbenzenesulfonate (0.70 g, 2.80 mmol) was heated to reflux in a round bottom flask equipped with a Dean-Stark trap and reflux condenser. After 44 hours of heating the mixture was cooled and then partitioned between ethyl acetate (50 mL) and brine (50 mL). The organic phase was washed with brine (2×50 mL) then dried (MgSO$_4$) and concentrated in vacuo. The crude product was purified by chromatography on silica gel (ethyl acetate-hexanes) to provide the title compound as an off white crystalline solid (1.487 g, 26%).

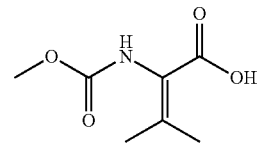

Intermediate 17B 2-(methoxycarbonylamino)-3-methylbut-2-enoic acid

The product from Intermediate 17A (0.373 g, 1.85 mmol) was dissolved in 2 mL of a 1:1(v/v) ethanol:water mixture at room temperature. To this was added lithium hydroxide (0.095 g, 3.99 mmol) in one portion. After stirring overnight, the reaction mixture was partitioned between ethyl acetate (25 mL) and 1 N HCl (5 mL) to which was added solid NaCl. The aqueous phase was extracted with ethyl acetate one time and the combined organics washed with brine (3×5 mL) then dried (MgSO$_4$) and concentrated to give the title compound (0.289 g, 90%) as an off white solid sufficiently pure for use as isolated.

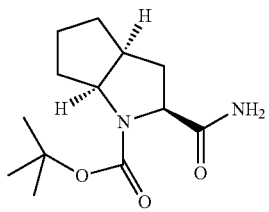 [SMILES: CC(C)(C)OC(=O)N1[C@H](C(N)=O)C[C@@H]2CCC[C@@H]21]

Intermediate 18

(2S,3aS,6aS)-tert-butyl 2-carbamoylhexahydrocyclopenta[b]pyrrole-1(2H)-carboxylate

Intermediate 18A (2S,3aS,6baS)-2-benzyl 1-tert-butyl hexahydrocyclopenta[b]pyrrole-1,2(2H)-dicarboxylate

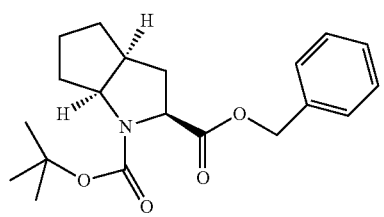 [SMILES: CC(C)(C)OC(=O)N1[C@H](C(=O)OCc2ccccc2)C[C@@H]2CCC[C@@H]21]

To a suspension of (2S,3aS,6aS)-benzyl octahydrocyclopenta[b]pyrrole-2-carboxylate hydrochloride (2.0 g, 7.10 mmol) in dichloromethane (36 mL) at room temperature was added di-tert-butyl dicarbonate (1.70 g, 7.81 mmol) followed by triethylamine (2.18 mL, 15.62 mmol). The solution rapidly becomes homogeneous along with vigorous gas evolution which quickly subsides. After two hours, the mixture was diluted with dichloromethane, washed with brine (3×60 mL), dried (MgSO$_4$) and concentrated. The crude product was purified by chromatography on silica gel (ethyl acetate-hexanes) to give the title compound (2.58 g, quantitative) as a clear oil.

Intermediate 18B (2S,3aS,6aS)-1-(tert-butoxycarbonyl)octahydrocyclopenta[b]pyrrole-2-carboxylic acid

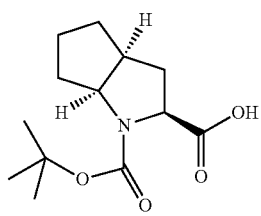 [SMILES: CC(C)(C)OC(=O)N1[C@H](C(=O)O)C[C@@H]2CCC[C@@H]21]

The product from Intermediate 18A (2.45 g, 7.1 mmol) was dissolved in methanol (35 mL) at room temperature. To this was added Pearlman's catalyst (0.153 g) followed by vacuum degassing (3×) and hydrogen addition (balloon). After one hour, the reaction mixture was vacuum filtered through diatomaceous earth and the filtrate concentrated to give a clear thick oil (1.89 g, quantitative) which was sufficiently pure for use as isolated.

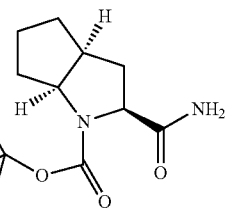

Intermediate 18C (2S,3aS,6aS)-tert-butyl 2-carbamoylhexahydrocyclopenta[b]pyrrole-1(2H)-carboxylate The product from Intermediate 18B (1.81 g, 7.1 mmol) was dissolved in THF (40 mL) at room temperature under nitrogen. To this was added N-methyl morpholine (1.0 mL, 9.09 mmol) and the resulting solution was cooled to −15° C. To the cold solution was added isobutylchloroformate (1.03 mL, 7.81 mmol) dropwise via syringe. A white precipitate forms at once. On completion of the addition, the mixture was allowed to stir in the cold for twenty minutes. Ammonia gas was then introduced by bubbling through the mixture for two minutes with additional cooling. On completion of the addition, the reaction was allowed to warm to ice bath temperature and stir for one half hour and then warmed to room temperature. After fifteen minutes at room temperature, the mixture was poured into brine (450 mL) and extracted with dichloromethane (6×50 mL). The combined extracts were dried (MgSO$_4$) and concentrated. The crude product was purified by chromatography on silica gel (ethyl acetate-hexanes) to give the title compound (1.68 g, 93%) as a sticky white foam.

Intermediate 19

(S,E)-tert-butyl 2-(5-(3-oxoprop-1-enyl)-1-((2-(trimethylsilyl)ethoxy)methyl)-1H-benzo[d]imidazol-2-yl)pyrrolidine-1-carboxylate

Intermediate 19A (S,E)-tert-butyl 2-(5-(3-ethoxy-3-oxoprop-1-enyl)-1-((2-(trimethylsilyl)ethoxy)methyl)-1H-benzo[d]imidazol-2-yl)pyrrolidine-1-carboxylate To (S)-tert-butyl 2-(5-bromo-1-((2-(trimethylsilyl)ethoxy)methyl)-1H-benzo[d]imidazol-2-yl)pyrrolidine-1-carboxylate (2.973 g, 5.99 mmol), ethyl acrylate (0.714 mL, 6.59 mmol), tri-tert-butylphosphonium tetrafluoroborate (0.104 g, 0.359 mmol), N,N-dicyclohexylmethylamine (1.461 mL, 6.89 mmol), and tris(dibenzylideneacetone)dipalladium(0) (0.164 g, 0.18 mmol) dissolved in THF (18 mL) had nitrogen bubbled through the solution for 15 minutes to remove the oxygen, and then the mixture heated at 60° C. for 2 hours. After cooling to room temperature the solution was filtered through diatomaceous earth and washed with EtOAc. The filtrated was then concentrated to a residue, and then the residue was dissolved in dichloromethane and extracted with water. The organic layer was then dried and concentrated. The residue was purified by chromatography (silica gel, hexanes in ethyl acetate) which afforded 2.56 g, (83%) of the title compound. MS (ESI) m/z 516 (M+H)$^+$.

Intermediate 19B (S,E)-tert-butyl 2-(5-(3-hydroxyprop-1-enyl)-1-((2-(trimethylsilyl)ethoxy)methyl)-1H-benzo[d]imidazol-2-yl)pyrrolidine-1-carboxylate Intermediate 19A (2.56 g, 4.97 mmol) was dissolved in THF (17 mL), and the mixture was cooled to −78° C. in a dry ice acetone bath. Then a solution of diisobutylaluminium hydride (1.0 N in THF, 22.75 mL, 24.75 mmol) was added dropwise. The resultant mixture was allowed to slowly warm to room temperature overnight, and then was quenched with a 1 N aqueous sodium hydroxide solution. The mixture was then added to ethyl acetate and extracted with an aqueous solution of Rochelle's salt (sodium, potassium tartrate). The organic layers were combined and dried, and then concentrated. The residue was purified by chromatography (silica gel, hexanes in ethyl acetate) which afforded 0.93 g, (40%) of the title compound. MS (ESI) m/z 474 (M+H)$^+$.

Intermediate 19C (S,E)-tert-butyl 2-(5-(3-oxoprop-1-enyl)-1-((2-(trimethylsilyl)ethoxy)methyl)-1H-benzo[d]imidazol-2-yl)pyrrolidine-1-carboxylate The product of Intermediate 19B (0.93 g, 1.96 mmol) was dissolved in dichloromethane (7.5 mL) and pyridinium dichromate (1.11 g, 2.95 mmol) was added, and the resultant mixture was stirred at room temperature overnight. The solution had hexanes added to it, and then it was filtered through diatomaceous earth. The filtrate was then concentrated to a residue which was then dissolved in dichloromethane and extracted with water. The organic layer was then dried, concentrated and the residue purified by chromatography (silica gel, hexanes in ethyl acetate) which afforded 0.3 g, (32%) of the title compound. $^1$H NMR (400 MHz, DMSO-d$_6$) δ ppm 9.65 (d, J=7.8 Hz, 1H), 8.05 (m, 1H), 7.82 (d, J=15.8 Hz, 1H), 7.70 (m, 2H), 6.87 (dd, J=15.8, 7.8 Hz, 1H), 5.70 (s, 2H), 5.14 (m, 1H), 3.57 (m, 2H), 3.42 (m, 1H), 2.40 (m, 5H), 1.30 (s, 4H), 0.95 (s, 5H), 0.80 (m, 2H), −0.10 (s, 9H); MS (ESI) m/z 472 (M+H)$^+$.

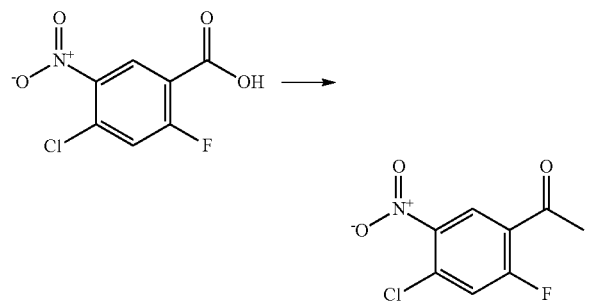

Intermediate 20A 1-(4-chloro-2-fluoro-5-nitrophenyl)ethanone

To a solution of 4-chloro-2-fluoro-5-nitrobenzoic acid (16.0 g, 72.9 mmol) in anhydrous CH$_2$Cl$_2$ (400 mL) was added oxalyl chloride (9.57 mL, 109 mmol) and DMF (2 drops), and the resulting mixture was stirred at room temperature until gas evolution ceased. The mixture was concentrated and dried in vacuo. In a separate, heat-dried reaction flask a mixture of ZnBr$_2$ (24.6 g, 109 mmol) in anhydrous THF (300 mL) at −78° C. was added a solution of CH$_3$MgBr (29.1 mL, 3.0 M in Et$_2$O, 87 mmol) dropwise. The resulting mixture was stirred at −78° C. for 15 minutes, and then the reaction mixture was allowed to warm to room temperature and stirred for 30 minutes. The mixture was cooled to −78° C. and a solution of the acid chloride in anhydrous THF (100 mL) was added dropwise, followed by Pd(PPh$_3$)$_4$ (1.68 g, 1.46 mmol). The resulting mixture was allowed to stir at −78° C. for 10 minutes, and was then allowed to warm to ambient temperature and stirred for an additional 16 hours. The mixture was quenched by adding aq. 1 M HCl, diluted with H$_2$O (100 mL), and extracted with CH$_2$Cl$_2$ (3×300 mL). The combined organic extracts were dried (MgSO$_4$), filtered and concentrated. The crude product was purified by column chromatography (silica gel, 5% EtOAc in hexanes) to afford the title compound (11.79 g, 74%).

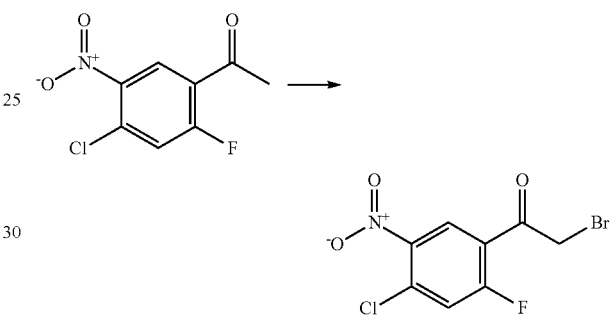

Intermediate 20B 2-bromo-1-(4-chloro-2-fluoro-5-nitrophenyl)ethanone

The product of Intermediate 20A (3.0 g, 13.79 mmol) dissolved in THF (100 mL) was treated with pyridinium bromide perbromide (4.63 g, 14.48 mmol) portionwise over several minutes. The resulting mixture stirred at ambient temperature for 2 hours and then filtered. The filtered solids were rinsed with EtOAc, and the filtrate was concentrated in vacuo. The crude product was purified by column chromatography (silica gel, 20% EtOAc in hexanes) to afford the title compound (3.8 g, 93%).

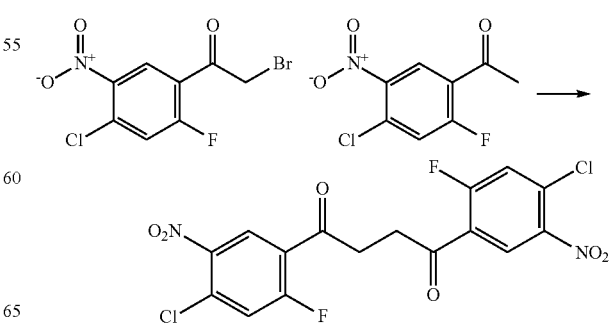

Intermediate 20C 1,4-bis(4-chloro-2-fluoro-5-nitrophenyl)butane-1,4-dione

Intermediate 20A (4.92 g, 22.62 mmol) and Intermediate 20B (4.47 g, 15.08 mmol) were processed using the method described in Intermediate 5B to afford the title compound (4.74 g, 73%).

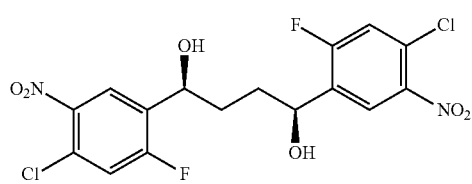 [SMILES: O=[N+]([O-])c1cc([C@@H](O)CC[C@H](O)c2cc([N+](=O)[O-])c(Cl)cc2F)c(F)cc1Cl]

Intermediate 20D (1S,4S)-1,4-bis(4-chloro-2-fluoro-5-nitrophenyl)butane-1,4-diol The product of Intermediate 20C (1.0 g, 2.309 mmol) was processed using the method described in Intermediate 5C to afford the title compound (0.96 g, 95%).

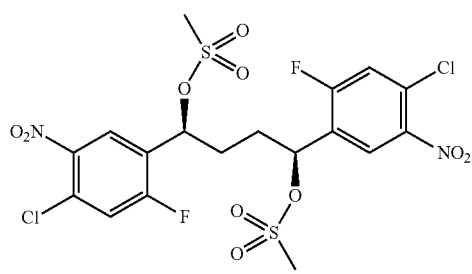 [SMILES: CS(=O)(=O)O[C@@H](CC[C@H](OS(C)(=O)=O)c1cc([N+](=O)[O-])c(Cl)cc1F)c1cc([N+](=O)[O-])c(Cl)cc1F]

Intermediate 20E (1S,4S)-1,4-bis(4-chloro-2-fluoro-5-nitrophenyl)butane-1,4-diyl dimethanesulfonate To a solution of Intermediate 20D (0.95 g, 2.17 mmol) in anhydrous $CH_2Cl_2$ (20 mL) at 0° C. was added methanesulfonyl chloride (0.42 mL, 5.43 mmol), followed by the dropwise addition of triethylamine (0.91 mL, 6.52 mmol). The resulting mixture was stirred at room temperature for 90 minutes, and was then concentrated in vacuo. Hexanes were added, and the resulting solids were collected by filtration, washed with $H_2O$, and dried in vacuo to provide the title compound (1.29 g, 100%).

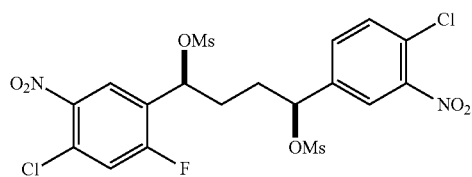 [SMILES: CS(=O)(=O)O[C@@H](CC[C@H](OS(C)(=O)=O)c1cc([N+](=O)[O-])c(Cl)cc1F)c1ccc(Cl)c([N+](=O)[O-])c1]

Intermediate 21

(1S,4S)-1-(4-chloro-2-fluoro-5-nitrophenyl)-4-(4-chloro-3-nitrophenyl)butane-1,4-diyl dimethanesulfonate Intermediate 21 can be made from Intermediate 20B and 1-(4-chloro-3-nitrophenyl)ethanone (commercially available from Aldrich) following the general methods to prepare Intermediate 20E.

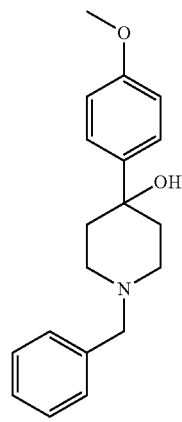 [SMILES: COc1ccc(C2(O)CCN(Cc3ccccc3)CC2)cc1]

Intermediate 22A 1-benzyl-4-(4-methoxyphenyl)piperidin-4-ol (4-Methoxyphenyl)magnesium bromide (0.5 M in THF, 90 mL, 45.0 mmol) was added slowly (~25 minutes) via cannula to a cold (0° C.) solution of 1-benzylpiperidin-4-one (5.4 mL, 30.2 mmol) in THF (60 mL). The reaction was stirred at 0° C. under nitrogen for 2 hours. The reaction was quenched with saturated aqueous $NH_4Cl$ then diluted with ether. The organic fraction was washed with saturated aqueous $NH_4Cl$ (2×) brine (1×) and concentrated. Purification using flash chromatography (5-100% EtOAc/hexane) provided 4.02 g (44%) of the titled compound. MS (DCI) m/z 298 (M+H)+.

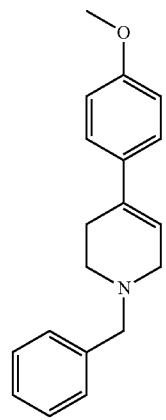 [SMILES: COc1ccc(C2=CCN(Cc3ccccc3)CC2)cc1]

Intermediate 22B 1-benzyl-4-(4-methoxyphenyl)-1,2,3,6-tetrahydropyridine

6 M HCl (100 mL, aqueous) was added to a solution of 1-benzyl-4-(4-methoxyphenyl)piperidin-4-ol (12.31 g, 41.36 mmol) in dioxane (50 mL), and the reaction was heated to strong reflux (110° C.). After 2 hours, the reaction was not complete. The heat was turned off and the reaction was left to stir at ambient temperature for 2 days. The reaction had progressed but was not complete so it was heated to 110° C. After 1 hour, the reaction was cooled and the volume was reduced by approximately one third. The solution was then cooled in an ice bath and neutralized with NaOH pellets. The thick suspension was filtered. The precipitate was rinsed with water and then dried under vacuum at 70° C. to afford 6.2 g (47%) of the titled compound. $^1$H NMR (400 MHz, CDCl$_3$) δ ppm 2.74-2.62 (m, 1H), 3.30-3.06 (m, 2H), 3.50 (d, J=18.5, 1H), 3.67-3.56 (m, 1H), 3.82 (s, 3H), 4.03-3.90 (m, 1H), 4.21 (dd, J=5.7, 13.0, 1H), 4.34 (dd, J=5.1, 13.0, 1H), 5.88 (s, 1H), 6.88 (d, J=8.7, 2H), 7.32 (d, J=8.7, 2H), 7.51-7.43 (m, 3H), 7.71 (dd, J=2.7, 6.3, 2H), 12.85 (s, 1H); MS (ESI) m/z 280 (M+H)$^+$; MS (DCI) m/z 280 (M+H)$^+$.

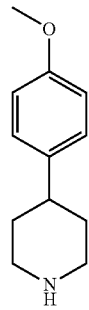

Intermediate 22C 4-(4-methoxyphenyl)piperidine

The product from Intermediate 22B (6.2 g) in trifluoroethanol (60 mL) was added to 20% Pd(OH)2-C, wet (1.240 g, 8.83 mmol) in a 250 mL stainless steel pressure bottle. The mixture was shaken under 30 psi of hydrogen at 50° C. for 23 hours. The mixture was filtered through a PTFE membrane, concentrated and dried under vacuum to afford 4.33 g of the desired product as the HCl salt. (HCl salt)$^1$H NMR (400 MHz, CDCl$_3$) δ ppm 2.03 (d, J=13.1, 2H), 2.28-2.11 (m, 2H), 2.72 (t, J=10.2, 1H), 3.08-2.91 (m, 2H), 3.62 (d, J=8.3, 2H), 3.79 (s, 3H), 6.86 (d, J=8.3, 2H), 7.16 (d, J=8.5, 2H), 9.65 (d, J=83.1, 2H); MS (DCI) m/z 192 (M+H)$^+$.

Intermediates 23, 24, and 25 can be prepared using the methodology used to prepare Intermediate 22C

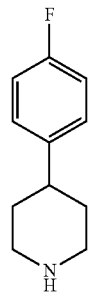 [SMILES: Fc1ccc(C2CCNCC2)cc1]

Intermediate 23

4-(4-fluorophenyl)piperidine

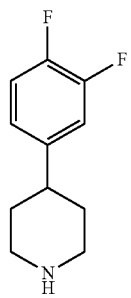

Intermediate 24

4-(3,4-difluorophenyl)piperidine

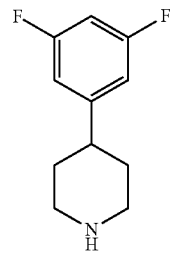 [SMILES: Fc1cc(F)cc(C2CCNCC2)c1]

Intermediate 25

4-(3,5-difluorophenyl)piperidine

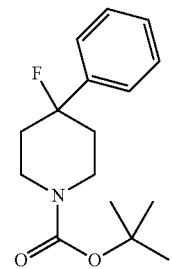 [SMILES: CC(C)(C)OC(=O)N1CCC(F)(c2ccccc2)CC1]

Intermediate 26A tert-butyl 4-fluoro-4-phenylpiperidine-1-carboxylate

A solution of diethylaminosulfur trifluoride (4 mL, 32.7 mmol) in dichloromethane (10 mL) was added to a cold (−78°

C.; dry ice/acetone bath) solution of tert-butyl 4-hydroxy-4-phenylpiperidine-1-carboxylate (8.05 g, 29.0 mmol) in dichloromethane (100 mL) under nitrogen. The reaction was stirred at −78° C. for ~1 hour. The reaction was removed from the bath and warmed to ambient temperature then stirred another 30 minutes. The reaction was quenched with saturated aqueous $NaHCO_3$ (100 mL). The organic fraction was washed with brine (~50 mL). Then 3-chloroperoxybenzoic acid (1.0995 g, 6.37 mmol) was added to the reaction and stirred at ambient temperature for 30 minutes. This step was quenched with saturated aqueous $NaHCO_3$ (100 mL). The organic fraction was washed with saturated aqueous $NaHCO_3$ (1×100 mL), water (1×100 mL), and brine (1×100 mL), dried ($MgSO_4$), tested for peroxide (3-10 ppm) and concentrated to light yellow oil. The oil was dried under vacuum to afford 8.27 g (100%) of the titled compound. $^1$H NMR (400 MHz, DMSO-$d_6$) δ ppm 1.42 (d, J=5.7, 9H), 1.96-1.85 (m, 3.5H), 2.03 (ddd, J=5.2, 13.3, 17.8, 1.5H), 3.06 (s, 2H), 3.98 (d, J=12.0, 2H), 7.33 (d, J=7.1, 1H), 7.46-7.36 (m, 4H); MS (DCI) m/z 280 (M+H$^+$, 60%), 297 (M+NH$_4^+$, 100%).

Intermediate 26B 4-fluoro-4-phenylpiperidine

Hydrochloric acid (4 M in dioxane, 20 mL, 80 mmol) was added to a solution of tert-butyl 4-fluoro-4-phenylpiperidine-1-carboxylate (8.27 g, 29.6 mmol) in dioxane (10 mL). The reaction was stirred at ambient temperature for 4 hours. The reaction was concentrated to an oil. Ether was added, and the resulting solid was sonicated and then stirred vigorously overnight to provide a tan solid. The solid was filtered, rinsed with ether and dried under vacuum at 60° C. for 3 hours to provide 5.56 g (87%) of the titled product. MS (DCI) m/z 180 (M+H)$^+$.

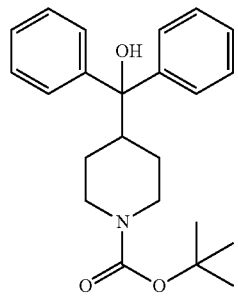 [SMILES: CC(C)(C)OC(=O)N1CCC(C(O)(c2ccccc2)c2ccccc2)CC1]

Intermediate 27A tert-butyl 4-(hydroxydiphenylmethyl)piperidine-1-carboxylate

A solution of di-tert-butyl dicarbonate (8.43 mL, 36.7 mmol) in dichloromethane (15 mL) was added to a solution of diphenyl(piperidin-4-yl)methanol (8.0721 g, 30.2 mmol) in dichloromethane (100 mL); triethylamine (5.1 mL, 36.6 mmol) was added and the reaction was stirred at ambient temperature for 2 hours. The reaction was diluted with dichloromethane and then washed with saturated aqueous NaHCO3 (2×), water (1×), and brine (1×), dried (MgSO4) and concentrated to afford 11.63 g (105%) of the titled compound. MS (ESI) m/z 367 (M+H)$^+$, 366 (M−H)$^+$.

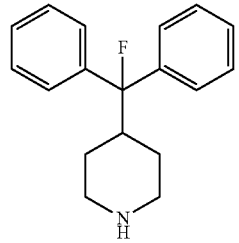 [SMILES: FC(c1ccccc1)(c1ccccc1)C1CCNCC1]

Intermediate 27B 4-(fluorodiphenylmethyl)piperidine

The title compound was prepared from tert-butyl 4-(hydroxydiphenylmethyl)piperidine-1-carboxylate using the general methods of Intermediates 26A and 26B. 3.37 g (100%) as HCl salt, MS (DCI) m/z 270 (M+H)$^+$.

General Procedures

General Procedure 1. Synthesis of 4-aminosubstituted anilines

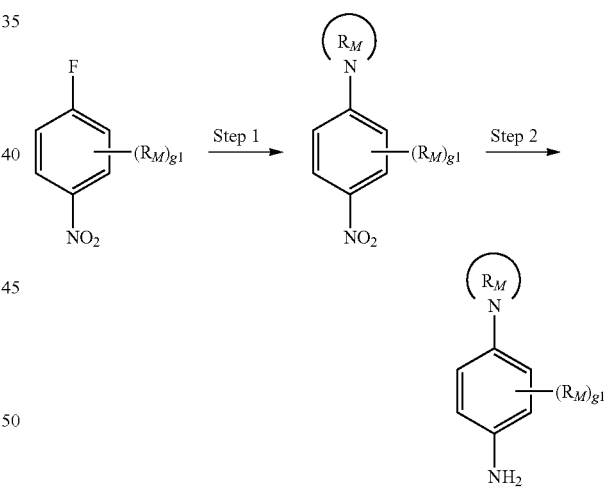

Intermediate anilines having an amino group para to the aniline can be made using a two-step procedure. Fluoronitrobenzenes, fluoronitropyridines, or fluoronitropyrimidines can be reacted in Step 1 with an appropriate amine

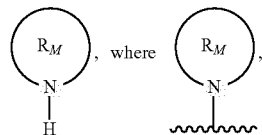

represents any amine group that can be present in $R_M$ and attached through nitrogen, in the presence of dibasic potassium phosphate (equivalents)) or potassium carbonate in a solvent such as DMSO optionally with heating and optional microwave irradiation. Step 2 can be accomplished by standard nitro reduction conditions such as catalytic hydrogenation using palladium on carbon or Raney-nickel. Alternatively, the reduction can be effected with iron/ammonium chloride in THF/methanol/water as solvent. Where the group

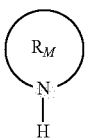

is an optionally substituted cyclic amine (e.g., piperidine, pyrrolidine), the optionally substituted cyclic amines can be accessed as described herein or using generally known methodologies. See for example the methods shown in Patel et al. *J Medicinal Chemistry* 49(25) 7450 (2006).

Illustration of General Procedure 1: General Procedure 1A

Step 1

1-(2,6-difluoro-4-nitrophenyl)-4-phenylpiperidine

In a 100 mL round-bottom flask was mixed 3,4,5-trifluoronitrobenzene (1.751 mL, 15 mmol) and potassium phosphate, dibasic (5.23 g, 30.0 mmol) in DMSO (15.00 mL) to give a yellow suspension. 4-Phenylpiperidine (2.419 g, 15.00 mmol) was added portion-wise as a solid over 10 minutes to produce a deeper yellow suspension and a mild exotherm. The mixture was stirred for 1 hour and partitioned between EtOAc and water. The EtOAc layer was washed 2× by 50 mL each with water and brine, dried ($Na_2SO_4$), filtered and concentrated to give the title compound as a yellow solid (4.53 g, 95% yield).

Step 2

3,5-difluoro-4-(4-phenylpiperidin-1-yl)aniline

In a 500 mL round-bottom flask was added 1-(2,6-difluoro-4-nitrophenyl)-4-phenylpiperidine (4.53 g, 14.23 mmol), iron (3.97 g, 71.2 mmol), and ammonium chloride (1.142 g, 21.35 mmol) in a solvent mixture of EtOH (60 mL)/THF (60 mL)/water (20 mL). The mixture was refluxed for 3 hours with vigorous stirring, cooled, filtered through diatomaceous earth and the filtrate was concentrated. The residue was partitioned between ethyl acetate and water. The organic layer was washed with brine, dried ($Na_2SO_4$), filtered and evaporated to give the title compound as yellow solid (3.93 g, 96% yield). $^1$H NMR (400 MHz, DMSO-$d_6$) δ ppm 1.63-1.81 (m, 4H) 2.54-2.64 (m, 1H) 2.95-3.03 (m, 2H) 3.09 (t, J=10.57 Hz, 2H) 5.42 (s, 2H) 6.10-6.21 (m, 2H) 7.15-7.22 (m, 1H) 7.25-7.34 (m, 4H); MS (ESI+) m/z 289 (M+H)$^+$.

Illustration of General Procedure 1: General Procedure 1B

Step 1

5-nitro-2-(pyrrolidin-1-yl)pyridine

To a slurry of 2-chloro-5-nitropyridine (10 g, 63.1 mmol) in EtOH (100 mL) at room temperature was added pyrrolidine (15.72 mL, 189 mmol) and the mixture was heated at 70° C. for 18 hours. The cooled solution was concentrated in vacuo and the residue partitioned between $CH_2Cl_2$ and 1 M NaOH. The organic layer was dried ($Na_2SO_4$), filtered and solvent removed in vacuo to give title compound (9.52 g, 78%). MS (ESI) m/z 194 (M+H)$^+$.

Step 2

6-(pyrrolidin-1-yl)pyridin-3-amine

5-Nitro-2-(pyrrolidin-1-yl)pyridine (9.52 g, 49.3 mmol) was dissolved in THF (50 mL) and DMF (40 mL) and added to a pressure bottle containing Raney-nickel 2800, water slurry (45%) (9.52 g, 162 mmol). The mixture was stirred for 2 hours at 30 psi under $H_2$ gas. The solution was filtered through a nylon membrane, washed with $CH_3OH$ and the filtrate concentrated in vacuo to give the title compound (7.78 g, 97%). $^1$H NMR (400 MHz, DMSO-$d_6$) δ ppm 1.81-1.91 (m, 4H) 3.17-3.29 (m, 4H) 4.30 (s, 2H) 6.25 (d, J=8.7, 1H), 6.90 (dd, J=2.8, 8.7, 1H), 7.55 (d, J=2.6, 1H); MS (ESI) m/z 164 (M+H)$^+$.

Illustration of General Procedure 1, step 2: General Procedure 1C 4-(3,5-dimethylpiperidin-1-yl)-3,5-difluoroaniline 1-(2,6-Difluoro-4-nitrophenyl)-3,5-dimethylpiperidine (14.01 g, 51.8 mmol) and THF (240 mL) were added to Raney-nickel 2800, water slurry (14.01 g, 239 mmol) in a 500 mL stainless steel pressure bottle. The mixture was stirred for 8 hours at 30 psi and room temperature. The mixture was filtered through a nylon membrane and concentrated to give the title compound.

Illustration of General Procedure 1, step 2: General Procedure 1D 3-methyl-4-(piperidin-1-yl)aniline To a solution of 1-(2-methyl-4-nitrophenyl)piperidine (6.75 g, 30.6 mmol) in ethyl acetate (50 mL) was added 10% palladium on carbon (0.033 g, 0.306 mmol) and the mixture hydrogenated (hydrogen balloon) at room temperature for 20 hours. The mixture was then filtered through diatomaceous earth and washed with ethyl acetate; the filtrate was then concentrated to afford 5.5 g (94%) of the title compound. MS (ESI) m/z 191 (M+H)$^+$.

Illustration of General Procedure 1, step 1: General Procedure 1E 1-(4-nitrophenyl)-4-phenylpiperidine An oven-dried 20 mL microwave tube was charged with 4-fluoronitrobenzene (0.752 mL, 7.02 mmol), 4-phenylpiperidine (1.166 g, 7.02 mmol), and potassium carbonate (0.970 g, 7.02 mmol) under nitrogen, anhydrous DMSO (7 mL) was added, the tube was sealed with an aluminum crimp cap, and heated in a microwave reactor (Personal Chemistry, 300 W, 2.4 bar) at 190° C. for 10 minutes. TLC ($SiO_2$, 5% EtOAc/hexanes) showed complete reaction. The reaction was poured into water (50 mL), stirred for 5 minutes, and vacuum filtered in a Büchner funnel. The collected yellow solids were washed with water (2×10 mL) and $Et_2O$ (5 mL), and the bright yellow solid was dried in vacuo to provide the title compound (1.712 g, 6.06 mmol, 86%). $^1$H NMR (400 MHz, CDCl$_3$) δ ppm 1.73-1.90 (m, 2H), 2.00 (d, J=13.34 Hz, 2H), 2.73-2.86 (m, 1H), 3.02-3.17 (m, 2H), 4.10 (d, J=13.23 Hz, 2H), 6.87 (d, J=9.43 Hz, 2H), 7.23 (t, J=7.75 Hz, 3H), 7.33 (t, J=7.43 Hz, 2H), 8.14 (d, J=9.33 Hz, 2H); MS (ESI+) m/z 283 (M+H)$^+$.

The following amines can be made using methods shown in the foregoing General Procedure 1:
4-(4,4-dimethylpiperidin-1-yl)-3,5-difluoroaniline;
4-(2-azabicyclo[2.2.2]octan-2-yl)-3,5-difluoroaniline;
3,5-difluoro-4-(4-isopropylpiperidin-1-yl)aniline;
3,5-difluoro-4-(4-(trifluoromethyl)piperidin-1-yl)aniline;
4-(4-tert-butylpiperidin-1-yl)-3,5-difluoroaniline;
3,5-difluoro-4-(6-azaspiro[2.5]octan-6-yl)aniline;
4-(3,3-dimethylazetidin-1-yl)-3,5-difluoroaniline;
4-(4,4-difluoropiperidin-1-yl)-3,5-difluoroaniline;
3,5-difluoro-4-(4-fluoropiperidin-1-yl)aniline;
3,5-difluoro-4-(piperidin-1-yl)aniline;
2,3,5,6-tetrafluoro-4-(piperidin-1-yl)aniline;
3-methyl-4-(piperidin-1-yl)aniline;
3,5-difluoro-4-((3aR,7aS)-1H-isoindol-2(3H,3aH,4H,5H,6H,7H,7aH)-yl)aniline;
N$^1$-tert-butyl-2-fluorobenzene-1,4-diamine;
3,5-difluoro-4-(4-methylpiperidin-1-yl)aniline;
3,5-dichloro-4-(piperidin-1-yl)aniline;
2,5-difluoro-4-(piperidin-1-yl)aniline;
4-((2R,6S)-2,6-dimethylpiperidin-1-yl)-3,5-difluoroaniline;
2,3,5-trifluoro-4-(piperidin-1-yl)aniline;
4-((1R,5S)-3-azabicyclo[3.2.0]heptan-3-yl)-3,5-difluoroaniline;
3-fluoro-4-(piperidin-1-yl)aniline;
3,5-difluoro-4-(3-azaspiro[5.5]undecan-3-yl)aniline;
3,5-difluoro-4-(isoindolin-2-yl)aniline;
3,5-difluoro-4-(1,4-dioxa-8-azaspiro[4.5]decan-8-yl)aniline;
4-(4-phenyl-5,6-dihydropyridin-1(2H)-yl)aniline;
3-fluoro-4-(4-phenylpiperidin-1-yl)aniline;
4-(4,4-diphenylpiperidin-1-yl)-3,5-difluoroaniline;
4-(4-phenylpiperidin-1-yl)aniline;
1-(1-(4-amino-2,6-difluorophenyl)-4-phenylpiperidin-4-yl)ethanone;
3,5-difluoro-4-(4-(3-phenylpropyl)piperidin-1-yl)aniline;
3,5-difluoro-4-(8-azaspiro[4.5]decan-8-yl)aniline;
3,5-difluoro-4-(3-phenylpiperidin-1-yl)aniline;
3,5-difluoro-4-(3-phenylpyrrolidin-1-yl)aniline;
3,5-difluoro-4-(4-(4-(trifluoromethyl)phenyl)piperazin-1-yl)aniline;
3,5-difluoro-4-(4-phenylpiperazin-1-yl)aniline;
4-(4-(2,6-difluorophenyl)piperazin-1-yl)-3,5-difluoroaniline;
3,5-difluoro-4-(4-(pyrimidin-2-yl)piperazin-1-yl)aniline;
3,5-difluoro-4-(2-phenylmorpholino)aniline;
(S)-3,5-difluoro-4-(2-phenylmorpholino)aniline
3,5-difluoro-4-(2-phenylpiperidin-1-yl)aniline;
4-((2S,6R)-2,6-dimethylmorpholino)-3,5-difluoroaniline;
4-(4-cyclohexylpiperidin-1-yl)-3,5-difluoroaniline;
4-(4-benzylpiperidin-1-yl)-3,5-difluoroaniline;
3,5-difluoro-4-(4-(4-methoxyphenyl)piperidin-1-yl)aniline;
3,5-difluoro-4-(4-(4-fluorophenyl)piperidin-1-yl)aniline;
4-(4-(3,4-difluorophenyl)piperidin-1-yl)-3,5-difluoroaniline;
4-(4-(3,5-difluorophenyl)piperidin-1-yl)-3,5-difluoroaniline;
3,5-difluoro-4-(4-fluoro-4-phenylpiperidin-1-yl)aniline;
3,5-difluoro-4-(4-(fluorodiphenylmethyl)piperidin-1-yl)aniline;
4-(4-fluoro-4-phenylpiperidin-1-yl)aniline;
3,5-difluoro-4-(4-(pyridin-2-yl)piperidin-1-yl)aniline;
3,5-difluoro-4-(4-(naphthalen-2-yl)piperidin-1-yl)aniline;
3,5-difluoro-4-(4-(naphthalen-1-yl)piperidin-1-yl)aniline; and
3,5-difluoro-4-(4-(4-(trimethylsilyl)phenyl)piperidin-1-yl)aniline.

General Procedure 1.1. 4-Alkoxy-substituted aniline

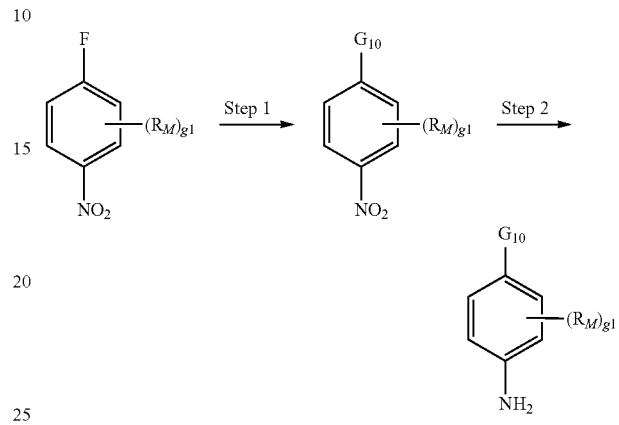

Intermediate anilines having an alkoxy substituent para to the aniline may be prepared through a two-step procedure wherein G$_{10}$ is —OR$_S$ (e.g., —O-t-butyl, —O-isopropyl, —O—CH$_2$-(3-ethyloxetan-3-yl), —O—CH$_2$-(1,3-dioxolan-4-yl), —O-cyclopentyl, —O-cyclohexyl, —O-(1,3-dioxan-5-yl)). In Step 1, fluoronitrobenzenes can be reacted with an appropriate alcohol and base (e.g., Cs$_2$CO$_3$, potassium tert-butoxide) in DMSO or like solvent with heating to between 50-100° C. Step 2 can be accomplished by standard nitro reduction conditions such as catalytic hydrogenation using palladium on carbon or Raney nickel as described elsewhere herein. Alternatively, the reduction can be effected with iron/ammonium chloride in THF/methanol/water as solvent.

Illustration of General Procedure 1.1: General Procedure 1.1A

Step 1

3-ethyl-3-((4-nitrophenoxy)methyl)oxetane

To a solution of 4-fluoronitrobenzene (3.76 mL, 35.4 mmol) in DMSO (35 mL) at room temperature was added cesium carbonate (7.09 mL, 89.0 mmol) followed by 3-ethyl-3-oxetanemethanol (4.48 mL, 42.5 mmol). The mixture was heated to 70° C. for 2 hours. After cooling water was added and the resulting precipitate was filtered, washed with water, and dried in a vacuum oven to provide the title compound (8.28 g, 98% yield).

Step 2

4-((3-ethyloxetan-3-yl)methoxy)aniline

To a solution of 3-ethyl-3-((4-nitrophenoxy)methyl)oxetane (8.28 g, 34.9 mmol) in a 3:3:1 mixture of THF:EtOH:water (140 mL) at room temperature was added ammonium chloride (2.80 g, 52.3 mmol) followed by iron powder (9.74 g, 174 mmol). The mixture was heated to 90° C. for 1 hour, then it was filtered hot through diatomaceous earth with a THF wash to complete the transfer. The filtrate was concentrated under reduced pressure, and the residue was taken up in ethyl acetate then washed with brine, dried (Na$_2$SO$_4$), and concentrated to provide the title compound (7.12 g, 98% yield) without further purification.

The following amines can be made using methods shown in the foregoing General Procedure 1:
4-((3-ethyloxetan-3-yl)methoxy)-3,5-difluoroaniline;
4-((1,3-dioxolan-4-yl)methoxy)aniline;
4-(1,3-dioxan-5-yloxy)aniline.

General Procedure 1.2. Aniline Formation through Suzuki-Type Reaction

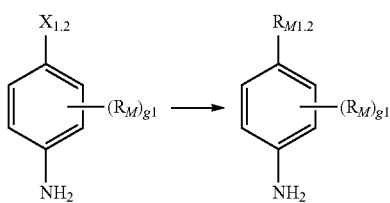

Certain intermediate anilines can be made from a bromide, iodide, or triflate (i.e., $X_{1,2}$=Br, I, or OTf) through a Suzuki, Stille, or other similar transition metal-mediated carbon-carbon bond forming reaction to form products where $R_{M1\ldots2}$ is cycloalkyl, aryl, heteroaryl, or cycloalkenyl. Above is an illustration of the process conducted on an aniline, however the process can be done also using other functionality which can be converted to an aniline (e.g., a nitro group).

Illustration of General Procedure 1.2. General Procedure 1.2A.

4-(cyclohexen-1-yl)-3-fluoroaniline

In a pressure tube, a solution of 3-fluoro-4-iodoaniline (2.29 g, 9.66 mmol) and potassium carbonate (1.74 g, 12.58 mmol) in 4:1 dimethoxyethane-water (33 mL) was degassed by nitrogen sparge for 40 minutes, followed by addition of 1-cyclohexenyl boronic acid pinacol ester (2.7 mL, 2.61 g, 12.56 mmol). Then 1,1'-bis(diphenylphosphino)ferrocene palladium (II) chloride dichloromethane complex (237 mg, 0.29 mmol) was added followed by degassing for another 5 minutes. The pressure tube was sealed and warmed at 100° C. for 18 hours. The mixture was cooled and diluted with ethyl acetate, followed by extraction with water and saturated sodium chloride solution. The solution was dried (Na$_2$SO$_4$) and stirred with 3-(mercaptopropyl) silica gel for 1 hour. Concentration in vacuo afforded a brown oil, which was chromatographed over a 340 g silica gel cartridge, eluting with 10-100% ethyl acetate in hexanes. These procedures afforded the title compound (1.16 g, 63%) as a light brown oil. $^1$H NMR (400 MHz, CDCl$_3$) δ ppm 7.00 (m, 1H), 6.37 (m, 2H), 5.84 (s, 1H), 3.71 (br s, 2H), 2.32 (m, 2H), 2.17 (m, 2H), 1.73 (m, 2H), 1.65 (m, 2H); MS (+DCI) m/z (rel abundance) 192 (100, M+H).

Illustration of General Procedure 1.2. General Procedure 1.2B.

4-cyclopropyl-3,5-difluoroaniline

To a pressure tube was added 4-bromo-3,5-difluoroaniline (1.0 g, 4.8 mmol), cesium carbonate (4.7 g, 14.4 mmol), toluene (10 mL) and water (1 mL). The solution was degassed with N$_2$ gas for 30 minutes, followed by the addition of cyclopropyltrifluoro-borate, potassium salt (0.8 g, 5.3 mmol), di(1-adamantyl)-n-butylphosphine hydroiodide (0.07 g, 0.14 mmol) and palladium(II) acetate (0.02 g, 0.096 mmol). Degassing was continued for 5 minutes, the tube was sealed and heated at 100° C. for 18 hours. The cooled solution was diluted with EtOAc, washed with H$_2$O and brine, dried (Na$_2$SO$_4$), and filtered. The filtrate was treated with 3-mercaptopropyl silica gel for 1 hour. The mixture was filtered and concentrated to give crude product which was purified by flash chromatography (0-30% EtOAc/hexane) to give the title compound (0.67 g, 4.0 mmol, 82%).

Illustration of General Procedure 1.2. General Procedure 1.2C.

4-cyclopropyl-2-fluoro-1-nitrobenzene

A solution of 4-bromo-2-fluoronitrobenzene (0.5 g, 2.27 mmol), cyclopropylboronic acid (0.293 g, 3.41 mmol), tribasic potassium phosphate (0.965 g, 4.55 mmol), tricyclohexylphosphonium tetrafluoroborate (0.021 g, 0.057 mmol) and palladium (II) acetate (6.12 mg 0.027 mmol) in 11 mL of a toluene-water mixture 10:1 (v/v) was nitrogen purged-vacuum degassed three times. The reaction mixture was then heated in an oil bath at 85° C. for four hours. The reaction mixture was partitioned with ethyl acetate and the organic phase water washed then dried (Na$_2$SO$_4$) and concentrated. The reaction mixture was partitioned between ethyl acetate and water. The organic phase was washed with water, dried (Na$_2$SO$_4$) and concentrated. The crude product was purified by chromatography on silica gel (ethyl acetate-hexane) to provide the title compound (0.382 g, 88%) as a yellow oil.

General Procedure 1.3

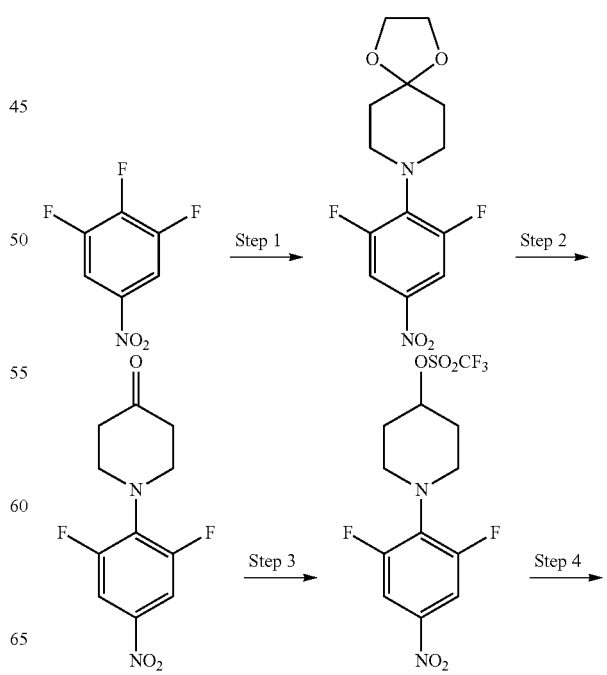

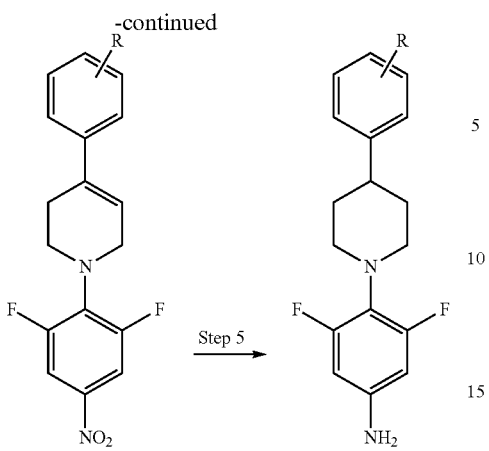

Certain intermediate anilines can be made using the general sequence outlined above and illustrated below. The sequence consists of reaction of a fluoronitrobenzene with a cyclic amine moiety (Step 1); conversion to a vinylic coupling partner (Steps 2 and 3); coupling of the vinylic coupling partner with another suitable partner (Step 4); and reduction of the nitro group and olefin (Step 5). Alternatively, this route may be adapted to prepare anilines wherein the olefin remains intact through selective reduction of the nitro group. Carbon-carbon bond forming reactions that may be suitable for Step 4 include, for example, the Suzuki reaction, the Stille reaction, or the Negishi reaction.

Illustration of General Procedure 1.3: General Procedure 1.3A

Step 1

8-(2,6-difluoro-4-nitrophenyl)-1,4-dioxa-8-azaspiro[4.5]decane

A mixture of 1,2,3-trifluoro-5-nitrobenzene (4.0 mL, 34.3 mmol), 1,4-dioxa-8-azaspiro[4.5]decane (6.59 mL, 51.4 mmol) and potassium carbonate (5.68 g, 41.1 mmol) in DMSO (35 mL) was heated at 100° C. for 3 hours and then cooled to room temperature. The mixture was partitioned between water and EtOAc, and the organic layer was dried over $Na_2SO_4$, filtered and concentrated in vacuo. The crude product was purified by column chromatography on silica gel using a solvent gradient of 0-20% EtOAc in hexanes to give a yellow oil.

Step 2

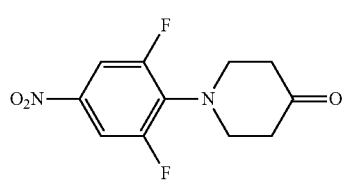 [SMILES: O=C1CCN(c2c(F)cc([N+](=O)[O-])cc2F)CC1]

1-(2,6-difluoro-4-nitrophenyl)piperidin-4-one

The crude 8-(2,6-difluoro-4-nitrophenyl)-1,4-dioxa-8-azaspiro[4.5]decane from the preceding procedure was dissolved in 4:1 acetone:water (100 mL). Concentrated HCl (5 mL) was added, and the resulting mixture was stirred at 50° C. for 8 hours and then cooled to room temperature. The mixture was concentrated in vacuo to approximately 20 mL, which was carefully added to concentrated aq. $NaHCO_3$ (100 mL) and extracted with EtOAc (2×100 mL). The combined organic extracts were dried over $Na_2SO_4$, filtered and concentrated in vacuo. The crude product was triturated with $Et_2O$ and hexanes to give a bright-yellow solid that was collected and dried to provide the title compound (7.13 g, 81%).

Step 3

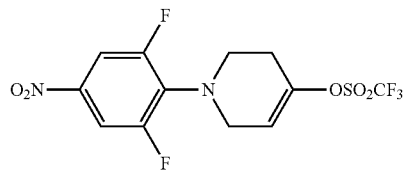

1-(2,6-difluoro-4-nitrophenyl)-1,2,3,6-tetrahydropyridin-4-yl trifluoromethanesulfonate To a solution of 1-(2,6-difluoro-4-nitrophenyl)piperidin-4-one (5.0 g, 19.52 mmol) in anhydrous THF (50 mL) at −78° C. under a dry $N_2$ atmosphere was added a 1 M THF solution of lithium bis(triethylsilyl)amide (29.3 ml, 29.3 mmol) in THF dropwise over 10 minutes. The resulting deep red solution was stirred at −78° C. for 5 minutes and 1,1,1-trifluoro-N-phenyl-N-(trifluoromethylsulfonyl)methanesulfonamide (7.67 g, 21.47 mmol) was added. The resulting mixture was stirred at −78° C. for 1 hour, and then the mixture was allowed to warm to room temperature. The mixture was diluted with EtOAc (100 mL) and washed with 1 N aq. NaOH (50 mL) and water (50 mL), and dried over $Na_2SO_4$. The drying agent was filtered off, and the solvent was removed in vacuo to give a crude product that was purified by column chromatography on silica gel using a solvent gradient of 0-40% EtOAc in hexanes. The title compound was obtained as a yellow oil that crystallized in vacuo (6.12 g, 81%).

Step 4

Suzuki Reaction

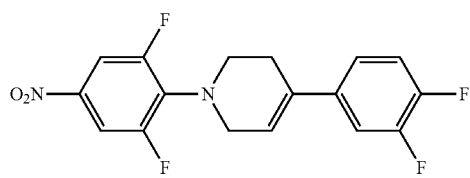 [SMILES: O=[N+]([O-])c1cc(F)c(N2CC=C(c3ccc(F)c(F)c3)CC2)c(F)c1]

1-(2,6-difluoro-4-nitrophenyl)-4-(3,4-difluorophenyl)-1,2,3,6-tetrahydropyridine A mixture of 1-(2,6-difluoro-4-nitrophenyl)-1,2,3,6-tetrahydropyridin-4-yl trifluoromethanesulfonate (1.18 g, 3.04 mmol), 2-(3,4-difluorophenyl)-4,4,5,5-tetramethyl-1,3,2-dioxaborolane (1.02 g, 4.25 mmol), lithium chloride (0.387 g, 9.12 mmol) and a 2.0 M aq. solution of sodium carbonate (4.56 mL, 9.12 mmol) in anhydrous DME (15 mL) was vigorously stirred while bubbling with N₂ gas for 20 minutes. Tetrakis(triphenylphosphine)palladium(0) (0.176 g, 0.152 mmol) was added, and the resulting mixture was degassed for 5 minutes more. The reaction flask was equipped with a condenser and placed in 100° C. oil bath. The dark mixture was stirred at 100° C. under a dry N₂ atmosphere for 16 hours, and was then cooled to room temperature and partitioned between water (50 mL) and EtOAc (2×50 mL). The combined organic layers were dried over Na₂SO₄, filtered and concentrated in vacuo, and the crude product was purified by column chromatography on silica gel using a solvent gradient of 0-40% EtOAc in hexanes to provide a yellow oil that solidified on standing. The solid was triturated with Et₂O and hexanes, filtered and dried to provide the title compound (0.67 g, 63%).

Step 5

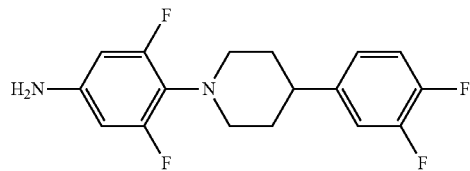 [SMILES: Nc1cc(F)c(N2CCC(c3ccc(F)c(F)c3)CC2)c(F)c1]

(4-(4-(3,4-difluorophenyl)piperidin-1-yl)-3,5-difluoroaniline

To a solution of 1-(2,6-difluoro-4-nitrophenyl)-4-(3,4-difluorophenyl)-1,2,3,6-tetrahydropyridine (0.67 g, 1.90 mmol) in THF (20 mL) was added 10% Pd on carbon (50 mg). The reaction flask was flushed with N₂ gas, and the resulting mixture was vigorously stirred under 1 atm H₂ gas for 24 hours. The mixture was filtered through diatomaceous earth and concentrated in vacuo to give the title compound as a solid (0.62 g, 100%).

The following amines can be made using methods shown in the foregoing General Procedure 1.3:

3,5-difluoro-4-(4-(4-fluorophenyl)piperidin-1-yl)aniline; and 3,5-difluoro-4-(4-(3-(trimethylsilyl)phenyl)piperidin-1-yl)aniline.

General Procedure 2. Pyrrolidine Formation from Amine and Dimesylate (5)

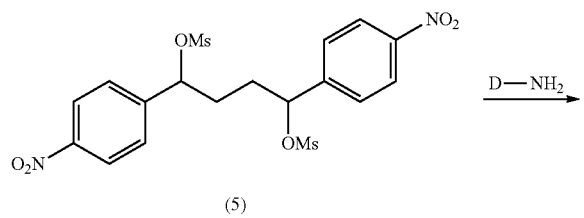

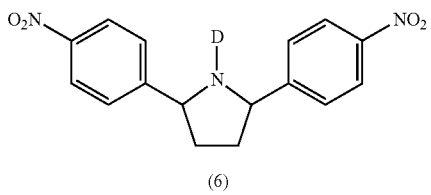

(6)

A dimesylate (5) (1 equivalent), as a single stereoisomer or mixture of isomers, may be reacted with between 1 to 20 equivalents of an amine, D-NH₂, either neat, or in solvents such as tetrahydrofuran or 2-methyltetrahydrofuran with or without a co-solvent such as DMF, at about room temperature to about 100° C., to give the pyrrolidines such as Formula (6). Where fewer equivalents of amine, D-NH₂, are employed (i.e., 1-2 equivalents), a base such as diisopropylethylamine can be added to promote the reaction. For example, the reaction of a dimesylate (1 equivalent) with excess of an aniline, D-NH₂, (about 5-10 equivalents) can be conducted by heating from 50 to 65° C. in 2-methyltetrahydrofuran or DMF until completion of the reaction. Or the dimesylate (1 equivalent) can be reacted neat with excess of an aniline, D-NH₂, (about 15-20 equivalents) at room temperature or with heating to around 65° C. The reaction can be partitioned between an organic solvent (e.g., ethyl acetate) and dilute aqueous HCl, followed by separation of the organic layer, optional washing of the organic with water, drying the organic layer with a drying agent (e.g., MgSO₄, Na₂SO₄), filtration and evaporation of solvent. The product can be purified by column chromatography over silica gel, eluting with standard solvents such as mixtures of ethyl acetate and hexane; or alternatively the product can be purified by trituration or recrystallization.

Illustration of General Procedure 2: General Procedure 2A (2S,5S)-1-(4-tert-butylphenyl)-2,5-bis(4-nitrophenyl)pyrrolidine To the crude product solution of Intermediate 6C (7.35 g, 13.39 mmol) was added 4-tert-butylaniline (13.4 g, 90 mmol) at 23° C. over 1 minute. The reaction was heated to 65° C. for 2 hours. After completion, the reaction mixture was cooled to 23° C. and diluted with 2-methyltetrahydrofuran (100 mL) and 1 M HCl (150 mL). After partitioning the phases, the organic phase was treated with 1 M HCl (140 mL), 2-methyltetrahydrofuran (50 mL), and 25 wt % aq. NaCl (100 mL), and the phases were partitioned. The organic phase was washed with 25 wt % aq. NaCl (50 mL), dried over MgSO₄, filtered, and concentrated in vacuo to approximately 20 mL. Heptane (30 mL) and additional 2-methyltetrahydrofuran were added in order to induce crystallization. The slurry was concentrated further, and additional heptane (40 mL) was slowly added and the slurry was filtered, washing with 2-methyltetrahydrofuran:heptane (1:4, 20 mL). The solids were suspended in CH₃OH (46 mL) for 3 hours, filtered, and the wet solid was washed with additional CH₃OH (18 mL). The solid was dried at 45° C. in a vacuum oven for 16 hours to provide the title compound (3.08 g).

General Procedure 3. Pyrrolidine Formation from amine and bisbromophenyldimesylate

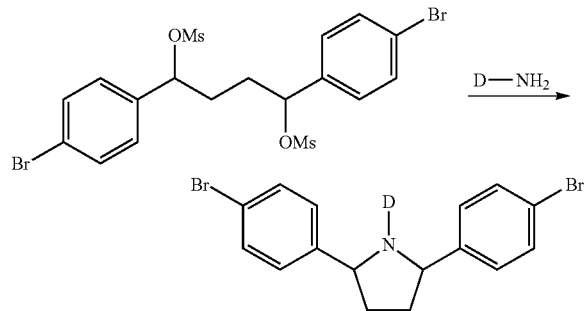

General Procedure 3 can be conducted using conditions substantially similar to the conditions of General Procedure 2.

Illustration of General Procedure 3: General Procedure 3A

(2S,5S)-2,5-bis(4-bromophenyl)-1-(4-tert-butylphenyl)pyrrolidine

Intermediate 7C was dissolved in anhydrous DMF (5 mL), and 4-tert-butylaniline (2.39 mL, 15 mmol) was added. The resulting mixture was stirred at 40° C. for 4 hours, and then it was partitioned between 1 N aq. HCl (30 mL) and EtOAc (30 mL). The organic layer was washed with $H_2O$ and dried over $Na_2SO_4$. The drying agent was filtered off, the solvent was removed in vacuo, and the crude product was purified by column chromatography on silica gel using a solvent gradient of 0-20% EtOAc in hexanes. The title compound was obtained as a colorless solid (0.71 g, 92%). $^1$H NMR indicated this material was a 87:13 mixture of trans:cis pyrrolidine isomers.

General Procedure 4. Pyrrolidine Formation from amine and dimesylate (52)

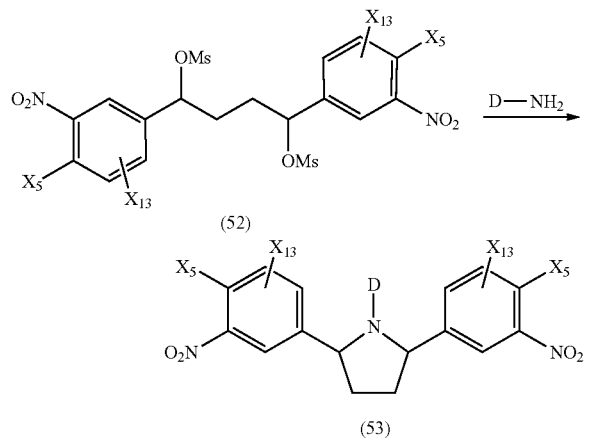

$X_5 = Cl$

General Procedure 4 can be conducted using conditions substantially similar to the conditions of General Procedure 2.

For example, a dimesylate (52) (1 equivalent), as a single stereoisomer or mixture of isomers, may be reacted with between 1 to 20 equivalents of an amine $D-NH_2$ either neat, or in solvents or mixtures of solvents including ethanol, acetonitrile, methylene chloride, tetrahydrofuran, 2-methyltetrahydrofuran, DMF, or DMA, at about room temperature to about 100° C., to give the pyrrolidines such as Formula (53). Alternatively, a dimesylate (52) (1 equivalent) can be reacted with an amine $D-NH_2$ (1-4 equivalents) in the presence of a base like diisopropylethylamine (3-10 equivalents) in solvents or mixtures of solvents including methylene chloride, tetrahydrofuran, 2-methyltetrahydrofuran, DMF, or DMA at temperatures from around room temperature to about 70° C. Where fewer equivalents of amine $D-NH_2$ are employed (i.e., 1-2 equivalents), greater amounts of a base (about 8-10 equivalents) such as diisopropylethylamine may be added to promote the reaction. For less reactive amines (e.g., 2,5-difluoro-4-(trifluoromethyl)aniline, 2-fluoropyridin-4-amine), a reaction time of several days may be required. The reaction can be partitioned between an organic solvent (e.g., ethyl acetate) and water or dilute aqueous HCl, followed by separation of the organic layer, optional washing of the organic with water and/or brine, drying the organic layer with a drying agent (e.g., $MgSO_4$, $Na_2SO_4$), filtration and evaporation of solvent. The product (53) can be purified by column chromatography over silica gel, eluting with standard solvents such as mixtures of ethyl acetate and hexane or methylene chloride in hexane. The methylene chloride/hexane system can be used to remove residual amine in cases where the reaction is quenched in water instead of aqueous HCl. In such cases a second chromatography using an ethyl acetate/hexane system may be necessary to separate cis from trans pyrrolidine products. Or alternatively, the product can be purified by trituration or recrystallization.

Illustration of General Procedure 4: General Procedure 4A

(2R,5R)-2,5-bis(4-chloro-3-nitrophenyl)-1-(4-cyclohexylphenyl)pyrrolidine

To Intermediate 5D (4.99 mmol) in dimethylformamide (8 mL) was added 4-cyclohexylaniline (5.24 g, 29.9 mmol), and the solution was heated at 65° C. for 2 hours. The reaction mixture was then poured into 1 M HCl and extracted into dichloromethane. The organic phase was concentrated and purified with a CombiFlash® 80 g silica column eluting with 0-20% ethyl acetate in hexanes to give 1.38 g (51%) of the title compound.

Illustration of General Procedure 4: General Procedure 4B

1-(4-((2R,5R)-2,5-bis(4-chloro-3-nitrophenyl)pyrrolidin-1-yl)-2,6-difluorophenyl)-4-phenylpiperidine A 250 mL flask was charged with 3,5-difluoro-4-(4-phenylpiperidin-1-yl)aniline (3.1 g, 10.76 mmol), Intermediate 5D (5.0 g, 8.97 mmol), DMF (15 mL) and diisopropylethylamine (15.7 mL, 90 mmol). The resulting slurry was placed in a 60° C. oil bath and heated under $N_2$ for 18 hours. The amber solution was cooled, diluted with 300 mL of ethyl acetate, washed 2×100 mL water, 2×100 mL with 1 N HCl, brine, dried ($Na_2SO_4$), filtered and concentrated. The crude material was flash chromatographed on a 330 g silica cartridge eluting with 50-80% dichloromethane in hexane to remove unreacted aniline. The column fractions containing the product were combined and concentrated to give an orange solid that was dissolved in 20 mL of hot ethyl acetate, treated with 15 mL hexane, and allowed to stir at ambient temperature overnight producing a precipitate (cis pyrrolidine) that was removed by filtration. The filtrate was concentrated and chromatographed again on a 330 g silica cartridge eluting with 40-70% methylene chloride in hexane to give 1-(4-((2R,5R)-2,5-bis(4-chloro-3-nitrophenyl)pyrrolidin-1-yl)-2,6-difluorophenyl)-4-phenylpiperidine as an orange foam (2.26 g, 36%). MS (ESI+) m/z 653 (M+H)$^+$.

Illustration of General Procedure 4: General Procedure 4C 1-(4-((2R,5R)-2,5-bis(4-chloro-3-nitrophenyl)pyrrolidin-1-yl)-2-fluorophenyl)-4-phenylpiperidine Intermediate 5D (6.0 g, 10.76 mmol), 3-fluoro-4-(4-phenylpiperidin-1-yl)aniline (4.37 g, 16.15 mmol), and diisopropylethylamine (15.04 mL, 86 mmol) were combined in N,N-dimethylacetamide (15 mL) and heated at 60° C. for 3 hours. The solution was diluted with water, extracted into dichloromethane and washed with brine. The organics were concentrated and purified by chromatography, eluting with 30-100% dichloromethane in hexanes to give 5.05 g (74%) of a yellow solid.

Illustration of General Procedure 4: General Procedure 4D (2R,5R)-2,5-bis(4-chloro-3-nitrophenyl)-1-(4-ethoxyphenyl)pyrrolidine Intermediate 5D (2.5805 g, 4.63 mmol) and 4-ethoxyaniline (2.4 mL, 18.60 mmol) were combined in DMF (30 mL) and stirred at room temperature overnight. The reaction was diluted with EtOAc/ether and washed with water (2×), brine (1×) and concentrated. The residue was purified by silica gel chromatography (hexane/EtOAc) to provide 1.8 g of the title compound (77%).

Illustration of General Procedure 4: General Procedure 4E 1-(4-((2R,5R)-2,5-bis(4-chloro-2-fluoro-5-nitrophenyl)pyrrolidin-1-yl)-2,6-difluorophenyl)piperidine To a solution of (1S,4S)-1,4-bis(4-chloro-2-fluoro-5-nitrophenyl)butane-1,4-diyl dimethanesulfonate (500 mg, 0.843 mmol) in CH$_3$CN (4.5 ml) was added 3,5-difluoro-4-(piperidin-1-yl)aniline (358 mg, 1.685 mmol) and Hunig's base (0.736 mL, 4.21 mmol). The suspension was heated at 75° C. for 24 hours. Solvent was removed by rotary evaporation and the residue was dissolved in EtOAc, washed with 1 N HCl, H$_2$O, brine, dried (MgSO$_4$), filtered and concentrated. The crude product was chromatographed on an ISCO 24 g silica gel cartridge eluting with 20-70% CH$_2$Cl$_2$/hexane to provide the title compound with some of the corresponding cis-pyrrolidine isomer.

The following substituted pyrrolidines can be made using the foregoing general methods:
1-(4-((2R,5R)-2,5-bis(4-chloro-3-nitrophenyl)pyrrolidin-1-yl)-2,6-difluorophenyl)-4,4-dimethylpiperidine;
2-(4-((2R,5R)-2,5-bis(4-chloro-3-nitrophenyl)pyrrolidin-1-yl)-2,6-difluorophenyl)-2-azabicyclo[2.2.2]octane;
1-(4-((2R,5R)-2,5-bis(4-chloro-3-nitrophenyl)pyrrolidin-1-yl)-2,6-difluorophenyl)-4-isopropylpiperidine;
1-(4-((2R,5R)-2,5-bis(4-chloro-3-nitrophenyl)pyrrolidin-1-yl)-2,6-difluorophenyl)-4-(trifluoromethyl)piperidine;
1-(4-((2R,5R)-2,5-bis(4-chloro-3-nitrophenyl)pyrrolidin-1-yl)-2,6-difluorophenyl)-4-tert-butylpiperidine;
6-(4-((2R,5R)-2,5-bis(4-chloro-3-nitrophenyl)pyrrolidin-1-yl)-2,6-difluorophenyl)-6-azaspiro[2.5]octane;
1-(4-((2R,5R)-2,5-bis(4-chloro-3-nitrophenyl)pyrrolidin-1-yl)-2,6-difluorophenyl)-4,4-dimethylpiperidine;
(2R,5R)-2,5-bis(4-chloro-3-nitrophenyl)-1-(4-(3,3-dimethylazetidin-1-yl)-3,5-difluorophenyl)pyrrolidine;
(2R,5R)-2,5-bis(4-chloro-3-nitrophenyl)-1-(4-phenoxyphenyl)pyrrolidine;
1-(4-((2R,5R)-2,5-bis(4-chloro-3-nitrophenyl)pyrrolidin-1-yl)phenyl)pyridin-2(1H)-one;
(2R,5R)-2,5-bis(4-chloro-3-nitrophenyl)-1-(2,5-difluoro-4-(trifluoromethyl)phenyl)pyrrolidine;
2-(4-((2R,5R)-2,5-bis(4-chloro-3-nitrophenyl)pyrrolidin-1-yl)phenyl)oxazole;
4-((2R,5R)-2,5-bis(4-chloro-3-nitrophenyl)pyrrolidin-1-yl)-2-fluoropyridine;
(2R,5R)-1-(4-chloro-3-fluorophenyl)-2,5-bis(4-chloro-3-nitrophenyl)pyrrolidine;
1-(4-((2R,5R)-2,5-bis(4-chloro-3-nitrophenyl)pyrrolidin-1-yl)-2,6-difluorophenyl)-4,4-difluoropiperidine;
1-(4-((2R,5R)-2,5-bis(4-chloro-3-nitrophenyl)pyrrolidin-1-yl)-2,6-difluorophenyl)-4-fluoropiperidine;
1-(4-((2R,5R)-2,5-bis(4-chloro-3-nitrophenyl)pyrrolidin-1-yl)-2,6-difluorophenyl)piperidine;
(2R,5R)-2,5-bis(4-chloro-3-nitrophenyl)-1-(4-fluorophenyl)pyrrolidine;
(2R,5R)-1-(4-tert-butylphenyl)-2,5-bis(4-chloro-3-nitrophenyl)pyrrolidine;
(2R,5R)-2,5-bis(4-chloro-3-nitrophenyl)-1-(4-cyclopropyl-3,5-difluorophenyl)pyrrolidine;
(2R,5R)-2,5-bis(4-chloro-3-nitrophenyl)-1-(4-cyclohexyl-3-fluorophenyl)pyrrolidine;
(2R,5R)-2,5-bis(4-chloro-3-nitrophenyl)-1-(3,4-difluorophenyl)pyrrolidine;
(2R,5R)-2,5-bis(4-chloro-3-nitrophenyl)-1-(4-(2,2-difluoroethoxy)phenyl)pyrrolidine;
1-(4-((2R,5R)-2,5-bis(4-chloro-3-nitrophenyl)pyrrolidin-1-yl)-2,6-difluorophenyl)-3,5-dimethylpiperidine;
(2R,5R)-2,5-bis(4-chloro-3-nitrophenyl)-1-[4-(pentafluoro-λ$^6$-sulfanyl)phenyl]pyrrolidine (ACD Name v12);
2-(4-((2R,5R)-2,5-bis(4-chloro-3-nitrophenyl)pyrrolidin-1-yl)phenyl)pyridine;
(2R,5R)-2,5-bis(4-chloro-3-nitrophenyl)-1-(3-chloro-4-(trifluoromethoxy)phenyl)pyrrolidine;
(2R,5R)-2,5-bis(4-chloro-3-nitrophenyl)-1-(4-(2-methoxyethoxy)-3-methylphenyl)pyrrolidine;
(2R,5R)-2,5-bis(4-chloro-3-nitrophenyl)-1-(4-chlorophenyl)pyrrolidine;
(2R,5R)-2,5-bis(4-chloro-3-nitrophenyl)-1-(4-((3-ethyloxetan-3-yl)methoxy)phenyl)pyrrolidine;
(2R,5R)-1-(biphenyl-4-yl)-2,5-bis(4-chloro-3-nitrophenyl)pyrrolidine;
(2R,5R)-1-(4-(1,3-dioxan-5-yloxy)phenyl)-2,5-bis(4-chloro-3-nitrophenyl)pyrrolidine;
(2R,5R)-1-(4-((1,3-dioxolan-4-yl)methoxy)phenyl)-2,5-bis(4-chloro-3-nitrophenyl)pyrrolidine;
(2R,5R)-2,5-bis(4-chloro-3-nitrophenyl)-1-(4-((3-ethyloxetan-3-yl)methoxy)-3,5-difluorophenyl)pyrrolidine;
1-(4-((2R,5R)-2,5-bis(4-chloro-3-nitrophenyl)pyrrolidin-1-yl)-2,3,5,6-tetrafluorophenyl)piperidine;
1-(4-((2R,5R)-2,5-bis(4-chloro-3-nitrophenyl)pyrrolidin-1-yl)-2-methylphenyl)piperidine;

(3aR,7aS)-2-(4-((2R,5R)-2,5-bis(4-chloro-3-nitrophenyl) pyrrolidin-1-yl)-2,6-difluorophenyl)octahydro-1H-isoindole;

4-((2R,5R)-2,5-bis(4-chloro-3-nitrophenyl)pyrrolidin-1-yl)-N-tert-butyl-2-fluoroaniline;

1-(4-((2R,5R)-2,5-bis(4-chloro-3-nitrophenyl)pyrrolidin-1-yl)-2,6-difluorophenyl)-4-methylpiperidine;

(2R,5R)-2,5-bis(4-chloro-3-nitrophenyl)-1-(4-(cyclopentyloxy)-3-fluorophenyl)pyrrolidine;

(2R,5R)-2,5-bis(4-chloro-3-nitrophenyl)-1-(3-fluoro-4-(methylthio)phenyl)pyrrolidine 1-(4-((2R,5R)-2,5-bis(4-chloro-3-nitrophenyl)pyrrolidin-1-yl)-2,6-dichlorophenyl)piperidine;

1-(4-((2R,5R)-2,5-bis(4-chloro-3-nitrophenyl)pyrrolidin-1-yl)-2,5-difluorophenyl)piperidine;

(2R,6S)-1-(4-((2R,5R)-2,5-bis(4-chloro-3-nitrophenyl)pyrrolidin-1-yl)-2,6-difluorophenyl)-2,6-dimethylpiperidine;

1-(4-((2R,5R)-2,5-bis(4-chloro-3-nitrophenyl)pyrrolidin-1-yl)-2,3,6-trifluorophenyl)piperidine;

(2R,5R)-2,5-bis(4-chloro-3-nitrophenyl)-1-(4-cyclopropylphenyl)pyrrolidine;

(1R,5S)-3-(4-((2R,5R)-2,5-bis(4-chloro-3-nitrophenyl)pyrrolidin-1-yl)-2,6-difluorophenyl)-3-azabicyclo[3.2.0]heptane;

(2R,5R)-2,5-bis(4-chloro-3-nitrophenyl)-1-(4-cyclopropyl-2-fluorophenyl)pyrrolidine;

1-(4-((2R,5R)-2,5-bis(4-chloro-3-nitrophenyl)pyrrolidin-1-yl)-2-fluorophenyl)piperidine;

1-(4-((2R,5R)-2,5-bis(4-chloro-3-nitrophenyl)pyrrolidin-1-yl)phenyl)-4-phenylpiperidine;

3-(4-((2R,5R)-2,5-bis(4-chloro-3-nitrophenyl)pyrrolidin-1-yl)-2,6-difluorophenyl)-3-azaspiro[5.5]undecane;

2-(4-((2R,5R)-2,5-bis(4-chloro-3-nitrophenyl)pyrrolidin-1-yl)-2,6-difluorophenyl)isoindoline;

8-(4-((2R,5R)-2,5-bis(4-chloro-3-nitrophenyl)pyrrolidin-1-yl)-2,6-difluorophenyl)-1,4-dioxa-8-azaspiro[4.5]decane;

1-(4-((2R,5R)-2,5-bis(4-chloro-3-nitrophenyl)pyrrolidin-1-yl)-2,6-difluorophenyl)-4-phenyl-1,2,3,6-tetrahydropyridine;

1-(4-((2R,5R)-2,5-bis(4-chloro-3-nitrophenyl)pyrrolidin-1-yl)-2,6-difluorophenyl)-4,4-diphenylpiperidine;

1-(1-(4-((2R,5R)-2,5-bis(4-chloro-3-nitrophenyl)pyrrolidin-1-yl)-2,6-difluorophenyl)-4-phenylpiperidin-4-yl)ethanone;

1-(4-((2R,5R)-2,5-bis(4-chloro-2-fluoro-5-nitrophenyl)pyrrolidin-1-yl)-2,6-difluorophenyl)piperidine;

1-(4-(2,5-bis(4-chloro-2-fluoro-5-nitrophenyl)pyrrolidin-1-yl)-2,6-difluorophenyl)piperidine;

1-(4-((2R,5R)-2,5-bis(4-chloro-3-nitrophenyl)pyrrolidin-1-yl)-2,6-difluorophenyl)-4-(3-phenylpropyl)piperidine;

8-(4-((2R,5R)-2,5-bis(4-chloro-3-nitrophenyl)pyrrolidin-1-yl)-2,6-difluorophenyl)-8-azaspiro[4.5]decane;

1-(4-((2R,5R)-2,5-bis(4-chloro-3-nitrophenyl)pyrrolidin-1-yl)-2,6-difluorophenyl)-4-(naphthalen-2-yl)piperidine;

2-(1-(4-((2R,5R)-2,5-bis(4-chloro-3-nitrophenyl)pyrrolidin-1-yl)-2,6-difluorophenyl)piperidin-4-yl)pyridine;

1-(4-((2R,5R)-2,5-bis(4-chloro-3-nitrophenyl)pyrrolidin-1-yl)-2,6-difluorophenyl)-4-(4-(trimethylsilyl)phenyl)piperidine;

1-(4-((2R,5R)-2,5-bis(4-chloro-3-nitrophenyl)pyrrolidin-1-yl)-2,6-difluorophenyl)-4-(naphthalen-1-yl)piperidine;

1-(4-((2R,5R)-2,5-bis(4-chloro-2-fluoro-5-nitrophenyl)pyrrolidin-1-yl)-2,6-difluorophenyl)-4-(3-phenylpropyl)piperidine;

6-(4-(2R,5R)-2,5-bis(4-chloro-2-fluoro-5-nitrophenyl)pyrrolidin-1-yl)-2,6-difluorophenyl)-6-azaspiro[2.5]octane;

1-(4-((2R,5R)-2,5-bis(4-chloro-2-fluoro-5-nitrophenyl)pyrrolidin-1-yl)-2,6-difluorophenyl)-4-tert-butylpiperidine;

1-(4-((2R,5R)-2,5-bis(4-chloro-2-fluoro-5-nitrophenyl)pyrrolidin-1-yl)-2,6-difluorophenyl)-4-(naphthalen-2-yl)piperidine;

1-(4-((2R,5R)-2,5-bis(4-chloro-2-fluoro-5-nitrophenyl)pyrrolidin-1-yl)-2,6-difluorophenyl)-3,5-dimethylpiperidine;

1'-(4-((2R,5R)-2,5-bis(4-chloro-2-fluoro-5-nitrophenyl)pyrrolidin-1-yl)-2,6-difluorophenyl)-2,3-dihydrospiro[indene-1,4'-piperidine];

1-(4-((2R,5R)-2,5-bis(4-chloro-3-nitrophenyl)pyrrolidin-1-yl)-2,6-difluorophenyl)-3-phenylpiperidine;

(2R,5R)-2,5-bis(4-chloro-3-nitrophenyl)-1-(3,5-difluoro-4-(3-phenylpyrrolidin-1-yl)phenyl)pyrrolidine;

1-(4-((2R,5R)-2,5-bis(4-chloro-3-nitrophenyl)pyrrolidin-1-yl)-2,6-difluorophenyl)-4-(4-methoxyphenyl)piperidine;

1-(4-((2R,5R)-2,5-bis(4-chloro-3-nitrophenyl)pyrrolidin-1-yl)-2,6-difluorophenyl)-4-fluoro-4-phenylpiperidine;

1-(4-((2R,5R)-2,5-bis(4-chloro-3-nitrophenyl)pyrrolidin-1-yl)phenyl)-4-fluoro-4-phenylpiperidine;

1-(4-((2R,5R)-2,5-bis(4-chloro-2-fluoro-5-nitrophenyl)pyrrolidin-1-yl)-2,6-difluorophenyl)-4-(fluorodiphenylmethyl)piperidine;

1-(4-((2R,5R)-2,5-bis(4-chloro-2-fluoro-5-nitrophenyl)pyrrolidin-1-yl)-2,6-difluorophenyl)-4-phenylpiperidine;

1-(4-((2R,5R)-2,5-bis(4-chloro-3-nitrophenyl)pyrrolidin-1-yl)-2,6-difluorophenyl)-4-(4-fluorophenyl)piperidine;

1-(4-((2R,5R)-2,5-bis(4-chloro-3-nitrophenyl)pyrrolidin-1-yl)-2,6-difluorophenyl)-4-(3,4-difluorophenyl)piperidine;

1-(4-((2R,5R)-2,5-bis(4-chloro-3-nitrophenyl)pyrrolidin-1-yl)-2,6-difluorophenyl)-4-(3,5-difluorophenyl)piperidine;

1-(4-((2R,5R)-2,5-bis(4-chloro-3-nitrophenyl)pyrrolidin-1-yl)-2,6-difluorophenyl)-4-(3-(trimethylsilyl)phenyl)piperidine;

(2R,5R)-1-(4-(benzyloxy)phenyl)-2,5-bis(4-chloro-3-nitrophenyl)pyrrolidine;

1-(4-((2R,5R)-2,5-bis(4-chloro-2-fluoro-5-nitrophenyl)pyrrolidin-1-yl)-2,6-difluorophenyl)-4-(4-(trifluoromethyl)phenyl)piperazine;

1-(4-((2R,5R)-2-(4-chloro-2-fluoro-5-nitrophenyl)-5-(4-chloro-3-nitrophenyl)pyrrolidin-1-yl)-2,6-difluorophenyl)piperidine;

4-benzyl-1-(4-((2R,5R)-2,5-bis(4-chloro-2-fluoro-5-nitrophenyl)pyrrolidin-1-yl)-2,6-difluorophenyl)piperidine;

4-(4-((2R,5R)-2,5-bis(4-chloro-3-nitrophenyl)pyrrolidin-1-yl)-2,6-difluorophenyl)-2-phenylmorpholine;

1-(4-((2R,5R)-2,5-bis(4-chloro-3-nitrophenyl)pyrrolidin-1-yl)-2,6-difluorophenyl)-2-phenylpiperidine;

(2S,6R)-4-(4-((2R,5R)-2,5-bis(4-chloro-2-fluoro-5-nitrophenyl)pyrrolidin-1-yl)-2,6-difluorophenyl)-2,6-dimethylmorpholine;

3-(4-((2R,5R)-2,5-bis(4-chloro-2-fluoro-5-nitrophenyl)pyrrolidin-1-yl)-2,6-difluorophenyl)-3-azaspiro[5.5]undecane;

1-(4-((2R,5R)-2,5-bis(4-chloro-2-fluoro-5-nitrophenyl)pyrrolidin-1-yl)-2,6-difluorophenyl)-4-cyclohexylpiperidine;

(S)-4-(4-((2R,5R)-2,5-bis(4-chloro-3-nitrophenyl)pyrrolidin-1-yl)-2,6-difluorophenyl)-2-phenylmorpholine;

1-(4-((2R,5R)-2,5-bis(4-chloro-2-fluoro-5-nitrophenyl)pyrrolidin-1-yl)-2,6-difluorophenyl)-4-(3,4-difluorophenyl)piperidine;

1-(4-((2R,5R)-2,5-bis(4-chloro-2-fluoro-5-nitrophenyl)pyrrolidin-1-yl)-2,6-difluorophenyl)-4-(4-fluorophenyl)piperidine;

1-(4-((2R,5R)-2,5-bis(4-chloro-3-nitrophenyl)pyrrolidin-1-yl)-2,6-difluorophenyl)-4-phenylpiperazine;

1-(4-((2R,5R)-2,5-bis(4-chloro-3-nitrophenyl)pyrrolidin-1-yl)-2,6-difluorophenyl)-4-(4-(trifluoromethyl)phenyl)piperazine;

1-(4-((2R,5R)-2,5-bis(4-chloro-2-fluoro-5-nitrophenyl)pyrrolidin-1-yl)-2,6-difluorophenyl)-4-(2,6-difluorophenyl)piperazine; and 2-(4-(4-((2R,5R)-2,5-bis(4-chloro-2-fluoro-5-nitrophenyl)pyrrolidin-1-yl)-2,6-difluorophenyl)piperazin-1-yl)pyrimidine.

General Procedure 5. Nitro Reduction

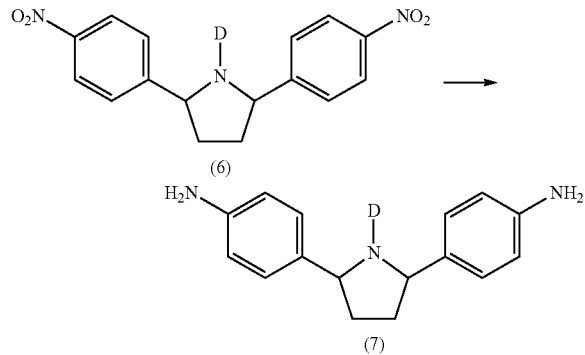

Compounds (6) (1 equivalent) can be reduced to (7) by reaction with iron powder (about 6 equivalents) and ammonium chloride (about 3 equivalents) in a solvent of THF:ethanol:water (1:1:0.2) with heating to about 60-80° C. The reaction can be worked up by cooling, filtering through diatomaceous earth, washing with ethanol and concentrating in vacuo. Alternatively, (6) (1 equivalent) can be reduced to (7) by hydrogenation (30 psi $H_2$) in the presence of $PtO_2$ (about 0.4 equivalents) in a solvent of ethanol:THF (about 1:1). The reaction can be worked up by filtration and evaporation of solvent. Alternatively, the reduction of (6) (1 equivalent) to (7) can be effected by exposure to 30 psig hydrogen gas in the presence of Raney-nickel Grace 2800 (50% by weight of reactant) in a solvent such as tetrahydrofuran with shaking. The reaction can be worked up by filtration and evaporation of solvent. The product (7) can be purified by chromatography over silica gel using typical organic solvents including mixtures of ethyl acetate and hexane.

General Procedure 5.1. Nitro Reduction for Pyrrole

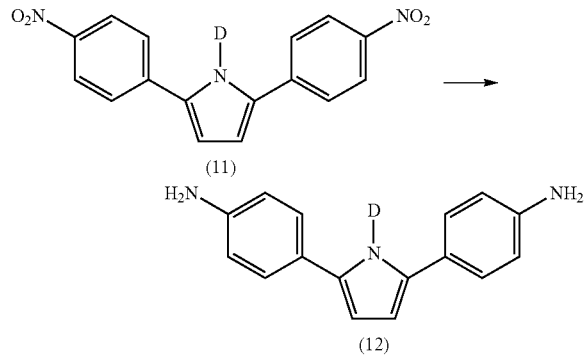

Compounds (11) can be converted to (12) using the conditions described generally for General Procedure 5, particularly through the iron reduction method.

Illustration of General Procedure 5.1: General Procedure 5.1A

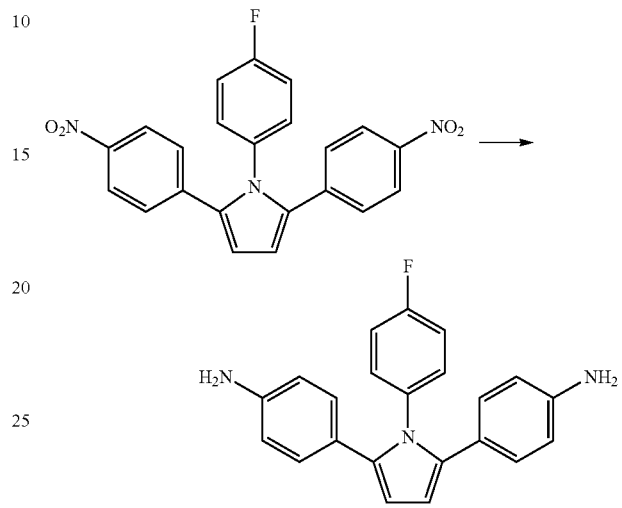

4,4'-(1-(4-Fluorophenyl)-1H-pyrrole-2,5-diyl)dianiline

To a solution of 1-(4-fluorophenyl)-2,5-bis(4-nitrophenyl)-1H-pyrrole (1.017 g, 2.496 mmol) in ethanol (15 mL) and THF (15 mL) was added iron powder (0.836 g, 14.98 mmol) followed by ammonium chloride (0.401 g, 7.49 mmol) and water (3.75 mL). The reaction mixture was refluxed for 45 minutes. The reaction mixture was slurry filtered through diatomaceous earth and washed with ethanol. The combined filtrates were concentrated, and the residue purified by column chromatography (gradient elution from 30% to 50% EtOAc:hexanes) to provide 1.09 g (77%) of the title compound.

General Procedure 6. Amide Coupling

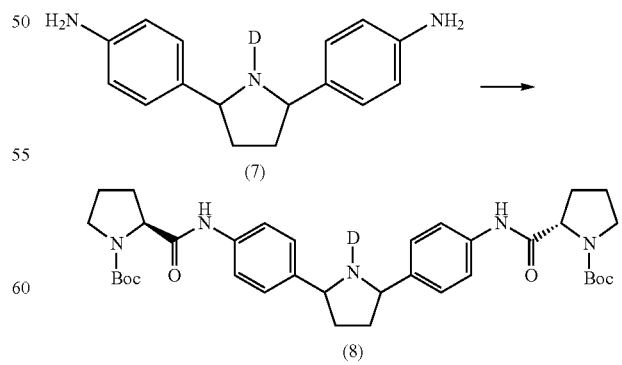

Compounds (7) (1 equivalent) can be converted to compounds (8) by reaction with 1-(tert-butoxycarbonyl)pyrrolidine-2-carboxylic acid (about 2.5 equivalents) and HATU (about 2 to 3 equivalents) in the presence of diisopropylethylamine (3-4 equivalents) in DMSO at about room temperature. Alternatively to using HATU, this reaction can be promoted using T3P or 1-ethyl-3-(3-dimethylaminopropyl)carbodiimide/1-hydroxybenzotriazole. The reaction can also be conducted in solvents such as tetrahydrofuran, ethyl acetate, or DMF. The reaction can be worked up by partitioning between an organic solvent (e.g., ethyl acetate) and water or dilute aqueous HCl, followed by separation of the organic layer, optional washing of the organic with water and/or brine, drying the organic layer with a drying agent (e.g., $MgSO_4$, $Na_2SO_4$), filtration and evaporation of solvent. The product (8) can be purified by column chromatography over silica gel, eluting with standard organic solvents including mixtures of ethyl acetate and hexane.

General Procedure 6.1. Amide Coupling for Pyrroles

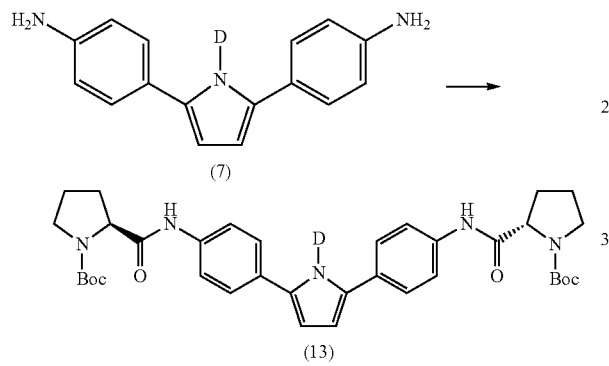

Aniline compounds (12) can be converted to amides (13) using the conditions described generally above in General Procedure 6.

Illustration of General Procedure 6.1: General Procedure 6.1A

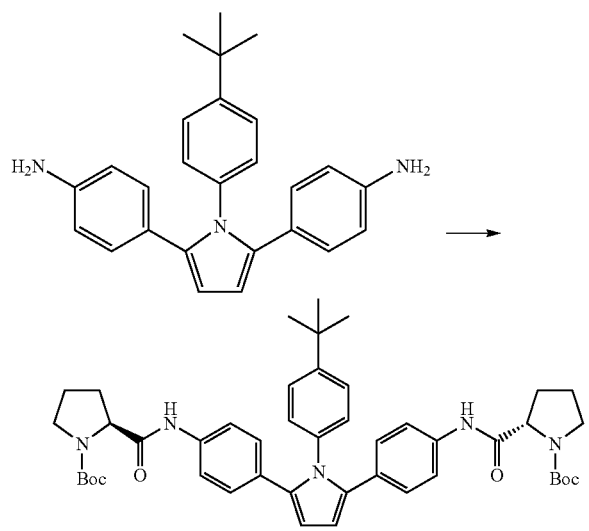

(2S,2'S)-tert-butyl 2,2'-(4,4'-(1-(4-tert-butylphenyl)-1H-pyrrole-2,5-diyl)bis(4,1-phenylene)bis(azanediyl)bis(oxomethylene))dipyrrolidine-1-carboxylate To a solution of 4,4'-(1-(4-tert-butylphenyl)-1H-pyrrole-2,5-diyl)dianiline (0.310 g, 0.813 mmol) in DMF (5 mL) was added (S)-1-(tert-butoxycarbonyl)pyrrolidine-2-carboxylic acid (0.385 g, 1.79 mmol) 1-hydroxybenzotriazole hydrate (0.274 g; 1.79 mmol) and N-(3-dimethylaminopropyl)-N'-ethylcarbodiimide hydrochloride (0.343 g, 1.79 mmol), and the mixture stirred overnight. The mixture was poured into water and extracted $CH_2Cl_2$. The organic extract was dried ($Na_2SO_4$), filtered and concentrated to give a crude product that was purified by trituration with ether to give 325 mg (51%) of the title compound. $^1$H NMR (400 MHz, DMSO-$d_6$) δ ppm 1.25 (s, 24H) 1.83 (s, 6H) 2.15 (s, 2H) 3.45 (m, 4H) 4.18 (s, 2H) 6.40 (s, 2H) 6.98 (s, 6H) 7.37 (s, 6H) 9.98 (s, 2H).

General Procedure 7. Suzuki Coupling

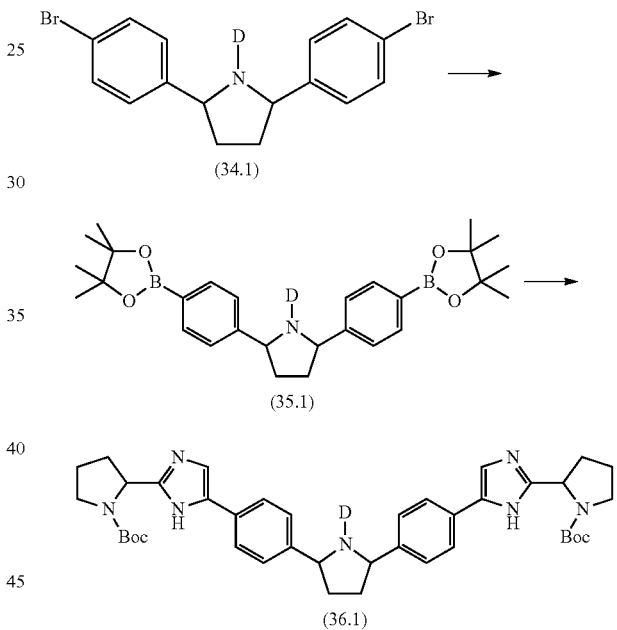

Dibromo compounds (34.1) (1 equivalent) can be converted to diboronate compounds (35.1) by mixing with bis(pinacolato)diborane (about 2 to 4 equivalents), potassium acetate (about 4-8 equivalents), and 1,1'-bis(diphenylphosphino)ferrocene-palladium(II) chloride dichloromethane complex ($PdCl_2$(dppf)) (about 0.1 to 0.2 equivalents) in a solvent such as DME, dioxane, or DMSO, degassing the mixture and heating to about 85° C. The reaction can be worked up by cooling to room temperature, diluting with methylene chloride, optionally washing the organics with water and/or brine, drying the organics with a drying agent (e.g., $MgSO_4$, $Na_2SO_4$), filtration and evaporation of solvent. Compounds (35.1) can be converted to compounds (36.1) by mixing with Intermediate 1D (about 1 to 2 equivalents), aqueous sodium carbonate solution (about 1 to 3.5 equivalents), and $PdCl_2$(dppf) (about 0.03 to 0.2 equivalents) in a solvent like dimethoxyethane or toluene:ethanol (1:1), degassing, and heating the reaction to around 80-100° C. The reaction can be worked up by cooling to room temperature, partition-

Illustration of General Procedure 7: General Procedure 7A

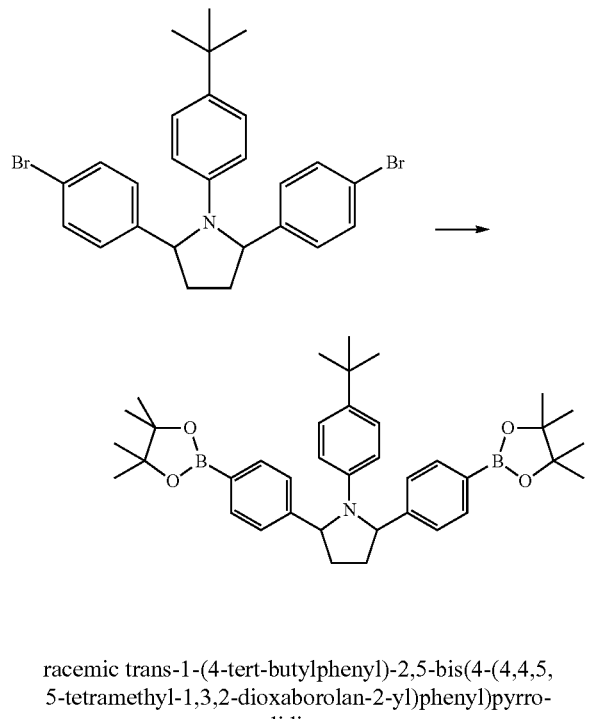

racemic trans-1-(4-tert-butylphenyl)-2,5-bis(4-(4,4,5,5-tetramethyl-1,3,2-dioxaborolan-2-yl)phenyl)pyrrolidine Racemic trans-2,5-bis(4-bromophenyl)-1-(4-tert-butylphenyl)pyrrolidine (3.88 g, 7.56 mmol), 4,4,4',4',5,5,5',5'-octamethyl-2,2'-bi(1,3,2-dioxaborolane) (6.72 g, 26.5 mmol), [1,1'-bis(diphenylphosphino)ferrocene]dichloropalladium(II) (0.617 g, 0.756 mmol), and potassium acetate (3.34 g, 34.0 mmol) were combined in dimethoxyethane (70 mL) and nitrogen gas was sparged through the solution for 10 minutes. The reaction mixture was then heated at 85° C. for 1 hour. The reaction solution was cooled to room temperature, filtered through diatomaceous earth and washed with ethyl acetate (20 mL). The filtrate was dried and concentrated, and the residue was purified by column chromatography on silica gel, eluting with a solvent gradient of 0-10% ethyl acetate in hexane followed by trituration of the resultant solid with diethyl ether to give the title compound (1.14 g, 25%) as a 1/1 mixture of trans stereoisomers.

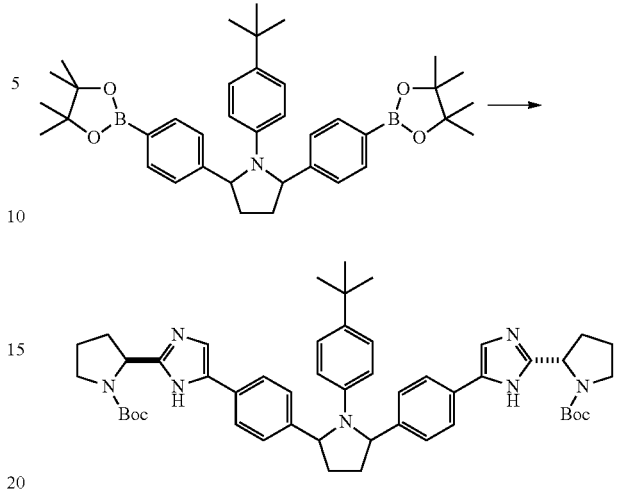

(2S,2'S)-tert-butyl 2,2'-(5,5'-(4,4'-(1-(4-tert-butylphenyl)pyrrolidine-2,5-diyl)bis(4,1-phenylene))bis(1H-imidazole-5,2-diyl))dipyrrolidine-1-carboxylate Racemic trans-1-(4-tert-butylphenyl)-2,5-bis(4-(4,4,5,5-tetramethyl-1,3,2-dioxaborolan-2-yl)phenyl)pyrrolidine (0.915 g, 1.506 mmol), Intermediate 1D (1.429 g, 4.52 mmol), and [1,1'-bis(diphenylphosphino)ferrocene]dichloropalladium(II) (0.123 g, 0.151 mmol) were dissolved in a mixture of toluene (7 mL), ethanol (7 mL) and a 2 N aq. sodium bicarbonate solution (2.64 mL, 5.28 mmol). Nitrogen gas was bubbled through the solution for 10 minutes, and then the reaction mixture was heated at 100° C. for 3 hours. The reaction solution was cooled to room temperature and water (20 mL) was added. Then the reaction mixture was extracted with dichloromethane (50 mL), dried, and concentrated. The residue was purified by column chromatography on silica gel eluting with a solvent gradient of 0-80% ethyl acetate in hexane to give the title compound (0.93 g, 75%) as a 1/1 mixture of trans stereoisomers.

General Procedure 7.1. Suzuki Coupling for Pyrroles

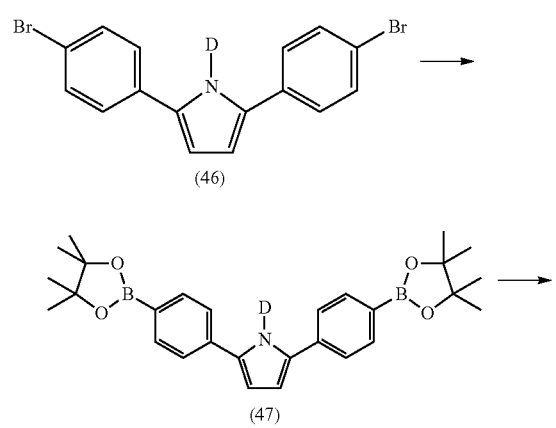

303

-continued

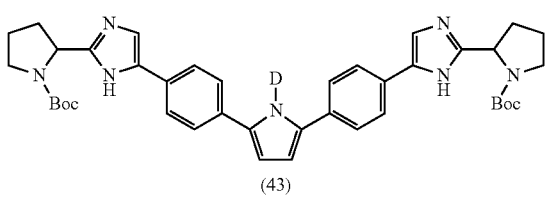

(43)

Dibromo compounds (46) can be converted sequentially to compounds (47) and (43) using the conditions described generally above in General Procedure 7.

Illustration of General Procedure 7.1: General Procedure 7.1B

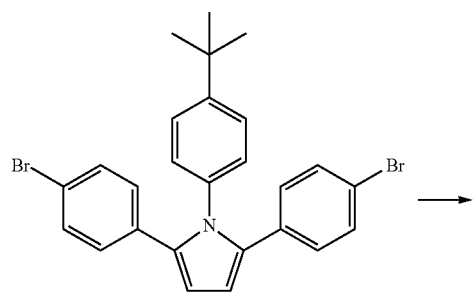

1-(4-tert-butylphenyl)-2,5-bis(4-(4,4,5,5-tetramethyl-1,3,2-dioxaborolan-2-yl)phenyl)-1H-pyrrole To a solution of 2,5-bis(4-bromophenyl)-1-(4-tert-butylphenyl)-1H-pyrrole (2.32 g, 4.56 mmol) in DMSO (26 mL) at room temperature were added bis(pinacolato)diborane (2.54 g, 10.02 mmol), potassium acetate (5.00 g, 36.4 mmol) and PdCl$_2$(dppf) (744 mg, 0.91 mmol). The mixture was degassed and heated to 85° C. After 4 hours, the mixture was cooled to room temperature, diluted with dichloromethane and washed with water followed by brine. The organic phase was dried (Na$_2$SO$_4$) and concentrated. The residue was taken up in 20% ethyl acetate/hexanes and filtered through a short plug of silica gel (elution with 20% ethyl acetate:hexanes) and concentrated to afford the title compound as a light yellow solid (1.62 g; 59% yield).

304

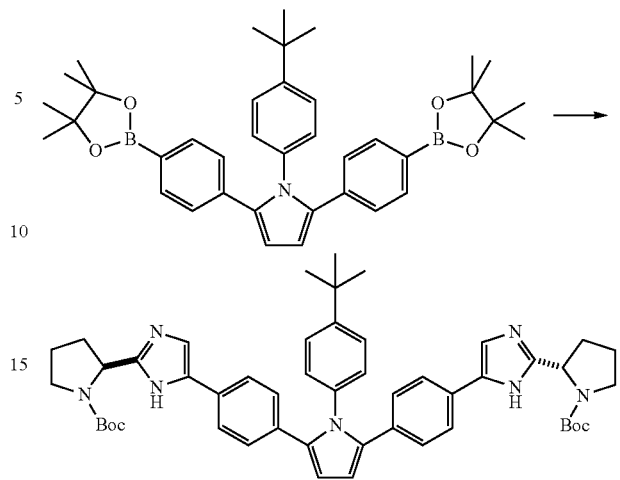

(2S,2'S)-tert-butyl 2,2'-(4,4'-(4,4'-(1-(4-tert-butylphenyl)-1H-pyrrole-2,5-diyl)bis(4,1-phenylene))bis(1H-imidazole-4,2-diyl))dipyrrolidine-1-carboxylate A mixture of Intermediate 1D (664 mg, 2.10 mmol), 1-(4-tert-butylphenyl)-2,5-bis(4-(4,4,5,5-tetramethyl-1,3,2-dioxaborolan-2-yl)phenyl)-1H-pyrrole (1.48 g, 2.45 mmol), 2 M sodium carbonate (1400 µL, 2.80 mmol), and Pd(dppf)Cl$_2$ (51.2 mg, 0.070 mmol) in DME (2800 µL) was subjected to microwave irradiation at 140° C. for 20 minutes. The mixture was diluted with ethyl acetate, then washed with water and brine, and dried over Na$_2$SO$_4$. The product was purified on silica gel eluting with 30 to 70% ethyl acetate:hexanes to provide the title compound (140 mg; 24% yield).

General Procedure 8. Buchwald Reaction

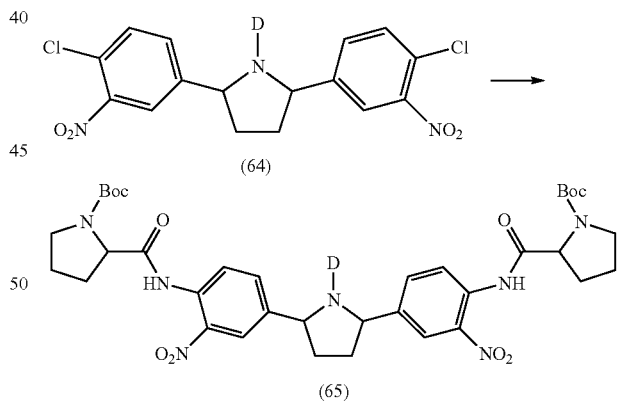

Compounds (64) (1 equivalent) can be converted to compounds (65) by mixing with tert-butyl 2-carbamoylpyrrolidine-1-carboxylate (about 3 equivalents), cesium carbonate (about 3 equivalents), 4,5-bis(diphenylphosphino)-9,9-dimethylxanthene (about 0.2 to 0.3 equivalents), and tris(dibenzylideneacetone)dipalladium(0) (about 0.1 to 0.2 equivalents) in dioxane, degassing the mixture, and heating to around 100° C. for between about 1 to 8 hours. The reaction can be conducted in a flask with a reflux condenser under inert atmosphere or in a sealed tube. The products (65) can be purified by silica gel chromatography eluting with standard solvents including ethyl acetate and methylene chloride.

Illustration of General Procedure 8: General Procedure 8A

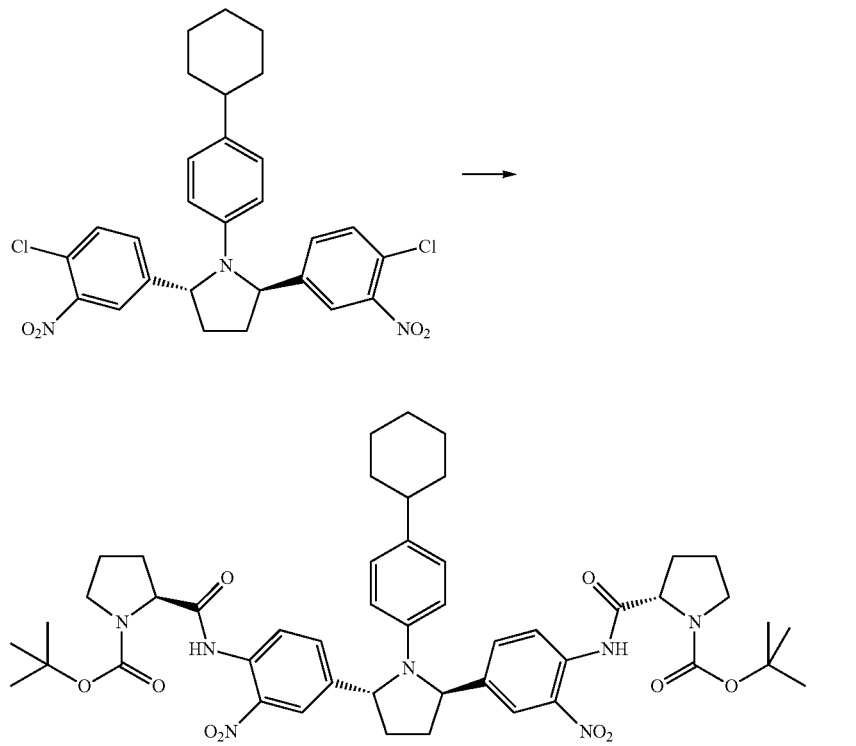

(2S,2'S)-tert-butyl 2,2'-(4,4'-((2R,5R)-1-(4-cyclohexylphenyl)pyrrolidine-2,5-diyl)bis(2-nitro-4,1-phenylene))bis(azanediyl)bis(oxomethylene)dipyrrolidine-1-carboxylate (2R,5R)-2,5-Bis(4-chloro-3-nitrophenyl)-1-(4-cyclohexylphenyl)pyrrolidine (General Procedure 4A) (1.29 g, 2.39 mmol), (S)-tert-butyl 2-carbamoylpyrrolidine-1-carboxylate (1.53 g, 7.16 mmol), cesium carbonate (2.33 g, 7.16 mmol), 4,5-bis(diphenylphosphino)-9,9-dimethylxanthene (0.33 g, 0.573 mmol), and tris(dibenzylideneacetone)dipalladium(0) (0.328 g, 0.358 mmol) were combined in dioxane (18 mL) and nitrogen was bubbled through the solution for 15 minutes. Then the flask was capped with a reflux condenser and the solution was heated at 100° C. for 8 hours. After filtering through diatomaceous earth and concentrating, the residue was purified with a CombiFlash® 80 g silica column, eluting with 0-20% ethyl acetate in dichloromethane to give 1.71 g (80%) of the title compound.

Illustration of General Procedure 8: General Procedure 8B, Example 1A

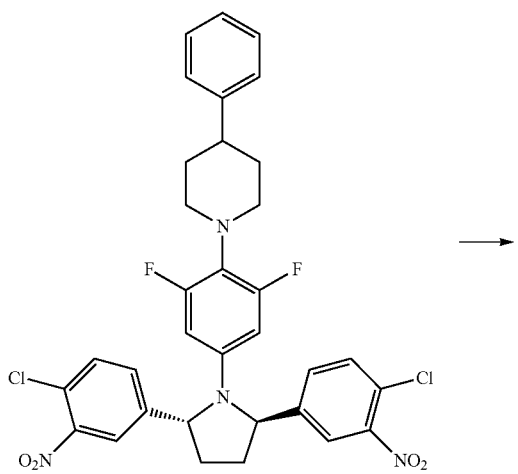

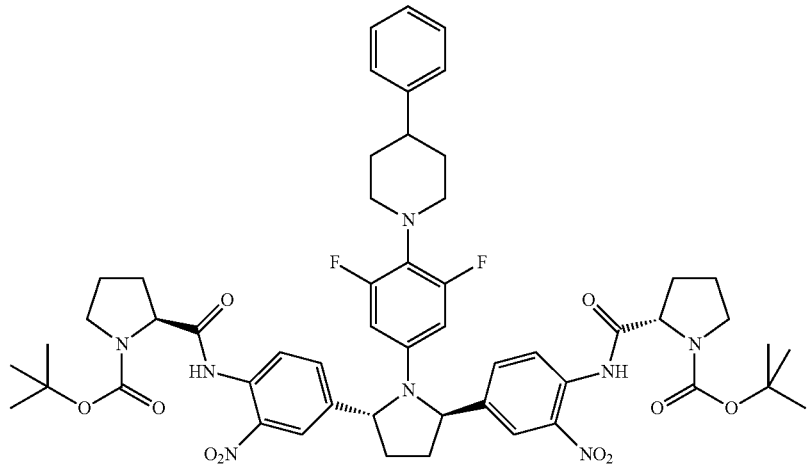

(2S,2'S)-tert-butyl 2,2'-(4,4'-((2R,5R)-1-(3,5-dif-
luoro-4-(4-phenylpiperidin-1-yl)phenyl)pyrrolidine-
2,5-diyl)bis(2-nitro-4,1-phenylene))bis(azanediyl)bis
(oxomethylene)dipyrrolidine-1-carboxylate To a 100 mL round-bottomed flask was added 1-(4-(2R,5R)-2,5-bis(4-chloro-3-nitrophenyl)pyrrolidin-1-0-2,6-difluorophenyl)-4-phenylpiperidine (2.26 g, 3.46 mmol), (S)-tert-butyl 2-carbamoylpyrrolidine-1-carboxylate (2.223 g, 10.37 mmol), cesium carbonate (3.38 g, 10.37 mmol), tris(dibenzyideneacetone)dipalladium(0) (0.190 g, 0.207 mmol) and (9,9-dimethyl-9H-xanthene-4,5-diyl)bis(diphenylphosphine) (0.300 g, 0.519 mmol) in dioxane (34.6 mL) to give a purple suspension. The mixture was sparged with $N_2$ for 20 minutes, heated under $N_2$ at 100° C. for 3 hours, cooled and poured into EtOAc. The EtOAc layer was washed 2×50 mL with $H_2O$ and then with saturated NaCl. The EtOAc layer was treated simultaneously for 1 hour with 3-mercaptopropyl silica and $Na_2SO_4$, filtered and concentrated. Purification using chromatography on a 120 g silica cartridge eluting with 1-3% methanol in methylene chloride gave material that was 90% pure by HPLC. A second column on a 120 g silica cartridge eluting with 15-50% EtOAc in hexane provided the title compound as an orange foam (2.6 g, 72%, 97% purity by HPLC). MS (ESI+) m/z 1009 (M+H)$^+$.

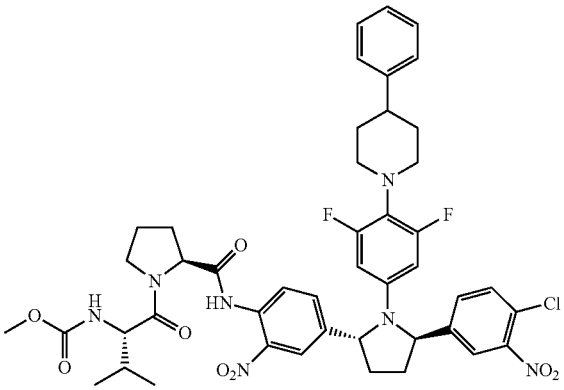 [SMILES: COC(=O)N[C@H](C(=O)N1CCC[C@H]1C(=O)Nc1ccc([C@H]2CC[C@H](c3ccc(Cl)c([N+](=O)[O-])c3)N2c2cc(F)c(N3CCC(c4ccccc4)CC3)c(F)c2)cc1[N+](=O)[O-])C(C)C]

Illustration of General Procedure 8: General
Procedure 8B, Example 1B (mono-displacement)

methyl (S)-1-((S)-2-(4-((2R,5R)-5-(4-chloro-3-nitro-
phenyl)-1-(3,5-difluoro-4-(4-phenylpiperidin-1-yl)
phenyl)pyrrolidin-2-yl)-2-nitrophenylcarbamoyl)
pyrrolidin-1-yl)-3-methyl-1-oxobutan-2-ylcarbamate 1-(4-((2R,5R)-2,5-Bis(4-chloro-3-nitrophenyl)pyrrolidin-1-yl)-2,6-difluorophenyl)-4-phenylpiperidine (0.745 g, 1.14 mmol) was dissolved in dioxane (12 mL) in a tube and treated with methyl (S)-1-((S)-2-carbamoylpyrrolidin-1-yl)-3-methyl-1-oxobutan-2-ylcarbamate (0.309 g, 1.14 mmol), cesium carbonate (0.409 g, 1.25 mmol), Xantphos (0.066 g, 0.11 mmol), and tris(dibenzylideneacetone)dipalladium(0) (0.052 g, 0.057 mmol). Nitrogen was bubbled through this mixture for 15 minutes, then the tube was sealed and heated at 100° C. for 2 hours. The mixture was diluted with water, extracted into dichloromethane, concentrated, and purified by chromatography, eluting with 0-5% methanol in dichloromethane to give 0.44 g (43%) of a dark yellow solid.

Illustration of General Procedure 8: General Procedure 8B, Example 2

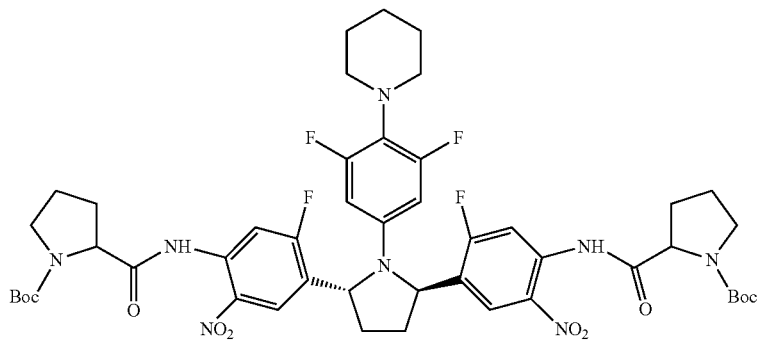 [SMILES: CC(C)(C)OC(=O)N1CCCC1C(=O)Nc1cc(F)c([C@H]2CC[C@H](c3cc([N+](=O)[O-])c(NC(=O)C4CCCN4C(=O)OC(C)(C)C)cc3F)N2c2cc(F)c(N3CCCCC3)c(F)c2)cc1[N+](=O)[O-]]

tert-butyl 2,2'-(4,4'-((2R,5R)-1-(3,5-difluoro-4-(piperidin-1-yl)phenyl)pyrrolidine-2,5-diyl)bis(5-fluoro-2-nitro-4,1-phenylene))bis(azanediyl)bis(oxomethylene)dipyrrolidine-1-carboxylate To a round bottom flask was combined 1-(4-((2R,5R)-2,5-bis(4-chloro-2-fluoro-5-nitrophenyl)pyrrolidin-1-yl)-2,6-difluorophenyl)piperidine (4.1 g, 6.68 mmol), (S)-tert-butyl 2-carbamoylpyrrolidine-1-carboxylate (4.30 g, 20.05 mmol), cesium carbonate (6.1 g, 18.72 mmol), and XantPhos (0.696 g, 1.203 mmol) followed by dioxane (30 ml) and the solution was de-gassed with N₂ gas for 30 minutes. The solution was stirred vigorously to keep the solids mixing and kept the flow rate of N₂ gas at a high rate to ensure complete de-gassing of the mixture. Tris(dibenzylideneacetone)dipalladium (0.367 g, 0.401 mmol) was added and the solution heated at 100° C. for 2 hours under N₂ gas. The solution was cooled and diluted with EtOAc, filtered through diatomaceous earth, washed with H₂O and brine, dried (Na₂SO₄), filtered, treated for 30 minutes with 3-mercaptopropyl-functionalized silica gel, filtered and concentrated to give crude product. Purification was run on an ISCO 120 g silica gel cartridge eluting with 0-40% EtOAc/hexane over 30 minutes to give the title compound (4.52 g, 4.66 mmol, 69.8%).

General Procedure 8.1. Buchwald with dipeptide

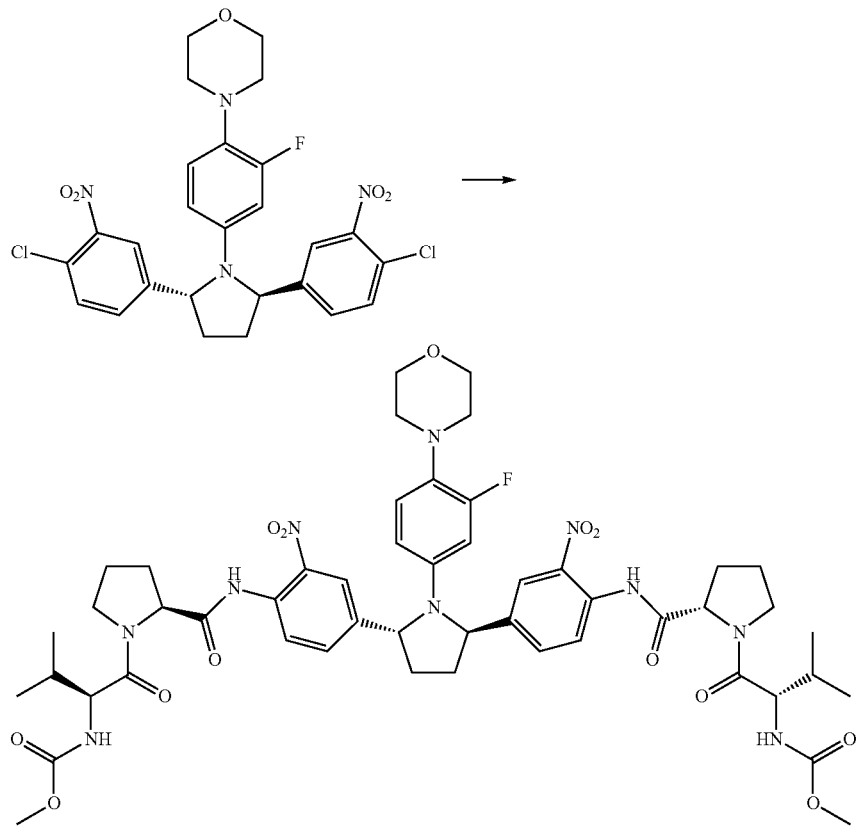

dimethyl (2R,2'R)-1,1'-((2S,2'S)-2,2'-(4,4'-((2R,5R)-1-(3-fluoro-4-morpholinophenyl)pyrrolidin-2,5-diyl)bis(2-nitro-4,1-phenylene))bis(azanediyl)bis(oxomethylene))bis(pyrrolidine-2,1-diyl))bis(3-methyl-1-oxobutane-2,1-diyl)dicarbamate In a microwave tube, a suspension of 4-(4-((2R,5R)-2,5-bis(4-chloro-3-nitrophenyl)pyrrolidin-1-yl)-2-fluorophenyl)morpholine (1.39 g, 2.48 mmoL), Intermediate 3B (2.02 g, 7.43 mmol), XantPhos (129 mg, 0.22 mmol) and cesium carbonate (2.42 g, 7.43 mmoL) in dioxane (14 mL) was degassed by nitrogen sparge for 30 minutes. The mixture was treated with tris(dibenzylideneacetone)dipalladium (0) (68 mg, 0.074 mmol) followed by degassing for another 5 minutes. The microwave tube was sealed and the mixture was warmed at 100° C. for 2 hours. The mixture was cooled and diluted with ethyl acetate and extracted with water (3×) and saturated sodium chloride solution. The solution was dried ($Na_2SO_4$) and stirred overnight with 3-(mercaptopropyl)silica gel. Filtration and concentration in vacuo afforded a solid which was chromatographed over a 340 g silica gel cartridge, eluting with 0-10% methanol in dichloromethane. These procedures afforded the title compound as an orange solid. $^1$H NMR (400 MHz, DMSO-$d_6$) δ ppm 0.80-0.90 (m, 12H) 1.74 (br s, 2H) 1.82-2.03 (m, 10H) 2.08-2.20 (m, 2H) 2.71-2.81 (m, 4H) 3.52 (s, 6H) 3.62 (m, 4H) 3.76 (s, 2H) 4.02 (m, 2H) 4.50 (d, J=4.4 Hz, 2H) 5.39 (s, 2H) 6.04-6.19 (m, 2H) 6.74f6.81 (m, 1H) 7.32 (d, J=8.4 Hz, 2H) 7.47-7.60 (m, 4H) 7.80 (d, J=1.5 Hz, 2H) 10.41 (s, 2H); MS (ESI) m/z 1031 (M+H)$^+$.

General Procedure 9. Nitro Reduction

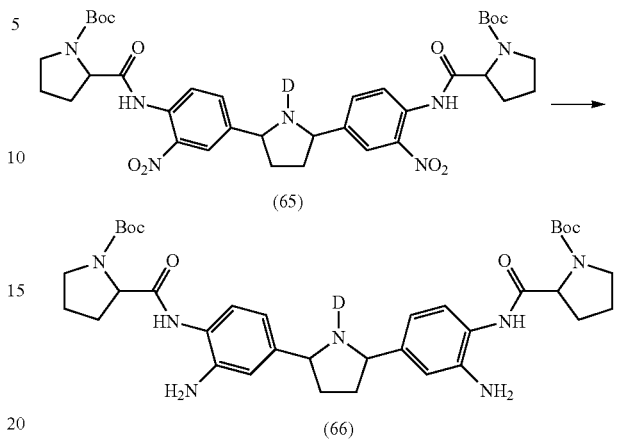

Compounds (65) (1 equivalent) can be converted to compounds (66) by hydrogenation with hydrogen gas (1-4 atm) over a catalyst such as $PtO_2$ (about 0.2 to 0.3 equivalents) or Raney-nickel (e.g., 50% aqueous; 1 equivalent by weight) in solvents such as tetrahydrofuran, ethanol, or mixtures thereof. The reaction can be worked up by filtration through diatomaceous earth or silica gel, and the filtrate concentrated to give compounds (66). Reduction of (65) (1 equivalent) can also be effected by reaction with iron powder (about 6 equivalents) and ammonium chloride (about 3 equivalents) in a solvent of THF:ethanol:water (1:1:0.2) with heating to about 60-100° C.

Illustration of General Procedure 9: General Procedure 9A, Example 1

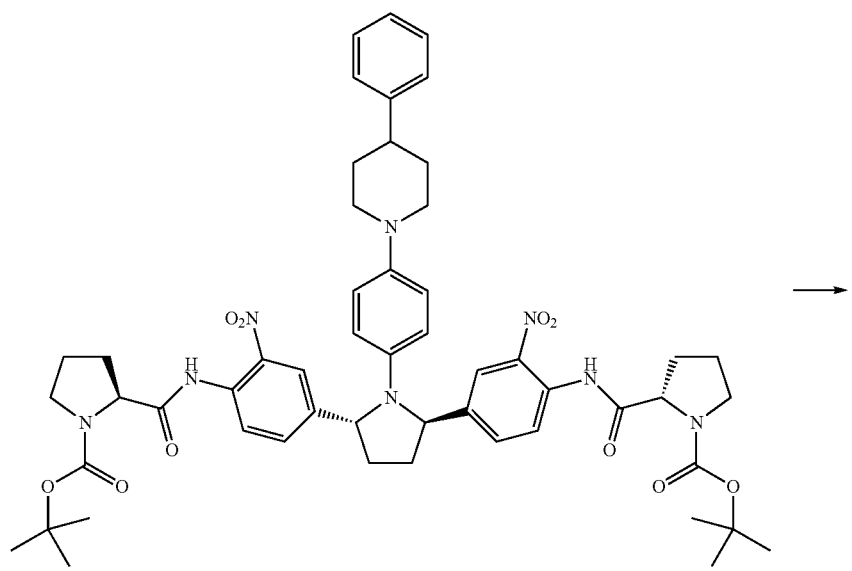

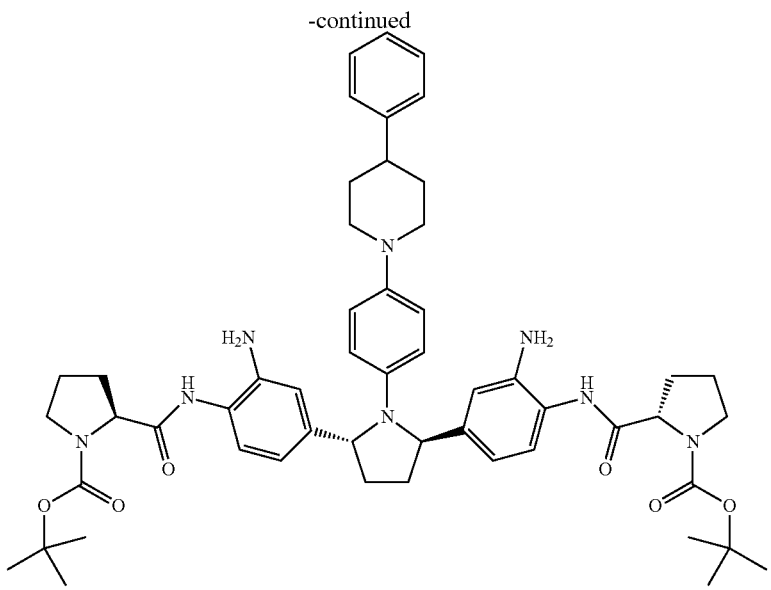

(2S,2'S)-tert-butyl 2,2'-(4,4'-((2R,5R)-1-(4-(4-phenylpiperidin-1-yl)phenyl)pyrrolidine-2,5-diyl)bis(2-amino-4,1-phenylene))bis(azanediyl)bis(oxomethylene)dipyrrolidine-1-carboxylate A solution of (2S,2'S)-tert-butyl 2,2'-(4,4'-((2R,5R)-1-(4-(4-phenylpiperidin-1-yl)phenyl)pyrrolidine-2,5-diyl)bis(2-nitro-4,1-phenylene))bis(azanediyl)bis(oxomethylene) dipyrrolidine-1-carboxylate (2.287 g, 2.350 mmol) in THF (60 mL) was added to $PtO_2$ (0.457 g, 2.014 mmol) in a 250 mL stainless steel pressure bottle and stirred for 4 hours at room temperature under 30 psi hydrogen pressure. The mixture was then filtered through a nylon membrane and the filtrate concentrated by rotary evaporation and dried in vacuo to give the title compound as a brown solid (2.02 g, 94%). $^1$H NMR (400 MHz, DMSO-$d_6$) δ ppm 1.30-1.44 (m, 18H), 1.53-1.98 (m, 11H), 2.08-2.29 (m, 1H), 2.43-2.60 (m, 3H), 3.35-3.50 (m, 4H), 4.16-4.29 (m, 2H), 4.79 (d, J=35.46 Hz, 4H), 4.97 (s, 2H), 6.21 (d, J=8.89 Hz, 2H), 6.41 (dd, J=20.66, 7.86 Hz, 2H), 6.53-6.61 (m, 2H), 6.66 (d, J=8.89 Hz, 2H), 6.93-7.06 (m, 2H), 7.17 (t, J=6.89 Hz, 1H), 7.21-7.32 (m, 4H), 9.18 (d, J=39.25 Hz, 2H); MS (ESI+) m/z 913 (M+H)$^+$; MS (ESI−) m/z 911 (M−H)$^−$.

Illustration of General Procedure 9: General Procedure 9A, Example 2 tert-butyl 2,2'-(4,4'-((2R,5R)-1-(3,5-difluoro-4-(piperidin-1-yl)phenyl)pyrrolidine-2,5-diyl)bis(2-amino-5-fluoro-4,1-phenylene))bis(azanediyl)bis(oxomethylene)dipyrrolidine-1-carboxylate tert-Butyl 2,2'-(4,4'-((2R,5R)-1-(3,5-difluoro-4-(piperidin-1-yl)phenyl)pyrrolidine-2,5-diyl)bis(5-fluoro-2-nitro-4,1-phenylene))bis(azanediyl)bis(oxomethylene)dipyrrolidine-1-carboxylate (4.5 g, 4.64 mmol) and THF (100 ml) were added to $PtO_2$ (0.900 g, 3.96 mmol) in a 250 ml stainless steel pressure bottle and stirred for 22 hours under a hydrogen atmosphere (30 psi) at room temperature. The mixture was filtered through a nylon membrane and concentrated to a yellow-orange foam.

Illustration of General Procedure 9: General Procedure 9B

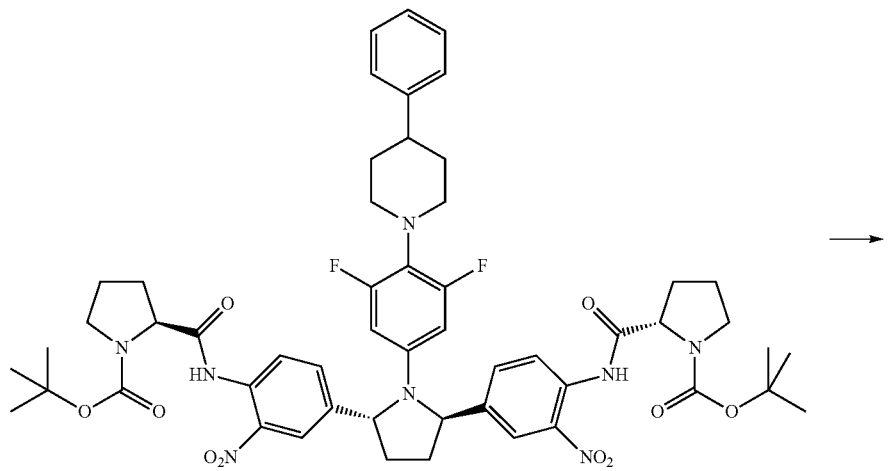

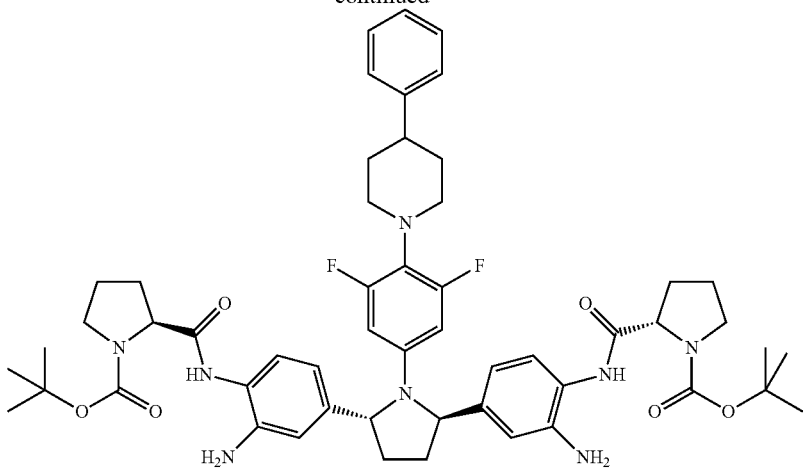

(2S,2'S)-tert-butyl 2,2'-(4,4'-((2R,5R)-1-(3,5-difluoro-4-(4-phenylpiperidin-1-yl)phenyl)pyrrolidine-2,5-diyl)bis(2-amino-4,1-phenylene))bis(azanediyl)bis(oxomethylene)dipyrrolidine-1-carboxylate In a 250 mL pressure bottle were combined (2S,2'S)-tert-butyl 2,2'-(4,4'-((2R,5R)-1-(3,5-difluoro-4-(4-phenylpiperidin-1-yl)phenyl)pyrrolidine-2,5-diyl)bis(2-nitro-4,1-phenylene))bis(azanediyl)bis(oxomethylene)dipyrrolidine-1-carboxylate (General Procedure 8B) (2.6 g, 2.58 mmol) and Raney-nickel 2800 (45% w/w in water, 2.6 g, 44 mmol) in THF (40 mL). The vessel was sealed and stirred under 30 psi H₂ for 5 hours. The solution was filtered through a nylon membrane and the filtrate was concentrated to afford the title compound as a tan foam (2.44 g, quantitative yield) that was used without purification. MS (ESI+) m/z 949 (M+H)⁺.

Illustration of General Procedure 9: General Procedure 9C dimethyl ([(2R,5R)-1-(4,5,6,7-tetrahydro-1,3-benzothiazol-2-yl)pyrrolidine-2,5-diyl]bis{(2-aminobenzene-4,1-diyl)carbamoyl(2S)pyrrolidine-2,1-diyl[(2S)-3-methyl-1-oxobutane-1,2-diyl]})biscarbamate (ACD Name v12))

Dimethyl ([(2R,5R)-1-(4,5,6,7-tetrahydro-1,3-benzothiazol-2-yl)pyrrolidine-2,5-diyl]bis{(2-nitrobenzene-4,1-diyl)carbamoyl(2S)pyrrolidine-2,1-diyl[(2S)-3-methyl-1-oxobutane-1,2-diyl]})biscarbamate (ACD Name v12)) (0.59 g, 0.596 mmol) was dissolved in tetrahydrofuran (15 mL) and treated with Raney-nickel slurry in water (0.25 mL). The flask was evacuated and opened to a hydrogen balloon and stirred at ambient temperature for 1 hour. The solution was filtered through a silica plug and concentrated to dryness to give the title compound.

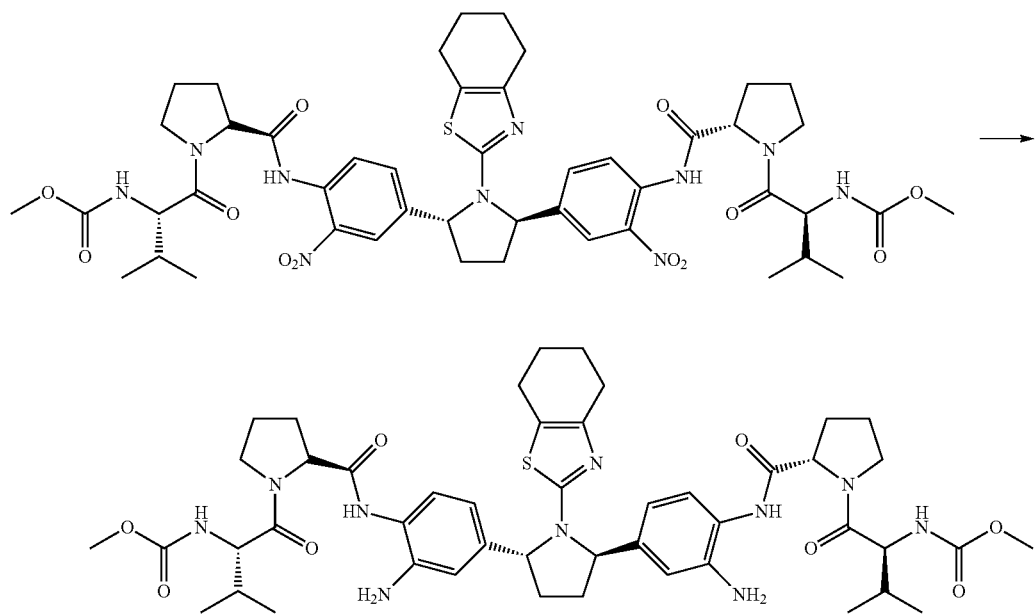

Illustration of General Procedure 9: General Procedure 9D

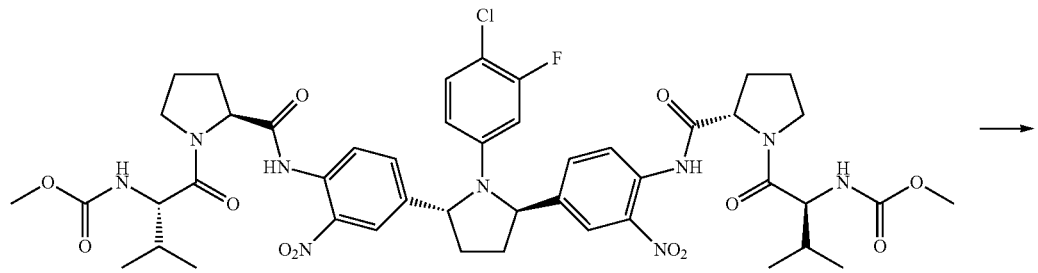

dimethyl (2S,2'S)-1,1'-((2S,2'S)-2,2'-(4,4'-((2R,5R)-1-(4-chloro-3-fluorophenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate Dimethyl (2S,2'S)-1,1'-((2S,2'S)-2,2'-(4,4'-((2R,5R)-1-(4-chloro-3-fluorophenyl)pyrrolidine-2,5-diyl)bis(2-nitro-4,1-phenylene))bis(azanediyl)bis(oxomethylene)bis(pyrrolidine-2,1-diyl))bis(3-methyl-1-oxobutane-2,1-diyl) dicarbamate (1.0 g, 1.02 mmol) and tetrahydrofuran (25 mL) were added to platinum oxide (0.20 g, 0.88 mmol) in a pressure bottle and stirred at ambient temperature under hydrogen at 30 psi for 1.5 hours. The solution was filtered through a nylon membrane and concentrated to dryness to give 100% yield of a brown residue that was used without purification.

Illustration of General Procedure 9: General Procedure 9E

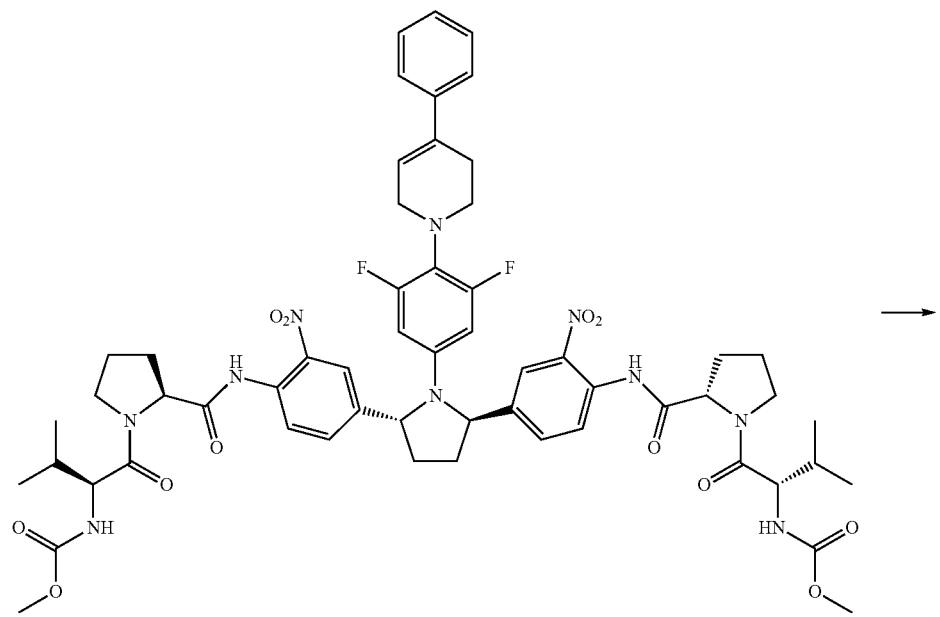

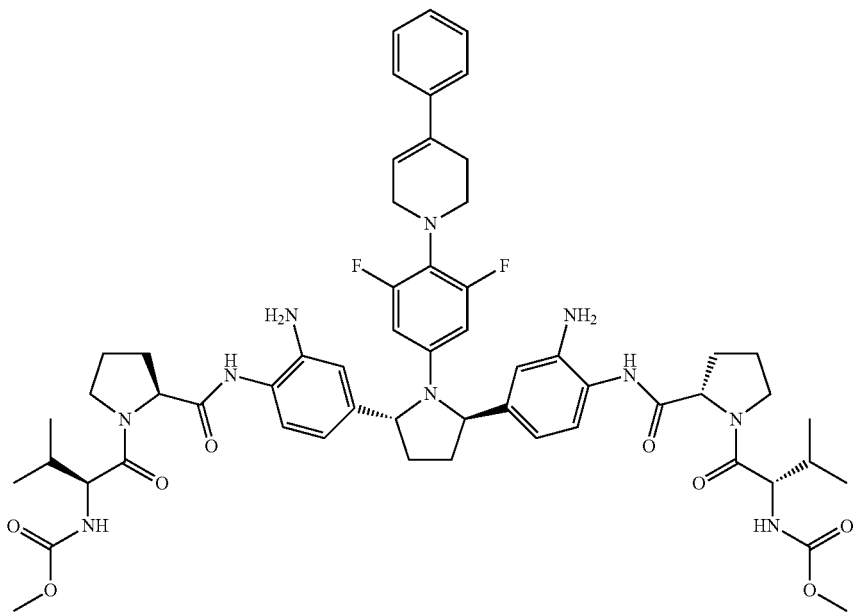

dimethyl (2S,2'S)-1,1'-((2S,2'S)-2,2'-(4,4'-((2R,5R)-1-(3,5-difluoro-4-(4-phenyl-5,6-dihydropyridin-1(2H)-yl)phenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate Dimethyl (2S,2'S)-1,1'-((2S,2'S)-2,2'-(4,4'-((2R,5R)-1-(3,5-difluoro-4-(4-phenyl-5,6-dihydropyridin-1(2H)-yl)phenyl)pyrrolidine-2,5-diyl)bis(2-nitro-4,1-phenylene))bis(azanediyl)bis(oxomethylene)bis(pyrrolidine-2,1-diyl))bis(3-methyl-1-oxobutane-2,1-diyl)dicarbamate (150 mg, 0.134 mmol) was dissolved in a mixture of THF (1 mL) and absolute EtOH (1 mL) under nitrogen. A solution of ammonium chloride (10.73 mg, 0.201 mmol) in water (0.333 mL), followed by iron powder (37.4 mg, 0.669 mmol) was added, and the mixture was heated under a reflux condenser in an oil bath at 90° C. After 1 hour, the reaction mixture was cooled to room temperature, vacuum filtered through a bed of Celite 545, and washed thoroughly with EtOAc. The filtrate was concentrated by rotary evaporation to remove the organic solvents. The residue was dissolved in EtOAc (50 mL), washed with water (2×25 mL) and brine (25 mL), dried over anhydrous $MgSO_4$, filtered, and concentrated by rotary evaporation. The residue was purified by $SiO_2$ flash chromatography (Alltech Extract-Clean column, 10 g bed) eluting with a step gradient of 3% to 4% methanol/$CH_2Cl_2$ to afford the product as a yellow solid (77 mg, 0.073 mmol, 54%). $^1$H NMR (400 MHz, DMSO-$d_6$) δ ppm 0.92 (dd, J=13.07, 6.56 Hz, 12H), 1.58-1.75 (m, 2H), 1.83-2.09 (m, 8H), 2.13-2.28 (m, 1H), 3.17 (s, 2H), 3.38-3.68 (m, 8H), 3.55 (s, 6H), 3.84 (s, 2H), 4.05 (t, J=8.35 Hz, 2H), 4.37-4.47 (m, 2H), 4.93 (s, 4H), 5.01 (d, J=5.10 Hz, 2H), 5.85-6.00 (m, 2H), 6.14 (s, 1H), 6.44 (d, J=8.02 Hz, 2H), 6.55-6.66 (m, 2H), 7.02 (d, J=7.81 Hz, 2H), 7.21-7.49 (m, 8H), 9.28 (s, 2H); MS (ESI+) m/z 1061 (M+H)$^+$; MS (ESI−) m/z 1059 (M−H)$^-$.

General Procedure 10. Benzimidazole Formation

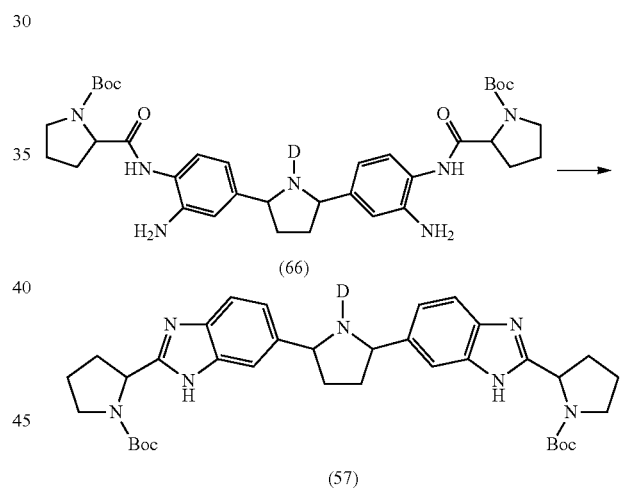

Compounds (66) can be converted to compounds (57) by heating neat in acetic acid or with acetic acid in toluene or dioxane at 50-80° C. The reaction can be worked up by concentrating the solution, neutralizing with aqueous sodium bicarbonate solution, extracting with an organic solvent (e.g., dichloromethane), drying the organic solvent mixture (e.g., $MgSO_4$, $Na_2SO_4$), filtering and concentrating in vacuo. The reaction can also be conducted in toluene as solvent with added acetic acid (about 3 to 5 equivalents) also with heating to 50-80° C. Workup can consist of simple solvent evaporation and the removal of residual acetic acid by the addition and evaporation of toluene. Compounds (57) can be purified by chromatography over silica gel eluting with ethyl acetate/dichloromethane or methanol/dichloromethane. Although the cyclization depicted above is shown with a t-butoxycarbonyl (Boc) group attached, the reaction can also be conducted with the groups -T-$R_D$ attached, wherein T and $R_D$ are as defined herein.

321

Illustration of General Procedure 10: General Procedure 10A; Example 1

322

(2S,2'S)-tert-butyl 2,2'-(5,5'-(1-(4-tert-butylphenyl)pyrrolidine-2,5-diyl)bis(1H-benzo[d]imidazole-5,2-diyl))dipyrrolidine-1-carboxylate

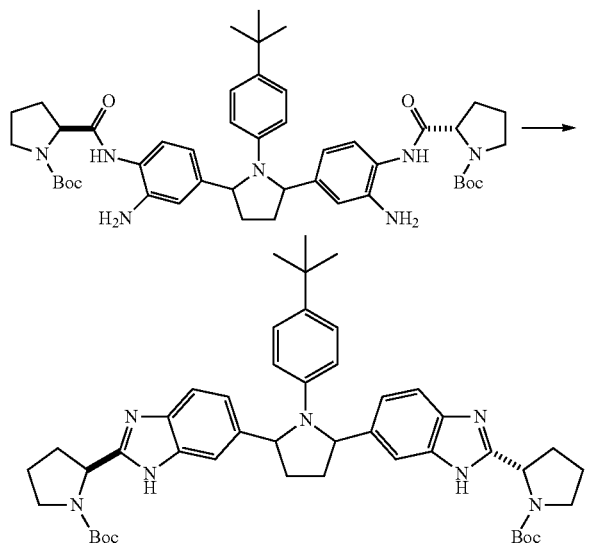

As a mixture of trans diastereomers, (2S,2'S)-tert-butyl 2,2'-(5,5'-(1-(4-tert-butylphenyl)pyrrolidine-2,5-diyl)bis(2-amino-5,1-phenylene)bis(azanediyl)bis(oxomethylene))dipyrrolidine-1-carboxylate (0.355 g) was dissolved in neat acetic acid (3 mL) and heated at 72° C. for 2 hours. The solution was concentrated and then poured into water where the pH was adjusted to ~7-8 with sodium bicarbonate. The product was extracted into dichloromethane, concentrated and purified by chromatography on silica gel with a 40 g column, eluting with 0-5% methanol/dichloromethane to give 0.185 g (55%) of the title compound as a light yellow solid.

Illustration of General Procedure 10: General Procedure 10A; Example 2

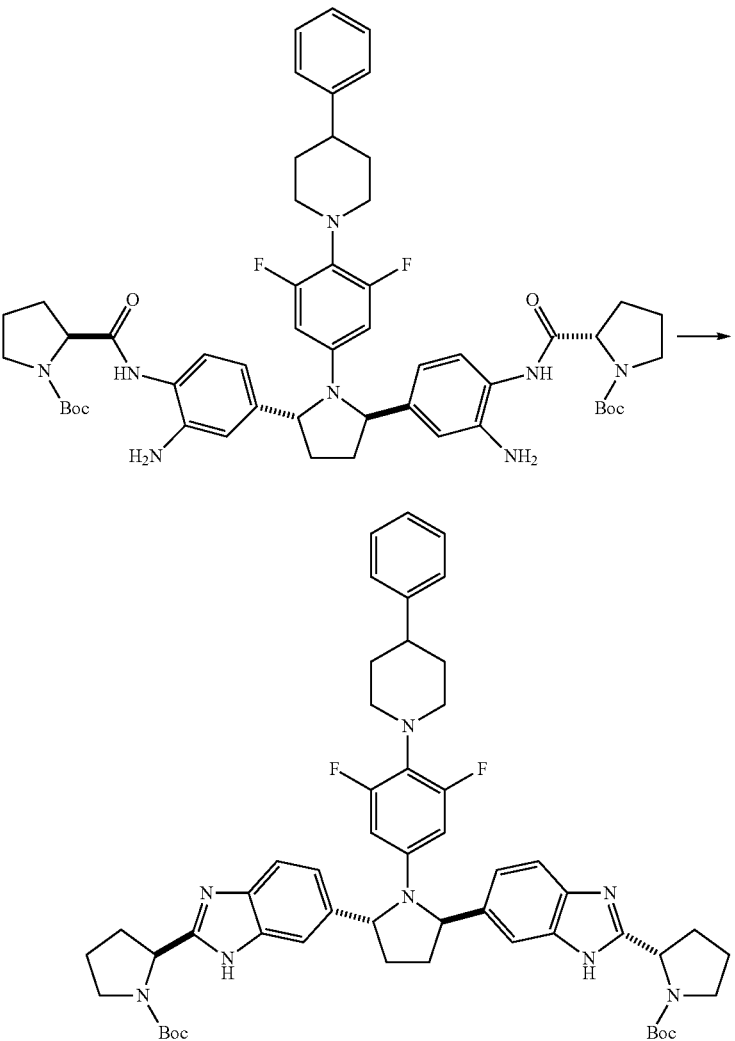

323

(2S,2'S)-tert-butyl 2,2'-(6,6'-((2R,5R)-1-(3,5-difluoro-4-(4-phenylpiperidin-1-yl)phenyl)pyrrolidine-2,5-diyl)bis(1H-benzo[d]imidazole-6,2-diyl))dipyrrolidine-1-carboxylate

A solution of (2S,2'S)-tert-butyl 2,2'-(4,4'-((2R,5R)-1-(3,5-difluoro-4-(4-phenylpiperidin-1-yl)phenyl)pyrrolidine-2,5-diyl)bis(2-amino-4,1-phenylene))bis(azanediyl)bis(oxomethylene)dipyrrolidine-1-carboxylate (2.4 g, 2.57 mmol) and acetic acid (1.54 g, 25.7 mmol) in toluene (50 mL) was heated at 70° C. for 2 hours, cooled and concentrated. The residue was azeotroped 3×15 mL with toluene and dried under vacuum to give a yellow foam (2.34 g, quantitative yield) that was used without purification. MS (ESI+) m/z 913 (M+H)$^+$.

Illustration of General Procedure 10: General Procedure 10A; Example 3

(2S,2'S)-tert-butyl 2,2'-(6,6'-((2R,5R)-1-(3,5-difluoro-4-(piperidin-1-yl)phenyl)pyrrolidine-2,5-diyl)bis(5-fluoro-1H-benzo[d]imidazole-6,2-diyl))dipyrrolidine-1-carboxylate

To crude tert-butyl 2,2'-(4,4'-((2R,5R)-1-(3,5-difluoro-4-(piperidin-1-yl)phenyl)pyrrolidine-2,5-diyl)bis(2-amino-5-fluoro-4,1-phenylene))bis(azanediyl)bis(oxomethylene)dipyrrolidine-1-carboxylate (from General Procedure 9A, Example 2) was added toluene (45 ml) followed by acetic acid (2.66 ml, 46.4 mmol) and the solution was stirred at 50° C. for 16 hours. The cooled solution was concentrated, azeotroped twice with toluene, and the crude residue was purified on an ISCO 40 g silica gel cartridge eluting with 0-5% CH$_3$OH/CH$_2$Cl$_2$ to give the title compound (2.85 g).

Illustration of General Procedure 10: General Procedure 10B, Example 1

324 methyl {(2S)-1-[(2S)-2-{5-[(2R,5R)-1-(4-chloro-3-fluorophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (ACD Name v12)

Dimethyl (2S,2'S)-1,1'-((2S,2'S)-2,2'-(4,4'-((2R,5R)-1-(4-chloro-3-fluorophenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate (General Procedure 9D) (0.98 g, 1.01 mmol) was dissolved in toluene (12 mL) and treated with glacial acetic acid (1.16 mL, 20.2 mmol) and heated at 65° C. for 1.5 hours. The mixture was concentrated, dissolved in dichloromethane, and washed with sodium bicarbonate solution. The organic reaction mixture was concentrated and purified by chromatography, eluting with 0-6% methanol in dichloromethane to give 0.17 g (19%) of the title compound as a dark yellow solid. $^1$H NMR (400 MHz, DMSO-d$_6$) δ ppm 0.77-0.90 (m, 12H) 1.66-1.78 (m, 2H) 1.88-1.95 (m, 2H) 1.96-2.06 (m, 4H) 2.15-2.24 (m, 4H) 2.54-2.60 (m, 2H) 3.54 (s, 6H) 3.79-3.86 (m, 4H) 4.06 (t, J=8.46 Hz, 2H) 5.10-5.18 (m, 2H) 5.37-5.45 (m, 2H) 6.16 (dd, J=9.49, 2.01 Hz, 1H) 6.22 (dd, J=13.55, 2.06 Hz, 1H) 7.00-7.11 (m, 3H) 7.22 (s, 1H) 7.28 (d, J=8.57 Hz, 2H) 7.32 (s, 1H) 7.40 (d, J=8.24 Hz, 1H) 7.47 (d, J=8.13 Hz, 1H) 12.07 (d, J=2.93 Hz, 2H); MS (APCI+) m/z 884 (M+H)$^+$.

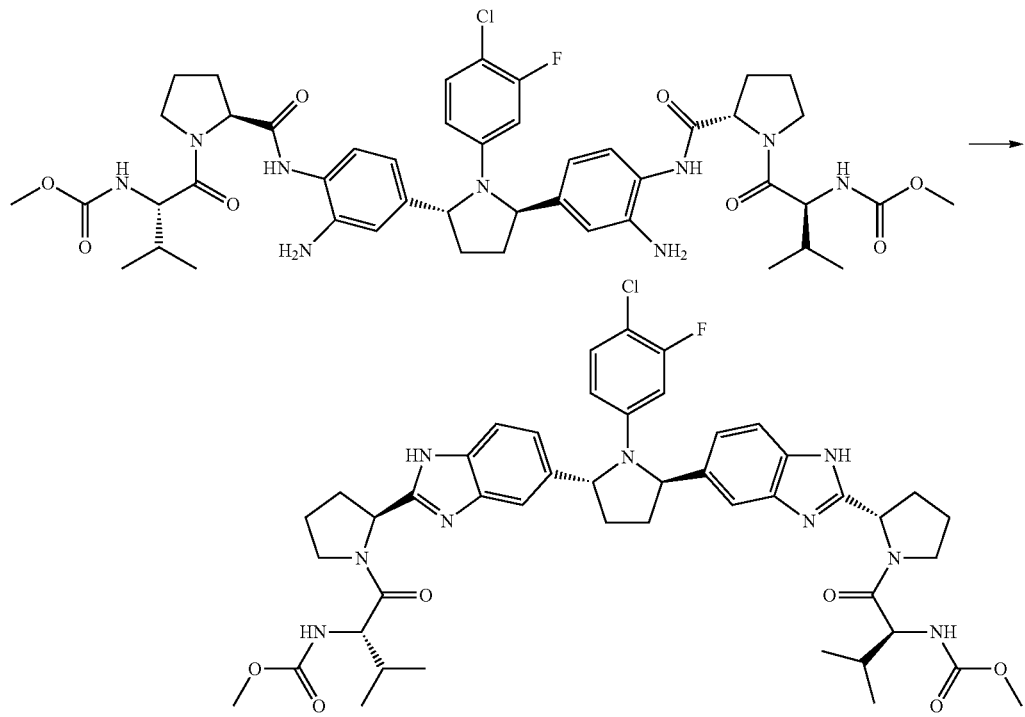

Illustration of General Procedure 10: General Procedure 10B; Example 2

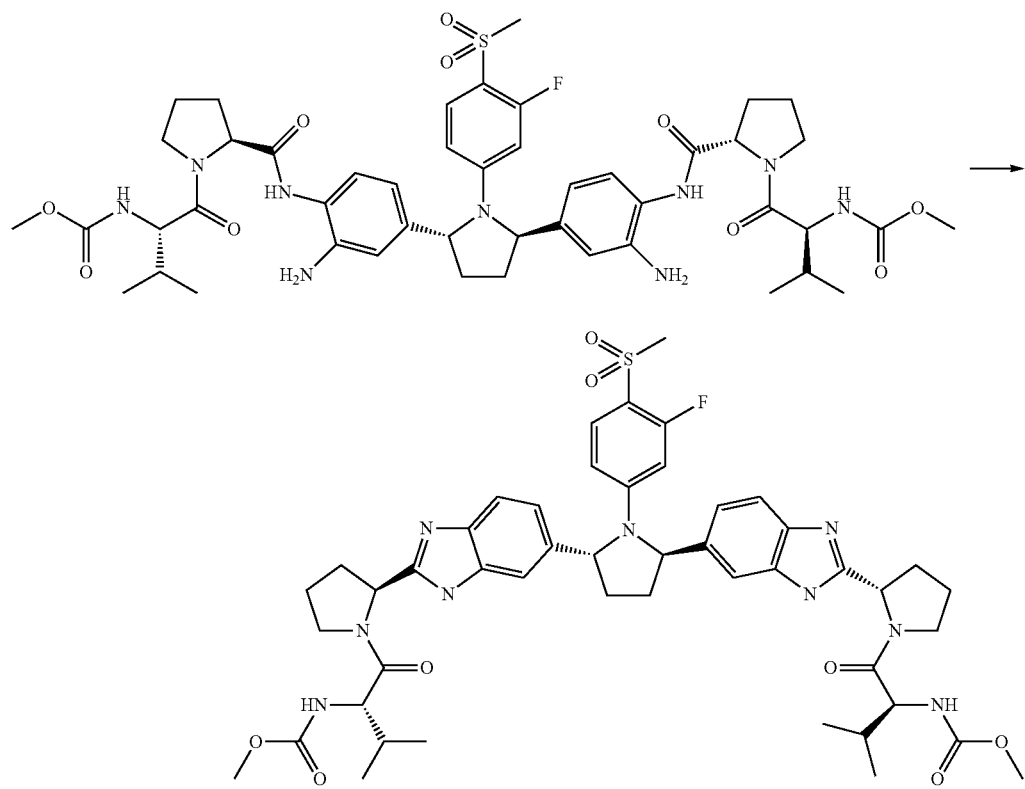

methyl {(2S)-1-[(2S)-2-{6-[(2R,5R)-1-[3-fluoro-4-(methylsulfonyl)phenyl]-5-{2-[(2S)-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate (ACD Name v12)

To a suspension of dimethyl (2S,2'S)-1,1'-((2S,2'S)-2,2'-(4,4'-((2R,5R)-1-(3-fluoro-4-(methylsulfonyl)phenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate (0.190 g, 0.197 mmol) in toluene (2 mL) was added acetic acid (1 mL, 17.48 mmol), and the reaction mixture was stirred at 60° C. overnight. LCMS shows completion of reaction. The reaction mixture was diluted with ethyl acetate and washed with a saturated solution of NaHCO₃. The organic extract was separated, dried over anhydrous sodium sulfate, filtered, concentrated on a rotovap and purified by reverse phase HPLC using 5-100% acetonitrile/water (TFA). Pure fractions were combined, neutralized with saturated solution of NaHCO₃, and concentrated. The residue was extracted with CH₂Cl₂. The organic extract was separated, dried over anhydrous sodium sulfate, filtered, and concentrated to supply the title compound (30 mg) as a white solid.

General Procedure 11. Procedure to Remove t-Butoxycarbonyl Protecting Groups

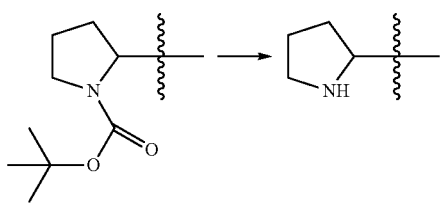 [SMILES: *C1CCCN1C(=O)OC(C)(C)C ; *C1CCCN1]

Removal of a t-butoxycarbonyl (Boc) protecting group, according to the above depiction can be effected using standard conditions such as by treatment with an acid, such as TFA, HCl, or formic acid. For example, reaction with TFA/CH₂Cl₂ or HCl in dioxane at room temperature can remove the Boc protecting group. Compounds may be used or isolated as the salt or free base.

After removal of the Boc-protecting groups and in cases where compounds have been processed through as mixtures of cis,

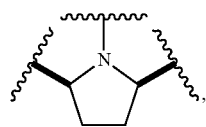 [SMILES: *[C@@H]1CC[C@H](*)N1*]

and trans,

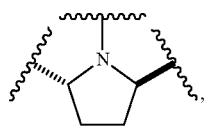 [SMILES: *[C@H]1CC[C@H](*)N1*]

pyrrolidines, the cis and trans diastereomers may be subject to separation using standard chromatographic methods (e.g., normal phase silica gel or reverse phase). For example, compounds of general type 11-1 and 11-2 can be separated in this manner.

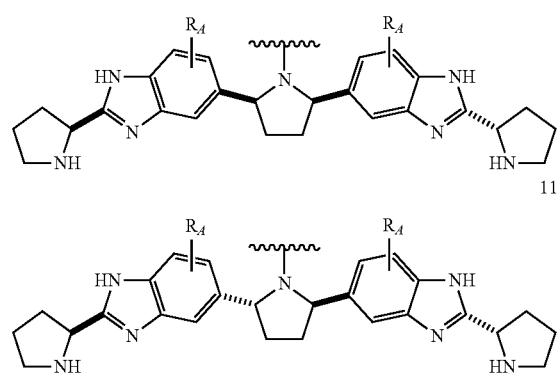

11-1

11-2

Illustration of General Procedure 11. General Procedure 11A (HCl-Dioxane), Example 1

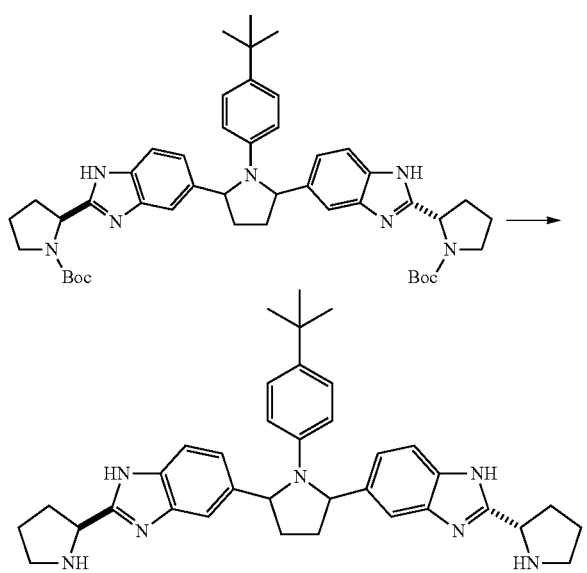

S)-5,5'-(1-(4-tert-butylphenyl)pyrrolidine-2,5-diyl) bis(2-((S)-pyrrolidin-2-yl)-1H-benzo[d]imidazole (2S,2'S)-tert-Butyl 2,2'-(5,5'-(1-(4-tert-butylphenyl)pyrrolidine-2,5-diyl)bis(1H-benzo[d]imidazole-5,2-diyl))dipyrrolidine-1-carboxylate (0.204 g, 0.264 mmol) was dissolved in THF (2 mL) at room temperature and treated with 4 M HCl in dioxane (2 mL). After completion of the reaction, the mixture was concentrated to dryness to provide the crude title compound.

Illustration of General Procedure 11. General Procedure 11A (HCl-Dioxane), Example 2

S)-6,6'-((2R,5R)-1-(3,5-difluoro-4-(4-phenylpiperidin-1-yl)phenyl)pyrrolidine-2,5-diyl)bis(2-((S)-pyrrolidin-2-yl)-1H-benzo[d]imidazole A solution of (2S,2'S)-tert-butyl 2,2'-(6,6'-((2R,5R)-1-(3,5-difluoro-4-(4-phenylpiperidin-1-yl)phenyl)pyrrolidine-2,5-diyl)bis(1H-benzo[d]imidazole-6,2-diyl))dipyrrolidine-1-carboxylate (2.34 g, 2.57 mmol) in dioxane (25 mL) was treated with 4 M hydrogen chloride in dioxane (16.06 mL, 64.3 mmol) to give a tan suspension. The mixture was sonicated for 10 minutes to break up solids into a fine suspension, stirred for 2 hours and concentrated. The residue was azeotroped 3×30 mL with toluene and dried to give the HCl salt of the title compound as a tan powder that was used without purification (assume quantitative yield, 2.57 mmol). MS (ESI+) m/z 713 (M+H)$^+$.

Illustration of General Procedure 11. General Procedure 11A (HCl-Dioxane), Example 3

6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12)

To a solution of (2S,2'S)-tert-butyl 2,2'-(6,6'-((2R,5R)-1-(3,5-difluoro-4-(piperidin-1-yl)phenyl)pyrrolidine-2,5-diyl) bis(5-fluoro-1H-benzo[d]imidazole-6,2-diyl))dipyrrolidine-1-carboxylate (2.85 g, 3.26 mmol) in dioxane (10 ml) was added 4 M HCl/dioxane (10.0 mL, 40.0 mmol) and the solution was vigorously stirred at room temperature for 1 hour. The solution was concentrated, dissolved in minimal H$_2$O and applied to an ISCO 130 g C18 cartridge and eluted with 0-100% CH$_3$CN/(0.1% TFA/H$_2$O). Desired fractions were combined, made basic with 10% NaHCO$_3$ solution, and extracted with EtOAc. The combined extracts were dried (MgSO$_4$), filtered and concentrated to give the title compound (932.5 mg, 1.386 mmol, 42.5%).

Illustration of General Procedure 11. General Procedure 11B (TFA-CH$_2$Cl$_2$)

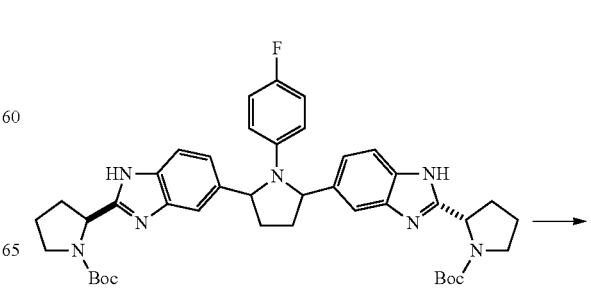

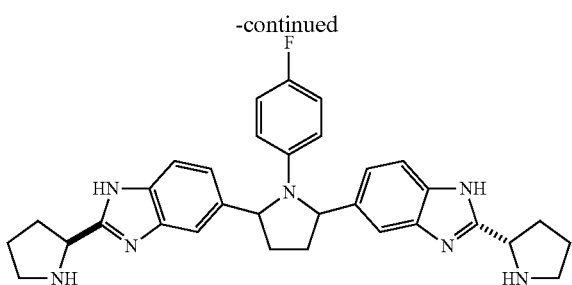

(S)-5,5'-(1-(4-fluorophenyl)pyrrolidine-2,5-diyl)bis(2-((S)-pyrrolidin-2-yl)-1H-benzo[d]imidazole (2S,2'S)-tert-Butyl 2,2'-(5,5'-(1-(4-fluorophenyl)pyrrolidine-2,5-diyl)bis(1H-benzo[d]imidazole-5,2-diyl))dipyrrolidine-1-carboxylate (0.120 g, 0.163 mmol) was dissolved in dichloromethane (2 mL) at room temperature and treated with TFA (1 mL). The mixture was concentrated to dryness, dissolved in 25% isopropanol/dichloromethane and washed with sodium bicarbonate solution. The resulting solids were filtered off and dried. The organic filtrate was concentrated and dried to give the more title compound. The batches of off-white solid were combined to give the titled compound (0.062 g 72% yield).

The following compounds as free base or salt can be made using General Procedure 8, General Procedure 9A (PtO$_2$), General Procedure 10/10A, and General Procedure 11/11A:

(S)-6,6'-((2R,5R)-1-(4-(pyridin-2-yl)phenyl)pyrrolidine-2,5-diyl)bis(2-((S)-pyrrolidin-2-yl)-1H-benzo[d]imidazole);

(S)-6,6'-((2R,5R)-1-(3-chloro-4-(trifluoromethoxy)phenyl)pyrrolidine-2,5-diyl)bis(2-((S)-pyrrolidin-2-yl)-1H-benzo[d]imidazole);

(S)-6,6'-((2R,5R)-1-(4-(2-methoxyethoxy)phenyl)pyrrolidine-2,5-diyl)bis(2-((S)-pyrrolidin-2-yl)-1H-benzo[d]imidazole);

(S)-6,6'-((2R,5R)-1-(4-chlorophenyl)pyrrolidine-2,5-diyl)bis(2-((S)-pyrrolidin-2-yl)-1H-benzo[d]imidazole);

(S)-6,6'-((2R,5R)-1-(3-methyl-4-(piperidin-1-yl)phenyl)pyrrolidine-2,5-diyl)bis(2-((S)-pyrrolidin-2-yl)-1H-benzo[d]imidazole);

(S)-6,6'-((2S,5S)-1-(4-cyclopropyl-3,5-difluorophenyl)pyrrolidine-2,5-diyl)bis(2-((S)-pyrrolidin-2-yl)-1H-benzo[d]imidazole);

(S)-6,6'-((2S,5S)-1-(4-cyclopropyl-2-fluorophenyl)pyrrolidine-2,5-diyl)bis(2-((S)-pyrrolidin-2-yl)-1H-benzo[d]imidazole);

(S)-6,6'-((2R,5R)-1-(3-fluoro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(trifluoromethyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4-tert-butylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(4-(4,4-dimethylpiperidin-1-yl)-3,5-difluorophenyl)pyrrolidine-2,5-diyl)bis(2-((S)-pyrrolidin-2-yl)-1H-benzo[a]imidazole);

(S)-6,6'-((2R,5R)-1-(3,5-difluoro-4-(6-azaspiro[2.5]octan-6-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(isoindolin-2-yl)phenyl)pyrrolidine-2,5-diyl)bis(2-((S)-pyrrolidin-2-yl)-1H-benzo[d]imidazole);

2-(4-((2R,5R)-2,5-bis(2-((S)-pyrrolidin-2-yl)-1H-benzo[d]imidazol-6-yl)pyrrolidin-1-yl)-2,6-difluorophenyl)-2-azabicyclo[2.2.2]octane;

(S)-6,6'-((2R,5R)-1-(3,5-difluoro-4-(4-isopropylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(3,3-dimethylazetidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(4-(4-phenylpiperidin-1-yl)phenyl)pyrrolidine-2,5-diyl)bis(2-((S)-pyrrolidin-2-yl)-1H-benzo[d]imidazole);

6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12);

(S)-6,6'-((2S,5R)-1-(3,5-difluoro-4-(piperidin-1-yl)phenyl)pyrrolidine-2,5-diyl)bis(5-fluoro-2-((S)-pyrrolidin-2-yl)-1H-benzo[d]imidazole)

(S,S,S)-6,6'-((2R,5R)-1-(3,5-difluoro-4-(piperidin-1-yl)phenyl)pyrrolidine-2,5-diyl)bis(5-fluoro-2-((2S,3aS,6aS)-octahydrocyclopenta[b]pyrrol-2-yl)-1H-benzo[d]imidazole);

(S,S,S)-6,6'-((2R,5R)-1-(3,5-difluoro-4-(piperidin-1-yl)phenyl)pyrrolidine-2,5-diyl)bis(2-((2S,3aS,6aS)-octahydrocyclopenta[b]pyrrol-2-yl)-1H-benzo[d]imidazole);

(S)-6,6'-((2R,5R)-1-(4-(2,3-dihydrospiro[indene-1,4'-piperidine]-1'-yl)-3,5-difluorophenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-(4-methoxyphenyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-fluoro-4-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4-fluoro-4-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(fluorodiphenylmethyl)piperidin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-phenylpiperidin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-(4-fluorophenyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(3-(trimethylsilyl)phenyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4-(3,4-difluorophenyl)piperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(4-(4-(3,5-difluorophenyl)piperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(4-(trifluoromethyl)phenyl)piperazin-1-yl)phenyl)pyrrolidine-2,5-diyl)bis(5-fluoro-2-((S)-pyrrolidin-2-yl)-1H-benzo[d]imidazole);

6-((2R,5R)-1-(3,5-difluoro-4-(piperidin-1-yl)phenyl)-5-(2-((S)-pyrrolidin-2-yl)-1H-benzo[d]imidazol-6-yl)pyrrolidin-2-yl)-5-fluoro-2-((S)-pyrrolidin-2-yl)-1H-benzo[d]imidazole;

(S)-6,6'-((2R,5R)-1-(4-(4-benzylpiperidin-1-yl)-3,5-difluorophenyl)pyrrolidine-2,5-diyl)bis(5-fluoro-2-((S)-pyrrolidin-2-yl)-1H-benzo[d]imidazole);

(S)-6,6'-((2R,5R)-1-(4-(4-benzylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2S,5R)-1-(3,5-difluoro-4-(4-phenylpiperidin-1-yl)phenyl)pyrrolidine-2,5-diyl)bis(2-((S)-pyrrolidin-2-yl)-1H-benzo[d]imidazole);

4-(4-((2R,5R)-2,5-bis(2-((S)-pyrrolidin-2-yl)-1H-benzo[d]imidazol-6-yl)pyrrolidin-1-yl)-2,6-difluorophenyl)-2-phenylmorpholine;

(S)-6,6'-((2R,5R)-1-(3,5-difluoro-4-(2-phenylpiperidin-1-yl)phenyl)pyrrolidine-2,5-diyl)bis(2-((S)-pyrrolidin-2-yl)-1H-benzo[d]imidazole);

(2S,6R)-4-(4-((2R,5R)-2,5-bis(5-fluoro-2-((S)-pyrrolidin-2-yl)-1H-benzo[d]imidazol-6-yl)pyrrolidin-1-yl)-2,6-difluorophenyl)-2,6-dimethylmorpholine;

(S)-6,6'-((2R,5R)-1-(3,5-difluoro-4-(3-azaspiro[5.5]undecan-3-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(4-(4-cyclohexylpiperidin-1-yl)-3,5-difluorophenyl)pyrrolidine-2,5-diyl)bis(5-fluoro-2-((S)-pyrrolidin-2-yl)-1H-benzo[d]imidazole);

(S)-4-(4-((2R,5R)-2,5-bis(5-fluoro-2-((S)-pyrrolidin-2-yl)-1H-benzo[d]imidazol-6-yl)pyrrolidin-1-yl)-2,6-difluorophenyl)-2-phenylmorpholine;

(S)-6,6'-((2R,5R)-1-(3,5-difluoro-4-(4-phenylpiperazin-1-yl)phenyl)pyrrolidine-2,5-diyl)bis(2-((S)-pyrrolidin-2-yl)-1H-benzo[d]imidazole);

(S,R)-6,6'-((2R,5R)-1-(3,5-difluoro-4-(piperidin-1-yl)phenyl)pyrrolidine-2,5-diyl)bis(2-((2S,4R)-4-fluoropyrrolidin-2-yl)-1H-benzo[d]imidazole);

(S)-6,6'-((2R,5R)-1-(4-(4-(2,6-difluorophenyl)piperazin-1-yl)-3,5-difluorophenyl)pyrrolidine-2,5-diyl)bis(5-fluoro-2-((S)-pyrrolidin-2-yl)-1H-benzo[d]imidazole);

(S)-6,6'-((2R,5R)-1-(4-(4-(3,4-difluorophenyl)piperidin-1-yl)-3,5-difluorophenyl)pyrrolidine-2,5-diyl)bis(5-fluoro-2-((S)-pyrrolidin-2-yl)-1H-benzo[d]imidazole); and (S)-6,6'-((2R,5R)-1-(3,5-difluoro-4-(4-(4-fluorophenyl)piperidin-1-yl)phenyl)pyrrolidine-2,5-diyl)bis(5-fluoro-2-((S)-pyrrolidin-2-yl)-1H-benzo[d]imidazole).

The following compounds as free base or salt can be made using General Procedure 8, General Procedure 9B (Raney-nickel), General Procedure 10/10A, and General Procedure 11/11A:

(S)-6,6'-((2R,5R)-1-(biphenyl-4-yl)pyrrolidine-2,5-diyl)bis(2-((S)-pyrrolidin-2-yl)-1H-benzo[d]imidazole);

(S)-6,6'-((2R,5R)-1-(4-(cyclopentyloxy)-3-fluorophenyl)pyrrolidine-2,5-diyl)bis(2-((S)-pyrrolidin-2-yl)-1H-benzo[d]imidazole);

(S)-6,6'-((2R,5R)-1-(3,5-difluoro-4-((3aR,7aS)-1H-isoindol-2(3H,3aH,4H,5H,6H,7H,7aH)-yl)phenyl)pyrrolidine-2,5-diyl)bis(2-((S)-pyrrolidin-2-yl)-1H-benzo[d]imidazole);

(S)-6,6'-((2R,5R)-1-(3,5-dichloro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(2,5-difluoro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-((2R,6S)-2,6-dimethylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(2,3,5-trifluoro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-cyclohexyl-3-fluorophenyl)pyrrolidine-2,5-diyl)bis(2-((S)-pyrrolidin-2-yl)-1H-benzo[d]imidazole);

(S)-6,6'-((2R,5R)-1-(3,4-difluorophenyl)pyrrolidine-2,5-diyl)bis(2-((S)-pyrrolidin-2-yl)-1H-benzo[d]imidazole);

(S)-6,6'-((2R,5R)-1-(4-ethoxyphenyl)pyrrolidine-2,5-diyl)bis(2-((S)-pyrrolidin-2-yl)-1H-benzo[d]imidazole);

(S)-6,6'-((2R,5R)-1-(4-(2,2-difluoroethoxy)phenyl)pyrrolidine-2,5-diyl)bis(2-((S)-pyrrolidin-2-yl)-1H-benzo[d]imidazole);

(S)-6,6'-((2R,5R)-1-(4-(3,5-dimethylpiperidin-1-yl)-3,5-difluorophenyl)pyrrolidine-2,5-diyl)bis(2-((S)-pyrrolidin-2-yl)-1H-benzo[d]imidazole);

6,6'-{(2R,5R)-1-[4-(pentafluoro-$\lambda^6$-sulfanyl)phenyl]pyrrolidine-2,5-diyl}bis{2-[(2S)-pyrrolidin-2-yl]-1H-benzimidazole} (ACD Name v12);

(S)-6,6'-((2S,5S)-1-(4-cyclopropylphenyl)pyrrolidine-2,5-diyl)bis(2-((S)-pyrrolidin-2-yl)-1H-benzo[d]imidazole);

(S)-6,6'-((2R,5R)-1-(4-tert-butylphenyl)pyrrolidine-2,5-diyl)bis(2-((S)-pyrrolidin-2-yl)-1H-benzo[d]imidazole);

(S,S)-6,6'-((2R,5R)-1-(3,5-difluoro-4-(piperidin-1-yl)phenyl)pyrrolidine-2,5-diyl)bis(2-((2S,4S)-4-methoxypyrrolidin-2-yl)-1H-benzo[d]imidazole);

(S,S)-6,6'-((2R,5R)-1-(3,5-difluoro-4-(piperidin-1-yl)phenyl)pyrrolidine-2,5-diyl)bis(2-((2S,4S)-4-fluoropyrrolidin-2-yl)-1H-benzo[d]imidazole);

(S,S)-6,6'-((2R,5R)-1-(4-fluorophenyl)pyrrolidine-2,5-diyl)bis(2-((2S,4S)-4-fluoropyrrolidin-2-yl)-1H-benzo[d]imidazole);

(S,S)-6,6'-((2R,5R)-1-(4-fluorophenyl)pyrrolidine-2,5-diyl)bis(2-((2S,4S)-4-methoxypyrrolidin-2-yl)-1H-benzo[d]imidazole);

(S)-6,6'-((2R,5R)-1-(4-tert-butylphenyl)pyrrolidine-2,5-diyl)bis(2-((S)-5,5-dimethylpyrrolidin-2-yl)-1H-benzo[d]imidazole);

(S,S)-6,6'-((2R,5R)-1-(4-tert-butylphenyl)pyrrolidine-2,5-diyl)bis(2-((2S,4S)-4-fluoropyrrolidin-2-yl)-1H-benzo[d]imidazole);

(S)-6,6'-((2R,5R)-1-(3,5-difluoro-4-(piperidin-1-yl)phenyl)pyrrolidine-2,5-diyl)bis(2-((3S)-2-azabicyclo[2.2.1]heptan-3-yl)-1H-benzo[d]imidazole);

(S)-6,6'-((2R,5R)-1-(3,5-difluoro-4-(piperidin-1-yl)phenyl)pyrrolidine-2,5-diyl)bis(2-((S)-indolin-2-yl)-1H-benzo[d]imidazole);

(S,R)-6,6'-((2R,5R)-1-(3,5-difluoro-4-(piperidin-1-yl)phenyl)pyrrolidine-2,5-diyl)bis(2-((2S,4R)-4-methoxypyrrolidin-2-yl)-1H-benzo[d]imidazole);

(S)-6,6'-((2R,5R)-1-(4-tert-butylphenyl)pyrrolidine-2,5-diyl)bis(2-((S)-4-methylenepyrrolidin-2-yl)-1H-benzo[d]imidazole);

(S)-6,6'-((2R,5R)-1-(4-(4,4-diphenylpiperidin-1-yl)-3,5-difluorophenyl)pyrrolidine-2,5-diyl)bis(2-((S)-pyrrolidin-2-yl)-1H-benzo[d]imidazole);

1-(1-(4-((2R,5R)-2,5-bis(2-((S)-pyrrolidin-2-yl)-1H-benzo[d]imidazol-6-yl)pyrrolidin-1-yl)-2,6-difluorophenyl)-4-phenylpiperidin-4-yl)ethanone;

(S)-6,6'-((2R,5R)-1-(3,5-difluoro-4-(piperidin-1-yl)phenyl)pyrrolidine-2,5-diyl)bis(2-((S)-pyrrolidin-2-yl)-1H-benzo[d]imidazole);

(S,S,S)-6,6'-((2R,5R)-1-(3,5-difluoro-4-(piperidin-1-yl)phenyl)pyrrolidine-2,5-diyl)bis(2-((2S,3aS,6aS)-octahydrocyclopenta[b]pyrrol-2-yl)-1H-benzo[d]imidazole);

(S,S,S)-6,6'-((2R,5R)-1-(4-tert-butylphenyl)pyrrolidine-2,5-diyl)bis(2-((2S,3aS,6aS)-octahydrocyclopenta[b]pyrrol-2-yl)-1H-benzo[d]imidazole);

(S)-6,6'-((2R,5R)-1-(3,5-difluoro-4-(3-azaspiro[5.5]unde-can-3-yl)phenyl)pyrrolidine-2,5-diyl)bis(2-((S)-pyrroli-din-2-yl)-1H-benzo[d]imidazole);

(S)-6,6'-((2R,5R)-1-(3-fluoro-4-(4-phenylpiperidin-1-yl)phenyl)pyrrolidine-2,5-diyl)bis(2-((S)-pyrrolidin-2-yl)-1H-benzo[d]imidazole);

(S,S,S)-6,6'-((2R,5R)-1-(3,5-difluoro-4-(4-phenylpiperidin-1-yl)phenyl)pyrrolidine-2,5-diyl)bis(2-((2S,3aS,6aS)-oc-tahydrocyclopenta[b]pyrrol-2-yl)-1H-benzo[d]imida-zole);

(S)-6,6'-((2R,5R)-1-(3,5-difluoro-4-(4-(naphthalen-2-yl)pi-peridin-1-yl)phenyl)pyrrolidine-2,5-diyl)bis(5-fluoro-2-((S)-pyrrolidin-2-yl)-1H-benzo[d]imidazole); and (S)-6,6'-((2R,5R)-1-(4-(benzyloxy)phenyl)pyrrolidine-2,5-diyl)bis(2-((S)-pyrrolidin-2-yl)-1H-benzo[d]imidazole).

Illustration of General Procedure 11. General Procedure 11C (monodeprotection)

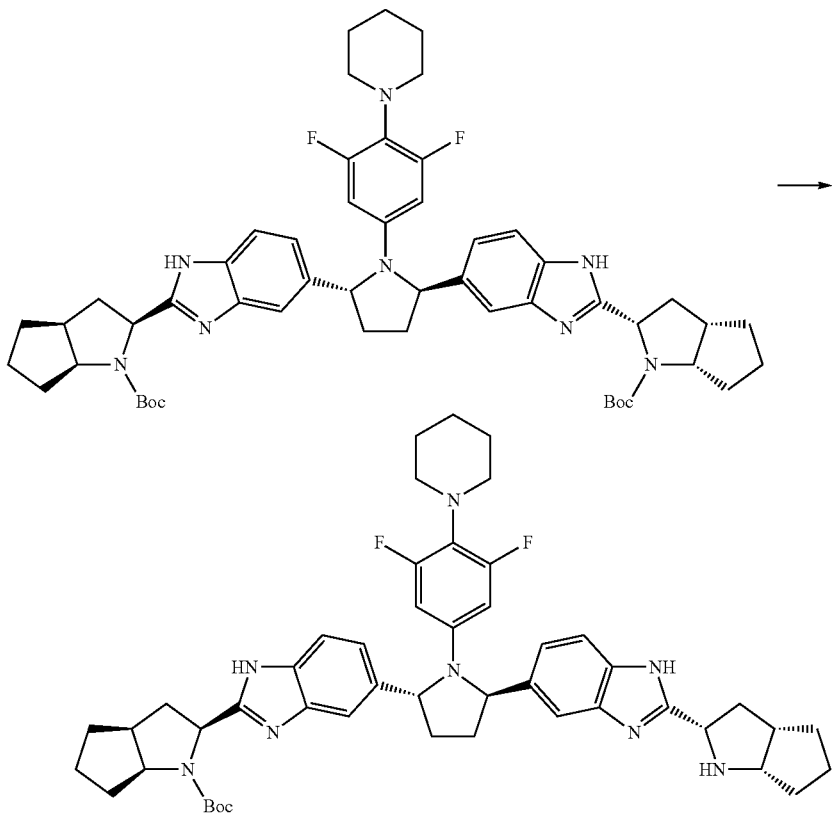

(S)-6,6'-((2R,5R)-1-(3,5-difluoro-4-(3-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(3-phenylpyrrolidin-1-yl)phenyl)pyrrolidine-2,5-diyl)bis(2-((S)-pyrrolidin-2-yl)-1H-benzo[d]imidazole); and (S)-6,6'-((2R,5R)-1-(3,5-difluoro-4-(4-(pyrimidin-2-yl)pip-erazin-1-yl)phenyl)pyrrolidine-2,5-diyl)bis(5-fluoro-2-((S)-pyrrolidin-2-yl)-1H-benzo[d]imidazole).

The following compounds as free base or salt can be made using General Procedure 8, General Procedure 9E (Fe/NH4Cl), General Procedure 10/10A, and General Procedure 11/11A:

(S)-6,6'-((2R,5R)-1-(3,5-difluoro-4-(4-(3-phenylpropyl)pip-eridin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(6-azaspiro[2.5]octan-6-yl)phenyl)pyrrolidine-2,5-diyl)bis(5-fluoro-2-((S)-pyr-rolidin-2-yl)-1H-benzo[d]imidazole);

(S)-6,6'-((2R,5R)-1-(4-(4-tert-butylpiperidin-1-yl)-3,5-dif-luorophenyl)pyrrolidine-2,5-diyl)bis(5-fluoro-2-((S)-pyr-rolidin-2-yl)-1H-benzo[d]imidazole);

(2S,3aS,6aS)-tert-butyl 2-(5-((2R,5R)-1-(3,5-dif-luoro-4-(piperidin-1-yl)phenyl)-5-(2-((2S,3aS,6aS)-octahydrocyclopenta[b]pyrrol-2-yl)-1H-benzo[d]imidazol-5-yl)pyrrolidin-2-yl)-1H-benzo[d]imidazol-2-yl)hexahydrocyclopenta[b]pyrrole-1(2H)-carboxylate The starting di-Boc-protected amine (1.24 g, 1.36 mmol) was dissolved in dichloromethane (12 mL) at ambient temperature and treated with aliquots of trifluoroacetic acid (0.10 mL, 1.35 mmol) every thirty minutes for 1.5 hours. The solution was concentrated to dryness then re-dissolved into dichloromethane and washed with sodium bicarbonate solution. After concentration, the residue was purified by chromatography, eluting with 0-20% methanol in dichloromethane to give 425 mg (38%) of the title mono-deprotected amine as a yellow powder.

General Procedure 12. Endcap Addition

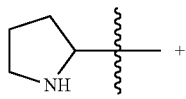 + but not limited to, 2-(methoxycarbonylamino)-3-methylbutanoic acid, 2-(methoxycarbonylamino)-3,3-dimethylbutanoic acid, 2-cyclohexyl-2-(methoxycarbonylamino)acetic acid, 2-(methoxycarbonylamino)-2-(tetrahydro-2H-pyran-4-yl)acetic acid, or those listed below under General Procedure 19.

Illustration of General Procedure 12. General Procedure 12A

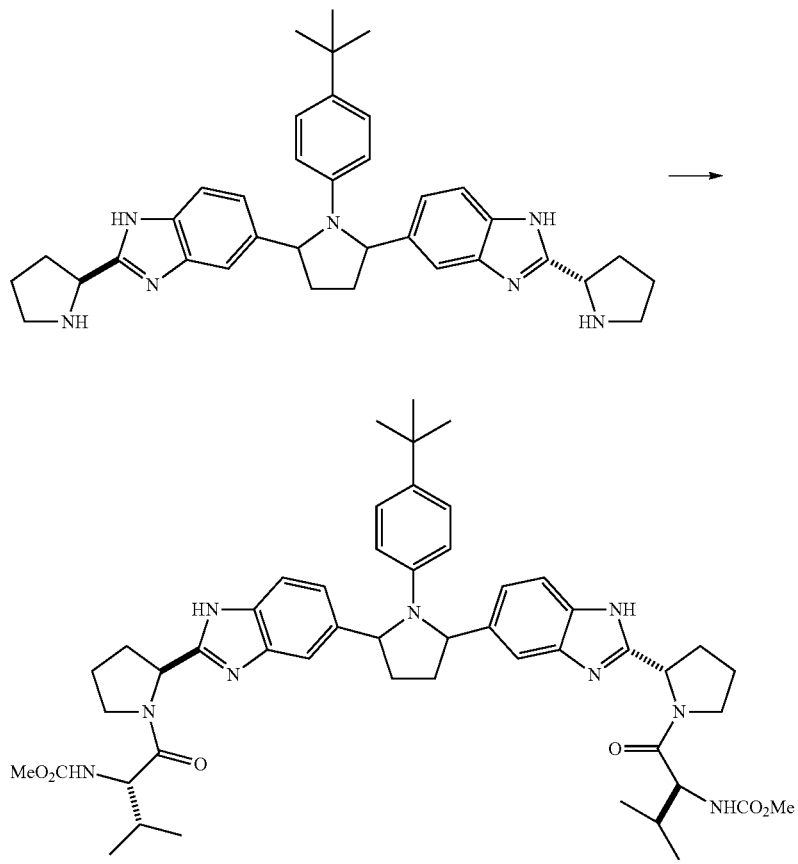

-continued

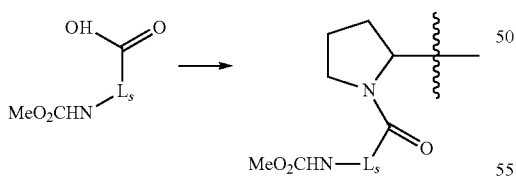

Reaction of an amine with an acid to form an amide as depicted above can be effected as described generally in Scheme 1 and other foregoing Schemes. The reaction can be promoted by a peptide coupling reagent, such as EDAC/HOBT, PyBOP, HATU, T3P or DEPBT, in a solvent such as THF, DMF, dichloromethane, ethyl acetate, or DMSO, with or without the addition of an amine base such as Hunig's base, N-methylmorpholine, pyridine, 2,6-lutidine, or triethylamine, to give amide products. For example, an amine (1 equivalent) can be reacted with acids (2 equivalents) such as, dimethyl (2S,2'S)-1,1'-((2S,2'S)-2,2'-(5,5'-((2R,5R)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate and dimethyl (2S,2'S)-1,1'-((2S,2'S)-2,2'-(5,5'-((2S,5S)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate (S)-5,5'-(1-(4-tert-butylphenyl)pyrrolidine-2,5-diyl)bis(2-((S)-pyrrolidin-2-yl)-1H-benzo[d]imidazole) (0.150 g, 0.261 mmol) and diisopropylethylamine (0.365 mL, 2.09 mmol) were dissolved in DMSO (3 mL) at room temperature and treated with (S)-2-(methoxycarbonylamino)-3-methylbutanoic acid (0.105 g, 0.601 mmol) followed by HATU (0.204 g, 0.536 mmol). The solution was stirred for 1 hour at room temperature then diluted with water. The solid product was filtered off and purified by chromatography on silica gel with a 12 g column, eluting with 0-8% methanol in dichloromethane to give 0.143 g (60%) of a yellow solid as a mixture of trans diastereomers. $^1$H NMR (400 MHz, DMSO-$d_6$) δ ppm 0.75-0.92 (m, 12H) 1.07 (s, 9H) 1.64-1.76 (m, 2H) 1.85-2.04 (m, 6H) 2.12-2.26 (m, 4H) 2.43 (dd, J=7.75, 4.07 Hz, 2H) 3.53 (s, 6H) 3.76-3.87 (m, 4H) 4.04 (dd, J=11.49, 6.51 Hz, 2H) 5.12 (t, J=7.59 Hz, 2H) 5.35 (d, J=3.25 Hz, 2H) 6.25 (d, J=8.46 Hz, 2H) 6.85-6.96 (m, 2H) 7.07 (t, J=7.97 Hz, 2H) 7.19 (s, 1H) 7.28 (d, J=8.35 Hz, 3H) 7.38 (dd, J=8.19, 1.90 Hz, 1H) 7.46 (d, J=8.13 Hz, 1H) 11.97-12.09 (m, 2H).

Illustration of General Procedure 12. General Procedure 12B filtered and evaporated. The residue was purified by chromatography on silica gel eluting with ethyl acetate in hexane (50% to 80%) to give a solid. The solid was triturated with ethyl acetate/hexane to give the title compound (13 mg, 29%) as a mixture of trans diastereomers. $^1$H NMR (400 MHz, DMSO-$d_6$) δ ppm 0.85-0.95 (m, 12H) 1.11 (s, 9H) 1.59-1.65 (m, 2H) 1.79-2.04 (m, 8H) 2.10-2.18 (m, 2H) 2.41-2.46 (m, 2H) 3.52 (s, 6H) 3.57-3.67 (m, 2H) 3.76-3.86 (m, 2H) 4.00 (t, J=7.56 Hz, 2H) 4.39-4.46 (m, 2H) 5.15 (d, J=7.00 Hz, 2H) 6.17 (d, J=7.70 Hz, 2H) 6.94 (d, J=8.78 Hz, 2H) 7.13 (d,

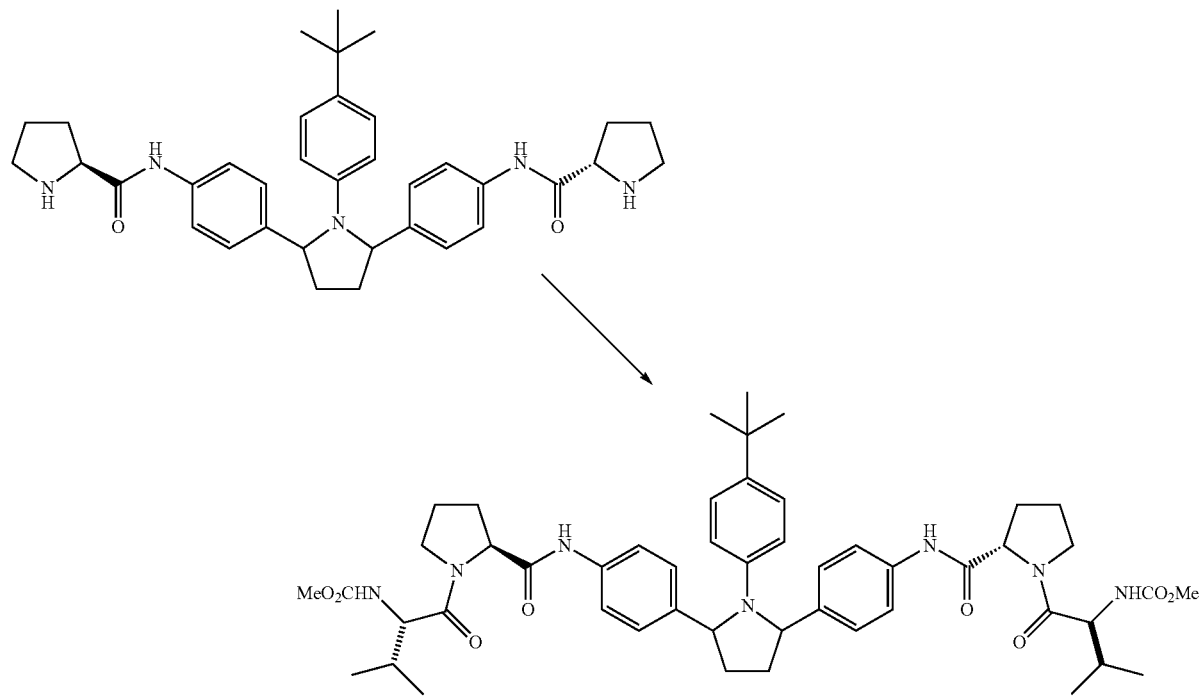

dimethyl (2S,2'S)-1,1'-(((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate and dimethyl (2S,2'S)-1,1'-(((2S,2'S)-2,2'-(4,4'-((2R,5R)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate (2S,2'S)—N,N'-(4,4'-((2S,5S)-1-(4-tert-Butylphenyl)pyrrolidine-2,5-diyl)bis(4,1-phenylene))dipyrrolidine-2-carboxamide and (2S,2'S)—N,N'-(4,4'-((2R,5R)-1-(4-tert-butylphenyl)pyrrolidine-2,5-diyl)bis(4,1-phenylene))dipyrrolidine-2-carboxamide (29.0 mg, 0.050 mmol), (S)-2-(methoxycarbonylamino)-3-methylbutanoic acid (19.27 mg, 0.110 mmol), EDAC (21.09 mg, 0.110 mmol), HOBT (16.85 mg, 0.110 mmol) and N-methylmorpholine (0.027 mL, 0.250 mmol) were combined in DMF (2 mL). The reaction mixture was stirred at room temperature for 3 hours. The mixture was partitioned between ethyl acetate and water. The organic layer was washed with brine twice, dried with sodium sulfate, J=7.37 Hz, 4H) 7.30 (d, J=8.20 Hz, 2H) 7.50 (d, J=8.24 Hz, 4H) 9.98 (s, 2H); MS (ESI+) m/z 895 (M+H)$^+$.

Illustration of General Procedure 12. General Procedure 12C

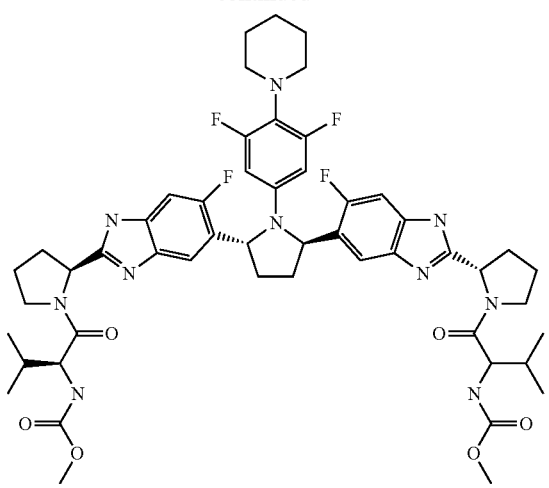

Teledyne/ISCO Combiflash® Rf System using a C18 cartridge eluting with 0-30% $CH_3CN/(0.1\%$ $TFA/H_2O)$ over 30 minutes. The desired fractions were made basic with 10% $NaHCO_3$ solution and extracted with EtOAc. The combined extracts were dried ($Na_2SO_4$), filtered and concentrated to give a white solid (545 mg). This material was then re-purified on a Waters preparative HPLC system using a C18 column eluting with 0-95% $CH_3CN/(0.1\%$ $TFA/H_2O)$ over 40 minutes to give material (195 mg) containing mostly the title compound and a residual amount of a diastereomeric product. To remove remaining amounts of the diastereomer, chiral chromatography was run on this sample using a Chiralpak® IA column (5 cm×15 cm, 20 mL/minute) and eluting with 55/30/15 hexane/THF/[$CH_3OH$/EtOH 8:2] to give the title compound (116 mg, 0.118 mmol). $^1H$ NMR (400 MHz, $CDCl_3$) δ ppm 10.51-10.60 (m, 1H) 10.33-10.41 (m, 1H) 7.43-7.50 (m, 1H) 7.32 (t, 1H) 7.13 (d, 1H) 6.93 (t, 1H) 5.82 (d, 2H) 5.28-5.48 (m, 6H) 4.26-4.39 (m, 2H) 3.78-3.90 (m, 2H) 3.70-3.71 (d, 6H) 3.57-3.67 (m, 2H) 3.44-3.57 (m, 1H) 2.99-3.12 (m, 2H) 2.79-2.98 (m, 4H) 1.78-2.58 (m, 12H) 1.41-1.51 (m, 2H) 0.80-0.95 (m, 12H); MS (ESI) m/z 987 $(M+H)^-$.

General Procedure 14. Chiral Separation

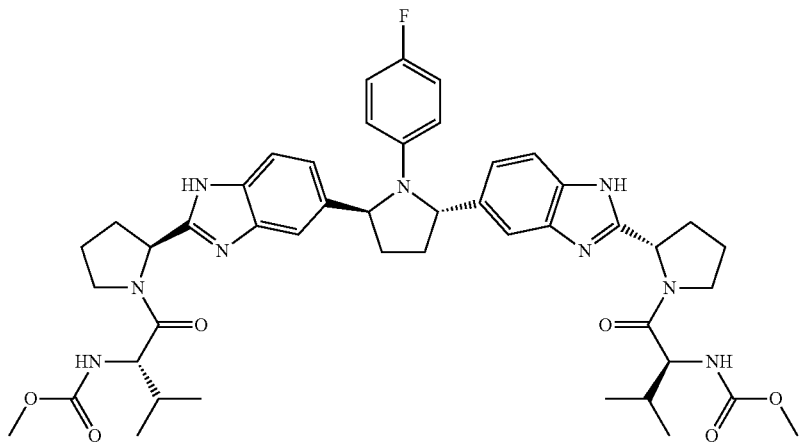

methyl {(2S)-1-[(2S)-2-{5-[(2R,5R)-1-[3,5-difluoro-4-(piperidin-1-yl)phenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate To a solution of (S)-2-(methoxycarbonylamino)-3-methylbutanoic acid (116 mg, 0.660 mmol) in $CH_2Cl_2$ (1.0 mL) was added EDC (127 mg, 0.660 mmol) and the solution was stirred at room temperature for 20 minutes. This solution was then cannulated into a solution of 6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12) (148 mg, 0.220 mmol) and Hunig's base (0.231 ml, 1.320 mmol) in $CH_2Cl_2$ (1.000 mL) followed by the addition of HOBT (101 mg, 0.660 mmol), and the solution was then stirred at room temperature for 1 hour. The solution was diluted with $CH_2Cl_2$, washed with $H_2O$, dried ($Na_2SO_4$), filtered and concentrated. The product may be subject to further purification.

From a separate experiment using the above coupling procedure, crude product (about 4 mmol) was purified on a dimethyl (2S,2'S)-1,1'-((2S,2'S)-2,2'-(5,5'-((2S,5S)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate The mixture of trans diastereomers was chromatographed by chiral chromatography on a Chiralpak IA column eluting with a mixture of hexane/EtOH/$CH_3OH$/1,2-dichloroethane/diethylamine (25/25/25/25/0.1) to give two separate isomers. $^1H$ NMR (400 MHz, DMSO-$d_6$) δ ppm 0.75-0.89 (m, 12H) 1.64-1.73 (m, 2H) 1.85-2.03 (m, 6H) 2.12-2.24 (m, 4H) 2.81-2.90 (m, 2H) 3.52 (s, 6H) 3.76-3.87 (m, 4H) 4.01-4.09 (m, 2H) 5.08-5.16 (m, 2H) 5.34 (q, J=6.65 Hz, 2H) 6.26 (dd, J=9.05, 4.50 Hz, 2H) 6.67-6.78 (m, 2H) 7.03 (t, J=8.02 Hz, 2H) 7.20 (s, 1H) 7.24-7.32 (m, 3H) 7.36 (d, J=8.13 Hz, 1H) 7.44 (d, J=7.92 Hz, 1H) 12.01-12.07 (m, 2H).

and

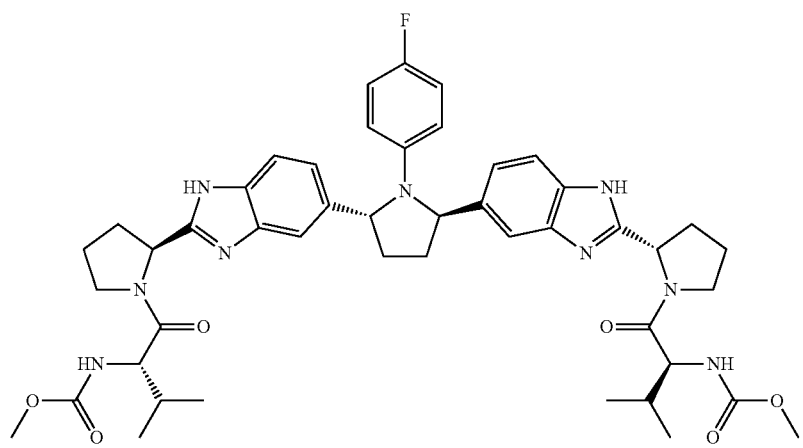

dimethyl (2S,2'S)-1,1'-((2S,2'S)-2,2'-(5,5'-((2R,5R)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate $^1$H NMR (400 MHz, DMSO-d$_6$) δ ppm 0.74-0.93 (m, 12H) 1.69 (t, J=9.65 Hz, 2H) 1.82-2.06 (m, 6H) 2.09-2.26 (m, 4H) 3.04-3.23 (m, 2H) 3.52 (s, 6H) 3.73-3.90 (m, 4H) 4.06 (t, J=8.46 Hz, 2H) 5.05-5.21 (m, 2H) 5.29-5.44 (m, 2H) 6.21-6.32 (m, 2H) 6.67-6.86 (m, 2H) 7.05 (t, J=8.78 Hz, 2H) 7.18 (s, 1H) 7.23-7.33 (m, 3H) 7.37 (d, J=8.13 Hz, 1H) 7.45 (d, J=8.02 Hz, 1H) 12.04 (d, J=14.96 Hz, 2H).

General Procedure 15. Benzimidazole Synthesis through methoxybenzylamine Displacement Route I Shown generally in Scheme VIII, is a method of preparing certain compounds (57) and (59). Illustrated below in General Procedure 15A is a representative synthesis of (57) where D is 4-tert-butylphenyl.

Illustration of General Procedure 15. General Procedure 15A

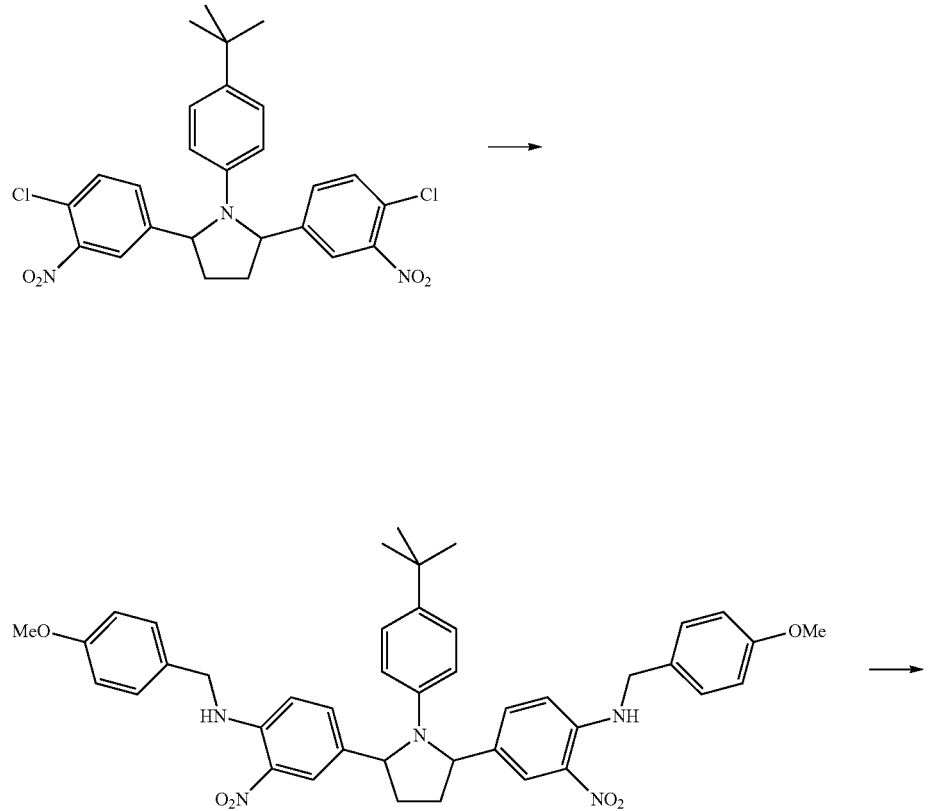

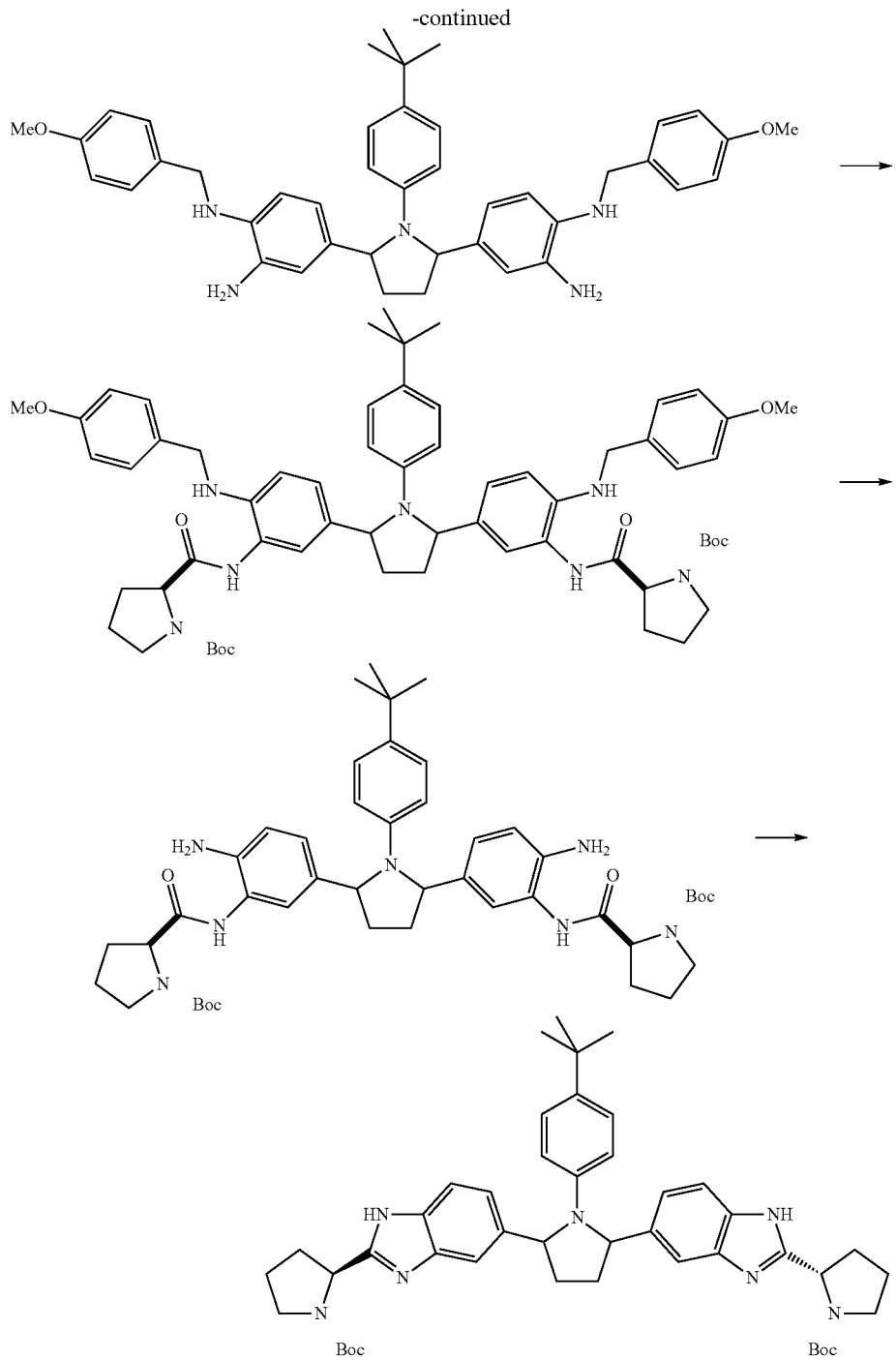

The five steps illustrated above are described by the following experimental procedures:

4,4'-(1-(4-tert-butylphenyl)pyrrolidine-2,5-diyl)bis(N-(4-methoxybenzyl)-2-nitroaniline)

1-(4-tert-Butylphenyl)-2,5-bis(4-chloro-3-nitrophenyl)pyrrolidine (4.41 g, 8.57 mmol) was combined, neat, with p-methoxy benzylamine (8.93 mL, 68.6 mmol) and heated at 145° C. for 1 hour. The mixture was diluted with dichloromethane and filtered. The filtrate was washed with 0.5 Al HCl, NaHCO₃ solution, and then brine. The organic phase was concentrated and purified by chromatography on silica gel with an 80 g column, eluting with 0-50% ethyl acetate/hexanes to give 4.13 g (67%) of an orange foamy solid.

4,4'-(1-(4-tert-Butylphenyl)pyrrolidine-2,5-diyl)bis(N1-(4-methoxybenzyl)benzene-1,2-diamine)

4,4'-(1-(4-tert-Butylphenyl)pyrrolidine-2,5-diyl)bis(N-(4-methoxybenzyl)-2-nitroaniline) (2 g, 2.79 mmol) was dissolved in a mixture of THF (15 mL), ethanol (15 mL), and ethyl acetate (5 mL). Then platinum oxide (0.254 g, 1.12 mmol) was added as a THF slurry. The flask was evacuated and purged with nitrogen twice, then evacuated and opened to a hydrogen balloon. The mixture was stirred at room temperature for 20 hours, then filtered through diatomaceous earth, concentrated, and purified by chromatography on silica gel with an 80 g column, eluting with 0-40% ethyl acetate/dichloromethane to give the first peak of trans product (0.508 g, 28%).

(2S,2'S)-tert-butyl 2,2'-(5,5'-(1-(4-tert-butylphenyl) pyrrolidine-2,5-diyl)bis(2-(4-methoxybenzylamino)-5,1-phenylene)bis(azanediyl)bis(oxomethylene)) dipyrrolidine-1-carboxylate 4,4'-(1-(4-tert-Butylphenyl)pyrrolidine-2,5-diyl)bis(N1-(4-methoxybenzyl)benzene-1,2-diamine) (0.422 g, 0.643 mmol) and diisopropylethylamine (0.674 mL, 3.86 mmol) were dissolved in DMSO (6 mL) at room temperature and treated with S-Boc-proline (0.319 g, 1.48 mmol) followed by HATU (0.514 g, 1.35 mmol). The solution was stirred for 1 hour at room temperature and then diluted with water. The solid product was filtered off and purified by chromatography on silica gel with a 40 g column, eluting with 0-50% ethyl acetate in dichloromethane to give the title compound (0.565 g, 84%) as a yellow solid.

(2S,2'S)-tert-butyl 2,2'-(5,5'-(1-(4-tert-butylphenyl) pyrrolidine-2,5-diyl)bis(2-amino-5,1-phenylene)bis (azanediyl)bis(oxomethylene))dipyrrolidine-1-carboxylate (2S,2'S)-tert-Butyl 2,2'-(5,5'-(1-(4-tert-butylphenyl)pyrrolidine-2,5-diyl)bis(2-(4-methoxybenzylamino)-5,1-phenylene)bis(azanediyl)bis(oxomethylene))dipyrrolidine-1-carboxylate (0.565 g, 0.538 mmol) was dissolved in dichloromethane (5 mL) and water (0.25 mL) at room temperature and treated with DDQ (0.244 g, 1.076 mmol) portionwise over 2 minutes. The mixture was diluted with sodium bicarbonate solution, extracted into dichloromethane, concentrated and purified by chromatography on silica gel with a 40 g column, eluting with 0-15% methanol/dichloromethane to give the title compound (0.355 g, 81%) as a yellow solid.

(2S,2'S)-tert-butyl 2,2'-(5,5'-(1-(4-tert-butylphenyl) pyrrolidine-2,5-diyl)bis(1H-benzo[d]imidazole-5,2-diyl))dipyrrolidine-1-carboxylate (2S,2'S)-tert-Butyl 2,2'-(5,5'-(1-(4-tert-butylphenyl)pyrrolidine-2,5-diyl)bis(2-amino-5,1-phenylene)bis(azanediyl) bis(oxomethylene))dipyrrolidine-1-carboxylate was dissolved in neat acetic acid (3 mL) and heated at 72° C. for 2 hours. The solution was concentrated and then poured into water. The pH was adjusted to ~7-8 with sodium bicarbonate. The product was extracted into dichloromethane, concentrated and purified by chromatography on silica gel with a 40 g column, eluting with 0-5% methanol/dichloromethane to give the title compound (0.185 g, 55%) as a light yellow solid.

General Procedure 16. Benzimidazole Synthesis through methoxybenzylamine Displacement Route II Shown generally in Scheme VIII, is a method of preparing certain compounds (57) and (59). Illustrated below in General Procedure 16A is a representative synthesis of (57) where D is 4-fluorophenyl.

Illustration of General Procedure 16. General Procedure 16A

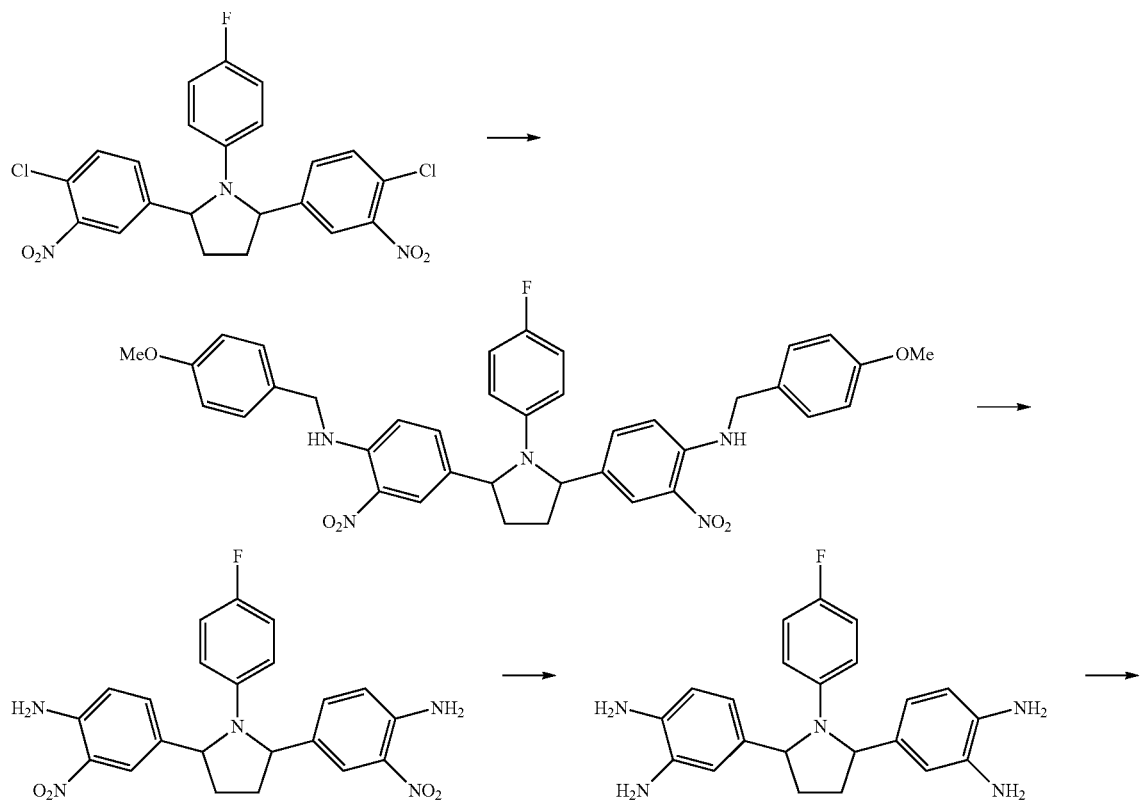

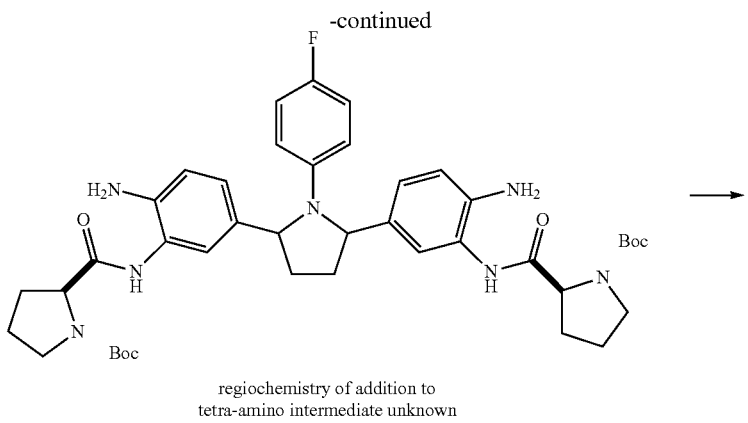

regiochemistry of addition to
tetra-amino intermediate unknown

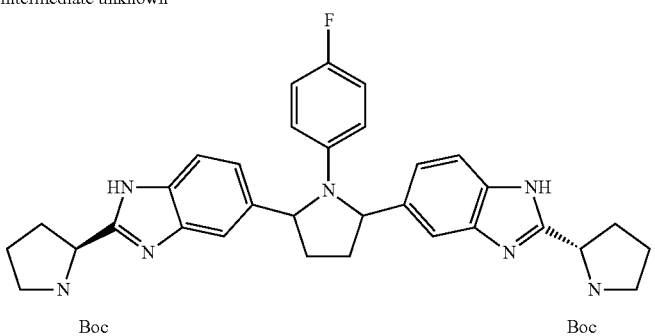

The five steps illustrated above are described by the following experimental procedures:

4,4'-(1-(4-fluorophenyl)pyrrolidine-2,5-diyl)bis(N-(4-methoxybenzyl)-2-nitroaniline)

2,5-Bis(4-chloro-3-nitrophenyl)-1-(4-fluorophenyl)pyrrolidine (0.88 g, 1.86 mmol) was combined with 4-methoxybenzylamine (3.64 mL, 28.0 mmol) and heated at 145° C. for 1 hour in a microwave reactor. The mixture was diluted with dichloromethane and filtered. The filtrate was concentrated and purified by chromatography on silica gel with a 330 g column, eluting with 0-60% ethyl acetate/hexanes to give 0.79 g (62%) of an orange foam solid.

4,4'-(1-(4-fluorophenyl)pyrrolidine-2,5-diyl)bis(2-nitroaniline)

4,4'-(1-(4-Fluorophenyl)pyrrolidine-2,5-diyl)bis(N-(4-methoxybenzyl)-2-nitroaniline) (0.78 g, 1.15 mmol) was dissolved in dichloromethane (10 mL) at room temperature and treated with TFA (1.8 mL, 23.0 mmol) for 3 hours. The residue was concentrated and partitioned between dichloromethane and sodium bicarbonate solution. The organics were concentrated and purified by chromatography on silica gel with a 40 g column, eluting with dichloromethane to give 0.218 g (43%) of the trans isomer.

4,4'-(1-(4-fluorophenyl)pyrrolidine-2,5-diyl)dibenzene-1,2-diamine 4,4'-(1-(4-Fluorophenyl)pyrrolidine-2,5-diyl)bis(2-nitroaniline) (0.218 g, 0.50 mmol) was dissolved in DMF (5 mL) then platinum oxide (0.226 g, 0.99 mmol) was added as a THF slurry. The flask was evacuated and purged with nitrogen twice, then evacuated and opened to hydrogen balloon. The mixture was stirred at room temperature for 20 hours. The solution was taken on to the next step without purification.

(2S,2'S)-tert-butyl 2,2'-(5,5'-(1-(4-fluorophenyl)pyrrolidine-2,5-diyl)bis(2-amino-5,1-phenylene))bis(azanediyl)bis(oxomethylene)dipyrrolidine-1-carboxylate The crude DMF solution of 4,4'-(1-(4-fluorophenyl)pyrrolidine-2,5-diyl)dibenzene-1,2-diamine was treated with diisopropylethylamine (0.296 mL, 1.70 mmol) and S-Boc-proline (0.192 g, 0.89 mmol) followed by HATU (0.322 g, 0.85 mmol). The solution was stirred for 1.5 hours at room temperature, and then the reaction mixture was diluted with water. The solid product was filtered off and purified by chromatography on silica gel with a 12 g column, eluting with 0-3% methanol in dichloromethane to give 0.235 g (72%) of a yellow solid, for which the regiochemistry of acylation was arbitrarily assigned as reacting at the meta-amino group.

(2S,2'S)-tert-butyl 2,2'-(5,5'-(1-(4-fluorophenyl)pyrrolidine-2,5-diyl)bis(1H-benzo[d]imidazole-5,2-diyl))dipyrrolidine-1-carboxylate (2S,2'S)-tert-Butyl 2,2'-(5,5'-(1-(4-fluorophenyl)pyrrolidine-2,5-diyl)bis(2-amino-5,1-phenylene))bis(azanediyl)bis(oxomethylene)dipyrrolidine-1-carboxylate was dissolved in neat acetic acid (2 mL) and heated at 60° C. for 1 hour. The solution was concentrated then poured into water and adjusted pH to ~7-8 with sodium bicarbonate. The product was extracted into dichloromethane, concentrated and purified by chromatography on silica gel with a 12 g column, eluting with 0-20% ethyl acetate in dichloromethane to give the title compound (0.124 g, 55%) as a light yellow solid.

General Procedure 17. Suzuki Couplings off N-Aryl Group

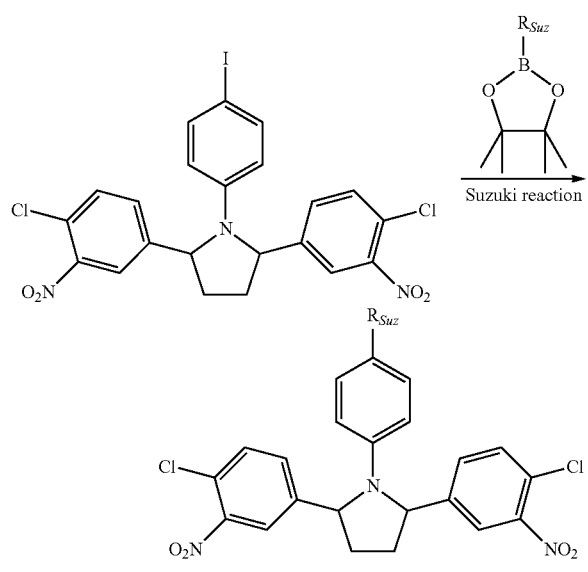

Intermediate compounds such as 2,5-bis(4-chloro-3-nitrophenyl)-1-(4-iodophenyl)pyrrolidine (or the corresponding triflate, nonaflate, or bromide) can be further elaborated through a Suzuki reaction as shown with an appropriate boronic acid or ester where $R_{Suz}$ represents a suitable cycloalkyl, aryl, cycloalkenyl, or heteroaryl group. Suitable conditions for effecting this Suzuki reaction include those described in Scheme V for the synthesis of compounds (37).

Illustration of General Procedure 17: General Procedure 17A

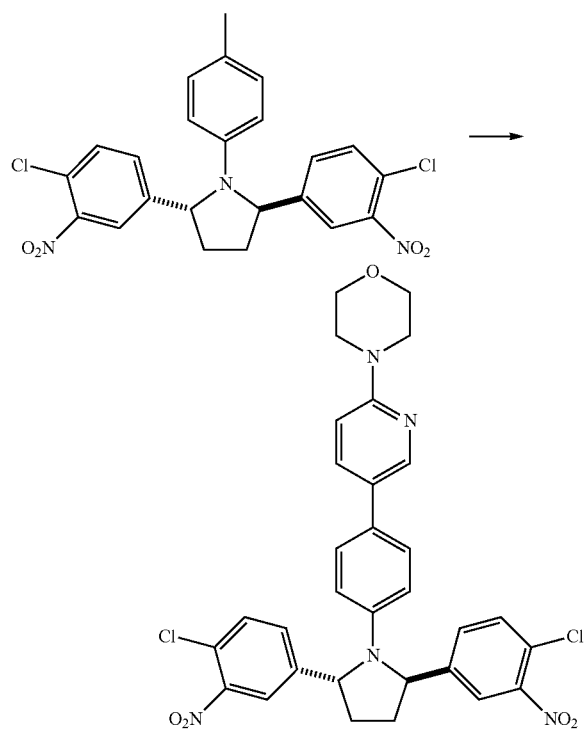

4-(5-(4-((2R,5R)-2,5-bis(4-chloro-3-nitrophenyl)pyrrolidin-1-yl)phenyl)pyridin-2-yl)morpholine (2R,5R)-2,5-Bis(4-chloro-3-nitrophenyl)-1-(4-iodophenyl)pyrrolidine (1.869 g, 3.2 mmol), 4-(5-(4,4,5,5-tetramethyl-1,3,2-dioxaborolan-2-yl)pyridin-2-yl)morpholine (0.929 g, 3.20 mmol), potassium phosphate (1.359 g, 6.40 mmol), tris(dibenzylideneacetone)dipalladium(0) (0.029 g, 0.032 mmol) and 1,3,5,7-tetramethyl-6-phenyl-2,4,8-trioxa-6-phosphaadamante (0.028 g, 0.096 mmol) were combined in THF (18 mL)/water (6 mL). The mixture was purged with nitrogen for 15 minutes and stirred at room temperature for 24 hours. The reaction mixture was partitioned between ethyl acetate and saturated sodium bicarbonate. The organic layer was washed with brine, dried with sodium sulfate, filtered and evaporated. The residue was purified by chromatography on silica gel eluting with ethyl acetate/hexane (20% to 40%) to give the title compound (1.01 g, 51%) as a solid.

General Procedure 18. Proline Amide Synthesis

Particular substituted proline amides can be made using methods such as those shown in General Procedures 18A-18C.

Illustration of General Procedure 18. General Procedure 18A

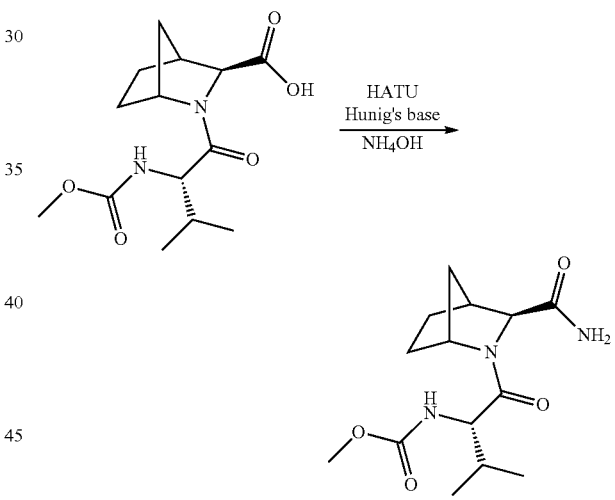

methyl (2S)-1-((3S)-3-carbamoyl-2-azabicyclo[2.2.1]heptan-2-yl)-3-methyl-1-oxobutan-2-ylcarbamate (3S)-2-((S)-2-(Methoxycarbonylamino)-3-methylbutanoyl)-2-azabicyclo[2.2.1]heptane-3-carboxylic acid (1.78 g, 5.97 mmol), 2-(3H-[1,2,3]triazolo[4,5-b]pyridin-3-yl)-1,1,3,3-tetramethylisouronium hexafluorophosphate (2.49 g, 5.56 mmol), and diisopropylethylamine (2.61 mL, 14.92 mmol) were dissolved in acetonitrile (30 mL) at ambient temperature and treated by dropwise addition with 28% ammonium hydroxide solution (2.49 g, 17.98 mmol). The resulting mixture was stirred for 1 hour and then diluted with water and extracted into dichloromethane. The organic layer was washed with brine, dried over sodium sulfate, filtered, and concentrated to give methyl (2S)-1-((3S)-3-carbamoyl-2-azabicyclo[2.2.1]heptan-2-yl)-3-methyl-1-oxobutan-2-ylcarbamate as a white waxy solid.

Illustration of General Procedure 18. General Procedure 18B

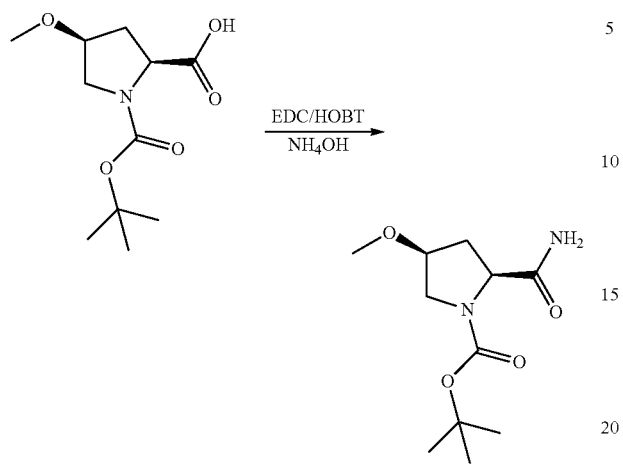

(2S,4S)-tert-butyl 2-carbamoyl-4-methoxypyrrolidine-1-carboxylate (2S,4S)-1-(tert-Butoxycarbonyl)-4-methoxypyrrolidine-2-carboxylic acid (2.9 g, 11.82 mmol) was dissolved in acetonitrile (150 mL) and cooled in an ice bath. $N^1$-((Ethylimino)methylene)-$N^3$,$N^3$-dimethylpropane-1,3-diamine hydrochloride (2.72 g, 14.19 mmol) and 1H-benzo[d][1,2,3]triazol-1-ol hydrate (2.17 g, 14.19 mmol) were added, and the mixture was stirred at ambient temperature for 15 hours, becoming clear. 28% Ammonium hydroxide (4.93 mL, 35.5 mmol) was added dropwise resulting in a precipitate. After stirring for 2 hours, then mixture was concentrated, diluted with water and extracted into ethyl acetate. The organic layer was washed with brine, dried over sodium sulfate, filtered, and concentrated to give 100% yield of (2S,4S)-tert-butyl 2-carbamoyl-4-methoxypyrrolidine-1-carboxylate as a white waxy solid.

Other amides that can be prepared using General Procedure 18B include:

(2S,4R)-tert-butyl 2-carbamoyl-4-methoxypyrrolidine-1-carboxylate;
(2S,4S)-tert-butyl 2-carbamoyl-4-fluoropyrrolidine-1-carboxylate; and
(S)-tert-butyl 5-carbamoyl-2,2-dimethylpyrrolidine-1-carboxylate.

Illustration of General Procedure 18. General Procedure 18C

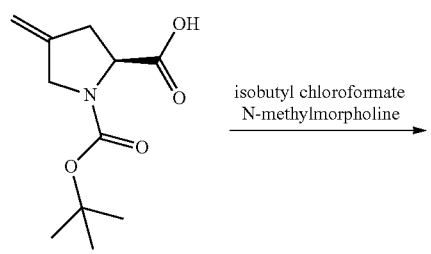

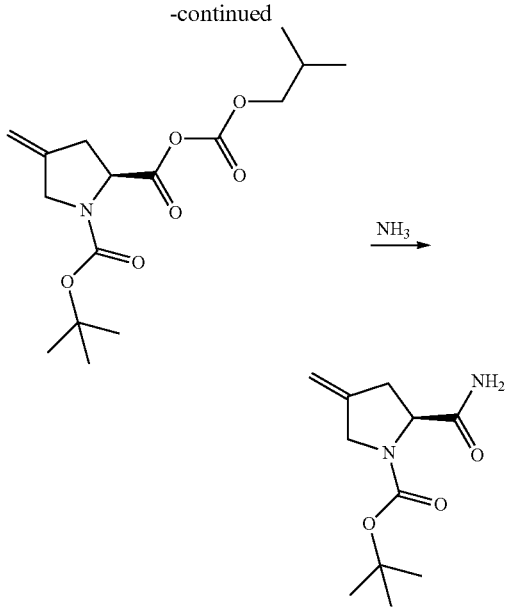

(S)-tert-butyl 2-carbamoyl-4-methylenepyrrolidine-1-carboxylate (S)-1-(tert-Butoxycarbonyl)-4-methylenepyrrolidine-2-carboxylic acid (1.05 g, 4.48 mmol) and N-methylmorpholine (0.64 mL, 5.83 mmol) were dissolved in tetrahydrofuran (25 mL) and cooled to −15° C. in a dry ice/acetone bath. Isobutyl chloroformate (0.65 mL, 4.93 mmol) was added dropwise and the solution was stirred for 15 minutes. The internal temperature was lowered to −25° C. and ammonia (g) was bubbled through the solution for 2 minutes, then the flask was transferred to an ice bath and stirred for another 20 minutes. The solution was poured into brine and extracted into ethyl acetate, dried over magnesium sulfate, filtered and concentrated. This residue was triturated with ether/hexanes, filtered, and dried to give 0.97 g (81%) of (S)-tert-butyl 2-carbamoyl-4-methylenepyrrolidine-1-carboxylate as a white solid.

General Procedure 19

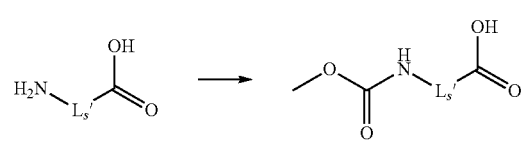

Amino acid carbamate intermediates can be made using the method and general illustration shown above to prepare Intermediate 2.

The following compounds can be made following General Procedure 19 starting from the appropriate amino acid:
(S)-2-(methoxycarbonylamino)-2-(tetrahydro-2H-pyran-4-yl)acetic acid;
(S)-2-cyclohexyl-2-(methoxycarbonylamino)acetic acid;
(S)-2-cyclopentyl-2-(methoxycarbonylamino)acetic acid;
(S)-2-cyclobutyl-2-(methoxycarbonylamino)acetic acid;
(S)-2-cyclopropyl-2-(methoxycarbonylamino)acetic acid;
(S)-2-(methoxycarbonylamino)-3,3-dimethylbutanoic acid;

(2S,3R)-3-methoxy-2-(methoxycarbonylamino)butanoic acid;
(2S,3S)-3-methoxy-2-(methoxycarbonylamino)butanoic acid;
(S)-2-(methoxycarbonylamino)-2-((R)-tetrahydrofuran-3-yl)acetic acid;
(S)-2-(methoxycarbonylamino)-2((S)-tetrahydrofuran-3-yl)acetic acid;
(S)-2-(2,3-dihydro-1H-inden-2-yl)-2-(methoxycarbonylamino)acetic acid.
(S)-3-ethyl-2-(methoxycarbonylamino)pentanoic acid; and
(S)-2-(ethoxycarbonylamino)-3-methylbutanoic acid.

General Procedure 20

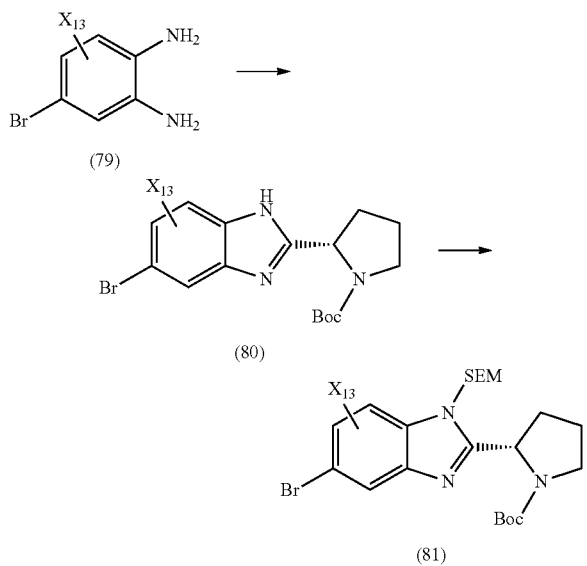

As described above generally in Scheme XIII, diamines (79) can be converted to benzimidazoles (81) in two steps.

Illustration of General Procedure 20. General Procedure 20A (S)-tert-butyl 2-(6-bromo-5-fluoro-1H-benzo[d]imidazol-2-yl)pyrrolidine-1-carboxylate To a solution of 4-bromo-5-fluorobenzene-1,2-diamine (1.7 g, 8.4 mmol) in DMSO (42 mL) was added (S)-1-(tert-butoxycarbonyl)pyrrolidine-2-carboxylic acid (1.8 g, 8.4 mmol) followed by HATU (3.5 g, 9.3 mmol) and N,N-diisopropyl-N-ethylamine (3.7 mL, 21.1 mmol), and the solution was stirred for 16 hours. The reaction mixture was diluted with EtOAc, washed with $H_2O$ and brine, dried ($Na_2SO_4$), filtered and concentrated. Acetic acid (40 mL) was added, and the mixture was stirred at 60° C. for 4 hours. Then, the reaction mixture was cooled and concentrated. The residue was azeotroped 2 times with toluene to give crude product which was purified by flash chromatography (0-50% EtOAc/hexane) to give the title compound (2.5 g, 6.4 mmol, 77%).

(S)-tert-butyl 2-(5-bromo-6-fluoro-1-((2-(trimethylsilyl)ethoxy)methyl)-1H-benzo[d]imidazol-2-yl)pyrrolidine-1-carboxylate To a solution of (S)-tert-butyl 2-(6-bromo-5-fluoro-1H-benzo[d]imidazol-2-yl)pyrrolidine-1-carboxylate (2.5 g, 6.4 mol) in THF (32 mL) was added sodium hydride (0.27 g, 6.8 mmol) and stirring was continued for 30 minutes. 2-(Trimethylsilyl)-ethoxymethyl chloride (1.2 mL, 6.8 mmol) was added and stirring was continued for 30 minutes. Water was added to quench the reaction. The mixture was diluted with EtOAc, washed with 1N HCl, $H_2O$, and brine, dried ($Na_2SO_4$), filtered and concentrated to an oil. The oil was purified by flash chromatography (0-30% EtOAc/hexane) to give the title compound (2.9 g, 5.7 mmol, 89%).

The following compounds of general formula (81) can be made following General Procedure 20 starting from the appropriate diamine:

(S)-tert-butyl 2-(5-bromo-1-((2-(trimethylsilyl)ethoxy)methyl)-1H-benzo[d]imidazol-2-yl)pyrrolidine-1-carboxylate;

(S)-tert-butyl 2-(5-bromo-4-methyl-1-((2-(trimethylsilyl)ethoxy)methyl)-1H-benzo[d]imidazol-2-yl)pyrrolidine-1-carboxylate;

(S)-tert-butyl 2-(5-bromo-4-chloro-1-((2-(trimethylsilyl)ethoxy)methyl)-1H-benzo[d]imidazol-2-yl)pyrrolidine-1-carboxylate;

(S)-tert-butyl 2-(5-bromo-4-fluoro-1-((2-(trimethylsilyl)ethoxy)methyl)-1H-benzo[d]imidazol-2-yl)pyrrolidine-1-carboxylate;

(S)-tert-butyl 2-(6-bromo-3-((2-(trimethylsilyl)ethoxy)methyl)-3H-imidazo[4,5-b]pyridin-2-yl)pyrrolidine-1-carboxylate;

(S)-tert-butyl 2-(5-bromo-7-methyl-1-((2-(trimethylsilyl)ethoxy)methyl)-1H-benzo[d]imidazol-2-yl)pyrrolidine-1-carboxylate;

(S)-tert-butyl 2-(5-bromo-6-methyl-1-((2-(trimethylsilyl)ethoxy)methyl)-1H-benzo[d]imidazol-2-yl)pyrrolidine-1-carboxylate;

(S)-tert-butyl 2-(5-bromo-6-(trifluoromethyl)-1-((2-(trimethylsilyl)ethoxy)methyl)-1H-benzo[d]imidazol-2-yl)pyrrolidine-1-carboxylate;

(S)-tert-butyl 2-(5-bromo-7-(trifluoromethyl)-1-((2-(trimethylsilyl)ethoxy)methyl)-1H-benzo[d]imidazol-2-yl)pyrrolidine-1-carboxylate;

(S)-tert-butyl 2-(5-bromo-6-methoxy-1-((2-(trimethylsilyl)ethoxy)methyl)-1H-benzo[d]imidazol-2-yl)pyrrolidine-1-carboxylate;

(S)-tert-butyl 2-(5-bromo-7-methoxy-1-((2-(trimethylsilyl)ethoxy)methyl)-1H-benzo[d]imidazol-2-yl)pyrrolidine-1-carboxylate; and (S)-methyl 5-bromo-2-(1-(tert-butoxycarbonyl)pyrrolidin-2-yl)-1-((2-(trimethylsilyl)ethoxy)methyl)-1H-benzo[d]imidazole-7-carboxylate.

General Procedure 21

As described above generally in Scheme XIII, compounds (81) can be converted to compounds (82.2). Illustrated below in General Procedure 21A is a representative synthesis of compounds (82.2) where $X_{13}$ is fluoro at the 6-position of the benzimidazole moiety. For convenient illustration, the SEM protecting groups on the benzimidazoles are shown attached to particular nitrogens of the benzimidazole. In General Procedures 21A and 22A, the actual substitution positions of the SEM groups were not determined and may be at either nitrogen.

Illustration of General Procedure 21. General Procedure 21A

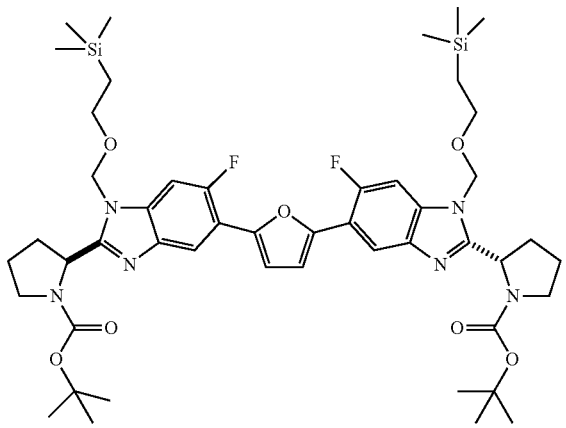

(2S,2'S)-tert-butyl 2,2'-(5,5'-(furan-2,5-diyl)bis(6-fluoro-1-((2-(trimethylsilyl)ethoxy)methyl)-1H-benzo[d]imidazole-5,2-diyl))dipyrrolidine-1-carboxylate In a pressure tube were combined (S)-tert-butyl 2-(5-bromo-6-fluoro-1-((2-(trimethylsilyl)ethoxy)methyl)-1H-benzo[d]imidazol-2-yl)pyrrolidine-1-carboxylate (600 mg, 1.2 mmol), 2,5-bis(4,4,5,5-tetramethyl-1,3,2-dioxaborolan-2-yl)furan (186 mg, 0.6 mmol), cesium fluoride (353 mg, 2.3 mmol) and DMF (4 mL), and the mixture was de-gassed with $N_2$ gas for 30 minutes. To this mixture was added [(t-Bu)$_2$PCl]$_2$PdCl$_2$ (PXPd) (15.7 mg, 0.03 mmol) and the tube was sealed and heated at 100° C. for 18 hours. The cooled solution was diluted with EtOAc, filtered through diatomaceous earth. The filtrate was washed with H$_2$O and brine, dried (Na$_2$SO$_4$), filtered and treated with 3-mercaptopropyl silica gel for 30 minutes. The mixture was filtered, and the filtrate concentrated to give crude product which was purified by flash chromatography (0-50% EtOAc/hexane) to give the title compound (269 mg, 0.29 mmol, 50%).

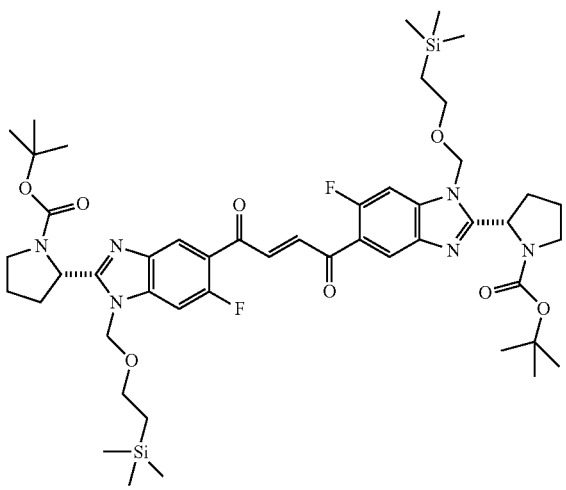 [SMILES: CC(C)(C)OC(=O)N1CCC[C@H]1c1nc2cc(C(=O)/C=C/C(=O)c3cc4nc([C@@H]5CCCN5C(=O)OC(C)(C)C)n(COCC[Si](C)(C)C)c4cc3F)c(F)cc2n1COCC[Si](C)(C)C]

di-tert-butyl (2S,2'S)-2,2'-{[(2E)-1,4-dioxobut-2-ene-1,4-diyl]bis(6-fluoro-1-{[2-(trimethylsilyl)ethoxy]methyl}-1H-benzimidazole-5,2-diyl)}dipyrrolidine-1-carboxylate (ACD Name v12)

To a solution of (2S,2'S)-tert-butyl 2,2'-(5,5'-(furan-2,5-diyl)bis(6-fluoro-1-((2-(trimethylsilyl)ethoxy)methyl)-1H-benzo[d]imidazole-5,2-diyl))dipyrrolidine-1-carboxylate (340 mg, 0.36 mmol) in THF (8 mL) was added Selectfluor® (1-chloromethyl-4-fluoro-1,4-diazoniabicyclo[2.2.2]octane bis(tetrafluoroborate)) (258 mg, 0.73 mmol) followed by H$_2$O (1 mL). The solution was stirred for 1 hour, diluted with EtOAc, washed with H$_2$O and brine, dried (Na$_2$SO$_4$), filtered and concentrated to give the title compound.

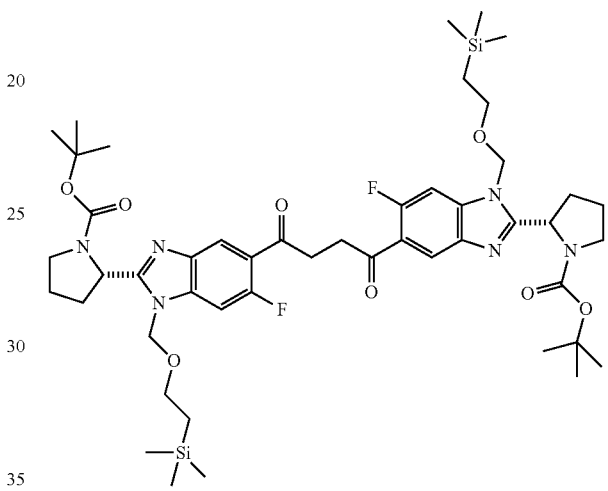

di-tert-butyl (2S,2'S)-2,2'-[(1,4-dioxobutane-1,4-diyl)bis(6-fluoro-1-{[2-(trimethylsilyl)ethoxy]methyl}-1H-benzimidazole-5,2-diyl)]dipyrrolidine-1-carboxylate (ACD Name v12)

To a solution of di-tert-butyl (2S,2'S)-2,2'-{[(2E)-1,4-dioxobut-2-ene-1,4-diyl]bis(6-fluoro-1-{[2-(trimethylsilyl)ethoxy]methyl}-1H-benzimidazole-5,2-diyl)}dipyrrolidine-1-carboxylate (346 mg, 0.36 mmol) in EtOAc (7 mL) was added platinum (3% on carbon) (71 mg, 0.36 mmol) and the solution was stirred under H$_2$ gas at 1 atm for 2 hours. The solution was filtered, washed with EtOAc and the filtrate concentrated to give a residue which was purified by flash chromatography (0-50% EtOAc/hexane) to give the title compound (269 mg, 0.28 mmol, 78%).

General Procedure 22

As described above generally in Scheme XIII, compounds (82.2) can be converted to compounds (84). Illustrated below in General Procedure 22A is a representative synthesis of compounds (84) where D is 4-tert-butylphenyl, the stereochemistries of the alcohols on the butane-1,4-diyl group are both (S), and $X_{13}$ is 6-fluoro. The cyclization to form the pyrrolidine can form the trans-pyrrolidine along with varying amounts of the cis-pyrrolidine. The cis-pyrrolidine may be separated after deprotection (see General Procedure 23) or after any step following the deprotection.

357

Illustration of General Procedure 22. General Procedure 22A

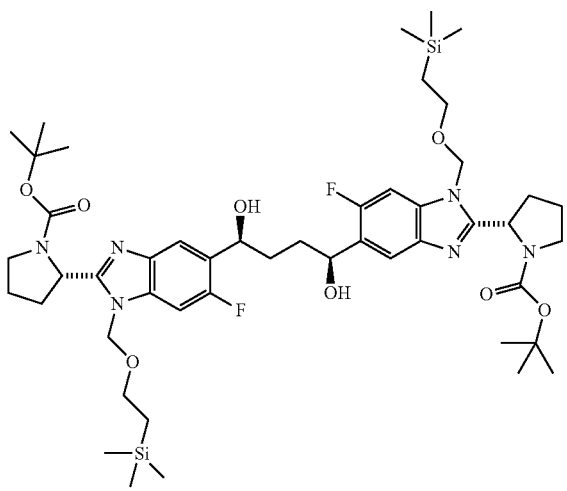 [SMILES: CC(C)(C)OC(=O)N1CCC[C@H]1c1nc2cc([C@@H](O)CC[C@H](O)c3cc4nc([C@@H]5CCCN5C(=O)OC(C)(C)C)n(COCC[Si](C)(C)C)c4cc3F)c(F)cc2n1COCC[Si](C)(C)C]

di-tert-butyl (2S,2'S)-2,2'-{[(1S,4S)-1,4-dihydroxybutane-1,4-diyl]bis(6-fluoro-1-{[2-(trimethylsilyl)ethoxy]methyl}-1H-benzimidazole-5,2-diyl)}dipyrrolidine-1-carboxylate (ACD Name v12)

To a solution of (R)-(+)-α,α-diphenyl-2-pyrrolidinemethanol (59.9 mg, 0.24 mmol) in THF (2.8 mL) was added trimethylborate (0.034 mL, 0.31 mmol), and the resultant solution was stirred for 90 minutes. The solution was cooled to 0° C. and N,N-diethylaniline borane (0.4 mL, 2.2 mmol) was added in portions over 30 minutes with stirring continued at 0° C. This solution was added via cannula to a 0° C. solution of di-tert-butyl (2S,2'S)-2,2'-[(1,4-dioxobutane-1,4-diyl)bis(6-fluoro-1-{[2-(trimethylsilyl)ethoxy]methyl}-1H-benzimidazole-5,2-diyl)]dipyrrolidine-1-carboxylate (265 mg, 0.28 mmol) in THF (2.8 mL) and then warmed to room temperature and stirred for 16 hours. The solution was cooled to 0° C. and CH₃OH (0.09 mL, 2.2 mmol) was added, and the solution was warmed to room temperature and stirred for 2 hours. 1N HCl was added, and the aqueous solution was extracted with EtOAc. The combined extracts were washed with brine, dried (Na₂SO₄), filtered and concentrated. Purification was run by flash chromatography (0-3% CH₃OH/CH₂Cl₂) to give the title compound (248 mg, 0.26 mmol, 93%).

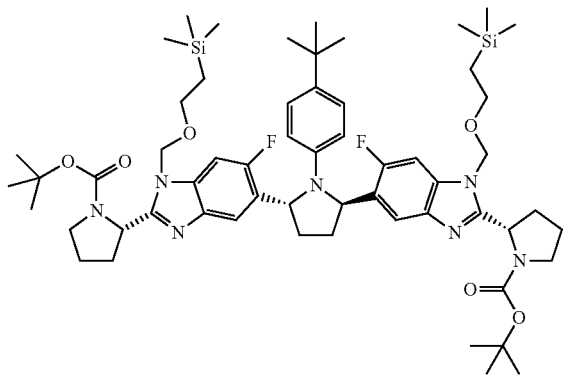 [SMILES: CC(C)(C)OC(=O)N1CCC[C@H]1c1nc2cc([C@H]3CC[C@H](c4cc5nc([C@@H]6CCCN6C(=O)OC(C)(C)C)n(COCC[Si](C)(C)C)c5cc4F)N3c3ccc(C(C)(C)C)cc3)c(F)cc2n1COCC[Si](C)(C)C]

358 di-tert-butyl (2S,2'S)-2,2'-{[(2R,5R)-1-(4-tert-butylphenyl)pyrrolidine-2,5-diyl]bis(6-fluoro-1-{[2-(trimethylsilyl)ethoxy]methyl}-1H-benzimidazole-5,2-diyl)}dipyrrolidine-1-carboxylate (ACD Name v12)

To a solution of di-tert-butyl (2S,2'S)-2,2'-{[(1S,4S)-1,4-dihydroxybutane-1,4-diyl]bis(6-fluoro-1-{[2-(trimethylsilyl)ethoxy]methyl}-1H-benzimidazole-5,2-diyl)}dipyrrolidine-1-carboxylate (100 mg, 0.10 mmol) in CH₂Cl₂ (1 mL) at −20° C. was added triethylamine (0.044 mL, 0.31 mmol) followed by mesyl chloride (0.018 mL, 0.23 mmol) and the solution stirred at −20° C. for 1 hour. 4-tert-Butyl aniline (0.083 mL, 0.52 mmol) was added in one portion, and the solution was allowed to warm to room temperature overnight, with stirring. The solution was diluted with EtOAc, washed with 1N HCl, H₂O, and brine, dried (Na₂SO₄), filtered and concentrated. Purification by flash chromatography (0-50% EtOAc/hexane) gave the title compound (46 mg, 0.04 mmol, 41%).

General Procedure 23. De-boc/de-SEM Procedure

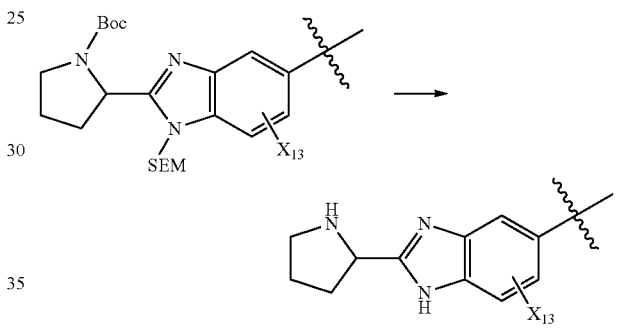

Simultaneous removal of Boc and SEM protecting groups, according to the above depiction can be effected using standard conditions such as by treatment with an acid, such as HCl in solvents such as dioxane or methanol or mixtures thereof at temperature from about room temperature to about 60° C. The compounds obtained on deprotection may consist of a mixture of stereoisomers that may be separated by reverse-phase HPLC. The de-protected compounds obtained may be isolated as either the salt directly from the reaction or reverse-phase HPLC or as the free base following neutralization, extraction into organic solvent and standard isolation.

Illustration of General Procedure 23. General Procedure 23A

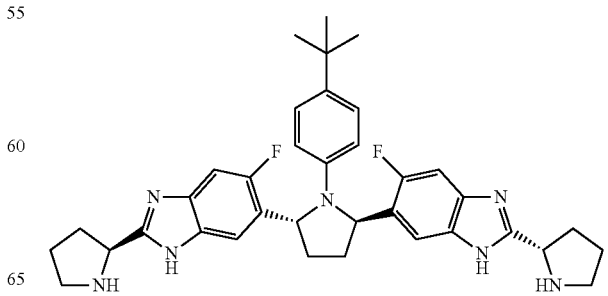

6,6'-[(2R,5R)-1-(4-tert-butylphenyl)pyrrolidine-2,5-diyl]bis {5-fluoro-2-[(2S)-pyrrolidin-2-yl]-1H-benzimidazole} (ACD Name v12)

To a solution of di-tert-butyl (2S,2'R)-2,2'-{[(2R,5R)-1-(4-tert-butylphenyl)pyrrolidine-2,5-diyl]bis(6-fluoro-1-{[2-(trimethylsilyl)ethoxy]methyl}-1H-benzimidazole-5,2-diyl)}dipyrrolidine-1-carboxylate (44 mg, 0.04 mmol) in dioxane (1 mL) was added 4 M HCl/dioxane (1 mL, 4.0 mmol) and the solution was stirred at 50° C. for 2 hours. The cooled solution was concentrated and placed under vacuum for 1 hour to provide the crude title compound that was used without purification.

The following list of diamines
4-bromo-3-methylbenzene-1,2-diamine;
5-bromo-3-fluorobenzene-1,2-diamine;
4-bromo-3-fluorobenzene-1,2-diamine;
4-bromo-3-chlorobenzene-1,2-diamine; and
4-bromo-5-fluorobenzene-1,2-diamine.
can be subjected to a sequence of General Procedures 20/20A, 21/21A, 22/22A, 23/23A to give the following compounds:
6,6'-[1-(4-tert-butylphenyl)pyrrolidine-2,5-diyl]bis{4-fluoro-2-[(2S)-pyrrolidin-2-yl]-1H-benzimidazole} (ACD Name v12);
6,6'-[(2R,5R)-1-(4-tert-butylphenyl)pyrrolidine-2,5-diyl]bis{7-fluoro-2-[(2S)-pyrrolidin-2-yl]-1H-benzimidazole} (ACD Name v12);
6,6'-[(2R,5S)-1-(4-tert-butylphenyl)pyrrolidine-2,5-diyl]bis{7-fluoro-2-[(2S)-pyrrolidin-2-yl]-1H-benzimidazole} (ACD Name v12);
6,6'-[(2R,5R)-1-(4-tert-butylphenyl)pyrrolidine-2,5-diyl]bis{7-chloro-2-[(2S)-pyrrolidin-2-yl]-1H-benzimidazole} (ACD Name v12);
6,6'-[(2R,5S)-1-(4-tert-butylphenyl)pyrrolidine-2,5-diyl]bis{7-chloro-2-[(2S)-pyrrolidin-2-yl]-1H-benzimidazole} (ACD Name v12);
6,6'-[(2R,5R)-1-(4-tert-butylphenyl)pyrrolidine-2,5-diyl]bis{7-methyl-2-[(2S)-pyrrolidin-2-yl]-1H-benzimidazole} (ACD Name v12);
6,6'-[(2R,5S)-1-(4-tert-butylphenyl)pyrrolidine-2,5-diyl]bis{7-methyl-2-[(2S)-pyrrolidin-2-yl]-1H-benzimidazole} (ACD Name v12);
6,6'-{(2R,5R)-1-[3-fluoro-4-(piperidin-1-yl)phenyl]pyrrolidine-2,5-diyl}bis{5-fluoro-2-[(2S)-pyrrolidin-2-yl]-1H-benzimidazole} (ACD Name v12);
6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12); and
6,6'-{(2R,5R)-1-[3,5-difluoro-4-(4-phenylpiperidin-1-yl)phenyl]pyrrolidine-2,5-diyl}bis{5-fluoro-2-[(2S)-pyrrolidin-2-yl]-1H-benzimidazole} (ACD Name v12).

EXAMPLES

The following example compounds 1.1-1.8 can be made from the appropriate listed substituted pyrrolidine following the methods of General Procedure 8.1, General Procedure 9C (Raney-nickel), and General Procedure 10B.
Pyrrolidines:
(2R,5R)-2,5-bis(4-chloro-3-nitrophenyl)-1-(4-phenoxyphenyl)pyrrolidine;
1-(4-((2R,5R)-2,5-bis(4-chloro-3-nitrophenyl)pyrrolidin-1-yl)phenyl)pyridin-2(1H)-one;
(2R,5R)-2,5-bis(4-chloro-3-nitrophenyl)-1-(2,5-difluoro-4-(trifluoromethyl)phenyl)pyrrolidine;
4-((2R,5R)-2,5-bis(4-chloro-3-nitrophenyl)pyrrolidin-1-yl)-2-fluoropyridine;
1-(4-((2R,5R)-2,5-bis(4-chloro-3-nitrophenyl)pyrrolidin-1-yl)-2,6-difluorophenyl)-4,4-difluoropiperidine;
1-(4-((2R,5R)-2,5-bis(4-chloro-3-nitrophenyl)pyrrolidin-1-yl)-2,6-difluorophenyl)-4-fluoropiperidine;
(2R,5R)-2,5-bis(4-chloro-3-nitrophenyl)-1-(4-((3-ethyloxetan-3-yl)methoxy)phenyl)pyrrolidine; and
(1R,5S)-3-(4-((2R,5R)-2,5-bis(4-chloro-3-nitrophenyl)pyrrolidin-1-yl)-2,6-difluorophenyl)-3-azabicyclo[3.2.0]heptane.

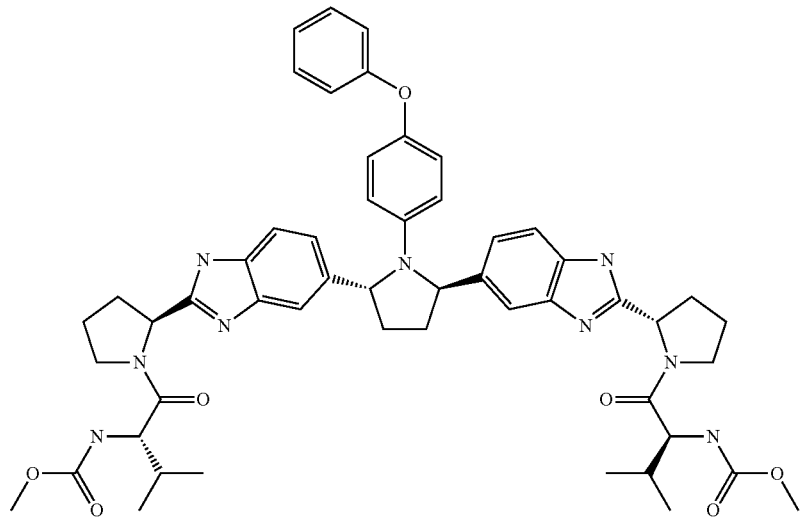

ABS

Example 1.1 methyl {(2S)-1-[(2S)-2-{5-[(2R,5R)-5-{2-[(2S)-1-
{(2S)-2-[(methoxycarbonyl)amino]-3-
methylbutanoyl}pyrrolidin-2-yl]-1H-benzimidazol-
5-yl}-1-(4-phenoxyphenyl)pyrrolidin-2-yl]-1H-benz-
imidazol-2-yl}pyrrolidin-1-yl]-3-methyl-1-oxobutan-
2-yl}carbamate $^1$H NMR (400 MHz, DMSO-d$_6$) δ ppm 0.78-0.91 (m, 12H) 1.70 (d, J=6.83 Hz, 2H) 1.86-1.96 (m, 2H) 1.99 (d, J=2.17 Hz, 4H) 2.15-2.25 (m, 4H) 2.55-2.61 (m, 2H) 3.54 (s, 6H) 3.82 (s, 4H) 4.06 (t, J=8.40 Hz, 2H) 5.13 (t, J=7.26 Hz, 2H) 5.35-5.43 (m, 2H) 6.35 (d, J=9.11 Hz, 2H) 6.62-6.69 (m, 2H) 6.71 (d, J=8.02 Hz, 2H) 6.93 (t, J=7.43 Hz, 1H) 7.08 (t, J=9.43 Hz, 2H) 7.18-7.25 (m, 3H) 7.27-7.34 (m, 3H) 7.39 (d, J=8.13 Hz, 1H) 7.47 (d, J=8.02 Hz, 1H) 12.05 (d, J=12.04 Hz, 2H); MS (ESI+) m/z 924.4 (M+H)$^+$.

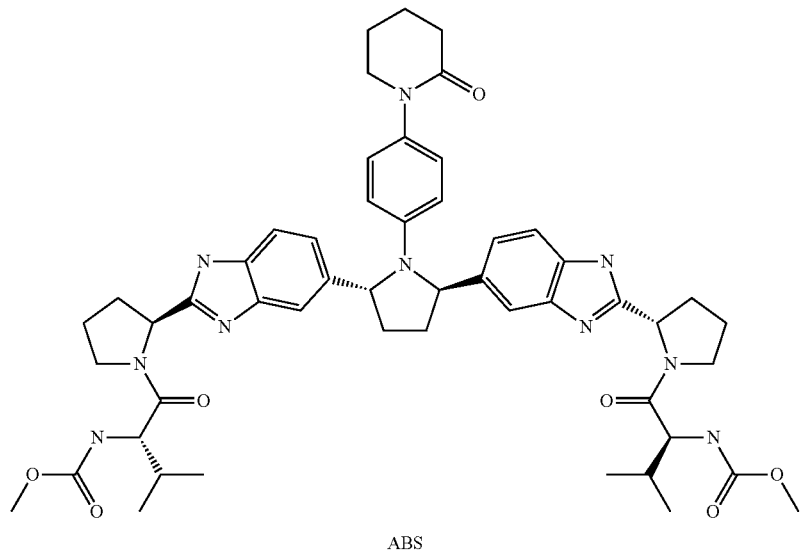

ABS

Example 1.2 methyl {(2S)-1-[(2S)-2-(5-{(2R,5R)-5-{2-[(2S)-1-
{(2S)-2-[(methoxycarbonyl)amino]-3-
methylbutanoyl}pyrrolidin-2-yl]-1H-benzimidazol-
5-yl}-1-[4-(2-oxopiperidin-1-yl)phenyl]pyrrolidin-2-
yl}-1H-benzimidazol-2-yl)pyrrolidin-1-yl]-3-
methyl-1-oxobutan-2-yl} carbamate $^1$H NMR (400 MHz, DMSO-d$_6$) δ ppm 0.76-0.92 (m, 12H) 1.66-1.76 (m, 6H) 1.91 (dd, J=13.61, 7.54 Hz, 2H) 1.95-2.04 (m, 4H) 2.20 (dd, J=16.26, 3.80 Hz, 6H) 2.58-2.64 (m, 2H) 3.39-3.45 (m, 2H) 3.54 (s, 6H) 3.82 (s, 4H) 4.02-4.09 (m, 2H) 5.09-5.19 (m, 2H) 5.35-5.43 (m, 2H) 6.29 (d, J=8.89 Hz, 2H) 6.70-6.78 (m, 2H) 7.07 (d, J=8.13 Hz, 2H) 7.22 (s, 1H) 7.29 (d, J=8.35 Hz, 2H) 7.33 (s, 1H) 7.38 (d, J=8.35 Hz, 1H) 7.47 (d, J=8.13 Hz, 1H) 12.04 (s, 2H); MS (ESI+) m/z 929.5 (M+H)$^-$.

ABS

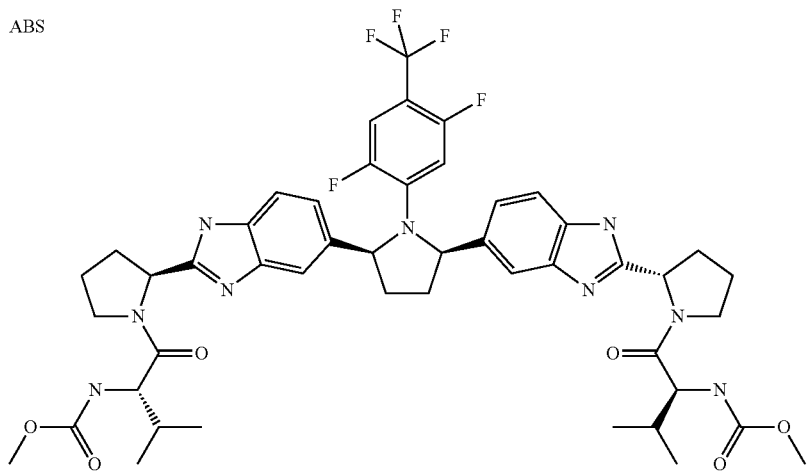

Example 1.3 methyl {(2S)-1-[(2S)-2-{5-[(2S,5R)-1-[2,5-difluoro-4-(trifluoromethyl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^{1}$H NMR (400 MHz, DMSO-d$_{6}$) δ ppm 0.76-0.94 (m, 12H) 1.83-2.07 (m, 8H) 2.14-2.28 (m, 4H) 2.35-2.45 (m, 2H) 3.54 (s, 6H) 3.75-3.94 (m, 4H) 4.07 (dd, J=8.19, 4.93 Hz, 2H) 5.19 (dd, J=31.50, 3.74 Hz, 4H) 6.48-6.61 (m, 1H) 7.20-7.35 (m, 5H) 7.40-7.46 (m, 1H) 7.49-7.56 (m, 2H) 7.58-7.65 (m, 1H) 12.12 (d, J=4.66 Hz, 2H); MS (APCI+) m/z 936.24 (M+H)$^{+}$.

Example 1.4 methyl {(2S)-1-[(2S)-2-{5-[(2R,5R)-1-(2-fluoropyridin-4-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^{1}$H NMR (400 MHz, DMSO-d$_{6}$) δ ppm 0.77-0.91 (m, 12H) 1.32 (td, J=14.99, 7.43 Hz, 1H) 1.53 (dt, J=21.23, 6.63 Hz, 1H) 1.74 (dd, J=11.93, 6.07 Hz, 2H) 1.86-2.05 (m, 6H) 2.14-2.23 (m, 4H) 3.54 (s, 6H) 3.77-3.86 (m, 4H) 4.05-4.10 (m, 2H) 5.11-5.18 (m, 2H) 5.45-5.59 (m, 2H) 5.79 (s, 1H) 6.18-6.23 (m, 1H) 7.03-7.13 (m, 2H) 7.23 (s, 1H) 7.29 (d, J=8.35 Hz, 2H) 7.34 (d, J=1.52 Hz, 1H) 7.42 (d, J=8.35 Hz, 1H) 7.47-7.56 (m, 2H) 12.11 (s, 2H); MS (ESI+) m/z 851.3 (M+H)$^{+}$.

ABS

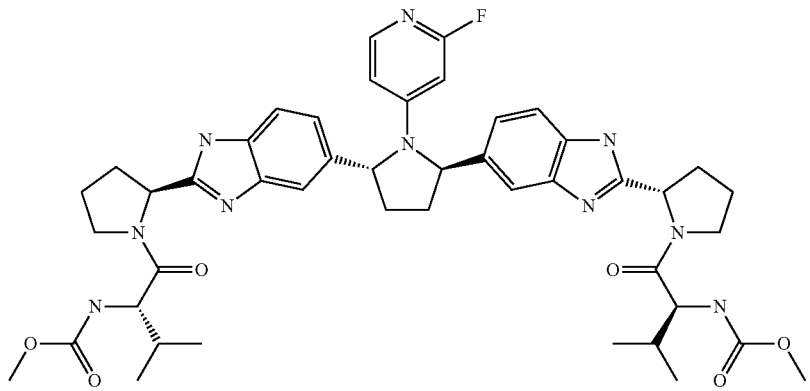

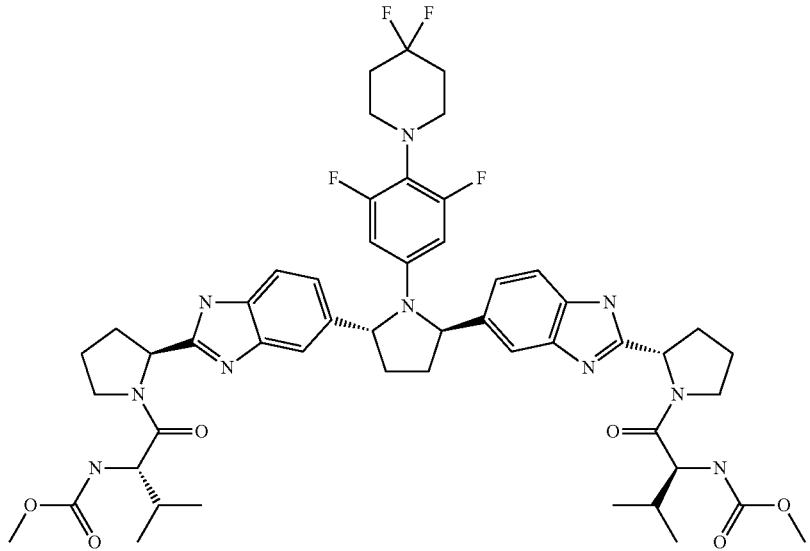
Example 1.5
methyl {(2S)-1-[(2S)-2-{5-[(2R,5R)-1-[4-(4,4-difluoropiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-$d_6$) δ ppm 0.74-0.93 (m, 12H) 1.63-1.74 (m, 2H) 1.85-2.06 (m, 12H) 2.19 (dd, J=9.49, 5.37 Hz, 4H) 2.86-2.96 (m, 4H) 3.54 (s, 6H) 3.76-3.86 (m, 4H) 4.07 (t, J=8.24 Hz, 2H) 5.09-5.20 (m, 2H) 5.33-5.42 (m, 2H) 5.92 (d, J=12.90 Hz, 2H) 7.07 (t, J=7.37 Hz, 2H) 7.21 (s, 1H) 7.26-7.33 (m, 3H) 7.41 (d, J=8.13 Hz, 1H) 7.49 (d, J=8.13 Hz, 1H) 12.08 (d, J=12.90 Hz, 2H); MS (ESI+) m/z 987.5 (M+H)$^+$.
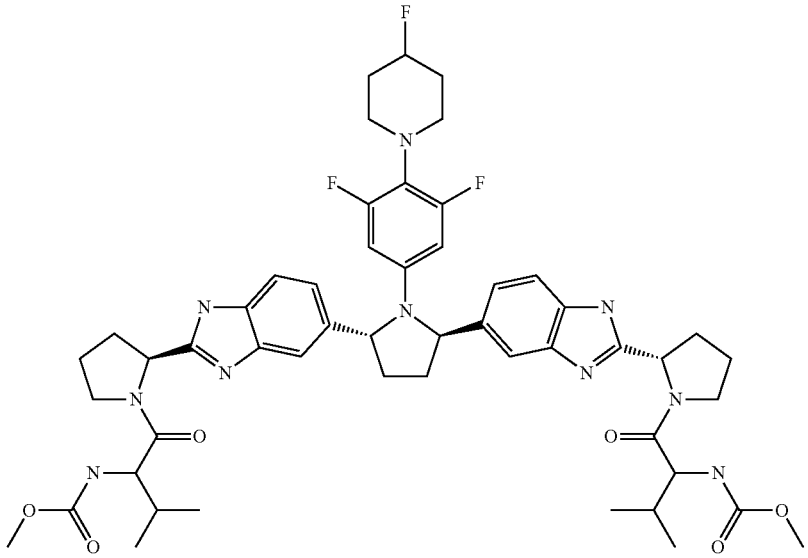

Example 1.6 methyl {1-[(2S)-2-{5-[(2R,5R)-1-[3,5-difluoro-4-(4-fluoropiperidin-1-yl)phenyl]-5-{2-[(2S)-1-{2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.74-0.91 (m, 12H) 1.63-1.71 (m, 6H) 1.76-1.97 (m, 4H) 1.98-2.07 (m, 4H) 2.14-2.23 (m, 4H) 2.71-2.78 (m, 2H) 2.90-3.00 (m, 2H) 3.54 (s, 6H) 3.82 (s, 4H) 4.06 (t, J=8.73 Hz, 2H) 4.58-4.78 (m, 1H) 5.11-5.18 (m, 2H) 5.33-5.43 (m, 2H) 5.90 (d, J=12.69 Hz, 2H) 7.07 (t, J=7.37 Hz, 2H) 7.20 (s, 1H) 7.26-7.32 (m, 3H) 7.41 (d, J=8.24 Hz, 1H) 7.49 (d, J=8.24 Hz, 1H) 12.07 (d, J=16.48 Hz, 2H); MS (ESI+) m/z 969.5 (M+H)$^+$.

ABS

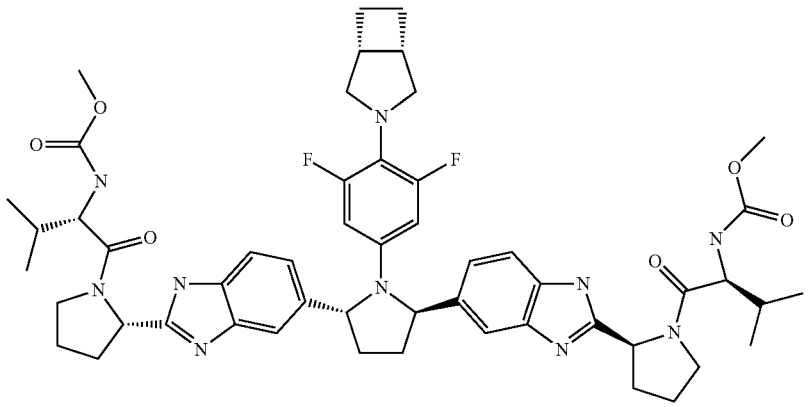

Example 1.7 methyl {(2S)-1-[(2S)-2-{5-[(2R,5R)-1-{4-[(3-ethyloxetan-3-yl)methoxy]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate

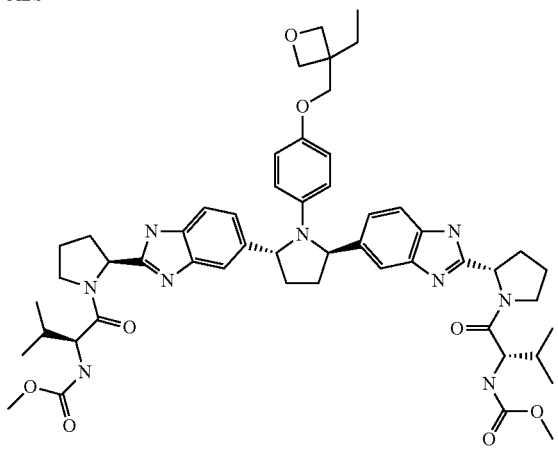

$^1$H NMR (400 MHz, DMSO-$d_6$) δ 12.26-11.98 (m, 2H), 7.44 (d, J=8.2, 1H), 7.37 (d, J=8.2, 1H), 7.33-7.18 (m, 4H), 7.05 (t, J=8.1, 2H), 6.62-6.53 (m, 2H), 6.26 (d, J=8.8, 2H), 5.40-5.30 (m, 2H), 5.17-5.08 (m, 2H), 4.29 (d, J=5.7, 2H), 4.22 (d, J=5.8, 2H), 4.06 (t, J=8.3, 2H), 3.86-3.75 (m, 6H), 3.53 (s, 6H), 2.54 (s, 2H), 2.24-2.12 (m, 4H), 2.06-1.83 (m, 6H), 1.75-1.62 (m, 4H), 0.91-0.74 (m, 15H); MS (ESI+) m/z 946.5 (M+H)$^+$.

Example 1.8 methyl {(2S)-1-[(2S)-2-{5-[(2R,5R)-1-{4-R1R,5S)-3-azabicyclo[3.2.0]hept-3-yl}-3,5-difluorophenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.82 (s, 12H) 1.61 (s, 3H) 1.71 (d, 2H) 1.97 (m, 9H) 2.20 (s, 2H) 2.74-2.78 (m, 2H) 2.85 (s, 5H) 3.53 (s, 6H) 3.82 (s, 3H) 4.06 (s, 2H) 5.14 (s, 2H) 5.38 (s, 2H) 5.91 (s, 2H) 7.09 (s, 1H) 7.37 (m, 6H) 7.63 (s, 1H) 7.88 (s, 1H) 12.05 (s, 2H); MS (ESI+) m/z 963.5 (M+H)$^-$, (ESI-) m/z 961.4 (M-H)$^-$.

The following example compounds 2.1-2.17 can be made from the appropriate listed substituted pyrrolidine following the methods of General Procedure 8.1, General Procedure 9D (PtO2), and General Procedure 10B.

Pyrrolidines:
2-(4-((2R,5R)-2,5-bis(4-chloro-3-nitrophenyl)pyrrolidin-1-yl)phenyl)oxazole;
(2R,5R)-1-(4-chloro-3-fluorophenyl)-2,5-bis(4-chloro-3-nitrophenyl)pyrrolidine;
(2R,5R)-1-(4-(1,3-dioxan-5-yloxy)phenyl)-2,5-bis(4-chloro-3-nitrophenyl)pyrrolidine;
(2R,5R)-1-(4-((1,3-dioxolan-4-yl)methoxy)phenyl)-2,5-bis(4-chloro-3-nitrophenyl)pyrrolidine;
(2R,5R)-2,5-bis(4-chloro-3-nitrophenyl)-1-(4-((3-ethyloxetan-3-yl)methoxy)-3,5-difluorophenyl)pyrrolidine;
1-(4-((2R,5R)-2,5-bis(4-chloro-3-nitrophenyl)pyrrolidin-1-yl)-2,3,5,6-tetrafluorophenyl)piperidine;
(2R,5R)-2,5-bis(4-chloro-3-nitrophenyl)-1-(3-fluoro-4-(methylsulfonyl)phenyl)pyrrolidine (obtained by mCPBA oxidation of (2R,5R)-2,5-bis(4-chloro-3-nitrophenyl)-1-(3-fluoro-4-(methylthio)phenyl)pyrrolidine);

4-((2R,5R)-2,5-bis(4-chloro-3-nitrophenyl)pyrrolidin-1-yl)-N-tert-butyl-2-fluoroaniline;

1-(4-((2R,5R)-2,5-bis(4-chloro-3-nitrophenyl)pyrrolidin-1-yl)-2,6-difluorophenyl)-4-methylpiperidine;

1-(4-((2R,5R)-2,5-bis(4-chloro-3-nitrophenyl)pyrrolidin-1-yl)-2,6-difluorophenyl)-4-(3-phenylpropyl)piperidine;

8-(4-((2R,5R)-2,5-bis(4-chloro-3-nitrophenyl)pyrrolidin-1-yl)-2,6-difluorophenyl)-8-azaspiro[4.5]decane;

1-(4-((2R,5R)-2,5-bis(4-chloro-3-nitrophenyl)pyrrolidin-1-yl)-2,6-difluorophenyl)-4-(naphthalen-2-yl)piperidine;

2-(1-(4-((2R,5R)-2,5-bis(4-chloro-3-nitrophenyl)pyrrolidin-1-yl)-2,6-difluorophenyl)piperidin-4-yl)pyridine;

1-(4-((2R,5R)-2,5-bis(4-chloro-3-nitrophenyl)pyrrolidin-1-yl)-2,6-difluorophenyl)-4-(4-(trimethylsilyl)phenyl)piperidine;

1-(4-((2R,5R)-2,5-bis(4-chloro-3-nitrophenyl)pyrrolidin-1-yl)-2,6-difluorophenyl)-4-(naphthalen-1-yl)piperidine;

1-(4-((2R,5R)-2,5-bis(4-chloro-2-fluoro-5-nitrophenyl)pyrrolidin-1-yl)-2,6-difluorophenyl)-3,5-dimethylpiperidine; and 1-(4-((2R,5R)-2,5-bis(4-chloro-3-nitrophenyl)pyrrolidin-1-yl)-2,6-difluorophenyl)-4-(4-(trifluoromethyl)phenyl)piperazine.

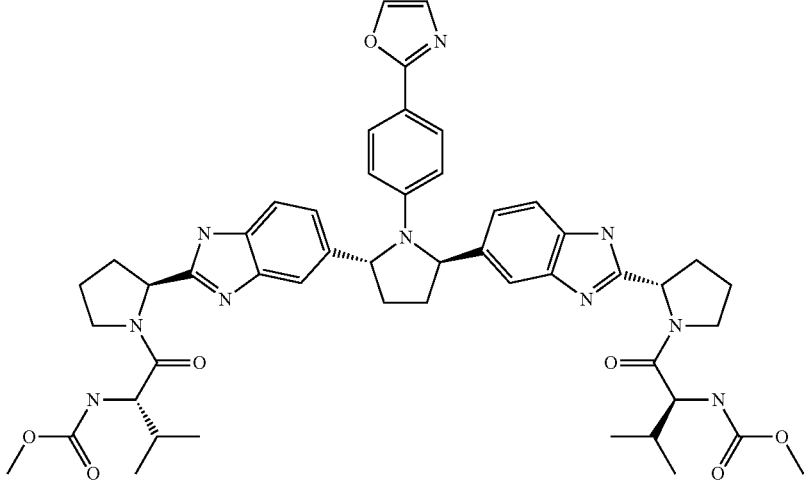

Example 2.1 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(1,3-oxazol-2-yl)phenyl]pyrrolidin-2-yl}-1H-benzimidazol-2-yl)pyrrolidin-1-yl]-3-methyl-1-oxobutan-2-yl}carbamate ¹H NMR (400 MHz, DMSO-$d_6$) δ ppm 0.74-0.91 (m, 12H) 1.70-1.79 (m, 2H) 1.89 (ddd, J=14.20, 7.05, 6.94 Hz, 2H) 1.95-2.04 (m, 4H) 2.13-2.23 (m, 4H) 2.55-2.61 (m, 2H) 3.53 (s, 6H) 3.77-3.84 (m, 4H) 4.05 (t, J=8.67 Hz, 2H) 5.09-5.18 (m, 2H) 5.46-5.54 (m, 2H) 6.45 (d, J=8.89 Hz, 2H) 7.08 (t, J=7.75 Hz, 2H) 7.13 (s, 1H) 7.23 (s, 1H) 7.28 (d, J=8.24 Hz, 2H) 7.33 (s, 1H) 7.39 (d, J=8.13 Hz, 1H) 7.45-7.56 (m, 3H) 7.94 (s, 1H) 12.06 (s, 2H); MS (ESI+) m/z 899.4 (M+H)⁺.

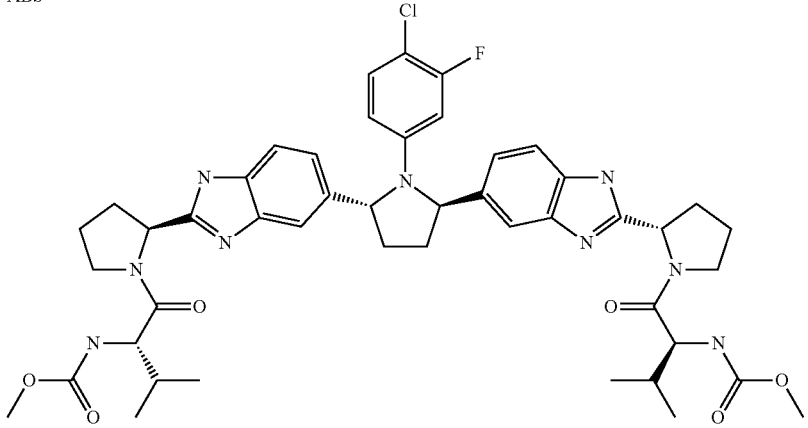

Example 2.2 methyl {(2S)-1-[(2S)-2-{5-[(2R,5R)-1-(4-chloro-3-fluorophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.77-0.90 (m, 12H) 1.66-1.78 (m, 2H) 1.88-1.95 (m, 2H) 1.96-2.06 (m, 4H) 2.15-2.24 (m, 4H) 2.54-2.60 (m, 2H) 3.54 (s, 6H) 3.79-3.86 (m, 4H) 4.06 (t, J=8.46 Hz, 2H) 5.10-5.18 (m, 2H) 5.37-5.45 (m, 2H) 6.16 (dd, J=9.49, 2.01 Hz, 1H) 6.22 (dd, J=13.55, 2.06 Hz, 1H) 7.00-7.11 (m, 3H) 7.22 (s, 1H) 7.28 (d, J=8.57 Hz, 2H) 7.32 (s, 1H) 7.40 (d, J=8.24 Hz, 1H) 7.47 (d, J=8.13 Hz, 1H) 12.07 (d, J=2.93 Hz, 2H); MS (APCI+) m/z 884 (M+H)$^+$.

ABS

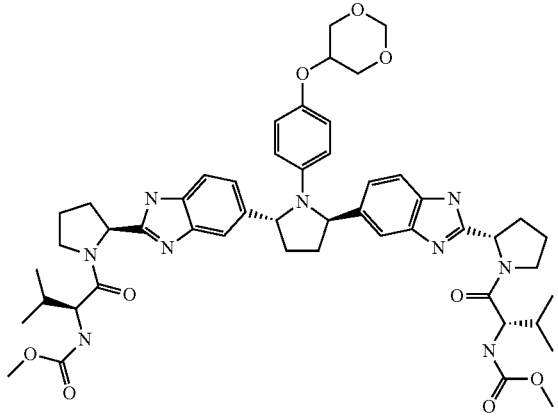

Example 2.3 methyl {(2S)-1-[(2S)-2-{5-[(2R,5R)-1-[4-(1,3-dioxan-5-yloxy)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.28-11.98 (m, 2H), 7.45 (d, J=8.1, 1H), 7.37 (d, J=8.2, 1H), 7.32-7.23 (m, 3H), 7.21 (s, 1H), 7.12-7.01 (m, 2H), 6.62-6.51 (m, 2H), 6.24 (d, J=8.9, 2H), 5.40-5.27 (m, 2H), 5.18-5.09 (m, 2H), 4.72 (d, J=6.1, 1H), 4.67 (d, J=6.2, 1H), 4.06 (t, J=8.4, 2H), 4.01-3.75 (m, 7H), 3.68-3.58 (m, 2H), 3.52 (d, J=15.9, 6H), 2.28-1.83 (m, 12H), 1.74-1.62 (m, 2H), 0.93-0.73 (m, 12H); MS (ESI+) m/z 934.5 (M+H)$^+$.

ABS

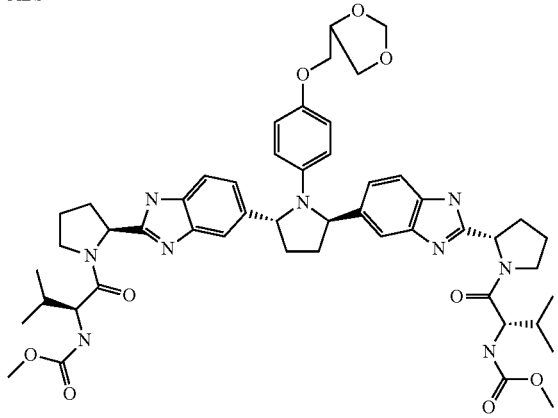

Example 2.4 methyl {(2S)-1-[(2S)-2-{5-[(2R,5R)-1-[4-(1,3-dioxolan-4-ylmethoxy)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.27-11.95 (m, 2H), 7.43 (d, J=8.1, 1H), 7.35 (d, J=8.2, 1H), 7.32-7.22 (m, 3H), 7.19 (s, 1H), 7.03 (t, J=7.4, 2H), 6.59-6.47 (m, 2H), 6.23 (d, J=8.8, 2H), 5.39-5.27 (m, 2H), 5.16-5.04 (m, 2H), 4.83 (d, J=2.6, 1H), 4.74 (s, 1H), 4.22-4.12 (m, 1H), 4.04 (t, J=8.3, 2H), 3.88 (t, J=7.5, 1H), 3.83-3.67 (m, 6H), 3.57-3.47 (m, 7H), 2.29-1.80 (m, 12H), 1.74-1.60 (m, 2H), 0.93-0.71 (m, 12H); MS (ESI+) m/z 934.4 (M+H)$^+$.

ABS

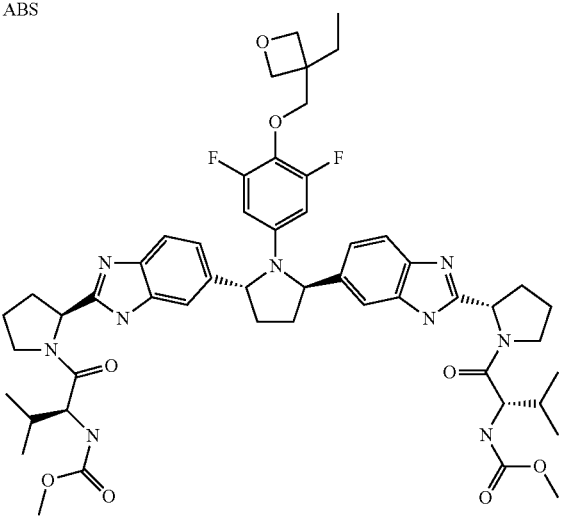 [SMILES: "ABS" ; CCC1(COc2c(F)cc(N3[C@@H](c4ccc5nc([C@@H]6CCCN6C(=O)[C@@H](NC(=O)OC)C(C)C)[nH]c5c4)CC[C@@H]3c3ccc4nc([C@@H]5CCCN5C(=O)[C@@H](NC(=O)OC)C(C)C)[nH]c4c3)cc2F)COC1]

373

Example 2.5 methyl {(2S)-1-[(2S)-2-{6-[(2R,5R)-1-{4-[(3-ethyloxetan-3-yl)methoxy]-3,5-difluorophenyl}-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ 12.30-12.02 (m, 2H), 7.47 (d, J=8.3, 1H), 7.40 (d, J=8.3, 1H), 7.34-7.16 (m, 4H), 7.06 (t, J=7.0, 2H), 5.98 (d, J=12.3, 2H), 5.46-5.30 (m, 2H), 5.24-5.05 (m, 2H), 4.29 (d, J=5.5, 2H), 4.21 (d, J=5.8, 2H), 4.05 (t, J=8.2, 2H), 3.90-3.72 (m, 6H), 3.52 (s, 6H), 2.27-1.81 (m, 12H), 1.73-1.60 (m, 4H), 0.91-0.69 (m, 15H); MS (ESI+) m/z 982.4 (M+H)$^+$.

374

Example 2.6 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-6-yl}-1-[2,3,5,6-tetrafluoro-4-(piperidin-1-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-d$_6$) δ 12.10 (dd, J=58.0, 37.7, 2H), 7.52-7.21 (m, 6H), 7.07 (t, J=8.1, 2H), 5.52-5.29 (m, 2H), 5.17-5.03 (m, 2H), 4.12-3.93 (m, 2H), 3.88-3.66 (m, 4H), 3.53 (s, 6H), 2.87-2.71 (m, 4H), 2.27-1.76 (m, 14H), 1.50-1.32 (m, 6H), 0.93-0.70 (m, 12H); MS (ESI+) m/z 987.3 (M+H)$^-$.

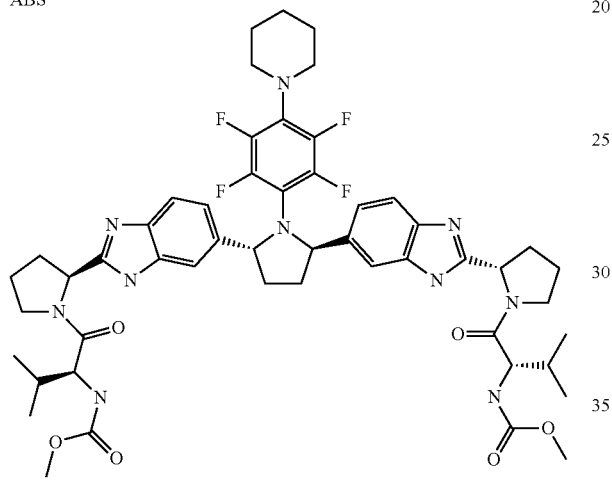

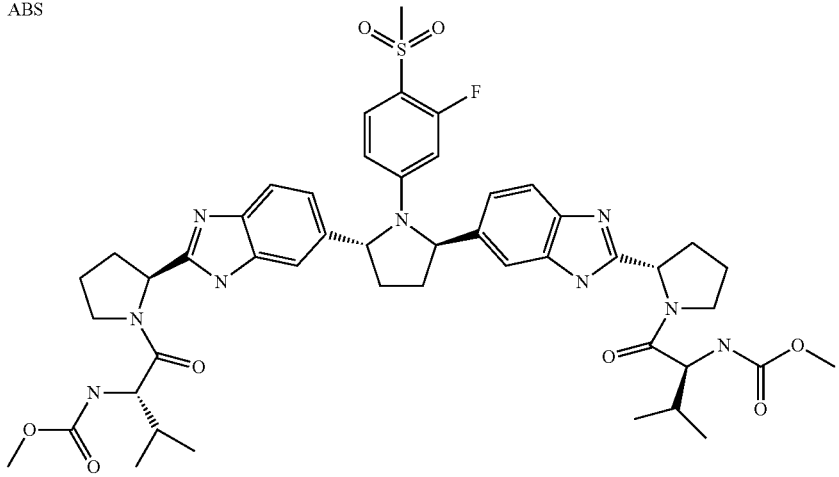

Example 2.7 methyl {(2S)-1-[(2S)-2-{6-[(2R,5R)-1-[3-fluoro-4-(methylsulfonyl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.81-0.97 (m, 12H), 1.30 (s, 2H), 1.82 (d, J=4.2 Hz, 2H), 1.90-2.35 (m, 12H), 3.60 (s, 6H), 3.88 (s, 3H), 4.13 (t, J=8.3 Hz, 2H), 5.20 (t, J=7.3 Hz, 2H), 5.62 (s, 2H), 6.26-6.40 (m, J=9.5 Hz, 2H), 7.15 (d, J=7.0 Hz, 2H), 7.30 (s, 1H), 7.32-7.45 (m, 4H), 7.49 (d, J=8.2 Hz, 1H), 7.56 (d, J=8.1 Hz, 1H), 12.16 (s, 2H); MS (ESI+) m/z 928.4 (M+H)$^+$, (ESI−) m/z 926.3 (M−H)$^−$.

methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate (ACD Name v12). The N-acetyl group was added by reaction with acetic anhydride/pyridine to provide the title compound. $^1$H NMR (400 MHz, DMSO-$d_6$) δ ppm 0.73-0.90 (m, 12H), 1.13 (d, J=5.20 Hz, 9H), 1.37-1.44 (m, 4H), 1.62-1.72 (m, 2H), 1.92-2.02 (m, 9H), 2.10-2.26 (m, 5H), 2.51-2.58 (m, 2H), 3.52 (s, 6H), 3.73-3.85 (m, 4H), 3.98-4.12 (m, 2H), 5.09-5.17 (m, 2H), 5.36-5.48 (m, 3H), 6.08-6.18 (m, 3H), 6.74-6.87 (m, 1H), 7.08 (dd, J=13.72, 8.29 Hz, 3H), 7.20 (s, 1H), 7.24-7.31 (m, 4H), 7.40 (d, J=8.24 Hz, 1H), 7.48 (d, J=8.13 Hz, 1H), 12.01 (s, 1H), 12.17 (s, 1H); MS (ESI+) m/z 964 (M+H)$^+$.

ABS

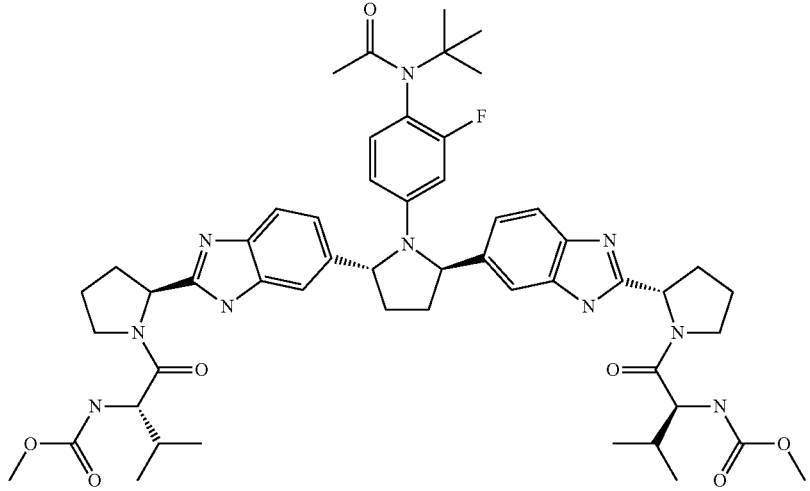

Example 2.8 methyl {(2S)-1-[(2S)-2-{6-[(2R,5R)-1-{4-[acetyl(tert-butyl)amino]-3-fluorophenyl}-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate Starting from 4-((2R,5R)-2,5-bis(4-chloro-3-nitrophenyl)pyrrolidin-1-yl)-N-tert-butyl-2-fluoroaniline, the initial product of the sequence outlined above was methyl {(2S)-1-[(2S)-2-{6-[(2R,5R)-1-[4-(tert-butylamino)-3-fluorophenyl]-5-{2-[(2S)-1-{(2S)-2-[(methoxycarbonyl)amino]-3-

ABS

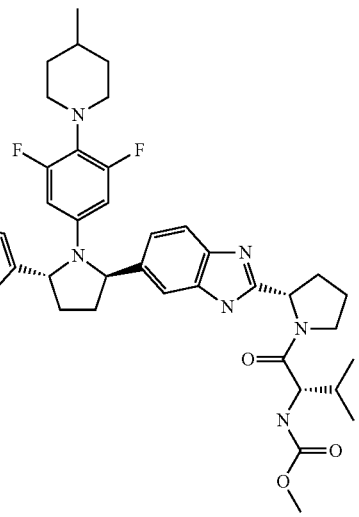

Example 2.9 methyl {(2S)-1-[(2S)-2-{6-[(2R,5R)-1-[3,5-difluoro-4-(4-methylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.75-0.90 (m, 12H), 1.05-1.18 (m, 2H), 1.24-1.37 (m, 2H), 1.45-1.54 (m, 2H), 1.62-1.73 (m, 2H), 1.84-2.05 (m, 7H), 2.12-2.25 (m, 5H), 2.69-2.81 (m, 4H), 3.52 (s, 6H), 3.77-3.86 (m, 4H), 4.05 (t, J=8.35 Hz, 2H), 5.10-5.18 (m, 2H), 5.35 (q, J=7.34 Hz, 2H), 5.87 (d, J=12.69 Hz, 2H), 7.02-7.10 (m, 2H), 7.19 (s, 1H), 7.24-7.32 (m, 3H), 7.39 (d, J=8.24 Hz, 1H), 7.47 (d, J=8.13 Hz, 1H), 12.06 (d, J=20.93 Hz, 2H); MS (ESI+) m/z 966 (M+H)$^+$.

ABS

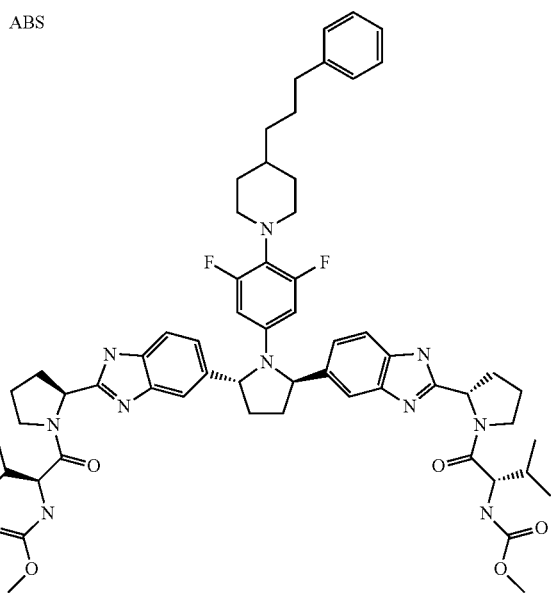

Example 2.10 methyl {(2S)-1-[(2S)-2-{5-[(2R,5R)-1-{3,5-difluoro-4-[4-(3-phenylpropyl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.72-0.95 (m, 12H), 1.00-1.31 (m, 9H), 1.46-1.59 (m, 4H), 1.61-1.79 (m, 2H), 1.83-2.08 (m, 6H), 2.11-2.27 (m, 4H), 2.77 (s, 4H), 3.54 (s, 6H), 3.82 (s, 4H), 4.06 (t, J=8.46 Hz, 2H), 5.08-5.19 (m, 2H), 5.28-5.46 (m, 2H), 5.88 (d, J=12.79 Hz, 2H), 7.01-7.10 (m, 2H), 7.10-7.33 (m, 9H), 7.40 (d, J=8.13 Hz, 1H), 7.48 (d, J=8.13 Hz, 1H), 11.71-12.51 (m, 2H); MS (ESI+) m/z 1069 (M+H)$^1$; MS (ESI−) m/z 1067 (M−H)$^−$.

ABS

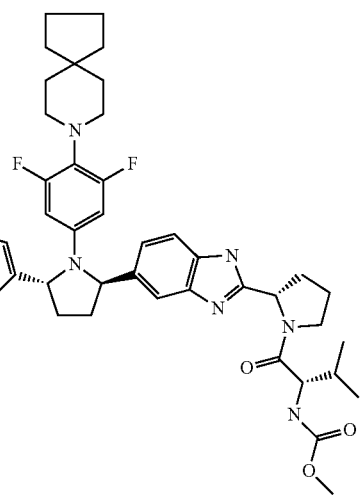

Example 2.11 methyl {(2S)-1-[(2S)-2-{5-[(2R,5R)-1-[4-(8-azaspiro[4.5]dec-8-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.73-0.93 (m, 12H), 1.29-1.43 (m, 9H), 1.52 (t, J=6.83 Hz, 5H), 1.68 (s, 2H), 1.81-2.08 (m, 6H), 2.10-2.26 (m, 4H), 2.75 (s, 4H), 3.54 (s, 6H), 3.82 (s, 4H), 4.06 (t, J=8.40 Hz, 2H), 5.09-5.19 (m, 2H), 5.29-5.46 (m, 2H), 5.88 (d, J=12.58 Hz, 2H), 7.03-7.11 (m, 2H), 7.20 (s, 1H), 7.25-7.33 (m, 3H), 7.40 (d, J=8.24 Hz, 1H), 7.49 (d, J=8.24 Hz, 1H), 11.63-12.57 (m, 2H); MS (ESI+) m/z 1005 (M+H)$^+$; MS (ESI−) m/z 1003 (M−H)$^−$.

ABS

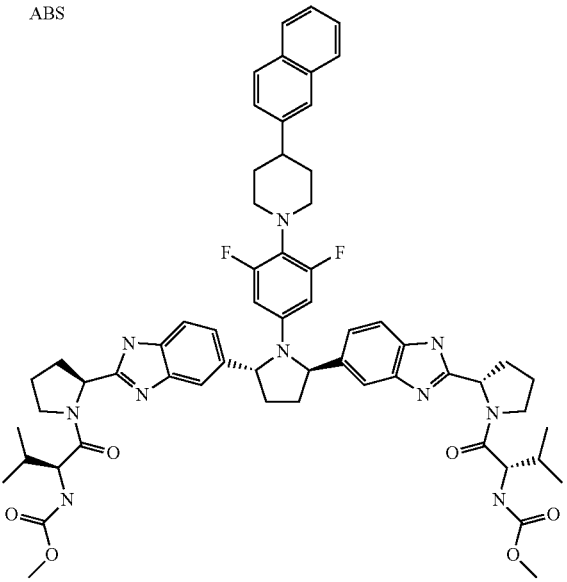 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(c5ccc6ccccc6c5)CC4)c(F)c3)ccc2[nH]1)C(C)C]

Example 2.12 methyl {(2S)-1-[(2S)-2-{5-[(2R,5R)-1-{3,5-difluoro-4-[4-(2-naphthyl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 0.76-0.91 (m, 12H), 1.24 (d, J=2.28 Hz, 2H), 1.63-2.08 (m, 12H), 2.20 (s, 4H), 2.86-3.19 (m, 5H), 3.53 (s, 6H), 3.82 (s, 4H), 4.06 (t, J=8.29 Hz, 2H), 5.10-5.22 (m, 2H), 5.32-5.48 (m, 2H), 5.93 (d, J=12.90 Hz, 2H), 7.03-7.16 (m, 2H), 7.19-7.36 (m, 4H), 7.39-7.55 (m, 5H), 7.69-7.89 (m, 4H), 11.71-12.63 (m, 2H); MS (ESI+) m/z 1077 (M+H)⁺; MS (ESI−) m/z 1075 (M−H)⁻.

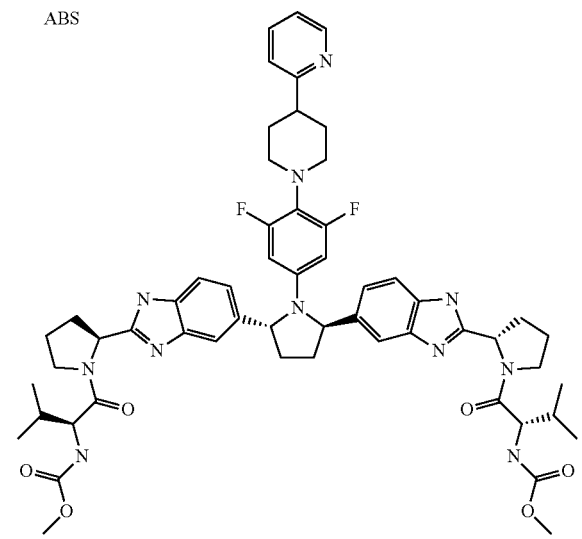 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(c5ccccn5)CC4)c(F)c3)ccc2[nH]1)C(C)C]

Example 2.13 methyl {(2S)-1-[(2S)-2-{5-[(2R,5R)-1-{3,5-difluoro-4-[4-(pyridin-2-yl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 0.71-1.02 (m, 12H), 1.62-1.83 (m, 6H), 1.81-2.08 (m, 7H), 2.10-2.29 (m, 4H), 2.47-2.63 (m, 2H), 2.81-3.07 (m, 4H), 3.53 (s, 6H), 3.82 (s, 4H), 4.06 (t, J=8.89 Hz, 2H), 5.10-5.21 (m, 2H), 5.31-5.47 (m, 2H), 5.91 (d, J=12.69 Hz, 2H), 7.04-7.13 (m, 2H), 7.14-7.20 (m, 1H), 7.20-7.34 (m, 5H), 7.41 (d, J=8.24 Hz, 1H), 7.49 (d, J=8.35 Hz, 1H), 7.62-7.72 (m, 1H), 8.45 (d, J=4.55 Hz, 1H), 11.74-12.57 (m, 2H); MS (ESI+) m/z 1028 (M+H)⁺; MS (ESI−) m/z 1026 (M−H)⁻.

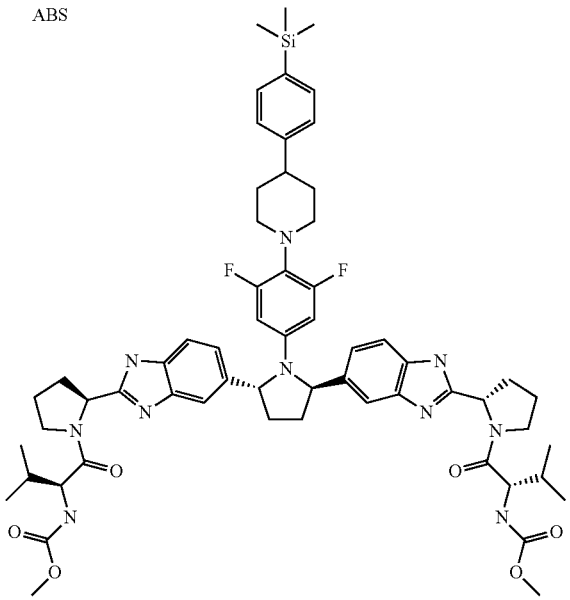 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(c5ccc([Si](C)(C)C)cc5)CC4)c(F)c3)ccc2[nH]1)C(C)C]

Example 2.14 methyl {(2S)-1-[(2S)-2-{5-[(2R,5R)-1-(3,5-difluoro-4-{4-[4-(trimethylsilyl)phenyl]piperidin-1-yl}phenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 0.20 (s, 9H), 0.74-0.94 (m, 12H), 1.59-1.75 (m, 6H), 1.83-2.09 (m, 7H), 2.13-2.29 (m, 4H), 2.44-2.59 (m, 2H), 2.84-3.15 (m, 4H), 3.53 (s, 6H), 3.82 (s, 4H), 4.06 (t, J=8.46 Hz, 2H), 5.15 (d, J=3.04 Hz, 2H), 5.31-5.47 (m, 2H), 5.92 (d, J=12.79 Hz, 2H), 7.04-7.14 (m, 2H), 7.21 (d, J=7.92 Hz, 3H), 7.27-7.37 (m, 3H), 7.37-7.45 (m, 3H), 7.50 (d, J=8.02 Hz, 1H), 12.10 (d, J=17.57 Hz, 2H); MS (ESI+) m/z 1099 (M+H)⁺; MS (ESI−) m/z 1097 (M−H)⁻.

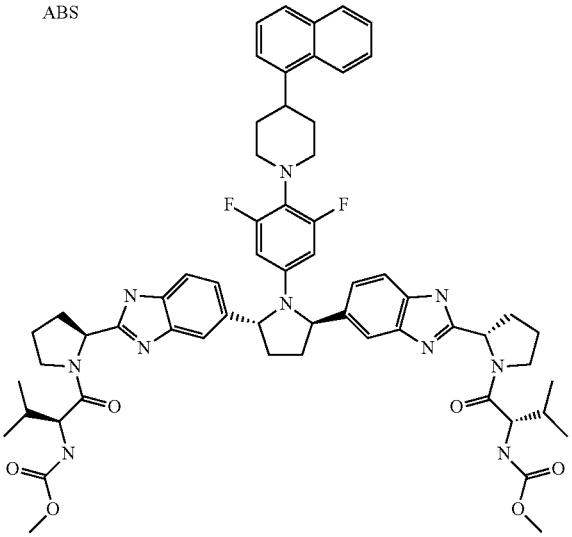 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(c5cccc6ccccc56)CC4)c(F)c3)ccc2[nH]1)C(C)C ; "ABS"]

Example 2.15 methyl {(2S)-1-[(2S)-2-{5-[(2R,5R)-1-{3,5-difluoro-4-[4-(1-naphthyl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.74-0.94 (m, 12H), 1.64-2.05 (m, 12H), 2.13-2.29 (m, 3H), 2.45-2.62 (m, 2H), 2.90-3.01 (m, J=11.06 Hz, 2H), 3.08-3.25 (m, 2H), 3.53 (s, 6H), 3.82 (s, 4H), 4.06 (t, J=8.29 Hz, 2H), 5.08-5.23 (m, 2H), 5.32-5.52 (m, 2H), 5.94 (d, J=12.69 Hz, 2H), 7.04-7.17 (m, 2H), 7.20-7.37 (m, 4H), 7.38-7.59 (m, 6H), 7.75 (d, J=8.35 Hz, 1H), 7.86-7.95 (m, 1H), 8.14 (d, J=8.24 Hz, 1H), 11.61-12.69 (m, 2H); MS (ESI+) m/z 1077 (M+H)$^+$; (ESI−) m/z 1075 (M−H)$^−$.

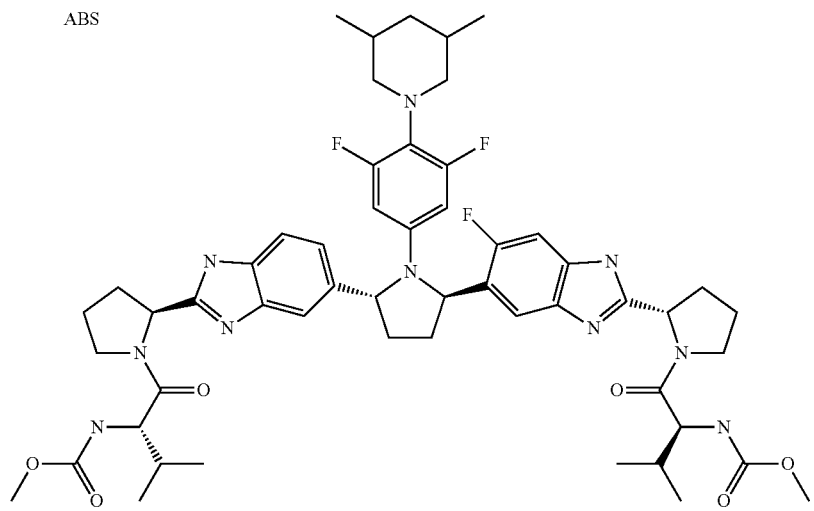

Example 2.16 methyl {(2S)-1-[(2S)-2-{5-[(5R)-1-[4-(3,5-dimethylpiperidin-1-yl)-3,5-difluorophenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, DMSO-d$_6$) δ ppm 0.64-0.94 (m, 18H) 1.56-1.73 (m, 4H) 1.75-1.93 (m, 6H) 1.95-2.06 (m, 6H) 2.12-2.26 (m, 4H) 2.69-2.79 (m, 1H) 3.20-3.29 (m, 1H) 3.53 (s, 6H) 3.74-3.89 (m, 4H) 3.97-4.10 (m, 2H) 5.05-5.19 (m, 2H) 5.48-5.62 (m, 2H) 5.87 (dd, J=11.49, 7.92 Hz, 2H) 7.02 (dd, J=3.90, 1.95 Hz, 1H) 7.12 (d, J=6.83 Hz, 1H) 7.26-7.37 (m, 3H) 7.40 (dd, J=11.11, 6.02 Hz, 1H) 12.08-12.16 (m, 1H) 12.23-12.31 (m, 1H); MS (APCI+) m/z 1016 (M+H)$^+$.

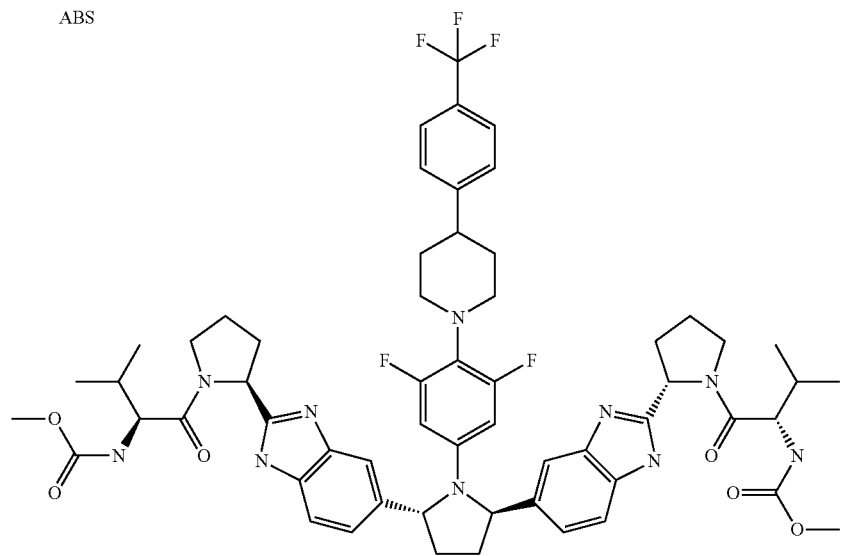

Example 2.17 methyl {(2S)-1-[(2S)-2-{5-[(2R,5R)-1-(3,5-difluoro-4-{4-[4-(trifluoromethyl)phenyl]piperazin-1-yl}phenyl)-5-{2-[(2S)-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.69-0.96 (m, 14H) 1.10-1.29 (m, 2H) 1.69 (m, 2H) 1.99 (m, 4H) 2.20 (m, 2H) 2.99 (m, 6H) 3.22-3.26 (m, 6H) 3.54 (s, 6H) 3.82 (m, 6H) 5.15 (m, 2H) 5.39 (m, 2H) 5.95 (m, 2H) 7.03 (d, J=8.78 Hz, 2H) 7.22 (m, 2H) 7.24-7.36 (m, 2H) 7.40-7.56 (m, 4H) 12.06 (s, 2H); MS (ESI+) m/z 1096.4, (ESI−) m/z 1094.3.

The following Example compounds 3.1-3.45 can be made from the appropriate listed intermediates following the methods of General Procedures 12/12A.

Intermediate Amines:
(S)-6,6'-((2R,5R)-1-(4-(pyridin-2-yl)phenyl)pyrrolidine-2,5-diyl)bis(2-((S)-pyrrolidin-2-yl)-1H-benzo[d]imidazole);
(S)-6,6'-((2R,5R)-1-(3-chloro-4-(trifluoromethoxy)phenyl)pyrrolidine-2,5-diyl)bis(2-((S)-pyrrolidin-2-yl)-1H-benzo[d]imidazole);
(S)-6,6'-((2R,5R)-1-(4-(2-methoxyethoxy)phenyl)pyrrolidine-2,5-diyl)bis(2-((S)-pyrrolidin-2-yl)-1H-benzo[d]imidazole);
(S)-6,6'-((2R,5R)-1-(4-chlorophenyl)pyrrolidine-2,5-diyl)bis(2-((S)-pyrrolidin-2-yl)-1H-benzo[d]imidazole);
(S)-6,6'-((2R,5R)-1-(biphenyl-4-yl)pyrrolidine-2,5-diyl)bis(2-((S)-pyrrolidin-2-yl)-1H-benzo[d]imidazole);
(S)-6,6'-((2R,5R)-1-(4-tert-butylphenyl)pyrrolidine-2,5-diyl)bis(2-((S)-pyrrolidin-2-yl)-1H-benzo[d]imidazole);
(S,S)-6,6'-((2R,5R)-1-(3,5-difluoro-4-(piperidin-1-yl)phenyl)pyrrolidine-2,5-diyl)bis(2-((2S,4S)-4-methoxypyrrolidin-2-yl)-1H-benzo[d]imidazole);
(S,S)-6,6'-((2R,5R)-1-(3,5-difluoro-4-(piperidin-1-yl)phenyl)pyrrolidine-2,5-diyl)bis(2-((2S,4S)-4-fluoropyrrolidin-2-yl)-1H-benzo[d]imidazole);
(S,S)-6,6'-((2R,5R)-1-(4-fluorophenyl)pyrrolidine-2,5-diyl)bis(2-((2S,4S)-4-fluoropyrrolidin-2-yl)-1H-benzo[d]imidazole);
(S,S)-6,6'-((2R,5R)-1-(4-fluorophenyl)pyrrolidine-2,5-diyl)bis(2-((2S,4S)-4-methoxypyrrolidin-2-yl)-1H-benzo[d]imidazole);
(S)-6,6'-((2R,5R)-1-(4-tert-butylphenyl)pyrrolidine-2,5-diyl)bis(2-((S)-5,5-dimethylpyrrolidin-2-yl)-1H-benzo[d]imidazole);
(S,S)-6,6'-((2R,5R)-1-(4-tert-butylphenyl)pyrrolidine-2,5-diyl)bis(2-((2S,4S)-4-fluoropyrrolidin-2-yl)-1H-benzo[d]imidazole);
(S)-6,6'-((2S,5S)-1-(4-cyclopropyl-2-fluorophenyl)pyrrolidine-2,5-diyl)bis(2-((S)-pyrrolidin-2-yl)-1H-benzo[d]imidazole);
(S)-6,6'-((2R,5R)-1-(3-fluoro-4-(piperidin-1-yl)phenyl)pyrrolidine-2,5-diyl)bis(2-((S)-pyrrolidin-2-yl)-1H-benzo[d]imidazole);
(S)-6,6'-((2R,5R)-1-(3,5-difluoro-4-(piperidin-1-yl)phenyl)pyrrolidine-2,5-diyl)bis(2-((S)-pyrrolidin-2-yl)-1H-benzo[d]imidazole);
(S)-6,6'-((2R,5R)-1-(3-fluoro-4-(4-phenylpiperidin-1-yl)phenyl)pyrrolidine-2,5-diyl)bis(2-((S)-pyrrolidin-2-yl)-1H-benzo[d]imidazole);
(S)-6,6'-((2R,5R)-1-(3,5-difluoro-4-(4-phenylpiperidin-1-yl)phenyl)pyrrolidine-2,5-diyl)bis(2-((S)-pyrrolidin-2-yl)-1H-benzo[d]imidazole);
(S)-6,6'-((2R,5R)-1-(3,5-difluoro-4-(piperidin-1-yl)phenyl)pyrrolidine-2,5-diyl)bis(2-((3S)-2-azabicyclo[2.2.1]heptan-3-yl)-1H-benzo[d]imidazole);
(S)-6,6'-((2R,5R)-1-(3,5-difluoro-4-(piperidin-1-yl)phenyl)pyrrolidine-2,5-diyl)bis(2-((S)-indolin-2-yl)-1H-benzo[d]imidazole);
(S)-6,6'-((2R,5R)-1-(4-tert-butylphenyl)pyrrolidine-2,5-diyl)bis(2-((S)-4-methylenepyrrolidin-2-yl)-1H-benzo[d]imidazole);
(S,S,S)-6,6'-((2R,5R)-1-(3,5-difluoro-4-(4-phenylpiperidin-1-yl)phenyl)pyrrolidine-2,5-diyl)bis(2-((2S,3aS,6aS)-octahydrocyclopenta[b]pyrrol-2-yl)-1H-benzo[d]imidazole);
(S,S,S)-6,6'-((2R,5R)-1-(3,5-difluoro-4-(piperidin-1-yl)phenyl)pyrrolidine-2,5-diyl)bis(2-((2S,3aS,6aS)-octahydrocyclopenta[b]pyrrol-2-yl)-1H-benzo[d]imidazole);

(S)-6,6'-((2R,5R)-1-(3,5-difluoro-4-(4-phenylpiperidin-1-yl)phenyl)pyrrolidine-2,5-diyl)bis(2-((S)-pyrrolidin-2-yl)-1H-benzo[d]imidazole);

6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12);

(S,S,S)-6,6'-((2R,5R)-1-(3,5-difluoro-4-(piperidin-1-yl)phenyl)pyrrolidine-2,5-diyl)bis(5-fluoro-2-((2S,3aS,6aS)-octahydrocyclopenta[b]pyrrol-2-yl)-1H-benzo[d]imidazole);

(S)-6,6'-((2R,5R)-1-(3,5-difluoro-4-(4-(4-fluorophenyl)piperidin-1-yl)phenyl)pyrrolidine-2,5-diyl)bis(2(S)-pyrrolidin-2-yl)-1H-benzo[d]imidazole);

(S)-6,6'-((2R,5R)-1-(3,5-difluoro-4-(4-(3-(trimethylsilyl)phenyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4-(3,4-difluorophenyl)piperidin-1-yl)-3,5-difluorophenyl)pyrrolidine-2,5-diyl)bis(2((S)-pyrrolidin-2-yl)-1H-benzo[d]imidazole); and (S)-6,6'-((2R,5R)-1-(4-(4-(3,5-difluorophenyl)piperidin-1-yl)-3,5-difluorophenyl)pyrrolidine-2,5-diyl)bis(2-((S)-pyrrolidin-2-yl)-1H-benzo[d]imidazole).

Intermediate Acids:
(S)-2-(methoxycarbonylamino)-3-methylbutanoic acid;
(S)-2-(methoxycarbonylamino)-2-(tetrahydro-2H-pyran-4-yl)acetic acid;
(S)-2-cyclohexyl-2-(methoxycarbonylamino)acetic acid;
(S)-2-cyclopentyl-2-(methoxycarbonylamino)acetic acid;
(S)-2-(methoxycarbonylamino)-3,3-dimethylbutanoic acid;
(2S,3R)-3-methoxy-2-(methoxycarbonylamino)butanoic acid;
(2S,3S)-3-methoxy-2-(methoxycarbonylamino)butanoic acid;
(S)-2-(methoxycarbonylamino)-2-((R)-tetrahydrofuran-3-yl)acetic acid;
(S)-2-(methoxycarbonylamino)-2-((S)-tetrahydrofuran-3-yl)acetic acid;
(S)-2-(2,3-dihydro-1H-inden-2-yl)-2-(methoxycarbonylamino)acetic acid;
2-(tert-butoxycarbonylamino)acetic acid;
2-(methoxycarbonylamino)-3-methylbut-2-enoic acid;
(S)-tetrahydrofuran-2-carboxylic acid
(S)-3-ethyl-2-(methoxycarbonylamino)pentanoic acid; and
(S)-2-(ethoxycarbonylamino)-3-methylbutanoic acid.

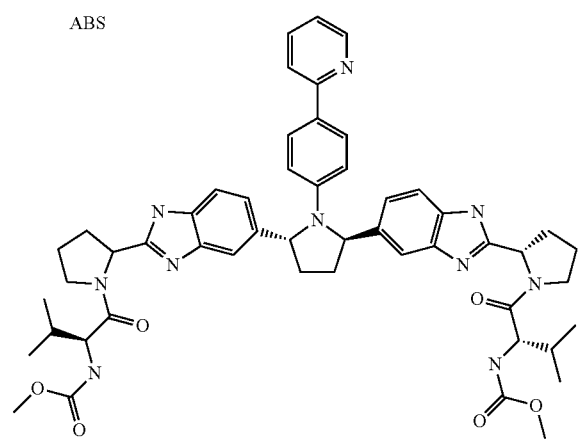 [SMILES: COC(=O)N[C@H](C(=O)N1CCCC1c1nc2cc([C@H]3CC[C@H](c4ccc5[nH]c([C@@H]6CCCN6C(=O)[C@@H](NC(=O)OC)C(C)C)nc5c4)N3c3ccc(-c4ccccn4)cc3)ccc2[nH]1)C(C)C ; "ABS"]

Example 3.1 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(pyridin-2-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-d$_6$) δ ppm 12.28-11.98 (m, 2H), 8.42 (d, J=4.4, 1H), 7.70-7.56 (m, 4H), 7.46 (d, J=8.2, 1H), 7.38 (d, J=8.2, 1H), 7.34 (s, 1H), 7.30-7.20 (m, 3H), 7.16-7.02 (m, 3H), 6.42 (d, J=8.7, 2H), 5.56-5.42 (m, 2H), 5.18-5.06 (m, 2H), 4.03 (t, J=9.3, 2H), 3.88-3.73 (m, 4H), 3.52 (s, 6H), 2.25-1.62 (m, 14H), 0.92-0.67 (m, 12H); MS (ESI+) m/z 909.5 (M+H)$^+$.

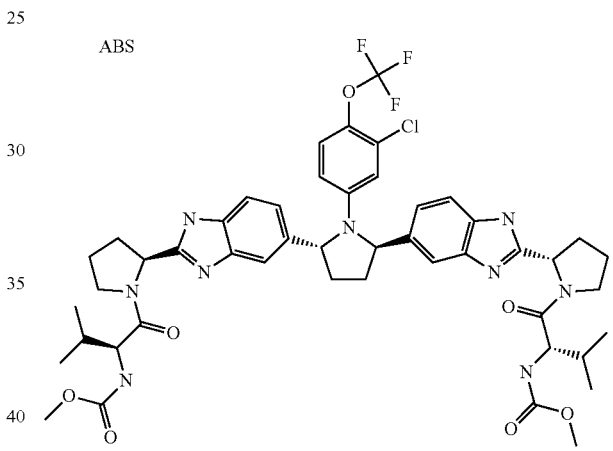

Example 3.2 methyl {(2S)-1-[(2S)-2-{5-((2R,5R)-1-[3-chloro-4-(trifluoromethoxy)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.31-12.01 (m, 2H), 7.48 (d, J=7.9, 1H), 7.40 (d, J=8.2, 1H), 7.34-7.17 (m, 4H), 7.15-6.99 (m, 3H), 6.44 (s, 1H), 6.30 (d, J=8.9, 1H), 5.55-5.37 (m, 2H), 5.19-5.04 (m, 2H), 4.04 (t, J=7.8, 2H), 3.89-3.73 (m, 4H), 3.52 (s, 6H), 2.28-1.79 (m, 12H), 1.77-1.59 (m, 2H), 0.92-0.64 (m, 12H); MS (ESI+) m/z 950.4 (M+H)$^+$.

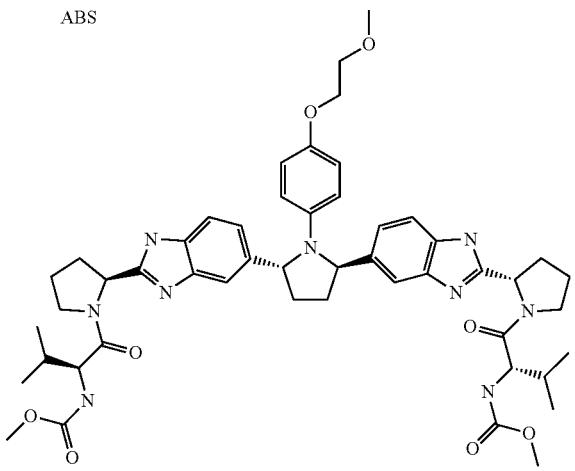 [SMILES: COCCOc1ccc(N2[C@@H](c3ccc4[nH]c([C@@H]5CCCN5C(=O)[C@@H](NC(=O)OC)C(C)C)nc4c3)CC[C@@H]2c2ccc3[nH]c([C@@H]4CCCN4C(=O)[C@@H](NC(=O)OC)C(C)C)nc3c2)cc1 ; "ABS"]

Example 3.3 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(2-methoxyethoxy)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-$d_6$) δ ppm 12.27-11.97 (m, 2H), 7.44 (d, J=8.4, 1H), 7.36 (d, J=7.7, 1H), 7.33-7.25 (m, 3H), 7.20 (s, 1H), 7.12-7.00 (m, 2H), 6.58-6.47 (m, 2H), 6.24 (d, J=9.0, 2H), 5.40-5.27 (m, 2H), 5.19-5.08 (m, 2H), 4.06 (t, J=8.3, 2H), 3.88-3.76 (m, 6H), 3.54 (s, 6H), 3.51-3.45 (m, 2H), 3.21 (s, 3H), 2.26-1.83 (m, 12H), 1.75-1.64 (m, 2H), 0.93-0.74 (m, 12H); MS (ESI+) m/z 906.4 (M+H)$^+$.

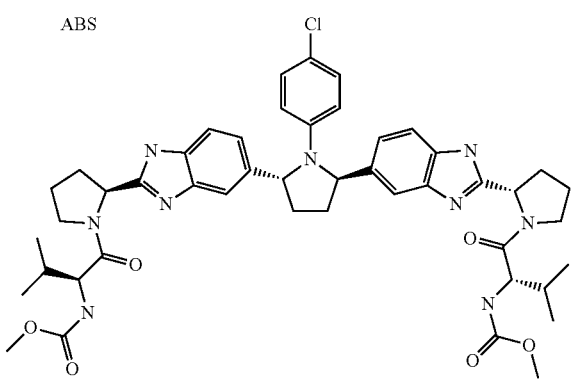 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(Cl)cc3)ccc2[nH]1)C(C)C ; "ABS"]

Example 3.4 methyl {(2S)-1-[(2S)-2-{5-[(2R,5R)-1-(4-chlorophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 12.05 (s, 2H), 7.44 (d, J=8.2, 1H), 7.36 (d, J=8.1, 1H), 7.31-7.22 (m, 3H), 7.19 (s, 1H), 7.03 (t, J=8.2, 2H), 6.94-6.83 (m, 2H), 6.29 (d, J=9.1, 2H), 5.42-5.32 (m, 2H), 5.16-5.04 (m, 2H), 4.04 (t, J=8.4, 2H), 3.85-3.75 (m, 4H), 3.51 (s, 6H), 2.25-1.58 (m, 14H), 0.90-0.73 (m, 12H); MS (ESI+) m/z 866.4 (M+H)$^+$.

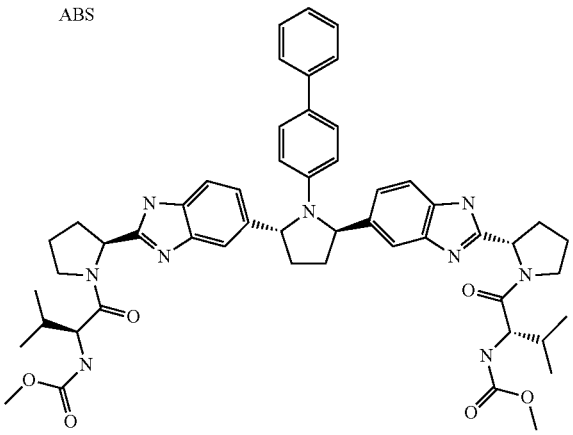 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(-c4ccccc4)cc3)ccc2[nH]1)C(C)C ; "ABS"]

Example 3.5 methyl {(2S)-1-[(2S)-2-{5-[(2R,5R)-1-(biphenyl-4-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ 12.11-11.66 (m, 2H), 7.47 (d, J=8.3, 1H), 7.43-7.33 (m, 4H), 7.32-7.19 (m, 7H), 7.17-7.06 (m, 3H), 6.43 (d, J=8.8, 2H), 5.52-5.41 (m, 2H), 5.18-5.09 (m, 2H), 4.05 (t, J=8.2, 2H), 3.87-3.76 (m, 4H), 3.53 (s, 6H), 2.25-2.11 (m, 4H), 2.05-1.62 (m, 10H), 0.91-0.74 (m, 12H); MS (ESI+) m/z 908.5 (M+H)$^+$.

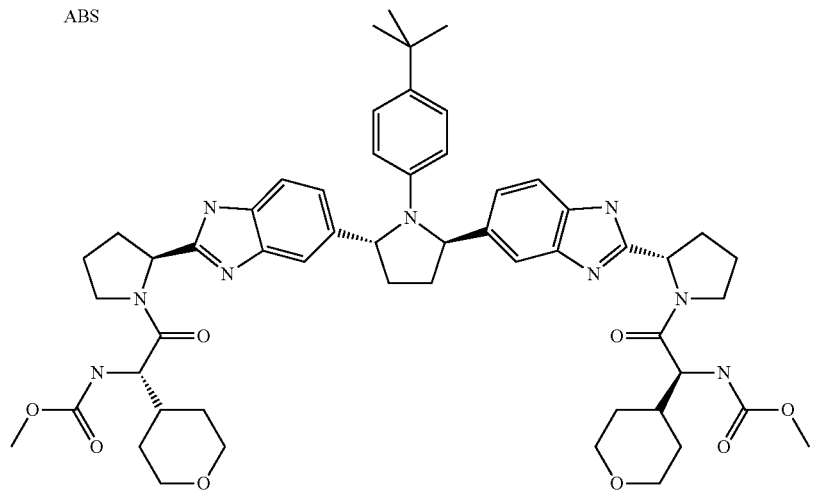

Example 3.6 dimethyl ([(2R,5R)-1-(4-tert-butylphenyl)pyrrolidine-2,5-diyl]bis{1H-benzimidazole-5,2-diyl(2S)pyrrolidine-2,1-diyl[(1S)-2-oxo-1-(tetrahydro-2H-pyran-4-yl)ethane-2,1-diyl]})biscarbamate $^1$H NMR (400 MHz, DMSO-d$_6$) δ ppm 1.07 (s, 9H) 1.22-1.32 (m, 2H) 1.42-1.57 (m, 4H) 1.64-1.72 (m, 2H) 1.82 (dd, J=21.90, 10.63 Hz, 4H) 1.92-2.02 (m, 4H) 2.10-2.25 (m, 4H) 2.90-2.99 (m, 1H) 3.04-3.19 (m, 4H) 3.53 (s, 6H) 3.56-3.63 (m, 1H) 3.66-3.79 (m, 4H) 3.83 (d, J=3.04 Hz, 4H) 4.14 (q, J=8.10 Hz, 2H) 5.07-5.15 (m, 2H) 5.33-5.40 (m, 2H) 6.24 (d, J=8.89 Hz, 2H) 6.85-6.94 (m, 2H) 7.09 (dd, J=14.10, 8.46 Hz, 2H) 7.16-7.22 (m, 2H) 7.30-7.41 (m, 3H) 7.44 (d, J=9.43 Hz, 1H) 11.99-12.12 (m, 2H); MS (ESI+) m/z 972.5 (M+H)$^+$.

Example 3.7 methyl {(2S)-1-[(2S,4S)-2-{5-[(2R,5R)-1-[3,5-difluoro-4-(piperidin-1-yl)phenyl]-5-{2-[(2S,4S)-4-methoxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-methoxypyrrolidin-1-yl]-3-methyl-1-oxobutan-2-yl}carbamate $^1$H NMR (500 MHz, DMSO-d$_6$) δ ppm 0.76-0.87 (m, 12H) 1.35-1.40 (m, 2H) 1.45 (s, 4H) 1.66-1.72 (m, 2H) 1.95 (dd, J=13.28, 7.17 Hz, 2H) 2.14 (td, J=12.32, 5.87 Hz, 2H) 2.41-2.46 (m, 2H) 2.76 (s, 4H) 3.03-3.18 (m, 2H) 3.25 (d, J=3.66 Hz, 6H) 3.54 (s, 6H) 3.64 (td, J=11.14, 5.65 Hz, 2H) 4.05-4.13 (m, 4H) 4.19-4.27 (m, 2H) 5.10-5.16 (m, 2H) 5.31-5.39 (m, 2H) 5.88 (d, J=12.66 Hz, 2H) 7.06 (t, J=8.47 Hz, 2H) 7.21-7.31 (m, 4H) 7.41 (d, J=8.09 Hz, 1H) 7.48 (dd, J=8.39, 1.83 Hz, 1H) 11.81-11.91 (m, 2H); MS (ESI+) m/z 1011.6 (M+H)$^+$.

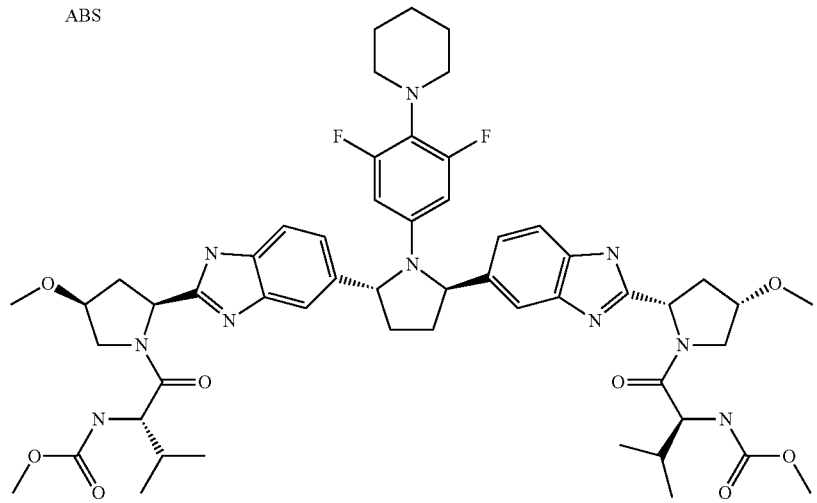

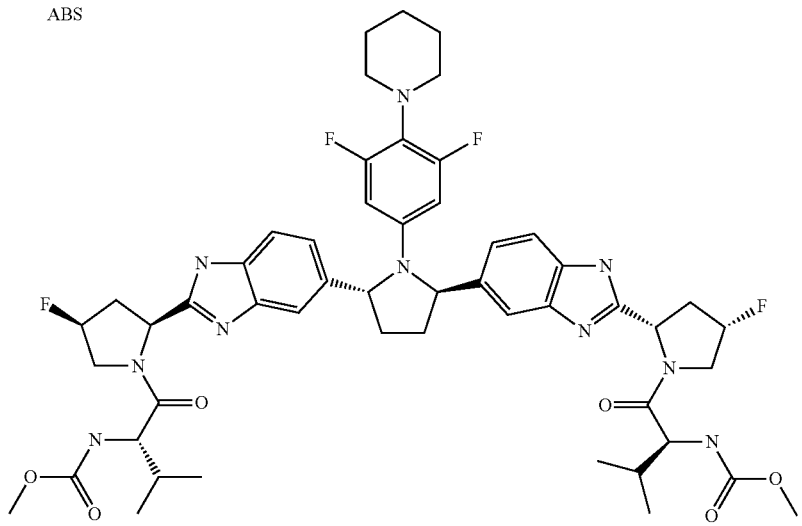

Example 3.8 methyl {(2S)-1-[(2S,4S)-2-{5-[(2R,5R)-1-[3,5-difluoro-4-(piperidin-1-yl)phenyl]-5-{2-[(2S,4S)-4-fluoro-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-fluoropyrrolidin-1-yl]-3-methyl-1-oxobutan-2-yl}carbamate ¹H NMR (500 MHz, DMSO-d₆) δ ppm 0.80-0.99 (m, 12H) 1.38 (d, J=4.73 Hz, 2H) 1.45 (s, 4H) 1.64-1.74 (m, 2H) 2.00-2.08 (m, 2H) 2.37-2.45 (m, 2H) 2.76 (s, 4H) 3.08-3.19 (m, 2H) 3.55 (s, 6H) 3.99-4.26 (m, 6H) 5.30-5.39 (m, 4H) 5.47 (d, J=53.41 Hz, 4H) 5.89 (d, J=12.66 Hz, 2H) 7.02-7.11 (m, 2H) 7.27 (d, J=25.02 Hz, 2H) 7.41 (d, J=8.09 Hz, 3H) 7.47 (d, J=7.93 Hz, 1H) 11.85 (d, J=31.74 Hz, 2H); MS (ESI+) m/z 987.5 (M+H)⁺.

Example 3.9 methyl {(2S)-1-[(2S,4S)-4-fluoro-2-{5-[(2R,5R)-5-{2-[(2S,4S)-4-fluoro-1-{(2S)-2-[(methoxycarbonyl)amino]-3-methylbutanoyl}pyrrolidin-2-yl]-1H-benzimidazol-5-yl}-1-(4-fluorophenyl)pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 0.82-0.98 (m, 12H) 1.68-1.77 (m, 2H) 1.91-2.09 (m, 4H) 2.36-2.44 (m, 2H) 2.59-2.66 (m, 2H) 3.52-3.57 (m, 6H) 3.72-3.98 (m, 2H) 4.07-4.18 (m, 4H) 5.19 (t, J=8.08 Hz, 1H) 5.31-5.44 (m, 4H) 5.48-5.57 (m, 1H) 6.24-6.31 (m, 2H) 6.70-6.78 (m, 2H) 7.02-7.12 (m, 2H) 7.17 (s, 1H) 7.24-7.34 (m, 2H) 7.39 (t, J=7.92 Hz, 2H) 7.47 (dd, J=20.38, 8.35 Hz, 1H) 11.78-12.06 (m, 2H); MS (ESI+) m/z 886.4 (M+H)⁺.

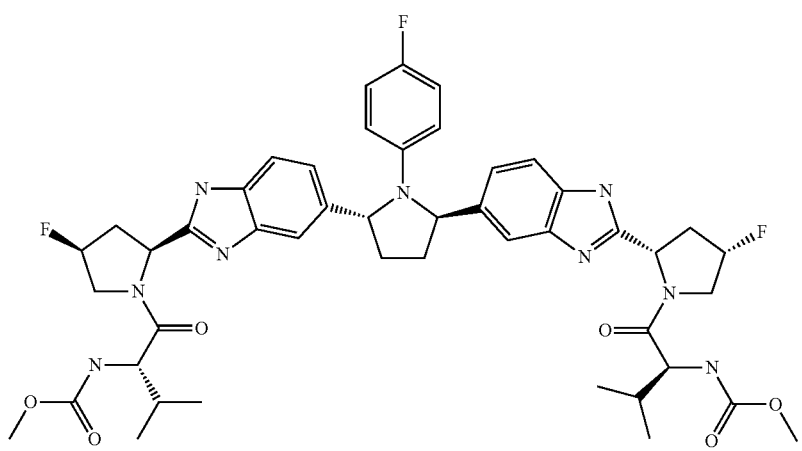

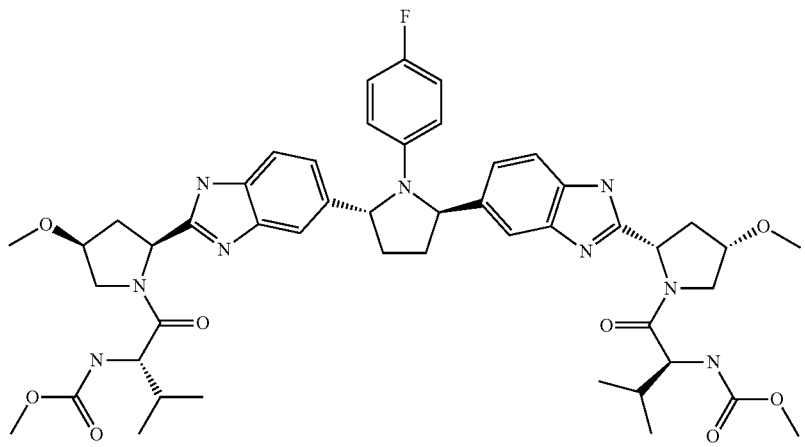

Example 3.10 methyl {(2S)-1-[(2S,4S)-2-{5-[(2R,5R)-1-(4-fluorophenyl)-5-{2-[(2S,4S)-4-methoxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-methoxypyrrolidin-1-yl]-3-methyl-1-oxobutan-2-yl}carbamate $^1$H NMR (400 MHz, DMSO-d$_6$) δ ppm 0.77-0.90 (m, 12H) 1.66-1.76 (m, 2H) 1.88-2.01 (m, 2H) 2.06-2.19 (m, 2H) 2.54-2.62 (m, 2H) 3.25 (d, J=5.86 Hz, 6H) 3.54 (s, 6H) 3.59-3.72 (m, 2H) 3.97-4.14 (m, 6H) 4.16-4.30 (m, 2H) 5.05-5.19 (m, 2H) 5.36 (d, J=3.25 Hz, 2H) 6.28 (dd, J=7.26, 4.34 Hz, 2H) 6.69-6.79 (m, 2H) 7.04 (d, J=8.57 Hz, 2H) 7.22-7.33 (m, 4H) 7.38 (d, J=8.02 Hz, 1H) 7.45 (d, J=8.24 Hz, 1H) 11.81 (s, 2H); MS (ESI+) m/z 910.4 (M+H)$^+$.

Example 3.11 methyl {(2S)-1-[(5S)-5-{5-[(2R,5R)-1-(4-tert-butylphenyl)-5-{2-[(2S)-1-{(2S)-2-[(methoxycarbonyl)amino]-3-methylbutanoyl}-5,5-dimethylpyrrolidin-2-yl]-1H-benzimidazol-5-yl}pyrrolidin-2-yl]-1H-benzimidazol-2-yl}-2,2-dimethylpyrrolidin-1-yl]-3-methyl-1-oxobutan-2-yl}carbamate $^1$H NMR (400 MHz, DMSO-d$_6$) δ ppm 0.81 (d, J=6.61 Hz, 6H) 0.89 (d, J=6.72 Hz, 6H) 1.07 (s, 9H) 1.38 (s, 6H) 1.62 (s, 6H) 1.68-1.77 (m, 4H) 1.82 (s, 2H) 1.94 (dd, J=13.61, 6.78 Hz, 2H) 2.10-2.18 (m, 2H) 2.27 (dd, J=4.12, 2.60 Hz, 2H) 3.15 (d, J=3.36 Hz, 6H) 3.96-4.03 (m, 2H) 5.30-5.43 (m, 6H) 6.24-6.31 (m, 2H) 6.70 (t, J=6.67 Hz, 2H) 6.84-6.91 (m, 2H) 7.05-7.13 (m, 2H) 7.24 (s, 1H) 7.36 (d, J=1.08 Hz, 1H) 7.40 (d, J=7.59 Hz, 1H) 7.49 (d, J=8.78 Hz, 1H) 12.16 (d, J=29.28 Hz, 2H); MS (ESI+) m/z 944.5 (M+H)$^+$.

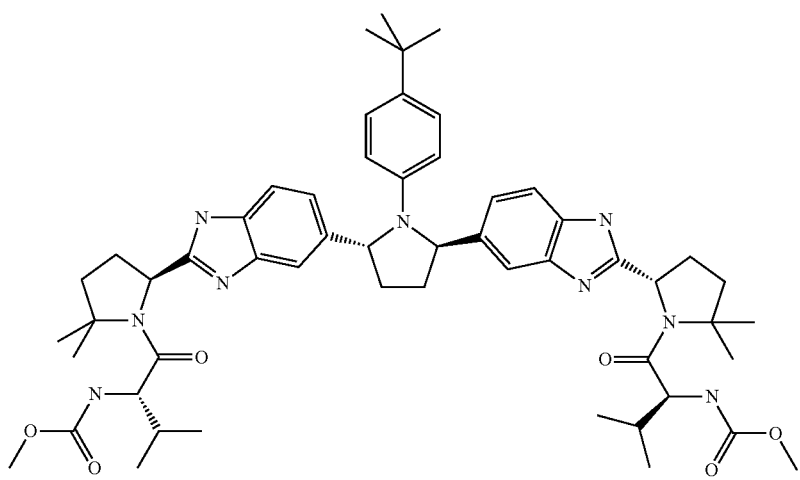

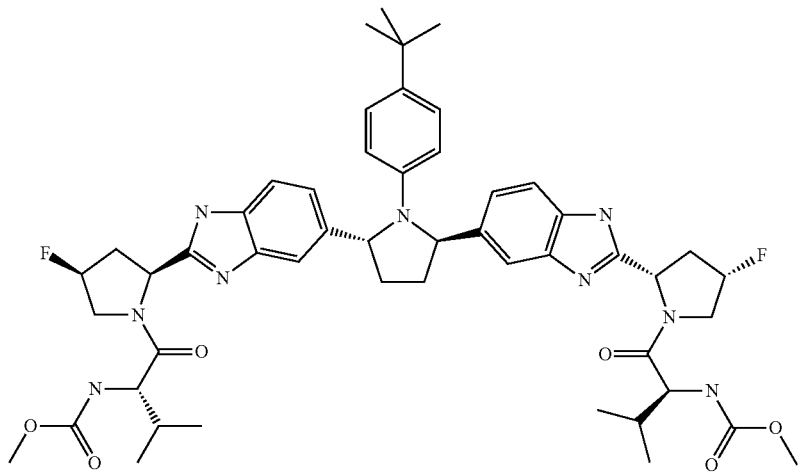
Example 3.12
methyl {(2S)-1-[(2S,4S)-2-{5-[(2R,5R)-1-(4-tert-butylphenyl)-5-{2-[(2S,4S)-4-fluoro-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-fluoropyrrolidin-1-yl]-3-methyl-1-oxobutan-2-yl}carbamate
$^1$H NMR (400 MHz, DMSO-d$_6$) δ ppm 0.79-0.97 (m, 12H) 1.07 (s, 9H) 1.66-1.75 (m, 2H) 1.99-2.08 (m, 2H) 2.40 (dd, J=17.02, 3.04 Hz, 2H) 3.09-3.21 (m, 4H) 3.55 (s, 6H) 4.05-4.13 (m, 4H) 4.16-4.27 (m, 2H) 5.35 (dd, J=8.51, 3.09 Hz, 4H) 5.46 (d, J=53.24 Hz, 2H) 6.23-6.29 (m, 2H) 6.91 (d, J=8.89 Hz, 2H) 7.03-7.11 (m, 2H) 7.23 (d, J=3.47 Hz, 1H) 7.28 (s, 1H) 7.39 (dd, J=8.08, 4.72 Hz, 3H) 7.44 (d, J=8.57 Hz, 1H) 11.80 (d, J=20.06 Hz, 2H); MS (ESI+) m/z 924.4 (M+H)$^+$.
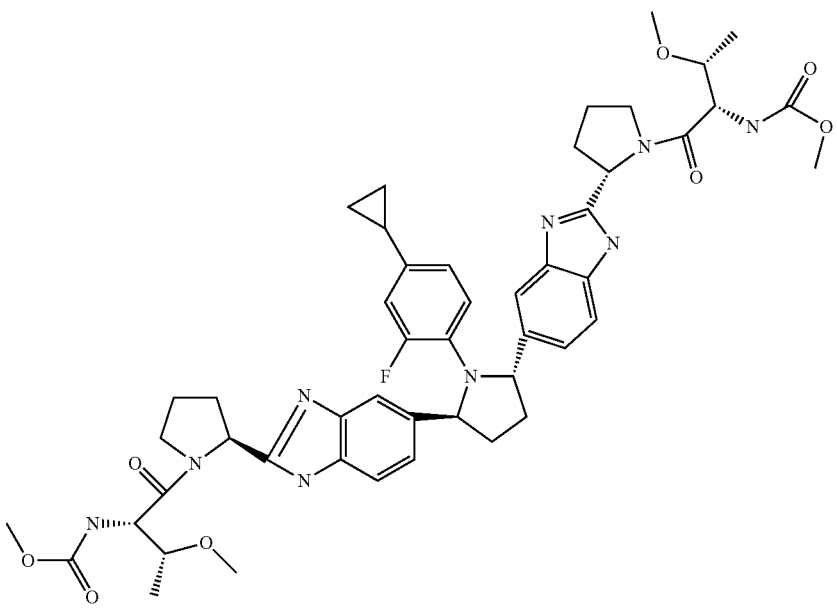

Example 3.13 methyl {(2S,3R)-1-[(2S)-2-{5-[(2S,5S)-1-(4-cyclo-
propyl-2-fluorophenyl)-5-(2-{(2S)-1-[N-(methoxy-
carbonyl)-O-methyl-l-threonyl]pyrrolidin-2-yl}-1H-
benzimidazol-5-yl)pyrrolidin-2-yl]-1H-
benzimidazol-2-yl}pyrrolidin-1-yl]-3-methoxy-1-
oxobutan-2-yl}carbamate $^1$H NMR (500 MHz, DMSO-d$_6$) δ ppm 0.35-0.57 (m, 2H) 0.66-0.85 (m, 2H) 1.07-1.17 (m, 7H) 1.59-1.69 (m, 1H) 1.82 (s, 2H) 1.95-2.12 (m, 5H) 2.13-2.33 (m, 5H) 3.17-3.35 (m, 6H) 3.48-3.65 (m, 6H) 3.85-3.95 (m, 4H) 4.29-4.38 (m, 2H) 5.11-5.25 (m, 2H) 5.58 (s, 2H) 6.44-6.57 (m, 2H) 6.59-6.70 (m, 1H) 7.07-7.19 (m, 2H) 7.25-7.32 (m, 2H) 7.35-7.41 (m, 2H) 7.45 (d, J=8.24 Hz, 2H) 12.05 (d, J=16.63 Hz, 2H); MS (ESI+) m/z 922.4 (M+H)$^+$, (ESI−) m/z 920.3 (M−H)$^-$.

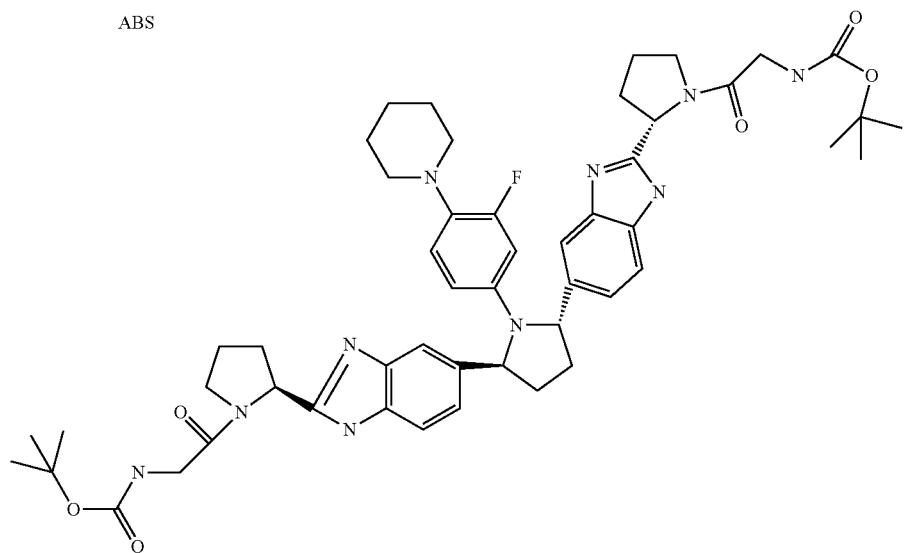 [SMILES: CC(C)(C)OC(=O)NCC(=O)N1CCC[C@H]1c1nc2cc([C@@H]3CC[C@@H](c4ccc5[nH]c([C@@H]6CCCN6C(=O)CNC(=O)OC(C)(C)C)nc5c4)N3c3ccc(N4CCCCC4)c(F)c3)ccc2[nH]1 ; "ABS"]

ABS

Example 3.14 tert-butyl {2-[(2S)-2-(5-{(2S,5S)-5-{2-[(2S)-1-
{[(tert-butoxycarbonyl)amino]acetyl}pyrrolidin-2-
yl]-1H-benzimidazol-5-yl}-1-[3-fluoro-4-(piperidin-
1-yl)phenyl]pyrrolidin-2-yl}-1H-benzimidazol-2-yl)
pyrrolidin-1-yl]-2-oxoethyl}carbamate $^1$H NMR (400 MHz, DMSO-d$_6$) δ ppm 1.16-1.43 (m, 18H) 1.42-2.27 (m, 14H) 2.58-2.70 (m, 5H) 3.38-4.02 (m, 9H) 5.14 (s, 2H) 5.33 (s, 3H) 6.04 (s, 2H) 6.74 (s, 3H) 7.04-7.60 (m, 7H) 11.83-12.43 (m, 2H); MS (ESI+) m/z 933.4 (M+H)$^+$, (ESI−) m/z 931.4 (M−H)$^-$.

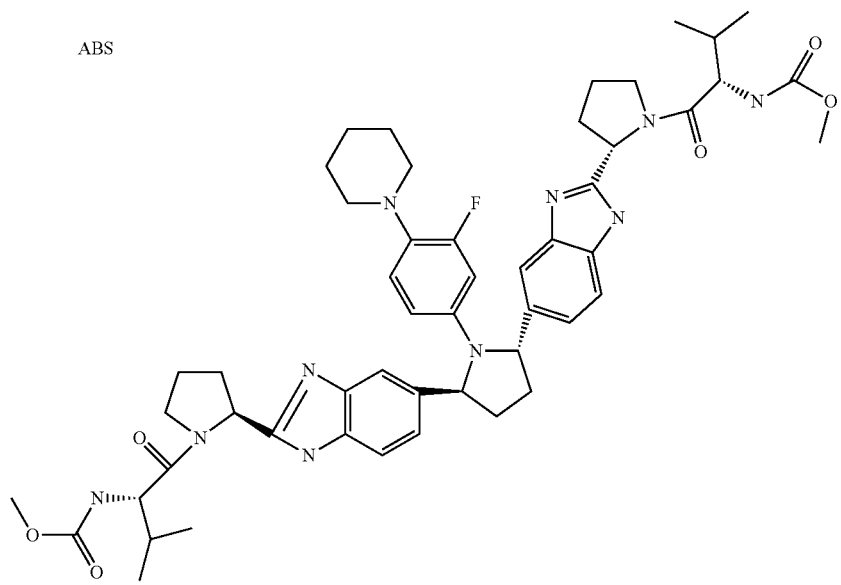 [SMILES: COC(=O)N[C@H](C(=O)N1CCC[C@H]1c1nc2cc([C@@H]3CC[C@@H](c4ccc5[nH]c([C@@H]6CCCN6C(=O)[C@@H](NC(=O)OC)C(C)C)nc5c4)N3c3ccc(N4CCCCC4)c(F)c3)ccc2[nH]1)C(C)C ; "ABS"]
Example 3.15
methyl {(2S)-1-[(2S)-2-{5-[(2S,5S)-1-[3-fluoro-4-(piperidin-1-yl)phenyl]-5-{2-[(2S)-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-d$_6$) δ ppm 0.73-0.93 (m, 12H) 1.32-1.57 (m, 6H) 1.58-2.06 (m, 14H) 2.18 (s, 4H) 2.67 (dd, J=3.69, 1.95 Hz, 4H) 3.75-3.87 (m, 6H) 4.07 (t, 2H) 5.13 (s, 2H) 5.37 (dd, J=6.02, 2.11 Hz, 2H) 6.04 (s, 2H) 6.65 (s, 1H) 7.09 (s, 2H) 7.16-7.23 (m, 1H) 7.23-7.48 (m, 5H) 12.01 (s, 2H); MS (ESI+) m/z 933.5 (M+H)$^+$, (ESI−) m/z 931.4 (M−H)$^−$.
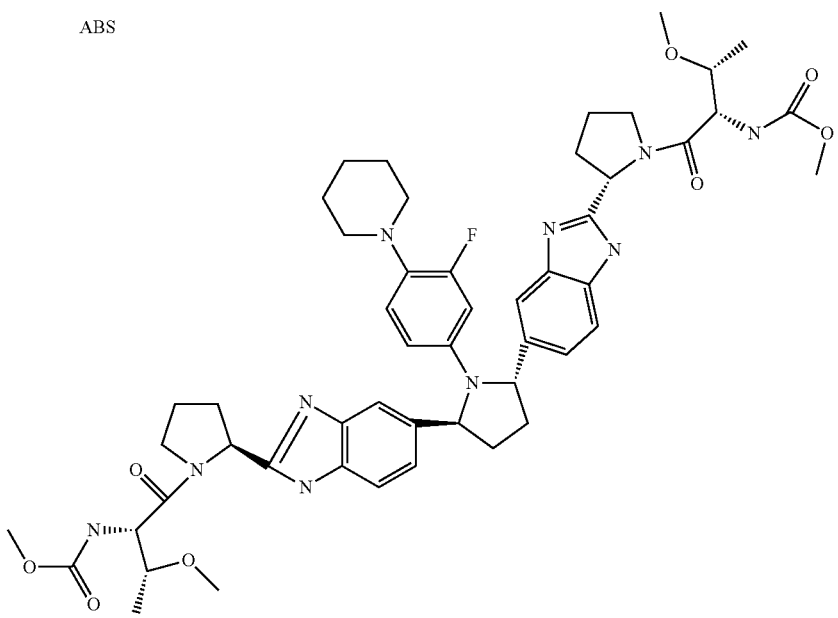 [SMILES: COC(=O)N[C@H](C(=O)N1CCC[C@H]1c1nc2cc([C@@H]3CC[C@@H](c4ccc5[nH]c([C@@H]6CCCN6C(=O)[C@@H](NC(=O)OC)[C@@H](C)OC)nc5c4)N3c3ccc(N4CCCCC4)c(F)c3)ccc2[nH]1)[C@@H](C)OC ; "ABS"]

Example 3.16 methyl {(2S,3R)-1-[(2S)-2-{5-[(2S,5S)-1-[3-fluoro-4-(piperidin-1-yl)phenyl]-5-(2-{(2S)-1-[N-(methoxycarbonyl)-O-methyl-l-threonyl]pyrrolidin-2-yl}-1H-benzimidazol-5-yl)pyrrolidin-2-yl]-1H-benzimidazol-2-yl}pyrrolidin-1-yl]-3-methoxy-1-oxobutan-2-yl}carbamate ¹H NMR (400 MHz, DMSO-d₆) δ ppm 1.00-1.14 (m, 6H) 1.33-1.55 (m, 6H) 1.59-2.28 (m, 14H) 2.58-2.71 (m, 4H) 3.10-3.27 (m, 6H) 3.54 (d, J=1.41 Hz, 6H) 3.71-3.90 (m, 6H) 4.21-4.33 (m, 2H) 5.02-5.22 (m, 2H) 5.37 (dd, J=6.02, 2.01 Hz, 2H) 6.04 (s, 2H) 6.58-6.84 (m, 1H) 7.06 (d, J=22.88 Hz, 2H) 7.16-7.32 (m, 2H) 7.39 (d, J=8.13 Hz, 2H) 11.90-12.34 (m, 2H); MS (ESI+) m/z 965.5 (M+H)⁺, (ESI−) m/z 963.3 (M−H)⁻.

ABS

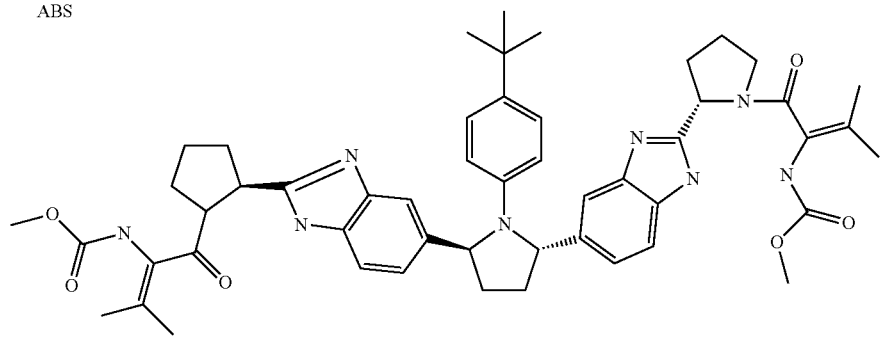 [SMILES: "ABS" ; COC(=O)NC(C(=O)C1CCC[C@H]1c1nc2cc([C@@H]3CC[C@@H](c4ccc5[nH]c([C@@H]6CCCN6C(=O)C(NC(=O)OC)=C(C)C)nc5c4)N3c3ccc(C(C)(C)C)cc3)ccc2[nH]1)=C(C)C]

Example 3.17 dimethyl {[(2S,5S)-1-(4-tert-butylphenyl)pyrrolidine-2,5-diyl]bis[1H-benzimidazole-5,2-diyl(2S)pyrrolidine-2,1-diyl(3-methyl-1-oxobut-2-ene-1,2-diyl)]}biscarbamate ¹H NMR (400 MHz, DMSO-d₆) δ ppm 0.87-1.20 (m, 9H) 1.60-1.77 (m, 14H) 1.80-2.35 (m, 10H) 3.16-3.79 (m, 10H) 5.14 (s, 2H) 5.37 (s, 2H) 6.24 (d, J=3.04 Hz, 2H) 6.92 (dd, J=8.57, 6.29 Hz, 2H) 7.11 (s, 3H) 7.31 (s, 1H) 7.39 (d, J=8.13 Hz, 1H) 7.50 (d, J=8.24 Hz, 1H) 8.89 (d, 2H) 11.64-12.14 (m, 2H); MS (ESI+) m/z 884.5 (M+H)¹, 918.4 (M+NH₃+NH₄)⁺.

ABS

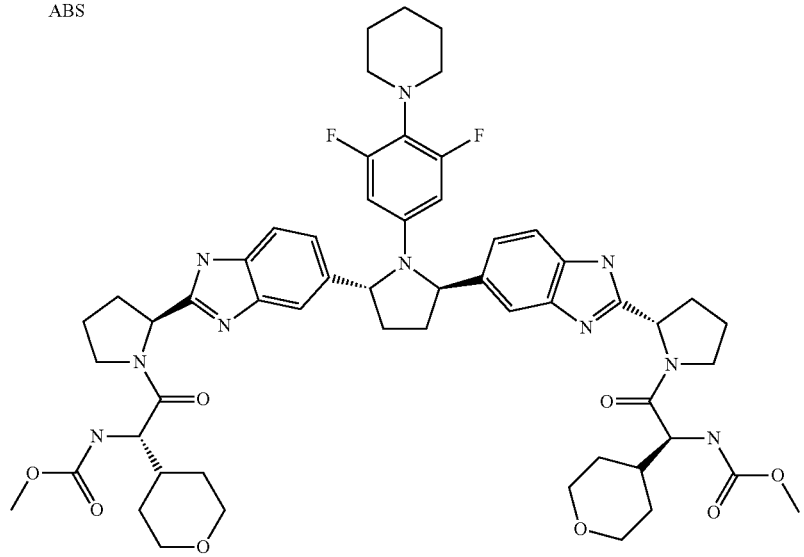

Example 3.18 dimethyl ({(2R,5R)-1-[3,5-difluoro-4-(piperidin-1-yl)phenyl]pyrrolidine-2,5-diyl}bis{1H-benzimidazole-5,2-diyl(2S)pyrrolidine-2,1-diyl[(1S)-2-oxo-1-(tetrahydro-2H-pyran-4-yl)ethane-2,1-diyl]}) biscarbamate ¹H NMR (400 MHz, DMSO-$d_6$) δ ppm 1.13-1.33 (m, 4H) 1.36-1.57 (m, 10H) 1.65-1.71 (m, 2H) 1.79-1.90 (m, 2H) 1.96-2.03 (m, 4H) 2.13-2.26 (m, 4H) 2.76 (s, 4H) 2.93-3.15 (m, 4H) 3.53 (s, 6H) 3.62 (dd, J=10.03, 2.01 Hz, 2H) 3.68-3.80 (m, 4H) 3.81-3.88 (m, 4H) 4.11-4.18 (m, 2H) 5.10-5.18 (m, 2H) 5.33-5.40 (m, 2H) 5.82-5.92 (m, 2H) 7.09 (dd, J=12.52, 8.29 Hz, 2H) 7.17-7.24 (m, 2H) 7.35 (t, J=8.35 Hz, 2H) 7.41 (d, J=7.92 Hz, 1H) 7.47 (d, J=6.94 Hz, 1H) 12.05 (d, J=1.73 Hz, 1H) 12.15 (d, J=2.17 Hz, 1H); MS (ESI+) m/z 1035.5 (M+H)⁺.

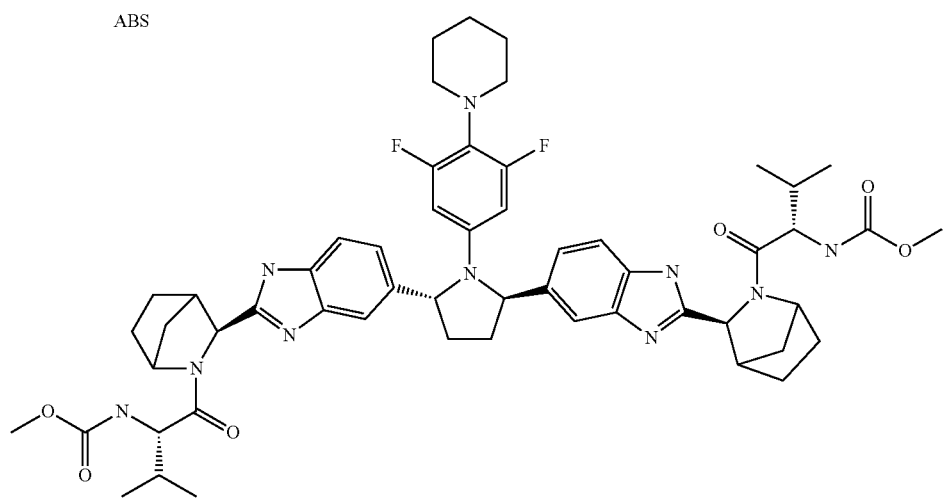

Example 3.19 methyl {(2S)-1-[(3S)-3-{5-[(2R,5R)-1-[3,5-difluoro-4-(piperidin-1-yl)phenyl]-5-{2-[(3S)-2-{(2S)-2-[(methoxycarbonyl)amino]-3-methylbutanoyl}-2-azabicyclo[2.2.1]hept-3-yl]-1H-benzimidazol-5-yl}pyrrolidin-2-yl]-1H-benzimidazol-2-yl}-2-azabicyclo[2.2.1]hept-2-yl]-3-methyl-1-oxobutan-2-yl}carbamate ¹H NMR (400 MHz, DMSO-$d_6$) δ ppm 0.80-0.87 (m, 6H) 0.93 (t, J=7.05 Hz, 6H) 1.36-1.48 (m, 10H) 1.49-1.57 (m, 2H) 1.64-1.70 (m, 4H) 1.72-1.79 (m, 4H) 1.84-1.90 (m, 2H) 1.92-1.98 (m, 2H) 2.61 (s, 2H) 2.72-2.78 (m, 4H) 3.54 (s, 6H) 4.10-4.17 (m, 2H) 4.50 (s, 2H) 4.59 (d, J=7.48 Hz, 2H) 5.32-5.41 (m, 2H) 5.89 (d, J=12.58 Hz, 2H) 7.07 (d, J=7.70 Hz, 2H) 7.18 (d, J=9.65 Hz, 2H) 7.21 (s, 1H) 7.32 (s, 1H) 7.40 (d, J=8.13 Hz, 1H) 7.49 (d, J=8.02 Hz, 1H) 12.01 (dd, J=12.58, 1.08 Hz, 2H); MS (ESI+) m/z 1003.4 (M+H)⁺.

405
ABS
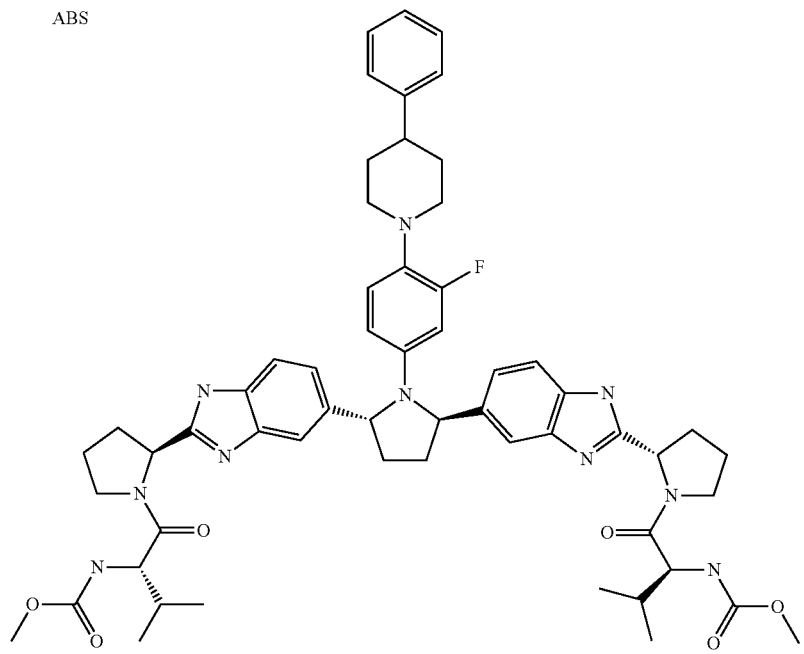
Example 3.20
methyl {(2S)-1-[(2S)-2-{5-[(2R,5R)-1-[3-fluoro-4-(4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-$d_6$) δ ppm 0.77-0.90 (m, 12H) 1.66-1.75 (m, 8H) 1.86-1.95 (m, 2H) 1.96-2.05 (m, 4H) 2.14-2.24 (m, 4H) 3.04-3.14 (m, 4H) 3.53 (s, 6H) 3.77-3.86 (m, 4H) 4.06 (t, J=8.40 Hz, 2H) 5.11-5.17 (m, 2H) 5.35 (q, J=6.83 Hz, 2H) 6.05-6.12 (m, 2H) 6.71 (ddd, J=13.99, 9.22, 4.34 Hz, 1H) 7.07 (t, J=7.05 Hz, 2H) 7.16 (t, J=6.94 Hz, 2H) 7.20-7.32 (m, 8H) 7.39 (d, J=8.13 Hz, 1H) 7.47 (d, J=8.46 Hz, 1H) 12.05 (d, J=5.64 Hz, 2H); MS (ESI+) m/z 1009.4 (M+H)$^+$.
406
ABS
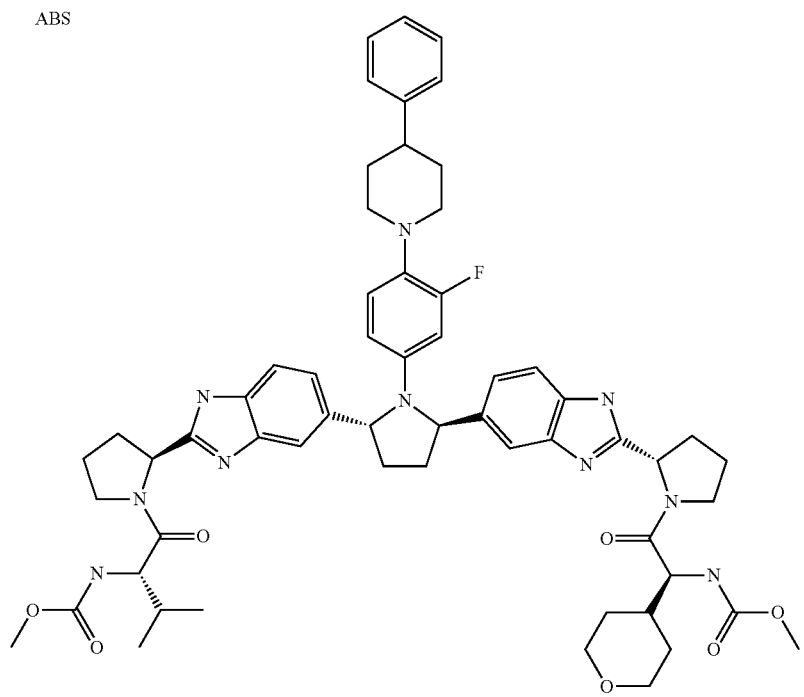

Example 3.21 methyl [(1S)-2-[(2S)-2-{5-[(2R,5R)-1-[3-fluoro-4-(4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-2-oxo-1-(tetrahydro-2H-pyran-4-yl)ethyl]carbamate $^1$H NMR (400 MHz, DMSO-d$_6$) δ ppm 0.76-0.92 (m, 6H) 1.47-1.57 (m, 2H) 1.65-1.76 (m, 8H) 1.81-1.94 (m, 2H) 1.94-2.04 (m, 4H) 2.15-2.23 (m, 4H) 3.03-3.15 (m, 4H) 3.53 (s, 6H) 3.57-3.67 (m, 2H) 3.70-3.79 (m, 2H) 3.79-3.89 (m, 4H) 4.07-4.20 (m, 2H) 5.10-5.19 (m, 2H) 5.32-5.41 (m, 2H) 6.04-6.11 (m, 2H) 6.66-6.75 (m, 1H) 7.03-7.36 (m, 12H) 7.39 (dd, J=8.78, 1.63 Hz, 1H) 7.46 (t, J=8.78 Hz, 1H) 12.02-12.14 (m, 2H); MS (APCI+) m/z 1051 (M+H)$^+$.

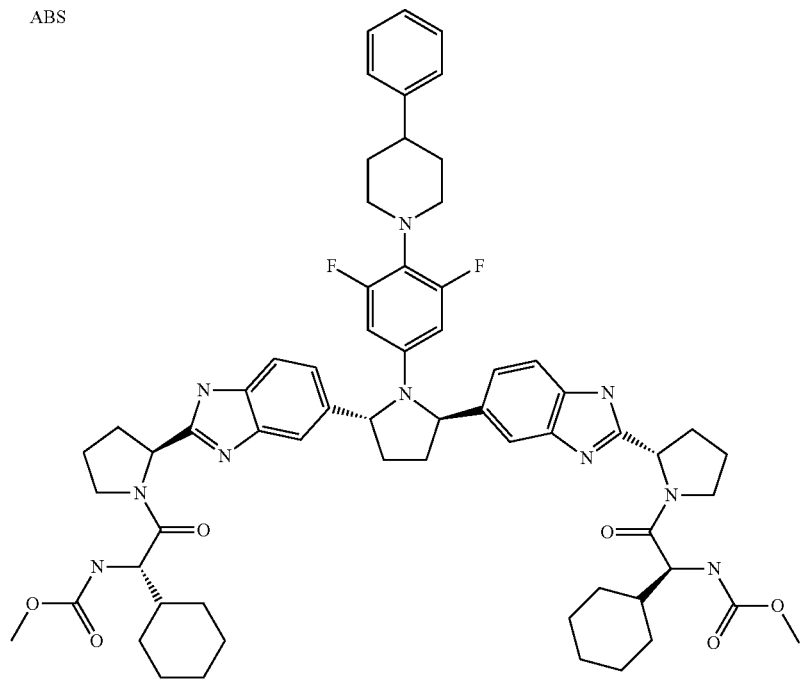

Example 3.22 dimethyl ({(2R,5R)-1-[3,5-difluoro-4-(4-phenylpiperidin-1-yl)phenyl]pyrrolidine-2,5-diyl}bis{1H-benzimidazole-5,2-diyl(2S)pyrrolidine-2,1-diyl[(1S)-1-cyclohexyl-2-oxoethane-2,1-diyl]})biscarbamate $^1$H NMR (400 MHz, DMSO-d$_6$) δ ppm 0.81-1.14 (m, 11H) 1.40-1.71 (m, 20H) 1.94-2.05 (m, 4H) 2.14-2.26 (m, 4H) 2.83-2.91 (m, 2H) 2.93-3.02 (m, 2H) 3.52 (d, J=3.80 Hz, 6H) 3.76-3.87 (m, 4H) 4.08 (q, J=8.53 Hz, 2H) 5.14 (d, J=5.86 Hz, 2H) 5.33-5.45 (m, 2H) 5.85-5.98 (m, 2H) 7.05-7.31 (m, 11H) 7.42 (d, J=9.76 Hz, 1H) 7.49 (d, J=8.24 Hz, 1H) 12.00 (s, 1H) 12.16 (d, J=3.58 Hz, 1H); MS (ESI+) m/z 1107.5 (M+H)$^+$.

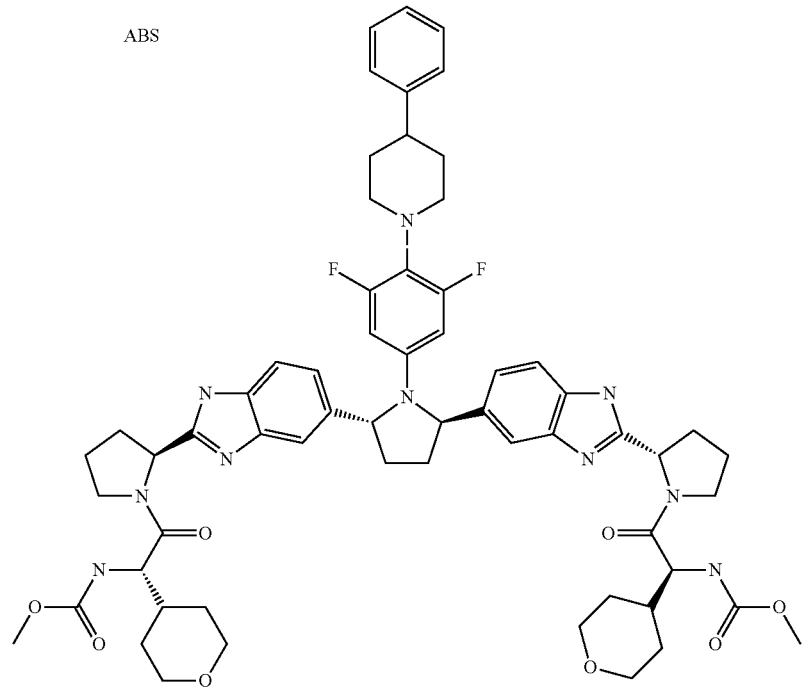
Example 3.23
dimethyl ({(2R,5R)-1-[3,5-difluoro-4-(4-phenylpiperidin-1-yl)phenyl]pyrrolidine-2,5-diyl}bis{1H-benzimidazole-5,2-diyl(2S)pyrrolidine-2,1-diyl[(1S)-2-oxo-1-(tetrahydro-2H-pyran-4-yl)ethane-2,1-diyl]}) biscarbamate
$^1$H NMR (400 MHz, DMSO-$d_6$) δ ppm 1.14-1.37 (m, 4H) 1.43-1.57 (m, 4H) 1.61-1.72 (m, 6H) 1.77-1.91 (m, 2H) 1.96-2.05 (m, 4H) 2.14-2.25 (m, 4H) 2.87-3.02 (m, 6H) 3.06-3.22 (m, 2H) 3.53 (s, 6H) 3.58-3.67 (m, 2H) 3.68-3.79 (m, 5H) 3.81-3.89 (m, 4H) 4.11-4.19 (m, 2H) 5.14 (dd, J=7.32, 2.98 Hz, 2H) 5.34-5.42 (m, 2H) 5.85-5.95 (m, 2H) 7.06-7.17 (m, 3H) 7.19-7.29 (m, 6H) 7.35 (t, J=9.05 Hz, 2H) 7.42 (d, J=8.57 Hz, 1H) 7.47 (d, J=8.78 Hz, 1H) 12.05 (s, 1H) 12.16 (d, J=1.41 Hz, 1H); MS (ESI+) m/z 1111.5 (M+H)$^+$.
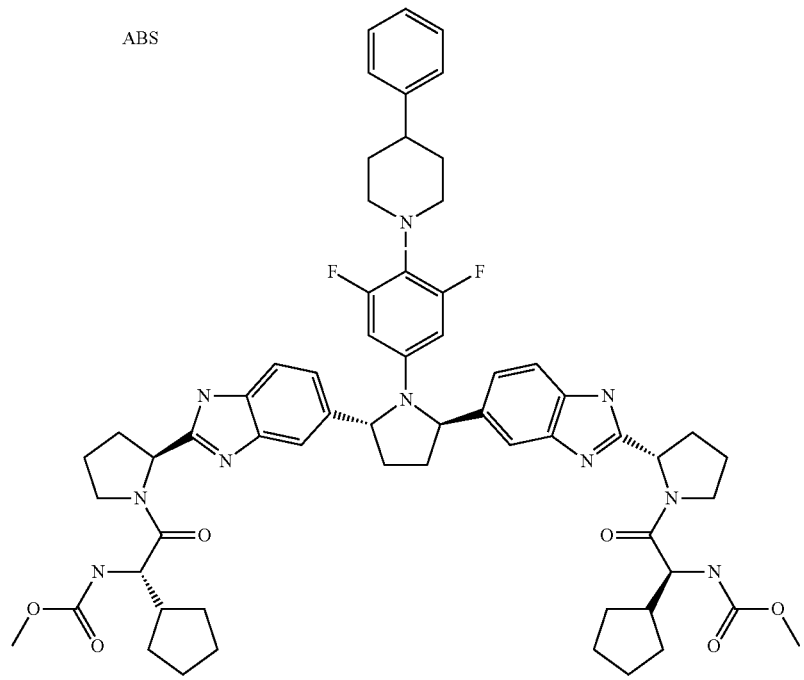

Example 3.24 dimethyl ({(2R,5R)-1-[3,5-difluoro-4-(4-phenylpip-
eridin-1-yl)phenyl]pyrrolidine-2,5-diyl}bis{1H-ben-
zimidazole-5,2-diyl(2S)pyrrolidine-2,1-diyl[(1S)-1-
cyclopentyl-2-oxoethane-2,1-diyl]})biscarbamate $^1$H NMR (400 MHz, DMSO-$d_6$) δ ppm 1.16-1.28 (m, 4H) 1.31-1.54 (m, 10H) 1.55-1.73 (m, 10H) 1.95-2.06 (m, 4H) 2.09-2.24 (m, 7H) 2.85-3.07 (m, 4H) 3.53 (s, 6H) 3.82 (s, 4H) 4.15 (t, J=8.51 Hz, 2H) 5.11-5.18 (m, 2H) 5.34-5.43 (m, 2H) 5.92 (d, J=12.69 Hz, 2H) 7.06-7.18 (m, 3H) 7.19-7.31 (m, 6H) 7.37-7.45 (m, 3H) 7.50 (d, J=8.35 Hz, 1H) 12.01 (s, 1H) 12.08 (s, 1H); MS (ESI+) m/z 1079.4 (M+H)$^+$.

(m, 4H) 2.74 (s, 6H) 3.08 (d, J=15.40 Hz, 6H) 3.69-3.89 (m, 2H) 4.27 (s, 1H) 5.26-5.39 (m, 2H) 5.77-6.01 (m, 4H) 7.01-7.33 (m, 12H) 7.37-7.53 (m, 2H) 8.12-8.25 (m, 2H) 12.34 (d, J=42.07 Hz, 2H); MS (ESI+) m/z 1047.4 (M+H)$^+$.

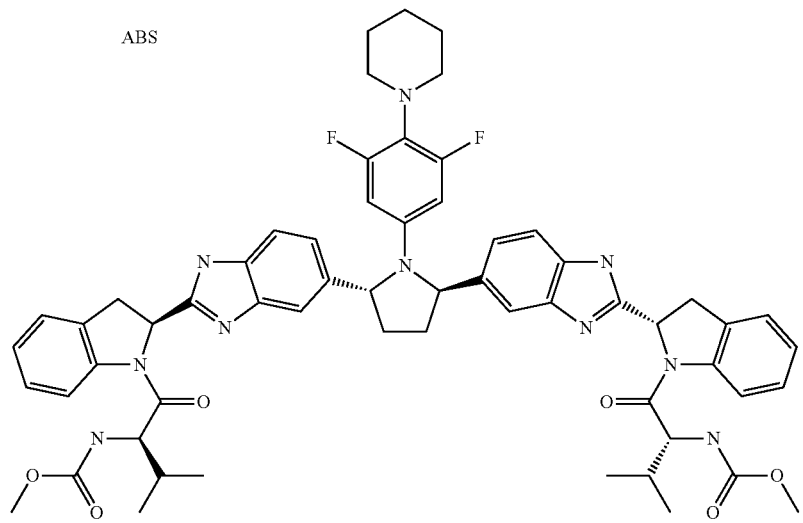

ABS

Example 3.25 methyl {(2R)-1-[(2S)-2-{5-[(2R,5R)-1-[3,5-difluoro-
4-(piperidin-1-yl)phenyl]-5-{2-[(2S)-1-{(2R)-2-
[(methoxycarbonyl)amino]-3-methylbutanoyl}-2,3-
dihydro-1H-indol-2-yl]-1H-benzimidazol-5-
yl}pyrrolidin-2-yl]-1H-benzimidazol-2-yl}-2,3-
dihydro-1H-indol-1-yl]-3-methyl-1-oxobutan-2-
yl}carbamate $^1$H NMR (400 MHz, DMSO-$d_6$) δ ppm 0.90 (dd, J=31.72, 6.23 Hz, 12H) 1.31-1.51 (m, 7H) 1.52-1.70 (m, 2H) 2.06-2.29

ABS

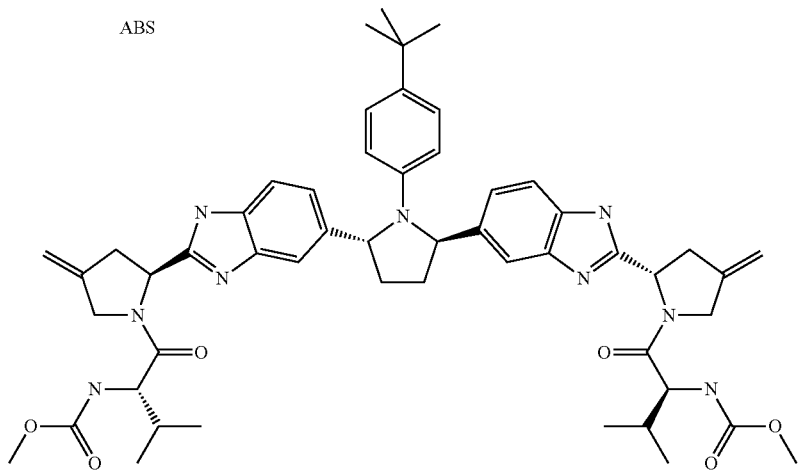

Example 3.26 methyl {(2S)-1-[(2S)-2-{5-[(2R,5R)-1-(4-tert-butylphenyl)-5-{2-[(2S)-1-{(2S)-2-[(methoxycarbonyl)amino]-3-methylbutanoyl}-4-methylidenepyrrolidin-2-yl]-1H-benzimidazol-5-yl}pyrrolidin-2-yl]-1H-benzimidazol-2-yl}-4-methylidenepyrrolidin-1-yl]-3-methyl-1-oxobutan-2-yl}carbamate 1H NMR (400 MHz, DMSO-$d_6$) δ ppm 0.74-0.92 (m, 12H) 1.07 (s, 9H) 1.68 (s, 2H) 1.91 (ddd, J=14.64, 7.64, 7.43 Hz, 2H) 2.61-2.75 (m, 2H) 2.97-3.09 (m, 2H) 3.13 (s, 1H) 3.54 (s, 6H) 3.94-4.08 (m, 2H) 4.46 (d, J=12.36 Hz, 2H) 4.60 (d, J=14.20 Hz, 2H) 5.02 (s, 3H) 5.10 (s, 2H) 5.31-5.45 (m, 4H) 6.24 (d, J=8.67 Hz, 2H) 6.86-6.94 (m, 2H) 7.07 (t, J=8.51 Hz, 2H) 7.20 (s, 1H) 7.26 (s, 1H) 7.34-7.50 (m, 4H) 12.05 (d, J=15.72 Hz, 2H); MS (ESI+) m/z 912.4 (M+H)$^+$.

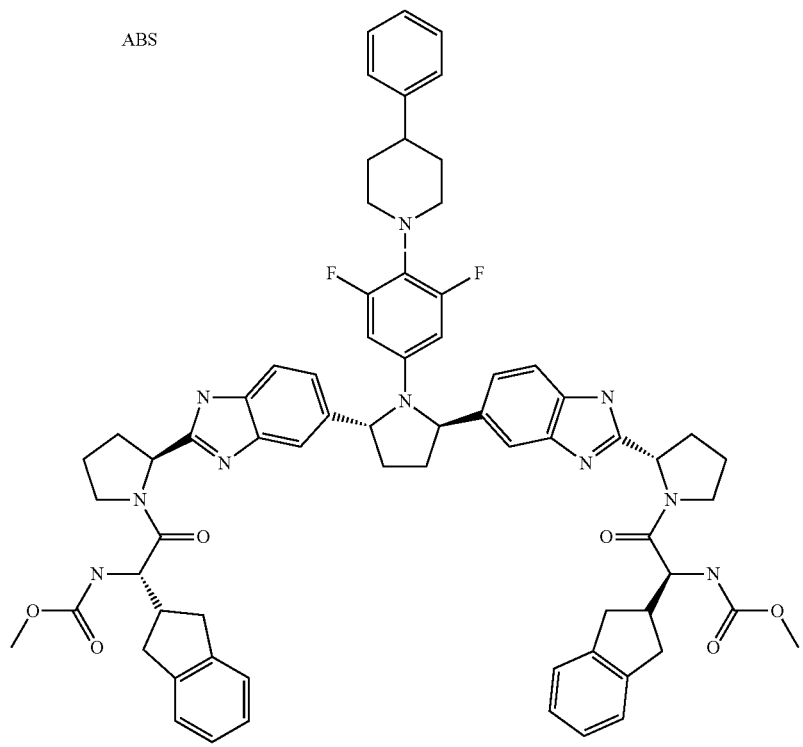

Example 3.27 dimethyl ({(2R,5R)-1-[3,5-difluoro-4-(4-phenylpiperidin-1-yl)phenyl]pyrrolidine-2,5-diyl}bis{1H-benzimidazole-5,2-diyl(2S)pyrrolidine-2,1-diyl[(1S)-1-(2,3-dihydro-1H-inden-2-yl)-2-oxoethane-2,1-diyl]})biscarbamate $^1$H NMR (400 MHz, DMSO-$d_6$) δ ppm 1.51-1.76 (m, 6H) 1.94-2.06 (m, 4H) 2.12-2.28 (m, 8H) 2.69-2.89 (m, 12H) 2.92-3.05 (m, 1H) 3.55 (s, 6H) 3.77-3.86 (m, 4H) 4.36-4.43 (m, 2H) 5.16-5.24 (m, 2H) 5.35-5.48 (m, 2H) 5.97 (d, J=12.90 Hz, 2H) 7.01-7.30 (m, 17H) 7.34 (s, 1H) 7.46 (d, J=8.35 Hz, 1H) 7.54-7.60 (m, 2H) 12.07 (s, 1H) 12.18 (s, 1H); MS (ESI+) m/z 1175.5 (M+H)$^+$.

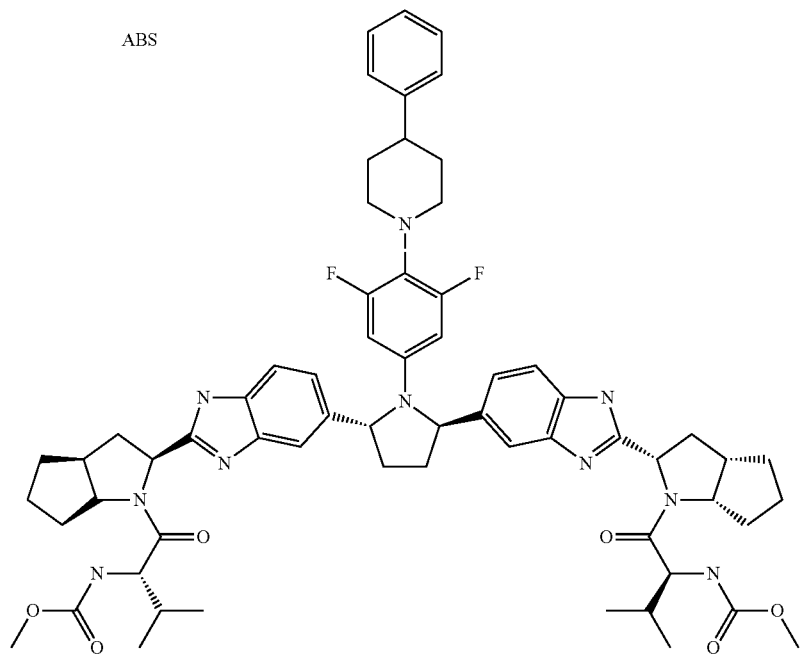

Example 3.28 methyl {(2S)-1-[(2S,3aS,6aS)-2-{5-[(2R,5R)-1-[3,5-difluoro-4-(4-phenylpiperidin-1-yl)phenyl]-5-{2-[(2S,3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-1H-benzimidazol-2-yl}hexahydrocyclopenta[b]pyrrol-1(2H)-yl]-3-methyl-1-oxobutan-2-yl}carbamate $^1$H NMR (400 MHz, DMSO-d$_6$) δ ppm 0.72-0.92 (m, 12H) 1.50-1.59 (m, 4H) 1.62-1.72 (m, 8H) 1.73-1.81 (m, 2H) 1.83-1.92 (m, 4H) 1.95-2.03 (m, 2H) 2.06-2.15 (m, 4H) 2.38-2.46 (m, 2H) 2.75-2.83 (m, 1H) 2.86-3.01 (m, 4H) 3.54 (s, 6H) 4.01 (td, J=13.28, 6.83 Hz, 4H) 4.78 (dd, J=7.70, 4.23 Hz, 2H) 5.13 (t, J=8.24 Hz, 2H) 5.33-5.45 (m, 2H) 5.92 (dd, J=12.90, 2.82 Hz, 2H) 7.07 (d, J=8.67 Hz, 2H) 7.15 (t, J=6.94 Hz, 1H) 7.20-7.29 (m, 5H) 7.34 (d, J=4.01 Hz, 1H) 7.39-7.47 (m, 3H) 7.50 (d, J=8.02 Hz, 1H) 11.97 (s, 1H) 12.06 (s, 1H); MS (ESI+) m/z 1107.4 (M+H)$^+$.

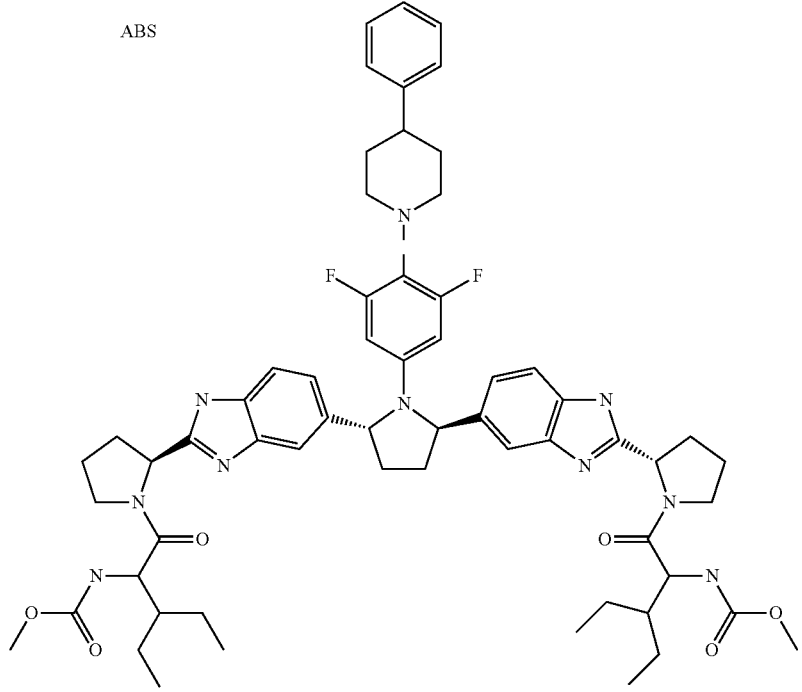

Example 3.29 methyl {1-[(2S)-2-{5-[(2R,5R)-1-[3,5-difluoro-4-(4-phenylpiperidin-1-yl)phenyl]-5-{2-[(2S)-1-{3-ethyl-2-[(methoxycarbonyl)amino]pentanoyl}pyrrolidin-2-yl]-1H-benzimidazol-5-yl}pyrrolidin-2-yl]-1H-benzimidazol-2-yl}pyrrolidin-1-yl]-3-ethyl-1-oxopentan-2-yl}carbamate

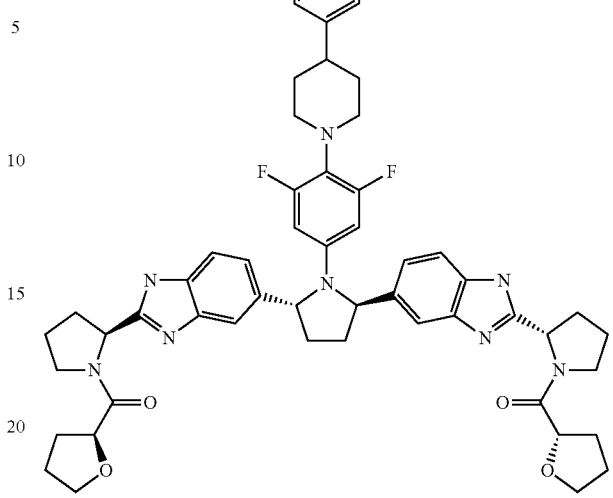

$^1$H NMR (400 MHz, DMSO-d$_6$) δ ppm 0.16 (t, J=6.02 Hz, 1H) 0.34 (t, J=6.89 Hz, 1H) 0.56-0.99 (m, 10H) 1.16-1.36 (m, 4H) 1.53-1.80 (m, 8H) 1.93-2.09 (m, 4H) 2.14-2.30 (m, 4H) 2.80-3.13 (m, 11H) 3.53 (s, 6H) 3.73-3.95 (m, 4H) 4.24-4.41 (m, 2H) 5.09-5.20 (m, 2H) 5.30-5.44 (m, 2H) 5.83-5.96 (m, 2H) 7.03-7.36 (m, 11H) 7.39-7.62 (m, 2H) 12.00 (s, 1H) 12.13-12.20 (m, 1H); MS (ESI+) m/z 1083.5 (M+H)$^+$.

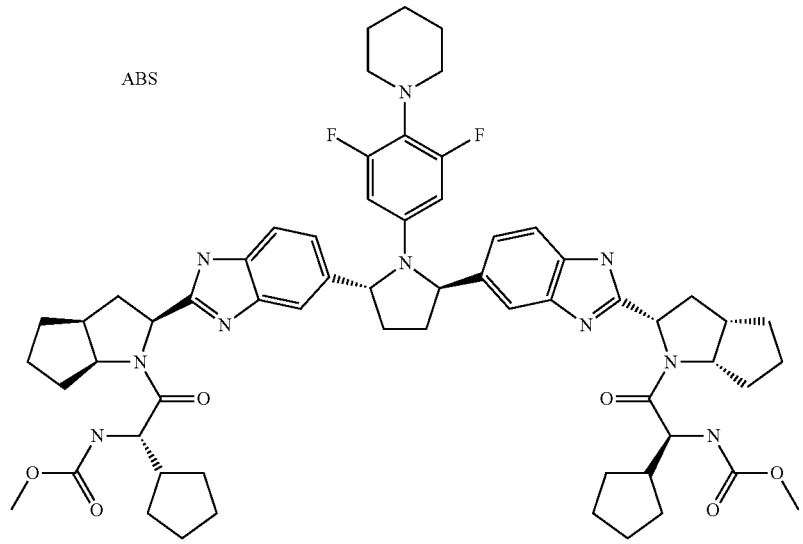

Example 3.30 dimethyl ({(2R,5R)-1-[3,5-difluoro-4-(piperidin-1-yl)phenyl]pyrrolidine-2,5-diyl}bis{1H-benzimidazole-5,2-diyl(2S,3aS,6aS)hexahydrocyclopenta[b]pyrrole-2,1(2H)-diyl[(1S)-1-cyclopentyl-2-oxoethane-2,1-diyl]})biscarbamate $^1$H NMR (400 MHz, DMSO-d$_6$) δ ppm 1.17-1.32 (m, 10H) 1.36-1.49 (m, 10H) 1.51-1.79 (m, 10H) 1.87 (dd, J=15.83, 7.26 Hz, 2H) 1.98 (dd, J=13.07, 8.40 Hz, 2H) 2.05-2.16 (m, 6H) 2.36-2.46 (m, 4H) 2.72-2.81 (m, 6H) 3.54 (s, 6H) 4.11 (q, J=9.40 Hz, 2H) 4.75-4.85 (m, 2H) 5.08-5.18 (m, 2H) 5.36 (dt, J=13.66, 6.83 Hz, 2H) 5.88 (ddd, J=12.69, 3.52, 3.42 Hz, 2H) 7.07 (d, J=8.35 Hz, 2H) 7.21 (s, 1H) 7.31 (d, J=4.01 Hz, 1H) 7.41 (d, J=8.24 Hz, 1H) 7.46-7.56 (m, 3H) 11.88 (d, J=2.49 Hz, 1H) 12.01 (d, J=3.36 Hz, 1H); MS (ESI+) m/z 1083.5 (M+H)$^+$.

Example 3.31

({(2R,5R)-1-[3,5-difluoro-4-(4-phenylpiperidin-1-yl)phenyl]pyrrolidine-2,5-diyl}bis[1H-benzimidazole-5,2-diyl(2S)pyrrolidine-2,1-diyl])bis[(2S)-tetrahydrofuran-2-ylmethanone]

$^1$H NMR (400 MHz, DMSO-d$_6$) δ ppm 1.36-1.49 (m, J=15.83 Hz, 2H) 1.60-1.75 (m, 8H) 1.77-1.91 (m, 6H) 1.94-2.12 (m, 8H) 2.16-2.27 (m, 2H) 2.86-3.08 (m, 5H) 3.74 (t, J=6.99 Hz, 6H) 4.57-4.63 (m, 2H) 5.13 (dd, J=9.00, 1.30 Hz, 2H) 5.33-5.43 (m, 2H) 5.93 (d, J=13.34 Hz, 2H) 7.06-7.16 (m, 3H) 7.20-7.29 (m, 5H) 7.32 (s, 1H) 7.42 (d, J=8.57 Hz, 1H) 7.52 (d, J=8.13 Hz, 1H) 12.00 (s, 1H) 12.08 (s, 1H); MS (ESI+) m/z 909.4 (M+H)$^+$.

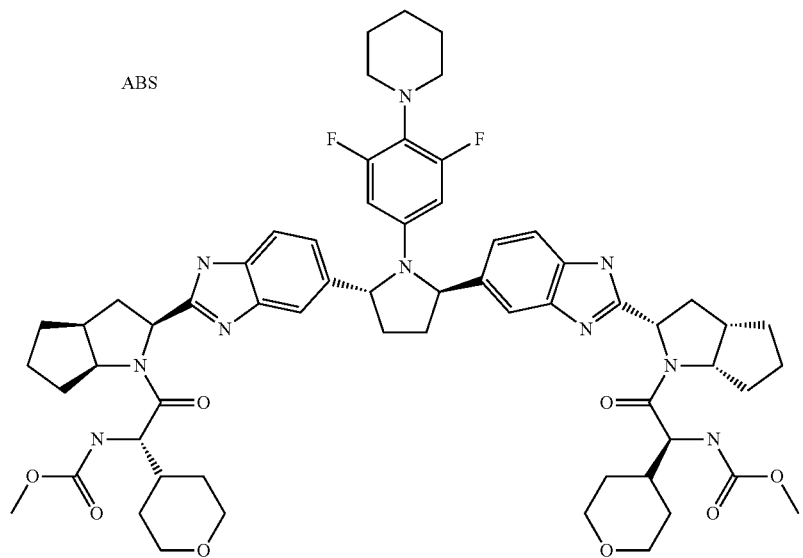

Example 3.32 dimethyl ({(2R,5R)-1-[3,5-difluoro-4-(piperidin-1-yl)phenyl]pyrrolidine-2,5-diyl}bis{1H-benzimidazole-5,2-diyl(2S,3aS,6aS)hexahydrocyclopenta[b]pyrrole-2,1(2H)-diyl[(1S)-2-oxo-1-(tetrahydro-2H-pyran-4-yl)ethane-2,1-diyl]})biscarbamate $^1$H NMR (400 MHz, DMSO-d$_6$) δ ppm 1.10-1.27 (m, 4H) 1.33-1.51 (m, 12H) 1.51-1.65 (m, 6H) 1.67-1.80 (m, 4H) 1.83-2.00 (m, 6H) 2.08-2.17 (m, 4H) 2.39-2.45 (m, 2H) 2.73-2.85 (m, 8H) 3.03-3.12 (m, 2H) 3.53 (s, 6H) 3.70-3.87 (m, 2H) 4.04-4.17 (m, 2H) 4.74-4.83 (m, 2H) 5.08-5.17 (m, 2H) 5.31-5.42 (m, 2H) 5.83-5.93 (m, 2H) 7.04-7.11 (m, 2H) 7.21 (d, J=15.83 Hz, 2H) 7.41 (d, J=8.02 Hz, 1H) 7.46-7.55 (m, 3H) 11.96 (d, J=4.12 Hz, 1H) 12.11 (d, J=4.55 Hz, 1H); MS (ESI+) m/z 1115.4 (M+H)$^+$.

Example 3.33 methyl {(2S,3R)-1-[(2S,3aS,6aS)-2-{5-[(2R,5R)-1-[3,5-difluoro-4-(piperidin-1-yl)phenyl]-5-(2-{(2S, 3aS,6aS)-1-[N-(methoxycarbonyl)-O-methyl-1-threonyl]octahydrocyclopenta[b]pyrrol-2-yl}-1H-benzimidazol-5-yl)pyrrolidin-2-yl]-1H-benzimidazol-2-yl}hexahydrocyclopenta[b]pyrrol-1(2H)-yl]-3-methoxy-1-oxobutan-2-yl}carbamate $^1$H NMR (400 MHz, DMSO-d$_6$) δ ppm 0.95 (d, J=6.18 Hz, 3H) 1.03 (d, J=5.75 Hz, 3H) 1.35-1.49 (m, 8H) 1.50-1.64 (m, 4H) 1.66-1.81 (m, 6H) 1.84-2.01 (m, 6H) 2.07-2.16 (m, 4H) 2.73-2.84 (m, 6H) 3.13 (s, 3H) 3.17 (s, 3H) 3.54 (s, 6H) 4.20-4.29 (m, 2H) 4.76-4.84 (m, 2H) 5.12 (t, J=8.19 Hz, 2H) 5.37 (dd, J=6.51, 4.88 Hz, 2H) 5.88 (d, J=13.45 Hz, 2H) 7.05 (d, J=8.13 Hz, 2H) 7.20 (s, 1H) 7.30 (s, 1H) 7.40 (d, J=7.81 Hz, 1H) 7.47-7.57 (m, 3H) 11.98-12.15 (m, 2H); MS (APCI+) m/z 1063.4 (M+H)$^+$.

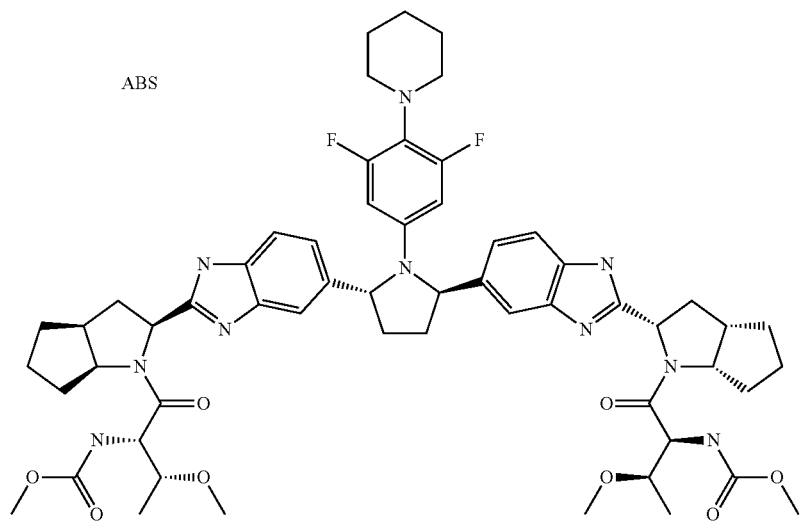

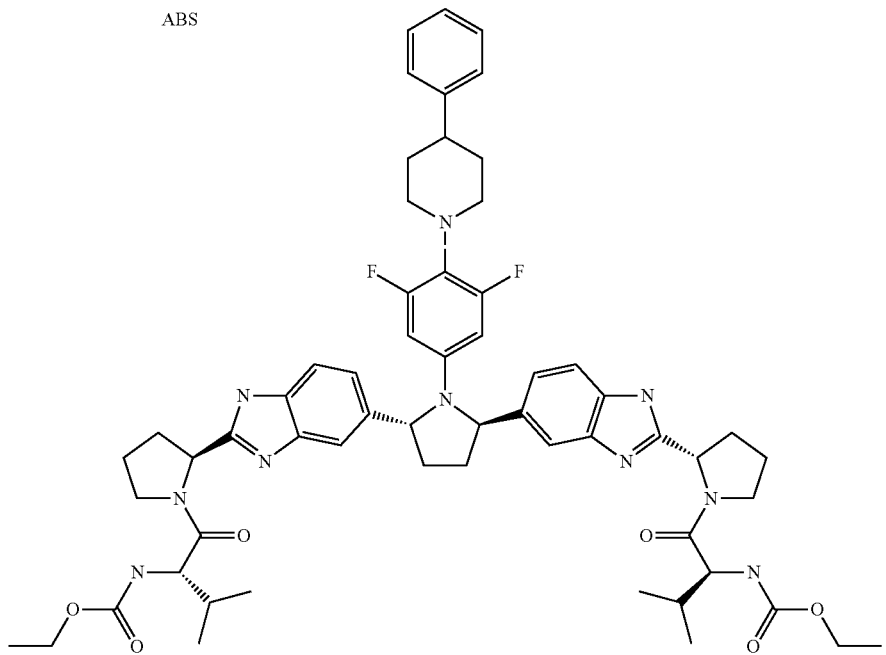 [SMILES: CCOC(=O)N[C@H](C(=O)N1CCC[C@H]1c1nc2cc([C@H]3CC[C@H](c4ccc5[nH]c([C@@H]6CCCN6C(=O)[C@@H](NC(=O)OCC)C(C)C)nc5c4)N3c3cc(F)c(N4CCC(c5ccccc5)CC4)c(F)c3)ccc2[nH]1)C(C)C ; "ABS"]
Example 3.34
ethyl {(2S)-1-[(2S)-2-{5-[(2R,5R)-1-[3,5-difluoro-4-(4-phenylpiperidin-1-yl)phenyl]-5-{2-[(2S)-1-{(2S)-2-[(ethoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-d$_6$) δ ppm 0.75-0.91 (m, 12H) 1.15 (t, J=7.43 Hz, 6H) 1.60-1.74 (m, 6H) 1.85-2.07 (m, 8H) 2.16-2.27 (m, 4H) 2.86-3.04 (m, 4H) 3.40-3.48 (m, 1H) 3.76-3.85 (m, 4H) 3.98 (q, J=7.08 Hz, 4H) 4.05 (t, J=8.29 Hz, 2H) 5.11-5.19 (m, 2H) 5.34-5.44 (m, 2H) 5.92 (d, J=12.69 Hz, 2H) 7.05-7.11 (m, 2H) 7.15 (t, J=6.94 Hz, 1H) 7.20-7.27 (m, 7H) 7.31 (s, 1H) 7.42 (d, J=8.24 Hz, 1H) 7.50 (d, J=7.92 Hz, 1H) 12.07 (s, 1H) 12.12 (s, 1H); MS (ESI+) m/z 1055.4 (M+H)$^+$.
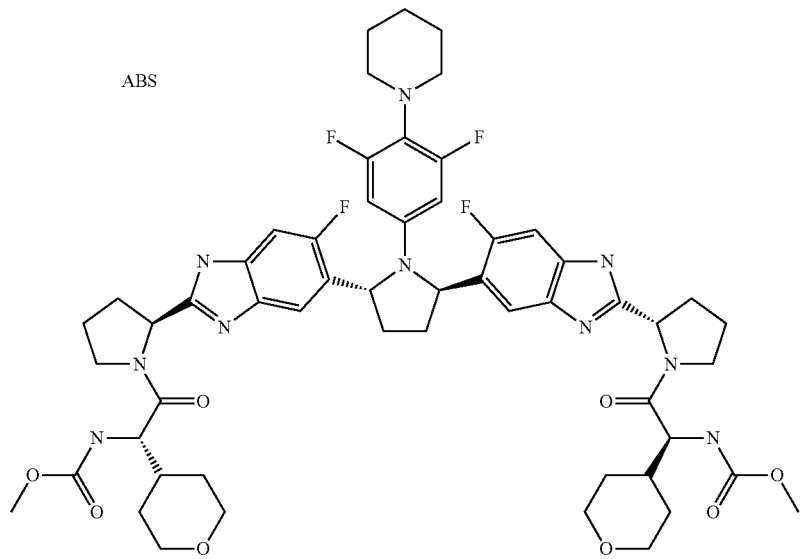

Example 3.35 dimethyl ({(2R,5R)-1-[3,5-difluoro-4-(piperidin-1-yl)phenyl]pyrrolidine-2,5-diyl}bis{(6-fluoro-1H-benzimidazole-5,2-diyl)(2S)pyrrolidine-2,1-diyl[(1S)-2-oxo-1-(tetrahydro-2H-pyran-4-yl)ethane-2,1-diyl]})biscarbamate $^1$H NMR (400 MHz, DMSO-$d_6$) δ ppm 1.12-1.33 (m, 4H) 1.38-1.55 (m, 10H) 1.66-1.90 (m, 6H) 1.94-2.04 (m, 4H) 2.11-2.24 (m, 2H) 2.75-2.85 (m, 6H) 3.01-3.19 (m, 2H) 3.52 (s, 6H) 3.63-3.77 (m, 4H) 3.78-3.89 (m, 6H) 4.08-4.18 (m, 2H) 5.07-5.16 (m, 2H) 5.46-5.63 (m, 2H) 5.81-5.93 (m, 2H) 6.99-7.12 (m, 2H) 7.31-7.44 (m, 4H) 12.04-12.15 (m, 1H) 12.28-12.35 (m, 1H); MS (APCI+) m/z 1071.2 (M+H)$^+$.

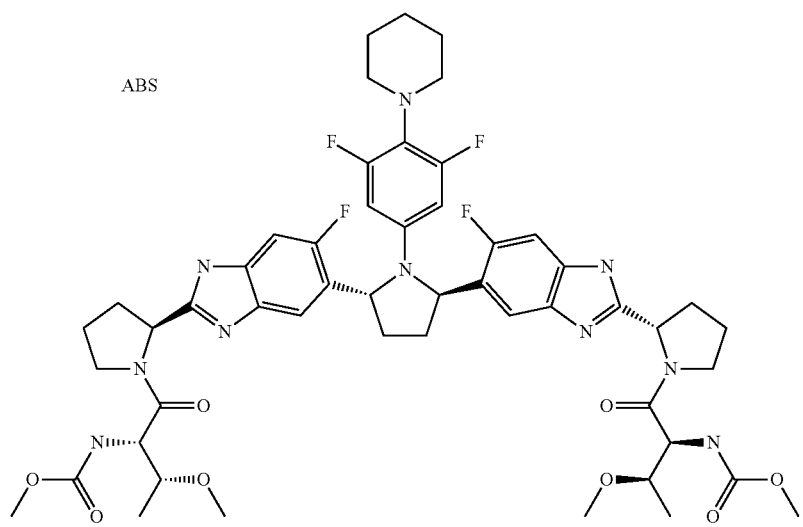

Example 3.36 methyl {(2S,3R)-1-[(2S)-2-{5-[(2R,5R)-1-[3,5-difluoro-4-(piperidin-1-yl)phenyl]-5-(6-fluoro-2-{(2S)-1-[N-(methoxycarbonyl)-O-methyl-L-threonyl]pyrrolidin-2-yl}-1H-benzimidazol-5-yl)pyrrolidin-2-yl]-6-fluoro-1H-benzimidazol-2-yl}pyrrolidin-1-yl]-3-methoxy-1-oxobutan-2-yl}carbamate $^1$H NMR (400 MHz, DMSO-$d_6$) δ ppm 0.87-1.11 (m, 8H) 1.35-1.52 (m, 6H) 1.71-1.84 (m, 2H) 1.91-2.07 (m, 4H) 2.12-2.26 (m, 4H) 2.79 (s, 4H) 3.08 (d, J=37.41 Hz, 6H) 3.41-3.48 (m, 2H) 3.53 (s, 6H) 3.82 (d, J=4.88 Hz, 4H) 4.18-4.30 (m, 2H) 5.11 (s, 2H) 5.47-5.63 (m, 2H) 5.81-5.97 (m, 2H) 6.99-7.28 (m, 4H) 7.37 (dd, J=25.54, 9.60 Hz, 2H) 12.10 (s, 1H) 12.22-12.35 (m, 1H); MS (ESI+) m/z 1019.4 (M+H)$^+$.

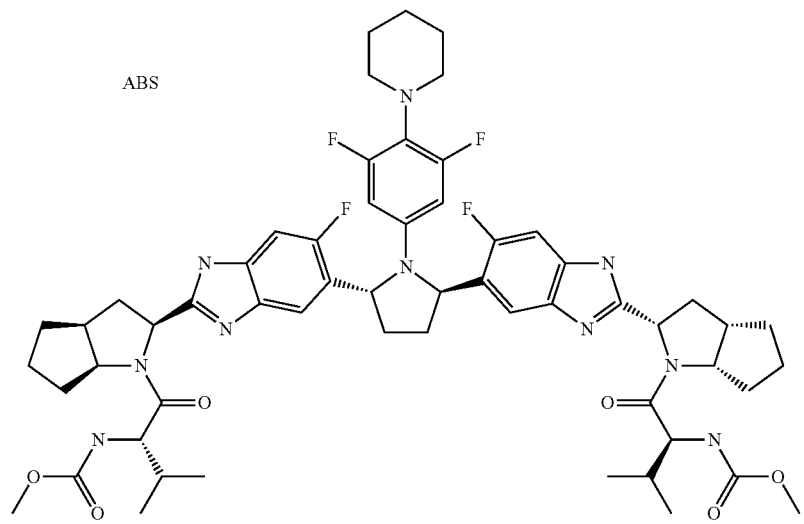

Example 3.37 methyl {(2S)-1-[(2S,3aS,6aS)-2-{5-[(2R,5R)-1-[3,5-difluoro-4-(piperidin-1-yl)phenyl]-5-{6-fluoro-2-[(2S,3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-6-fluoro-1H-benzimidazol-2-yl}hexahydrocyclopenta[b]pyrrol-1 (2H)-yl]-3-methyl-1-oxobutan-2-yl}carbamate ¹H NMR (400 MHz, DMSO-d₆) δ ppm 0.80 (dd, J=24.13, 6.45 Hz, 12H) 1.36-1.67 (m, 10H) 1.69-1.87 (m, 8H) 1.92-2.17 (m, 6H) 2.37-2.47 (m, 2H) 2.78 (s, 6H) 3.53 (s, 6H) 3.92-4.07 (m, 2H) 4.69-4.84 (m, 2H) 5.08 (t, J=8.29 Hz, 2H) 5.36-5.68 (m, 4H) 5.86 (dd, J=11.71, 8.67 Hz, 2H) 7.10 (dd, J=31.39, 6.89 Hz, 2H) 7.28-7.51 (m, 4H) 12.02 (s, 1H) 12.21 (d, J=7.27 Hz, 1H); MS (ESI+) m/z 1067.4 (M+H)⁺.

Example 3.38 methyl {(2S,3R)-1-[(2S,3aS,6aS)-2-{5-R2R,5R)-1-[3,5-difluoro-4-(piperidin-1-yl)phenyl]-5-(6-fluoro-2-{(2S,3aS,6aS)-1-[N-(methoxycarbonyl)-O-methyl-L-threonyl]octahydrocyclopenta[b]pyrrol-2-yl}-1H-benzimidazol-5-yl)pyrrolidin-2-yl]-6-fluoro-1H-benzimidazol-2-yl}hexahydrocyclopenta[b]pyrrol-1 (2H)-yl]-3-methoxy-1-oxobutan-2-yl}carbamate ¹H NMR (400 MHz, DMSO-d₆) δ ppm 0.78-1.07 (m, 8H) 1.36-1.51 (m, 8H) 1.51-1.67 (m, 4H) 1.75 (dd, J=12.20, 6.56 Hz, 4H) 1.90 (dd, J=20.22, 8.95 Hz, 4H) 2.00-2.14 (m, 4H) 2.37-2.47 (m, 2H) 2.79 (s, 6H) 3.04-3.20 (m, 6H) 3.54 (s, 6H) 4.14-4.29 (m, 2H) 4.77 (dd, J=18.00, 7.48 Hz, 2H) 5.07 (t, J=8.24 Hz, 2H) 5.47-5.65 (m, 2H) 5.80-5.94 (m, 2H) 7.08 (dd, J=27.27, 6.78 Hz, 2H) 7.28-7.57 (m, 4H) 12.04 (s, 1H) 12.26 (s, 1H); MS (ESI+) m/z 1099.4 (M+H)⁺.

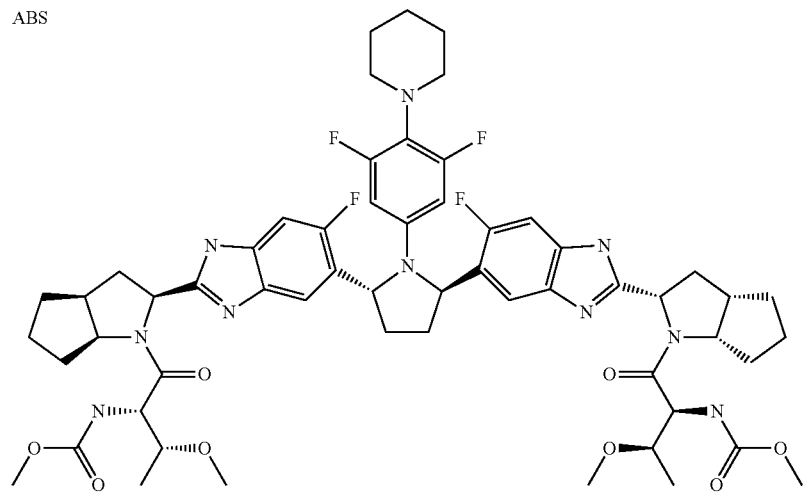

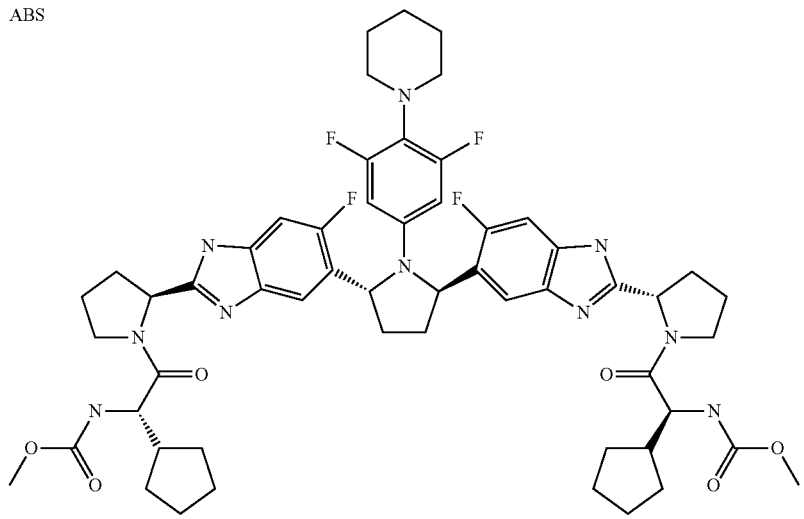

Example 3.39 dimethyl ({(2R,5R)-1-[3,5-difluoro-4-(piperidin-1-yl)phenyl]pyrrolidine-2,5-diyl}bis{(6-fluoro-1H-benzimidazole-5,2-diyl)(2S)pyrrolidine-2,1-diyl[(1S)-1-cyclopentyl-2-oxoethane-2,1-diyl]})biscarbamate $^1$H NMR (400 MHz, DMSO-$d_6$) δ ppm 1.10-1.29 (m, 6H) 1.34-1.62 (m, 18H) 1.71-1.86 (m, 2H) 1.94-2.10 (m, 4H) 2.11-2.24 (m, 4H) 2.74-2.84 (m, 4H) 2.94-3.12 (m, 2H) 3.53 (s, 6H) 3.73-3.87 (m, 4H) 4.06-4.17 (m, 2H) 5.07-5.18 (m, 2H) 5.47-5.63 (m, 2H) 5.82-5.95 (m, 2H) 7.03 (d, J=6.40 Hz, 1H) 7.13 (d, J=7.37 Hz, 1H) 7.30-7.46 (m, 4H) 12.07 (s, 1H) 12.23 (s, 1H); MS (APCI+) m/z 1040.3 (M+H)$^+$.

Example 3.40 dimethyl ({(2R,5R)-1-[3,5-difluoro-4-(piperidin-1-yl)phenyl]pyrrolidine-2,5-diyl}bis{(6-fluoro-1H-benzimidazole-5,2-diyl)(2S,3aS,6aS)hexahydrocyclopenta[b]pyrrole-2,1(2H)-diyl[(1S)-1-cyclopentyl-2-oxoethane-2,1-diyl]})biscarbamate $^1$H NMR (400 MHz, DMSO-$d_6$) δ ppm 1.12-1.25 (m, 8H) 1.35-1.64 (m, 18H) 1.70-1.88 (m, 6H) 1.92-2.15 (m, 8H) 2.36-2.46 (m, 4H) 2.78 (s, 6H) 3.53 (s, 6H) 4.07 (dt, J=18.38, 9.24 Hz, 2H) 4.72-4.83 (m, 2H) 5.07 (t, J=8.08 Hz, 2H) 5.46-5.65 (m, 2H) 5.81-5.91 (m, 2H) 7.06 (d, J=6.07 Hz, 1H) 7.11-7.19 (m, 1H) 7.34 (dd, J=10.63, 4.88 Hz, 1H) 7.43 (dd, J=11.22, 7.21 Hz, 1H) 7.51 (dd, J=13.99, 7.92 Hz, 2H) 11.95 (s, 1H) 12.20 (s, 1H); MS (ESI+) m/z 1119.4 (M+H)$^+$.

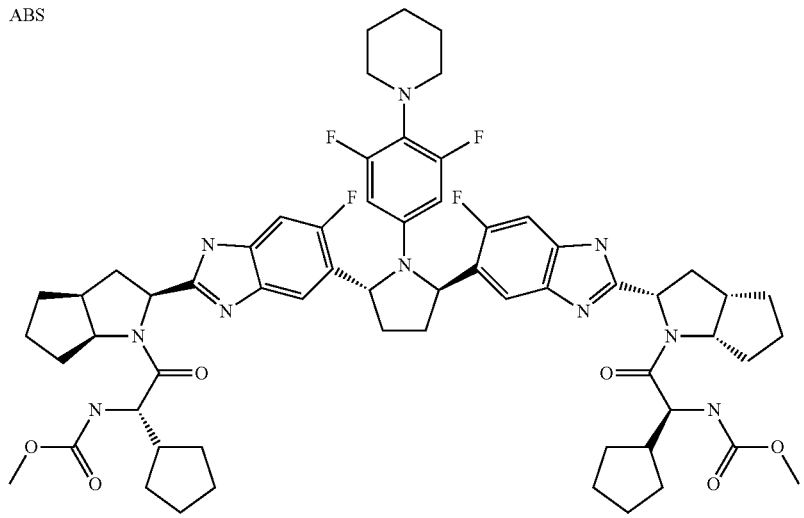

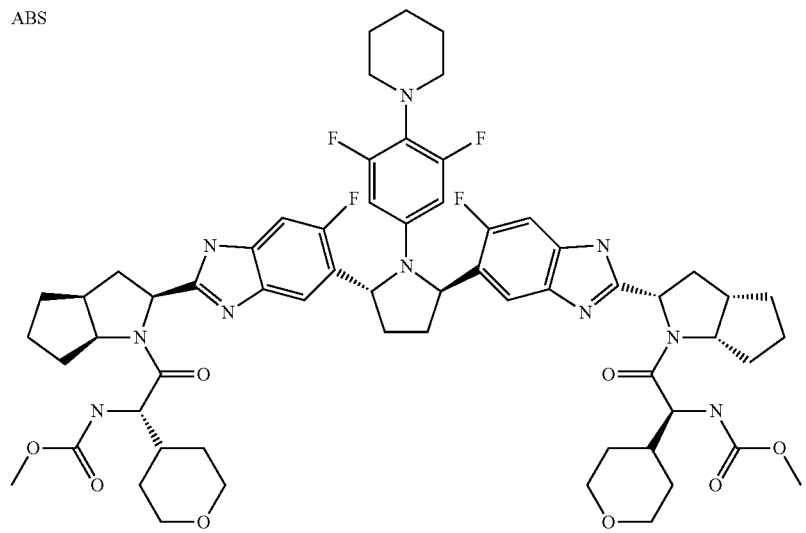

Example 3.41 dimethyl ({(2R,5R)-1-[3,5-difluoro-4-(piperidin-1-yl)phenyl]pyrrolidine-2,5-diyl}bis{(6-fluoro-1H-benzimidazole-5,2-diyl)(2S,3aS,6aS)hexahydrocyclopenta[b]pyrrole-2,1(2H)-diyl[(1S)-2-oxo-1-(tetrahydro-2H-pyran-4-yl)ethane-2,1-diyl]}) biscarbamate $^1$H NMR (400 MHz, DMSO-d$_6$) δ ppm 1.30-1.65 (m, 18H) 1.69-1.94 (m, 12H) 2.05-2.15 (m, 4H) 2.37-2.45 (m, 4H) 2.73-2.87 (m, 6H) 2.97-3.11 (m, 3H) 3.53 (s, 6H) 3.77 (dd, J=27.65, 10.08 Hz, 4H) 4.06-4.14 (m, 2H) 4.71-4.81 (m, 2H) 5.07 (t, J=8.35 Hz, 2H) 5.43-5.65 (m, 2H) 5.78-5.92 (m, 2H) 6.99-7.05 (m, 1H) 7.09 (t, J=6.94 Hz, 1H) 7.33 (dd, J=10.03, 6.13 Hz, 1H) 7.50 (dd, J=18.16, 7.86 Hz, 2H) 11.99 (s, 1H) 12.29 (d, J=5.75 Hz, 1H); MS (ESI+) m/z 1151.4 (M+H)$^+$.

Example 3.42 methyl {(2S)-1-[(2S)-2-{5-[(2R,5R)-1-{3,5-difluoro-4-[4-(4-fluorophenyl)piperidin-1-yl]phenyl}-5-{2-[(2S)-1-[(2S)-2-[(methoxycarbonyl)amino]-3-methylbutanoyl 1 pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.08 (d, J=18.9, 2H), 7.50 (d, J=8.0, 1H), 7.41 (d, J=8.3, 1H), 7.33-7.18 (m, 6H), 7.13-7.01 (m, 4H), 5.91 (d, J=13.1, 2H), 5.42-5.33 (m, 2H), 5.19-5.10 (m, 2H), 4.06 (t, J=8.6, 2H), 3.86-3.77 (m, 4H), 3.53 (s, 6H), 3.03-2.83 (m, 5H), 2.28-1.54 (m, 18H), 0.91-0.73 (m, 12H); MS (ESI+) m/z 1045.4 (M+H)$^+$.

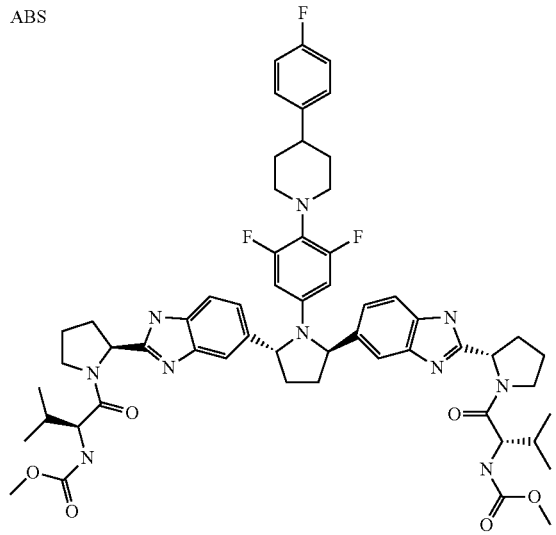

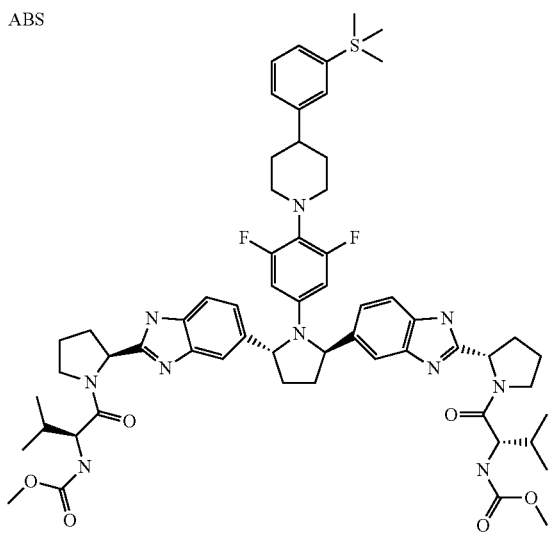

Example 3.43 methyl {(2S)-1-[(2S)-2-{5-[(2R,5R)-1-(3,5-difluoro-4-{4-[3-(trimethylsilyl)phenyl]piperidin-1-yl}phenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.31-12.04 (m, 2H), 7.49 (d, J=8.4, 1H), 7.40 (d, J=8.2, 1H), 7.34-7.17 (m, 8H), 7.11-7.04 (m, 2H), 5.95-5.86 (m, 2H), 5.43-5.31 (m, 2H), 5.18-5.09 (m, 2H), 4.05 (t, J=8.3, 2H), 3.86-3.76 (m, 4H), 3.52 (s, 6H), 3.12-2.82 (m, 4H), 2.58-2.52 (m, 2H), 2.26-1.83 (m, 11H), 1.72-1.58 (m, 6H), 0.90-0.73 (m, 12H), 0.20 (s, 9H); MS (ESI+) m/z 1099.4 (M+H)$^+$.

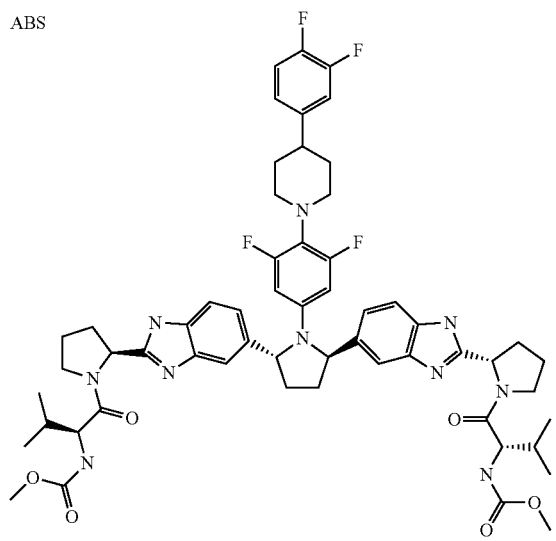

ABS

Example 3.44 methyl {(2S)-1-[(2S)-2-{5-[(2R,5R)-1-{4-[4-(3,4-difluorophenyl)piperidin-1-yl]-3,5-difluorophenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.32-12.04 (m, 2H), 7.50 (d, J=8.5, 1H), 7.41 (d, J=8.3, 1H), 7.36-7.25 (m, 5H), 7.21 (s, 1H), 7.12-7.05 (m, 3H), 5.91 (d, J=12.8, 2H), 5.37 (dd, J=6.0, 2.1, 2H), 5.18-5.11 (m, 2H), 4.06 (t, J=8.3, 2H), 3.86-3.79 (m, 4H), 3.53 (s, 6H), 3.12-2.83 (m, 4H), 2.27-2.10 (m, 4H), 2.08-1.49 (m, 15H), 0.93-0.67 (m, 12H); MS (ESI+) m/z 1063.3 (M+H)$^+$.

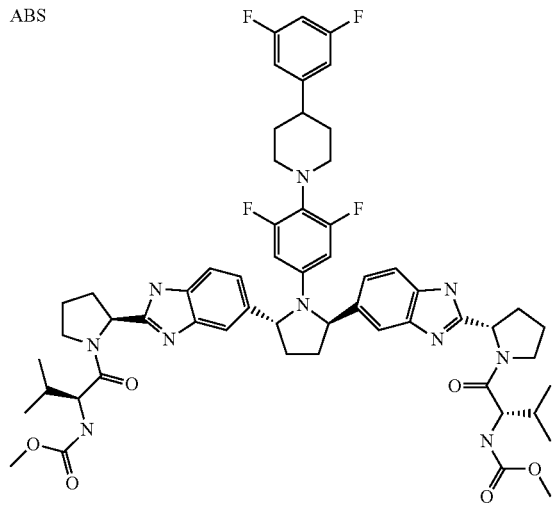

ABS

Example 3.45 methyl {(2S)-1-[(2S)-2-{5-[(2R,5R)-1-{4-[4-(3,5-difluorophenyl)piperidin-1-yl]-3,5-difluorophenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-pyrrolidin-1-yl]-3-methyl-1-oxobutan-2-yl}carbamate $^1$H NMR (400 MHz, DMSO-d$_6$) δ ppm 12.47-11.91 (m, 2H), 7.52-7.40 (m, 2H), 7.36-7.19 (m, 4H), 7.10 (d, J=7.9, 2H), 7.04-6.92 (m, 3H), 5.92 (d, J=12.7, 2H), 5.46-5.32 (m, 2H), 5.20-5.10 (m, 2H), 4.06 (t, J=8.3, 2H), 3.89-3.75 (m, 4H), 3.53 (s, 6H), 3.13-2.82 (m, 4H), 2.63-2.54 (m, 3H), 2.28-2.12 (m, 4H), 2.08-1.84 (m, 6H), 1.77-1.56 (m, 6H), 0.91-0.71 (m, 12H); MS (ESI+) m/z 1063.4 (M+H)$^+$.

The following Example compounds 4.1-4.60 can be made from the appropriate listed intermediate following the methods of General Procedures 12/12B.

Intermediate Amines:

(S)-6,6'-((2R,5R)-1-(4-(cyclopentyloxy)-3-fluorophenyl)pyrrolidine-2,5-diyl)bis(2-((S)-pyrrolidin-2-yl)-1H-benzo[d]imidazole);

(S)-6,6'-((2R,5R)-1-(3-methyl-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-((3aR,7aS)-1H-isoindol-2(3H,3aH,4H,5H,6H,7H,7aH)-yl)phenyl)pyrrolidine-2,5-diyl)bis(2-((S)-pyrrolidin-2-yl)-1H-benzo[d]imidazole);

(S)-6,6'-((2R,5R)-1-(3,5-dichloro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(2,5-difluoro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-((2R,6S)-2,6-dimethylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(2,3,5-trifluoro-4-(piperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-cyclohexyl-3-fluorophenyl)pyrrolidine-2,5-diyl)bis(2-((S)-pyrrolidin-2-yl)-1H-benzo[d]imidazole);

(S)-6,6'-((2R,5R)-1-(3,4-difluorophenyl)pyrrolidine-2,5-diyl)bis(2-((S)-pyrrolidin-2-yl)-1H-benzo[d]imidazole);

(S)-6,6'-((2R,5R)-1-(4-ethoxyphenyl)pyrrolidine-2,5-diyl) bis(2-((S)-pyrrolidin-2-yl)-1H-benzo[d]imidazole);

(S)-6,6'-((2R,5R)-1-(4-(2,2-difluoroethoxy)phenyl)pyrrolidine-2,5-diyl)bis(2-((S)-pyrrolidin-2-yl)-1H-benzo[d] imidazole);

(S)-6,6'-((2R,5R)-1-(4-(3,5-dimethylpiperidin-1-yl)-3,5-difluorophenyl)pyrrolidine-2,5-diyl)bis(2-((S)-pyrrolidin-2-yl)-1H-benzo[d]imidazole);

6,6'-{(2R,5R)-1-[4-(pentafluoro-$\lambda^6$-sulfanyl)phenyl]pyrrolidine-2,5-diyl}bis{2-[(2S)-pyrrolidin-2-yl]-1H-benzimidazole} (ACD Name v12);

(S)-6,6'-((2S,5S)-1-(4-cyclopropylphenyl)pyrrolidine-2,5-diyl)bis(2-((S)-pyrrolidin-2-yl)-1H-benzo[d]imidazole);

(S)-6,6'-((2S,5S)-1-(4-cyclopropyl-3,5-difluorophenyl)pyrrolidine-2,5-diyl)bis(2-((S)-pyrrolidin-2-yl)-1H-benzo[d] imidazole);

(S)-6,6'-((2R,5R)-1-(4-tert-butylphenyl)pyrrolidine-2,5-diyl)bis(2-((S)-pyrrolidin-2-yl)-1H-benzo[d]imidazole);

1-(1-(4-((2R,5R)-2,5-bis(2-((S)-pyrrolidin-2-yl)-1H-benzo [d]imidazol-6-yl)pyrrolidin-1-yl)-2,6-difluorophenyl)-4-phenylpiperidin-4-yl)ethanone;

(S,S,S)-6,6'-((2R,5R)-1-(3,5-difluoro-4-(piperidin-1-yl)phenyl)pyrrolidine-2,5-diyl)bis(2-((2S,3aS,6aS)-octahydrocyclopenta[b]pyrrol-2-yl)-1H-benzo[d]imidazole);

(S,S,S)-6,6'-((2R,5R)-1-(4-tert-butylphenyl)pyrrolidine-2,5-diyl)bis(2S,3aS,6aS)-octahydrocyclopenta[b]pyrrol-2-yl)-1H-benzo[d]imidazole);

2-(4-((2R,5R)-2,5-bis(2-((S)-pyrrolidin-2-yl)-1H-benzo[d] imidazol-6-yl)pyrrolidin-1-yl)-2,6-difluorophenyl)-2-azabicyclo[2.2.2]octane;

(S)-6,6'-((2R,5R)-1-(3,5-difluoro-4-(4-isopropylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4,4-dimethylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(4-(3,3-dimethylazetidin-1-yl)-3,5-difluorophenyl)pyrrolidine-2,5-diyl)bis(2-((S)-pyrrolidin-2-yl)-1H-benzo[d]imidazole);

(S)-6,6'-((2R,5R)-1-(4-(4-phenylpiperidin-1-yl)phenyl)pyrrolidine-2,5-diyl)bis(2-((S)-pyrrolidin-2-yl)-1H-benzo[d] imidazole);

(S)-6,6'-((2R,5R)-1-(3,5-difluoro-4-(4-(3-phenylpropyl)piperidin-1-yl)phenyl)pyrrolidine-2,5-diyl)bis(5-fluoro-2 ((S)-pyrrolidin-2-yl)-1H-benzo[d]imidazole);

(S)-6,6'-((2R,5R)-1-(4-(4-tert-butylpiperidin-1-yl)-3,5-difluorophenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-(naphthalen-2-yl)piperidin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(4-(2,3-dihydrospiro[indene-1,4'-piperidine]-1'-yl)-3,5-difluorophenyl)pyrrolidine-2,5-diyl) bis(5-fluoro-2((S)-pyrrolidin-2-yl)-1H-benzo[d]imidazole);

(S)-6,6'-((2R,5R)-1-(3,5-difluoro-4-(3-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(3-phenylpyrrolidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(4-methoxyphenyl)piperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-fluoro-4-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(4-(4-fluoro-4-phenylpiperidin-1-yl)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(fluorodiphenylmethyl)piperidin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-phenylpiperidin-1-yl)phenyl)pyrrolidine-2,5-diyl)bis(5-fluoro-2((S)-pyrrolidin-2-yl)-1H-benzo[d]imidazole);

(S)-6,6'-((2R,5R)-1-(4-(benzyloxy)phenyl)pyrrolidine-2,5-diyl)bis(2-((S)-pyrrolidin-2-yl)-1H-benzo[d]imidazole);

(S)-6,6'-((2R,5R)-1-(3,5-difluoro-4-(4-(4-(trifluoromethyl) phenyl)piperazin-1-yl)phenyl)pyrrolidine-2,5-diyl)bis(5-fluoro-2-((S)-pyrrolidin-2-yl)-1H-benzo[d]imidazole);

6-((2R,5R)-1-(3,5-difluoro-4-(piperidin-1-yl)phenyl)-5-(2-((S)-pyrrolidin-2-yl)-1H-benzo[d]imidazol-6-yl)pyrrolidin-2-yl)-5-fluoro-2-((S)-pyrrolidin-2-yl)-1H-benzo[d] imidazole;

(S)-6,6'-((2R,5R)-1-(4-(4-benzylpiperidin-1-yl)-3,5-difluorophenyl)pyrrolidine-2,5-diyl)bis(5-fluoro-2-((S)-pyrrolidin-2-yl)-1H-benzo[d]imidazole);

(S)-6,6'-((2R,5R)-1-(4-(4-benzylpiperidin-1-yl)-3,5-difluorophenyl)pyrrolidine-2,5-diyl)bis(2-((S)-pyrrolidin-2-yl)-1H-benzo[d]imidazole);

(S)-6,6'-((2S,5R)-1-(3,5-difluoro-4-(4-phenylpiperidin-1-yl)phenyl)pyrrolidine-2,5-diyl)bis(2-((S)-pyrrolidin-2-yl)-1H-benzo[d]imidazole);

4-(4-((2R,5R)-2,5-bis(2-((S)-pyrrolidin-2-yl)-1H-benzo[d] imidazol-6-yl)pyrrolidin-1-yl)-2,6-difluorophenyl)-2-phenylmorpholine;

(S)-6,6'-((2R,5R)-1-(3,5-difluoro-4-(2-phenylpiperidin-1-yl)phenyl)pyrrolidine-2,5-diyl)bis(2-((S)-pyrrolidin-2-yl)-1H-benzo[d]imidazole);

(2S,6R)-4-(4-((2R,5R)-2,5-bis(5-fluoro-2-((S)-pyrrolidin-2-yl)-1H-benzo[d]imidazol-6-yl)pyrrolidin-1-yl)-2,6-difluorophenyl)-2,6-dimethylmorpholine;

(S)-6,6'-((2R,5R)-1-(3,5-difluoro-4-(3-azaspiro[5.5]undecan-3-yl)phenyl)pyrrolidine-2,5-diyl)bis(5-fluoro-2((S)-pyrrolidin-2-yl)-1H-benzo[d]imidazole);

(S)-6,6'-((2R,5R)-1-(4-(4-cyclohexylpiperidin-1-yl)-3,5-difluorophenyl)pyrrolidine-2,5-diyl)bis(5-fluoro-2-((S)-pyrrolidin-2-yl)-1H-benzo[d]imidazole);

(S)-4-(4-((2R,5R)-2,5-bis(5-fluoro-2((S)-pyrrolidin-2-yl)-1H-benzo[d]imidazol-6-yl)pyrrolidin-1-yl)-2,6-difluorophenyl)-2-phenylmorpholine;

(S)-6,6'-((2S,5R)-1-(3,5-difluoro-4-(piperidin-1-yl)phenyl) pyrrolidine-2,5-diyl)bis(5-fluoro-2-((S)-pyrrolidin-2-yl)-1H-benzo[d]imidazole);

(S)-6,6'-((2R,5R)-1-(3,5-difluoro-4-(4-phenylpiperazin-1-yl)phenyl)pyrrolidine-2,5-diyl)bis(2-((S)-pyrrolidin-2-yl)-1H-benzo[d]imidazole);

(S,R)-6,6'-((2R,5R)-1-(3,5-difluoro-4-(piperidin-1-yl)phenyl)pyrrolidine-2,5-diyl)bis(2-((2S,4R)-4-fluoropyrrolidin-2-yl)-1H-benzo[d]imidazole);

(S)-6,6'-((2R,5R)-1-(3,5-difluoro-4-(4-(pyrimidin-2-yl)piperazin-1-yl)phenyl)pyrrolidine-2,5-diyl)bis(5-fluoro-2-((S)-pyrrolidin-2-yl)-1H-benzo[d]imidazole);

(S)-6,6'-((2R,5R)-1-(4-(4-(3,4-difluorophenyl)piperidin-1-yl)-3,5-difluorophenyl)pyrrolidine-2,5-diyl)bis(5-fluoro-2-((S)-pyrrolidin-2-yl)-1H-benzo[d]imidazole); and (S)-6,6'-((2R,5R)-1-(3,5-difluoro-4-(4-(4-fluorophenyl)piperidin-1-yl)phenyl)pyrrolidine-2,5-diyl)bis(5-fluoro-2-((S)-pyrrolidin-2-yl)-1H-benzo[d]imidazole).

Intermediate Acids:

(S)-2-(methoxycarbonylamino)-3-methylbutanoic acid;

(S)-2-(methoxycarbonylamino)-2-(tetrahydro-2H-pyran-4-yl)acetic acid;

(2S,3R)-3-methoxy-2-(methoxycarbonylamino)butanoic acid;

(S)-2-cyclopropyl-2-(methoxycarbonylamino)acetic acid;

(2S,3R)-3-tert-butoxy-2-(methoxycarbonylamino)butanoic acid;

(S)-2-(methoxycarbonylamino)-2-(tetrahydro-2H-pyran-4-yl)acetic acid;
(S)-2-cyclopentyl-2-(methoxycarbonylamino)acetic acid; and
(2S,3R)-3-methoxy-2-(methoxycarbonylamino)butanoic acid.

ABS

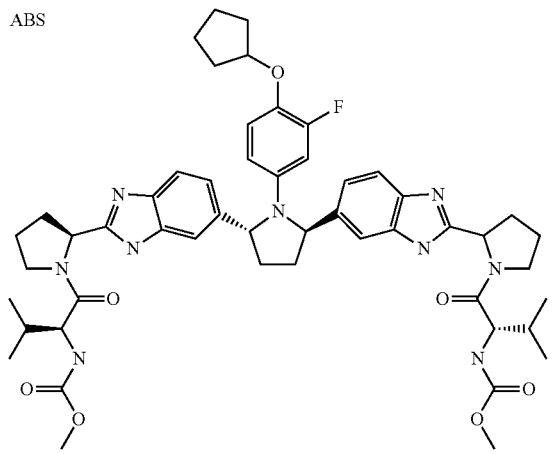 [SMILES: "ABS" ; COC(=O)N[C@H](C(=O)N1CCCC1c1nc2ccc([C@H]3CC[C@H](c4ccc5nc([C@@H]6CCCN6C(=O)[C@@H](NC(=O)OC)C(C)C)[nH]c5c4)N3c3ccc(OC4CCCC4)c(F)c3)cc2[nH]1)C(C)C]

Example 4.1 methyl {(2S)-1-[(2S)-2-{6-[(2R,5R)-1-[4-(cyclopentyloxy)-3-fluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl]pyrrolidin-1-yl]-3-methyl-1-oxobutan-2-yl}carbamate ¹H NMR (400 MHz, DMSO-d₆) δ ppm 0.74-0.89 (m, 12H), 1.37-1.77 (m, 12H), 1.81-2.06 (m, 6H), 2.11-2.29 (m, 4H), 3.54 (s, 6H), 3.72-3.92 (m, 4H), 3.95-4.16 (m, 2H), 4.40-4.52 (m, 1H), 5.07-5.23 (m, 2H), 5.26-5.44 (m, 2H), 5.96-6.17 (m, 2H), 6.63-6.98 (m, 2H), 7.00-7.16 (m, 2H), 7.16-7.35 (m, 4H), 7.35-7.54 (m, J=31.23 Hz, 2H), 11.93-12.32 (m, 2H); MS (ESI) m/z=934.5 (M+H)⁻.

ABS

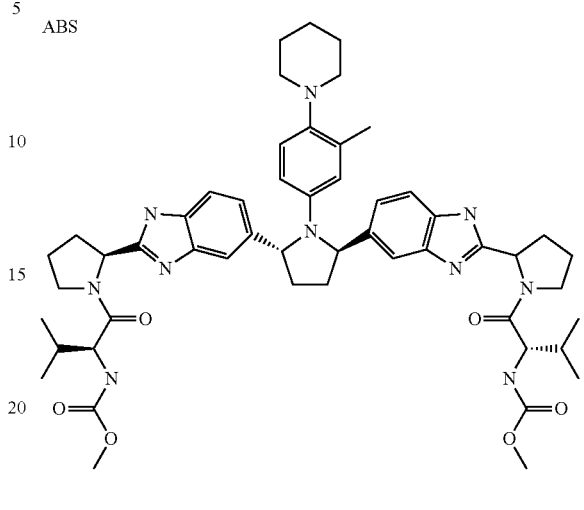

Example 4.2 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[3-methyl-4-(piperidin-1-yl)phenyl]pyrrolidin-2-yl}-1H-benzimidazol-2-yl)pyrrolidin-1-yl]-3-methyl-1-oxobutan-2-yl}carbamate ¹H NMR (400 MHz, DMSO-d₆) δ ppm 0.74-0.89 (m, 12H) 1.35-1.41 (m, 2H) 1.44-1.52 (m, 4H) 1.62-1.67 (m, 2H) 1.86-1.93 (m, 5H) 1.94-2.03 (m, 4H) 2.15-2.24 (m, 4H) 2.48-2.54 (m, 6H) 3.52 (s, 6H) 3.74-3.84 (m, 4H) 4.00-4.09 (m, 2H) 5.06-5.18 (m, 2H) 5.28-5.37 (m, 2H) 6.07-6.12 (m, 1H) 6.17-6.21 (m, 1H) 6.56-6.62 (m, 1H) 6.99-7.30 (m, 6H) 7.35 (d, J=8.24 Hz, 1H) 7.44 (d, J=8.24 Hz, 1H) 11.94-12.04 (m, 2H); MS (ESI+) m/z 929.5 (M+H)⁺.

ABS

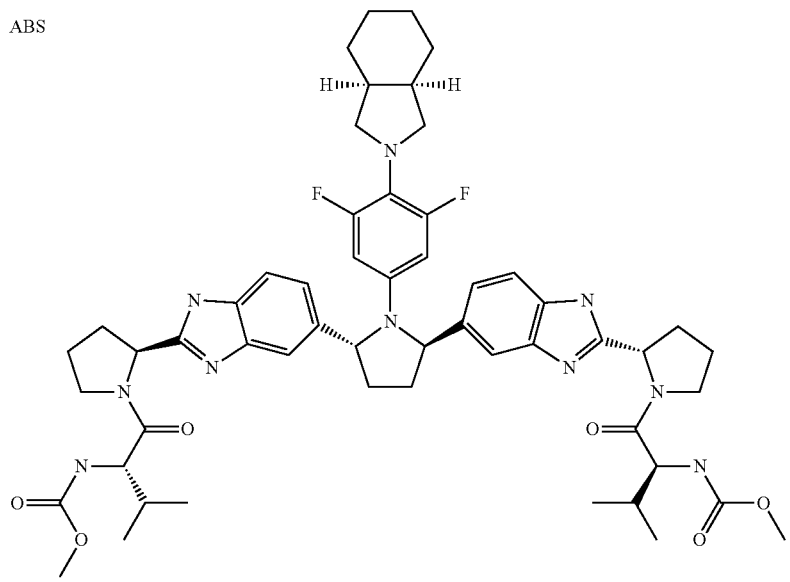 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4C[C@H]5CCCC[C@H]5C4)c(F)c3)ccc2[nH]1)C(C)C]

Example 4.3 methyl {(2S)-1-[(2S)-2-{5-[(2R,5R)-1-{3,5-difluoro-4-[(3aR,7aS)-octahydro-2H-isoindol-2-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.71-0.94 (m, 12H) 1.22-1.31 (m, 2H) 1.35-1.53 (m, 6H) 1.66-1.74 (m, 2H) 1.86-2.24 (m, 12H) 2.90-2.97 (m, 2H) 3.05-3.15 (m, 2H) 3.36-3.42 (m, 2H) 3.54 (s, 6H) 3.77-3.86 (m, 4H) 4.06 (t, J=8.29 Hz, 2H) 5.09-5.20 (m, 2H) 5.29-5.40 (m, 2H) 5.89 (d, J=12.25 Hz, 2H) 7.03-7.13 (m, 2H) 7.18-7.33 (m, 4H) 7.40 (d, J=8.13 Hz, 1H) 7.48 (d, J=8.24 Hz, 1H) 11.95-12.25 (m, 2H); MS (ESI+) m/z 991.5 (M+H)$^+$.

ABS

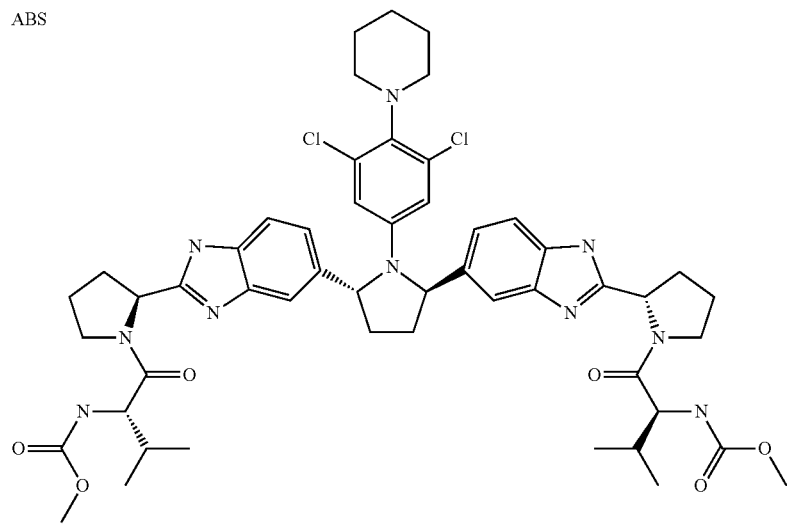 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(Cl)c(N4CCCCC4)c(Cl)c3)ccc2[nH]1)C(C)C]

Example 4.4 methyl {(2S)-1-[(2S)-2-{5-[(2R,5R)-1-[3,5-dichloro-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.68-0.94 (m, 12H) 1.36-2.28 (m, 20H) 2.84 (s, 4H) 3.54 (s, 6H) 3.82 (s, 4H) 4.04-4.09 (m, 2H) 5.09-5.19 (m, 2H) 5.33-5.50 (m, 2H) 6.30 (t, J=2.49 Hz, 2H) 6.99-7.57 (m, 8H) 12.04 (s, 1H) 12.09 (s, 1H); MS (ESI+) m/z 983 (M+H)$^+$.

ABS

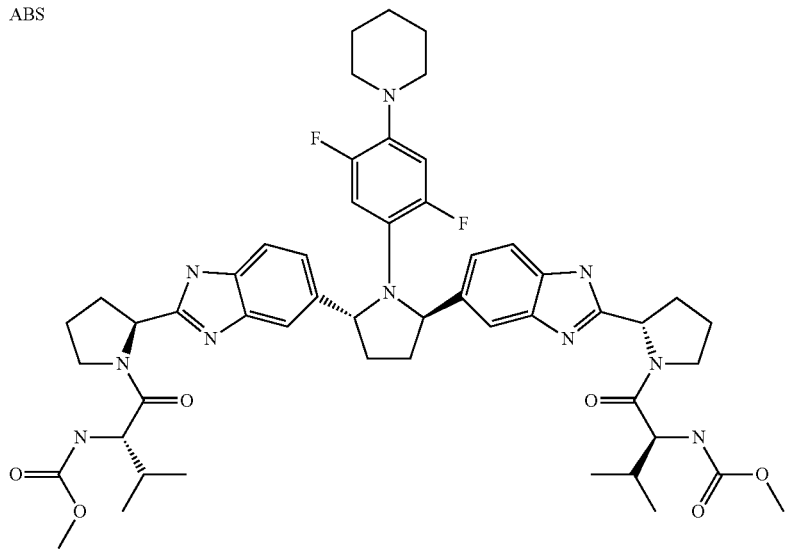 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCCCC4)cc3F)ccc2[nH]1)C(C)C]

Example 4.5 methyl {(2S)-1-[(2S)-2-{5-[(2R,5R)-1-[2,5-difluoro-4-(piperidin-1-yl)-phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.80 (s, 12H) 1.08-2.71 (m, 24H) 3.53 (s, 6H) 3.81 (s, 4H) 3.97-4.11 (m, 2H) 5.13 (s, 2H) 5.51 (s, 2H) 6.34-6.70 (m, 2H) 7.00-7.60 (m, 8H) 11.87-12.30 (m, 2H); MS (ESI+) m/z 952 (M+H)$^+$.

Example 4.6 methyl {(2S)-1-[(2S)-2-{5-[(2R,5R)-1-{4-[(2R,6S)-2,6-dimethylpiperidin-1-yl]-3,5-difluorophenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.58 (s, 6H) 0.73-0.92 (m, 12H) 1.08-2.37 (m, 20H) 3.53 (s, 6H) 3.82 (s, 4H) 4.06 (q, J=7.92 Hz, 2H) 5.15 (s, 2H) 5.39 (s, 2H) 5.88 (d, J=13.01 Hz, 2H) 7.02-7.58 (m, 10H) 12.01 (s, 1H) 12.18 (s, 1H); MS (ESI+) m/z 979 (M+H)$^+$.

ABS

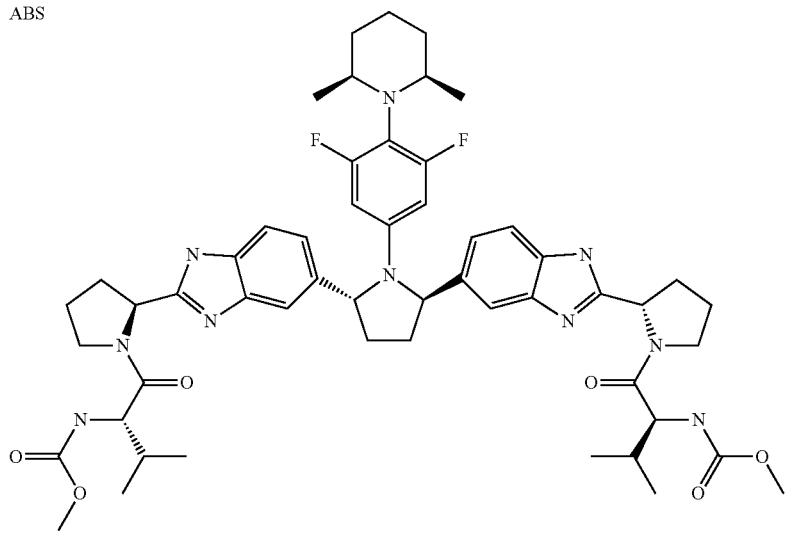 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4[C@H](C)CCC[C@@H]4C)c(F)c3)ccc2[nH]1)C(C)C]

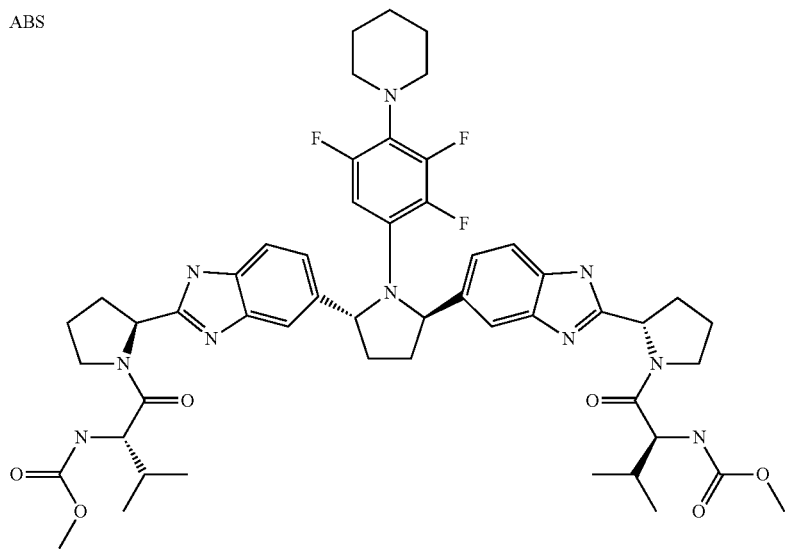 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCCCC4)c(F)c3F)ccc2[nH]1)C(C)C]

Example 4.7 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[2,3,5-trifluoro-4-(piperidin-1-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-$d_6$) δ ppm 0.72-0.93 (m, 12H) 1.34-2.38 (m, 20H) 2.77 (s, 4H) 3.53 (s, 6H) 3.82 (s, 4H) 4.00-4.13 (m, 2H) 5.14 (s, 2H) 5.56 (s, 2H) 6.27-6.47 (m, 1H) 6.97-7.49 (m, 8H) 12.01 (s, 1H) 12.08 (d, J=1.84 Hz, 1H); MS (ESI+) m/z 970 (M+H)$^+$.

Example 4.8 methyl {(2S)-1-[(2S)-2-{5-[(2R,5R)-1-(4-cyclohexyl-3-fluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, CDCl$_3$) δ ppm 10.48 (m, 1H), 10.32 (s, 1H), 7.70 (d, J=8.0 Hz, 1H), 7.53 (s, 1H), 7.34 (d, J=8.1 Hz, 1H), 7.13 (d, J=5.5 Hz, 3H), 6.72 (s, 1H), 6.03 (m, 2H), 5.40 (m, 5H), 5.26 (d, J=1.7 Hz, 3H), 4.34 (dd, J=8.7, 7.0 Hz, 2H), 3.84 (d, J=7.6 Hz, 2H), 3.70 (s, 6H), 3.62 (m, 3H), 3.09 (m, 2H), 2.57 (m, 4H), 2.33 (m, 2H), 2.17 (m, 5H), 1.97 (m, 3H), 1.73 (m, 8H), 1.17 (m, 8H), 0.89 (t, J=6.4, 12H); MS (ESI+) m/z (rel abundance) 933 (100, M+H), 934 (53).

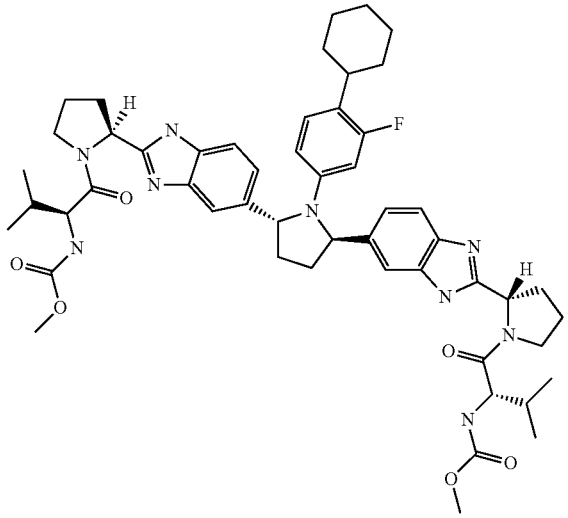

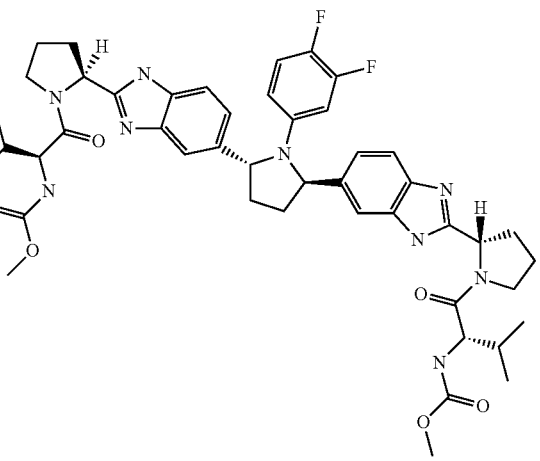

Example 4.9 methyl {(2S)-1-[(2S)-2-{5-[(2R,5R)-1-(3,4-difluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, CDCl$_3$) δ ppm 10.49 (d, J=9.0 Hz, 1H), 10.38 (s, 1H), 7.70 (d, J=8.1 Hz, 1H), 7.51 (s, 1H), 7.35 (d, J=8.3 Hz, 1H), 7.12 (dd, J=10.9, 6.3 Hz, 3H), 6.69 (dd, J=9.4, 5.7 Hz, 1H), 6.13 (d, J=7.2 Hz, 1H), 6.00 (s, 1H), 5.41 (m, 4H), 5.27 (m, 2H), 4.34 (m, 2H), 4.06 (d, J=6.6 Hz, 1H), 3.85 (m, 2H), 3.73 (s, 6H), 3.64 (m, 2H), 3.08 (m, 2H), 2.61 (m, 2H), 2.34 (m, 2H), 2.19 (m, 4H), 1.96 (m, 2H), 1.79 (m, 2H), 1.64 (m, 4H), 0.92 (m, 12H); MS (ESI+) m/z (rel abundance) 868 (100, M+H), 869 (43).

ABS

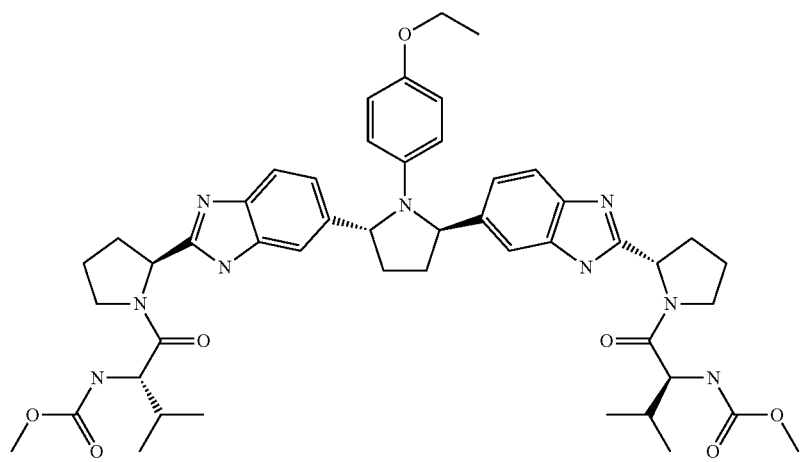

Example 4.10 methyl {(2S)-1-[(2S)-2-{6-[(2R,5R)-1-(4-ethoxyphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.92-0.75 (m, 12H), 1.21-1.10 (m, 3H), 1.33-1.21 (m, 1H), 1.76-1.64 (m, 2H), 2.06-1.85 (m, 7H), 2.28-2.08 (m, 4H), 3.54 (s, 6H), 3.73 (q, J=7.0, 2H), 3.81 (s, 4H), 4.11-3.99 (m, 2H), 5.18-5.06 (m, 2H), 5.33 (s, 2H), 6.24 (d, J=8.9, 2H), 6.51 (dt, J=4.9, 9.4, 2H), 7.04 (t, J=7.7, 2H), 7.34-7.18 (m, 4H), 7.36 (d, J=8.2, 1H), 7.44 (d, J=8.2, 1H), 12.02 (s, 2H); MS (ESI) m/z 876 (M+H)$^+$, 874 (M−H)$^−$.

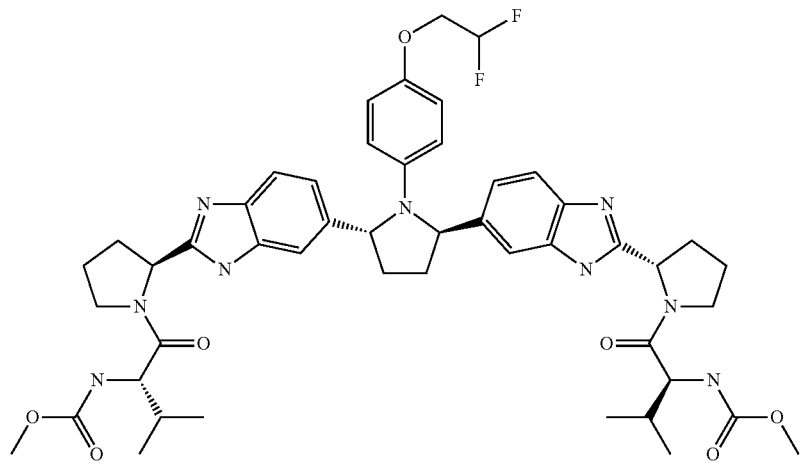

Example 4.11 methyl {(2S)-1-[(2S)-2-{6-[(2R,5R)-1-[4-(2,2-difluoroethoxy)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, methanol-d$_4$) δ ppm 0.85 (dd, J=6.7, 20.0, 12H), 1.88-1.75 (m, 2H), 2.06-1.95 (m, 3H), 2.22-2.06 (m, 3H), 2.34-2.23 (m, 2H), 2.49-2.34 (m, 2H), 2.71-2.56 (m, 2H), 3.64 (s, 6H), 4.13-3.76 (m, 6H), 4.22 (dd, J=5.4, 10.3, 1H), 5.28-5.17 (m, 2H), 5.37 (t, J=6.4, 2H), 5.96 (tt, J=3.9, 55.2, 1H), 6.31 (t, J=9.7, 2H), 6.60-6.51 (m, 2H), 6.98 (d, J=8.4, 1H), 7.23 (d, J=8.3, 2H), 7.35 (d, J=17.8, 2H), 7.50 (d, J=8.3, 2H); MS (ESI) m/z 912 (M+H)$^+$, 910 (M−H)$^-$.

Example 4.12 methyl {(2S)-1-[(2S)-2-{6-[(2R,5R)-1-[4-(3,5-dimethylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.50 (q, J=11.9, 1H), 0.97-0.64 (m, 18H), 1.32-1.20 (m, 2H), 1.81-1.46 (m, 5H), 2.09-1.80 (m, 6H), 2.32-2.13 (m, 5H), 2.75 (dd, J=10.0, 40.2, 2H), 3.18-3.05 (m, 1H), 3.54 (s, 6H), 3.82 (s, 4H), 4.14-3.95 (m, 2H), 5.14 (s, 2H), 5.36 (d, J=7.2, 2H), 5.88 (d, J=12.8, 2H), 7.14-7.02 (m, 2H), 7.19 (s, 1H), 7.33-7.23 (m, 3H), 7.41 (d, J=8.2, 1H), 7.49 (d, J=8.2, 1H), 12.37-11.98 (m, 2H); MS (ESI) m/z 979 (M+H)$^+$.

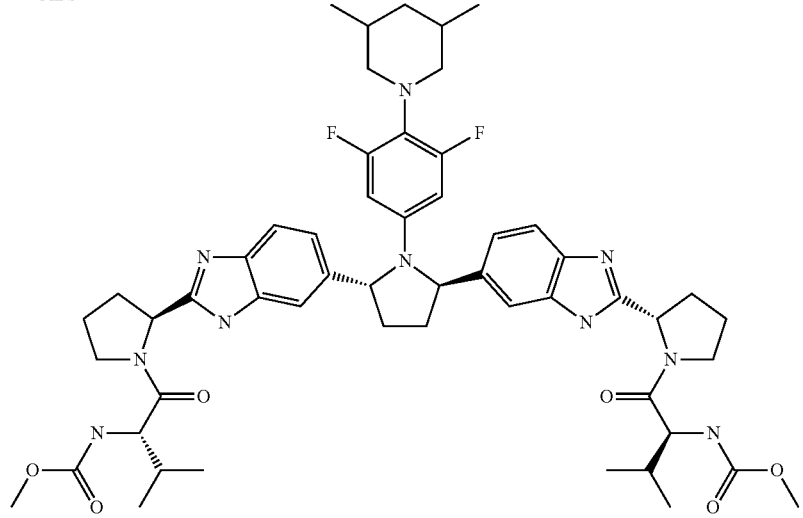

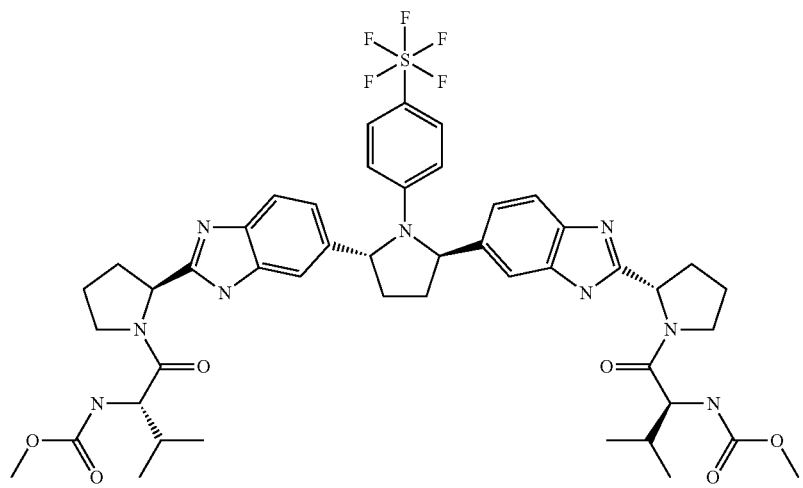

Example 4.13 methyl {(2S)-1-[(2S)-2-(6-{(2R,5R)-5-{2-[(2S)-1-{(2S)-2-[methoxycarbonyl)amino]-3-methylbutanoyl}pyrrolidin-2-yl]-1H-benzimidazol-6-yl}-1-[4-(pentafluoro-lambda~6~-sulfanyl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-$d_6$) δ ppm 0.92-0.69 (m, 12H), 2.08-1.61 (m, 8H), 2.20 (s, 4H), 3.53 (s, 6H), 3.82 (s, 4H), 4.05 (t, J=8.0, 2H), 5.13 (dt, J=4.9, 9.8, 2H), 5.49 (dd, J=10.8, 15.8, 2H), 6.37 (d, J=8.6, 2H), 7.13-6.81 (m, 3H), 7.20 (d, J=8.8, 1H), 7.28 (dd, J=4.6, 9.9, 3H), 7.45-7.34 (m, 4H), 7.48 (d, J=8.2, 1H), 12.16 (dd, J=22.6, 68.2, 2H); MS (ESI) m/z 958 (M+H)$^+$, 956 (M=H)$^-$.

Example 4.14 methyl {(2S,3R)-1-[(2S)-2-{5-[(2S,5S)-1-(4-cyclopropylphenyl)-5-(2-{(2S)-1-[N-(methoxycarbonyl)-O-methyl-L-threonyl]pyrrolidin-2-yl}-1H-benzimidazol-5-yl)pyrrolidin-2-yl]-1H-benzimidazol-2-yl}pyrrolidin-1-yl]-3-methoxy-1-oxobutan-2-yl}carbamate $^1$H NMR (400 MHz, DMSO-$d_6$) δ ppm 0.37 (m, 2H) 0.68, (s, 2H) 1.08 (d, 6H) 1.54-1.64 (m, 2H) 1.69 (s, 2H) 1.99 (s, 4H) 2.17 (s, 7H) 3.18 (s, 6H) 3.42-3.53 (m, 2H) 3.54 (s, J=1.41 Hz, 6H) 3.84 (s, 3H) 4.28 (s, 2H) 5.12 (s, 2H) 5.34 (s, 2H) 6.22 (s, 2H) 6.61 (s, 2H) 7.05 (s, 2H) 7.16 (s, 2H) 7.36 (s, 2H) 11.97 (s, 1H),12.08 (s, 1H); MS (ESI+) m/z 904.5 (M+H)$^+$, (ESI−) m/z 902.3 (M−H)$^-$.

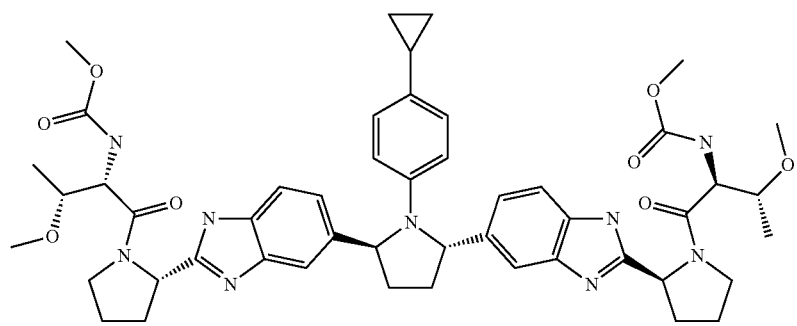

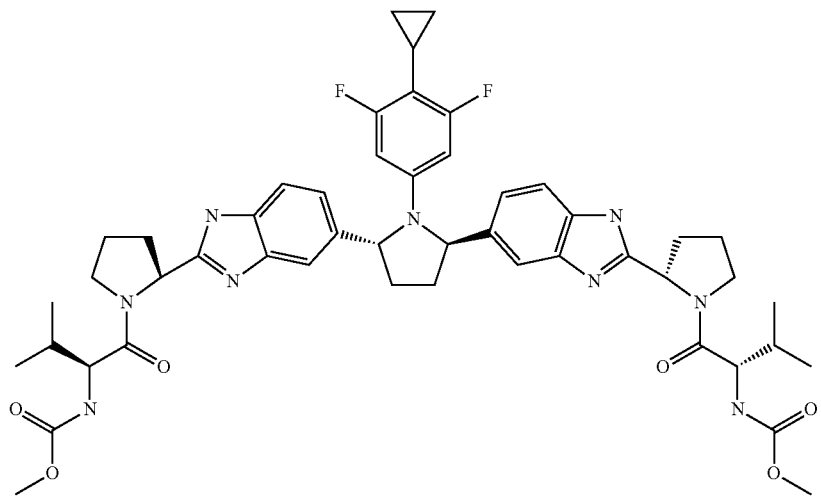

Example 4.15 methyl {(2S)-1-[(2S)-2-{6-[(2R,5R)-1-(4-cyclopropyl-3,5-difluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, CDCl$_3$) δ ppm 10.47 (br s, 1H) 10.30-10.41 (br s, 1H) 7.69 (br s, 1H) 7.49 (s, 1H) 7.30-7.43 (br s, 1H) 7.04-7.20 (m, 3H) 5.75-5.89 (m, 2H) 5.37 (m, 4H) 5.23 (s, 2H) 4.34 (t, 2H) 3.83 (m, 2H) 3.71 (s, 6H) 3.56-3.67 (m, 2H) 3.11 (m, 2H) 2.58 (br s, 2H) 2.33 (m, 2H) 2.08-2.27 (m, 4H) 2.01 (m, 2H) 1.78 (br s, 2H) 0.82-0.96 (m, 12H) 0.71 (m, 4H).

Example 4.16 dimethyl([[(2R,5R)-1-(4-tert-butylphenyl)pyrrolidine-2,5-diyl]bis{1H-benzimidazole-6,2-diyl(2S)pyrrolidine-2,1-diyl[(1S)-1-cyclopropyl-2-oxoethane-2,1-diyl]})biscarbamate $^1$H NMR (500 MHz, DMSO-d$_6$) δ ppm 0.48-0.24 (m, 7H), 0.89-0.81 (m, 1H), 1.01 (s, 3H), 1.07 (s, 6H), 1.14 (dd, J=8.7, 16.6, 1H), 1.32-1.17 (m, 4H), 1.75-1.64 (m, 1H), 2.05-1.78 (m, 4H), 2.24-2.09 (m, 3H), 2.45-2.39 (m, 2H), 3.21-3.12 (m, 1H), 3.53 (s, 6H), 3.72-3.63 (m, 2H), 3.76 (s, 2H), 4.03-3.85 (m, 2H), 5.17-5.04 (m, 1H), 5.44-5.26 (m, 2H), 6.26 (d, J=8.8, 1H), 6.95-6.81 (m, 2H), 7.06-6.95 (m, 1H), 7.09 (t, J=8.3, 1H), 7.20 (d, J=4.3, 1H), 7.35-7.25 (m, 1H), 7.55-7.36 (m, 4H), 12.28-11.84 (m, 2H); MS (ESI+) m/z 884 (M+H)$^+$, (ESI−) m/z 882 (M−H)$^−$.

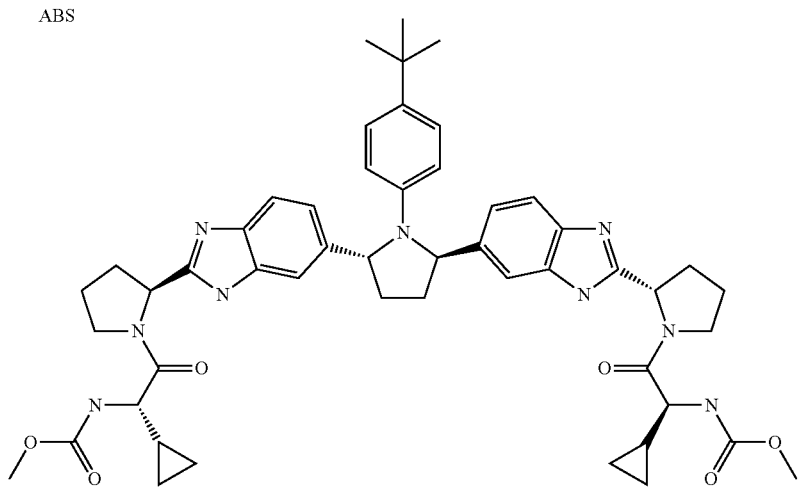

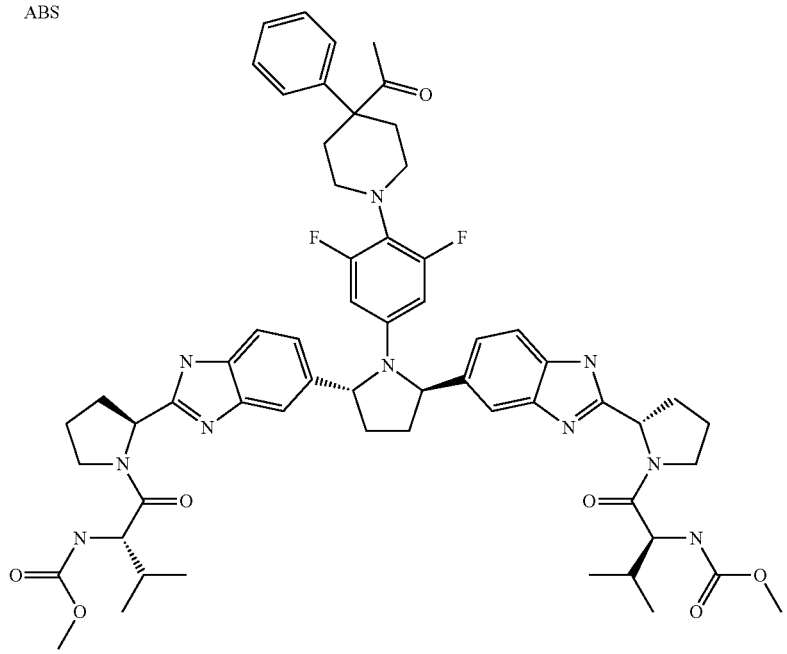 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(C(C)=O)(c5ccccc5)CC4)c(F)c3)ccc2[nH]1)C(C)C]

Example 4.17 methyl {(2S)-1-[(2S)-2-{5-[(2R,5R)-1-[4-(4-acetyl-4-phenylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.75-0.91 (m, 12H) 1.68 (d, J=4.66 Hz, 2H) 1.83 (s, 3H) 1.87-2.38 (m, 16H) 2.78-2.90 (m, 4H) 3.54 (s, 6H) 3.82 (s, 4H) 4.06 (t, J=8.35 Hz, 2H) 5.09-5.18 (m, 2H) 5.27-5.41 (m, 2H) 5.88 (d, J=12.90 Hz, 2H) 7.02-7.51 (m, 13H) 12.07 (d, J=16.91 Hz, 2H); MS (ESI+) m/z 1070 (M+H)$^+$.

Example 4.18 methyl {(2S)-1-[(2S,3aS,6aS)-2-{5-[(2R,5R)-1-[3,5-difluoro-4-(piperidin-1-yl)phenyl]-5-{2-[(3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-1H-benzimidazol-2-yl}hexahydrocyclopenta[b]pyrrol-1(2H)-yl]-3-methyl-1-oxobutan-2-yl}carbamate $^1$H NMR (400 MHz, DMSO-d$_6$) δ ppm 0.64-0.96 (m, 13H) 1.31-2.18 (m, 21H) 3.50-3.57 (m, 6H) 3.93-4.07 (m, 2H) 4.72-4.85 (m, 1H) 5.13 (t, 1H) 5.37 (s, 2H) 5.90 (dd, 2H) 7.06 (d, 2H) 7.21 (s, 1H) 7.33 (d, 1H) 7.36-7.56 (m, J=8.13 Hz, 4H) 11.96 (s, 1H) 12.03-12.08 (m, 1H) 12.24 (none, 1H); MS (ESI+) m/z 1031.5 (M+H)$^+$, (ESI−) m/z 1029.4 (M−H)$^-$.

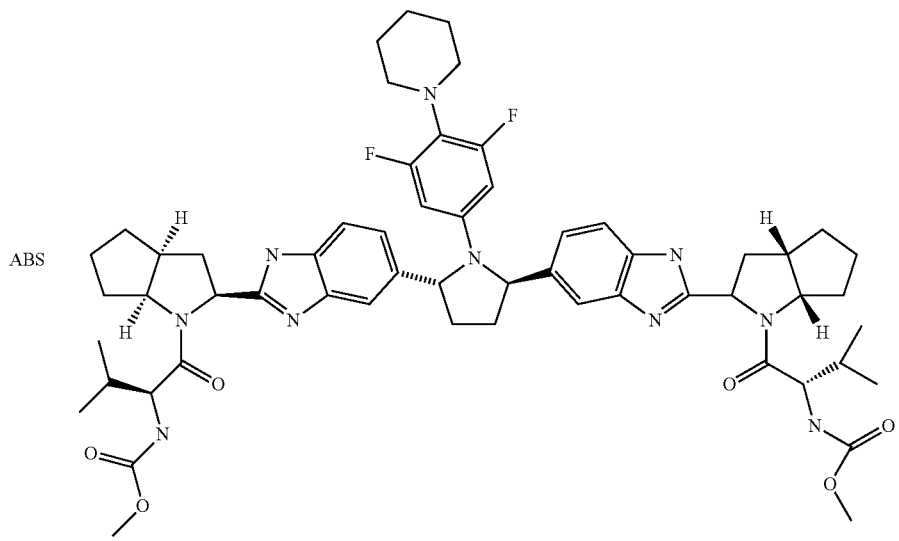 [SMILES: "ABS" ; COC(=O)N[C@H](C(=O)N1C(c2nc3cc([C@H]4CC[C@H](c5ccc6[nH]c([C@@H]7C[C@@H]8CCC[C@@H]8N7C(=O)[C@@H](NC(=O)OC)C(C)C)nc6c5)N4c4cc(F)c(N5CCCCC5)c(F)c4)ccc3[nH]2)C[C@@H]2CCC[C@@H]21)C(C)C]

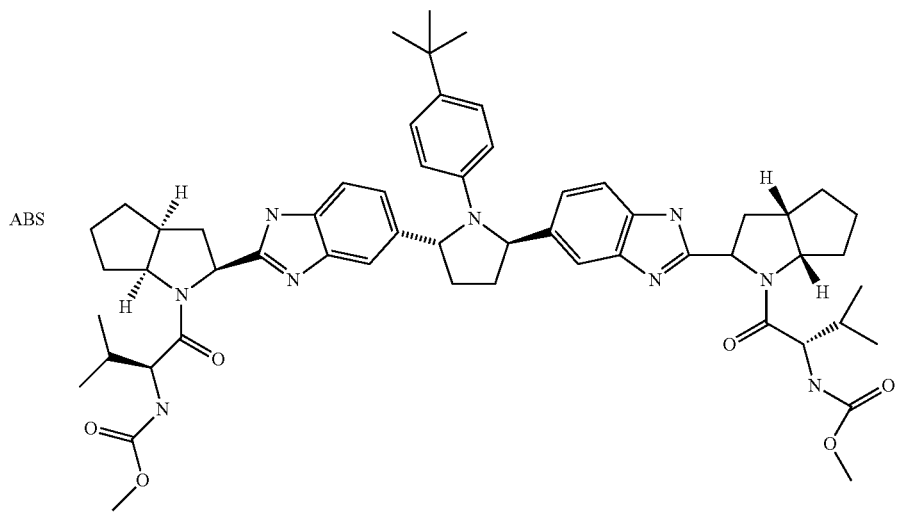 [SMILES: "ABS" ; COC(=O)N[C@H](C(=O)N1C(c2nc3cc([C@H]4CC[C@H](c5ccc6[nH]c([C@@H]7C[C@@H]8CCC[C@@H]8N7C(=O)[C@@H](NC(=O)OC)C(C)C)nc6c5)N4c4ccc(C(C)(C)C)cc4)ccc3[nH]2)C[C@@H]2CCC[C@@H]21)C(C)C]

Example 4.19 methyl {(2S)-1-[(2S,3aS,6aS)-2-{5-[(2R,5R)-1-(4-tert-butylphenyl)-5-{2-[(3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-1H-benzimidazol-2-yl}hexahydrocyclopenta[b]pyrrol-1(2H)-yl]-3-methyl-1-oxobutan-2-yl}carbamate $^1$H NMR (400 MHz, DMSO-d$_6$) δ ppm 0.62-0.93 (m, 13H) 1.42-2.16 (m, 25H) 2.78 (s, 1H) 3.54 (s, 6H) 4.01 (s, 2H) 4.77 (s, 1H) 5.11 (t, J=8.08 Hz, 2H) 5.35 (s, 2H) 6.26 (d, J=8.67 Hz, 2H) 6.83-6.97 (m, 2H) 7.05 (s, 2H) 7.21 (s, 1H) 7.27-7.32 (m, 1H) 7.34-7.55 (m, 4H) 11.92 (s, 1H) 12.01 (s, 1H); MS (ESI+) m/z 968.5 (M+H)$^+$, (ESI−) m/z 966.4 (M−H)$^−$, 1011.7 (M+COOH−H)$^−$.

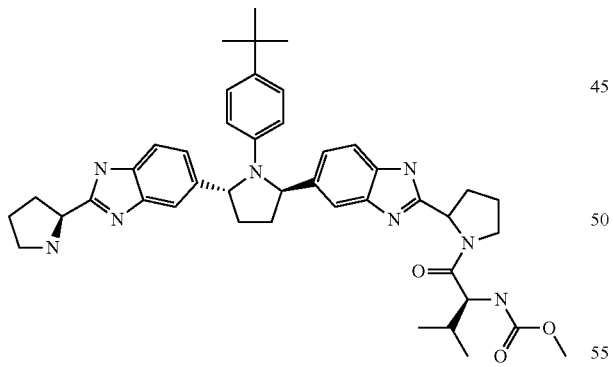

Example 4.20 methyl[(2S)-1-(2-{5-[(2R,5R)-1-(4-tert-butylphenyl)-5-{2-[(2S)-pyrrolidin-2-yl]-1H-benzimidazol-5-yl}pyrrolidin-2-yl]-1H-benzimidazol-2-yl}pyrrolidin-1-yl)-3-methyl-1-oxobutan-2-yl]carbamate The title compound can be prepared by reacting the amine with one equivalent of an acid instead of two. $^1$H NMR (400 MHz, DMSO-d$_6$) δ ppm 0.67-0.90 (m, 6H) 0.97-1.17 (m, 9H) 1.53-2.46 (m, 13H) 3.26-3.42 (m, J=11.39 Hz, 2H) 3.54 (s, 3H) 3.85 (d, J=4.34 Hz, 2H) 4.07-4.13 (m, 1H) 4.88-4.98 (m, 1H) 5.15-5.23 (m, 1H) 5.45 (d, J=7.16 Hz, 1H) 5.50 (d, J=6.94 Hz, 1H) 6.26 (d, J=8.78 Hz, 2H) 6.92 (d, J=8.78 Hz, 2H) 7.19-7.77 (m, 7H) 9.15 (s, 1H) 9.66 (s, 1H); MS (ESI+) m/z 731 (M+H)$^+$.

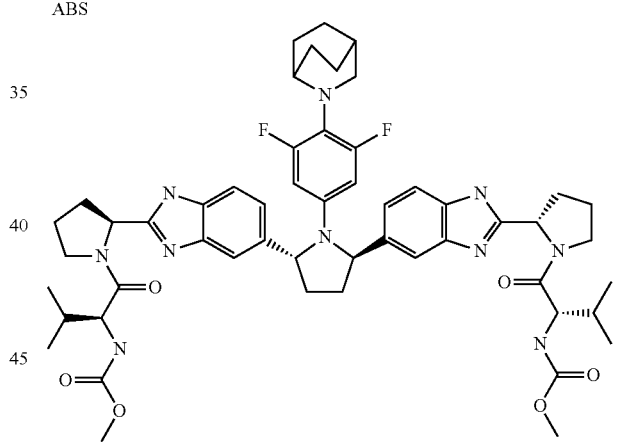

Example 4.21 methyl {(2S)-1-[(2S)-2-{5-[(2R,5R)-1-[4-(2-azabicyclo[2.2.2]oct-2-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.74-1.02 (m, 12H), 1.41-2.27 (m, 26H), 2.65 (s, 1H), 3.05-3.26 (m, 3H), 3.54 (s, 6H), 4.06 (t, J=8.35 Hz, 2H), 5.07-5.20 (m, 2H), 5.26-5.45 (m, 2H), 5.89 (d, J=12.36 Hz, 2H), 7.00-7.14 (m, 2H), 7.16-7.33 (m, 4H), 7.44 (dd, J=32.42, 8.24 Hz, 2H), 12.06 (two s, 2H); MS (ESI+) m/z 977 (M+H)$^+$, (ESI−) m/z 975 (M−H)$^−$.

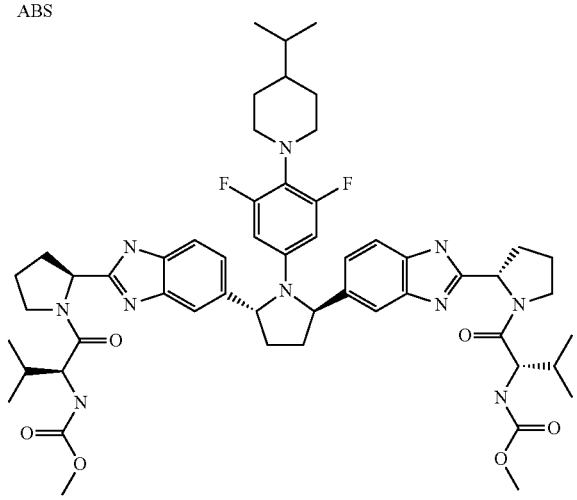 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(C(C)C)CC4)c(F)c3)ccc2[nH]1)C(C)C]

Example 4.22 methyl {(2S)-1-[(2S)-2-{5-[(2R,5R)-1-{3,5-difluoro-4-[4-(propan-2-yl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 0.74-0.91 (m, 18H), 0.91-1.05 (m, 1H), 1.07-1.21 (m, 3H), 1.31-1.43 (m, 1H), 1.51 (d, J=11.17 Hz, 2H), 1.63-1.77 (m, 2H), 1.84-2.26 (m, 11H), 2.72-2.88 (m, 4H), 3.54 (s, 6H) 3.82 (br s, 4H), 4.06 (t, J=8.35 Hz, 2H), 5.07-5.23 (m, 2H), 5.29-5.45 (m, 2H), 5.88 (d, J=12.79 Hz, 2H), 7.02-7.12 (m, 2H), 7.16-7.32 (m, 4H), 7.41 (d, J=8.13 Hz, 1H), 7.49 (d, J=8.13 Hz, 1H), 12.07 (two s, 2H); MS (ESI+) m/z 994 (M+H)⁺.

Example 4.23 dimethyl({(2R,5R)-1-[4-(4,4-dimethylpiperidin-1-yl)-3,5-difluorophenyl]pyrrolidine-2,5-diyl}bis{1H-benzimidazole-5,2-diyl(2S)pyrrolidine-2,1-diyl[(1S)-2-oxo-1-(tetrahydro-2H-pyran-4-yl)ethane-2,1-diyl]})biscarbamate ¹H NMR (400 MHz, DMSO-d₆) δ ppm 0.87 (s, 6H), 1.18-1.34 (m, 9H), 1.34-1.59 (m, 4H), 1.61-1.93 (m, 5H), 1.93-2.06 (m, 4H), 2.09-2.27 (m, 4H), 2.77 (s, 4H), 2.90-3.27 (m, 4H), 3.53 (s, 6H), 3.62 (d, J=11.71 Hz, 1H), 3.67-3.89 (m, 7H), 4.14 (q, J=8.10 Hz, 2H), 5.08-5.20 (m, 2H), 5.30-5.43 (m, 2H), 5.81-5.94 (m, 2H), 7.03-7.52 (m, 8H), 12.10 (two s, 2H); MS (ESI+) m/z 1063 (M+H)⁺, (ESI−) m/z 1061 (M−H)⁻.

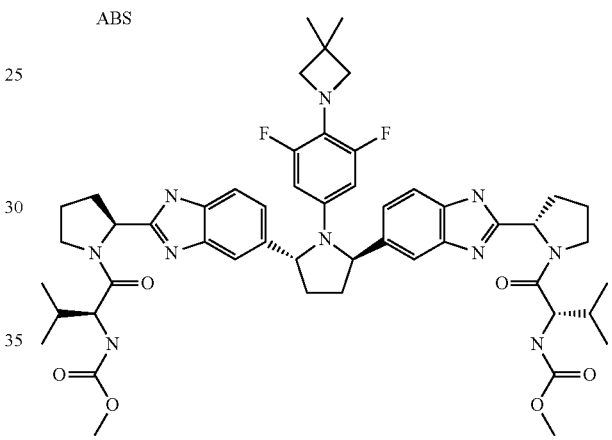

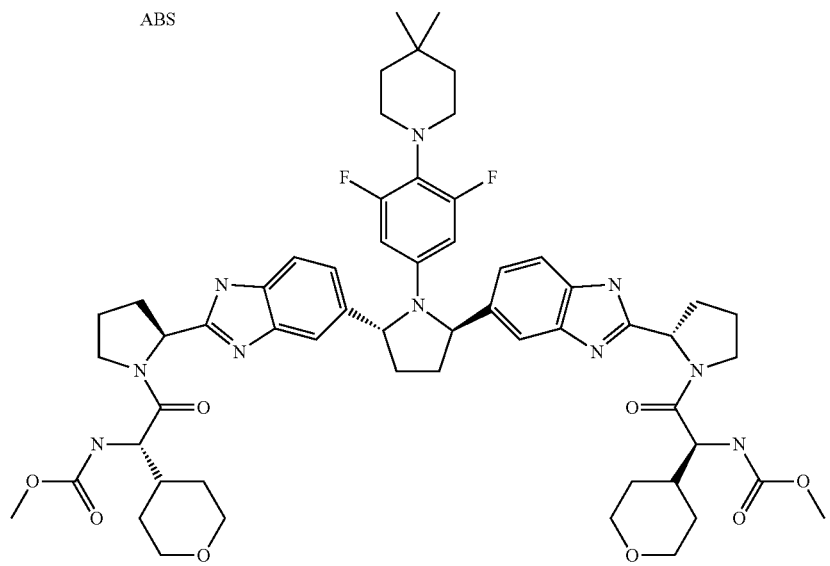

Example 4.24 methyl {(2S)-1-[(2S)-2-{5-[(2R,5R)-1-[4-(3,3-dimethylazetidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.76-0.94 (m, 12H), 1.13 (s, 6H), 1.61-1.74 (m, 2H), 1.81-2.28 (m, 9H), 3.07-3.18 (m, 1H), 3.49 (s, 4H), 3.54 (s, 6H), 3.82 (br s, 4H), 4.07 (t, J=8.24 Hz, 2H), 5.14 (t, J=7.54 Hz, 2H), 5.25-5.40 (m, 2H), 5.79-5.94 (m, 2H), 7.01-7.07 (m, 2H), 7.08-7.34 (m, 4H), 7.39 (d, J=8.13 Hz, 1H), 7.47 (d, J=8.24 Hz, 1H), 12.05 (two s, 2H); MS (ESI+) m/z 951 (M+H)$^+$.

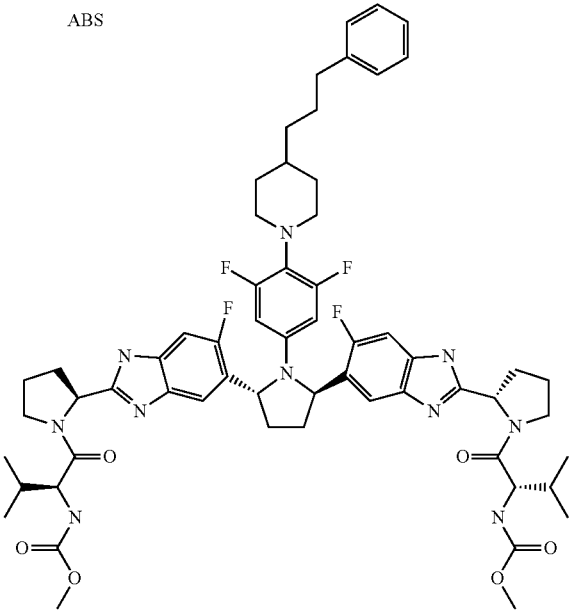

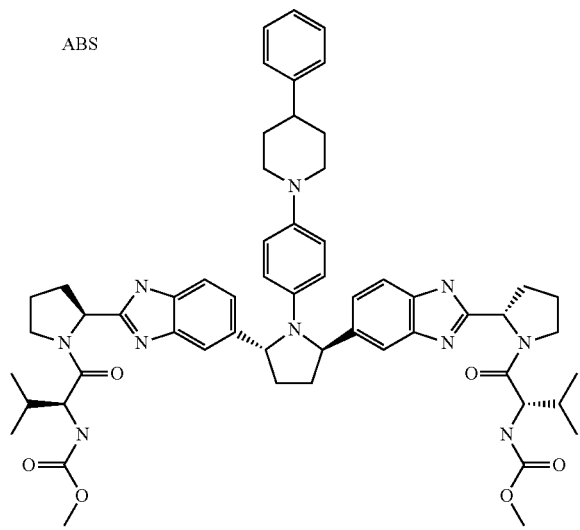 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCC(c5ccccc5)CC4)cc3)ccc2[nH]1)C(C)C ; "ABS"]

Example 4.25 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(4-phenylpiperidin-1-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-d$_6$) δ ppm 0.74-0.93 (m, 12H), 1.61-1.79 (m, 6H), 1.84-2.09 (m, 6H), 2.11-2.27 (m, 4H), 2.40-2.60 (m, 4H), 3.35 (s, 3H), 3.53 (s, 6H), 3.82 (s, 4H), 4.06 (t, J=8.29 Hz, 2H), 5.08-5.19 (m, 2H), 5.28-5.46 (m, 2H), 6.26 (d, J=8.67 Hz, 2H), 6.55-6.67 (m, 2H), 7.06 (t, J=7.32 Hz, 2H), 7.13-7.32 (m, 9H), 7.37 (d, J=8.24 Hz, 1H), 7.45 (d, J=8.24 Hz, 1H), 12.02 (s, 2H); MS (ESI+) m/z 991 (M+H)$^+$, (ESI−) m/z 989 (M−H)$^-$.

Example 4.26 methyl {(2S)-1-[(2S)-2-{5-[(2R,5R)-1-{3,5-difluoro-4-[4-(3-phenylpropyl)piperidin-1-yl]phenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, DMSO-d$_6$) δ ppm 0.68-0.84 (m, 12H), 0.98-1.30 (m, 8H), 1.47-1.60 (m, 5H), 1.63-2.07 (m, 9H), 2.09-2.24 (m, 3H), 2.78 (s, 4H), 3.51 (s, 6H), 3.71-3.87 (m, 4H), 3.97-4.12 (m, 2H), 5.03-5.17 (m, 2H), 5.43-5.63 (m, 2H), 5.78-5.96 (m, 2H), 7.02 (dd, J=6.78, 2.33 Hz, 1H), 7.08-7.19 (m, 4H), 7.19-7.35 (m, 5H), 7.39 (dd, J=11.28, 6.29 Hz, 1H), 11.50-12.73 (m, 2H); MS (ESI+) m/z 1105 (M+H)$^+$; MS (ESI−) m/z 1103 (M−H)$^-$.

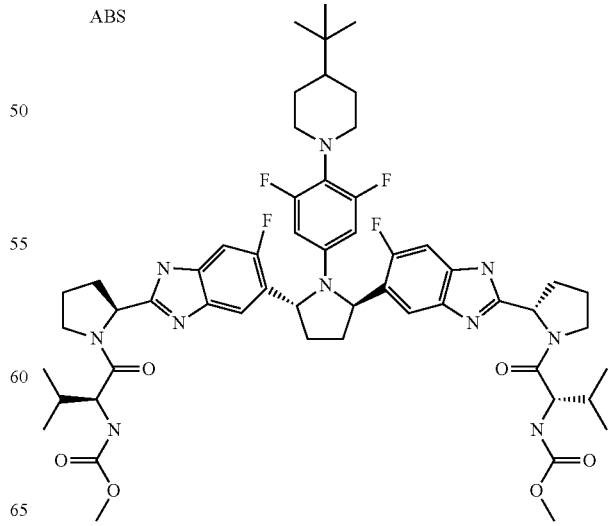

Example 4.27 methyl {(2S)-1-[(2S)-2-{5-[(2R,5R)-1-[4-(4-tert-butylpiperidin-1-yl)-3,5-difluorophenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, DMSO-d₆) δ ppm 0.69-0.76 (m, 4H), 0.76-0.91 (m, 17H), 1.13-1.27 (m, 3H), 1.55 (d, J=11.39 Hz, 2H), 1.67-2.09 (m, 9H), 2.11-2.26 (m, 4H), 2.72-2.94 (m, 4H), 3.50-3.57 (m, 6H), 3.62-3.86 (m, 5H), 3.99-4.11 (m, 2H), 5.03-5.17 (m, 2H), 5.46-5.63 (m, 2H), 5.87 (dd, J=12.52, 7.21 Hz, 2H), 7.03 (d, J=6.40 Hz, 1H), 7.13 (d, J=6.94 Hz, 1H), 7.25-7.37 (m, 3H), 7.40 (dd, J=11.17, 6.29 Hz, 1H), 11.67-12.63 (m, 2H); MS (ESI+) m/z 1043 (M+H)⁺; MS (ESI−) m/z 1041 (M−H)⁻.

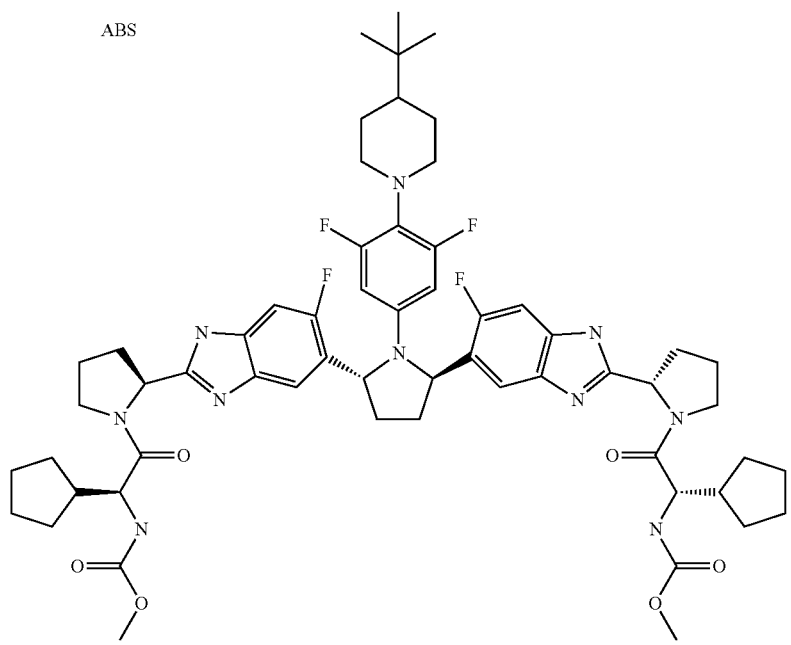 [SMILES: COC(=O)N[C@H](C(=O)N1CCC[C@H]1c1nc2cc([C@H]3CC[C@H](c4cc5nc([C@@H]6CCCN6C(=O)[C@@H](NC(=O)OC)C6CCCC6)[nH]c5cc4F)N3c3cc(F)c(N4CCC(C(C)(C)C)CC4)c(F)c3)c(F)cc2[nH]1)C1CCCC1 ; "ABS"]

Example 4.28 dimethyl({(2R,5R)-1-[4-(4-tert-butylpiperidin-1-yl)-3,5-difluorophenyl]pyrrolidine-2,5-diyl}bis{(6-fluoro-1H-benzimidazole-5,2-diyl)(2S)pyrrolidine-2,1-diyl[(1S)-1-cyclopentyl-2-oxoethane-2,1-diyl]})biscarbamate ¹H NMR (400 MHz, DMSO-d₆) δ ppm 0.80 (s, 9H), 1.08-1.63 (m, 24H), 1.65-1.87 (m, 3H), 1.92-2.25 (m, 10H), 2.37-2.45 (m, 1H), 2.73-2.93 (m, 4H), 3.60-3.91 (m, 4H), 4.13 (t, J=8.24 Hz, 2H), 5.11 (d, J=6.83 Hz, 2H), 5.45-5.63 (m, 2H), 5.80-5.97 (m, 2H), 6.95-7.08 (m, 1H), 7.13 (d, J=6.61 Hz, 1H), 7.34 (dd, J=10.25, 3.74 Hz, 1H), 7.37-7.46 (m, 3H), 11.73-12.50 (m, 2H); MS (ESI+) m/z 1095 (M+H)⁺; MS (ESI−) m/z 1093 (M−H)⁻.

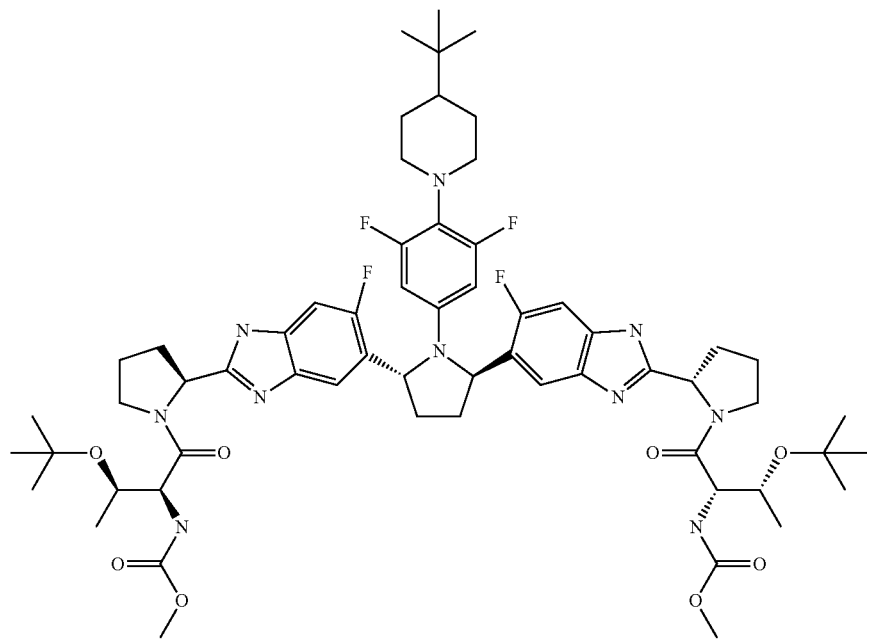
Example 4.29
methyl {(2S,3R)-3-tert-butoxy-1-[(2S)-2-(5-{(2R,5R)-5-{2-[(2S)-1-{(2S,3R)-3-tert-butoxy-2-[(methoxycarbonyl)amino]butanoyl}pyrrolidin-2-yl]-6-fluoro-1H-benzimidazol-5-yl}-1-[4-(4-tert-butylpiperidin-1-yl)-3,5-difluorophenyl]pyrrolidin-2-yl}-6-fluoro-1H-benzimidazol-2-yl)pyrrolidin-1-yl]-1-oxobutan-2-yl}carbamate
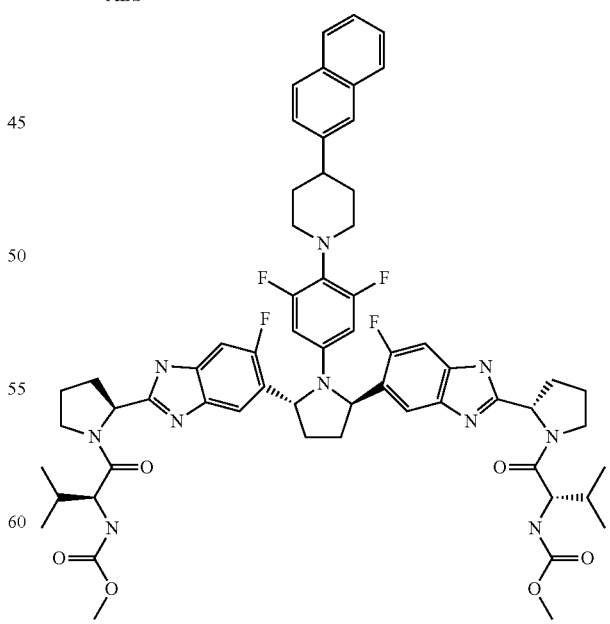
$^1$H NMR (400 MHz, DMSO-$d_6$) δ ppm 0.82 (d, J=14.64 Hz, 13H), 0.88-0.96 (m, 4H), 1.02 (s, 7H), 1.12 (d, J=33.83 Hz, 11H), 1.49-2.31 (m, 9H), 2.69-2.93 (m, 4H), 3.27 (s, 1H), 3.50-3.57 (m, 6H), 3.64-3.94 (m, 9H), 4.03-4.31 (m, 3H), 5.06-5.23 (m, 1H), 5.38-5.69 (m, 2H), 5.78-5.95 (m, 2H), 6.46-6.63 (m, 1H), 6.70-6.87 (m, 1H), 6.92-7.04 (m, 1H), 7.08-7.29 (m, 1H), 7.34 (dd, J=10.63, 1.84 Hz, 1H), 7.38-7.55 (m, 1H), 11.40-12.88 (m, 2H); MS (ESI+) m/z 1159 (M+H)$^+$.

Example 4.30 methyl {(2S)-1-[(2S)-2-{5-[(2R,5R)-1-{3,5-difluoro-4-[4-(2-naphthyl)piperidin-1-yl]phenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, DMSO-d₆) δ ppm 0.73 (d, J=6.51 Hz, 4H), 0.76-0.85 (m, 8H), 1.19-1.32 (m, 2H), 1.69-2.08 (m, 12H), 2.11-2.25 (m, 3H), 2.67-2.78 (m, 1H), 2.92-3.18 (m, 5H), 3.52 (d, J=1.19 Hz, 6H), 3.72-3.87 (m, 4H), 3.99-4.11 (m, 2H), 5.06-5.19 (m, 2H), 5.49-5.67 (m, 2H), 5.83-6.00 (m, 2H), 7.01-7.09 (m, 1H), 7.16 (d, J=7.05 Hz, 1H), 7.25-7.37 (m, 3H), 7.38-7.53 (m, 4H), 7.68-7.93 (m, 4H), 11.88-12.65 (m, 2H); MS (ESI+) m/z 1113 (M+H)⁺; MS (ESI−) m/z 1111 (M−H)⁻.

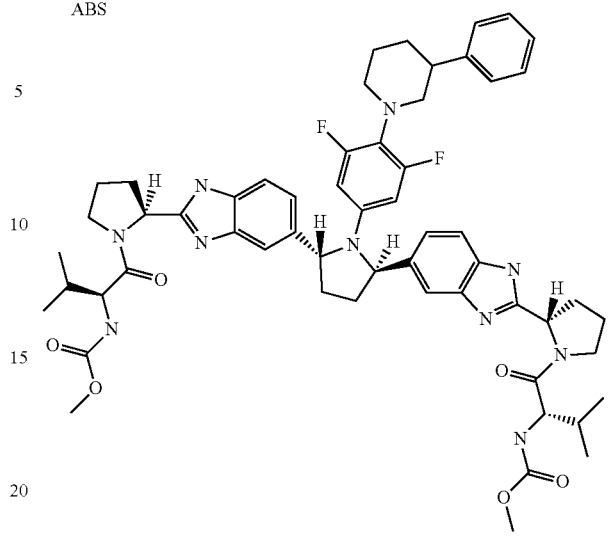

Example 4.31 methyl {(2S)-1-[(2S)-2-{5-[(2R,5R)-1-[4-(2,3-dihydro-1'H-spiro[indene-1,4'-piperidin]-1'-yl)-3,5-difluorophenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, CDCl₃) δ ppm 10.53-10.63 (m, 1H) 10.31-10.41 (m, 1H) 7.43-7.52 (m, 1H) 7.30-7.40 (m, 1H) 7.10-7.25 (m, 5H) 6.92-7.00 (m, 1H) 5.86 (d, 2H) 5.23-5.51 (m, 6H) 4.26-4.40 (m, 2H) 3.77-3.91 (m, 2H) 3.68-3.72 (m, 6H) 3.56-3.66 (m, 2H) 2.83-3.26 (m, 8H) 1.81-2.61 (m, 16H) 0.71-1.10 (m, 12H); MS (ESI) m/z 1089 (M+H)⁺.

Example 4.32 methyl {(2S)-1-[(2S)-2-{5-[(2R,5R)-1-[3,5-difluoro-4-(3-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ¹H NMR (400 MHz, DMSO-d₆) δ ppm 12.07 (s, 1H), 12.01 (s, 1H), 7.48 (d, J=8.3 Hz, 1H), 7.38 (m, 2H), 7.20 (s, 8H), 7.09 (m, 2H), 5.90 (d, J=12.9 Hz, 2H), 5.36 (d, J=7.5 Hz, 2H), 5.14 (s, 2H), 4.05 (t, J=8.1 Hz, 2H), 3.81 (s, 4H), 3.54 (s, 6H), 2.85 (s, 4H), 2.18 (s, 5H), 1.94 (m, 7H), 1.61 (m, 5H), 0.77 (m, 12H); MS (ESI+) m/z (rel abundance) 1027 (100, M+H)⁺.

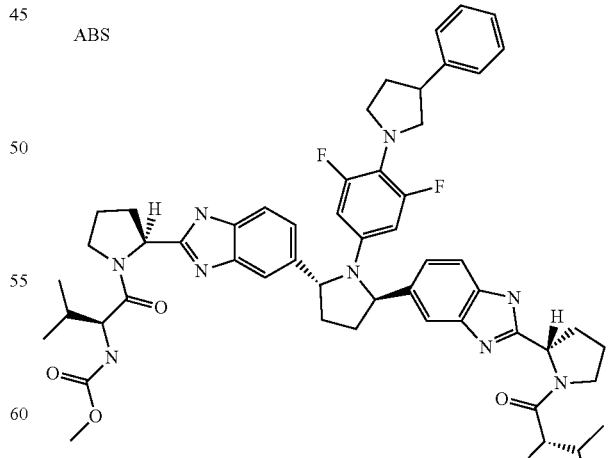

Example 4.33 methyl {(2S)-1-[(2S)-2-{5-[(2R,5R)-1-[3,5-difluoro-
4-(3-phenylpyrrolidin-1-yl)phenyl]-5-{2-[(2S)-1-
{(2S)-2-[(methoxycarbonyl)amino]-3-
methylbutanoyl}pyrrolidin-2-yl]-1H-benzimidazol-
6-yl}pyrrolidin-2-yl]-1H-benzimidazol-2-
yl}pyrrolidin-1-yl]-3-methyl-1-oxobutan-2-
yl}carbamate ¹H NMR (400 MHz, DMSO-d$_6$) δ ppm 12.09 (d, J=14.8 Hz, 2H), 7.47 (m, 2H), 7.45 (m, 2H), 7.24 (m, 8H), 7.08 (s, 2H), 5.93 (d, J=12.1 Hz, 2H), 5.38 (s, 2H), 5.15 (s, 2H), 4.06 (t, J=8.4 Hz, 2H), 3.82 (s, 4H), 3.53 (s, 6H), 3.13 (m, 4H), 2.19 (s, 4H), 1.90 (m, 6H), 1.70 (s, 2H), 0.80 (m, 12H); MS (ESI+) m/z (rel abundance) 1013 (100, M+H)⁺, 1014 (58).

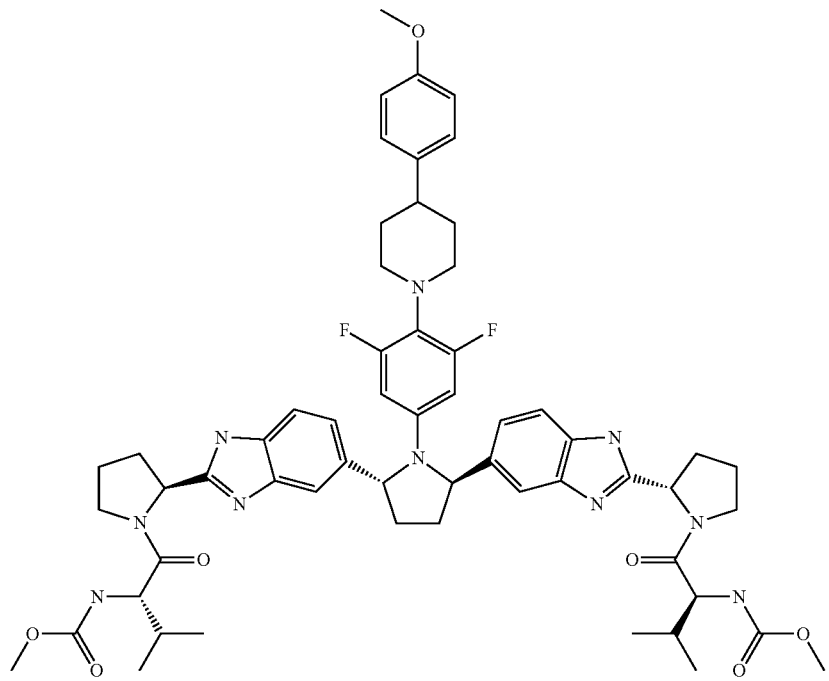

Example 4.34 methyl {(2S)-1-[(2S)-2-{6-[(2R,5R)-1-{3,5-difluoro-
4-[4-(4-methoxyphenyl)piperidin-1-yl]phenyl}-5-{2-
[(2S)-1-{(2S)-2-[(methoxycarbonyl)amino]-3-
methylbutanoyl}pyrrolidin-2-yl]-1H-benzimidazol-
6-yl}pyrrolidin-2-yl]-1H-benzimidazol-2-
yl}pyrrolidin-1-yl]-3-methyl-1-oxobutan-2-
yl}carbamate ¹H NMR (400 MHz, DMSO-d$_6$) δ ppm 0.97-0.69 (m, 12H), 1.24 (s, 1H), 1.78-1.50 (m, 6H), 2.10-1.85 (m, 7H), 2.19 (s, 4H), 2.47-2.38 (m, 1H), 3.03-2.80 (m, 4H), 3.53 (s, 6H), 3.69 (s, 3H), 3.82 (s, 4H), 4.17-3.93 (m, 2H), 5.22-5.08 (m, 2H), 5.45-5.29 (m, 2H), 5.91 (d, J=12.8, 2H), 6.81 (d, J=8.7, 2H), 7.17-7.02 (m, 4H), 7.21 (s, 1H), 7.34-7.26 (m, 3H), 7.41 (d, J=8.2, 1H), 7.50 (d, J=8.2, 1H), 12.17 (dd, J=19.9, 74.7, 2H); MS (ESI) m/z 1057 (M+H)⁺, 1055 (M−H)⁺.

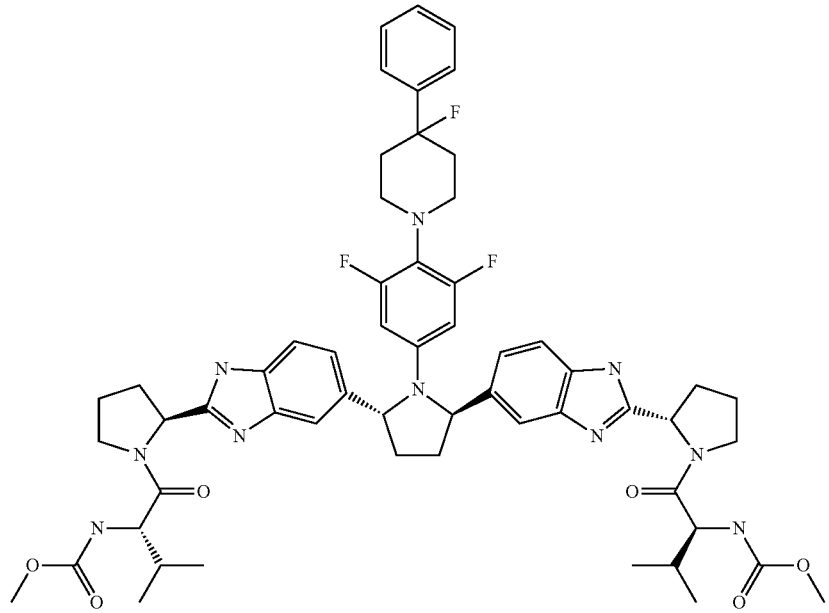
Example 4.35
methyl {(2S)-1-[(2S)-2-{6-[(2R,5R)-1-[3,5-difluoro-4-(4-fluoro-4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-$d_6$) δ ppm 0.91-0.75 (m, 12H), 2.11-1.60 (m, 12H), 2.28-2.12 (m, 4H), 2.55 (d, J=5.5, 2H), 2.84-2.71 (m, 2H), 3.28-3.06 (m, 2H), 3.53 (s, 6H), 3.83 (s, 4H), 4.11-3.99 (m, 2H), 5.19-5.09 (m, 2H), 5.45-5.30 (m, 2H), 5.94 (d, J=12.8, 2H), 7.13-7.05 (m, 2H), 7.45-7.18 (m, 10H), 7.50 (d, J=8.3, 1H), 12.11 (d, J=15.2, 2H); MS (ESI) m/z 1045 (M+H)$^+$, 1043 (M–H)$^+$.
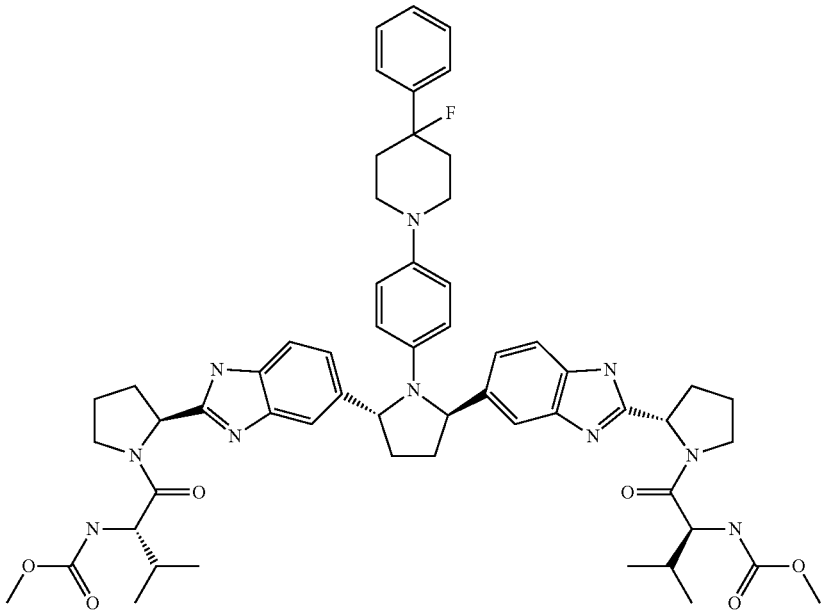

Example 4.36 methyl {(2S)-1-[(2S)-2-{6-[(2R,5R)-1-[4-(4-fluoro-
4-phenylpiperidin-1-yl)phenyl]-5-{2-[(2S)-1-{(2S)-
2-[(methoxycarbonyl)amino]-3-
methylbutanoyl}pyrrolidin-2-yl]-1H-benzimidazol-
6-yl}pyrrolidin-2-yl]-1H-benzimidazol-2-
yl}pyrrolidin-1-yl]-3-methyl-1-oxobutan-2-
yl}carbamate $^1$H NMR (400 MHz, DMSO-d$_6$) δ ppm 0.92-0.74 (m, 12H), 1.23 (d, J=3.9, 1H), 1.69 (d, J=3.6, 2H), 2.09-1.80 (m, 9H), 2.26-2.09 (m, 5H), 2.81-2.69 (m, 2H), 3.26-3.10 (m, 3H), 3.53 (s, 6H), 3.89-3.74 (m, 4H), 4.05 (t, J=8.4, 2H), 5.18-5.06 (m, 2H), 5.34 (d, J=4.5, 2H), 6.27 (d, J=8.7, 2H), 6.65 (dt, J=4.2, 8.6, 2H), 7.06 (t, J=7.8, 2H), 7.21 (s, 1H), 7.43-7.26 (m, 9H), 7.45 (d, J=8.2, 1H), 12.04 (s, 2H); MS (ESI) m/z 1009 (M+H)$^-$, 1007 (M−H)$^+$.

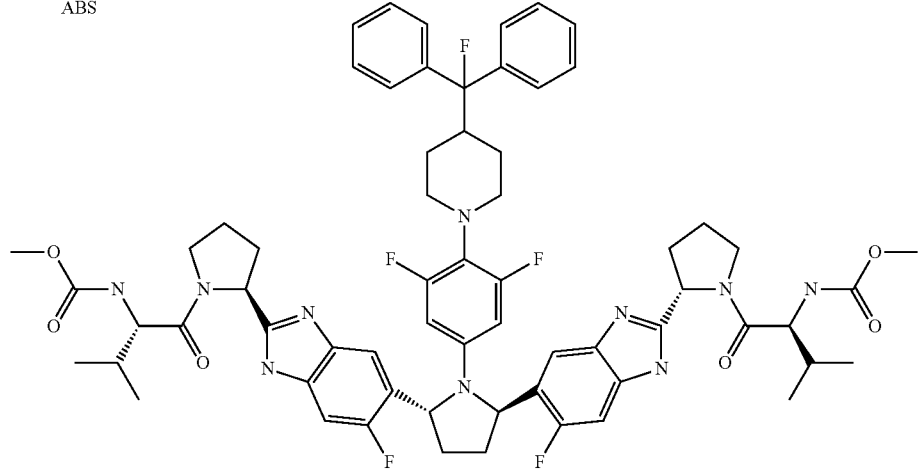

ABS

Example 4.37 methyl {(2S)-1-[(2S)-2-{5-[(2R,5R)-1-(3,5-difluoro-
4-{4-[fluoro(diphenyl)methyl]piperidin-1-
yl}phenyl)-5-{6-fluoro-2-[(2S)-1-{(2S)-2-[(meth-
oxycarbonyl)amino]-3-methylbutanoyl}pyrrolidin-2-
yl]-1H-benzimidazol-5-yl}pyrrolidin-2-yl]-6-fluoro-
1H-benzimidazol-2-yl}pyrrolidin-1-yl]-3-methyl-1-
oxobutan-2-yl}carbamate $^1$H NMR (400 MHz, methanol-d$_4$) δ ppm 0.99-0.69 (m, 12H), 1.42-1.26 (m, 3H), 1.55 (dd, J=12.0, 24.4, 2H), 2.42-1.85 (m, 12H), 2.62-2.43 (m, 3H), 3.01-2.74 (m, 4H), 3.63 (s, 6H), 3.90-3.77 (m, 2H), 4.05-3.90 (m, 2H), 4.20 (d, J=7.4, 1H), 5.24-5.08 (m, 2H), 5.52 (t, J=5.8, 2H), 5.92-5.72 (m, 2H), 7.07 (s, 1H), 7.18 (t, J=7.3, 2H), 7.29 (t, J=7.5, 6H), 7.33 (s, 1H), 7.43 (d, J=7.3, 4H); MS (ESI) m/z 1171 (M+H)$^+$.

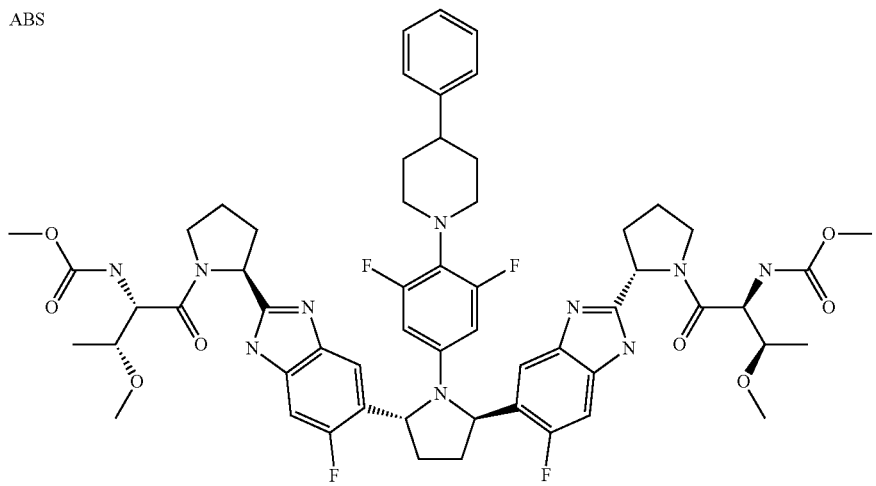

Example 4.38 methyl {(2S,3R)-1-[(2S)-2-{5-[(2R,5R)-1-[3,5-difluoro-4-(4-phenylpiperidin-1-yl)phenyl]-5-(6-fluoro-2-{(2S)-1-[N-(methoxycarbonyl)-O-methyl-L-threonyl]pyrrolidin-2-yl}-1H-benzimidazol-5-yl)pyrrolidin-2-yl]-6-fluoro-1H-benzimidazol-2-yl}pyrrolidin-1-yl]-3-methoxy-1-oxobutan-2-yl}carbamate $^1$H NMR (400 MHz, DMSO-d$_6$) δ ppm 0.92 (d, J=5.5, 2H), 1.04 (dd, J=5.8, 12.0, 4H), 1.68 (s, 4H), 1.80 (s, 2H), 2.09-1.91 (m, 4H), 2.27-2.10 (m, 4H), 3.01-2.82 (m, 3H), 3.03 (s, 4H), 3.13 (s, 4H), 3.25 (s, 2H), 3.44 (dd, J=6.5, 12.8, 3H), 3.53 (s, 6H), 3.81 (s, 3H), 4.31-4.14 (m, 2H), 5.17-5.02 (m, 2H), 5.66-5.41 (m, 2H), 5.97-5.80 (m, 2H), 7.13-6.99 (m, 2H), 7.19-7.13 (m, 2H), 7.31-7.19 (m, 5H), 7.38 (dd, J=9.8, 26.3, 2H), 12.39-12.01 (m, 2H); MS (ESI) m/z 1095 (M+H)$^+$, 1093 (M−H)$^+$.

Example 4.39 dimethyl({(2R,5R)-1-[3,5-difluoro-4-(4-phenylpiperidin-1-yl)phenyl]pyrrolidine-2,5-diyl}bis{(6-fluoro-1H-benzimidazole-5,2-diyl)(2S)pyrrolidine-2,1-diyl[(1S)-2-oxo-1-(tetrahydro-2H-pyran-4-yl)ethane-2,1-diyl]})biscarbamate $^1$H NMR (400 MHz, DMSO-d$_6$) δ ppm 1.37-1.07 (m, 6H), 1.56-1.36 (m, 4H), 1.73-1.60 (m, 4H), 1.78 (s, 4H), 2.06-1.93 (m, 4H), 2.26-2.06 (m, 4H), 3.26-2.81 (m, 8H), 3.52 (s, 6H), 3.91-3.60 (m, 8H), 4.12 (dd, J=6.9, 15.8, 2H), 5.11 (s, 2H), 5.54 (d, J=10.0, 2H), 5.99-5.81 (m, 2H), 7.05 (dd, J=6.3, 23.5, 2H), 7.16 (t, J=6.9, 1H), 7.31-7.20 (m, 5H), 7.45-7.30 (m, 4H), 12.23 (d, J=83.3, 2H); MS (ESI) m/z 1147 (M+H)$^+$.

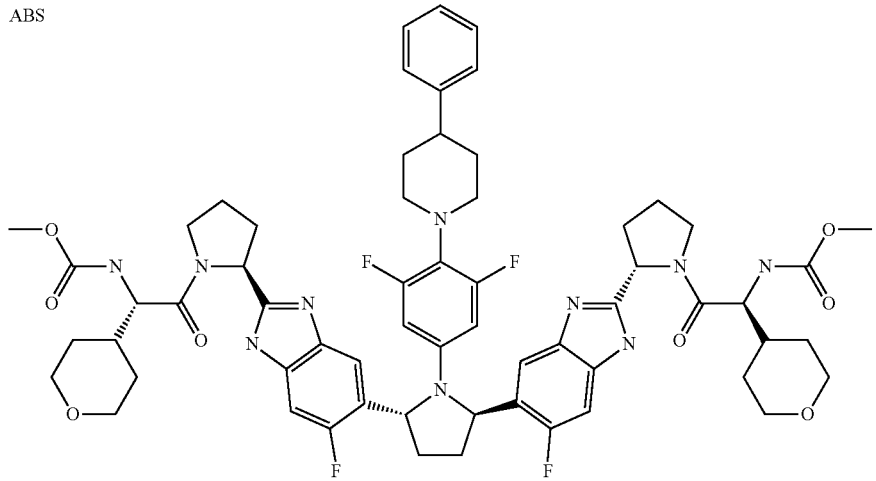

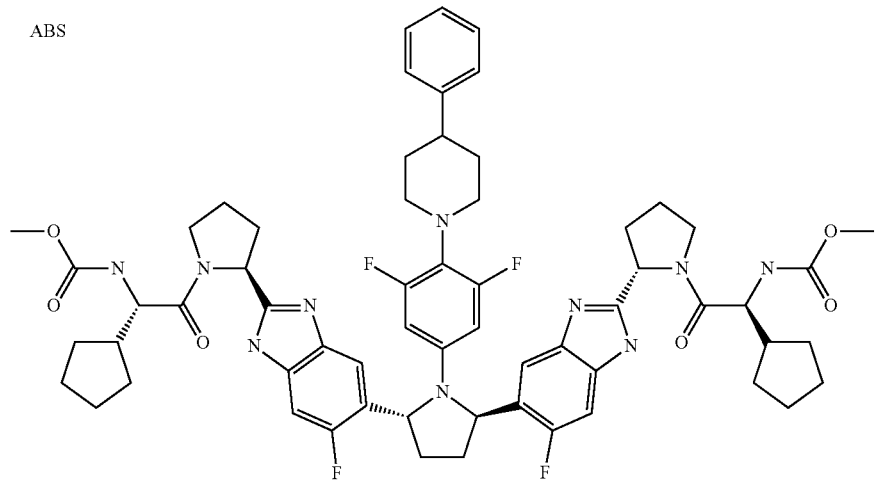

Example 4.40 dimethyl({(2R,5R)-1-[3,5-difluoro-4-(4-phenylpip-
eridin-1-yl)phenyl]pyrrolidine-2,5-diyl}bis{(6-
fluoro-1H-benzimidazole-5,2-diyl)(2S)pyrrolidine-2,
1-diyl[(1S)-1-cyclopentyl-2-oxoethane-2,1-diyl]})
biscarbamate $^1$H NMR (400 MHz, DMSO-d$_6$) δ ppm 1.61-1.10 (m, 18H), 1.67 (s, 4H), 1.90-1.72 (m, 2H), 2.13-1.93 (m, 6H), 2.18 (s, 4H), 3.08-2.86 (m, 4H), 3.17 (d, J=5.1, 1H), 3.52 (s, 6H), 3.89-3.70 (m, 4H), 4.20-4.01 (m, 2H), 5.11 (s, 2H), 5.56 (d, J=21.5, 2H), 5.96-5.83 (m, 2H), 7.04 (d, J=6.7, 1H), 7.16 (t, J=7.0, 2H), 7.31-7.20 (m, 4H), 7.39 (dt, J=8.1, 25.5, 4H), 12.16 (d, J=61.1, 2H); MS (ESI) m/z 1115 (M+H)$^+$, 1113 (M−H)$^+$.

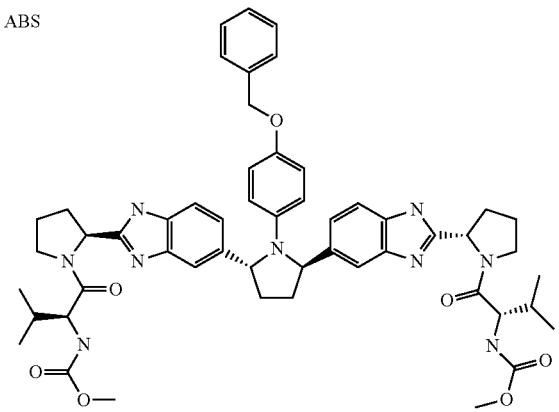 [SMILES: "ABS" ; COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(OCc4ccccc4)cc3)ccc2[nH]1)C(C)C]

Example 4.41 methyl {(2S)-1-[(2S)-2-{5-[(2R,5R)-1-[4-(benzy-
loxy)phenyl]-5-{2-[(2S)-1-{(2S)-2-[(methoxycarbo-
nyl)amino]-3-methylbutanoyl}pyrrolidin-2-yl]-1H-
benzimidazol-5-yl}pyrrolidin-2-yl]-1H-
benzimidazol-2-yl}pyrrolidin-1-yl]-3-methyl-1-
oxobutan-2-yl}carbamate $^1$H NMR (400 MHz, DMSO-d$_6$) δ ppm 12.02 (s, 2H), 7.28 (m, 13H), 6.60 (m, 2H), 6.23 (m, 2H), 5.33 (m, 2H), 5.14 (m, 2H), 4.90 (m, 2H), 3.81 (m, 4H), 3.56 (s, 6H), 2.20 (m, 6H), 1.98 (m, 6H), 1.70 (m, 2H), 0.86 (m, 12H); MS (ESI) m/z 938 (M+H)$^+$.

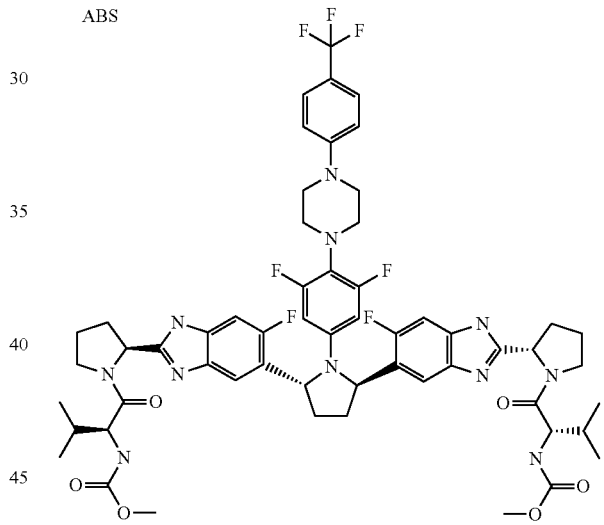

Example 4.42 methyl {(2S)-1-[(2S)-2-{5-[(2R,5R)-1-(3,5-difluoro-
4-{4-[4-(trifluoromethyl)phenyl]piperazin-1-
yl}phenyl)-5-{6-fluoro-2-[(2S)-1-{(2S)-2-[(meth-
oxycarbonyl)amino]-3-methylbutanoyl}pyrrolidin-2-
yl]-1H-benzimidazol-5-yl}pyrrolidin-2-yl]-6-fluoro-
1H-benzimidazol-2-yl}pyrrolidin-1-yl]-3-methyl-1-
oxobutan-2-yl}carbamate $^1$H NMR (400 MHz, DMSO-d$_6$) δ ppm 7.55 (m, 2H), 7.48 (d, J=8.8 Hz, 2H), 7.34 (m, 2H), 7.18 (m, 2H), 7.04 (d, J=7.8 Hz, 2H), 5.99 (m, 2H), 5.63 (m, 2H), 5.13 (m, 2H), 4.06 (m, 2H), 3.80 (m, 2H), 3.53 (s, 6H), 3.25 (m, 8H), 2.99 (m, 4H), 2.05 (m, 12H), 0.81 (m, 12H); MS (ESI) m/z 1132 (M+H)$^+$.

Example 4.43

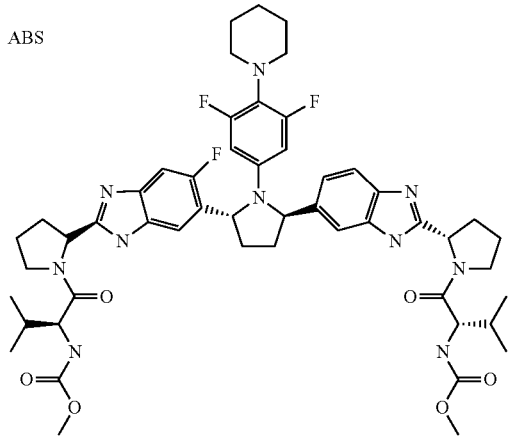

methyl {(2S)-1-[(2S)-2-{6-[(2R,5R)-1-[3,5-difluoro-
4-(piperidin-1-yl)phenyl]-5-{5-fluoro-2-[(2S)-1-
{(2S)-2-[(methoxycarbonyl)amino]-3-
methylbutanoyl}pyrrolidin-2-yl]-1H-benzimidazol-
6-yl}pyrrolidin-2-yl]-1H-benzimidazol-2-
yl}pyrrolidin-1-yl]-3-methyl-1-oxobutan-2-
yl}carbamate $^1$H NMR (400 MHz, DMSO-d$_6$) δ ppm 0.68-0.89 (m, 12H) 1.34-1.50 (m, 6H) 1.65-2.06 (m, 9H) 2.12-2.24 (m, 4H) 2.70-2.82 (m, 4H) 3.52 (d, J=2.49 Hz, 6H) 3.73-3.86 (m, 4H) 3.99-4.08 (m, 2H) 5.06-5.19 (m, 2H) 5.26-5.43 (m, 1H) 5.46-5.56 (m, 1H) 5.86 (d, J=12.04 Hz, 2H) 6.98 (d, J=6.51 Hz, 1H) 7.02-7.11 (m, 1H) 7.21 (d, J=6.94 Hz, 1H) 7.26-7.35 (m, 2H) 7.39 (d, J=8.35 Hz, 1H) 7.45-7.51 (m, 1H) 12.01-12.26 (m, 2H); MS (ESI+) m/z 969 (M+H)$^+$.

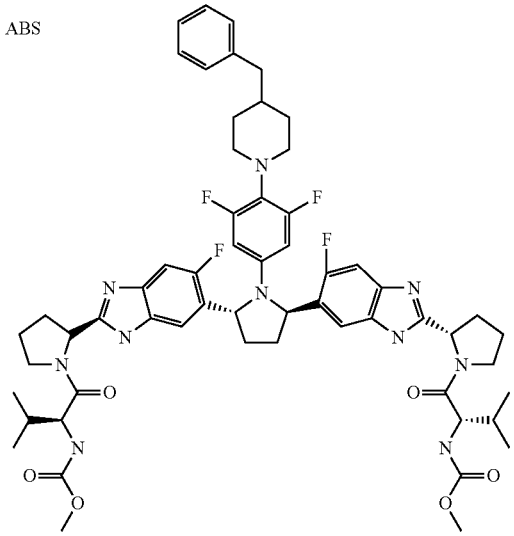

Example 4.44 methyl {(2S)-1-[(2S)-2-{6-[(2R,5R)-1-[4-(4-ben-
zylpiperidin-1-yl)-3,5-difluorophenyl]-5-{5-fluoro-
2-[(2S)-1-{(2S)-2-[(methoxycarbonyl)amino]-3-
methylbutanoyl}pyrrolidin-2-yl]-1H-benzimidazol-
6-yl}pyrrolidin-2-yl]-5-fluoro-1H-benzimidazol-2-
yl}pyrrolidin-1-yl]-3-methyl-1-oxobutan-2-
yl}carbamate $^1$H NMR (400 MHz, DMSO-d$_6$) δ ppm 0.67-0.88 (m, 12H) 1.22 (s, 12H) 1.42-1.51 (m, 5H) 1.73-2.04 (m, 12H) 2.12-2.21 (m, 4H) 2.72-2.81 (m, 5H) 3.48-3.54 (m, 6H) 3.72-3.83 (m, 3H), 3.97-4.06 (m, 2H) 5.05-5.13 (m, 2H) 5.46-5.58 (m, 2H) 5.79-5.89 (m, 2H) 6.99-7.04 (m, 1H), 7.09-7.16 (m, 5H) 7.20-7.34 (m, 6H) 7.35-7.42 (m, 1H) 7.51-7.64 (m, 3H) 12.10 (s, 1H) 12.23 (s, 1H); MS (ESI+) m/z 1077 (M+H)$^+$.

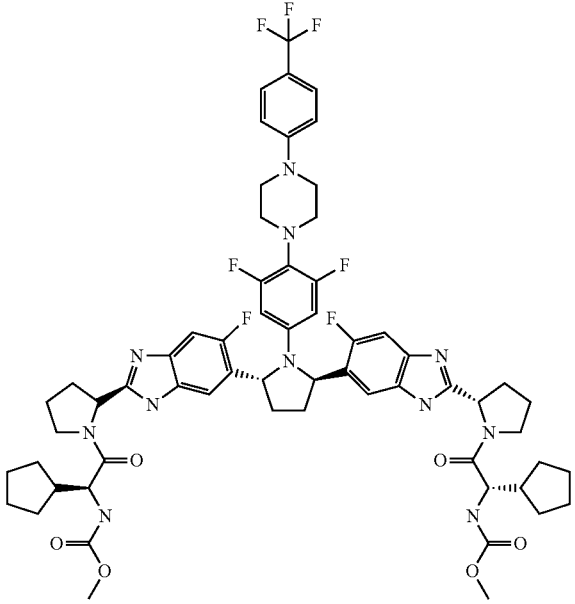

Example 4.45 dimethyl([(2R,5R)-1-(3,5-difluoro-4-{4-[4-(trifluo-
romethyl)phenyl]piperazin-1-yl}phenyl)pyrrolidine-
2,5-diyl]bis{(5-fluoro-1H-benzimidazole-6,2-diyl)
(2S)pyrrolidine-2,1-diyl[(1S)-1-cyclopentyl-2-
oxoethane-2,1-diyl]})bis carbamate $^1$H NMR (400 MHz, DMSO-d$_6$) δ ppm 1.09-1.64 (m, 18H) 1.71-1.86 (m, 2H) 1.92-2.23 (m, 10H) 2.91-3.03 (m, 5H) 3.22-3.30 (m, 4H) 3.52 (s, 6H) 3.71-3.87 (m, 4H) 4.12 (t, J=8.40 Hz, 2H) 5.05-5.16 (m, 2H) 5.48-5.65 (m, 2H) 5.85-5.99 (m, 2H) 7.03 (d, J=8.89 Hz, 3H) 7.14 (d, J=6.29 Hz, 1H) 7.30-7.38 (m, 1H) 7.40 (d, J=9.54 Hz, 2H) 7.46 (d, J=8.67 Hz, 2H), 12.08 (s, 1H) 12.20 (s, 1H); MS (ESI+) m/z 1184 (M+H)$^+$.

ABS
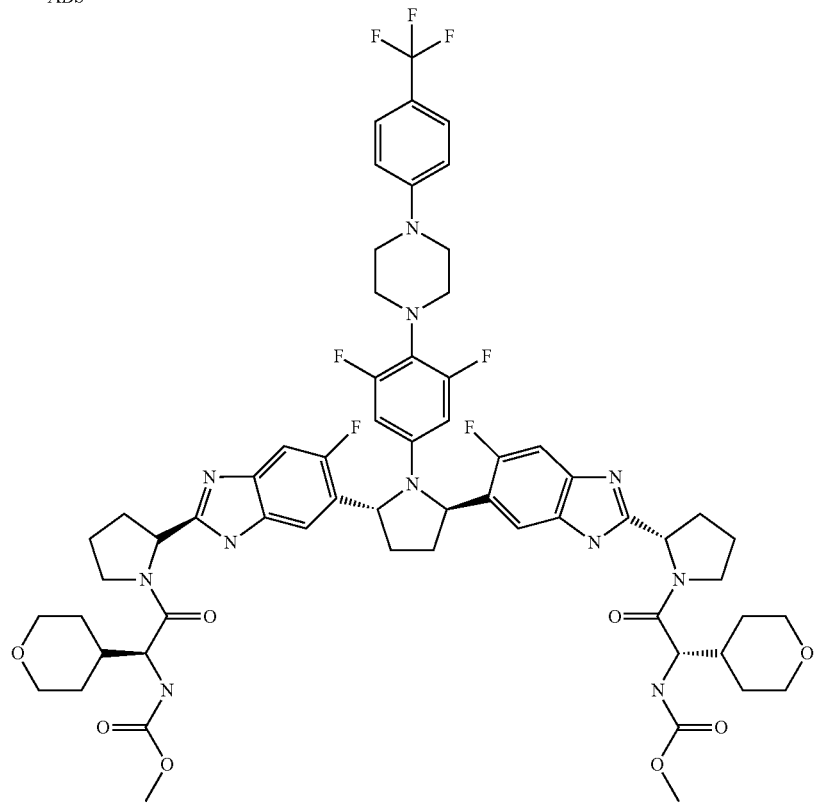
Example 4.46
dimethyl([(2R,5R)-1-(3,5-difluoro-4-{4-[4-(trifluoromethyl)phenyl]piperazin-1-yl}phenyl)pyrrolidine-2,5-diyl]bis{(5-fluoro-1H-benzimidazole-6,2-diyl)(2S)pyrrolidine-2,1-diyl[(1S)-2-oxo-1-(tetrahydro-2H-pyran-4-yl)ethane-2,1-diyl]})biscarbamate
$^1$H NMR (400 MHz, DMSO-$d_6$) δ ppm 1.09-1.33 (m, 4H) 1.38-1.54 (m, 4H) 1.70-1.88 (m, 4H), 1.92-2.05 (m, 4H) 2.10-2.25 (m, 3H) 2.95-3.03 (m, 4H) 3.03-3.20 (m, 3H) 3.21-3.29 (m, 4H) 3.51 (s, 6H) 3.62-3.89 (m, 6H) 4.05-4.17 (m, 2H) 5.06-5.15 (m, 2H) 5.48-5.64 (m, 2H), 5.83-5.98 (m, 2H) 7.03 (d, J=8.67 Hz, 3H) 7.07 (d, J=6.29 Hz, 1H) 7.29-7.42 (m, 3H) 7.46 (d, J=8.78 Hz, 2H) 12.11 (s, 1H) 12.32 (s, 1H); MS (ESI+) m/z 1216 (M+H)$^-$.
ABS
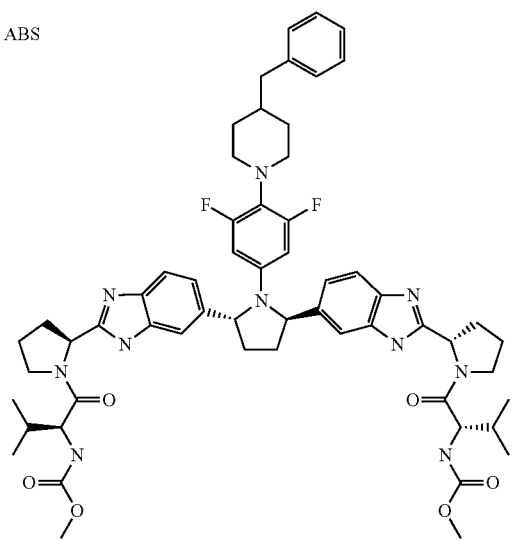 [SMILES: "ABS" ; COC(=O)N[C@H](C(=O)N1CCC[C@H]1c1nc2ccc([C@H]3CC[C@H](c4ccc5nc([C@@H]6CCCN6C(=O)[C@@H](NC(=O)OC)C(C)C)[nH]c5c4)N3c3cc(F)c(N4CCC(Cc5ccccc5)CC4)c(F)c3)cc2[nH]1)C(C)C]

Example 4.47 methyl {(2S)-1-[(2S)-2-{6-[(2R,5R)-1-[4-(4-benzylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 12.07 (d, J=19.1, 2H), 7.48 (d, J=8.3, 2H), 7.40 (d, J=8.1, 2H), 7.34-7.10 (m, 8H), 7.07 (s, 2H), 5.87 (d, J=12.3, 2H), 5.35 (s, 2H), 5.14 (s, 1H), 3.78 (d, J=28.9, 2H), 3.54 (s, 6H), 2.76 (s, 3H), 2.19 (s, 4H), 2.07-1.80 (m, 6H), 1.68 (s, 2H), 1.46 (d, J=10.4, 3H), 1.25-1.08 (m, 2H), 0.92-0.71 (m, 12H); MS (ESI+) m/z 1041.4 (M+H)$^+$, (ESI−) m/z 1039.3 (M−H)$^-$.

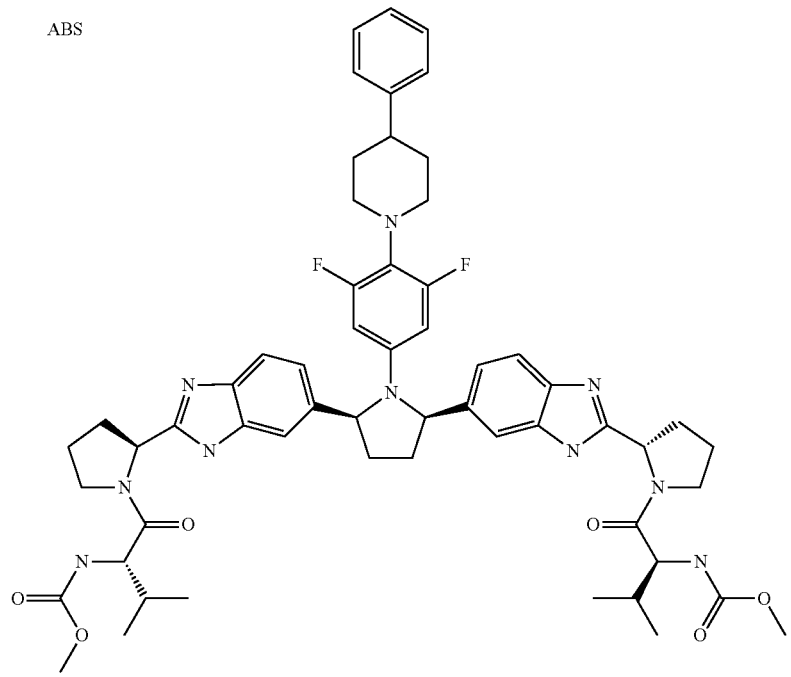 [SMILES: "ABS" ; COC(=O)N[C@H](C(=O)N1CCC[C@H]1c1nc2ccc([C@H]3CC[C@@H](c4ccc5nc([C@@H]6CCCN6C(=O)[C@@H](NC(=O)OC)C(C)C)[nH]c5c4)N3c3cc(F)c(N4CCC(c5ccccc5)CC4)c(F)c3)cc2[nH]1)C(C)C]

Example 4.48 methyl {(2S)-1-[(2S)-2-{5-[(2S,5R)-1-[3,5-difluoro-4-(4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-d$_6$) δ ppm 0.76-0.94 (m, 12H), 1.60-2.30 (m, 14H), 2.88-3.09 (m, 4H), 3.54 (s, 6H), 3.84 (s, 3H), 4.02-4.15 (m, J=8.1, 8.1 Hz, 2H), 4.77-4.97 (m, 2H), 5.17 (d, J=2.9 Hz, 2H), 5.95-6.10 (m, 2H), 7.08-7.70 (m, 13H), 12.09-12.23 (m, 2H).

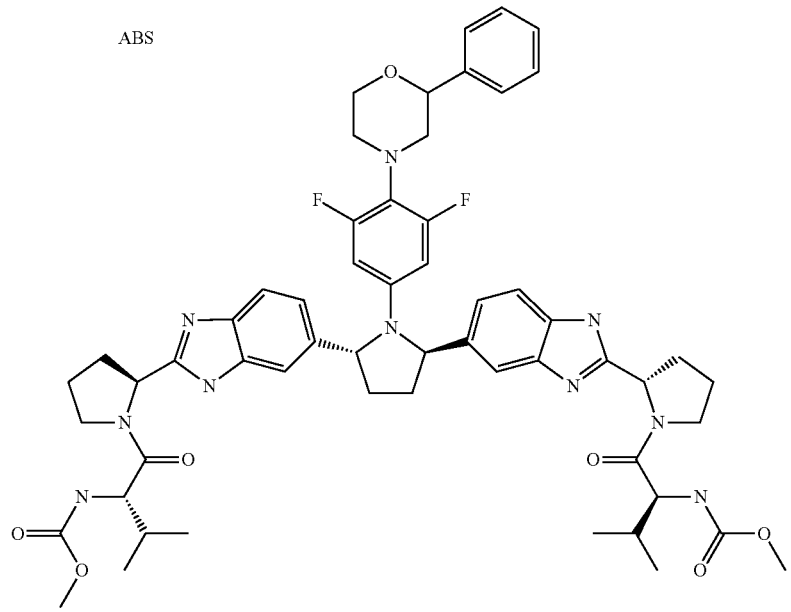 [SMILES: COC(=O)N[C@H](C(=O)N1CCC[C@H]1c1nc2cc([C@H]3CC[C@H](c4ccc5nc([C@@H]6CCCN6C(=O)[C@@H](NC(=O)OC)C(C)C)[nH]c5c4)N3c3cc(F)c(N4CCOC(c5ccccc5)C4)c(F)c3)ccc2[nH]1)C(C)C ; "ABS"]
Example 4.49
methyl {(2S)-1-[(2S)-2-{5-[(2R,5R)-1-[3,5-difluoro-4-(2-phenylmorpholin-4-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate
$^1$H NMR (400 MHz, DMSO-$d_6$) δ ppm 0.69-0.92 (m, 12H), 1.69 (d, J=5.1 Hz, 2H), 1.82-2.30 (m, 12H), 2.70-3.16 (m, J=63.6 Hz, 6H), 3.54 (s, 6H), 3.81 (s, 3H), 3.99-4.12 (m, 2H), 4.47 (dd, J=9.1, 3.7 Hz, 1H), 5.08-5.19 (m, 2H), 5.29-5.48 (m, 2H), 5.92 (d, J=13.4 Hz, 2H), 7.07 (t, J=7.9 Hz, 2H), 7.16-7.35 (m, J=0.8 Hz, 10H), 7.40 (d, J=8.1 Hz, 1H), 7.49 (d, J=8.3 Hz, 1H), 12.06 (s, 1H), 12.11 (s, 1H); MS (APCI+) m/z 1030.1 (M+H).
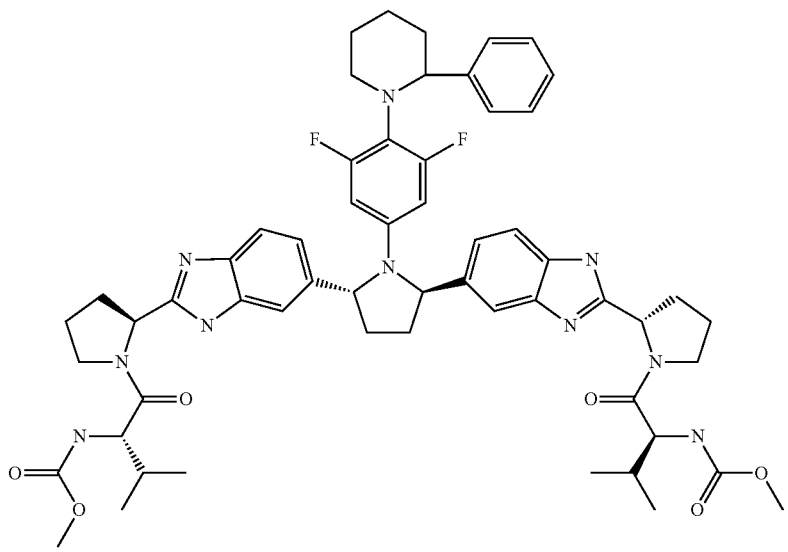

Example 4.50 methyl {(2S)-1-[(2S)-2-{5-[(2R,5R)-1-[3,5-difluoro-4-(2-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.81-1.01 (m, 12H), 1.24-2.35 (m, 22H), 3.60 (s, 6H), 3.89 (s, 4H), 3.94-4.20 (m, 3H), 5.22 (s, 2H), 5.30 (d, J=4.3 Hz, 2H), 5.73 (dd, J=13.1, 3.6 Hz, 2H), 6.92-7.44 (m, 13H), 7.48 (d, J=8.1 Hz, 1H), 12.08 (s, 1H), 12.17 (s, 1H); MS (APCI+) m/z 1028.2 (M+H)$^+$.

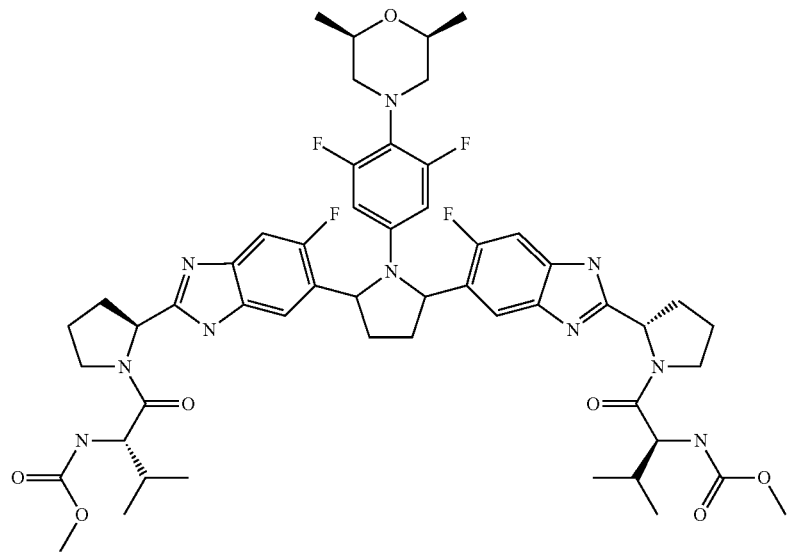

Example 4.51 methyl[(2S)-1-{(2S)-2-[5-(1-{4-[(2R,6S)-2,6-dimethylmorpholin-4-yl]-3,5-difluorophenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl)-6-fluoro-1H-benzimidazol-2-yl]pyrrolidin-1-yl}-3-methyl-1-oxobutan-2-yl]carbamate $^1$H NMR (400 MHz, DMSO-$d_6$) δ ppm 0.67-0.90 (m, 12H), 0.96 (s, 6H), 1.01-1.31 (m, 2H), 1.68-2.25 (m, 12H), 3.51 (s, 6H), 3.78 (s, 3H), 4.01 (q, J=7.2 Hz, 2H), 5.10 (d, J=4.8 Hz, 2H), 5.43-5.65 (m, 2H), 5.79-5.97 (m, 2H), 7.02 (d, J=5.3 Hz, 1H), 7.11 (d, J=6.8 Hz, 1H), 7.21-7.46 (m, 4H), 12.11 (s, 1H), 12.24 (s, 1H); MS (ESI) m/z 1017.4 (M+H)$^+$.

ABS

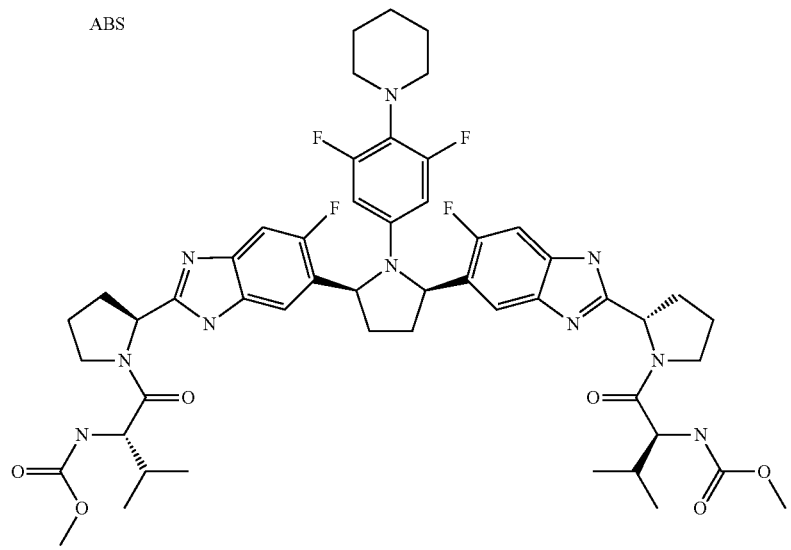 [SMILES: COC(=O)N[C@H](C(=O)N1CCC[C@H]1c1nc2cc([C@H]3CC[C@@H](c4cc5[nH]c([C@@H]6CCCN6C(=O)[C@@H](NC(=O)OC)C(C)C)nc5cc4F)N3c3cc(F)c(N4CCCCC4)c(F)c3)c(F)cc2[nH]1)C(C)C ; "ABS"]

Example 4.32 methyl {(2S)-1-[(2S)-2-{5-[(2S,5R)-1-[3,5-difluoro-4-(piperidin-1-yl)phenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, DMSO-d₆) δ ppm 0.72-0.94 (m, J=10.5, 10.5 Hz, 12H), 1.36-1.58 (m, 6H), 1.77-2.28 (m, 14H), 2.83 (s, 4H), 3.53 (s, 6H), 3.82 (s, 4H), 3.97-4.14 (m, 2H), 4.92-5.07 (m, 2H), 5.09-5.20 (m, 2H), 5.83-6.02 (m, 2H), 7.21-7.79 (m, 6H), 12.14-12.44 (m, 2H); MS (APCI+) m/z 987.8 (M+H)⁺.

Example 4.53 methyl {(2S)-1-[(2S)-2-{5-[(2R,5R)-1-[4-(3-azaspiro[5.5]undec-3-yl)-3,5-difluorophoenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, DMSO-d₆) δ ppm 0.64-0.94 (m, 12H), 1.21-1.44 (m, 16H), 1.68-2.25 (m, J=78.0 Hz, 12H), 2.78 (s, 4H), 3.53 (s, 6H), 3.80 (s, 4H), 4.04 (t, J=7.1 Hz, 2H), 5.11 (s, 2H), 5.55 (dd, J=19.8, 4.2 Hz, 2H), 5.79-5.99 (m, 2H), 7.03 (d, J=6.0 Hz, 1H), 7.13 (d, J=6.5 Hz, 1H), 7.24-7.48 (m, 4H), 12.12 (s, 1H), 12.24 (s, 1H); MS (ESI) m/z 1055.4 (M+H)⁺.

ABS

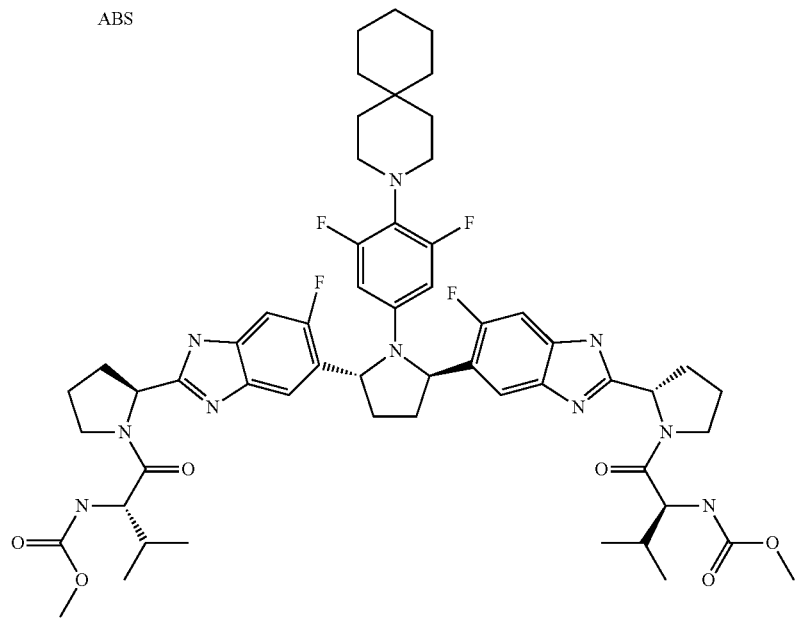 [SMILES: COC(=O)N[C@H](C(=O)N1CCC[C@H]1c1nc2cc([C@H]3CC[C@H](c4cc5nc([C@@H]6CCCN6C(=O)[C@@H](NC(=O)OC)C(C)C)[nH]c5cc4F)N3c3cc(F)c(N4CCC5(CCCCC5)CC4)c(F)c3)c(F)cc2[nH]1)C(C)C ; "ABS"]

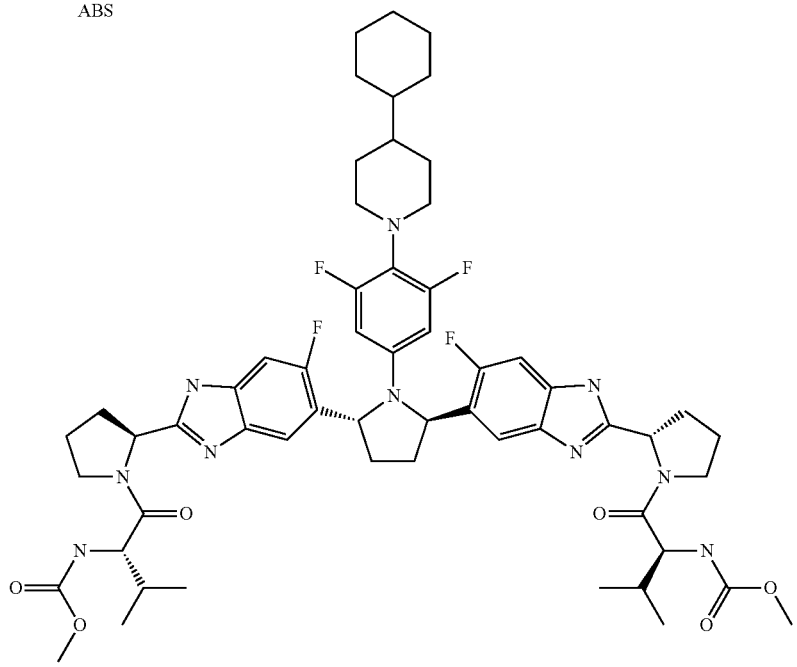 [SMILES: COC(=O)N[C@H](C(=O)N1CCC[C@H]1c1nc2cc([C@H]3CC[C@H](c4cc5nc([C@@H]6CCCN6C(=O)[C@@H](NC(=O)OC)C(C)C)[nH]c5cc4F)N3c3cc(F)c(N4CCC(C5CCCCC5)CC4)c(F)c3)c(F)cc2[nH]1)C(C)C ; "ABS"]
Example 4.54
methyl {(2S)-1-[(2S)-2-{5-[(2R,5R)-1-[4-(4-cyclohexylpiperidin-1-yl)-3,5-difluorophenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate
¹H NMR (400 MHz, DMSO-d₆) δ ppm 0.65-0.97 (m, 12H), 0.98-1.33 (m, 10H), 1.50-2.25 (m, 20H), 2.72-2.91 (m, 4H), 3.53 (s, 6H), 3.79 (s, 4H), 4.04 (t, J=8.1 Hz, 2H), 5.11 (s, 2H), 5.54 (dd, J=14.7, 6.7 Hz, 2H), 5.79-5.97 (m, 2H), 7.03 (d, J=6.7 Hz, 1H), 7.13 (d, J=6.9 Hz, 1H), 7.24-7.46 (m, 4H), 12.11 (s, 1H); 12.23 (s, 1H); MS (ESI+) m/z 1069.5 (M+H)⁺.
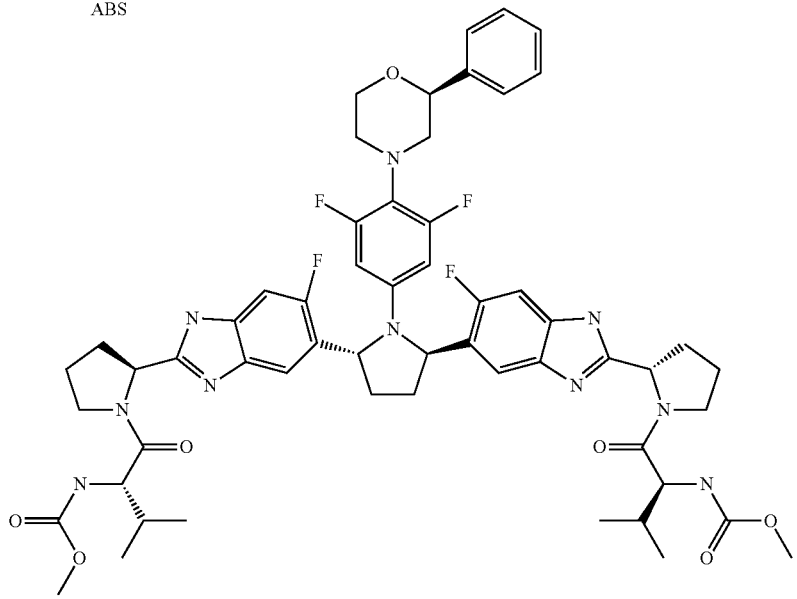 [SMILES: COC(=O)N[C@H](C(=O)N1CCC[C@H]1c1nc2cc([C@H]3CC[C@H](c4cc5nc([C@@H]6CCCN6C(=O)[C@@H](NC(=O)OC)C(C)C)[nH]c5cc4F)N3c3cc(F)c(N4CCO[C@@H](c5ccccc5)C4)c(F)c3)c(F)cc2[nH]1)C(C)C ; "ABS"]

Example 4.55 methyl {(2S)-1-[(2S)-2-{5-[(2R,5R)-1-{3,5-difluoro-4-[(2S)-2-phenylmorpholin-4-yl]phenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, DMSO-d$_6$) δ ppm 0.60-0.95 (m, 12H), 1.64-2.08 (m, 10H), 2.09-2.25 (m, 4H), 2.70-3.18 (m, 4H), 3.53 (s, 6H), 3.64-3.86 (m, 4H), 3.91 (d, J=11.4 Hz, 1H), 4.03 (t, J=8.2 Hz, 2H), 4.48 (d, J=7.5 Hz, 1H), 5.10 (s, 2H), 5.43-5.69 (m, 2H), 5.80-6.03 (m, 2H), 7.03 (d, J=6.8 Hz, 1H), 7.14 (d, J=6.7 Hz, 1H), 7.20-7.45 (m, 10H), 12.10 (s, 1H), 12.24 (s, 1H); MS (ESI+) m/z 1065.4 (M+H)$^+$.

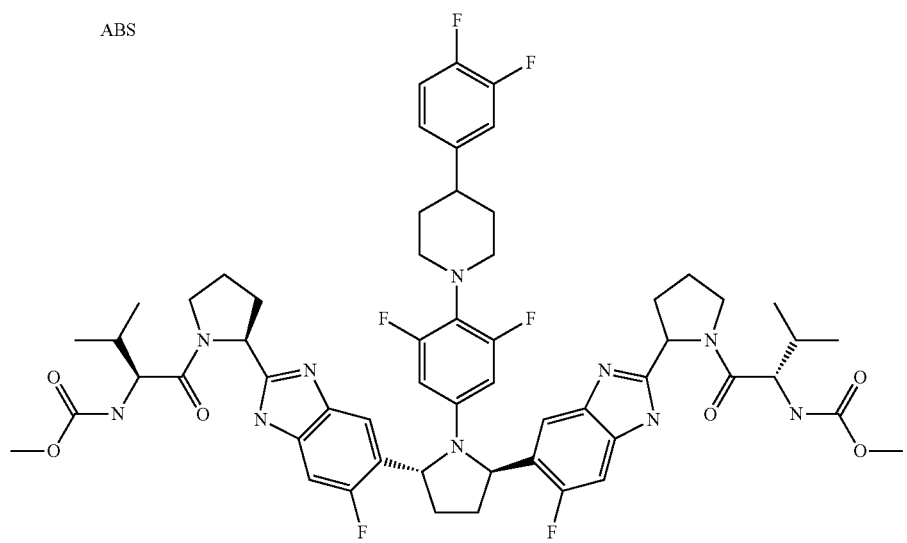

Example 4.56 methyl {(2S)-1-[(2S)-2-{5-[(2R,5R)-1-{4-[4-(3,4-difluorophenyl)piperidin-1-yl]-3,5-difluorophenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, DMSO-d$_6$) δ ppm 0.68-0.92 (m, 14H), 1.58-2.08 (m, 11H), 2.09-2.27 (m, 4H), 2.71-3.14 (m, 6H), 3.52 (s, 6H), 3.68-3.89 (m, 4H), 3.98-4.10 (m, 2H), 5.05-5.17 (m, 2H), 5.48-5.68 (m, 2H), 5.83-5.99 (m, 2H), 6.95-7.08 (m, 2H), 7.09-7.21 (m, 2H), 7.25-7.46 (m, 5H), 12.06-12.39 (m, 2H); MS (ESI+) m/z 1099.3 (M+H)$^+$.

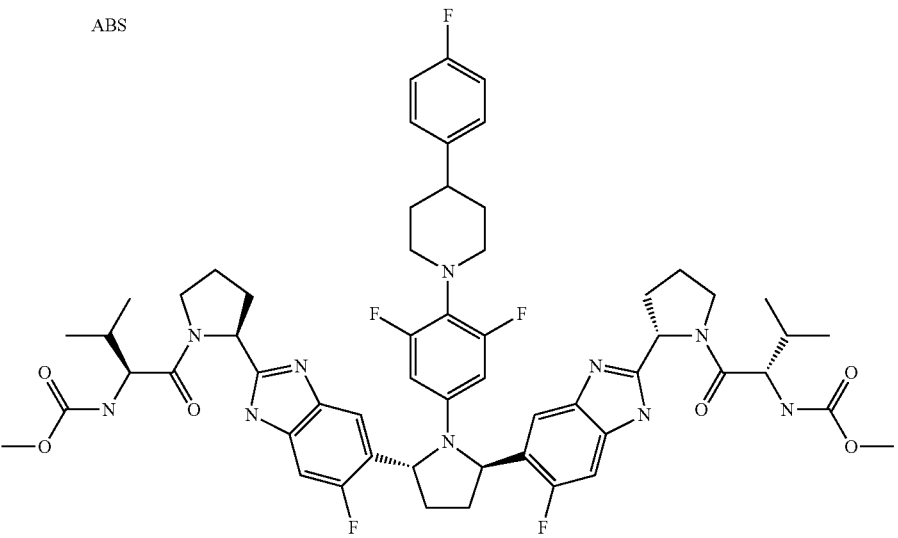

Example 4.57 methyl {(2S)-1-[(2S)-2-{5-[(2R,5R)-1-{3,5-difluoro-4-[4-(4-fluorophenyl)piperidin-1-yl]phenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, DMSO-$d_6$) δ ppm 0.67-0.93 (m, 14H), 1.53-2.09 (m, 11H), 2.10-2.25 (m, 4H), 2.83-3.15 (m, 6H), 3.53 (s, 6H), 3.69-3.88 (m, 4H), 3.98-4.10 (m, 2H), 5.05-5.17 (m, 2H), 5.48-5.67 (m, 2H), 5.83-5.99 (m, 2H), 6.99-7.20 (m, 4H), 7.22-7.47 (m, 6H), 12.02-12.47 (m, 2H); MS (ESI+) m/z 1081.4 (M+H)$^+$.

Example 4.58 methyl {(2S)-1-[(2S)-2-{5-[(2R,5R)-1-[3,5-difluoro-4-(4-phenylpiperazin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate $^1$H NMR (400 MHz, DMSO-$d_6$) δ ppm 0.72-0.95 (m, 12H) 1.69 (s, 1H) 1.84-2.11 (m, 2H) 2.20 (s, 4H) 2.97 (s, 4H) 3.09 (s, 4H) 3.54 (s, 6H) 3.82 (s, 4H) 4.03 (q, J=7.05 Hz, 6H) 5.15 (s, 2H) 5.39 (s, 2H) 5.95 (s, 2H) 6.75 (s, 2H) 6.90 (d, J=8.24 Hz, 2H) 7.08 (t, 2H) 7.17 (t, J=7.92 Hz, 2H) 7.30 (s, 2H) 7.48 (s, 2H) 7.66 (s, 2H) 7.92 (s, 2H) 12.09 (s, 2H); MS (ESI+) m/z 1028.4, (ESI−) m/z 1026.4 (M−H)$^-$.

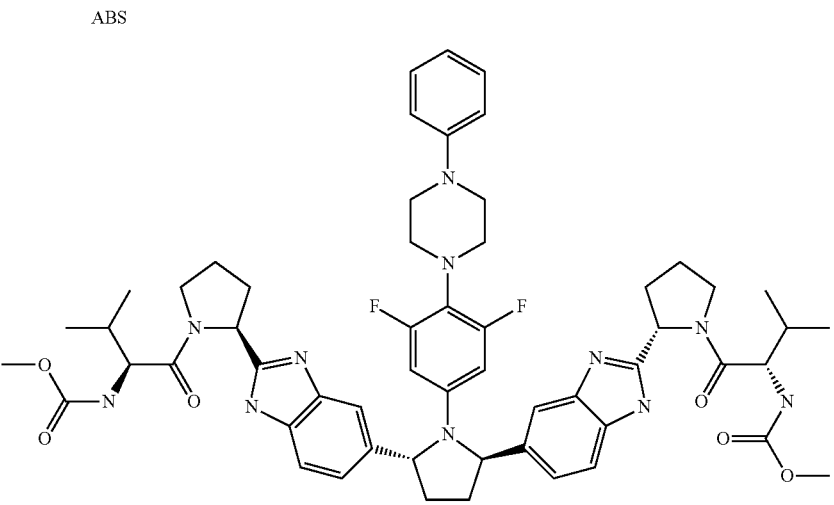

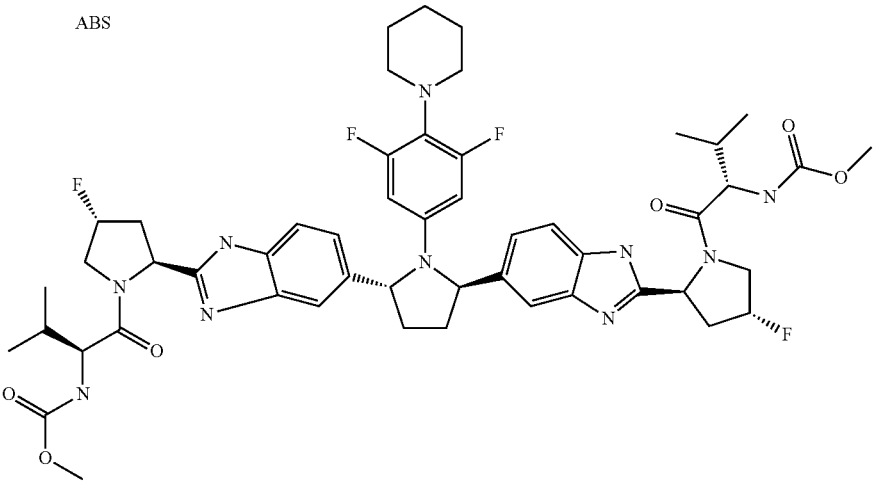 [SMILES: COC(=O)N[C@H](C(=O)N1C[C@H](F)C[C@H]1c1nc2cc([C@H]3CC[C@H](c4ccc5[nH]c([C@@H]6C[C@@H](F)CN6C(=O)[C@@H](NC(=O)OC)C(C)C)nc5c4)N3c3cc(F)c(N4CCCCC4)c(F)c3)ccc2[nH]1)C(C)C ; "ABS"]

Example 4.59 methyl {(2S)-1-[(2S,4R)-2-{5-[(2R,5R)-1-[3,5-difluoro-4-(piperidin-1-yl)phenyl]-5-{2-[(2S,4R)-4-fluoro-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-fluoropyrrolidin-1-yl]-3-methyl-1-oxobutan-2-yl}carbamate ¹H NMR (400 MHz, DMSO-d₆) δ ppm 0.76 (m, 16H) 0.89 (m, 3H) 1.45 (m, 5H) 1.70 (m, 2H) 1.85 (m, 1H) 2.76 (d, 2H) 3.17 (d, J=5.10 Hz, 2H) 3.53 (s, 6H) 3.87-4.13 (m, 4H) 4.31 (m, 1H) 5.17 (d, 2H) 5.36 (m, 3H) 5.57 (s, 1H) 5.89 (d, 2H) 7.09 (m, 2H) 7.18-7.25 (m, 1H) 7.29 (m, 3H) 7.48 (m, 3H) 12.22 (s, 2H); MS (ESI+) m/z 987.4, (ESI−) m/z 985.2 (M−H)⁻.

Example 4.60 methyl {(2S)-1-[(2S)-2-{5-[(2R,5R)-1-{3,5-difluoro-4-[4-(pyrimidin-2-yl)piperazin-1-yl]phenyl}-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate ¹H NMR (400 MHz, DMSO-d₆) δ ppm 0.67-0.93 (m, 12H) 1.99 (m, 16H) 2.18 (m, 4H) 2.87 (m, 4H) 3.53 (s, 6H) 3.56 m, 2H) 3.74 (m, 10H) 5.11 (m, 2H) 5.53 (m, 2H) 5.90 (m, 2H) 6.60 (t, J=4.72 Hz, 1H) 7.04 (m, 2H) 7.32 (m, 4H) 8.33 (d, J=4.77 Hz, 2H) 12.14 (s, 1H) 12.22 (s, 1H); MS (ESI+) m/z 1066.4, (ESI−) m/z 1064.1 (M−H)⁻.

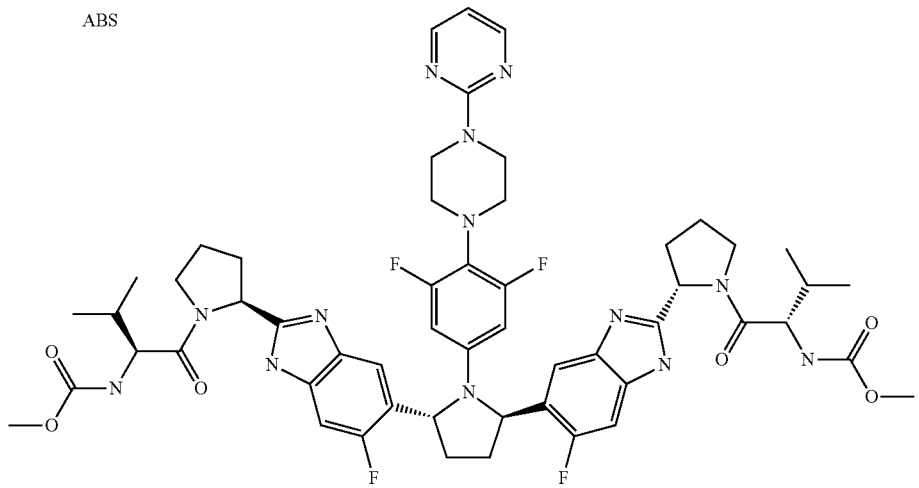

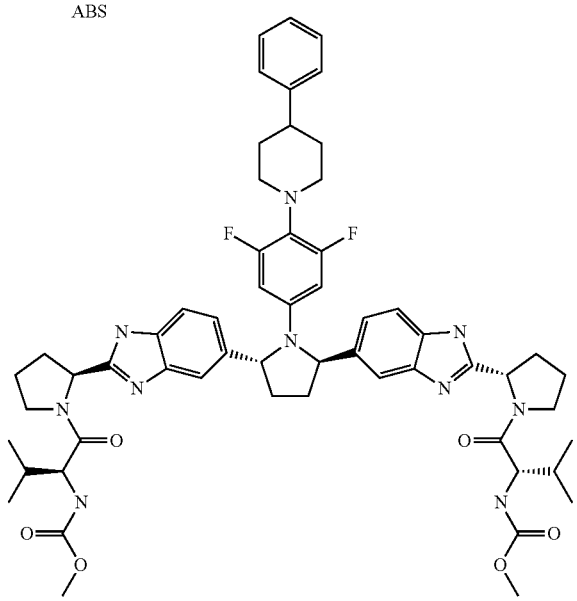 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(c5ccccc5)CC4)c(F)c3)ccc2[nH]1)C(C)C ; "ABS"]

din-1-yl)phenyl)pyrrolidine-2,5-diyl)bis(2-((S)-pyrrolidin-2-yl)-1H-benzo[d]imidazole) (2.57 mmol), (S)-2-(methoxycarbonylamino)-3-methylbutanoic acid (0.945 g, 5.40 mmol) and 1H-benzo[d][1,2,3]triazol-1-ol hydrate (0.984 g, 6.43 mmol) in DMF (25 mL) to give an orange solution. 4-Methylmorpholine (2.83 mL, 25.7 mmol) and $N^1$-((ethylimino)methylene)-$N^3,N^3$-dimethylpropane-1,3-diamine hydrochloride (1.232 g, 6.43 mmol) were added, and the mixture was stirred at ambient temperature for 2 hours and then diluted into EtOAc. The EtOAc layer was washed with aqueous saturated NaHCO$_3$, H$_2$O, and saturated NaCl. The organic layer was treated with 3-mercaptopropyl silica for 1 hour, dried (Na$_2$SO$_4$), filtered and concentrated to a yellow foam (2.74 g). Purification by flash chromatography on a 120 g silica cartridge eluting with 2-5% methanol in dichloromethane afforded 1.7 g (61%) of the title compound as a yellow powder. The title compound can additionally be purified by recrystallization from acetonitrile. $^1$H NMR (400 MHz, DMSO-d$_6$) δ ppm 0.73-0.91 (m, 12H) 1.60-1.74 (m, 6H) 1.86-2.04 (m, 6H) 2.17-2.30 (m, 4H) 2.52-2.53 (m, 4H) 2.84-3.02 (m, 4H) 3.52-3.56 (m, 6H) 3.78-3.87 (m, 3H) 4.00-4.12 (m, 2H) 5.10-5.18 (m, 2H) 5.32-5.42 (m, 2H) 5.88-5.95 (m, 2H) 7.05-7.33 (m, 11H) 7.41 (d, J=8.24 Hz, 1H) 7.50 (d, J=8.35 Hz, 1H) 11.97-12.30 (m, 2H); MS (ESI+) m/z 1027 (M+H)$^+$.

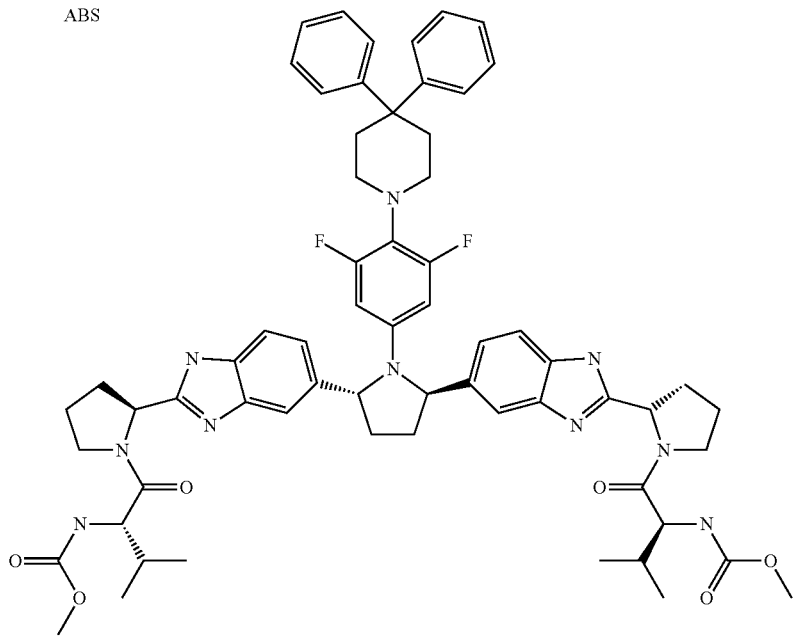

Example 5.1 methyl {(2S)-1-[(2S)-2-{5-[(2R,5R)-1-[3,5-difluoro-4-(4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate In a 250 mL round-bottomed flask cooled in an ice bath was added (S)-6,6'-((2R,5R)-1-(3,5-difluoro-4-(4-phenylpiperi- Example 5.2 methyl {(2S)-1-[(2S)-2-{5-[(2R,5R)-1-[4-(4,4-diphenylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate In a 100 mL round bottom was added (S)-6,6'-((2R,5R)-1-(4-(4,4-diphenylpiperidin-1-yl)-3,5-difluorophenyl)pyrrolidine-2,5-diyl)bis(2-((S)-pyrrolidin-2-yl)-1H-benzo[d]imidazole) (0.385 g, 0.488 mmol), (S)-2-(methoxycarbonylamino)-3-methylbutanoic acid (0.180 g, 1.025 mmol), and 1H-benzo[d][1,2,3]triazol-1-ol hydrate (0.187 g, 1.220 mmol) in DMF (25 mL) to give an orange solution. 4-Methylmorpholine (0.537 mL, 4.88 mmol) and $N^1$-((ethylimino)methylene)-$N^3$,$N^3$-dimethylpropane-1,3-diamine hydrochloride (0.234 g, 1.220 mmol) were added, and the mixture was stirred at ambient temperature for 2 hours and then diluted with EtOAc. The organic solution was washed sequentially with saturated NaHCO$_3$, H$_2$O, and saturated NaCl. The organic layer was treated with 3-mercaptopropyl silica for 1 hour, dried (Na2SO4), filtered and concentrated to a yellow foam. Purification by flash chromatography on a 24 g silica cartridge eluting with 2-7% methanol in CH$_2$Cl$_2$ provided material that was 90% pure by HPLC. A second chromatography of selected fractions on a 12 g silica cartridge eluting with 2-5% methanol in CH$_2$Cl$_2$ gave the title compound as a cream colored solid (100 mg, 17%). $^1$H NMR (400 MHz, DMSO-d$_6$) δ ppm 0.76-0.91 (m, 12H) 1.68 (d, J=4.01 Hz, 2H) 1.85-2.07 (m, 6H) 2.19 (s, 4H) 2.38 (s, 4H) 2.86 (s, 4H) 3.54 (s, 6H) 3.82 (s, 4H) 4.06 (t, J=8.35 Hz, 2H) 5.10-5.17 (m, 2H) 5.34 (d, J=7.16 Hz, 2H) 5.85 (d, J=12.79 Hz, 2H) 6.84-7.54 (m, 20H) 12.06 (d, J=18.98 Hz, 2H); MS (ESI+) m/z 1103 (M+H)$^+$.

Example 5.3 methyl {(2S,3R)-1-[(2S)-2-{5-[(2R,5R)-1-[3,5-difluoro-4-(4-phenylpiperidin-1-yl)phenyl]-5-(2-{(2S)-1-[N-(methoxycarbonyl)-O-methyl-L-threonyl]pyrrolidin-2-yl}-1H-benzimidazol-5-yl)pyrrolidin-2-yl]-1H-benzimidazol-2-yl}pyrrolidin-1-yl]-3-methoxy-1-oxobutan-2-yl}carbamate (S)-6,6'-((2R,5R)-1-(3,5-Difluoro-4-(4-phenylpiperidin-1-yl)phenyl)pyrrolidine-2,5-diyl)bis(2-((S)-pyrrolidin-2-yl)-1H-benzo[d]imidazole)hydrochloride (0.12 g) was dissolved in dimethyl sulfoxide (2 mL) and treated with diisopropylethylamine (0.195 mL, 1.12 mmol) at ambient temperature followed by (2S,3R)-3-methoxy-2-(methoxycarbonylamino)butanoic acid (0.059 g, 0.307 mmol) and HATU (0.112 g, 0.293 mmol). After 1 hour, the solution was diluted with water and extracted into dichloromethane, concentrated and purified by chromatography, eluting with 0-8% methanol in dichloromethane to give 0.071 g of a yellow solid (48%). $^1$H NMR (400 MHz, DMSO-d$_6$) δ ppm 1.03 (dd, J=18.22, 6.18 Hz, 6H) 1.63-1.72 (m, 6H) 1.99-2.08 (m, 6H) 2.15-2.26 (m, 6H) 2.87-3.00 (m, 2H) 3.10 (s, 3H) 3.15 (s, 3H) 3.17-3.20 (m, 1H) 3.43-3.52 (m, 2H) 3.54 (s, 6H) 3.79-3.89 (m, 4H) 4.25-4.30 (m, 2H) 5.11-5.18 (m, 2H) 5.35-5.42 (m, 2H) 5.87-5.95 (m, 2H) 7.09 (t, J=8.19 Hz, 2H) 7.12-7.32 (m, 9H) 7.41 (d, J=8.35 Hz, 1H) 7.49 (d, J=8.78 Hz, 1H) 12.03 (s, 1H) 12.10 (s, 1H); MS (ESI+) m/z 1059.4 (M+H)$^+$.

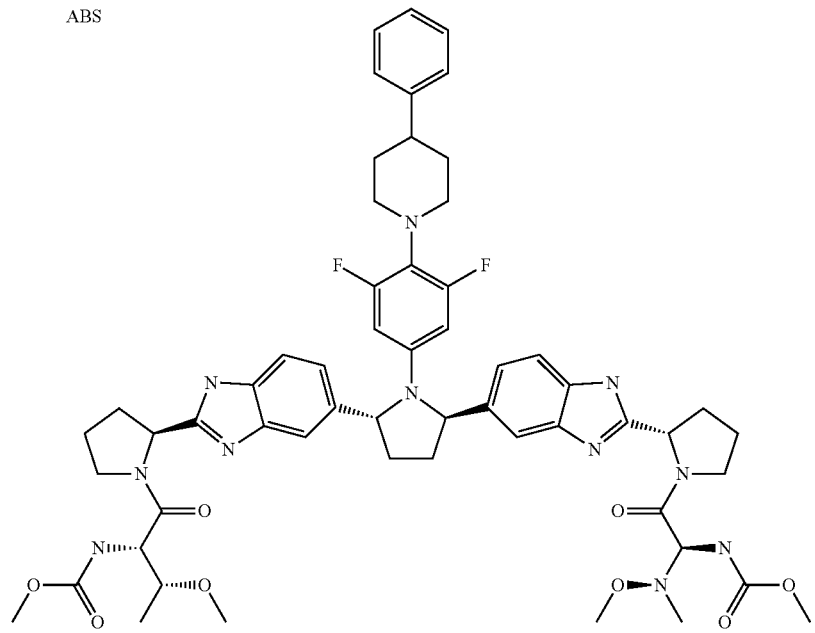

ABS

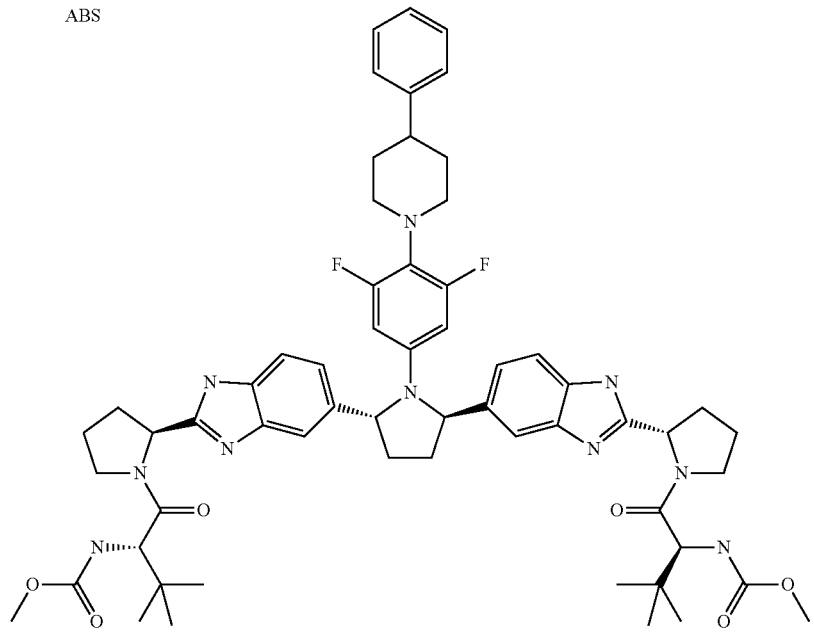

Example 5.4 methyl {(2S)-1-[(2S)-2-{5-[(2R,5R)-1-[3,5-difluoro-4-(4-phenylpiperidin-1-yl)phenyl]-5-{2-[(2S)-1-{(2S)-2-[(methoxycarbonyl)amino]-3,3-dimethylbutanoyl}pyrrolidin-2-yl]-1H-benzimidazol-5-yl}pyrrolidin-2-yl]-1H-benzimidazol-2-yl}pyrrolidin-1-yl]-3,3-dimethyl-1-oxobutan-2-yl}carbamate (S)-6,6'-((2R,5R)-1-(3,5-Difluoro-4-(4-phenylpiperidin-1-yl)phenyl)pyrrolidine-2,5-diyl)bis(2((S)-pyrrolidin-2-yl)-1H-benzo[d]imidazole)hydrochloride (0.12 g) was dissolved in dimethyl sulfoxide (2 mL) and treated with diisopropylethylamine (0.195 mL, 1.12 mmol) at ambient temperature followed by (S)-2-(methoxycarbonylamino)-3,3-dimethylbutanoic acid (0.058 g, 0.307 mmol) and HATU (0.112 g, 0.293 mmol). After 1 hour, the solution was diluted with water and extracted into dichloromethane. The organic phases were concentrated and purified by chromatography, eluting with 0-6% methanol in dichloromethane to give the title compound (0.065 g, 44%) as a yellow solid. $^1$H NMR (400 MHz, DMSO-$d_6$) δ ppm 0.89 (d, J=13.88 Hz, 18H) 1.61-1.73 (m, 8H) 1.95-2.08 (m, 4H) 2.15-2.24 (m, 6H) 2.86-3.02 (m, 4H) 3.55 (s, 6H) 3.78-3.85 (m, 4H) 4.23 (dd, J=8.89, 4.66 Hz, 2H) 5.13-5.22 (m, 2H) 5.33-5.43 (m, 2H) 5.92 (dd, J=12.85, 2.98 Hz, 2H) 7.05-7.18 (m, 4H) 7.20-7.29 (m, 5H) 7.33 (s, 1H) 7.42 (d, J=8.13 Hz, 1H) 7.49 (d, J=8.46 Hz, 1H) 12.05 (d, J=1.63 Hz, 1H) 12.09 (d, J=1.30 Hz, 1H); MS (ESI+) m/z 1055.4 (M+H)$^+$.

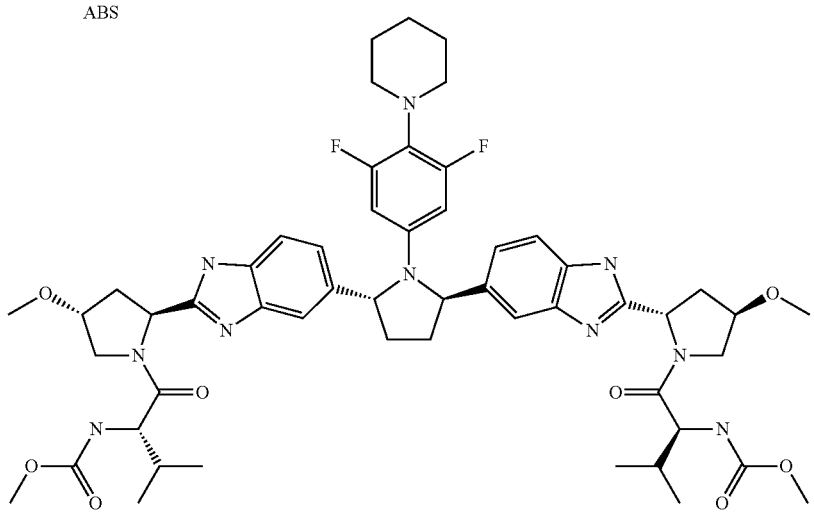

Example 5.5 methyl {(2S)-1-[(2S,4R)-2-{5-[(2R,5R)-1-[3,5-difluoro-4-(piperidin-1-yl)phenyl]-5-{2-[(2S,4R)-4-methoxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-methoxypyrrolidin-1-yl]-3-methyl-1-oxobutan-2-yl}carbamate (S,R)-6,6'-((2R,5R)-1-(3,5-Difluoro-4-(piperidin-1-yl)phenyl)pyrrolidine-2,5-diyl)bis(2-((2S,4R)-4-methoxypyrrolidin-2-yl)-1H-benzo[d]imidazole) (0.20 g, 0.287 mmol) was dissolved dimethyl sulfoxide (3 mL) and treated with diisopropylethylamine (0.400 mL, 2.29 mmol) at ambient temperature followed by (S)-2-(methoxycarbonylamino)-3-methylbutanoic acid (0.111 g, 0.631 mmol) and HATU (0.229 g, 0.603 mmol). After 2 hours, the solution was diluted with water and extracted into dichloromethane. The organic layer was concentrated and purified by chromatography, eluting with 0-6% methanol in dichloromethane to give the title compound (0.163 g, 56%) as a yellow solid. $^1$H NMR (400 MHz, DMSO-$d_6$) δ ppm 0.71-0.84 (m, 12H) 1.35-1.49 (m, 8H) 1.69 (d, J=5.42 Hz, 2H) 1.83-1.94 (m, 2H) 2.22-2.32 (m, 4H) 2.76 (s, 4H) 3.29 (s, 6H) 3.54 (s, 6H) 3.87 (dd, J=11.11, 3.85 Hz, 2H) 4.03 (q, J=7.05 Hz, 4H) 4.21 (s, 2H) 5.02-5.15 (m, 2H) 5.36 (d, J=3.25 Hz, 2H) 5.84-5.94 (m, 2H) 7.04-7.11 (m, 2H) 7.19 (s, 1H) 7.27-7.34 (m, 3H) 7.41 (d, J=8.24 Hz, 1H) 7.48 (d, J=8.24 Hz, 1H) 12.13 (s, 1H) 12.19 (s, 1H); MS (ESI+) m/z 1011.6 (M+H)$^+$.

Example 5.6 dimethyl({(2R,5R)-1-[3,5-difluoro-4-(piperidin-1-yl)phenyl]pyrrolidine-2,5-diyl}bis{1H-benzimidazole-5,2-diyl(2S)pyrrolidine-2,1-diyl[(1S)-1-cyclohexyl-2-oxoethane-2,1-diyl]})biscarbamate (S)-6,6'-((2R,5R)-1-(3,5-Difluoro-4-(piperidin-1-yl)phenyl)pyrrolidine-2,5-diyl)bis(2-((S)-pyrrolidin-2-yl)-1H-benzo[d]imidazole) (0.192 g, 0.302 mmol) was dissolved in dimethyl sulfoxide (4 mL) and treated with diisopropylethylamine (0.421 mL, 2.41 mmol) at ambient temperature followed by (S)-2-cyclohexyl-2-(methoxycarbonylamino)acetic acid (0.143 g, 0.663 mmol) and HATU (0.241 g, 0.633 mmol). After 1 hour, the solution was diluted with water and extracted into dichloromethane. The organic phase was concentrated, and the residue was purified by chromatography, eluting with 0-8% methanol in dichloromethane to give the title compound (0.166 g, 53%) as a yellow solid. $^1$H NMR (400 MHz, DMSO-$d_6$) δ ppm 0.80-1.12 (m, 8H) 1.36-1.70 (m, 24H) 1.98 (d, J=4.45 Hz, 4H) 2.15-2.25 (m, 4H) 2.75 (s, 4H) 3.52 (s, 6H) 3.81 (d, J=2.39 Hz, 4H) 4.08 (q, J=8.57 Hz, 2H) 5.14 (d, J=4.23 Hz, 2H) 5.36 (d, J=3.58 Hz, 2H) 5.82-5.93 (m, 2H) 7.10 (dd, J=13.93, 8.30 Hz, 2H) 7.15-7.28 (m, 4H) 7.42 (d, J=7.37 Hz, 1H) 7.48 (dd, J=8.35, 1.84 Hz, 1H) 12.00 (s, 1H) 12.16 (s, 1H); MS (ESI+) m/z 1031.4 (M+H)$^+$.

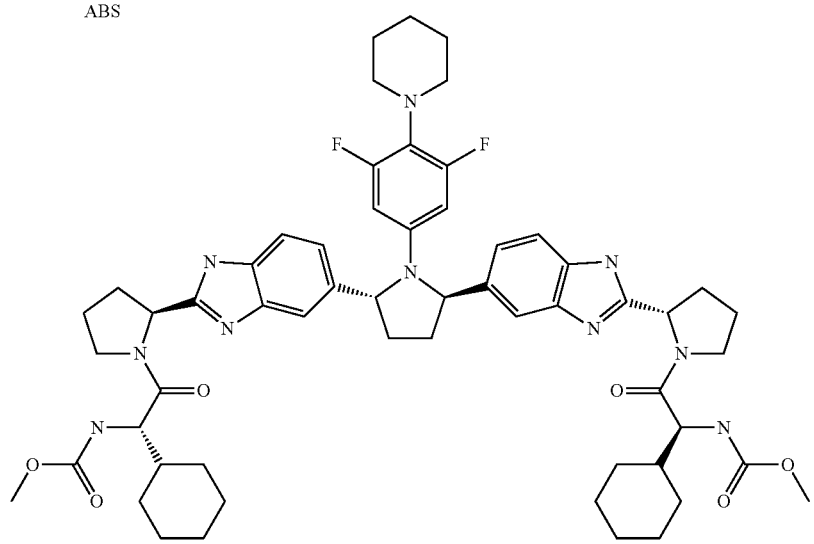

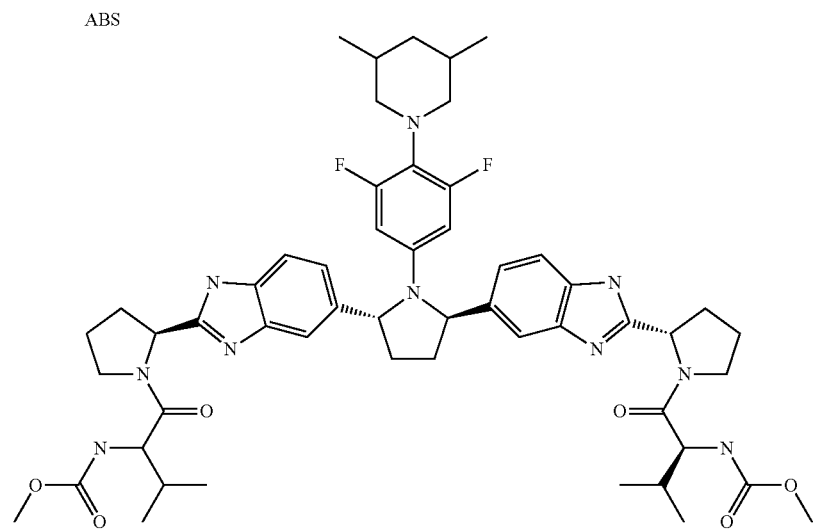

Example 5.7 methyl {(2S)-1-[(2S)-2-{6-[(2R,5R)-1-[4-(3,5-dimethylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate Diisopropylethylamine (3 mL, 17.18 mmol) was added to a suspension of (S)-6,6'-((2R,5R)-1-(4-(3,5-dimethylpiperidin-1-yl)-3,5-difluorophenyl)pyrrolidine-2,5-diyl)bis(2-((S)-pyrrolidin-2-yl)-1H-benzo[d]imidazole) (1.045 g, 1.572 mmol), (S)-2-(methoxycarbonylamino)-3-methylbutanoic acid (0.6852 g, 3.91 mmol), and HATU (1.4995 g, 3.94 mmol) in dichloromethane (20 mL). The reaction mixture was stirred at ambient temperature for 30 minutes. The reaction was diluted with dichloromethane, washed with water (2×), brine (1×), and concentrated. The residue was purified by flash chromatography (2-5% methanol/dichloromethane) to afford the title compound (0.7107 g, 46%). $^1$H NMR (400 MHz, DMSO-$d_6$) δ ppm 0.50 (q, J=11.9, 1H), 0.97-0.64 (m, 18H), 1.32-1.20 (m, 2H), 1.81-1.46 (m, 5H), 2.09-1.80 (m, 6H), 2.32-2.13 (m, 5H), 2.75 (dd, J=10.0, 40.2, 2H), 3.18-3.05 (m, 1H), 3.54 (s, 6H), 3.82 (s, 4H), 4.14-3.95 (m, 2H), 5.14 (s, 2H), 5.36 (d, J=7.2, 2H), 5.88 (d, J=12.8, 2H), 7.14-7.02 (m, 2H), 7.19 (s, 1H), 7.33-7.23 (m, 3H), 7.41 (d, J=8.2, 1H), 7.49 (d, J=8.2, 1H), 12.37-11.98 (m, 2H); MS (ESI+) m/z 979 (M+H)$^+$.

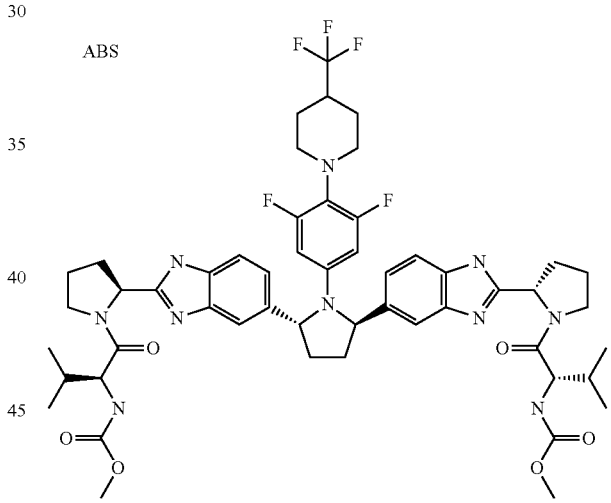

Example 5.8 methyl {(2S)-1-[(2S)-2-{5-[(2R,5R)-1-{3,5-difluoro-4-[4-(trifluoromethyl)piperidin-1-yl]phenyl}-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(3,5-Difluoro-4-(4-(trifluoromethyl)piperidin-1-yl)phenyl)pyrrolidin-2,5-diyl)bis(2-((S)-pyrroli din-2-yl)-1H-benzo[d]imidazole)tetrahydrochloride (250 mg, 0.294 mmol) and (S)-2-(methoxycarbonylamino)-3-methylbutanoic acid (113 mg, 0.647 mmol) were combined in anhydrous DMF (3 mL) under nitrogen. HOBT hydrate (113 mg, 0.735 mmol) and EDAC (144 mg, 0.735 mmol) were added. The amber-colored solution was cooled to 0° C. 4-Methylmorpholine (0.323 mL, 2.94 mmol) was added, the cooling bath was removed, and the reaction mixture was stirred at 20° C. After 2 hours, the reaction was diluted with EtOAc (50 mL) and washed with water (3×25 mL) and brine (25 mL). The organic phase was dried over anhydrous MgSO$_4$, filtered, and concentrated by rotary evaporation to a tan solid (300 mg). An aliquot (50 mg) of crude material was dissolved in 2 mL acetonitrile and 2 mL 0.1% TFA in H$_2$O, and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute (10 mL fractions). Pure fractions were treated with saturated aq NaHCO$_3$ (2 mL/tube), each tube was vortexed to thoroughly neutralize TFA, and the neutralized solutions were combined in a 250-mL round bottom flask. The acetonitrile was removed by rotary evaporation, and extracted the remaining aqueous phase with EtOAc (2×50 mL). The combined organic extracts were dried over anhydrous MgSO$_4$, filtered, and concentrated by rotary evaporation to afford the title compound as a white solid (18 mg). Repeated purification of an additional 100 mg as above by prep-HPLC in two 50-mg injections. Workup as above afforded additional title compound as a white solid (34 mg). $^1$H NMR (400 MHz, DMSO-d$_6$) δ ppm 0.73-0.90 (m, 12H), 1.23 (s, 1H), 1.34-1.49 (m, 2H), 1.63-1.76 (m, 4H), 1.83-2.04 (m, 6H), 2.11-2.25 (m, 4H), 2.84 (m, 4H), 3.52 (s, 6H), 3.81 (br s, 4H), 4.00-4.09 (m, 2H), 5.08-5.18 (m, 2H), 5.28-5.42 (m, 2H), 5.89 (d, J=12.79 Hz, 2H), 7.06 (t, J=7.26 Hz, 2H), 7.16-7.32 (m, 4H), 7.39 (d, J=8.24 Hz, 1H), 7.47 (d, J=8.13 Hz, 1H), 12.06 (two s, 2H); MS (ESI+) m/z 1019 (M+H)$^+$.

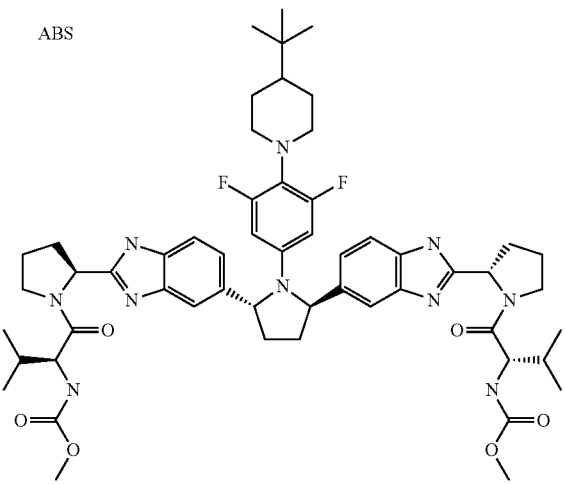 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC(C(C)(C)C)CC4)c(F)c3)ccc2[nH]1)C(C)C ; "ABS"]

Example 5.9 methyl {(2S)-1-[(2S)-2-{5-[(2R,5R)-1-[4-(4-tert-butylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(4-(4-tert-Butylpiperidin-1-yl)-3,5-difluorophenyl)pyrrolidine-2,5-diyl)bis(2-((S)-pyrrolidin-2-yl)-1H-benzo[d]imidazole)tetrahydrochloride (250 mg, 0.298 mmol) and (S)-2-(methoxycarbonylamino)-3-methylbutanoic acid (115 mg, 0.656 mmol) were combined in anhydrous DMF (3 mL) under nitrogen. HOBT hydrate (114 mg, 0.745 mmol) and EDAC (146 mg, 0.745 mmol) were added, and then the amber-colored solution was cooled to 0° C. 4-Methylmorpholine (0.328 mL, 2.98 mmol) was added, the cooling bath was removed, and the reaction mixture was stirred at 20° C. After 18 hours, the reaction mixture was diluted with EtOAc (50 mL), washed with water (3×25 mL) and brine (25 mL). The organic phase was dried over anhydrous MgSO$_4$, filtered, and concentrated by rotary evaporation to a yellow solid. Pre-purified by SiO$_2$ flash chromatography (Alltech Extract-Clean™ column, 10 g bed) eluting with 3% CH$_3$OH/CH$_2$Cl$_2$ afforded a yellow solid (119 mg). An aliquot (50 mg) of the residue was dissolved in 2 mL acetonitrile and 2 mL 0.1% TFA in H$_2$O, and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute (10 mL fractions). Pure fractions were treated with saturated aq NaHCO$_3$ (2 mL/tube), each tube was vortexed to thoroughly neutralize TFA, and the solutions were combined in a 250-mL round bottom flask. The remaining 69 mg of material was purified by prep-HPLC as described above. The pure product-containing fractions were treated with saturated aq NaHCO$_3$ as above and combined in the same 250-mL round bottom flask. The acetonitrile was removed by rotary evaporation, the remaining aqueous phase was extracted with EtOAc (2×50 mL). The combined organic extracts were dried over anhydrous MgSO$_4$, filtered, and concentrated by rotary evaporation to afford the title compound as a white solid (56 mg). $^1$H NMR (400 MHz, DMSO-d$_6$) δ ppm 0.68-0.93 (m, 22H), 1.09-1.25 (m, 2H), 1.53 (d, J=11.93 Hz, 2H), 1.63-1.75 (m, 2H), 1.80-2.08 (m, 7H), 2.12-2.27 (m, 4H), 2.71-2.91 (m, 5H), 3.54 (s, 6H), 3.82 (br s, 4H), 4.06 (t, J=8.35 Hz, 2H), 5.09-5.19 (m, 2H), 5.30-5.44 (m, 2H), 5.89 (d, J=12.69 Hz, 2H), 7.02-7.11 (m, 2H), 7.17-7.32 (m, 4H), 7.40 (d, J=8.24 Hz, 1H), 7.49 (d, J=8.13 Hz, 1H), 12.07 (two s, 2H); MS (ESI+) m/z 1007 (M+H)$^+$.

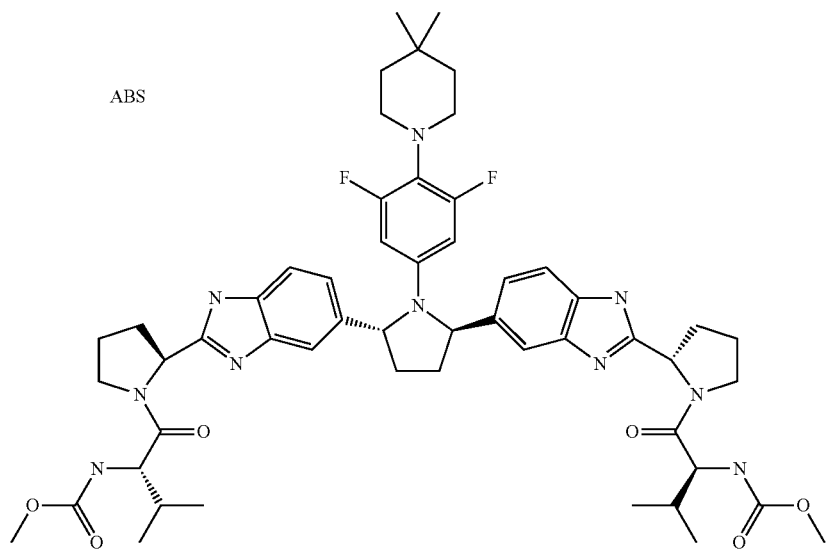

Example 5.10 methyl {(2S)-1-[(2S)-2-{5-[(2R,5R)-1-[4-(4,4-dimethylpiperidin-1-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(4-(4,4-Dimethylpiperidin-1-yl)-3,5-difluorophenyl)pyrrolidine-2,5-diyl)bis(2-((S)-pyrrolidin-2-yl)-1H-benzo[d]imidazole)pentahydrochloride (250 mg, 0.295 mmol) and (S)-2-(methoxycarbonylamino)-3-methylbutanoic acid (109 mg, 0.620 mmol) were combined in anhydrous DMF (3 mL) under nitrogen. HOBT hydrate (104 mg, 0.679 mmol), and EDAC (133 mg, 0.679 mmol) were added, and then the amber-colored solution was cooled to 0° C. 4-Methylmorpholine (0.325 mL, 2.95 mmol) was added, the cooling bath was removed, and the reaction mixture was stirred at 20° C. After 2 hours, the reaction mixture was diluted with EtOAc (50 mL), and washed with water (3×25 mL) and brine (25 mL). The organic phase was dried over anhydrous MgSO₄, filtered, and concentrated by rotary evaporation to a tan solid. Purification by SiO₂ flash chromatography (3.8 cm×15 cm) eluting with a step gradient of 3% to 4% CH₃OH/CH₂Cl₂ afforded the title compound as a solid (115 mg). An aliquot (50 mg) was dissolved in 1.5 mL acetonitrile and 1.5 mL 0.1% TFA in H₂O, and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H₂O/acetonitrile to 25:75 0.1% TFA in H₂O/acetonitrile, then 10 minutes to 100% acetonitrile at 20 mL/minute (10 mL fractions). Pure fractions were treated with saturated aq NaHCO₃ (2 mL/tube), each tube was vortexed to thoroughly neutralize TFA, and the solutions were combined in a 250-mL round bottom flask. Acetonitrile was removed by concentration in vacuo. The remaining aqueous phase was extracted with EtOAc (2×50 mL). The combined organic extracts were dried over anhydrous MgSO₄, filtered, and concentrated by rotary evaporation to afford the title compound as a white solid (33 mg). The remaining 65 mg of impure product (from silica gel column) were purified by RP-C18 prep HPLC as described above to obtain additional title compound as a white solid (33 mg). $^1$H NMR (400 MHz, DMSO-$d_6$) δ ppm 0.75-0.91 (m, 12H), 0.87 (s, 6H), 1.21-1.35 (m, 4H), 1.63-1.77 (m, 2H), 1.81-2.09 (m, 6H), 2.11-2.29 (m, 4H), 2.49-2.59 (m, 2H), 2.76 (s, 4H), 3.54 (s, 6H), 3.82 (br s, 4H), 4.06 (t, J=8.46 Hz, 2H), 5.09-5.22 (m, 2H), 5.30-5.44 (m, 2H), 5.89 (d, J=12.79 Hz, 2H), 7.03-7.11 (m, 2H), 7.17-7.32 (m, 4H), 7.41 (d, J=8.13 Hz, 1H), 7.49 (d, J=8.02 Hz, 1H), 12.07 (two s, 2H); (ESI+) m/z 979 (M+H)⁺; MS (ESI−) m/z 977 (M−H)⁻.

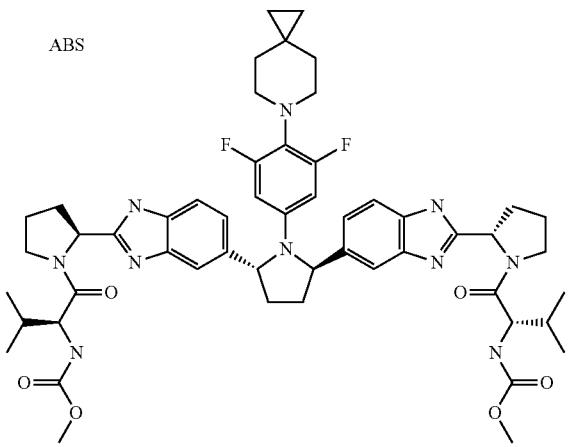 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCC5(CC4)CC5)c(F)c3)ccc2[nH]1)C(C)C ; "ABS"]

Example 5.11 methyl {(2S)-1-[(2S)-2-{5-[(2R,5R)-1-[4-(6-azaspiro[2.5]oct-6-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(3,5-Difluoro-4-(6-azaspiro[2.5]octan-6-yl)phenyl)pyrrolidine-2,5-diyl)bis(2-((S)-pyrrolidin- 2-yl)-1H-benzo[d]imidazole)tetrahydrochloride (250 mg, 0.309 mmol) and (S)-2-(methoxycarbonylamino)-3-methylbutanoic acid (119 mg, 0.680 mmol) were combined in anhydrous DMF (3 mL) under nitrogen. HOBT hydrate (118 mg, 0.773 mmol) and EDAC (151 mg, 0.773 mmol), were added, and then the amber-colored solution was cooled to 0° C. 4-Methylmorpholine (0.340 mL, 3.09 mmol) was added, the cooling bath was removed, and the reaction mixture was stirred at 20° C. After 16.5 hours, the reaction mixture was diluted with EtOAc (50 mL), and washed with water (3×25 mL) and brine (25 mL). The organic phase was dried over anhydrous MgSO$_4$, filtered, and concentrated by rotary evaporation to a yellow solid. Pre-purification by SiO$_2$ flash chromatography (Alltech Extract-Clean™ column, 10 g bed) eluting with 3% CH$_3$OH/CH$_2$Cl$_2$ to afforded a beige solid (172 mg). An aliquot (50 mg) was dissolved in 1.5 mL acetonitrile and 1.5 mL 0.1% TFA in H$_2$O, and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute (10 mL fractions). Pure fractions were treated with saturated aq NaHCO$_3$ (2 mL/tube), each tube was vortexed to thoroughly neutralize TFA, and the solutions were combined in a 250-mL round bottom flask. Two additional 50 mg lots were purified by prep-HPLC as described above, and the pure product-containing fractions were treated with saturated aq NaHCO$_3$ as above and combined in the same 250-mL round bottom flask. The acetonitrile was removed by concentration in vacuo, and the remaining aqueous phase was extracted with EtOAc (2×50 mL). The combined organic phases were dried over anhydrous MgSO$_4$, filtered, and concentrated by rotary evaporation to afford the title compound as a white solid (42 mg). $^1$H NMR (400 MHz, DMSO-d$_6$) δ ppm 0.22 (s, 4H), 0.72-0.93 (m, 12H), 1.21-1.36 (m, 5H), 1.61-1.78 (m, 2H), 1.83-2.08 (m, 7H), 2.13-2.27 (m, 4H), 2.81 (br s, 4H), 3.53 (s, 6H), 3.82 (br s, 4H), 4.06 (t, J=8.40 Hz, 2H), 5.10-5.19 (m, 2H), 5.29-5.45 (m, 2H), 5.90 (d, J=12.79 Hz, 2H), 7.02-7.32 (m, 6H), 7.41 (d, J=8.24 Hz, 1H), 7.49 (d, J=8.24 Hz, 1H), 12.07 (two s, 2H); MS (ESI+) m/z 977 (M+H)$^+$.

ABS

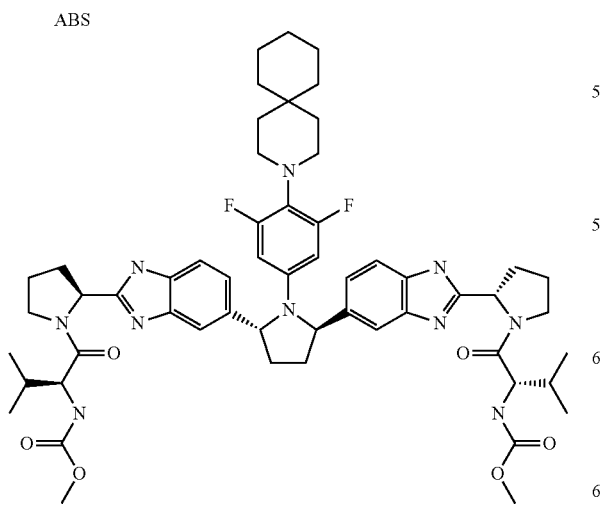

Example 5.12 methyl {(2S)-1-[(2S)-2-{5-[(2R,5R)-1-[4-(3-azaspiro[5.5]undec-3-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(3,5-Difluoro-4-(3-azaspiro[5.5]undecan-3-yl)phenyl)pyrrolidine-2,5-diyl)bis(2((S)-pyrrolidin-2-yl)-1H-benzo[d]imidazole)tetrahydrochloride (250 mg, 0.294 mmol) and (S)-2-(methoxycarbonylamino)-3-methylbutanoic acid (113 mg, 0.646 mmol) were combined in anhydrous DMF (3 mL) under nitrogen. HOBT hydrate (113 mg, 0.735 mmol) and EDAC (144 mg, 0.735 mmol), were added, and then the mixture was cooled to 0° C. 4-Methylmorpholine (0.323 mL, 2.94 mmol) was added, the cooling bath was removed, and the reaction mixture was stirred at 20° C. for 18 hours. The reaction mixture was diluted with EtOAc (50 mL) and washed with water (3×25 mL) and brine (25 mL). The organic phase was dried over anhydrous MgSO$_4$, filtered, and concentrated by rotary evaporation to a beige foam. The crude material was purified by SiO$_2$ flash chromatography (3.8 cm×15 cm) eluting with 4% CH$_3$OH/CH$_2$Cl$_2$ to afford the title compound as a white solid (82 mg). $^1$H NMR (400 MHz, DMSO-d$_6$) δ ppm 0.72-0.93 (m, 12H), 1.22-1.41 (m, 15H), 1.63-1.74 (m, 2H), 1.80-2.07 (m, 7H), 2.12-2.27 (m, 4H), 2.75 (s, 4H), 3.54 (s, 6H), 3.82 (s, 4H), 4.06 (t, J=8.40 Hz, 2H), 5.14 (d, J=1.19 Hz, 2H), 5.27-5.42 (m, 2H), 5.88 (d, J=12.69 Hz, 2H), 7.03-7.11 (m, 2H), 7.20 (s, 1H), 7.29 (d, J=5.96 Hz, 3H), 7.40 (d, J=8.24 Hz, 1H), 7.49 (d, J=8.24 Hz, 1H), 12.07 (m, 2H); MS (ESI+) m/z 1019 (M+H)$^+$, (ESI−) m/z 1017 (M−H)$^-$.

ABS

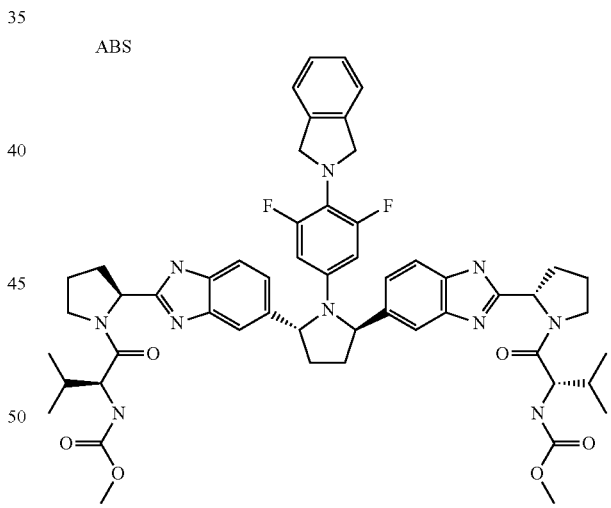

Example 5.13 methyl {(2S)-1-[(2S)-2-{5-[(2R,5R)-1-[4-(1,3-dihydro-2H-isoindol-2-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (S)-6,6'-((2R,5R)-1-(3,5-Difluoro-4-(isoindolin-2-yl)phenyl)pyrrolidine-2,5-diyl)bis(2-((S)-pyrrolidin-2-yl)-1H- benzo[d]imidazole)tetrahydrochloride (250 mg, 0.306 mmol) and (S)-2-(methoxycarbonylamino)-3-methylbutanoic acid (118 mg, 0.673 mmol) were combined in anhydrous DMF (3 mL) under nitrogen. HOBT hydrate (117 mg, 0.765 mmol) and EDAC (150 mg, 0.765 mmol) were added, then the amber-colored solution was cooled to 0° C. 4-Methylmorpholine (0.337 mL, 3.06 mmol) was added, the cooling bath was removed, and the reaction mixture was stirred at 20° C. for 16 hours. The reaction mixture was diluted with EtOAc (50 mL) and this mixture was washed with water (3×25 mL) and brine (25 mL). The organic phase over dried over anhydrous MgSO$_4$, filtered, and concentrated by rotary evaporation to a greenish-yellow solid. The solid was purified by SiO$_2$ flash chromatography (3.8 cm×15 cm) eluting with 4% CH$_3$OH/CH$_2$Cl$_2$ to afford an off-white solid (104 mg). An aliquot (52 mg) was dissolved acetonitrile (2 mL) and 0.1% TFA in H$_2$O (2 mL) and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute (10 mL fractions). Pure fractions were treated with saturated aq NaHCO$_3$ (2 mL/tube), each tube was vortexed to thoroughly neutralize TFA, and the solutions were combined in a 500-mL round bottom flask. The remaining 52 mg of material were purified by prep-HPLC as described above and the pure product-containing fractions were treated with saturated aq NaHCO$_3$ as described above. The product containing fractions were combined in the same 500-mL round bottom flask. The acetonitrile was removed by rotary evaporation. The remaining aqueous phase was extracted with EtOAc (2×50 mL). The combined organic phases were dried over anhydrous MgSO$_4$, filtered, and concentrated by rotary evaporation to afford the title compound as a white solid (88 mg). $^1$H NMR (400 MHz, DMSO-d$_6$) δ ppm 0.75-0.92 (m, 12H), 1.61-2.08 (m, 8H), 2.11-2.26 (m, 3H), 2.57 (s, 2H), 3.54 (s, 6H), 3.83 (s, 4H), 4.07 (t, J=8.29 Hz, 2H), 4.26-4.43 (m, 4H), 5.10-5.23 (m, 2H), 5.33-5.50 (m, 2H), 5.99 (d, J=12.79 Hz, 2H), 7.09 (t, J=6.83 Hz, 2H), 7.20 (s, 4H), 7.22-7.37 (m, 4H), 7.42 (d, J=8.24 Hz, 1H), 7.50 (d, J=8.13 Hz, 1H), 12.09 (m, 2H); MS (ESI+) m/z 985 (M+H)$^+$, (ESI−) m/z 983 (M−H)$^−$.

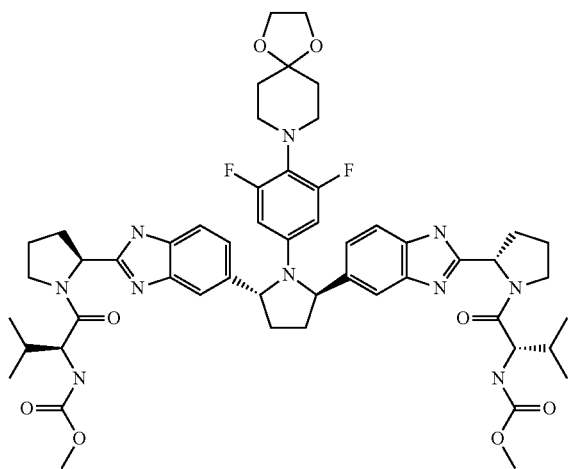

Example 5.14 methyl {(2S)-1-[(2S)-2-{5-[(2R,5R)-1-[4-(1,4-dioxa-8-azaspiro[4.5]dec-8-yl)-3,5-difluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate Part A The compound 8-(4-((2R,5R)-2,5-bis(4-chloro-3-nitrophenyl)pyrrolidin-1-yl)-2,6-difluorophenyl)-1,4-dioxa-8-azaspiro[4.5]decane can be transformed following the methods of General Procedure 8.1 and General Procedure 9D (PtO2) to obtain dimethyl (2S,2'S)-1,1'-((2S,2'S)-2,2'-(4,4'-((2R,5R)-1-(3,5-difluoro-4-(1,4-dioxa-8-azaspiro[4.5]decan-8-yl)phenyl)pyrrolidine-2,5-diyl)bis(2-amino-4,1-phenylene))bis(azanediyl))bis(oxomethylene)bis(pyrrolidine-2,1-diyl))bis(3-methyl-1-oxobutane-2,1-diyl)dicarbamate.

Part B

In an oven-dried 10-mL round bottom flask, dimethyl(2S,2'S)-1,1'-((2S,2'S)-2,2'-(4,4'-((2R,5R)-1-(3,5-difluoro-4-(1,4-dioxa-8-azaspiro[4.5]decan-8-yl)phenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate (200 mg, 0.191 mmol) was dissolved in anhydrous toluene (2 mL) under nitrogen. Glacial acetic acid (0.110 mL, 1.914 mmol) was added, and the solution was stirred in an oil bath at 60° C. After 1.5 hours, the reaction mixture was cooled to room temperature, diluted with EtOAc (50 mL), and washed with saturated aq NaHCO$_3$ (25 mL). The organic phase was dried over anhydrous MgSO$_4$, filtered, and concentrated by rotary evaporation to afford the crude title compound as a tan solid (185 mg). An aliquot (93 mg) of the impure material was dissolved acetonitrile (2 mL) and 0.1% TFA in H$_2$O (2 mL) and purified by RP-C18 HPLC (Waters Prep LC, 40 mm Module with Nova Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute. Pure fractions were immediately treated with saturated aq NaHCO$_3$ (2 mL/tube), each tube was vortexed to thoroughly neutralize TFA, and the solutions were combined in a 500-mL round bottom flask. The remaining 92 mg were purified by preparative-HPLC as described above and the pure product-containing fractions were treated with saturated aq NaHCO$_3$ as described above. The additional fractions were combined in the same 500-mL round bottom flask. The acetonitrile was removed by rotary evaporation, and the remaining aqueous phase was extracted with EtOAc (2×50 mL). The combined organic extracts were dried over anhydrous MgSO$_4$, filtered, and concentrated by rotary evaporation to afford the title compound as a white solid (103 mg). 1H NMR (400 MHz, DMSO-d$_6$) δ ppm 0.73-0.94 (m, 12H), 1.51-1.61 (m, 4H), 1.63-1.75 (m, 2H), 1.83-2.10 (m, 8H), 2.13-2.29 (m, 4H), 2.86 (s, 4H), 3.54 (s, 6H), 3.83 (s, 8H), 4.06 (t, J=8.51 Hz, 2H), 5.09-5.21 (m, 2H), 5.30-5.42 (m, 2H), 5.90 (d, J=12.69 Hz, 2H), 7.01-7.12 (m, 2H), 7.17-7.32 (m, 4H), 7.40 (s, 1H), 7.49 (d, J=8.24 Hz, 1H), 11.71-12.53 (m, 2H); MS (ESI+) m/z 1009 (M+H)$^+$, (ESI−) m/z 1007 (M−H)$^−$.

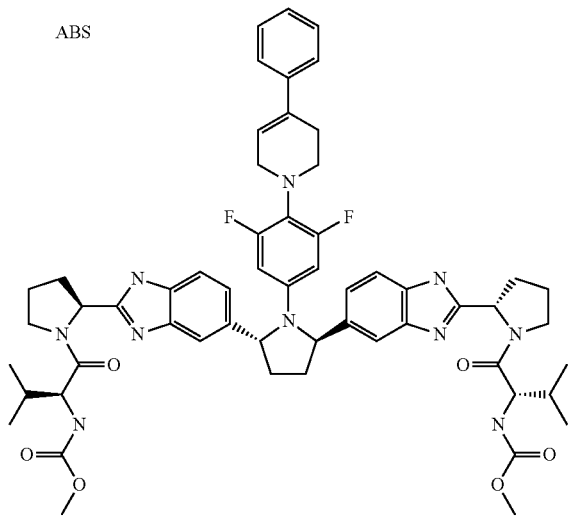 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CC=C(c5ccccc5)CC4)c(F)c3)ccc2[nH]1)C(C)C ; "ABS"]

Example 5.15 methyl {(2S)-1-[(2S)-2-{5-[(2R,5R)-1-[3,5-difluoro-4-(4-phenyl-3,6-dihydropyridin-1(2H)-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate Part A The compound 1-(4-((2R,5R)-2,5-bis(4-chloro-3-nitrophenyl)pyrrolidin-1-yl)-2,6-difluorophenyl)-4-phenyl-1,2,3,6-tetrahydropyridine can be transformed following the methods of General Procedure 8.1 and General Procedure 9E to obtain dimethyl (2S,2'S)-1,1'-((2S,2'S)-2,2'-(4,4'-((2R,5R)-1-(3,5-difluoro-4-(4-phenyl-5,6-dihydropyridin-1(2H)-yl)phenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate.

Part B

In an oven-dried 5-mL round bottom flask, dimethyl(2S,2'S)-1,1'-((2S,2'S)-2,2'-(4,4'-((2R,5R)-1-(3,5-difluoro-4-(4-phenyl-5,6-dihydropyridin-1(2H)-yl)phenyl)pyrrolidine-2,5-diyl)bis(2-amino-4,1-phenylene))bis(azanediyl)bis(oxomethylene)bis(pyrrolidine-2,1-diyl))bis(3-methyl-1-oxobutane-2,1-diyl)dicarbamate (75 mg, 0.071 mmol) was dissolved in anhydrous toluene (1 mL) under nitrogen. Glacial acetic acid (0.041 mL, 0.707 mmol) was added, and the solution was stirred in an oil bath at 60° C. After 1.5 hours, the yellow reaction mixture was cooled to room temperature, diluted in EtOAc (50 mL), and washed with saturated aq NaHCO$_3$ (25 mL). The organic phase was dried over anhydrous MgSO$_4$, filtered, and concentrated by rotary evaporation to a yellow solid (~80 mg). The residue was dissolved in 2 mL acetonitrile and 2 mL 0.1% TFA in H$_2$O, and purified by RP-C18 HPLC (Waters Prep LC, 40 mm Module with Nova-Pak HR C18 6 μm 40×100 mm Prep Pak cartridge) eluting with a 30 minutes gradient of 95:5 0.1% TFA in H$_2$O/acetonitrile to 25:75 0.1% TFA in H$_2$O/acetonitrile, then 10 minutes to 100% acetonitrile at 20 mL/minute (10 mL fractions). Pure fractions were treated with saturated aq NaHCO$_3$ (2 mL/tube), each tube was vortexed to thoroughly neutralize TFA, and the solutions were combined in a 250-mL round bottom flask. The acetonitrile was removed by rotary evaporation, and the remaining aqueous phase was extracted with EtOAc (2×50 mL). The organic phase was dried over anhydrous MgSO$_4$, filtered, and concentrated by rotary evaporation to afford the product as an off-white solid (34 mg). $^1$H NMR (400 MHz, DMSO-d$_6$) δ ppm 0.76-0.94 (m, 12H), 1.70 (d, J=4.55 Hz, 2H), 1.83-2.10 (m, 6H), 2.11-2.26 (m, 3H), 2.44 (s, 1H), 2.56 (s, 4H), 3.09 (s, 2H), 3.48 (s, 2H), 3.54 (s, 6H), 3.82 (s, 4H), 4.07 (t, J=8.35 Hz, 2H), 5.09-5.22 (m, 2H), 5.30-5.46 (m, 2H), 5.95 (d, J=12.90 Hz, 2H), 6.09 (s, 1H), 7.04-7.17 (m, 2H), 7.19-7.25 (m, 2H), 7.26-7.34 (m, 5H), 7.36-7.45 (m, 3H), 7.50 (d, J=8.35 Hz, 1H), 11.71-12.63 (m, 2H); MS (ESI+) m/z 1025 (M+H)$^+$, (ESI−) m/z 1023 (M−H)$^−$.

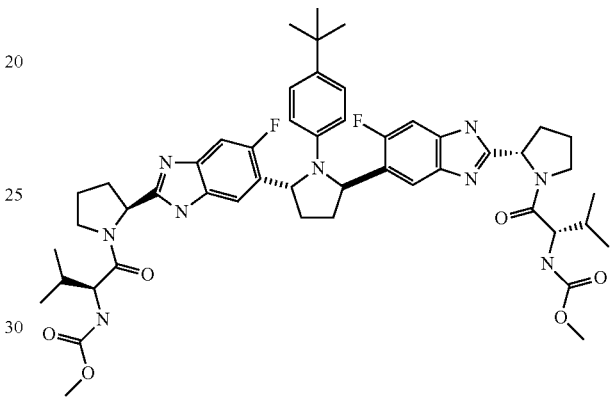

Example 6.1 methyl {(2S)-1-[(2S)-2-{5-[(2R,5R)-1-(4-tert-butylphenyl)-5-{5-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-6-fluoro-1H-benzimidazol-2-yl}pyrrolidin-1-yl]-3-methyl-1-oxobutan-2-yl}carbamate To 6,6'-[(2R,5R)-1-(4-tert-butylphenyl)pyrrolidine-2,5-diyl]bis{5-fluoro-2-[(2S)-pyrrolidin-2-yl]-1H-benzimidazole} was added DMF (1.0 mL) followed by N-methylmorpholine (0.045 mL, 0.41 mmol), (S)-2-(methoxycarbonylamino)-3-methylbutanoic acid (15 mg, 0.09 mmol), EDC (20 mg, 0.1 mmol) and HOBT (16 mg, 0.1 mmol). The solution was stirred at room temperature for 18 hours. The reaction mixture was diluted with EtOAc, washed with H$_2$O and brine, dried (Na$_2$SO$_4$), filtered and concentrated. The product was purified by reverse-phase HPLC chromatography (5-100% CH$_3$CN/0.1% TFA-H$_2$O); the desired fractions were neutralized with aqueous NaHCO$_3$ solution, extracted with EtOAc, dried, filtered and solvent evaporated to give the title compound (6.7 mg, 7.2 μmol, 18%): $^1$H NMR (400 MHz, CDCl$_3$) δ ppm 10.48 (m, 1H) 10.25 (m, 1H) 7.39 (m, 1H) 7.14 (m, 1H) 6.98 (m, 3H) 6.29 (m, 1H) 5.54 (br s, 1H) 5.34 (br s, 4H) 4.31 (m, 1H) 3.82 (m, 2H) 3.70 (s, 6H) 3.51-3.65 (m, 2H) 3.03 (br s, 2H) 2.51 (br s, 2H) 2.23-2.40 (m, 2H) 2.14 (m, 4H) 1.95 (m, 4H) 1.72 (m, 2H) 1.09-1.23 (m, 9H) 1.07 (m, 3H) 0.87 (m, 9H) 0.67-0.79 (m, 2H); MS (ESI) m/z 924 (M+H)$^+$.

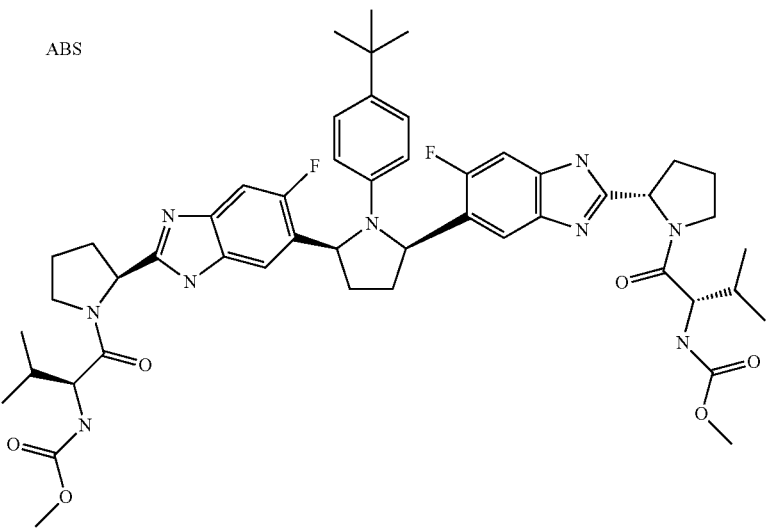 [SMILES: COC(=O)N[C@H](C(=O)N1CCC[C@H]1c1nc2cc([C@H]3CC[C@@H](c4cc5[nH]c([C@@H]6CCCN6C(=O)[C@@H](NC(=O)OC)C(C)C)nc5cc4F)N3c3ccc(C(C)(C)C)cc3)c(F)cc2[nH]1)C(C)C ; "ABS"]

Example 6.2 methyl {(2S)-1-[(2S)-2-{5-[(2R,5S)-1-(4-tert-butylphenyl)-5-{5-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-6-fluoro-1H-benzimidazol-2-yl}pyrrolidin-1-yl]-3-methyl-1-oxobutan-2-yl}carbamate From the HPLC purification of Example 6.1, the cis isomer (6.4 mg, 6.9 μmol, 17%) was also obtained: $^1$H NMR (400 MHz, CDCl$_3$) δ ppm 11.62 (s, 1H) 11.37 (s, 1H) 7.45-7.55 (m, 3H) 7.36 (d, 1H) 7.04 (d, 2H) 6.92 (d, 1H) 6.77 (d, 1H) 6.41 (d, 2H) 5.36-5.40 (m, 2H) 5.33 (m, 1H) 5.07 (t, 1H) 3.98-4.07 (m, 1H) 3.93 (m, 1H) 3.74-3.86 (m, 2H) 3.72 (m, 1H) 3.59 (m, 2H) 2.80 (m, 1H) 2.50 (s, 6H) 2.32 (s, 4H) 1.86-2.27 (m, 7H) 1.78 (m, 1H) 1.17 (s, 9H) 0.86-1.01 (m, 9H); MS (ESI) m/z 924 (M+H)$^+$.

The following example compounds 6.3-6.11 can be made from the appropriate listed intermediate amine following generally the method of Example 6.1:

Intermediate Amines:

6,6'-[(2R,5R)-1-(4-tert-butylphenyl)pyrrolidine-2,5-diyl]bis{7-fluoro-2-[(2S)-pyrrolidin-2-yl]-1H-benzimidazole} (ACD Name v12);

6,6'-[(2R,5S)-1-(4-tert-butylphenyl)pyrrolidine-2,5-diyl]bis{7-fluoro-2-[(2S)-pyrrolidin-2-yl]-1H-benzimidazole} (ACD Name v12);

6,6'-[(2R,5R)-1-(4-tert-butylphenyl)pyrrolidine-2,5-diyl]bis{7-chloro-2-[(2S)-pyrrolidin-2-yl]-1H-benzimidazole} (ACD Name v12);

6,6'-[(2R,5S)-1-(4-tert-butylphenyl)pyrrolidine-2,5-diyl]bis{7-chloro-2-[(2S)-pyrrolidin-2-yl]-1H-benzimidazole} (ACD Name v12);

6,6'-[(2R,5R)-1-(4-tert-butylphenyl)pyrrolidine-2,5-diyl]bis{7-methyl-2-[(2S)-pyrrolidin-2-yl]-1H-benzimidazole} (ACD Name v12);

6,6'-[(2R,5S)-1-(4-tert-butylphenyl)pyrrolidine-2,5-diyl]bis{7-methyl-2-[(2S)-pyrrolidin-2-yl]-1H-benzimidazole} (ACD Name v12);

6,6'-{(2R,5R)-1-fluoro-4-(piperidin-1-yl)phenyl]pyrrolidine-2,5-diyl}bis{5-fluoro-2-[(2S)-pyrrolidin-2-yl]-1H-benzimidazole} (ACD Name v12);

6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (ACD Name v12); and 6,6'-{(2R,5R)-1-[3,5-difluoro-4-(4-phenylpiperidin-1-yl)phenyl]pyrrolidine-2,5-diyl}bis{5-fluoro-2-[(2S)-pyrrolidin-2-yl]-1H-benzimidazole} (ACD Name v12).

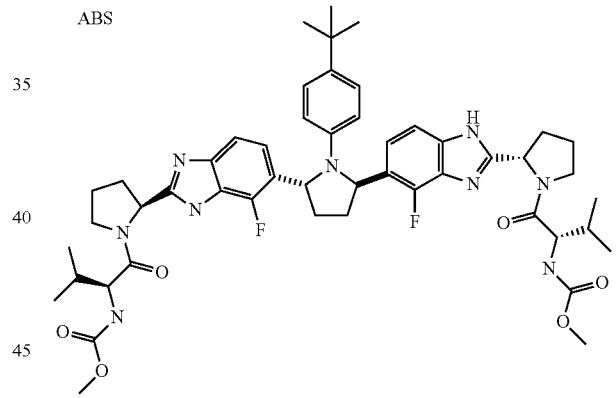

Example 6.3 methyl {(2S)-1-[(2S)-2-{5-[(2R,5R)-1-(4-tert-butylphenyl)-5-{7-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-4-fluoro-1H-benzimidazol-2-yl}pyrrolidin-1-yl]-3-methyl-1-oxobutan-2-yl}carbamate $^1$H NMR (400 MHz, CDCl$_3$) δ ppm 10.41-10.64 (m, 2H) 6.84-7.06 (m, 6H) 6.25-6.36 (m, 2H) 5.55-5.68 (m, 1H) 5.25-5.46 (m, 4H) 4.27-4.40 (m, 1H) 3.79-3.92 (m, 2H) 3.71 (s, 6H) 3.56-3.67 (m, 2H) 3.03-3.27 (m, 2H) 1.83-2.66 (m, 10H) 1.14 (s, 9H) 0.77-1.31 (m, 14H); MS (ESI) m/z 924 (M+H)$^+$.

ABS

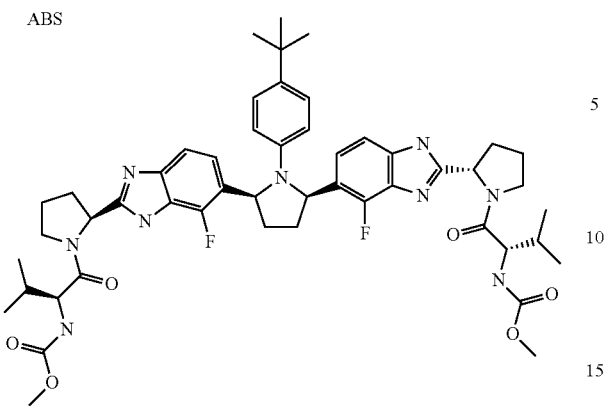

Example 6.4 methyl {(2S)-1-[(2S)-2-{5-[(2R,5S)-1-(4-tert-butylphenyl)-5-{7-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-4-fluoro-1H-benzimidazol-2-yl}pyrrolidin-1-yl]-3-methyl-1-oxobutan-2-yl}carbamate $^1$H NMR (400 MHz, CDCl$_3$) δ ppm 10.54-10.71 (m, 2H) 7.54-7.68 (m, 2H) 7.00-7.21 (m, 4H) 6.43-6.54 (m, 2H) 5.27-5.50 (m, 4H) 5.20 (br s, 2H) 4.29-4.42 (m, 1H) 3.80-3.94 (m, 2H) 3.71 (s, 6H) 3.59-3.69 (m, 2H) 3.04-3.29 (m, 2H) 1.86-2.66 (m, 10H) 1.18 (s, 9H) 0.79-1.33 (m, 14H); MS (ESI) m/z 924 (M+H)$^+$.

ABS

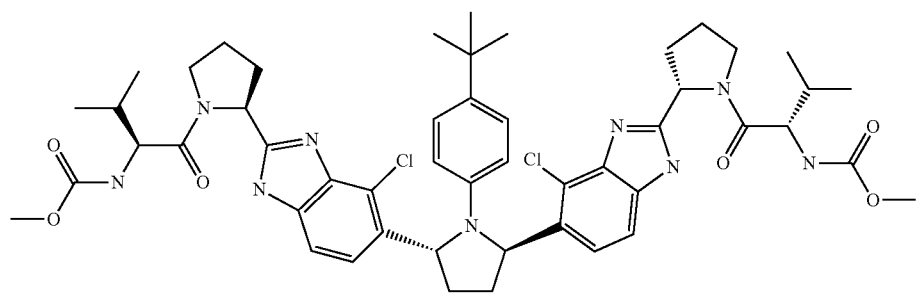

Example 6.5 methyl {(2S)-1-[(2S)-2-{5-[(2R,5R)-1-(4-tert-butylphenyl)-5-{4-chloro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-4-chloro-1H-benzimidazol-2-yl}pyrrolidin-1-yl]-3-methyl-1-oxobutan-2-yl}carbamate $^1$H NMR (400 MHz, DMSO-d$_6$) δ 12.70 (s, 0H), 12.39 (s, 1H), 8.07 (s, 1H), 7.32 (dd, J=26.1, 8.1, 3H), 6.91 (d, J=37.0, 4H), 6.08 (d, J=7.9, 1H), 5.64 (s, 1H), 5.17 (s, 1H), 4.66 (s, 1H), 4.10 (d, J=5.2, 1H), 3.86 (s, 3H), 3.52 (d, J=14.1, 6H), 3.17 (d, J=5.2, 1H), 2.30-2.10 (m, 2H), 2.00 (s, 4H), 1.77 (s, 1H), 1.23 (s, 1H), 1.18-1.01 (m, 9H), 1.01-0.72 (m, 11H); MS (APCI+) m/z 958.76 (M+H)$^+$.

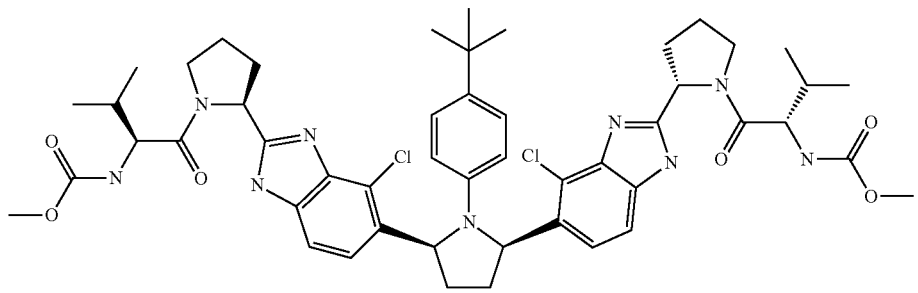

Example 6.6 methyl {(2S)-1-[(2S)-2-{5-[(2R,5S)-1-(4-tert-bu-tylphenyl)-5-{4-chloro-2-[(2S)-1-{(2S)-2-[(meth-oxycarbonyl)amino]-3-methylbutanoyl}pyrrolidin-2-yl]-1H-benzimidazol-5-yl}pyrrolidin-2-yl]-4-chloro-1H-benzimidazol-2-yl}pyrrolidin-1-yl]-3-methyl-1-oxobutan-2-yl}carbamate $^1$H NMR (400 MHz, DMSO-d$_6$) δ 12.45 (s, 1H), 8.06 (d, J=3.3, 1H), 7.68 (d, J=8.6, 2H), 7.48 (t, J=12.5, 2H), 7.31 (d, J=8.2, 2H), 7.00 (d, J=8.1, 2H), 6.20 (d, J=8.7, 2H), 5.16 (d, J=32.0, 4H), 4.66 (s, 1H), 4.11 (s, 1H), 3.88 (s, 3H), 3.56 (d, J=8.1, 6H), 2.30-2.09 (m, 5H), 2.02 (s, 7H), 1.80 (s, 2H), 1.23 (s, 2H), 1.09 (s, 9H), 1.00-0.78 (m, 12H); MS(APCI+) m/z 958.64 (M+H)$^+$.

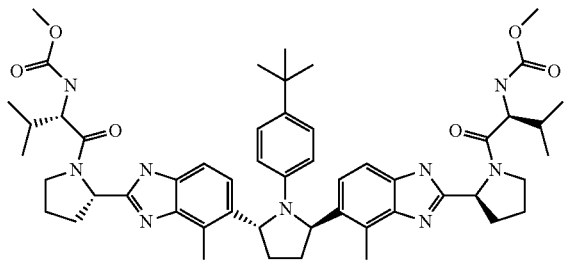

Example 6.7 methyl {(2S)-1-[(2S)-2-{5-[(2R,5R)-1-(4-tert-bu-tylphenyl)-5-{2-[(2S)-1-{(2S)-2-[(methoxycarbonyl)amino]-3-methylbutanoyl}pyrrolidin-2-yl]-4-methyl-1H-benzimidazol-5-yl}pyrrolidin-2-yl]-4-methyl-1H-benzimidazol-2-yl}pyrrolidin-1-yl]-3-methyl-1-oxobutan-2-yl}carbamate $^1$H NMR (400 MHz, DMSO-d$_6$) δ ppm 0.78-1.05 (m, 14H), 1.06 (s, 9H), 1.86-2.06 (m, 8H), 2.09-2.31 (m, 4H), 2.58-2.72 (m, 6H), 3.54 (s, 6H), 3.79-3.93 (m, 4H), 4.02-4.17 (m, 2H), 5.11-5.23 (m, 2H), 5.42-5.51 (m, 2H), 6.02-6.12 (m, 2H), 6.71-6.83 (m, 2H), 6.83-6.96 (m, 2H), 7.04-7.19 (m, 2H), 7.24-7.35 (m, 2H), 11.84-12.26 (m, 2H).

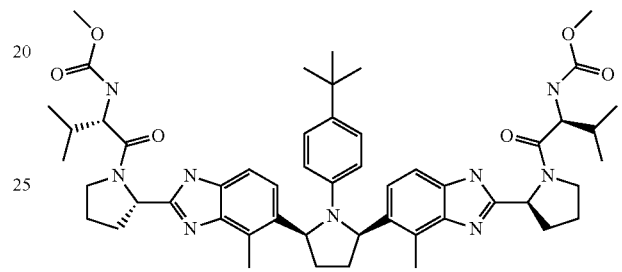

Example 6.8 methyl {(2S)-1-[(2S)-2-{5-[(2R,5S)-1-(4-tert-bu-tylphenyl)-5-{2-[(2S)-1-{(2S)-2-[(methoxycarbonyl)amino]-3-methylbutanoyl}pyrrolidin-2-yl]-4-methyl-1H-benzimidazol-5-yl}pyrrolidin-2-yl]-4-methyl-1H-benzimidazol-2-yl}pyrrolidin-1-yl]-3-methyl-1-oxobutan-2-yl}carbamate $^1$H NMR (400 MHz, DMSO-d$_6$) δ ppm 0.79-1.06 (m, 12H), 1.23 (s, 9H), 1.87-2.31 (m, J=30.69 Hz, 12H), 2.58-2.65 (m, J=3.25 Hz, 6H), 3.55 (s, 6H), 3.81-3.96 (m, 4H), 4.01-4.19 (m, 2H), 4.92 (s, 2H), 5.12-5.26 (m, 2H), 6.14-6.26 (m, 2H), 6.86-7.02 (m, 2H), 7.22-7.39 (m, 4H), 7.57-7.79 (m, 2H), 11.90-12.32 (m, 2H); MS (ESI) m/z=916.4 (M+H)$^+$.

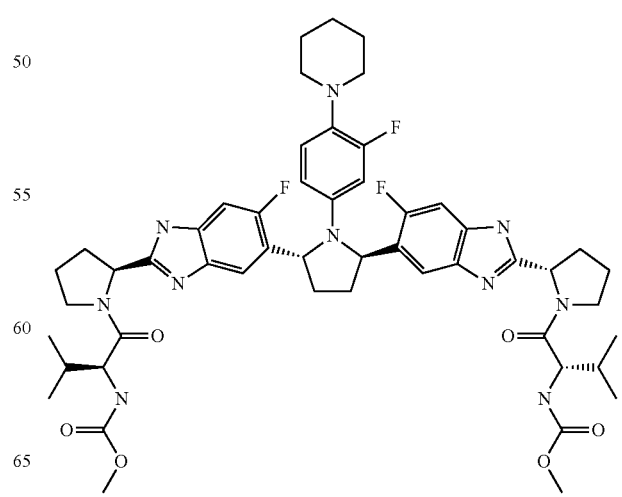

Example 6.9 methyl {(2S)-1-[(2S)-2-(6-fluoro-5-{(2R,5R)-5-{6-fluoro-2-[(2S)-1-{(2S)-2-[(methoxycarbonyl)amino]-3-methylbutanoyl}pyrrolidin-2-yl]-1H-benzimidazol-5-yl}-1-[3-fluoro-4-(piperidin-1-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, CDCl$_3$) δ ppm 10.21-10.67 (m, 2H) 6.55-7.99 (m, 6H) 5.95-6.14 (m, 1H) 5.19-5.56 (m, 6H) 4.25-4.39 (m, 1H) 3.77-3.92 (m, 2H) 3.70 (s, 6H) 3.42-3.76 (m, 3H) 2.95-3.17 (m, 2H) 2.64-2.95 (m, 2H) 2.43-2.64 (m, 1H) 1.78-2.42 (m, 11H) 0.62-1.78 (m, 18H); MS (ESI) m/z 969 (M+H)$^+$.

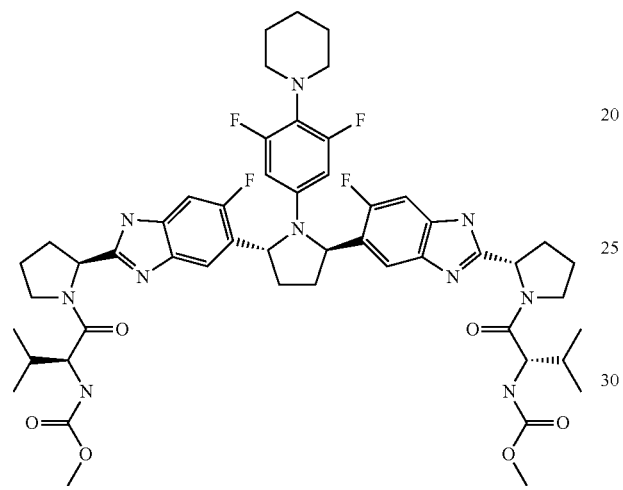

Example 6.10 methyl {(2S)-1-[(2S)-2-{5-[(2R,5R)-1-[3,5-difluoro-4-(piperidin-1-yl)phenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate To a solution of 6,6'-{(2R,5R)-1-[3,5-difluoro-4-(piperidin-1-yl)phenyl]pyrrolidine-2,5-diyl}bis{5-fluoro-2-[(2S)-pyrrolidin-2-yl]-1H-benzimidazole} (64 mg, 0.095 mmol) in DMF (2378 μL) was added (S)-2-(methoxycarbonylamino)-3-methylbutanoic acid (35.0 mg, 0.200 mmol), EDC (45.6 mg, 0.238 mmol), HOBT (36.4 mg, 0.238 mmol) and N-methylmorpholine (105 μL, 0.951 mmol), and the resultant solution was stirred at ambient temperature overnight. The reaction solution was diluted with EtOAc, washed with H$_2$O and brine, dried (MgSO4), filtered and concentrated. The crude material was dissolved in 1:1 CH$_3$CN:0.1% TFA/H$_2$O and purified by HPLC (C18, 0-100% CH$_3$CN/0.1% TFA/H$_2$O). The product containing fractions were combined, made basic with saturated sodium bicarbonate solution, and extracted with EtOAc. The organic layer was dried (MgSO$_4$), filtered and concentrated to give the title compound (43.3 mg, 0.044 mmol, 46.1% yield). The title compound can also be prepared according to General Procedure 12C described above. $^1$H NMR (400 MHz, CDCl$_3$) δ ppm 10.25-10.70 (m, 2H) 6.83-7.53 (m, 4H) 5.70-5.91 (m, 2H) 5.20-5.52 (m, 4H) 4.21-4.42 (m, 2H) 3.70 (s, 6H) 3.53-3.94 (m, 6H) 1.75-3.17 (m, 16H) 0.63-1.74 (m, 18H); MS (ESI) m/z 987 (M+H)$^+$.

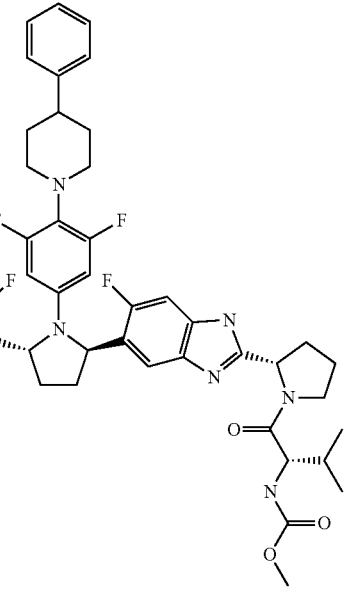

Example 6.11 methyl {(2S)-1-[(2S)-2-{5-[(2R,5R)-1-[3,5-difluoro-4-(4-phenylpiperidin-1-yl)phenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate $^1$H NMR (400 MHz, CDCl$_3$) δ ppm 10.54 (br s, 2H) 7.09-7.33 (m, 9H) 5.77-5.92 (m, 2H), 5.23-5.52 (m, 4H) 4.24-4.39 (m, 2H) 3.79-3.91 (m, 2H) 3.70 (s, 6H) 3.55-3.67 (m, 2H) 2.92-3.21 (m, 5H) 1.73-2.65 (m, 10H) 0.97-1.74 (m, 8H) 0.76-0.96 (m, 12H); MS (ESI) m/z 1063 (M+H)$^+$.

ABS

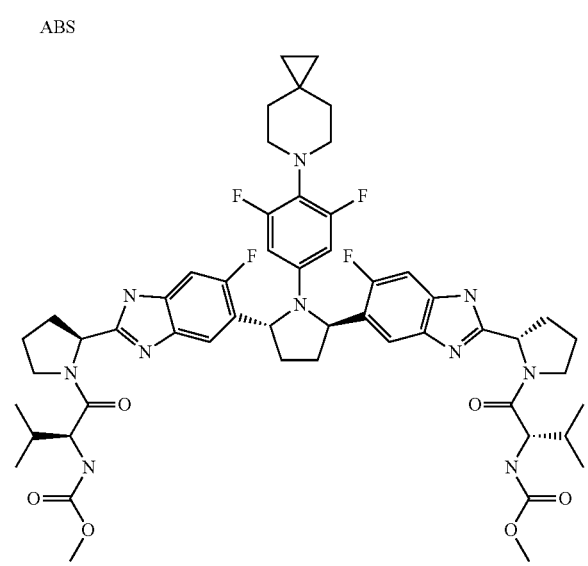 [SMILES: "ABS" ; COC(=O)N[C@H](C(=O)N1CCC[C@H]1c1nc2cc([C@H]3CC[C@H](c4cc5nc([C@@H]6CCCN6C(=O)[C@@H](NC(=O)OC)C(C)C)[nH]c5cc4F)N3c3cc(F)c(N4CCC5(CC4)CC5)c(F)c3)c(F)cc2[nH]1)C(C)C]

Example 6.12 methyl {(2S)-1-[(2S)-2-{5-[(2R,5R)-1-[4-(6-azaspiro [2.5]oct-6-yl)-3,5-difluorophenyl]-5-{6-fluoro-2-[(2S)-1-{(2S)-2-[(methoxycarbonyl)amino]-3-methylbutanoyl}pyrrolidin-2-yl]-1H-benzimidazol-5-yl}pyrrolidin-2-yl]-6-fluoro-1H-benzimidazol-2-yl}pyrrolidin-1-yl]-3-methyl-1-oxobutan-2-yl}carbamate In an oven-dried 5-mL pear-shaped flask, dissolved (S)-2-(methoxycarbonylamino)-3-methylbutanoic acid (56.6 mg, 0.323 mmol) in anhydrous $CH_2Cl_2$ (1 mL) under nitrogen, added EDAC (63.2 mg, 0.323 mmol), and stirred at 20° C. for 20 min. The resulting solution was added via gas-tight syringe to a solution of (S)-6,6'-((2R,5R)-1-(3,5-difluoro-4-(6-azaspiro[2.5]octan-6-yl)phenyl)pyrrolidine-2,5-diyl)bis(5-fluoro-2-((S)-pyrrolidin-2-yl)-1H-benzo[d]imidazole)hydrochloride (91 mg) and diisopropylethylamine (0.188 mL, 1.077 mmol) in anhydrous $CH_2Cl_2$ (2 mL) under nitrogen, added HOBt hydrate (49.5 mg, 0.323 mmol), and stirred at 20° C. for 1 hr. The reaction was diluted with $CH_2Cl_2$ (50 mL), washed with water (25 mL), dried over anhydrous $Na_2SO_4$, filtered, and concentrated by rotary evaporation to a dark yellow foam (~140 mg). Dissolved 70 mg of the impure material in 2 mL Acetonitrile and 2 mL 0.1% TFA in $H_2O$, and purified by RP-$C_{18}$ HPLC (Waters Prep LC, 40 mm Module with Nova Pak HR C18 6 µm 40×100 mm Prep Pak cartridge) eluting with a 30 min gradient of 95:5 0.1% TFA in $H_2O$/Acetonitrile to 25:75 0.1% TFA in $H_2O$/Acetonitrile, then 10 min to 100% Acetonitrile at 20 mL/min. Pure fractions were treated with saturated aqueous $NaHCO_3$ (2 mL/tube), vortexed each tube to thoroughly neutralize TFA, and combined the solutions in a 500-mL round bottom flask. Purified the remaining 70 mg by prep-HPLC as above and the pure product-containing fractions were treated with saturated aqueous $NaHCO_3$ as above and combined in the same 500-mL round bottom flask. Removed the Acetonitrile by rotary evaporation, extracted the remaining aqueous phase with EtOAc (2×50 mL), dried the combined organic extracts over anhydrous $MgSO_4$, filtered, and concentrated by rotary evaporation to afford the product as a white solid (49 mg, 0.048 mmol). $^1H$ NMR (400 MHz, DMSO-$d_6$) δ ppm 0.24 (s, 4H), 0.68-0.91 (m, 12H), 1.21-1.35 (m, 5H), 1.67-2.07 (m, 9H), 2.13-2.24 (m, 4H), 2.84 (s, 4H), 3.53 (s, 6H), 3.73-3.87 (m, 4H), 3.99-4.11 (m, 2H), 5.02-5.23 (m, 2H), 5.45-5.65 (m, 2H), 5.81-5.99 (m, 2H), 7.04 (d, J=6.07 Hz, 1H), 7.14 (d, J=6.94 Hz, 1H), 7.26-7.36 (m, 3H), 7.41 (dd, J=11.06, 6.18 Hz, 1H), 11.73-12.63 (m, 2H); MS (ESI+) m/z 1013 (M+H)$^+$; MS (ESI−) m/z 1011 (M−H)$^-$.

ABS

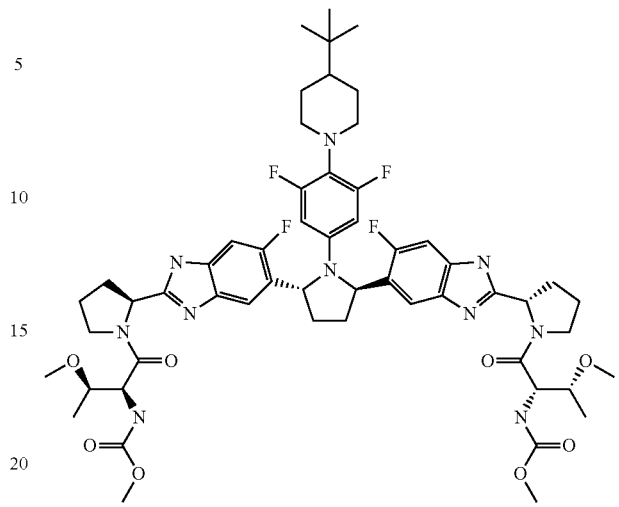

Example 6.13 methyl {(2S,3R)-1-[(2S)-2-{5-[(2R,5R)-1-[4-(4-tert-butylpiperidin-1-yl)-3,5-difluorophenyl]-5-(6-fluoro-2-{(2S)-1-[N-(methoxycarbonyl)-O-methyl-L-threonyl]pyrrolidin-2-yl}-1H-benzimidazol-5-yl)pyrrolidin-2-yl]-6-fluoro-1H-benzimidazol-2-yl}pyrrolidin-1-yl]-3-methoxy-1-oxobutan-2-yl}carbamate (2S,3R)-3-Methoxy-2-(methoxycarbonylamino)butanoic acid (65.6 mg, 0.343 mmol) was dissolved in anhydrous $CH_2Cl_2$ (1 mL) under nitrogen. EDAC (67.1 mg, 0.343 mmol) was added, and the mixture was stirred at 20° C. for 20 minutes. The resulting solution was added via to a solution of (S)-6,6'-((2R,5R)-1-(4-(4-tert-butylpiperidin-1-yl)-3,5-difluorophenyl)pyrrolidine-2,5-diyl)bis(5-fluoro-2-((S)-pyrrolidin-2-yl)-1H-benzo[d]imidazole)hydrochloride (100 mg) and diisopropylamine (0.200 mL, 1.143 mmol) in anhydrous $CH_2Cl_2$ (2 mL) under nitrogen. HOBt hydrate (52.5 mg, 0.343 mmol) was added, and the mixture was stirred at 20° C. for 1 hour. The reaction was diluted with $CH_2Cl_2$ (50 mL), washed with water (25 mL), dried over anhydrous $Na_2SO_4$, filtered, and concentrated by rotary evaporation to a dark yellow foam (140 mg). The crude material (70 mg) was dissolved in acetonitrile (2 mL) and 0.1% TFA in $H_2O$ (2 mL), and purified by RP-$C_{18}$ HPLC (Waters Prep LC, 40 mm module with Nova-Pak® HR C18 6 µm 40×100 mm Prep Pak cartridge) eluting with a 30 minute gradient of 95:5 0.1% TFA in $H_2O$/acetonitrile to 25:75 0.1% TFA in $H_2O$/acetonitrile, then 10 minutes to 100% acetonitrile at 20 mL/minute. Pure fractions were treated with saturated aqueous $NaHCO_3$ (2 mL/tube), each tube was vortexed to thoroughly neutralize TFA, and the fractions were combined in a 500-mL round bottom flask. The remaining 70 mg of material was purified by prep-HPLC as described above and the pure product-containing fractions were treated with saturated aqueous $NaHCO_3$ as above and combined in the same 500-mL round bottom flask. The acetonitrile was removed by rotary evaporation, the remaining aqueous phase was extracted with EtOAc (2×50 mL), the combined organic extracts were dried over anhydrous MgSO$_4$, filtered, and concentrated by rotary evaporation to afford the product as a white solid (62 mg, 0.057 mmol). $^1$H NMR (400 MHz, DMSO-d$_6$) δ ppm 0.80 (s, 9H), 0.92 (d, J=6.07 Hz, 2H), 0.98-1.09 (m, 4H), 1.12-1.22 (m, 2H), 1.44-1.63 (m, 3H), 1.65-1.89 (m, 3H), 1.91-2.10 (m, 4H), 2.11-2.28 (m, 4H), 2.73-2.92 (m, 4H), 3.04 (d, J=1.73 Hz, 2H), 3.13 (s, 3H), 3.25 (d, J=3.47 Hz, 1H), 3.41-3.50 (m, 3H), 3.53 (s, 6H), 3.72-3.92 (m, 4H), 4.25 (q, J=7.99 Hz, 2H), 5.02-5.17 (m, 2H), 5.46-5.63 (m, 2H), 5.79-6.00 (m, 2H), 7.02 (d, J=6.72 Hz, 1H), 7.08-7.18 (m, 2H), 7.24 (d, J=8.02 Hz, 1H), 7.33 (dd, J=10.36, 4.50 Hz, 1H), 7.40 (dd, J=11.22, 6.23 Hz, 1H), 11.84-12.63 (m, 2H); MS (ESI+) m/z 1075 (M+H)$^+$; MS (ESI−) m/z 1073 (M−H)$^−$.

mg) and diisopropylethylamine (0.200 mL, 1.143 mmol) in anhydrous CH$_2$Cl$_2$ (2 mL) under nitrogen. HOBt hydrate (52.5 mg, 0.343 mmol) was added, and the mixture was stirred at 20° C. for 1 hour. The reaction was diluted with CH$_2$Cl$_2$ (50 mL), washed with water (25 mL), dried over anhydrous Na$_2$SO$_4$, filtered, and concentrated by rotary evaporation to a dark yellow solid (210 mg). The impure material (70 mg) was dissolved in 2 mL acetonitrile and 2 mL 0.1% TFA in H$_2$O, and purified by RP-C$_{18}$ HPLC (Waters Prep LC, 40 mm module with Nova-Pak® HR C18 6 μm 40×100 mm Prep Pak cartridge) eluting with a 30 minute gradient of 95:5 0.1% TFA in H$_2$O/acetonitrile to 25:75 0.1% TFA in H$_2$O/acetonitrile, then 10 minutes to 100% acetonitrile at 20 mL/minute. Pure fractions were treated with saturated aqueous NaHCO$_3$ (2 mL/tube), each tube was vortexed to thoroughly neutralize TFA, and the fractions were com-

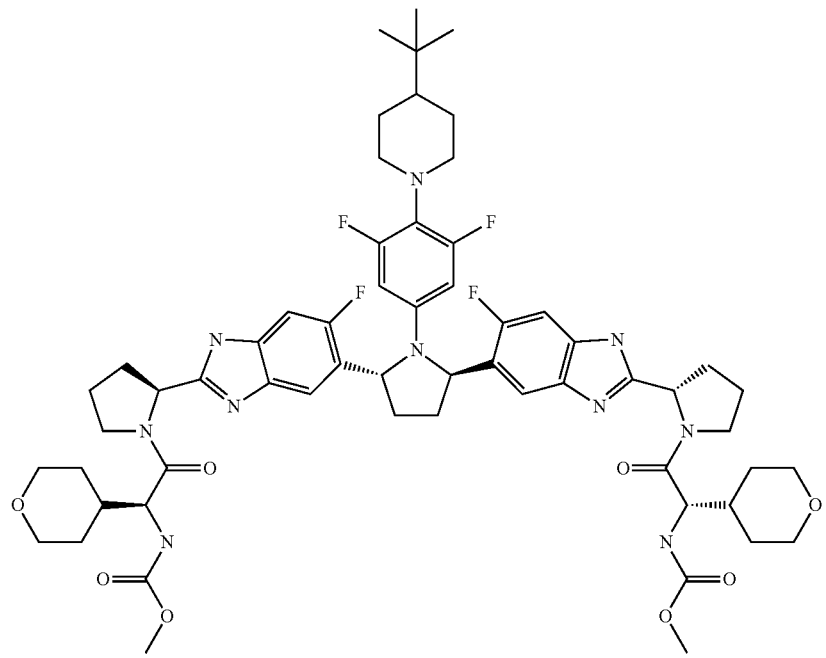

ABS

Example 6.14 dimethyl({(2R,5R)-1-[4-(4-tert-butylpiperidin-1-yl)-3,5-difluorophenyl]pyrrolidine-2,5-diyl}bis{(6-fluoro-1H-benzimidazole-5,2-diyl)(2S)pyrrolidine-2,1-diyl[(1S)-2-oxo-1-(tetrahydro-2H-pyran-4-yl)ethane-2,1-diyl]})biscarbamate (S)-2-(Methoxycarbonylamino)-2-(tetrahydro-2H-pyran-4-yl)acetic acid (74.5 mg, 0.343 mmol) was dissolved in anhydrous CH$_2$Cl$_2$ (1 mL) under nitrogen. EDAC (67.1 mg, 0.343 mmol) was added, and the mixture was stirred at 20° C. for 20 minutes. The resulting solution was added to a solution of (S)-6,6'-((2R,5R)-1-(4-(4-tert-butylpiperidin-1-yl)-3,5-difluorophenyl)pyrrolidine-2,5-diyl)bis(5-fluoro-2-((S)-pyrrolidin-2-yl)-1H-benzo[d]imidazole)hydrochloride (100 bined in a 500-mL round bottom flask. The remaining material was purified in two 70 mg injections by prep-HPLC as described above, and the pure product-containing fractions were treated with saturated aqueous NaHCO$_3$ as above and combined in the same 500-mL round bottom flask. The acetonitrile was removed by rotary evaporation, the remaining aqueous phase was extracted with EtOAc (2×50 mL), the combined organic extracts were dried over anhydrous MgSO$_4$, filtered, and concentrated by rotary evaporation to afford the product as a white solid (69 mg, 0.060 mmol). $^1$H NMR (400 MHz, DMSO-d$_6$) δ ppm 0.80 (s, 9H), 0.89-1.01 (m, 1H), 1.07-1.38 (m, 7H), 1.39-1.63 (m, 6H), 1.67-1.91 (m, 5H), 1.92-2.05 (m, 4H), 2.10-2.26 (m, 4H), 2.71-2.95 (m, 5H), 2.96-3.25 (m, 3H), 3.52 (s, 6H), 3.62-3.92 (m, 8H), 4.06-4.23 (m, 2H), 5.10 (t, J=6.23 Hz, 2H), 5.39-5.65 (m, 2H), 5.77-5.99 (m, 2H), 7.01 (d, J=6.72 Hz, 1H), 7.07 (d, J=7.05 Hz, 1H), 7.28-7.49 (m, 4H), 11.78-12.42 (m, 2H); MS (ESI+) m/z 1127 (M+H)$^+$; MS (ESI−) m/z 1125 (M−H)$^−$.

527

ABS

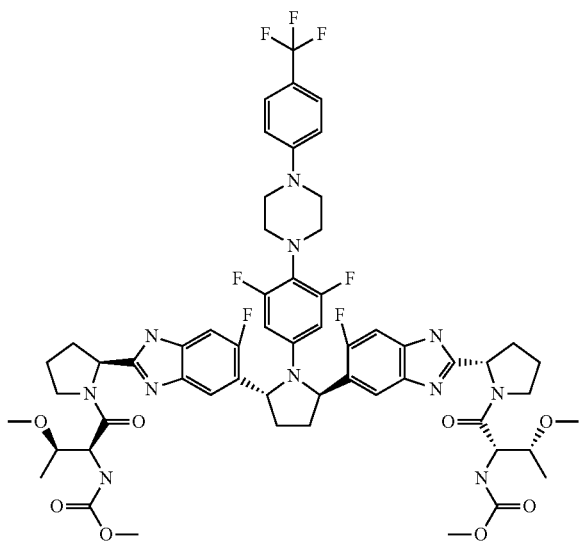

Example 6.15 methyl {(2S,3R)-1-[(2S)-2-{5-[(2R,5R)-1-(3,5-difluoro-4-{4-[4-(trifluoromethyl)phenyl]piperazin-1-yl}phenyl)-5-(6-fluoro-2-{(2S)-1-[N-(methoxycarbonyl)-O-methyl-L-threonyl]pyrrolidin-2-yl}-1H-benzimidazol-5-yl)pyrrolidin-2-yl]-6-fluoro-1H-benzimidazol-2-yl}pyrrolidin-1-yl]-3-methoxy-1-oxobutan-2-yl}carbamate (S)-6,6'-((2R,5R)-1-(3,5-Difluoro-4-(4-(4-(trifluoromethyl)phenyl)piperazin-1-yl)phenyl)pyrrolidine-2,5-diyl)bis(5-fluoro-2-((S)-pyrrolidin-2-yl)-1H-benzo[d]imidazole)hydrochloride (88 mg), (2S,3R)-3-methoxy-2-(methoxycarbonylamino)butanoic acid (41 mg, 0.216 mmol), N-(3-dimethylaminopropyl)-N'-ethylcarbodiimide hydrochloride (46 mg, 0.238 mmol), 1-hydroxybenzotriazole hydrate (36 mg, 0.238 mmol) and 4-methylmorpholine (0.095 mL, 0.864 mmol) were dissolved in DMF (3.0 mL), and the mixture stirred at room temperature for 3 hours. Afterwards, an isopropyl alcohol and chloroform mixture was added then extracted with 1 N aqueous hydrochloric acid. The organic extract was dried, filtered and concentrated, and then the residue was purified by chromatography (silica gel, methanol in dichloromethane) which afforded 71 mg of the title compound. $^1$H NMR (400 MHz, DMSO-$d_6$) δ ppm 7.56 (m, 2H), 7.48 (d, J=8.8 Hz, 2H), 7.34 (m, 2H), 7.18 (m, 2H), 7.04 (d, J=8.6 Hz, 2H), 5.97 (m, 2H), 5.62 (m, 2H), 5.17 (m, 2H), 4.28 (m, 2H), 3.82 (m, 2H), 3.60 (m, 2H), 3.54 (s, 6H), 3.25 (m, 8H), 3.17 (s, 6H), 2.99 (m, 4H), 2.05 (m, 12H), 1.25 (m, 6H); MS (ESI) m/z 1164 (M+H)$^+$.

ABS

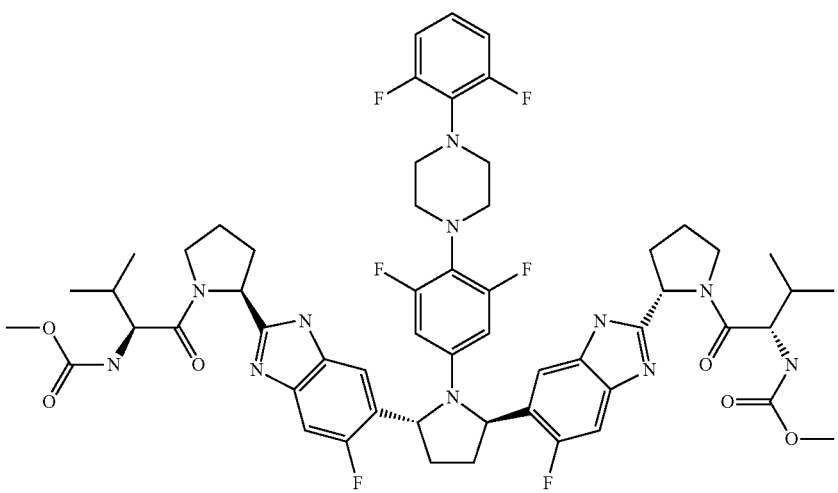

Example 6.16 methyl {(2S)-1-[(2S)-2-{6-[(2R,5R)-1-{4-[4-(2,6-difluorophenyl)piperazin-1-yl]-3,5-difluorophenyl}-5-{5-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-5-fluoro-1H-benzimidazol-2-yl}pyrrolidin-1-yl]-3-methyl-1-oxobutan-2-yl}carbamate (S)-2-(Methoxycarbonylamino)-3-methylbutanoic acid (0.072 g, 0.410 mmole) and HOBt (0.063 g, 0.410 mmole) were combined in DMF (2 mL). To the clear solution was added EDAC (0.079 g, 0.410 mmole) with a 0.2 ml DMF rinse, and the resulting clear solution was stirred at room temperature for 20 minutes. (S)-6,6'-((2R,5R)-1-(4-(4-(2,6-Difluorophenyl)piperazin-1-yl)-3,5-difluorophenyl)pyrrolidine-2,5-diyl)bis(5-fluoro-2-((S)-pyrrolidin-2-yl)-1H-benzo[d]imidazole)hydrochloride (0.160 g) was dissolved in 2 ml DMF, treated with N-methylmorpholine (1.863 mmol, 0.205 ml), and then treated with the activated amino acid solution and the resulting clear brown solution was stirred at room temperature for 1 hour. The pH of the solution was measured to be 8 by pH paper. Reaction progress was determined by LC-MS at 1 hour and analysis deemed reaction complete. The reaction mixture was concentrated in vacuo to a brown mobile oil. The oil was diluted with 50 ml EtOAc and washed with 30 mL 10% NaHCO$_3$. The layers were separated and the aqueous layer was extracted with another 50 mL EtOAc. The combined organic extracts were washed with 10% NaCl, dried over anhydrous Na$_2$SO$_4$(s), filtered and solvent removed in vacuo leaving a brown oily residue. The residue was purified on a 12 g silica gel column eluted with a gradient of CH$_2$Cl$_2$/CH$_3$OH, 99/1 to 95/5 over 13 minutes, then 95/5 to 90/10 over 8 minutes. The fractions containing product were combined and repurified on a 12 g gold column eluted with a gradient of CH$_2$Cl$_2$/CH$_3$OH, 98/2 to 90/10 over 15 minutes. The fractions were concentrated in vacuo leaving a light brown solid as the title compound (50.3 mg). $^1$H NMR (400 MHz, DMSO-d$_6$) δ ppm 0.82 (m, 12H) 1.99 (m, 9H) 2.18 (m, 2H) 2.95 (m, 4H) 3.05-3.17 (m, 5H) 3.53 (s, 6H) 3.79 (m, 4H) 3.95-4.11 (m, 4H) 5.11 (m, 2H) 5.55 (m, 2H) 5.91 (m, 2H) 7.01 (m, 5H) 7.29 (m, 4H) 12.14 (m, 2H); MS (ESI+) m/z 1100.3, (ESI−) m/z 1098.3 (M−H)$^-$.

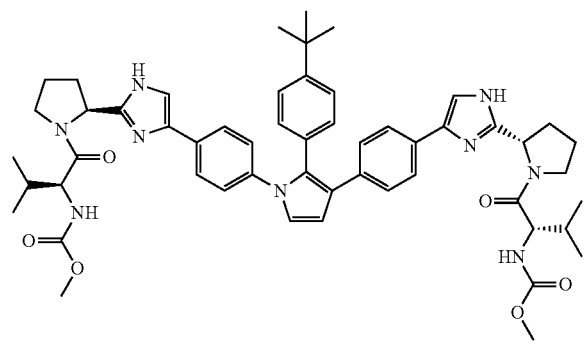 [SMILES: COC(=O)N[C@H](C(=O)N1CCC[C@H]1c1nc(-c2ccc(-c3ccn(-c4ccc(-c5c[nH]c([C@@H]6CCCN6C(=O)[C@@H](NC(=O)OC)C(C)C)n5)cc4)c3-c3ccc(C(C)(C)C)cc3)cc2)c[nH]1)C(C)C]

Example 7.1 methyl {(2S)-1-[(2S)-2-(4-{4-[2-(4-tert-butylphenyl)-1-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-3-yl]phenyl}-1H-imidazol-2-yl)pyrrolidin-1-yl]-3-methyl-1-oxobutan-2-yl}carbamate

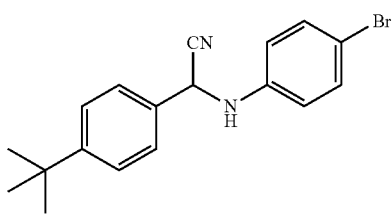 [SMILES: CC(C)(C)c1ccc(C(C#N)Nc2ccc(Br)cc2)cc1]

Example 7.1A 2-(4-bromophenylamino)-2-(4-tert-butylphenyl)acetonitrile

To a solution of 4-bromoaniline (10.0 g, 58.1 mmol) in THF (100 mL) was added 4-tert-butylbenzaldehyde (9.72 mL, 58.1 mmol), acetic acid (13.3 mL, 233 mmol), potassium cyanide (3.79 g, 58.1 mmol) and water (50 mL). The resultant mixture was stirred at room temperature for 16 hours. The resultant solid that formed was collected by vacuum filtration, washed with hexane, and then dried to afford 15.3 g, (77%) of the title compound. $^1$H NMR (400 MHz, CDCl$_3$) δ ppm 7.49 (m, 4H), 7.37 (d, J=8.7 Hz, 2H), 6.66 (d, J=8.8 Hz, 2H), 5.34 (d, J=8.1 Hz, 1H), 4.02 (d, J=8.0 Hz, 1H), 1.34 (s, 9H).

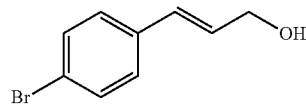 [SMILES: OC/C=C/c1ccc(Br)cc1]

Example 7.1B (E)-3-(4-bromophenyl)prop-2-en-1-ol

To a solution of (E)-ethyl 3-(4-bromophenyl)acrylate (10.0 g, 39.2 mmol) in dichloromethane (151 mL) cooled to −78° C. was added a solution of diisobutylaluminum hydride (1.0 M in dichloromethane, 82 mL, 82 mmol) dropwise over 15 minutes time. The solution was then stirred for an additional 2 hours followed by the addition of a solution of 10% aqueous sodium hydroxide (250 mL). The mixture was allowed to warm to room temperature, and then the mixture was extracted with dichloromethane. The organic layer was dried and concentrated to afford 8.35 g (100%) of the title compound used directly in the next reaction.

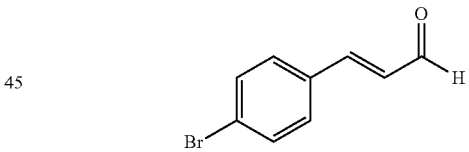

Example 7.1C (E)-3-(4-bromophenyl)acrylaldehyde

To the product of Example 7.1B (8.35 g, 39.2 mmol) dissolved in dichloromethane (151 mL) was added pyridinium dichromate (22.11 g, 58.8 mmol), and the resultant mixture was stirred for 16 hours at room temperature. A solution of hexane was added, and the resultant mixture filtered through diatomaceous earth, and then concentrated. Water was added to the residue, and the mixture was extracted with ethyl acetate. The organic layers were combined, dried and then concentrated. The residue was purified by chromatography (silica gel, hexanes in ethyl acetate) which afforded 5.5 g, (67%) of the title compound. $^1$H NMR (400 MHz, CDCl$_3$) δ ppm 9.62 (d, J=7.6 Hz, 1H), 7.57 (d, J=8.5 Hz, 2H), 7.42 (m, 3H), 6.70 (dd, J=15.9, 7.6 Hz, 1H).

531

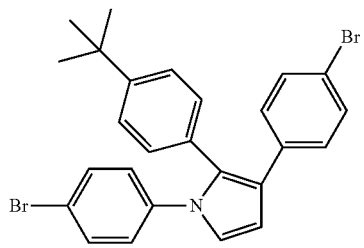 [SMILES: CC(C)(C)c1ccc(-c2c(-c3ccc(Br)cc3)ccn2-c2ccc(Br)cc2)cc1]

Example 7.1D 1,3-bis(4-bromophenyl)-2-(4-tert-butylphenyl)-1H-pyrrole

To the product of Example 7.1C (0.676 g, 3.2 mmol) and the product from Example 7.1A (1.0 g, 2.91 mmol) was added ethanol (30 mL) followed by potassium hydroxide (0.163 g, 2.91 mmol), and the mixture was stirred at room temperature for 16 hours. Afterwards the mixture was concentrated. The residue was partitioned between water and ethyl acetate. The organic layers were combined, dried and then concentrated. The residue was purified by chromatography (silica gel, hexanes in ethyl acetate) which afforded 150 mg, (10%) of the title compound. $^1$H NMR (400 MHz, CDCl$_3$) δ ppm 7.37 (m, 3H), 7.32 (d, J=8.5, 2H), 7.21 (d, J=8.4 Hz, 2H), 7.06 (d, J=8.3 Hz, 2H), 6.93 (m, 4H), 6.51 (dd, J=2.9 Hz, 1H), 1.29 (s, 9H).

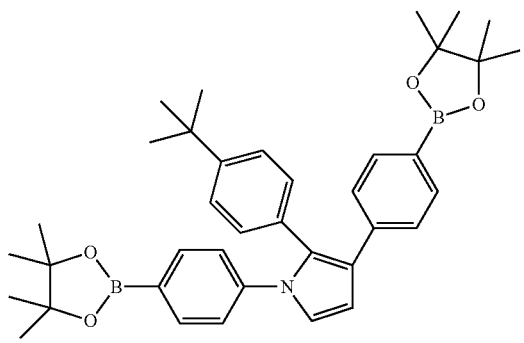

Example 7.1E 2-(4-tert-butylphenyl)-1,3-bis(4-(4,4,5,5-tetramethyl-1,3,2-dioxaborolan-2-yl)phenyl)-1H-pyrrole A solution of the product from Example 7.1D (150 mg, 0.295 mmol), 4,4,4',4',5,5,5',5'-octamethyl-2,2'-bi(1,3,2-dioxaborolane) (165 mg, 0.648 mmol), potassium acetate (87 mg, 8.84 mmol) and [1,1'-bis(diphenylphosphino)ferrocene]dichloropalladium(II), complex with dichloromethane (21.6 mg, 0.029 mmol) in dioxane (5.5 mL) was heated at 100° C. for 18 hours. The mixture was then filtered through diatomaceous earth and concentrated to an oil which was dissolved in EtOAc and extracted with brine. The organic extract was concentrated to afford 230 mg of the title compound that was used directly in the next step.

532

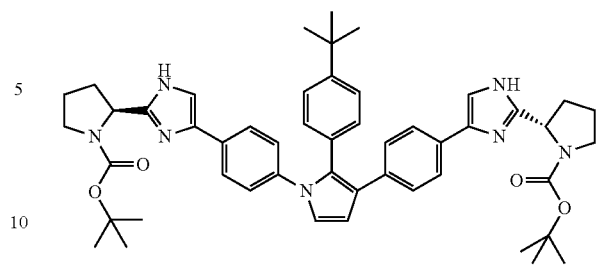

Example 7.1F di-tert-butyl(2S,2'S)-2,2'-{[2-(4-tert-butylphenyl)-1H-pyrrole-1,3-diyl]bis(benzene-4,1-diyl-1H-imidazole-4,2-diyl)}dipyrrolidine-1-carboxylate (ACD Name v12)

The product from Example 7.1E (227 mg, 0.376 mmol), (S)-tert-butyl 2-(5-bromo-1H-imidazol-2-yl)pyrrolidine-1-carboxylate or (S)-tert-butyl 2-(4-bromo-1H-imidazol-2-yl)pyrrolidine-1-carboxylate (357 mg, 1.13 mmol), [1,1'-bis(diphenylphosphino)ferrocene]dichloropalladium(II), complex with dichloromethane (27.5 mg, 0.038 mmol), and a solution of sodium carbonate (1.0 M in water, 1.13 mL, 1.13 mmol) were heated in a solution of ethanol (3 mL) and toluene (3 mL) at 85° C. for 18 hours. The mixture then had water (10 mL) added followed by extraction with EtOAc (2×10 mL). The organic extract was dried, filtered and concentrated, and then the residue was purified by chromatography (silica gel, methanol in dichloromethane) which afforded 29 mg, (9%) of the title compound; MS (ESI) m/z 823 (M+H)$^+$.

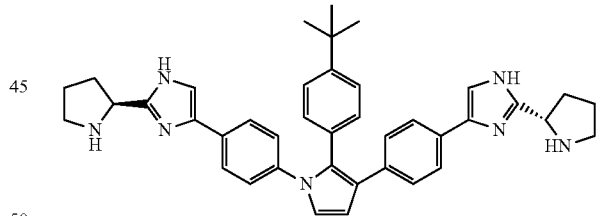

Example 7.1G 4,4'-{[2-(4-tert-butylphenyl)-1H-pyrrole-1,3-diyl]dibenzene-4,1-diyl}bis{2-yl]-1H-imidazole} (ACD Name v12)

The product of Example 7.1F (29 mg, 0.035 mmol) was dissolved in dioxane (0.5 mL) and hydrochloric acid in dioxane (4.0 N, 0.14 mL, 0.54 mmol) was added. The mixture was stirred at room temperature for 4 hours. Afterwards the mixture was concentrated to afford the title compound as a hydrochloride salt. MS (ESI) m/z 622 (M+H)$^+$.

533

Example 7.1H methyl {(2S)-1-[(2S)-2-(4-{4-[2-(4-tert-butylphenyl)-1-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-3-yl]phenyl}-1H-imidazol-2-yl)pyrrolidin-1-yl]-3-methyl-1-oxobutan-2-yl}carbamate The product from Example 7.1G (22 mg, 0.036 mmol), (S)-2-(methoxycarbonylamino)-3-methylbutanoic acid (12.7 mg, 0.072 mmol), N-(3-dimethylaminopropyl)-N'-ethylcarbodiimide hydrochloride (15.2 mg, 0.079 mmol), 1-hydroxybenzotriazole hydrate (12.2 mg, 0.079 mmol) and 4-methylmorpholine (0.021 mL, 0.29 mmol) were dissolved in DMF (0.7 mL), and the mixture was stirred at room temperature for 3 hours. Afterwards, 1 N aqueous hydrochloric acid (5 mL) was added followed by extraction with dichloromethane (2×5 mL). The organic extract was dried, filtered and concentrated. Then the residue was purified by chromatography (silica gel, methanol in dichloromethane) which afforded 3.3 mg, (10%) of the title compound. $^1$H NMR (400 MHz, DMSO-$d_6$) δ ppm 10.57 (s, 1H), 10.26 (s, 1H), 7.62 (m, 4H), 7.20 (m, 8H), 6.99 (m, 4H), 5.37 (m, 2H), 5.24 (m, 2H), 4.30 (m, 2H), 3.80 (m, 2H), 3.08 (m, 1H), 2.96 (s, 3H), 2.88 (s, 3H), 2.30 (m, 2H), 2.19 (m, 2H), 2.08 (m, 2H), 1.92 (m, 2H), 1.23 (m, 9H), 0.85 (m, 12H); MS (ESI) m/z 936 (M+H)$^-$.

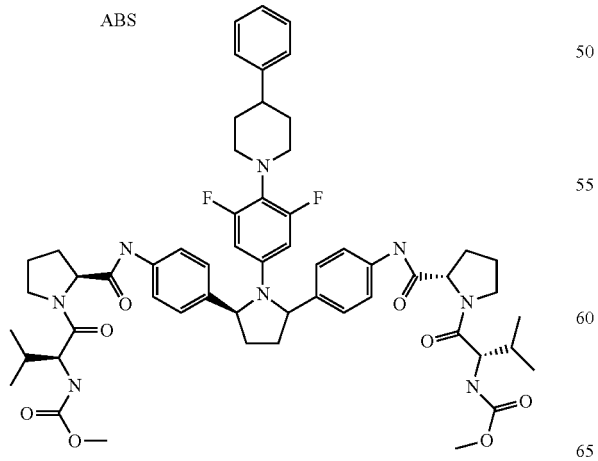

534

Example 8 dimethyl({(2S)-1-[3,5-difluoro-4-(4-phenylpiperidin-1-yl)phenyl]pyrrolidine-2,5-diyl}bis{4,1-phenylenecarbamoyl(2S)pyrrolidine-2,1-diyl[(2S)-3-methyl-1-oxobutane-1,2-diyl]})biscarbamate

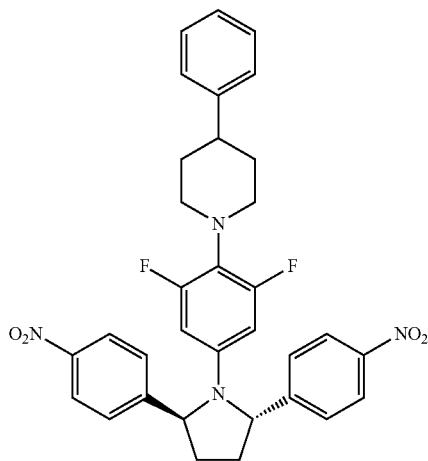

Example 8A 1-(4-((2S,5S)-2,5-bis(4-nitrophenyl)pyrrolidin-1-yl)-2,6-difluorophenyl)-4-phenylpiperidine A mixture of Intermediate 6 (2.68 g, 5.49 mmol), 3,5-difluoro-4-(4-phenylpiperidin-1-yl)aniline (1.90 g, 6.58 mmol) and diisopropylethylamine (9.58 mL, 54.9 mmol) in DMF (18.3 mL) was heated at 60° C. for 18 hours. Afterwards ethyl acetate was added to the solution followed by extraction with water. The organic extract was dried, filtered and concentrated then the residue purified by chromatography (silica gel, ethyl acetate in hexanes) which afforded 197 mg, (6%) of the title compound. MS (ESI) m/z 585 (M+H)$^+$.

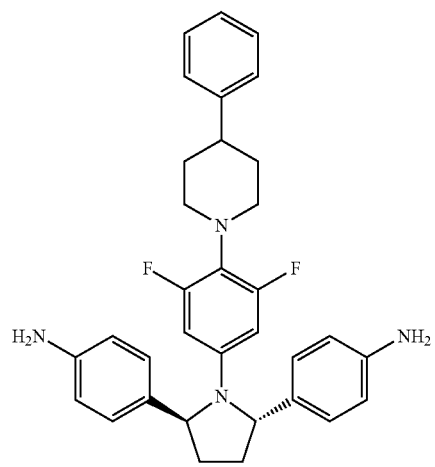 [SMILES: O=[N+]([O-])c1ccc([C@@H]2CC[C@@H](c3ccc([N+](=O)[O-])cc3)N2c2cc(F)c(N3CCC(c4ccccc4)CC3)c(F)c2)cc1]

Example 8B 4,4'-((2S,5S)-1-(3,5-difluoro-4-(4-phenylpiperidin-1-yl)phenyl)pyrrolidin-2,5-diyl)dianiline The product of Example 8A (197 mg, 0.337 mmol) was dissolved in a mixture of THF (3 mL), ethanol (3 mL) and water (0.5 mL), and then iron (95 mg, 1.69 mmol) and ammonium chloride (27 mg, 0.506 mmol) were added and the mixture heated at 80° C. for 3 hours. Afterwards ethyl acetate was added to the solution followed by extraction with sodium bicarbonate. The organic extract was dried, filtered and concentrated which afforded 177 mg (100%) of the title compound. MS (ESI) m/z 525 (M+H)+.

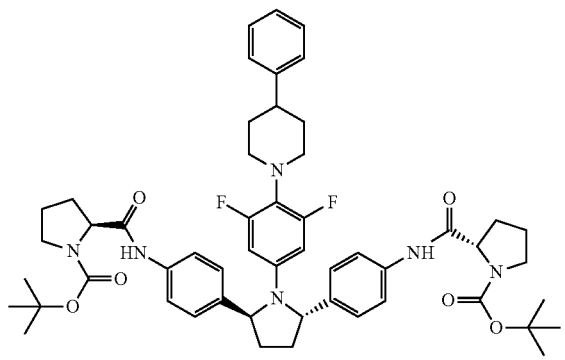 [SMILES: CC(C)(C)OC(=O)N1CCC[C@H]1C(=O)Nc1ccc([C@@H]2CC[C@@H](c3ccc(NC(=O)[C@@H]4CCCN4C(=O)OC(C)(C)C)cc3)N2c2cc(F)c(N3CCC(c4ccccc4)CC3)c(F)c2)cc1]

Example 8C (2S,2'S)-tert-butyl 2,2'-(4,4'-((2S,5S)-1-(3,5-difluoro-4-(4-phenylpiperidin-1-yl)phenyl)pyrrolidine-2,5-diyl)bis(4,1-phenylene))bis(azanediyl)bis(oxomethylene)dipyrrolidine-1-carboxylate The product from Example 8B (177 mg, 0.337 mmol), (S)-1-(tert-butoxycarbonyl)pyrrolidine-2-carboxylic acid (160 mg, 0.742 mmol), N-(3-dimethylaminopropyl)-N'-ethylcarbodiimide hydrochloride (162 mg, 0.843 mmol), 1-hydroxybenzotriazole hydrate (129 mg, 0.843 mmol) and 4-methylmorpholine (0.370 mL, 3.37 mmol) were dissolved in dichloromethane (3.5 mL), and the mixture stirred at room temperature for 19 hours. Afterwards, aqueous sodium bicarbonate was added followed by extraction with dichloromethane. The organic extract was dried, filtered and concentrated, and then the residue was purified by chromatography (silica gel, methanol in dichloromethane) which afforded 130 mg, (42%) of the title compound. MS (ESI) m/z 920 (M+H)+.

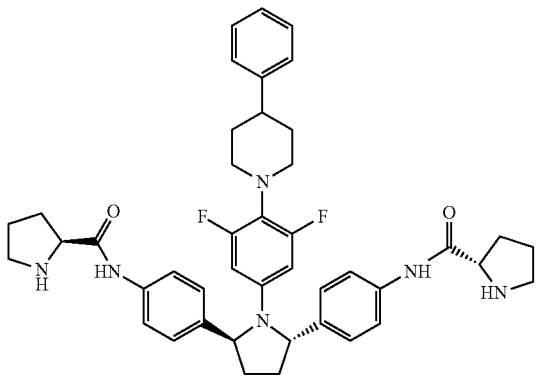 [SMILES: O=C(Nc1ccc([C@@H]2CC[C@@H](c3ccc(NC(=O)[C@@H]4CCCN4)cc3)N2c2cc(F)c(N3CCC(c4ccccc4)CC3)c(F)c2)cc1)[C@@H]1CCCN1]

Example 8D (2S,2'S)—N,N'-(4,4'-((2S,5S)-1-(3,5-difluoro-4-(4-phenylpiperidin-1-yl)phenyl)pyrrolidine-2,5-diyl)bis(4,1-phenylene))dipyrrolidine-2-carboxamide The product of Example 8C (130 mg, 0.141 mmol) was dissolved in dichloromethane (2.7 mL) and trifluoroacetic acid (0.27 mL, 3.5 mmol) and the mixture was stirred at room temperature for 1 hour. Afterwards the mixture was concentrated, the residue was dissolved in an isopropyl alcohol and chloroform mixture and then extracted with aqueous sodium bicarbonate. The organic phase was then dried and concentrated to afford 100 mg (99%) of the title compound. MS (ESI) m/z 719 (M+H)+.

Example 8E dimethyl({(2S)-1-[3,5-difluoro-4-(4-phenylpiperidin-1-yl)phenyl]pyrrolidine-2,5-diyl}bis{4,1-phenylenecarbamoyl(2S)pyrrolidine-2,1-diyl[(2S)-3-methyl-1-oxobutane-1,2-diyl]})biscarbamate The product from Example 8D (100 mg, 0.142 mmol), (S)-2-(methoxycarbonylamino)-3-methylbutanoic acid (60 mg, 0.341 mmol), N-(3-dimethylaminopropyl)-N'-ethylcarbodiimide hydrochloride (68 mg, 0.355 mmol), 1-hydroxybenzotriazole hydrate (54 mg, 0.355 mmol) and 4-methylmorpholine (0.156 mL, 1.42 mmol) were dissolved in DMF (1.5 mL), and the mixture was stirred at room temperature for 19 hours. Afterwards, an isopropyl alcohol and chloroform mixture was added and then extracted with aqueous sodium bicarbonate. The organic extract was dried, filtered and concentrated, and then the residue was purified by chromatography (silica gel, methanol in dichloromethane) which afforded 20 mg, (14%) of the title compound. $^1$H NMR (400 MHz, DMSO-$d_6$) δ ppm 10.03 (s, 2H), 7.53 (d, J=8.5 Hz, 4H), 7.30 (m, 9H), 5.83 (d, J=12.6 Hz, 2H), 5.18 (m, 2H), 5.08 (m, 2H), 4.43 (m, 2H), 4.02 (m, 4H), 3.61 (m, 2H), 3.54 (s, 6H), 2.98 (m, 4H), 2.18 (m, 2H), 1.93 (m, 6H), 1.70 (m, 6H), 0.81 (m, 12H); MS (ESI) m/z 1033 (M+H)+.

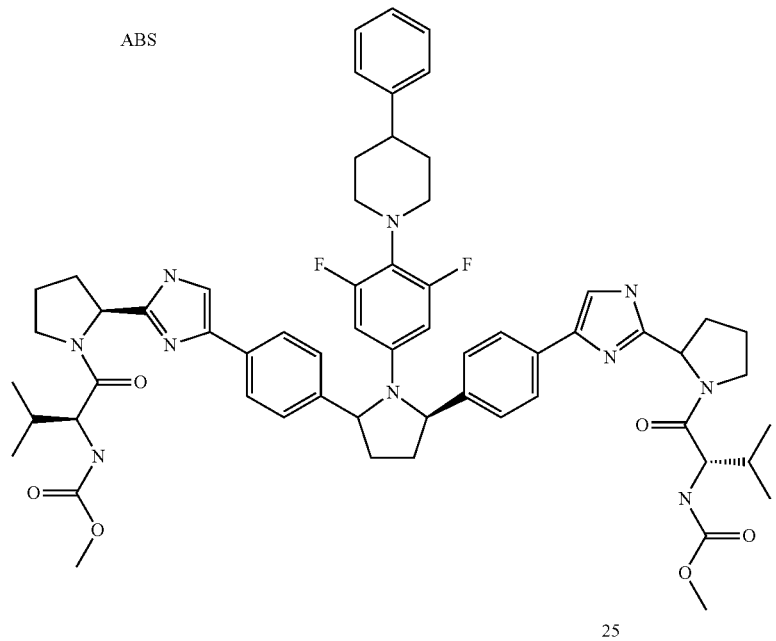

Example 9 methyl {(2S)-1-[(2S)-2-(4-{4-[(2R,5R)-1-[3,5-difluoro-4-(4-phenylpiperidin-1-yl)phenyl]-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

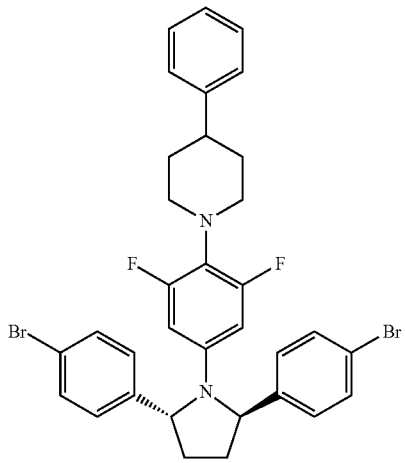 [SMILES: Fc1cc(N2[C@@H](c3ccc(Br)cc3)CC[C@@H]2c2ccc(Br)cc2)cc(F)c1N1CCC(c2ccccc2)CC1]

Example 9A 1-(4-((2R,5R)-2,5-bis(4-bromophenyl)pyrrolidin-1-yl)-2,6-difluorophenyl)-4-phenylpiperidine A mixture of Intermediate 7 (2.35 g, 4.22 mmol), 3,5-difluoro-4-(4-phenylpiperidin-1-yl)aniline (2.44 g, 8.45 mmol) and diisopropylethylamine (2.21 mL, 12.67 mmol) in acetonitrile (25 mL) was heated at 80° C. for 9 hours. Afterwards the resultant solid was removed by filtration and purified by chromatography (silica gel, hexanes in ethyl acetate then dichloromethane in hexanes) which afforded 130 mg, (4.7%) of the title compound. MS (ESI+) m/z 653 (M+H)$^+$.

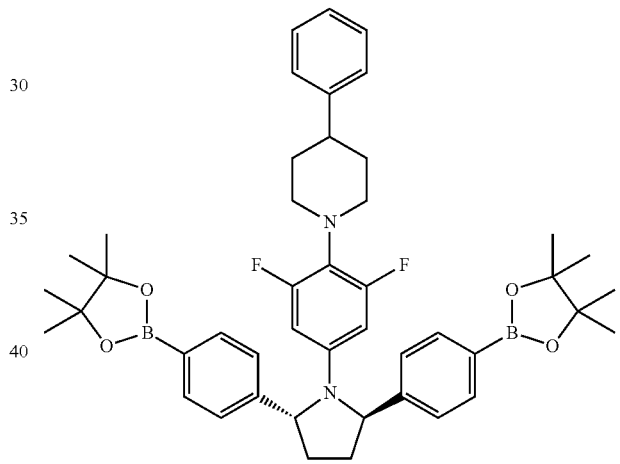

Example 9B 1-(4-((2R,5R)-2,5-bis(4-(4,4,5,5-tetramethyl-1,3,2-dioxaborolan-2-yl)phenyl)pyrrolidin-1-yl)-2,6-difluorophenyl)-4-phenylpiperidine A solution of the product from Example 9A (130 mg, 0.199 mmol), 4,4,4',4',5,5,5',5'-octamethyl-2,2'-bi(1,3,2-dioxaborolane) (121 mg, 0.478 mmol), potassium acetate (59 mg, 0.598 mmol) and [1,1'-bis(diphenylphosphino)ferrocene]dichloropalladium(II) (29 mg, 0.04 mmol) in dioxane (4.5 mL) was heated at 100° C. for 3 hours. The mixture was then filtered through diatomaceous earth and concentrated to an oil which was dissolved in EtOAc and extracted with 1 N aqueous hydrochloric acid. The organic extract was dried, filtered and concentrated, and then the residue was purified by chromatography (silica gel, ethyl acetate in hexanes) which afforded 50 mg, (34%) of the title compound. MS (ESI) m/z 747 (M+H)$^+$.

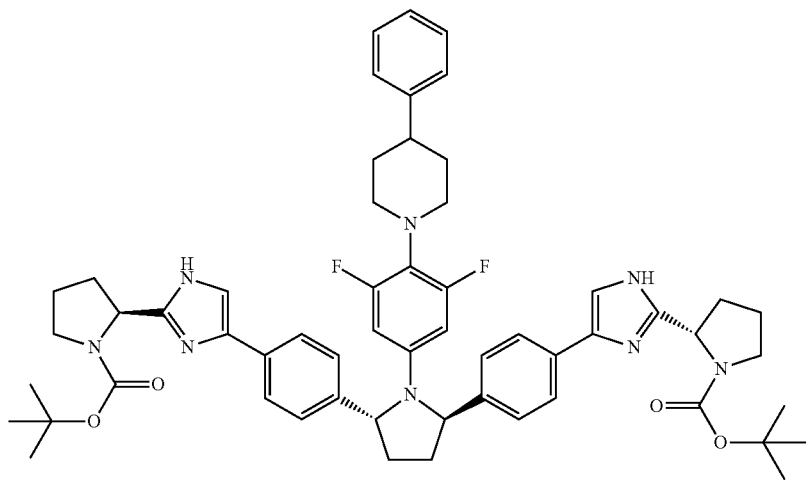 [SMILES: CC(C)(C)OC(=O)N1CCC[C@H]1c1nc(-c2ccc([C@H]3CC[C@H](c4ccc(-c5c[nH]c([C@@H]6CCCN6C(=O)OC(C)(C)C)n5)cc4)N3c3cc(F)c(N4CCC(c5ccccc5)CC4)c(F)c3)cc2)c[nH]1]

Example 9C (2S,2'S)-tert-butyl 2,2'-(4,4'-(4,4'-((2R,5R)-1-(3,5-difluoro-4-(4-phenylpiperidin-1-yl)phenyl)pyrrolidine-2,5-diyl)bis(4,1-phenylene))bis(1H-imidazole-4,2-diyl))dipyrrolidine-1-carboxylate The product from Example 9B (50 mg, 0.067 mmol), Intermediate 1 (64 mg, 0.201 mmol), [1,1'-bis(diphenylphosphino)ferrocene]dichloropalladium(II) (6.1 mg, 0.0084 mmol), and sodium carbonate (1.0 M in water, 0.27 mL, 0.27 mmol) were heated in ethanol (1.5 mL) and toluene (1.5 mL) at 85° C. for 17 hours. Water (10 mL) was added to the mixture followed by extraction with dichloromethane. The organic extract was dried, filtered and concentrated, and then the residue was purified by chromatography (silica gel, methanol in dichloromethane) which afforded 51 mg, (79%) of the title compound. MS (ESI) m/z 966 (M+H)+.

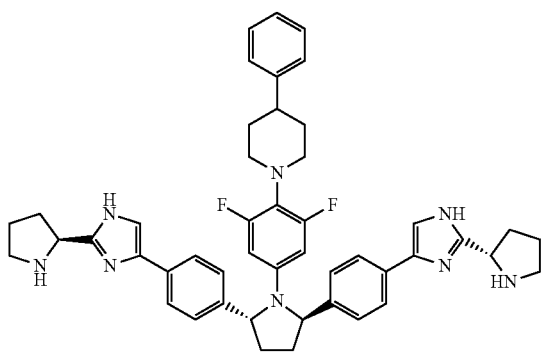 [SMILES: Fc1cc(N2[C@@H](c3ccc(-c4c[nH]c([C@@H]5CCCN5)n4)cc3)CC[C@@H]2c2ccc(-c3c[nH]c([C@@H]4CCCN4)n3)cc2)cc(F)c1N1CCC(c2ccccc2)CC1]

Example 9D 1-(4-((2R,5R)-2,5-bis(4-(2-((S)-pyrrolidin-2-yl)-1H-imidazol-4-yl)phenyl)pyrrolidin-1-yl)-2,6-difluorophenyl)-4-phenylpiperidine The product of Example 9C (50 mg, 0.052 mmol) was dissolved in dioxane (1.5 mL) and hydrochloric acid in dioxane (4.0 N, 0.65 mL, 2.6 mmol), and the mixture was stirred at room temperature for 4 hours. Afterwards the mixture was concentrated to afford the title compound as a hydrochloride salt. MS (ESI) m/z 765 (M+H)+.

Example 9E methyl {(2S)-1-[(2S)-2-(4-{4-[(2R,5R)-1-[3,5-difluoro-4-(4-phenylpiperidin-1-yl)phenyl]-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 9D (40 mg, 0.052 mmol), (S)-2-(methoxycarbonylamino)-3-methylbutanoic acid (18.3 mg, 0.105 mmol), N-(3-dimethylaminopropyl)-N'-ethylcarbodiimide hydrochloride (22.1 mg, 0.115 mmol), 1-hydroxybenzotriazole hydrate (17.6 mg, 0.115 mmol) and 4-methylmorpholine (0.046 mL, 0.418 mmol) were dissolved in DMF (1.5 mL), and the mixture was stirred at room temperature for 19 hours. Afterwards, 1 N aqueous hydrochloric acid was added followed by extraction with dichloromethane. The organic extract was dried, filtered and concentrated, and then the residue was purified by chromatography (silica gel, methanol in dichloromethane) which afforded 25 mg, (44%) of the title compound. $^1$H NMR (400 MHz, DMSO-$d_6$) δ ppm 7.64 (m, 5H), 7.23 (m, 11H), 5.89 (d, J=12.8 Hz, 2H), 5.23 (m, 2H), 5.08 (m, 2H), 4.06 (m, 2H), 3.80 (m, 4H), 3.53 (s, 6H), 2.96 (m, 4H), 2.18 (m, 2H), 1.99 (m, 6H), 1.70 (m, 6H), 0.83 (m, 12H); MS (ESI) m/z 1080 (M+H)+.

From the product of General Procedure 11C, the compounds of Examples 10.1 and 10.2 can be obtained by the steps of: (1) coupling with (S)-2-(methoxycarbonylamino)-3-methylbutanoic acid; (2) removal of the single Boc protecting group; and (3) coupling with a second selected carbamate-protected amino acid.

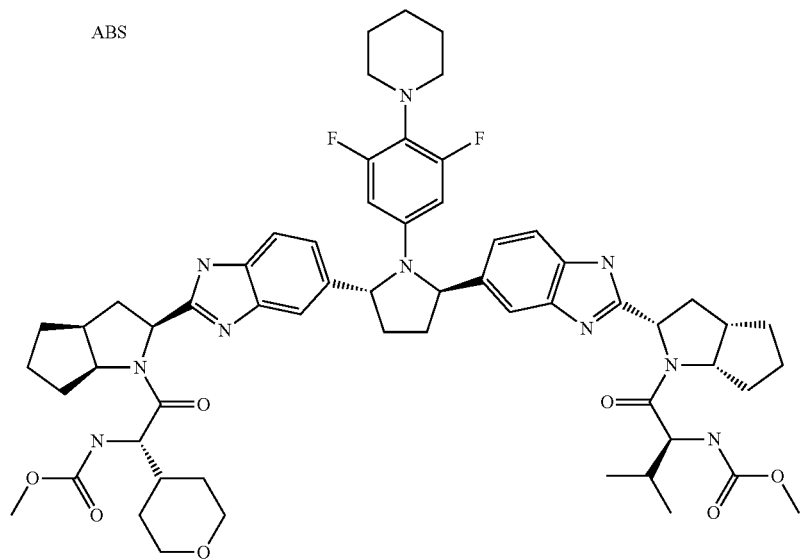

Example 10.1 methyl[(1S)-2-[(2S,3aS,6aS)-2-{5-[(2R,5R)-1-[3,5-difluoro-4-(piperidin-1-yl)phenyl]-5-{2-[(2S,3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-1H-benzimidazol-2-yl}hexahydrocyclopenta[b]pyrrol-1(2H)-yl]-2-oxo-1-(tetrahydro-2H-pyran-4-yl)ethyl]carbamate $^1$H NMR (400 MHz, DMSO-$d_6$) δ ppm 0.70-0.91 (m, 6H) 1.10-1.27 (m, 2H) 1.34-1.49 (m, 8H) 1.50-1.64 (m, 4H) 1.65-1.81 (m, 4H) 1.84-2.03 (m, 6H) 2.05-2.18 (m, 4H) 2.36-2.46 (m, 4H) 2.72-2.86 (m, 6H) 3.02-3.21 (m, 2H) 3.54 (s, 6H) 3.70-3.89 (m, 2H) 3.97-4.17 (m, 2H) 4.72-4.86 (m, 2H) 5.07-5.20 (m, 2H) 5.32-5.43 (m, 2H) 5.84-5.94 (m, 2H) 7.07 (t, J=10.08 Hz, 2H) 7.17-7.27 (m, 2H) 7.30-7.56 (m, 4H) 11.92-11.99 (m, 1H) 12.03-12.13 (m, 1H); MS (ESI+) m/z 1073.4 (M+H)$^+$.

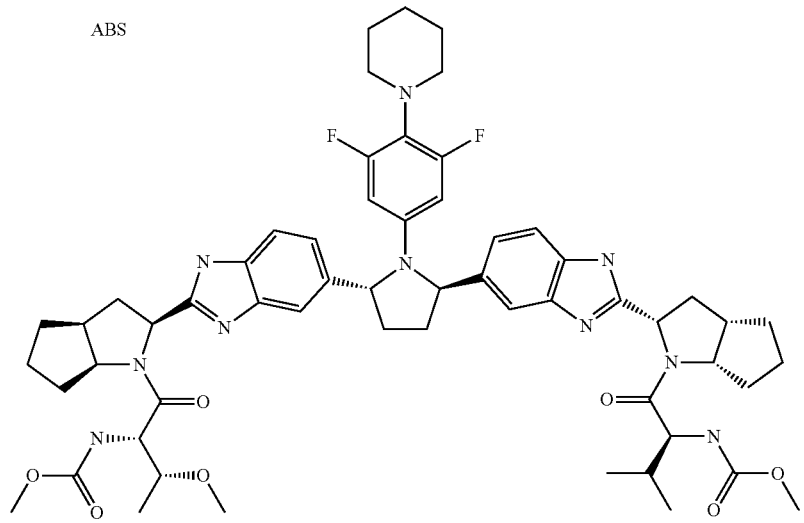

543
Example 10.2 methyl {(2S,3R)-1-[(2S,3aS,6aS)-2-{5-[(2R,5R)-1-[3,5-difluoro-4-(piperidin-1-yl)phenyl]-5-{2-[(2S,3aS,6aS)-1-{(2S)-2-[(methoxycarbonyl)amino]-3-methylbutanoyl}octahydrocyclopenta[b]pyrrol-2-yl]-1H-benzimidazol-5-yl}pyrrolidin-2-yl]-1H-benzimidazol-2-yl}hexahydrocyclopenta[b]pyrrol-1(2H)-yl]-3-methoxy-1-oxobutan-2-yl}carbamate $^1$H NMR (400 MHz, DMSO-d$_6$) δ ppm 0.70-0.89 (m, 6H) 0.99 (ddd, J=34.43, 6.29, 3.31 Hz, 3H) 1.35-1.48 (m, 6H) 1.50-1.63 (m, 4H) 1.66-1.80 (m, 6H) 1.83-2.00 (m, 6H) 2.05-2.16 (m, 4H) 2.72-2.83 (m, 4H) 3.17 (s, 3H) 3.21-3.28 (m, 4H) 3.54 (s, 6H) 4.02 (t, J=7.48 Hz, 1H) 4.20-4.30 (m, 1H) 4.80 (t, J=7.97 Hz, 2H) 5.08-5.17 (m, 2H) 5.32-5.43 (m, 2H) 5.83-5.94 (m, 2H) 7.05 (dd, J=8.24, 1.30 Hz, 2H) 7.21 (s, 1H) 7.30 (d, J=3.14 Hz, 1H) 7.40 (d, J=7.92 Hz, 1H) 7.45-7.56 (m, 3H) 11.99 (dd, J=9.87, 1.63 Hz, 1H) 12.04-12.13 (m, 1H); MS (ESI+) m/z 1047.5 (M+H)$^+$.

From the product of General Procedure 8B, Example 1B (mono-displacement), the compounds of Examples 11.1 and 11.2 can be obtained by the steps of: (1) Buchwald reaction with an appropriate second amide (see General Procedure 8); (2) nitro reduction (see General Procedure 9); and (3) cyclization (see General Procedure 10).

544
Example 11.1 methyl[(1S)-2-[(2S)-2-{5-[(2R,5R)-1-[3,5-difluoro-4-(4-phenylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-2-oxo-1-(tetrahydro-2H-pyran-4-yl)ethyl]carbamate $^1$H NMR (400 MHz, DMSO-d$_6$) δ ppm 0.74-0.91 (m, 6H) 1.44-1.56 (m, 2H) 1.62-1.75 (m, 6H) 1.82-1.95 (m, 2H) 1.97-2.07 (m, 4H) 2.16-2.26 (m, 4H) 2.87-3.16 (m, 7H) 3.43-3.50 (m, 2H) 3.53 (s, 6H) 3.58-3.66 (m, 2H) 3.70-3.78 (m, 2H) 3.80-3.89 (m, 4H) 4.06 (t, J=8.51 Hz, 2H) 5.11-5.19 (m, 2H) 5.33-5.43 (m, 2H) 5.86-5.95 (m, 2H) 7.06-7.11 (m, 2H) 7.12-7.37 (m, 9H) 7.42 (dd, J=7.92, 1.73 Hz, 1H) 7.46-7.53 (m, 1H) 12.04-12.20 (m, 2H); MS (ESI+) m/z 1069.4 (M+H)$^+$.

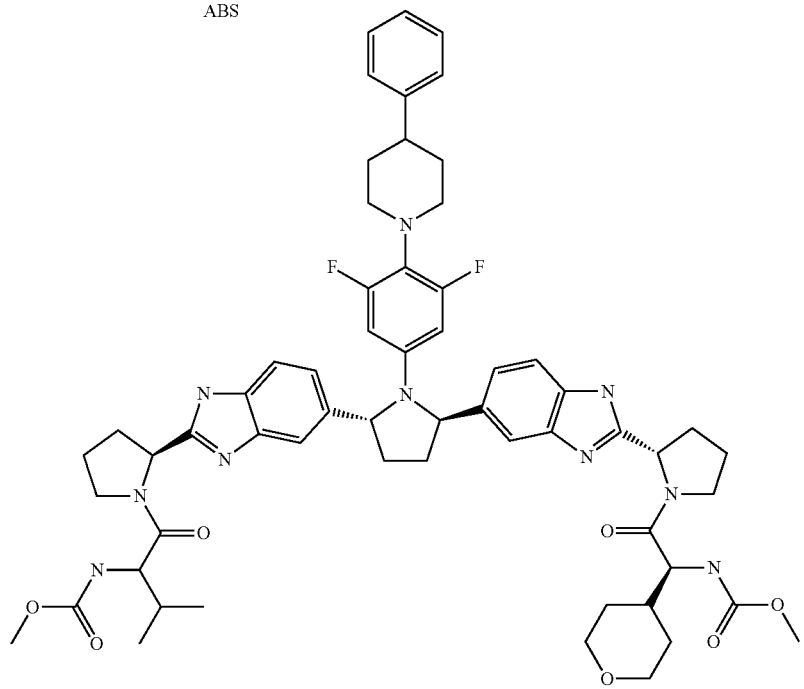

ABS

ABS

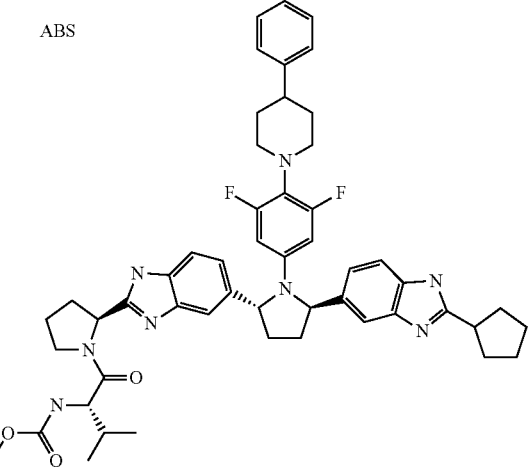

Example 11.2 methyl {(2S)-1-[(2S)-2-(5-{(2R,5R)-5-(2-cyclopentyl-1H-benzimidazol-5-yl)-1-[3,5-difluoro-4-(4-phenylpiperidin-1-yl)phenyl]pyrrolidin-2-yl}-1H-benzimidazol-2-yl)pyrrolidin-1-yl]-3-methyl-1-oxobutan-2-yl}carbamate $^1$H NMR (400 MHz, DMSO-$d_6$) δ ppm 0.76-0.91 (m, 6H) 1.59-1.73 (m, 10H) 1.73-1.80 (m, 2H) 1.83-1.94 (m, 4H) 1.97-2.08 (m, 4H) 2.16-2.24 (m, 1H) 2.86-3.04 (m, 6H) 3.19-3.29 (m, 1H) 3.53 (s, 3H) 3.79-3.87 (m, 2H) 5.11-5.19 (m, 1H) 5.34-5.42 (m, 2H) 5.88-5.95 (m, 2H) 7.03-7.11 (m, 2H) 7.13-7.19 (m, 2H) 7.20-7.27 (m, 4H) 7.28-7.34 (m, 2H) 7.40 (dd, J=13.88, 8.24 Hz, 1H) 7.50 (d, J=8.02 Hz, 1H) 12.05 (d, J=10.63 Hz, 1H) 12.12 (d, J=3.90 Hz, 1H); MS (ESI+) m/z 869.4 (M+H)$^+$.

The present invention also contemplates pharmaceutically acceptable salts of each title compound described in the above examples. All of the examples disclosed in U.S. patent application Ser. No. 12/813,301, filed Jun. 10, 2010 and now U.S. Pat. No. 8,691,938, are also incorporated herein by reference.

When tested using HCV 1b-Con1 replicon assays in the presence of 5% FBS, each title compound in 1.1, 1.3, 1.5, 1.6, 1.7, 1.8, 2.1, 2.2, 2.4, 2.5, 2.6, 2.9, 2.10, 2.11, 2.12, 2.13, 2.14, 2.15, 2.16, 2.17, 3.1, 3.11, 3.12, 3.13, 3.15, 3.17, 3.18, 3.19, 3.2, 3.20, 3.21, 3.22, 3.23, 3.24, 3.25, 3.26, 3.27, 3.28, 3.29, 3.30, 3.31, 3.32, 3.33, 3.34, 3.35, 3.36, 3.37, 3.38, 3.39, 3.4, 3,42, 3.43, 3.44, 3.45, 3.5, 3.6, 3.7, 3.8, 4.1, 4.10, 4.11, 4.12, 4.13, 4.14, 4.15, 4.16, 4.17, 4.18, 4.19, 4.2, 4.20, 4.21, 4.22, 4.23, 4.24, 4.26, 4.27, 4.28, 4.29, 4.3, 4.30, 4.31, 4.32, 4.33, 4.34, 4.35, 4.36, 4.37, 4.4, 4.41, 4.42, 4.43, 4.44, 4.47, 4.49, 4.5, 4.50, 4.51, 4.52, 4.56, 4.58, 4.59, 4.6, 4.60, 4.7, 4.8, 4.9, 5.10, 5.1, 5.11, 5.12, 5.13, 5.14, 5.15, 5.2, 5.3, 5.4, 5.5, 5.6, 5.7, 5.8, 5.9, 6.1, 6.10, 6.11, 6.12, 6.13, 6.14, 6.15, 6.16, 6.2, 6.3, 6.4, 6.5, 6.6, 6.7, 6.8, 6.9, 7.1, 8, 9, 10.1, 10.2, 11.1, and 11.2 showed showed an $EC_{50}$ value of less than about 0.1 nM. When tested using HCV 1b-Con1 replicon assays in the presence of 5% FBS, each title compound in Examples 1.4, 2.8, 3.10, 3.16, 3.3, 3.9 and 4.25 showed an $EC_{50}$ value of from about 0.1 to about 1 nM. When tested using HCV 1b-Con1 replicon assays in the presence of 5% FBS, each title compound in Examples 2.3 and 2.7 showed an $EC_{50}$ value of from about 1 to about 10 nM. The tile compounds of Example 1.2 and 3.14 showed an $EC_{50}$ value of over 10 μM when tested using HCV 1b-Con1 replicon assays in the presence of 5% FBS.

Each compound's anti-HCV activity can be determined by measuring the activity of the luciferase reporter gene in the replicon in the presence of 5% FBS. The luciferase reporter gene is placed under the translational control of the poliovirus IRES instead of the HCV IRES, and HuH-7 cells are used to support the replication of the replicon.

The inhibitory activities of the compounds of the present invention can be evaluated using a variety of assays known in the art. For instance, two stable subgenomic replicon cell lines can be used for compound characterization in cell culture: one derived from genotype 1a-H77 and the other derived from genotype 1b-Con1, obtained from University of Texas Medical Branch, Galveston, Tex. or Apath, LLC, St. Louis, Mo., respectively. The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the HCV 5' UTR, 3' UTR, and NS3-NS5B coding region are derived from the 1b-Con1 strain, and the adaptive mutations are K1609E, K1846T and Y3005C. In addition, the 1b-Con1 replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 μl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 μl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators after which time 30 μl of Passive Lysis buffer (Promega) can be added to each well, and then the plates are incubated for 15 minutes with rocking to lyse the cells. Luciferin solution (100 μl, Promega) can be added to each well, and luciferase activity can be measured with a Victor II luminometer (Perkin-Elmer). The percent inhibition of HCV RNA replication can be calculated for each compound concentration and the $EC_{50}$ value can be calculated using nonlinear regression curve fitting to the 4-parameter logistic equation and GraphPad Prism 4 software. Using the above-described assays or similar cell-based replicon assays, representative compounds of the present invention showed significantly inhibitory activities against HCV replication.

The present invention also features pharmaceutical compositions comprising the compounds of the invention. A pharmaceutical composition of the present invention can comprise one or more compounds of the invention, each of which has Formula I (or $I_A$, $I_B$, $I_C$, $I_D$, $I_E$, $I_F$ or $I_G$).

In addition, the present invention features pharmaceutical compositions comprising pharmaceutically acceptable salts, solvates, or prodrugs of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt, solvate or prodrug thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immuno-modulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio-025, NIM-811, R7128, R1626, R4048, T-1106, PSI-7851 (Pharmasset) (nucleoside polymerase inhibitor), PSI-938 (Pharmasset) (nucleoside polymerase inhibitor), PF-00868554, ANA-598, IDX184 (nucleoside polymerase inhibitor), IDX102, IDX375 (non-nucleoside polymerase inhibitor), GS-9190 (non-nucleoside polymerase inhibitor), VCH-759, VCH-916, MK-3281, BCX-4678, MK-3281, VBY708, ANA598, GL59728, GL60667, BMS-790052 (NS5A inhibitor), BMS-791325 (protease Inhibitor), BMS-650032, BMS-824393, GS-9132, ACH-1095 (protease inhibitor), AP-H005, A-831 (Arrow Therapeutics) (NS5A inhibitor), A-689 (Arrow Therapeutics) (NS5A inhibitor), INX08189 (Inhibitex) (polymerase inhibitor), AZD2836, telaprevir (protease Inhibitor), boceprevir (protease Inhibitor), ITMN-191 (Intermune/Roche), BI-201335 (protease Inhibitor), VBY-376, VX-500 (Vertex) (protease Inhibitor), PHX-B, ACH-1625, IDX136, IDX316, VX-813 (Vertex) (protease Inhibitor), SCH 900518 (Schering-Plough), TMC-435 (Tibotec) (protease Inhibitor), ITMN-191 (Intermune, Roche) (protease Inhibitor), MK-7009 (Merck) (protease Inhibitor), IDX-PI (Novartis), BI-201335 (Boehringer Ingelheim), R7128 (Roche) (nucleoside polymerase inhibitor), MK-3281 (Merck), MK-0608 (Merck) (nucleoside polymerase inhibitor), PF-868554 (Pfizer) (non-nucleoside polymerase inhibitor), PF-4878691 (Pfizer), IDX-184 (Novartis), IDX-375 (Pharmasset), PPI-461 (Presidio) (NS5A inhibitor), BILB-1941 (Boehringer Ingelheim), GS-9190 (Gilead), BMS-790052 (BMS), Albuferon (Novartis), ABT-450 (Abbott/Enanta) (protease Inhibitor), ABT-333 (Abbott) (non-nucleoside polymerase inhibitor), ABT-072 (Abbott) (non-nucleoside polymerase inhibitor), ritonavir, another cytochrome P450 monooxygenase inhibitor, or any combination thereof.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. For example, a pharmaceutical composition of the present invention can comprise a compound(s) of the present invention having Formula I, $I_A$, $I_B$, $I_C$, $I_D$, $I_E$, $I_F$ or $I_G$ (or a salt, solvate or prodrug thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NS5A inhibitors.

In yet another embodiment, a pharmaceutical composition of the present invention comprises one or more compounds of the present invention (or salts, solvates or prodrugs thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art.

In a preferred embodiment, a pharmaceutical composition of the invention comprises a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), and a HCV protease inhibitor. In another preferred embodiment, a pharmaceutical composition of the invention comprises a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), and a HCV polymerase inhibitor (e.g., a non-nucleoside polymerase inhibitor, or preferably a nucleoside polymerase inhibitor). In yet another preferred embodiment, a pharmaceutical composition of the present invention comprises (1) a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), (2) a HCV protease inhibitor, and (3) a HCV polymerase inhibitor (e.g., a non-nucleoside polymerase inhibitor, or preferably a nucleoside polymerase inhibitor). Non-limiting examples of protease and polymerase inhibitors are described above.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

In a preferred embodiment, a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof) is formulated in a solid dispersion, where the compound of the invention can be molecularly dispersed in an amorphous matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt-extrusion, spray-drying, co-precipitation, freeze drying, or other solvent evaporation techniques, with melt-extrusion and spray-drying being preferred. In one example, a compound of the invention is formulated in a solid dispersion comprising copovidone and vitamin E TPGS. In another example, a compound of the invention is formulated in a solid dispersion comprising copovidone and Span 20.

A solid dispersion described herein may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion described herein may also contain at least 1% by weight of a pharmaceutically acceptable surfactant or a combination of such surfactants. Preferably, the solid dispersion contains at least 2% by weight of a pharmaceutically acceptable surfactant or a combination of such surfactants. More preferably, the solid dispersion contains from 4% to 20% by weight of the surfactant(s), such as from 5% to 10% by weight of the surfactant(s). In addition, a solid dispersion described herein may contain at least 1% by weight of a compound of the invention, preferably at least 5%, including, e.g., at least 10%. In one example, the solid dispersion comprises 5% of a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), which is molecularly dispersed in a an amorphous matrix comprising 7% Vitamin E-TPGS and 88% copovidone; the solid dispersion can also be mixed with other excipients such as mannitol/aerosil (99:1), and the weight ratio of the solid dispersion over the other excipients can range from 5:1 to 1:5 with 1:1 being preferred. In another example, the solid dispersion comprises 5% of a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), which is molecularly dispersed in a an amorphous matrix comprising 5% Span 20 and 90% copovidone; the solid dispersion can also be mixed with other excipients such as mannitol/aerosil (99:1), the solid dispersion can also be mixed with other excipients such as mannitol/aerosil (99:1), and the weight ratio of the solid dispersion over the other excipients can range from 5:1 to 1:5 with 1:1 being preferred.

Various additives can also be included in or mixed with the solid dispersion. For instance, at least one additive selected from flow regulators, binders, lubricants, fillers, disintegrants, plasticizers, colorants, or stabilizers may be used in compressing the solid dispersion to tablets. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like. Non-limiting examples of stabilizers include antioxidants, light stabilizers, radical scavengers, or stabilizers against microbial attack.

The present invention further features methods of using the compounds of the present invention (or salts, solvates or prodrugs thereof) to inhibit HCV replication. The methods comprise contacting cells infected with HCV virus with an effective amount of a compound of the present invention (or a salt, solvate or prodrug thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may inhibit one or more HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c, 3a or 4a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. The methods typically comprise administering a therapeutic effective amount of a compound of the present invention (or a salt, solvate or prodrug thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof), or a pharmaceutical composition comprising the same, to an HCV patient, thereby reducing the HCV viral level in the blood or liver of the patient.

A compound of the present invention (or a salt, solvate or prodrug thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention. In one embodiment, the present invention features methods of treating HCV infection, wherein said methods comprise administering a compound of the invention (e.g., a compound of Formula I, $I_A$, $I_B$, $I_C$, $I_D$, $I_E$, $I_F$ or $I_G$, or preferably a compound described hereinabove, or a salt, solvate or prodrug thereof), interferon and ribavirin to an HCV patient. The interferon preferably is α-interferon, and more preferably, pegylated interferon-α such as PEGASYS (peginterferon alfa-2a).

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The present invention further features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

The compounds of the present invention can also be isotopically substituted. Preferred isotopic substitution include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 5 mol % (e.g., at least 10 mol %) of hydrogen in a compound of the present invention is substituted with deuterium. In another example, at least 25 mole % of hydrogen in a compound of the present invention is substituted with deuterium. In a further example, at least 50, 60,70, 80 or 90 mole % of hydrogen in a compound of the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound having Formula I, or a pharmaceutically acceptable salt thereof,

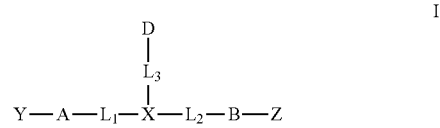

wherein:
X is $C_3$-$C_{12}$carbocycle or 3- to 12-membered heterocycle, and is optionally substituted with one or more $R_A$;
$L_1$, $L_2$, and $L_3$ are bond;
A is 5- to 6-membered heterocycle;
B is $C_3$-$C_{12}$carbocycle or 3- to 12-membered heterocycle;
D is phenyl, and is optionally substituted with one or more $R_A$;
Y is —C($R_1R_2$)N($R_5$)—C(O)-$L_Y$-N($R_B$")C(O)-$L_S$-$R_E$, wherein $L_Y$ is $C_1$-$C_6$alkylene, and $R_B$" is hydrogen;
$R_1$ is hydrogen, and $R_2$ and $R_5$, taken together with the atoms to which they are attached, form a 5- to 6-membered heterocycle;
Z is —C($R_8R_9$)N($R_{12}$)—C(O)-$L_Y$-N($R_B$")C(O)-$L_S$-$R_E$, wherein $L_Y$ and $R_B$" are as defined above;

$R_8$ is hydrogen, and $R_9$ and $R_{12}$, taken together with the atoms to which they are attached, form a 5- to 6-membered heterocycle;

$R_A$ is independently selected at each occurrence from halogen, nitro, oxo, phosphonoxy, phosphono, thioxo, cyano, or $-L_S-R_E$, wherein two adjacent $R_A$, taken together with the atoms to which they are attached and any atoms between the atoms to which they are attached, can optionally form carbocycle or heterocycle;

$R_E$ is independently selected at each occurrence from —O—$R_S$, —S—$R_S$, —C(O)$R_S$, —OC(O)$R_S$, —C(O)O$R_S$, —N($R_S R_S'$), —S(O)$R_S$, —SO$_2 R_S$, —C(O)N($R_S R_S'$), —N($R_S$)C(O)$R_S'$, —N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$O$R_S$, —S(O)O$R_S$, —OC(O)O$R_S$, —N($R_S$)C(O)O$R_S'$, —OC(O)N($R_S R_S'$), —N($R_S$)S(O)—$R_S'$, —S(O)N($R_S R_S'$) or —C(O)N($R_S$)C(O)—$R_S'$; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl;

$L_S$ is each independently selected at each occurrence from bond; or C$_1$-C$_6$alkylene, C$_2$-C$_6$alkenylene or C$_2$-C$_6$alkynylene; and $R_S$, $R_S'$ and $R_S''$ are each independently selected at each occurrence from hydrogen; C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_S$, $R_S'$ or $R_S'$ is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$' C$_6$alkenyl, C$_2$-C$_6$alkynyl, C$_1$-C$_6$haloalkyl, C$_2$-C$_6$haloalkenyl or C$_2$-C$_6$haloalkynyl.

2. The compound or salt according to claim 1, wherein $R_2$ and $R_5$, taken together with the atoms to which they are attached, form

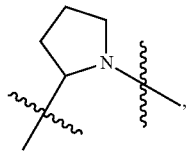 [SMILES: *C1CCCN1*]

and $R_9$ and $R_{12}$, taken together with the atoms to which they are attached, form

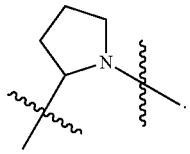 [SMILES: *C1CCCN1*]

3. The compound or salt according to claim 2, wherein B is 5- to 6-membered heterocycle.

4. The compound or salt according to claim 3, wherein X is a ring system comprising a 6- to 12-membered bicycle which is substituted with one or more $R_A$, and wherein two adjacent $R_A$, taken together with the atoms to which they are attached, form carbocycle or heterocycle.

5. The compound or salt according to claim 3, wherein D is phenyl.

6. The compound or salt according to claim 4, wherein D is phenyl.

7. A pharmaceutical composition comprising the compound or salt of claim 1.

* * * * *